United States Patent
Chen et al.

(10) Patent No.: US 11,685,746 B2
(45) Date of Patent: Jun. 27, 2023

(54) HETEROARYL COMPOUNDS FOR TREATING HUNTINGTON'S DISEASE

(71) Applicant: PTC THERAPEUTICS, INC., South Plainfield, NJ (US)

(72) Inventors: Guangming Chen, Bridgewater, NJ (US); Anuradha Bhattacharyya, Edison, NJ (US); Yao Jiang, South Plainfield, NJ (US); Gary Mitchell Karp, Princeton Junction, NJ (US); Jana Narasimhan, Scotch Plains, NJ (US); Anthony Turpoff, Hillsborough, NJ (US); Nanjing Zhang, Princeton, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 207 days.

(21) Appl. No.: 17/254,848

(22) PCT Filed: Jun. 25, 2019

(86) PCT No.: PCT/US2019/038900
§ 371 (c)(1),
(2) Date: Dec. 21, 2020

(87) PCT Pub. No.: WO2020/005882
PCT Pub. Date: Jan. 2, 2020

(65) Prior Publication Data
US 2021/0380603 A1 Dec. 9, 2021

Related U.S. Application Data

(60) Provisional application No. 62/690,605, filed on Jun. 27, 2018.

(51) Int. Cl.
*C07D 513/04* (2006.01)
*C07D 519/00* (2006.01)

(52) U.S. Cl.
CPC ......... *C07D 513/04* (2013.01); *C07D 519/00* (2013.01)

(58) Field of Classification Search
CPC ............................ C07D 513/04; C07D 519/00
USPC ......................................................... 514/249
See application file for complete search history.

(56) References Cited

U.S. PATENT DOCUMENTS

| | | |
|---|---|---|
| 3,558,618 A | 1/1971 | Trepanier |
| 4,122,274 A | 10/1978 | Juby |
| 4,342,870 A | 8/1982 | Kennis et al. |
| 5,089,633 A | 2/1992 | Powers et al. |
| 5,599,816 A | 2/1997 | Chu et al. |
| 5,916,916 A | 6/1999 | Hauser et al. |
| 6,468,607 B1 | 10/2002 | Takehara et al. |
| 6,630,488 B1 | 10/2003 | Lamothe et al. |
| 6,977,255 B2 | 12/2005 | Robertson et al. |
| 7,326,711 B2 | 2/2008 | Wang et al. |
| 7,399,767 B2 | 7/2008 | Zhang et al. |
| 7,569,337 B2 | 8/2009 | Auberson |
| 7,655,657 B2 | 2/2010 | Stoner et al. |
| 7,897,792 B2 | 3/2011 | Iikura et al. |
| 7,910,578 B2 | 3/2011 | Peters et al. |
| 8,314,119 B2 | 11/2012 | Schrimpf et al. |

(Continued)

FOREIGN PATENT DOCUMENTS

| | | |
|---|---|---|
| DE | 2345064 A1 | 4/1974 |
| EP | 1227084 A1 | 7/2002 |

(Continued)

OTHER PUBLICATIONS

International Search Report for PCT/EP2016/076905, dated Feb. 9, 2017.

(Continued)

*Primary Examiner* — Kahsay Habte
(74) *Attorney, Agent, or Firm* — Hoffmann & Baron, LLP

(57) ABSTRACT

The present description relates to compounds, forms, and pharmaceutical compositions thereof and methods of using such compounds, forms, or compositions thereof for treating or ameliorating Huntington's disease.

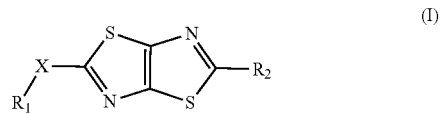

(I)

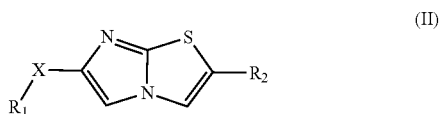

(II)

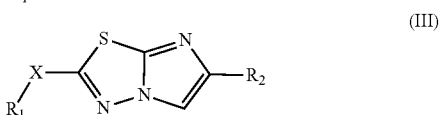

(III)

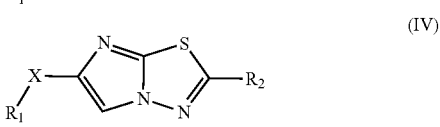

(IV)

In particular, the present description relates to substituted bicyclic heteroaryl compounds of Formula (I), Formula (II), Formula (III), or Formula (IV), forms and pharmaceutical compositions thereof and methods of using such compounds, forms, or compositions thereof for treating or ameliorating Huntington's disease.

9 Claims, No Drawings

(56) References Cited

U.S. PATENT DOCUMENTS

| | | |
|---|---|---|
| 8,337,941 B2 | 12/2012 | Gubernator et al. |
| 8,563,550 B2 | 10/2013 | Pevarello et al. |
| 8,633,019 B2 | 1/2014 | Paushkin et al. |
| 8,846,661 B2 | 9/2014 | Schrimpf et al. |
| 8,921,361 B2 | 12/2014 | Cmiljanovic et al. |
| 9,371,336 B2 | 6/2016 | Lee et al. |
| 9,399,649 B2 | 7/2016 | Chen et al. |
| 9,617,268 B2 | 4/2017 | Woll et al. |
| 9,969,754 B2 | 5/2018 | Ratni et al. |
| 2002/0099208 A1 | 7/2002 | Yu et al. |
| 2003/0004164 A1 | 1/2003 | Bebbington et al. |
| 2003/0199526 A1 | 10/2003 | Choquette et al. |
| 2005/0159597 A1 | 7/2005 | Ji et al. |
| 2006/0205741 A1 | 9/2006 | Zhang et al. |
| 2007/0078144 A1 | 4/2007 | Stockwell et al. |
| 2007/0191374 A1 | 8/2007 | Hodgetts |
| 2008/0171792 A1 | 7/2008 | Jobdevairakkam et al. |
| 2008/0255162 A1 | 10/2008 | Bruendl et al. |
| 2009/0163464 A1 | 6/2009 | Black et al. |
| 2009/0163515 A1 | 6/2009 | Birault et al. |
| 2009/0264433 A1 | 10/2009 | Russell et al. |
| 2010/0004233 A1 | 1/2010 | Iikura et al. |
| 2010/0035279 A1 | 2/2010 | Gubernator et al. |
| 2010/0267721 A1 | 10/2010 | Hohlweg et al. |
| 2011/0086833 A1 | 4/2011 | Paushkin et al. |
| 2011/0118289 A1 | 5/2011 | Giordani et al. |
| 2012/0083495 A1 | 4/2012 | Heemskerk et al. |
| 2014/0051672 A1 | 2/2014 | Cheung et al. |
| 2014/0206661 A1 | 7/2014 | Axford et al. |
| 2014/0329825 A1 | 11/2014 | Heback et al. |
| 2015/0005289 A1 | 1/2015 | Qi et al. |
| 2015/0057218 A1 | 2/2015 | Zhong et al. |
| 2015/0080383 A1 | 3/2015 | Yang et al. |
| 2015/0119380 A1 | 4/2015 | Woll et al. |
| 2017/0000794 A1 | 1/2017 | Naryshkin |
| 2017/0002016 A1 | 1/2017 | Shishido et al. |
| 2017/0096411 A1 | 4/2017 | Vechorkin et al. |
| 2017/0121197 A1 | 5/2017 | Tale |

FOREIGN PATENT DOCUMENTS

| | | |
|---|---|---|
| EP | 2560008 A2 | 2/2013 |
| FR | 2914188 A1 | 10/2008 |
| GB | 1047935 | 11/1966 |
| GB | 1383409 | 2/1975 |
| JP | 1981-150091 A | 3/1983 |
| JP | 2006219453 A | 8/2006 |
| WO | 1993/023398 A1 | 11/1993 |
| WO | 1996/039407 A1 | 12/1996 |
| WO | 1998/025930 A1 | 6/1998 |
| WO | 2002/062290 A2 | 8/2002 |
| WO | 2002/087589 A1 | 11/2002 |
| WO | 2004/009558 A1 | 1/2004 |
| WO | 2004/029053 A1 | 4/2004 |
| WO | 2004/113335 A2 | 12/2004 |
| WO | 2005/012288 A1 | 2/2005 |
| WO | 2005/019215 A1 | 3/2005 |
| WO | 2005/061513 A1 | 7/2005 |
| WO | 2005/072720 A1 | 8/2005 |
| WO | 2005/105801 A1 | 11/2005 |
| WO | 2007/003604 A2 | 1/2007 |
| WO | 2007/018738 A1 | 2/2007 |
| WO | 2007/109211 A2 | 9/2007 |
| WO | 2007/130383 A2 | 11/2007 |
| WO | 2007/133561 A2 | 11/2007 |
| WO | 2007/133756 A2 | 11/2007 |
| WO | 2007/135121 A1 | 11/2007 |
| WO | 2008/011109 A2 | 1/2008 |
| WO | 2008/049864 A1 | 5/2008 |
| WO | 2008/077188 A1 | 7/2008 |
| WO | 2009/042907 A1 | 4/2009 |
| WO | 2009/114874 A2 | 9/2009 |
| WO | 2009/126635 A1 | 10/2009 |
| WO | 2009/151546 A2 | 12/2009 |
| WO | 2009/156861 A2 | 12/2009 |
| WO | 2010/000032 A1 | 1/2010 |
| WO | 2010/019236 A1 | 2/2010 |
| WO | 2010/071819 A1 | 6/2010 |
| WO | 2010/093425 A1 | 8/2010 |
| WO | 2010/130934 A2 | 11/2010 |
| WO | 2010/145208 A1 | 12/2010 |
| WO | 2011/050245 A1 | 4/2011 |
| WO | 2011/057204 A2 | 5/2011 |
| WO | 2011/062853 A1 | 5/2011 |
| WO | 2011/085990 A1 | 7/2011 |
| WO | 2012/075393 A2 | 6/2012 |
| WO | 2012/104823 A2 | 8/2012 |
| WO | 2012/116965 A1 | 9/2012 |
| WO | 2013/020993 A1 | 2/2013 |
| WO | 2013/059606 A1 | 4/2013 |
| WO | 2013/068769 A1 | 5/2013 |
| WO | 2013/101974 A1 | 7/2013 |
| WO | 2013/112788 A1 | 8/2013 |
| WO | 2013/119916 A1 | 8/2013 |
| WO | 2013/130689 A1 | 9/2013 |
| WO | 2013/142236 A1 | 9/2013 |
| WO | 2013/163190 A1 | 10/2013 |
| WO | 2014/012050 A2 | 1/2014 |
| WO | 2014/028459 A1 | 2/2014 |
| WO | 2014/116845 A1 | 7/2014 |
| WO | 2014/135244 A1 | 9/2014 |
| WO | 2014/184163 A1 | 11/2014 |
| WO | 2014/209841 A2 | 12/2014 |
| WO | 2015/024876 A2 | 12/2014 |
| WO | 2015/017589 A1 | 2/2015 |
| WO | 2015/095446 A1 | 6/2015 |
| WO | 2015/095449 A1 | 6/2015 |
| WO | 2015/105657 A1 | 7/2015 |
| WO | 2015/110446 A1 | 7/2015 |
| WO | 2017/080967 A1 | 7/2015 |
| WO | 2015/173181 A1 | 11/2015 |
| WO | 2015/197503 A1 | 12/2015 |
| WO | 2016/131776 A1 | 8/2016 |
| WO | 2016/170163 A1 | 10/2016 |
| WO | 2017/023987 A1 | 2/2017 |
| WO | 2017/081111 A1 | 5/2017 |
| WO | 2017/100726 A1 | 6/2017 |
| WO | 2017/175068 A1 | 10/2017 |
| WO | 2017/189829 A1 | 11/2017 |
| WO | 2017/210134 A1 | 12/2017 |
| WO | 2018/081091 A1 | 5/2018 |
| WO | 2018/218133 A1 | 11/2018 |
| WO | 2018/226622 A1 | 12/2018 |
| WO | 2019/005980 A1 | 1/2019 |
| WO | 2019/005993 A1 | 1/2019 |
| WO | 2019/028440 A1 | 2/2019 |
| WO | 2019/191092 A1 | 10/2019 |
| WO | 2019/191229 A1 | 10/2019 |
| WO | 2020/005873 A1 | 1/2020 |
| WO | 2020/005877 A1 | 1/2020 |
| WO | 2020/005882 A1 | 1/2020 |

OTHER PUBLICATIONS

Written Opinion of the International Searching Authority for PCT/EP2016/076905, dated Feb. 9, 2017.
International Search Report for PCT/EP2016/077190, dated Mar. 1, 2017.
Written Opinion of the International Searching Authority for PCT/EP2016/077190, dated Mar. 1, 2017.
International Search Report for PCT/EP2016/079816, dated Jan. 19, 2016.
Written Opinion of the International Searching Authority for PCT/EP2016/079816, dated Jan. 19, 2016.
International Search Report for PCT/US2013/025292, dated Aug. 30, 2013.
Written Opinion of the International Searching Authority for PCT/US2013/025292, dated Aug. 30, 2013.
International Search Report in PCT/US2018/039794, dated Oct. 25, 2018.
Written Opinion of the International Searching Authority in PCT/US2018/039794, dated Oct. 25, 2018.

(56) References Cited

OTHER PUBLICATIONS

International Search Report from PCT/US2020/041300, dated Oct. 16, 2020.
Written Opinion from PCT/US2020/041300, dated Oct. 16, 2020.
Pubchem, Substance Record for SID 249779947, Mar. 31, 2015, "4H-Quinolizin-4-one1; Hydrobromide".
Potkin et al., "New directions in therapeutics for Huntington disease", Future Neurology, vol. 13(2):101-121, May 2018.
Wermuth, "The Practice of Medicinal Chemistry", 2nd ed., 2003, Chapters 9-10.
H. Kubinyi, "3D QSAR in Drug Design—Theory Methods and Applications", pp. vii-ix and pp. 243-244, 1998.
Chloé Copin et al, "SnAr versus Buchwald-Hartwig Amination/Amidation in the Imidazo[2,1-b][1,3,4]thiadiazole Series", European Journal of Organic Chemistry, vol. 2015(31), Sep. 29, 2015, p. 6932-6942.
Database Registry, Chemical Abstracts Service, Feb. 22, 2018, Database Accession No. 2178867-25-7.
Database Registry, Chemical Abstracts Service, Sep. 18, 2017, Database Accession No. 2128311-64-6.
Database Registry, Chemical Abstracts Service, Sep. 24, 2017, Database Accession No. 2130300-22-8.
Database Registry, Chemical Abstracts Service, Sep. 25, 2017, Database Accession No. 2130694-60-7.
Fascio Mirta L et al, "Synthesis and antiviral activity of some imidazo[1,2-b][1,3,4]thiadiazole carbohydrate derivatives", Carbohydrate Research,vol. 480, May 21, 2019 , p. 61-66.
Ingo Knepper et al., "3-Acylindoles as versatile starting materials for pyridine ring annulation: synthesis of 1-deazapurine isosteres", Tetrahedron,vol. 67(29):5293-5303, May 14, 2011.
K.K. Abdul Khader et al., "Regioselective synthesis of C-2 substituted imidazo[4,5-b]pyridines utilizing palladium catalysed C—N bond forming reactions with enolizable heterocy", Tetrahedron Letters, vol. 55(10):1778-1783, Feb. 1, 2014.
Mariusz Mojzych et al., "Synthesis of pyrazolo[4,3-e][1,2,4]triazine sulfonamides, novel Sildenafil analogs with tyrosinase inhibitory activity", Bioorganic & Medicinal Chemistry, vol. 22, pp. 6616-6624, Oct. 18, 2014.
Mazzone G et al, "Sintesi e valutazione biologica preliminare di imidazo[2,1-b]-1,3-4-tiadiazoli-2,6-diarilsostituti", Farmaco, Edizione Scientifica, Societa Chimica Italiana, Pavia, IT,vol. 39(7), Jan. 1, 1984, p. 585-598. English Abstract Only.
Patel Harun M et al, "2,5,6-Trisubstituted imidazo[2,1-b][1,3,4]thiadiazoles: Search for antihyperlipidemic agents", European Journal of Medicinal Chemistry, Editions Scientifique Elsevier, Paris, FR, vol. 65, Apr. 18, 2013, p. 119-133.
ISR in PCT/US2019/038889, dated Aug. 8, 2019.
WO in PCT/US2019/038889, mailed Aug. 8, 2019.
ISR in PCT/US2019/038895, dated Aug. 14, 2019.
WO in PCT/US2019/038895, mailed Aug. 14, 2019.
ISR in PCT/US19/38900, dated Aug. 20, 2019.
WO in PCT/US19/38900, mailed Aug. 20, 2019.
J. S. Nair et al: "Synthesis and Fluorescence Properties of 3-Benzoxa- and Thiazol-2-ylquinoline-5 or 7-maleimides.", Cheminform, vol. 36, No. 2, Sep. 1, 2004 (Sep. 1, 2004), pp. 1944-1949.
Naik et al: "Studies in the Vilsmeier-Haack reaction: Part XVI., Synthesis of 7-amino-3-hetrarylquinoline fluorophore and derivatives", Indian Journal of Chemistry, Council of Scientific and Industrial Research (CS I R), DE, vol. 15B, No. 6, Jan. 1, 1977 (Jan. 1, 1977), pp. 506-508.
USPTO, Office Action dated Feb. 4, 2021 in U.S. Appl. No. 16/617,450. See whole document in general and compounds on pp. 10-14 and 15-18 in particular.
Macdonald et al., "Quantification Assays for Total and Polyglutamine-Expanded Huntingtin Proteins", PLOS One, 2014, vol. 9(5), dated May 2014, e96854, pp. 1-17.
Palacino et al., "SMN2 splice modulators enhance U1-pre-mRNA association and rescue SM0A mice", Nature: Chemical Biology, pp. 511-517 and 5 Supplemental Pages + S1-S20, vol. 11, Jun. 1, 2015.

Pryor et al., "Huntingtin promotes mTORC1 signaling in the pathogenesis of Huntington's disease", Sci. Signal, dated Oct. 28, 2014, vol. 7, Issue 349, ra103, pp. 1-12.
Cheung et al., "Discovery of Small Molecule Splicing Modulators of Survival Motor Neuron-2 (SMN2) for the Treatment of Spinal Muscular Atrophy (SMA)", J. Med. Chem. XXXX, XXX, XXX-XXX, Aug. 15, 2018 (received), Nov. 8, 2018 (published), pp. A-P.
Brunhilde Wirth et al., "Moving towards treatments for spinal muscular atrophy: hopes and limits", Expert Opinion on Emerging drugs, 20(3):353-356, Apr. 28, 2015.
Chiara Zanetta et al., "Molecular Therapeutic Strategies for Spinal Muscular Atrophies: Current and Future Clinical Trials", Clinical Therapeutics, 36(1):128-140, Dec. 17, 2013.
Coady et al., 2010, "Trans-splicing-mediated improvement in a severe mouse model of spinal muscular atrophy", J. Neurosci., vol. 30(1), pp. 126-130, 2010.
Combring et al., "Respiratory syncytial virus fusion inhibitors. Part 6: An examination of the effect of structural variation for the benzimidazol-2-one heterocycle moiety", Bioorganic & Medicinal Chemistry Letters, 17(17):4784-4790, Aug. 4, 2007.
European Patent Office, Communication pursuant to Article 94(3) EPC, European Application No. 14877918.4, dated Mar. 23, 2018.
Greene, Protective Groups in Organic Syntehsis, 1991, Wiley, New York, pp. v-xxi and 1-17.
Higuchi and W. Stella, "Pro-drugs as novel delivery systems", vol. 14 of the A.C.S., Symposium Series and in Bioreversible Carriers in Drug Design, ed., Edward B. Roche, American Pharmaceutical Association and Pergamon Press (1975).
Hua et al., "Peripheral SMN restoration is essential or long-term rescue of a severe SMA mouse model", Nature, vol. 478(7367), pp. 123-126, 2012.
Jarecki et al., "Diverse small-molecule modulators of SMN expression found by high-throughput compound screening: early leads towards a therapeutic for spinal muscular atrophy", Human molecular genetics, 14(14):2003-2018, 2005.
Knight et al., "Isoform-specific phosphoinositide 3-kinase inhibitors from an arylmorpholine scaffold", Bioorganic & Medicinal Chemistry, vol. 12(17):4749-4759, 2004.
Kocar, Transformations of 3-aminopyridazines. Synthesis of 4-oxo-4H-pyrimido [1,2-b]pyridazine and 1-(substituted pyridazin-3-yl)-1H-1,2,3-triazole derivatives, Arkivoc, vol. 8, 2002, 143-156.
Le et al., "SMND7, the major product of the centromeric survival motor neuron (SMN2) gene, extends survival in mice with spinal muscular atrophy and associates with full-length SMN", Human Molecular Genetics, vol. 14(5), pp. 845-857, 2005.
Liu et al., "A novel nuclear structure containing the survival of motor neurons protein", EMBO J. vol. 15(14), pp. 3555-3565 (1996).
Makhortova et al., "A screen for regulators of survival of motor neuron proteins levels", Nature chemical biology, vol. 7(8):544-552, 2011.
Markus Riessland et al., "The benzamide M344, a novel histone deacetylase inhibitor, significantly increases SMN2 RNA/protein levels in spinal muscular atrophy cells", Hum Genet 120:101-110, May 26, 2006.
Naryshkin et al., "SMN2 splicing modifiers improve motor function and longevity in mice with spinal muscular atrophy", Science, vol. 345(6197):688-693, 2014 (including supplementary materials).
Passini et al., "Antisense Oligonucleotides delivered to the mouse CNS ameliorate symptoms of severe spinal muscular atrophy", Sci Transl. Med., vol. 3(72), 2001.
Peng, Lijie et al., "Identification of pyrido[1,2-alpha]pyrimidine-4-ones as new molecules improving the transcriptional functions of estrogen-related receptor alpha", Journal of medicinal chemistry, vol. 54(21):7729-7733, 2011.
PubChem/NCBI Database accession No. CID 377422 [online], 2005, retrieved on Jul. 4, 2016, URL http://pubchem.nci.nlm.nih.gov/compound/377422.
Seisuke Mimori et al., "Protective Effects of 4-phenylbutyrate derivatives on the neuronal cell death and endoplasmic reticulum stress," Biological & Pharmaceutical Bulletin of Japan, 35(1):84-90, Jan. 1, 2012.

(56) References Cited

OTHER PUBLICATIONS

Shao, Ning et al., "Synthesis and structure-activity relationship (SAR) study of 4-azabenzoxazole analogues as H3 antagonists", Bioorganic & Medicinal chemistry letters, vol. 22(5):2075-2078, 2012.

Sin et al., "Respiratory syncytial virus fusion inhibitors. Part 7: Structure-activity relationships associated with a series of isatin oximes that demonstrate antiviral activity in vivo", Bioorganic & Medicinal Chemistry Letters, 19(16):4857-4862, Aug. 15, 2009.

Yuo et al., 2008, "5-(N-ethyl-N-isopropyl)-amiloride enhances SMN2 exon 7 inclusion and protein expression in spinal muscular atrophy cells", Annals of neurology, vol. 63(1):26-34, 2008.

Lazarev et al., "Factors Affecting Aggregate Formation in Cell Models of Huntington's Disease and Amyotrophic Lateral Sclerosis", Acta Naturae, vol. 5(2):81-89, Apr. 2013.

International Search Report for PCT/US2018/035954, dated Oct. 1, 2018.

Written Opinion of the International Searching Authority for PCT/US2018/035954, dated Oct. 1, 2018.

International Search Report for PCT/US2018/039775, dated Oct. 29, 2018.

Written Opinion of the International Searching Authority for PCT/US2018/039775, dated Oct. 29, 2018.

International Search Report in PCT/US2016/066042, dated Mar. 16, 2017.

Written Opinion of the International Searching Authority for PCT/US2016/066042, dated Mar. 16, 2017.

International Search Report for PCT/US2019/024068, dated Jul. 10, 2019.

Written Opinion of the International Searching Authority for PCT/US2019/024068, dated Jul. 10, 2019.

International Search Report for PCT/US2019/024278, dated May 28, 2019.

Written Opinion of the International Searching Authority for PCT/US2019/024278, dated May 28, 2019.

International Search Report for PCT/EP2012/065499, dated Sep. 28, 2012.

Written Opinion of the International Searching Authority for PCT/EP2012/065499, dated Sep. 28, 2012.

International Search Report for PCT/EP2014/059699, dated Aug. 25, 2014.

Written Opinion of the International Searching Authority for PCT/EP2014/059699, dated Aug. 25, 2014.

International Search Report for PCT/EP2015/051066, dated Feb. 19, 2015.

Written Opinion of the International Searching Authority for PCT/EP2015/051066, dated Feb. 19, 2015.

International Search Report for PCT/EP2015/060343, dated Jul. 13, 2015.

Written Opinion of the International Searching Authority for PCT/EP2015/060343, dated Jul. 13, 2015.

International Search Report for PCT/EP2016/060952, dated Jun. 29, 2016.

Written Opinion of the International Searching Authority for PCT/EP2016/060952, dated Jun. 29, 2016.

International Search Report for PCT/EP2016/063894, dated Jan. 19, 2017.

Written Opinion of the International Searching Authority for PCT/EP2016/063894, dated Jan. 19, 2017.

HETEROARYL COMPOUNDS FOR TREATING HUNTINGTON'S DISEASE

CROSS-REFERENCE TO RELATED APPLICATIONS

This application is a U.S. National Stage filing under 35 U.S.C. § 371 of International Application No. PCT/US2019/038900, filed Jun. 25, 2019, which in turn claims priority to U.S. Provisional Application No. 62/690,605, filed Jun. 27, 2018, the entire contents of which are incorporated by reference herein.

An aspect of the present description relates to compounds, forms, and pharmaceutical compositions thereof and methods of using such compounds, forms, or compositions thereof useful for treating or ameliorating Huntington's disease. In particular, another aspect of the present description relates to substituted bicyclic heteroaryl compounds, forms and pharmaceutical compositions thereof and methods of using such compounds, forms, or compositions thereof for treating or ameliorating Huntington's disease.

BACKGROUND

Huntington's disease (HD) is a progressive, autosomal dominant neurodegenerative disorder of the brain, having symptoms characterized by involuntary movements, cognitive impairment, and mental deterioration. Death, typically caused by pneumonia or coronary artery disease, usually occurs 13 to 15 years after the onset of symptoms. The prevalence of HD is between three and seven individuals per 100,000 in populations of western European descent. In North America, an estimated 30,000 people have HD, while an additional 200,000 people are at risk of inheriting the disease from an affected parent. The disease is caused by an expansion of uninterrupted trinucleotide CAG repeats in the "mutant" huntingtin (Htt) gene, leading to production of HTT (Htt protein) with an expanded poly-glutamine (polyQ) stretch, also known as a "CAG repeat" sequence. There are no current small molecule therapies targeting the underlying cause of the disease, leaving a high unmet need for medications that can be used for treating or ameliorating HD. Consequently, there remains a need to identify and provide small molecule compounds for treating or ameliorating HD.

All other documents referred to herein are incorporated by reference into the present application as though fully set forth herein.

SUMMARY

An aspect of the present description includes compounds comprising, a compound of Formula (I), Formula (II), Formula (III), or Formula (IV):

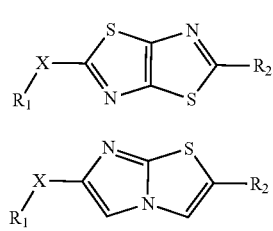

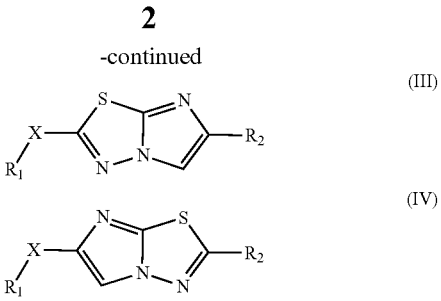

or a form thereof, wherein X, $R_1$, and $R_2$ are as defined herein.

An aspect of the present description includes a method for treating or ameliorating HD in a subject in need thereof comprising, administering to the subject an effective amount of a compound of Formula (I), Formula (II), Formula (III), or Formula (IV) or a form thereof.

An aspect of the present description includes a method for use of a compound of Formula (I), Formula (II), Formula (III), or Formula (IV) or a form or composition thereof for treating or ameliorating HD in a subject in need thereof comprising, administering to the subject an effective amount of the compound of Formula (I), Formula (II), Formula (III), or Formula (IV) or a form or composition thereof.

An aspect of the present description includes a use for a compound of Formula (I), Formula (II), Formula (III), or Formula (IV) or a form thereof for treating or ameliorating HD in a subject in need thereof comprising, administering to the subject an effective amount of the compound of Formula (I), Formula (II), Formula (III), or Formula (IV) or a form thereof.

An aspect of the present description includes a use for a compound of Formula (I), Formula (II), Formula (III), or Formula (IV) or a form thereof in the manufacture of a medicament for treating or ameliorating HD in a subject in need thereof comprising, administering to the subject an effective amount of the medicament.

An aspect of the present description includes a use for a compound of Formula (I), Formula (II), Formula (III), or Formula (IV) or a form thereof in a combination product with one or more therapeutic agents for treating or ameliorating HD in a subject in need thereof comprising, administering to the subject an effective amount of the compound of Formula (I), Formula (II), Formula (III), or Formula (IV) or a form thereof in combination with an effective amount of the one or more agents.

DETAILED DESCRIPTION

An aspect of the present description relates to compounds comprising, a compound of Formula (I), Formula (II), Formula (III), or Formula (IV):

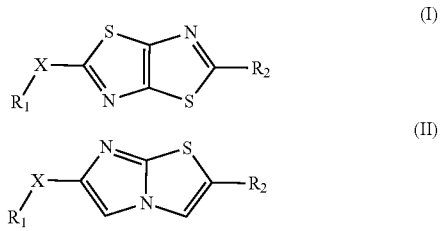

-continued

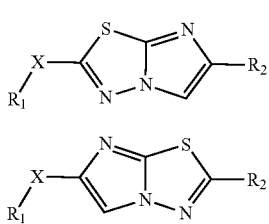

or a form thereof, wherein:

X is selected from N—R$_b$, O, and a bond;

R$_b$ is selected from hydrogen and C$_{1-6}$alkyl;

R$_1$ is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, and wherein each instance of heterocyclyl is optionally substituted where allowed by available valences with one, two, three, or four R$_3$ substituents;

R$_3$ is, in each instance, independently selected from cyano, halogen, hydroxy, C$_{1-6}$alkyl, deutero-C$_{1-4}$alkyl, halo-C$_{1-6}$alkyl, C$_{1-6}$alkoxy, halo-C$_{1-6}$alkoxy, C$_{1-6}$alkoxy-C$_{1-6}$alkyl, amino, C$_{1-6}$alkyl-amino, (C$_{1-6}$alkyl)$_2$-amino, amino-C$_{1-6}$alkyl, hydroxy-C$_{1-6}$alkyl, and C$_{3-10}$cycloalkyl;

R$_2$ is selected from phenyl and heteroaryl, wherein heteroaryl is a 3-7 membered monocyclic or 6-10 membered bicyclic ring system having 1, 2, 3, or 4 heteroatom ring members independently selected from N, O, or S, and wherein each instance of phenyl or heteroaryl is optionally substituted where allowed by available valences with one, two, or three R$_4$ substituents and optionally, with one additional R$_5$ substituent or, wherein, alternatively, each instance of phenyl or heteroaryl is optionally substituted where allowed by available valences with one, two, three, or four R$_4$ substituents;

R$_4$ is, in each instance, independently selected from cyano, halogen, hydroxy, C$_{1-6}$alkyl, deutero-C$_{1-4}$alkyl, halo-C$_{1-6}$alkyl, C$_{1-6}$alkoxy, halo-C$_{1-6}$alkoxy, C$_{1-6}$alkoxy-C$_{1-6}$alkyl, C$_{1-6}$alkoxy-carbonyl, amino, C$_{1-6}$alkyl-amino, (C$_{1-6}$alkyl)$_2$-amino, amino-C$_{1-6}$alkyl, and hydroxy-C$_{1-6}$alkyl;

R$_5$ is heteroaryl;

wherein heteroaryl is a 3-7 membered monocyclic or 6-10 membered bicyclic ring system having 1, 2, 3, or 4 heteroatom ring members independently selected from N, O, or S, and wherein, each instance of heteroaryl is optionally substituted where allowed by available valences with one, two or three R$_6$ substituents; and R$_6$ is, in each instance, independently selected from cyano, halogen, hydroxy, C$_{1-6}$alkyl, deutero-C$_{1-4}$alkyl, halo-C$_{1-6}$alkyl, C$_{1-6}$alkoxy, halo-C$_{1-6}$alkoxy, C$_{1-6}$alkoxy-C$_{1-6}$alkyl, C$_{1-6}$alkoxy-carbonyl, amino, C$_{1-6}$alkyl-amino, (C$_{1-6}$alkyl)$_2$-amino, amino-C$_{1-8}$alkyl, and hydroxy-C$_{1-6}$alkyl;

wherein a form of the compound is selected from the group consisting of a salt, hydrate, solvate, racemate, enantiomer, diastereomer, stereoisomer, and tautomer form thereof.

Aspects of the Description

Another aspect of the present description relates to compounds comprising, a compound of Formula (I), Formula (II), Formula (III), or Formula (IV):

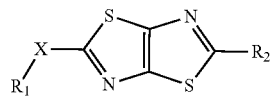

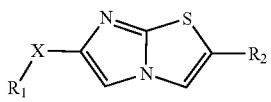

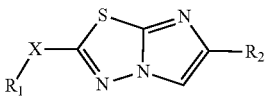

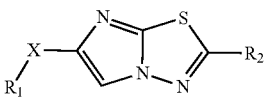

or a form thereof, wherein:

X is selected from N—R$_b$, O, and a bond;

R$_b$ is selected from hydrogen and C$_{1-6}$alkyl;

R$_1$ is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, and wherein each instance of heterocyclyl is optionally substituted where allowed by available valences with one, two, three, or four R$_3$ substituents;

R$_3$ is, in each instance, independently selected from cyano, halogen, hydroxy, C$_{1-6}$alkyl, deutero-C$_{1-4}$alkyl, halo-C$_{1-6}$alkyl, C$_{1-6}$alkoxy, halo-C$_{1-6}$alkoxy, C$_{1-6}$alkoxy-C$_{1-6}$alkyl, amino, C$_{1-6}$alkyl-amino, (C$_{1-6}$alkyl)$_2$-amino, amino-C$_{1-6}$alkyl, hydroxy-C$_{1-6}$alkyl, and C$_{3-10}$cycloalkyl;

R$_2$ is selected from phenyl and heteroaryl, wherein heteroaryl is a 3-7 membered monocyclic or 6-10 membered bicyclic ring system having 1, 2, 3, or 4 heteroatom ring members independently selected from N, O, or S, and wherein each instance of phenyl or heteroaryl is optionally substituted where allowed by available valences with one, two, or three R$_4$ substituents and optionally, with one additional R$_5$ substituent or, wherein, alternatively, each instance of phenyl or heteroaryl is optionally substituted where allowed by available valences with one, two, three, or four R$_4$ substituents;

R$_4$ is, in each instance, independently selected from cyano, halogen, hydroxy, C$_{1-6}$alkyl, deutero-C$_{1-4}$alkyl, halo-C$_{1-6}$alkyl, C$_{1-6}$alkoxy, halo-C$_{1-6}$alkoxy, C$_{1-6}$alkoxy-C$_{1-6}$alkyl, C$_{1-6}$alkoxy-carbonyl, amino, C$_{1-6}$alkyl-amino, (C$_{1-6}$alkyl)$_2$-amino, amino-C$_{1-6}$alkyl, and hydroxy-C$_{1-6}$alkyl;

R$_5$ is heteroaryl;

wherein heteroaryl is a 3-7 membered monocyclic or 6-10 membered bicyclic ring system having 1, 2, 3, or 4 heteroatom ring members independently selected from N, O, or S, and wherein, each instance of heteroaryl is optionally substituted where allowed by available valences with one, two or three $R_6$ substituents; and $R_6$ is, in each instance, independently selected from cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, $C_{1-6}$alkoxy-carbonyl, amino, $C_{1-6}$alkyl-amino, $(C_{1-6}$alkyl$)_2$-amino, amino-$C_{1-8}$alkyl, and hydroxy-$C_{1-6}$alkyl;

wherein a form of the compound is selected from the group consisting of a salt, hydrate, solvate, racemate, enantiomer, diastereomer, stereoisomer, and tautomer form thereof.

One aspect includes a compound of Formula (I), Formula (II), Formula (III), or Formula (IV), wherein X is selected from N—$R_b$, O, and a bond.

Another aspect includes a compound of Formula (I), Formula (II), Formula (III), or Formula (IV), wherein X is N—$R_b$.

Another aspect includes a compound of Formula (I), Formula (II), Formula (III), or Formula (IV), wherein X is O.

Another aspect includes a compound of Formula (I), Formula (II), Formula (III), or Formula (IV), wherein X is a bond.

One aspect includes a compound of Formula (I), Formula (II), Formula (III), or Formula (IV), wherein $R_b$ is selected from hydrogen and $C_{1-6}$alkyl.

Another aspect includes a compound of Formula (I), Formula (II), Formula (III), or Formula (IV), wherein $R_b$ is hydrogen.

Another aspect includes a compound of Formula (I), Formula (II), Formula (III), or Formula (IV), wherein $R_b$ is $C_{1-6}$alkyl.

Another aspect includes a compound of Formula (I), Formula (II), Formula (III), or Formula (IV), wherein $R_b$ is $C_{1-6}$alkyl selected from methyl, ethyl, propyl, isopropyl, and tert-butyl.

Another aspect includes a compound of Formula (I), Formula (II), Formula (III), or Formula (IV), wherein $R_b$ is $C_{1-6}$alkyl selected from methyl and ethyl.

One aspect includes a compound of Formula (I), Formula (II), Formula (III), or Formula (IV), wherein $R_1$ is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, and wherein each instance of heterocyclyl is optionally substituted where allowed by available valences with one, two, three, or four $R_3$ substituents.

Another aspect includes a compound of Formula (I), Formula (II), Formula (III), or Formula (IV), wherein $R_1$ is heterocyclyl selected from pyrrolidinyl, piperidinyl, piperazinyl, 1,2,3,6-tetrahydropyridinyl, octahydroindolizinyl, hexahydropyrrolo[3,4-c]pyrrol-(1H)-yl, 8-azabicyclo[3.2.1]octyl, 8-azabicyclo[3.2.1]oct-2-enyl, 1,6-diazaspiro[3.5]nonyl, 1,7-diazaspiro[3.5]nonyl, 2,7-diazaspiro[3.5]nonyl, and 8'-azaspiro[azetidine-3,3'-bicyclo[3.2.1]octan]-yl, optionally substituted where allowed by available valences with one, two, three, or four $R_3$ substituents.

Another aspect includes a compound of Formula (I), Formula (II), Formula (III), or Formula (IV), wherein $R_1$ is heterocyclyl selected from pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,2,3,6-tetrahydropyridin-2-yl, 1,2,3,6-tetrahydropyridin-3-yl, 1,2,3,6-tetrahydropyridin-4-yl, octahydroindolizin-7-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, 8-azabicyclo[3.2.1]oct-3-yl, 8-azabicyclo[3.2.1]oct-2-en-3-yl, 1,6-diazaspiro[3.5]non-1-yl, 1,7-diazaspiro[3.5]non-1-yl, 2,7-diazaspiro[3.5]non-2-yl, and 8'-azaspiro[azetidine-3,3'-bicyclo[3.2.1]octan]-1-yl, optionally substituted where allowed by available valences with one, two, three, or four $R_3$ substituents.

Another aspect includes a compound of Formula (I), Formula (II), Formula (III), or Formula (IV), wherein $R_1$ is heterocyclyl selected from pyrrolidin-1-yl, pyrrolidin-3-yl, piperidin-3-yl, piperidin-4-yl, piperazin-1-yl, 1,2,3,6-tetrahydropyridin-4-yl, octahydroindolizin-7-yl, hexahydropyrrolo[3,4-c]pyrrol-2(1H)-yl, 8-azabicyclo[3.2.1]oct-3-yl, 8-azabicyclo[3.2.1]oct-2-en-3-yl, 1,6-diazaspiro[3.5]non-1-yl, 1,7-diazaspiro[3.5]non-1-yl, 2,7-diazaspiro[3.5]non-2-yl, and 8'-azaspiro[azetidine-3,3'-bicyclo[3.2.1]octan]-1-yl, optionally substituted where allowed by available valences with one, two, three, or four $R_3$ substituents.

One aspect includes a compound of Formula (I), Formula (II), Formula (III), or Formula (IV), wherein $R_3$ is, in each instance, independently selected from cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, amino, $C_{1-6}$alkyl-amino, $(C_{1-6}$alkyl$)_2$-amino, amino-$C_{1-6}$alkyl, hydroxy-$C_{1-6}$alkyl, and $C_{3-10}$cycloalkyl.

Another aspect includes a compound of Formula (I), Formula (II), Formula (III), or Formula (IV), wherein $R_3$ is, in each instance, independently selected from $C_{1-6}$alkyl, $C_{1-6}$alkyl-amino, hydroxy-$C_{1-6}$alkyl, and $C_{3-10}$cycloalkyl.

Another aspect includes a compound of Formula (I), Formula (II), Formula (III), or Formula (IV), wherein $R_3$ is $C_{1-6}$alkyl selected from methyl, ethyl, propyl, isopropyl, and tert-butyl.

Another aspect includes a compound of Formula (I), Formula (II), Formula (III), or Formula (IV), wherein $R_3$ is $C_{1-6}$alkyl selected from methyl, ethyl, propyl, and isopropyl.

Another aspect includes a compound of Formula (I), Formula (II), Formula (III), or Formula (IV), wherein $R_3$ is $C_{1-6}$alkyl-amino wherein $C_{1-6}$alkyl is selected from methyl, ethyl, propyl, isopropyl, butyl, isobutyl, sec-butyl, tert-butyl, 2-methylbutyl, and 3-methylpentyl.

Another aspect includes a compound of Formula (I), Formula (II), Formula (III), or Formula (IV), wherein $R_3$ is tert-butylamino.

Another aspect includes a compound of Formula (I), Formula (II), Formula (III), or Formula (IV), wherein $R_3$ is hydroxyl-$C_{1-6}$alkyl, wherein $C_{1-6}$alkyl is selected from methyl, ethyl, propyl, isopropyl, butyl, isobutyl, sec-butyl, and tert-butyl partially or completely substituted with one or more hydroxyl groups where allowed by available valences.

Another aspect includes a compound of Formula (I), Formula (II), Formula (III), or Formula (IV), wherein $R_3$ is hydroxymethyl.

Another aspect includes a compound of Formula (I), Formula (II), Formula (III), or Formula (IV), wherein $R_3$ is $C_{3-10}$cycloalkyl selected from cyclopropyl, cylcobutyl, cyclopentyl, cyclohexyl, cycloheptyl, cyclooctyl, bicyclo[2.2.1]hexanyl, and adamantyl.

Another aspect includes a compound of Formula (I), Formula (II), Formula (III), or Formula (IV), wherein $R_3$ is cyclopropyl.

One aspect includes a compound of Formula (I), Formula (II), Formula (III), or Formula (IV), wherein $R_2$ is selected from phenyl and heteroaryl, wherein heteroaryl is a 3-7 membered monocyclic or 6-10 membered bicyclic ring system having 1, 2, 3, or 4 heteroatom ring members independently selected from N, O, or S, and wherein each instance of phenyl or heteroaryl is optionally substituted where allowed by available valences with one, two, or three $R_4$ substituents and optionally, with one additional $R_5$ substituent or, wherein, alternatively, each instance of phenyl or heteroaryl is optionally substituted where allowed by available valences with one, two, three, or four $R_4$ substituents.

Another aspect includes a compound of Formula (I), Formula (II), Formula (III), or Formula (IV), wherein $R_2$ is phenyl, optionally substituted where allowed by available valences with one, two, or three $R_4$ substituents and optionally, with one additional $R_5$ substituent or, alternatively, optionally substituted where allowed by available valences with one, two, three, or four $R_4$ substituents.

Another aspect includes a compound of Formula (I), Formula (II), Formula (III), or Formula (IV), wherein $R_2$ is heteroaryl selected from 1H-pyrazolyl, thiazolyl, isothiazolyl, oxazolyl, 1H-imidazolyl, 1H-1,2,3-triazolyl, 2H-1,2,3-triazolyl, 1H-1,2,4-triazolyl, 2H-tetrazolyl, pyridinyl, pyridin-2(1H)-on-yl, pyrimidinyl, pyrimidin-4(3H)-on-yl, pyridazinyl, pyrazinyl, 1,2,4-triazinyl, 1H-indolyl, 1H-indazolyl, 2H-indazolyl, 1H-benzimidazolyl, 1H-pyrazolo[3,4-c]pyridinyl, 1H-pyrrolo[2,3-b]pyridinyl, 1H-pyrrolo[2,3-c]pyridinyl, imidazo[1,2-a]pyridinyl, imidazo[1,2-b]pyridazinyl, imidazo[1,2-a]pyrazinyl, imidazo[1,2-c]pyrimidinyl, 1H-imidazo[4,5-c]pyridinyl, 3H-imidazo[4,5-c]pyridinyl, imidazo[2,1-b][1,3]thiazolyl, and [1,2,4]triazolo[4,3-a]pyridinyl, optionally substituted where allowed by available valences with one, two, or three $R_4$ substituents and optionally, with one additional $R_5$ substituent or, alternatively, optionally substituted where allowed by available valences with one, two, three, or four $R_4$ substituents.

Another aspect includes a compound of Formula (I), Formula (II), Formula (III), or Formula (IV), wherein $R_2$ is heteroaryl selected from 1H-imidazolyl, pyridinyl, pyridin-2(1H)-on-yl, pyrimidinyl, pyrimidin-4(3H)-on-yl, pyridazinyl, pyrazinyl, 1,2,4-triazinyl, 1H-indolyl, 1H-indazolyl, 2H-indazolyl, 1H-benzimidazolyl, 1H-pyrazolo[3,4-c]pyridinyl, 1H-pyrrolo[2,3-b]pyridinyl, 1H-pyrrolo[2,3-c]pyridinyl, imidazo[1,2-a]pyridinyl, imidazo[1,2-b]pyridazinyl, imidazo[1,2-a]pyrazinyl, imidazo[1,2-c]pyrimidinyl, 1H-imidazo[4,5-c]pyridinyl, 3H-imidazo[4,5-c]pyridinyl, and imidazo[2,1-b][1,3]thiazolyl, optionally substituted where allowed by available valences with one, two, or three $R_4$ substituents and optionally, with one additional $R_5$ substituent or, alternatively, optionally substituted where allowed by available valences with one, two, three, or four $R_4$ substituents.

One aspect includes a compound of Formula (I), Formula (II), Formula (III), or Formula (IV), wherein $R_4$ is, in each instance, independently selected from cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, $C_{1-6}$alkoxy-carbonyl, amino, $C_{1-6}$alkyl-amino, $(C_{1-6}$alkyl$)_2$-amino, amino-$C_{1-6}$alkyl, and hydroxy-$C_{1-6}$alkyl.

Another aspect includes a compound of Formula (I), Formula (II), Formula (III), or Formula (IV), wherein $R_4$ is, in each instance, independently selected from cyano, halogen, hydroxy, $C_{1-6}$alkyl, and $C_{1-6}$alkoxy.

Another aspect includes a compound of Formula (I), Formula (II), Formula (III), or Formula (IV), wherein $R_4$ is cyano.

Another aspect includes a compound of Formula (I), Formula (II), Formula (III), or Formula (IV), wherein $R_4$ is halogen selected from bromo, chloro, fluoro, and iodo.

Another aspect includes a compound of Formula (I), Formula (II), Formula (III), or Formula (IV), wherein $R_4$ is halogen selected from bromo, chloro, and fluoro.

Another aspect includes a compound of Formula (I), Formula (II), Formula (III), or Formula (IV), wherein $R_4$ is hydroxy.

Another aspect includes a compound of Formula (I), Formula (II), Formula (III), or Formula (IV), wherein $R_4$ is $C_{1-6}$alkyl selected from methyl, ethyl, propyl, isopropyl, and tert-butyl.

Another aspect includes a compound of Formula (I), Formula (II), Formula (III), or Formula (IV), wherein $R_4$ is methyl.

Another aspect includes a compound of Formula (I), Formula (II), Formula (III), or Formula (IV), wherein $R_4$ is $C_{1-6}$alkoxy selected from methoxy, ethoxy, propoxy, isopropoxy, butoxy, and tert-butoxy.

Another aspect includes a compound of Formula (I), Formula (II), Formula (III), or Formula (IV), wherein $R_4$ is methoxy.

One aspect includes a compound of Formula (I), Formula (II), Formula (III), or Formula (IV), wherein $R_5$ is heteroaryl selected from 1H-pyrazolyl, thiazolyl, isothiazolyl, oxazolyl, 1H-imidazolyl, 1H-1,2,3-triazolyl, 2H-1,2,3-triazolyl, 1H-1,2,4-triazolyl, 2H-tetrazolyl, pyridinyl, pyridin-2(1H)-on-yl, pyrimidinyl, pyrimidin-4(3H)-on-yl, pyridazinyl, pyrazinyl, 1,2,4-triazinyl, 1H-indolyl, 1H-indazolyl, 2H-indazolyl, 1H-benzimidazolyl, 1H-pyrazolo[3,4-c]pyridinyl, 1H-pyrrolo[2,3-b]pyridinyl, imidazo[1,2-a]pyridinyl, imidazo[1,2-b]pyridazinyl, imidazo[1,2-a]pyrazinyl, imidazo[1,2-c]pyrimidinyl, 1H-imidazo[4,5-c]pyridinyl, 3H-imidazo[4,5-c]pyridinyl, imidazo[2,1-b][1,3]thiazolyl, and [1,2,4]triazolo[4,3-a]pyridinyl, optionally substituted where allowed by available valences with one, two or three $R_6$ substituents.

Another aspect includes a compound of Formula (I), Formula (II), Formula (III), or Formula (IV), wherein $R_5$ is heteroaryl selected from 1H-pyrazolyl, thiazolyl, isothiazolyl, oxazolyl, 1H-imidazolyl, 1H-1,2,3-triazolyl, 2H-1,2,3-triazolyl, 1H-1,2,4-triazolyl, 2H-tetrazolyl, pyridinyl, pyridin-2(1H)-on-yl, pyrimidinyl, pyridazinyl, and [1,2,4]triazolo[4,3-a]pyridinyl, optionally substituted where allowed by available valences with one, two or three $R_6$ substituents.

One aspect includes a compound of Formula (I), Formula (II), Formula (III), or Formula (IV), wherein $R_6$ is, in each instance, independently selected from cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, $C_{1-6}$alkoxy-carbonyl, amino, $C_{1-6}$alkyl-amino, $(C_{1-6}$alkyl$)_2$-amino, amino-$C_{1-6}$alkyl, and hydroxy-$C_{1-6}$alkyl.

Another aspect includes a compound of Formula (I), Formula (II), Formula (III), or Formula (IV), wherein $R_6$ is, in each instance, independently selected from halogen, hydroxy, $C_{1-6}$alkyl, deutero-$C_{1-4}$alkyl, and $C_{1-6}$alkoxy.

Another aspect includes a compound of Formula (I), Formula (II), Formula (III), or Formula (IV), wherein $R_6$ is halogen selected from bromo, chloro, fluoro, and iodo.

Another aspect includes a compound of Formula (I), Formula (II), Formula (III), or Formula (IV), wherein $R_6$ is halogen selected from chloro, and fluoro.

Another aspect includes a compound of Formula (I), Formula (II), Formula (III), or Formula (IV), wherein $R_6$ is hydroxy.

Another aspect includes a compound of Formula (I), Formula (II), Formula (III), or Formula (IV), wherein $R_6$ is $C_{1-6}$alkyl selected from methyl, ethyl, propyl, isopropyl, and tert-butyl.

Another aspect includes a compound of Formula (I), Formula (II), Formula (III), or Formula (IV), wherein $R_6$ is $C_{1-6}$alkyl selected from methyl and ethyl.

Another aspect includes a compound of Formula (I), Formula (II), Formula (III), or Formula (IV), wherein $R_6$ is deutero-$C_{1-4}$alkyl wherein $C_{1-4}$alkyl is selected from methyl, ethyl, propyl, isopropyl, butyl, isobutyl, sec-butyl, and tert-butyl partially or completely substituted with one or more deuterium atoms where allowed by available valences.

Another aspect includes a compound of Formula (I), Formula (II), Formula (III), or Formula (IV), wherein $R_6$ is ($^2H_3$)methyl.

Another aspect includes a compound of Formula (I), Formula (II), Formula (III), or Formula (IV), wherein $R_6$ is $C_{1-6}$alkoxy selected from methoxy, ethoxy, propoxy, isopropoxy, butoxy, and tert-butoxy.

Another aspect includes a compound of Formula (I), Formula (II), Formula (III), or Formula (IV), wherein $R_6$ is methoxy.

One aspect of the compound of Formula (I), Formula (II), Formula (III), or Formula (IV) includes the compound of Formula (I):

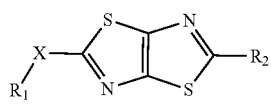

or a form thereof.

One aspect includes a compound of Formula (I) wherein X is selected from N—$R_b$, O, and a bond.

Another aspect includes a compound of Formula (I), wherein X is N—$R_b$.

Another aspect includes a compound of Formula (I), wherein X is O.

Another aspect includes a compound of Formula (I), wherein X is a bond.

One aspect includes a compound of Formula (I), wherein $R_b$ is selected from hydrogen and $C_{1-6}$alkyl.

Another aspect includes a compound of Formula (I), wherein $R_b$ is hydrogen.

Another aspect includes a compound of Formula (I), wherein $R_b$ is $C_{1-6}$alkyl.

Another aspect includes a compound of Formula (I), wherein $R_b$ is $C_{1-6}$alkyl selected from methyl, ethyl, propyl, isopropyl, and tert-butyl.

Another aspect includes a compound of Formula (I), wherein $R_b$ is $C_{1-6}$alkyl selected from methyl and ethyl.

One aspect includes a compound of Formula (I), wherein $R_1$ is heterocyclyl,
wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, and
wherein each instance of heterocyclyl is optionally substituted where allowed by available valences with one, two, three, or four $R_3$ substituents.

Another aspect includes a compound of Formula (I), wherein $R_1$ is heterocyclyl selected from pyrrolidinyl, piperidinyl, piperazinyl, 1,2,3,6-tetrahydropyridinyl, octahydroindolizinyl, hexahydropyrrolo[3,4-c]pyrrol-(1H)-yl, 8-azabicyclo[3.2.1]octyl, 8-azabicyclo[3.2.1]oct-2-enyl, 1,6-diazaspiro[3.5]nonyl, 1,7-diazaspiro[3.5]nonyl, 2,7-diazaspiro[3.5]nonyl, and 8'-azaspiro[azetidine-3,3'-bicyclo[3.2.1]octan]-yl, optionally substituted where allowed by available valences with one, two, three, or four $R_3$ substituents.

Another aspect includes a compound of Formula (I), wherein $R_1$ is heterocyclyl selected from pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,2,3,6-tetrahydropyridin-2-yl, 1,2,3,6-tetrahydropyridin-3-yl, 1,2,3,6-tetrahydropyridin-4-yl, hexahydropyrrolo[3,4-c]pyrrol-1(1H)-yl, octahydroindolizin-7-yl, hexahydropyrrolo[3,4-c]pyrrol-2(1H)-yl, hexahydropyrrolo[3,4-c]pyrrol-5(1H)-yl, 8-azabicyclo[3.2.1]oct-3-yl, 8-azabicyclo[3.2.1]oct-2-en-3-yl, 1,6-diazaspiro[3.5]non-1-yl, 1,7-diazaspiro[3.5]non-1-yl, 2,7-diazaspiro[3.5]non-2-yl, and 8'-azaspiro[azetidine-3,3'-bicyclo[3.2.1]octan]-1-yl, optionally substituted where allowed by available valences with one, two, three, or four $R_3$ substituents.

Another aspect includes a compound of Formula (I), wherein $R_1$ is heterocyclyl selected from pyrrolidin-1-yl, pyrrolidin-3-yl, piperidin-3-yl, piperidin-4-yl, piperazin-1-yl, 1,2,3,6-tetrahydropyridin-4-yl, hexahydropyrrolo[3,4-c]pyrrol-2(1H)-yl, octahydroindolizin-7-yl, 8-azabicyclo[3.2.1]oct-3-yl, 8-azabicyclo[3.2.1]oct-2-en-3-yl, 1,6-diazaspiro[3.5]non-1-yl, 1,7-diazaspiro[3.5]non-1-yl, 2,7-diazaspiro[3.5]non-2-yl, and 8'-azaspiro[azetidine-3,3'-bicyclo[3.2.1]octan]-1-yl, optionally substituted where allowed by available valences with one, two, three, or four $R_3$ substituents.

One aspect includes a compound of Formula (I), wherein $R_3$ is, in each instance, independently selected from cyano, halogen, hydroxy, $C_{1-6}$alkyl, deutero-C1-4alkyl, halo-$C_{1-6}$alkyl, $C_{1-6}$alkoxy, halo-$C_{1-6}$alkoxy, $C_{1-6}$alkoxy-$C_{1-6}$alkyl, amino, $C_{1-6}$alkyl-amino, ($C_{1-6}$alkyl)$_2$-amino, amino-$C_{1-6}$alkyl, hydroxy-$C_{1-6}$alkyl, and $C_{3-10}$cycloalkyl.

Another aspect includes a compound of Formula (I), wherein $R_3$ is, in each instance, independently selected from $C_{1-6}$alkyl, $C_{1-6}$alkyl-amino, hydroxy-$C_{1-6}$alkyl, and $C_{3-10}$cycloalkyl.

Another aspect includes a compound of Formula (I), wherein $R_3$ is $C_{1-6}$alkyl selected from methyl, ethyl, propyl, isopropyl, and tert-butyl.

Another aspect includes a compound of Formula (I), wherein $R_3$ is $C_{1-6}$alkyl selected from methyl, ethyl, propyl, and isopropyl.

Another aspect includes a compound of Formula (I), wherein $R_3$ is $C_{1-6}$alkyl-amino wherein $C_{1-6}$alkyl is selected from methyl, ethyl, propyl, isopropyl, butyl, isobutyl, sec-butyl, tert-butyl, 2-methylbutyl, and 3-methylpentyl.

Another aspect includes a compound of Formula (I), wherein $R_3$ is tert-butylamino.

Another aspect includes a compound of Formula (I), wherein $R_3$ is hydroxyl-$C_{1-6}$alkyl, wherein $C_{1-6}$alkyl is selected from methyl, ethyl, propyl, isopropyl, butyl, isobutyl, sec-butyl, and tert-butyl partially or completely substituted with one or more hydroxyl groups where allowed by available valences.

Another aspect includes a compound of Formula (I), wherein $R_3$ is hydroxymethyl.

Another aspect includes a compound of Formula (I), wherein $R_3$ is $C_{3-10}$cycloalkyl selected from cyclopropyl, cylcobutyl, cyclopentyl, cyclohexyl, cycloheptyl, cyclooctyl, bicyclo[2.2.1]hexanyl, and adamantyl.

Another aspect includes a compound of Formula (I), wherein $R_3$ is cyclopropyl.

One aspect includes a compound of Formula (I), wherein $R_2$ is selected from phenyl and heteroaryl, wherein heteroaryl is a 3-7 membered monocyclic or 6-10 membered bicyclic ring system having 1, 2, 3, or 4 heteroatom ring members independently selected from N, O, or S, and wherein each instance of phenyl or heteroaryl is optionally substituted where allowed by available valences with one, two, or three $R_4$ substituents and optionally, with one additional $R_5$ substituent or, wherein, alternatively, each instance of phenyl or heteroaryl is optionally substituted where allowed by available valences with one, two, three, or four $R_4$ substituents.

Another aspect includes a compound of Formula (I), wherein $R_2$ is phenyl, optionally substituted where allowed by available valences with one, two, or three $R_4$ substituents and optionally, with one additional $R_5$ substituent or, alternatively, optionally substituted where allowed by available valences with one, two, three, or four $R_4$ substituents.

Another aspect includes a compound of Formula (I), wherein $R_2$ is heteroaryl selected from 1H-pyrazolyl, thiazolyl, isothiazolyl, oxazolyl, 1H-imidazolyl, 1H-1,2,3-triazolyl, 2H-1,2,3-triazolyl, 1H-1,2,4-triazolyl, 2H-tetrazolyl, pyridinyl, pyridin-2(1H)-on-yl, pyrimidinyl, pyrimidin-4(3H)-on-yl, pyridazinyl, pyrazinyl, 1,2,4-triazinyl, 1H-indolyl, 1H-indazolyl, 2H-indazolyl, 1H-benzimidazolyl, 1H-pyrazolo[3,4-c]pyridinyl, 1H-pyrrolo[2,3-b]pyridinyl, 1H-pyrrolo[2,3-c]pyridinyl, imidazo[1,2-c]pyridinyl, imidazo[1,2-b]pyridazinyl, imidazo[1,2-c]pyrazinyl, imidazo[1,2-c]pyrimidinyl, 1H-imidazo[4,5-c]pyridinyl, 3H-imidazo[4,5-c]pyridinyl, imidazo[2,1-b][1,3]thiazolyl, and [1,2,4]triazolo[4,3-a]pyridinyl, optionally substituted where allowed by available valences with one, two, or three $R_4$ substituents and optionally, with one additional $R_5$ substituent or, alternatively, optionally substituted where allowed by available valences with one, two, three, or four $R_4$ substituents.

Another aspect includes a compound of Formula (I), wherein $R_2$ is heteroaryl selected from 1H-imidazolyl, pyridinyl, pyridin-2(1H)-on-yl, pyrimidinyl, pyrimidin-4(3H)-on-yl, pyridazinyl, pyrazinyl, 1,2,4-triazinyl, 1H-indolyl, 1H-indazolyl, 2H-indazolyl, 1H-benzimidazolyl, 1H-pyrazolo[3,4-c]pyridinyl, 1H-pyrrolo[2,3-b]pyridinyl, 1H-pyrrolo[2,3-c]pyridinyl, imidazo[1,2-c]pyridinyl, imidazo[1,2-b]pyridazinyl, imidazo[1,2-c]pyrazinyl, imidazo[1,2-c]pyrimidinyl, 1H-imidazo[4,5-c]pyridinyl, 3H-imidazo[4,5-c]pyridinyl, and imidazo[2,1-b][1,3]thiazolyl, optionally substituted where allowed by available valences with one, two, or three $R_4$ substituents and optionally, with one additional $R_5$ substituent or, alternatively, optionally substituted where allowed by available valences with one, two, three, or four $R_4$ substituents.

One aspect includes a compound of Formula (I), wherein $R_4$ is, in each instance, independently selected from cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, $C_{1-6}$alkoxy-carbonyl, amino, $C_{1-6}$alkyl-amino, $(C_{1-6}$alkyl$)_2$-amino, amino-$C_{1-6}$alkyl, and hydroxy-$C_{1-6}$alkyl.

Another aspect includes a compound of Formula (I), wherein $R_2$ is, in each instance, independently selected from cyano, halogen, hydroxy, $C_{1-6}$alkyl, and $C_{1-6}$alkoxy.

Another aspect includes a compound of Formula (I), wherein $R_4$ is cyano.

Another aspect includes a compound of Formula (I), wherein $R_4$ is halogen selected from bromo, chloro, fluoro, and iodo.

Another aspect includes a compound of Formula (I), wherein $R_4$ is halogen selected from bromo, chloro and fluoro.

Another aspect includes a compound of Formula (I), wherein $R_4$ is hydroxy.

Another aspect includes a compound of Formula (I), wherein $R_4$ is $C_{1-6}$alkyl selected from methyl, ethyl, propyl, isopropyl, and tert-butyl.

Another aspect includes a compound of Formula (I), wherein $R_4$ is methyl.

Another aspect includes a compound of Formula (I), wherein $R_4$ is $C_{1-6}$alkoxy selected from methoxy, ethoxy, propoxy, isopropoxy, butoxy, and tert-butoxy.

Another aspect includes a compound of Formula (I), wherein $R_4$ is methoxy.

One aspect includes a compound of Formula (I), wherein $R_5$ is heteroaryl selected from 1H-pyrazolyl, thiazolyl, isothiazolyl, oxazolyl, 1H-imidazolyl, 1H-1,2,3-triazolyl, 2H-1,2,3-triazolyl, 1H-1,2,4-triazolyl, 2H-tetrazolyl, pyridinyl, pyridin-2(1H)-on-yl, pyrimidinyl, pyrimidin-4(3H)-on-yl, pyridazinyl, pyrazinyl, 1,2,4-triazinyl, 1H-indolyl, 1H-indazolyl, 2H-indazolyl, 1H-benzimidazolyl, 1H-pyrazolo[3,4-c]pyridinyl, 1H-pyrrolo[2,3-b]pyridinyl, imidazo[1,2-a]pyridinyl, imidazo[1,2-b]pyridazinyl, imidazo[1,2-a]pyrazinyl, imidazo[1,2-c]pyrimidinyl, 1H-imidazo[4,5-c]pyridinyl, 3H-imidazo[4,5-c]pyridinyl, imidazo[2,1-b][1,3]thiazolyl, and [1,2,4]triazolo[4,3-a]pyridinyl, optionally substituted where allowed by available valences with one, two or three $R_6$ substituents.

Another aspect includes a compound of Formula (I), wherein $R_5$ is heteroaryl selected from 1H-pyrazolyl, thiazolyl, isothiazolyl, oxazolyl, 1H-imidazolyl, 1H-1,2,3-triazolyl, 2H-1,2,3-triazolyl, 1H-1,2,4-triazolyl, 2H-tetrazolyl, pyridinyl, pyridin-2(1H)-on-yl, pyrimidinyl, pyridazinyl, and [1,2,4]triazolo[4,3-a]pyridinyl, optionally substituted where allowed by available valences with one, two or three $R_6$ substituents.

One aspect includes a compound of Formula (I), wherein $R_6$ is, in each instance, independently selected from cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, $C_{1-6}$alkoxy-carbonyl, amino, $C_{1-6}$alkyl-amino, $(C_{1-6}$alkyl$)_2$-amino, amino-$C_{1-6}$alkyl, and hydroxy-$C_{1-6}$alkyl.

Another aspect includes a compound of Formula (I), wherein $R_6$ is, in each instance, independently selected from halogen, hydroxy, $C_{1-6}$alkyl, deutero-$C_{1-4}$alkyl, and $C_{1-6}$alkoxy.

Another aspect includes a compound of Formula (I), wherein $R_6$ is halogen selected from bromo, chloro, fluoro, and iodo.

Another aspect includes a compound of Formula (I), wherein $R_6$ is halogen selected from chloro and fluoro.

Another aspect includes a compound of Formula (I), wherein $R_6$ is hydroxy.

Another aspect includes a compound of Formula (I), wherein $R_6$ is $C_{1-6}$alkyl selected from methyl, ethyl, propyl, isopropyl, and tert-butyl.

Another aspect includes a compound of Formula (I), wherein $R_6$ is $C_{1-6}$alkyl selected from methyl and ethyl.

Another aspect includes a compound of Formula (I), wherein $R_6$ is deutero-$C_{1-4}$alkyl wherein $C_{1-4}$alkyl is selected from methyl, ethyl, propyl, isopropyl, butyl, isobutyl, sec-butyl, and tert-butyl partially or completely substituted with one or more deuterium atoms where allowed by available valences.

Another aspect includes a compound of Formula (I), wherein $R_6$ is $(^2H_3)$methyl.

Another aspect includes a compound of Formula (I), wherein $R_4$ is $C_{1-6}$alkoxy selected from methoxy, ethoxy, propoxy, isopropoxy, butoxy, and tert-butoxy.

Another aspect includes a compound of Formula (I), wherein $R_6$ is methoxy.

One aspect of the compound of Formula (I), Formula (II), Formula (III), or Formula (IV) includes the compound of Formula (II):

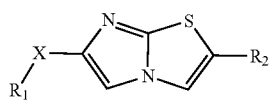

or a form thereof.

One aspect includes a compound of Formula (II) wherein X is selected from N—$R_b$, O, and a bond.

Another aspect includes a compound of Formula (II), wherein X is a bond.

One aspect includes a compound of Formula (II), wherein $R_1$ is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, and wherein each instance of heterocyclyl is optionally substituted where allowed by available valences with one, two, three, or four $R_3$ substituents.

Another aspect includes a compound of Formula (II), wherein $R_1$ is heterocyclyl selected from pyrrolidinyl, piperidinyl, piperazinyl, 1,2,3,6-tetrahydropyridinyl, octahydroindolizinyl, hexahydropyrrolo[3,4-c]pyrrol-(1H)-yl, 8-azabicyclo[3.2.1]octyl, 8-azabicyclo[3.2.1]oct-2-enyl, 1,6-diazaspiro[3.5]nonyl, 1,7-diazaspiro[3.5]nonyl, 2,7-diazaspiro[3.5]nonyl, and 8'-azaspiro[azetidine-3,3'-bicyclo[3.2.1]octan]-yl, optionally substituted where allowed by available valences with one, two, three, or four $R_3$ substituents.

Another aspect includes a compound of Formula (II), wherein $R_1$ is piperidinyl, optionally substituted where allowed by available valences with one, two, three, or four $R_3$ substituents.

Another aspect includes a compound of Formula (II), wherein $R_1$ is heterocyclyl selected from pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,2,3,6-tetrahydropyridin-2-yl, 1,2,3,6-tetrahydropyridin-3-yl, 1,2,3,6-tetrahydropyridin-4-yl, octahydroindolizin-7-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, 8-azabicyclo[3.2.1]oct-3-yl, 8-azabicyclo[3.2.1]oct-2-en-3-yl, 1,6-diazaspiro[3.5]non-1-yl, 1,7-diazaspiro[3.5]non-1-yl, 2,7-diazaspiro[3.5]non-2-yl, and 8'-azaspiro[azetidine-3,3'-bicyclo[3.2.1]octan]-1-yl, optionally substituted where allowed by available valences with one, two, three, or four $R_3$ substituents.

Another aspect includes a compound of Formula (II), wherein $R_1$ is piperidin-4-yl, optionally substituted where allowed by available valences with one, two, three, or four $R_3$ substituents.

One aspect includes a compound of Formula (II), wherein $R_3$ is, in each instance, independently selected from cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, amino, $C_{1-6}$alkyl-amino, $(C_{1-6}$alkyl$)_2$-amino, amino-$C_{1-6}$alkyl, hydroxy-$C_{1-6}$alkyl, and $C_{3-10}$cycloalkyl.

One aspect includes a compound of Formula (II), wherein $R_2$ is selected from phenyl and heteroaryl, wherein heteroaryl is a 3-7 membered monocyclic or 6-10 membered bicyclic ring system having 1, 2, 3, or 4 heteroatom ring members independently selected from N, O, or S, and wherein each instance of phenyl or heteroaryl is optionally substituted where allowed by available valences with one, two, or three $R_4$ substituents and optionally, with one additional $R_5$ substituent or, wherein, alternatively, each instance of phenyl or heteroaryl is optionally substituted where allowed by available valences with one, two, three, or four $R_4$ substituents.

Another aspect includes a compound of Formula (II), wherein $R_2$ is heteroaryl selected from 1H-pyrazolyl, thiazolyl, isothiazolyl, oxazolyl, 1H-imidazolyl, 1H-1,2,3-triazolyl, 2H-1,2,3-triazolyl, 1H-1,2,4-triazolyl, 2H-tetrazolyl, pyridinyl, pyridin-2(1H)-on-yl, pyrimidinyl, pyrimidin-4(3H)-on-yl, pyridazinyl, pyrazinyl, 1,2,4-triazinyl, 1H-indolyl, 1H-indazolyl, 2H-indazolyl, 1H-benzimidazolyl, 1H-pyrazolo[3,4-c]pyridinyl, 1H-pyrrolo[2,3-b]pyridinyl, 1H-pyrrolo[2,3-c]pyridinyl, imidazo[1,2-a]pyridinyl, imidazo[1,2-b]pyridazinyl, imidazo[1,2-a]pyrazinyl, imidazo[1,2-c]pyrimidinyl, 1H-imidazo[4,5-c]pyridinyl, 3H-imidazo[4,5-c]pyridinyl, imidazo[2,1-b][1,3]thiazolyl, and [1,2,4]triazolo[4,3-a]pyridinyl, optionally substituted where allowed by available valences with one, two, or three $R_4$ substituents and optionally, with one additional $R_5$ substituent or, alternatively, is optionally substituted where allowed by available valences with one, two, three, or four $R_4$ substituents.

Another aspect includes a compound of Formula (II), wherein $R_2$ is 2H-indazolyl, optionally substituted where allowed by available valences with one, two, or three $R_4$ substituents and optionally, with one additional $R_5$ substituent or, alternatively, optionally substituted where allowed by available valences with one, two, three, or four $R_4$ substituents.

One aspect includes a compound of Formula (II), wherein $R_4$ is, in each instance, independently selected from cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, $C_{1-6}$alkoxy-carbonyl, amino, $C_{1-6}$alkyl-amino, $(C_{1-6}$alkyl$)_2$-amino, amino-$C_{1-6}$alkyl, and hydroxy-$C_{1-6}$alkyl.

Another aspect includes a compound of Formula (II), wherein $R_4$ is $C_{1-6}$alkyl selected from methyl, ethyl, propyl, isopropyl, and tert-butyl.

Another aspect includes a compound of Formula (II), wherein $R_4$ is methyl.

One aspect includes a compound of Formula (II), wherein $R_5$ is heteroaryl selected from 1H-pyrazolyl, thiazolyl, isothiazolyl, oxazolyl, 1H-imidazolyl, 1H-1,2,3-triazolyl, 2H-1,2,3-triazolyl, 1H-1,2,4-triazolyl, 2H-tetrazolyl, pyridinyl, pyridin-2(1H)-on-yl, pyrimidinyl, pyrimidin-4(3H)-on-yl, pyridazinyl, pyrazinyl, 1,2,4-triazinyl, 1H-indolyl, 1H-indazolyl, 2H-indazolyl, 1H-benzimidazolyl, 1H-pyrazolo[3,4-c]pyridinyl, 1H-pyrrolo[2,3-b]pyridinyl, imidazo[1,2-a]pyridinyl, imidazo[1,2-b]pyridazinyl, imidazo[1,2-a]pyrazinyl, imidazo[1,2-c]pyrimidinyl, 1H-imidazo[4,5-c]pyridinyl, 3H-imidazo[4,5-c]pyridinyl, imidazo[2,1-b][1,3]

thiazolyl, and [1,2,4]triazolo[4,3-a]pyridinyl, optionally substituted where allowed by available valences with one, two or three $R_6$ substituents.

One aspect includes a compound of Formula (II), wherein $R_6$ is, in each instance, independently selected from cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, $C_{1-6}$alkoxy-carbonyl, amino, $C_{1-6}$alkyl-amino, ($C_{1-6}$alkyl)$_2$-amino, amino-$C_{1-6}$alkyl, and hydroxy-$C_{1-6}$alkyl.

One aspect of the compound of Formula (I), Formula (II), Formula (III), or Formula (IV) includes the compound of Formula (III):

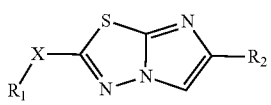

or a form thereof.

One aspect includes a compound of Formula (III) wherein X is selected from N—$R_b$, O, and a bond.

Another aspect includes a compound of Formula (III), wherein X is N—$R_b$.

Another aspect includes a compound of Formula (III), wherein X is a bond.

One aspect includes a compound of Formula (III), wherein $R_b$ is selected from hydrogen and $C_{1-6}$alkyl.

Another aspect includes a compound of Formula (III), wherein $R_b$ is $C_{1-6}$alkyl.

Another aspect includes a compound of Formula (III), wherein $R_b$ is $C_{1-6}$alkyl selected from methyl, ethyl, propyl, isopropyl, and tert-butyl.

Another aspect includes a compound of Formula (III), wherein $R_b$ is methyl.

One aspect includes a compound of Formula (III), wherein $R_1$ is heterocyclyl,
wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, and
wherein each instance of heterocyclyl is optionally substituted where allowed by available valences with one, two, three, or four $R_3$ substituents.

Another aspect includes a compound of Formula (III), wherein $R_1$ is heterocyclyl selected from pyrrolidinyl, piperidinyl, piperazinyl, 1,2,3,6-tetrahydropyridinyl, octahydroindolizinyl, hexahydropyrrolo[3,4-c]pyrrol-(1H)-yl, 8-azabicyclo[3.2.1]octyl, 8-azabicyclo[3.2.1]oct-2-enyl, 1,6-diazaspiro[3.5]nonyl, 1,7-diazaspiro[3.5]nonyl, 2,7-diazaspiro[3.5]nonyl, and 8'-azaspiro[azetidine-3,3'-bicyclo[3.2.1]octan]-yl, optionally substituted where allowed by available valences with one, two, three, or four $R_3$ substituents.

Another aspect includes a compound of Formula (III), wherein $R_1$ is heterocyclyl selected from piperidinyl, 8-azabicyclo[3.2.1]octyl, and 8-azabicyclo[3.2.1]oct-2-enyl, optionally substituted where allowed by available valences with one, two, three, or four $R_3$ substituents.

Another aspect includes a compound of Formula (III), wherein $R_1$ is heterocyclyl selected from pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,2,3,6-tetrahydropyridin-2-yl, 1,2,3,6-tetrahydropyridin-3-yl, 1,2,3,6-tetrahydropyridin-4-yl, octahydroindolizin-7-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, 8-azabicyclo[3.2.1]oct-3-yl, 8-azabicyclo[3.2.1]oct-2-en-3-yl, 1,6-diazaspiro[3.5]non-1-yl, 1,7-diazaspiro[3.5]non-1-yl, 2,7-diazaspiro[3.5]non-2-yl, and 8'-azaspiro[azetidine-3,3'-bicyclo[3.2.1]octan]-1-yl, optionally substituted where allowed by available valences with one, two, three, or four $R_3$ substituents.

Another aspect includes a compound of Formula (III), wherein $R_1$ is heterocyclyl selected from piperidin-4-yl, 8-azabicyclo[3.2.1]oct-3-yl, and 8-azabicyclo[3.2.1]oct-2-en-3-yl, optionally substituted where allowed by available valences with one, two, three, or four $R_3$ substituents.

One aspect includes a compound of Formula (III), wherein $R_3$ is, in each instance, independently selected from cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, amino, $C_{1-6}$alkyl-amino, ($C_{1-6}$alkyl)$_2$-amino, amino-$C_{1-6}$alkyl, hydroxy-$C_{1-6}$alkyl, and $C_{3-14}$cycloalkyl.

Another aspect includes a compound of Formula (III), wherein $R_3$ is $C_{1-6}$alkyl selected from methyl, ethyl, propyl, isopropyl, and tert-butyl.

Another aspect includes a compound of Formula (III), wherein $R_3$ is methyl.

One aspect includes a compound of Formula (III), wherein $R_2$ is selected from phenyl and heteroaryl,
wherein heteroaryl is a 3-7 membered monocyclic or 6-10 membered bicyclic ring system having 1, 2, 3, or 4 heteroatom ring members independently selected from N, O, or S, and
wherein each instance of phenyl or heteroaryl is optionally substituted where allowed by available valences with one, two, or three $R_4$ substituents and optionally, with one additional $R_5$ substituent or,
wherein, alternatively, each instance of phenyl or heteroaryl is optionally substituted where allowed by available valences with one, two, three, or four $R_4$ substituents.

Another aspect includes a compound of Formula (III), wherein $R_2$ is phenyl, optionally substituted where allowed by available valences with one, two, or three $R_4$ substituents and optionally, with one additional $R_5$ substituent or, alternatively, optionally substituted where allowed by available valences with one, two, three, or four $R_4$ substituents.

Another aspect includes a compound of Formula (III), wherein $R_2$ is heteroaryl selected from 1H-pyrazolyl, thiazolyl, isothiazolyl, oxazolyl, 1H-imidazolyl, 1H-1,2,3-triazolyl, 2H-1,2,3-triazolyl, 1H-1,2,4-triazolyl, 2H-tetrazolyl, pyridinyl, pyridin-2(1H)-on-yl, pyrimidinyl, pyrimidin-4(3H)-on-yl, pyridazinyl, pyrazinyl, 1,2,4-triazinyl, 1H-indolyl, 1H-indazolyl, 2H-indazolyl, 1H-benzimidazolyl, 1H-pyrazolo[3,4-c]pyridinyl, 1H-pyrrolo[2,3-b]pyridinyl, 1H-pyrrolo[2,3-c]pyridinyl, imidazo[1,2-a]pyridinyl, imidazo[1,2-b]pyridazinyl, imidazo[1,2-a]pyrazinyl, imidazo[1,2-c]pyrimidinyl, 1H-imidazo[4,5-c]pyridinyl, 3H-imidazo[4,5-c]pyridinyl, imidazo[2,1-b][1,3]thiazolyl, and [1,2,4]triazolo[4,3-a]pyridinyl, optionally substituted where allowed by available valences with one, two, or three $R_4$ substituents and optionally, with one additional $R_5$ substituent or, alternatively, optionally substituted where allowed by available valences with one, two, three, or four $R_4$ substituents.

Another aspect includes a compound of Formula (III), wherein $R_2$ is 2H-indazolyl, optionally substituted where allowed by available valences with one, two, or three $R_4$ substituents and optionally, with one additional $R_5$ substituent or, alternatively, optionally substituted where allowed by available valences with one, two, three, or four $R_4$ substituents.

One aspect includes a compound of Formula (III), wherein $R_4$ is, in each instance, independently selected from cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, $C_{1-6}$alkoxy-carbonyl, amino, $C_{1-6}$alkyl-amino, ($C_{1-6}$alkyl)$_2$-amino, amino-$C_{1-6}$alkyl, and hydroxy-$C_{1-6}$alkyl.

Another aspect includes a compound of Formula (III), wherein $R_4$ is, in each instance, independently selected from cyano and hydroxy.

Another aspect includes a compound of Formula (III), wherein $R_4$ is hydroxy.

One aspect includes a compound of Formula (III), wherein $R_5$ is heteroaryl selected from 1H-pyrazolyl, thiazolyl, isothiazolyl, oxazolyl, 1H-imidazolyl, 1H-1,2,3-triazolyl, 2H-1,2,3-triazolyl, 1H-1,2,4-triazolyl, 2H-tetrazolyl, pyridinyl, pyridin-2(1H)-on-yl, pyrimidinyl, pyrimidin-4 (3H)-on-yl, pyridazinyl, pyrazinyl, 1,2,4-triazinyl, 1H-indolyl, 1H-indazolyl, 2H-indazolyl, 1H-benzimidazolyl, 1H-pyrazolo[3,4-c]pyridinyl, 1H-pyrrolo[2,3-b]pyridinyl, imidazo[1,2-a]pyridinyl, imidazo[1,2-b]pyridazinyl, imidazo[1,2-a]pyrazinyl, imidazo[1,2-c]pyrimidinyl, 1H-imidazo[4,5-c]pyridinyl, 3H-imidazo[4,5-c]pyridinyl, imidazo[2,1-b][1,3]thiazolyl, and [1,2,4]triazolo[4,3-a]pyridinyl, wherein, optionally substituted where allowed by available valences with one, two or three $R_6$ substituents.

Another aspect includes a compound of Formula (III), wherein $R_5$ is 1H-pyrazolyl, optionally substituted where allowed by available valences with one, two or three $R_6$ substituents.

One aspect includes a compound of Formula (III), wherein $R_6$ is, in each instance, independently selected from cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, $C_{1-6}$alkoxy-carbonyl, amino, $C_{1-6}$alkyl-amino, ($C_{1-6}$alkyl)$_2$-amino, amino-$C_{1-6}$alkyl, and hydroxy-$C_{1-6}$alkyl.

One aspect of the compound of Formula (I), Formula (II), Formula (III), or Formula (IV) includes the compound of Formula (IV):

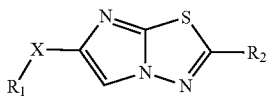

(IV)

or a form thereof.

One aspect includes a compound of Formula (IV) wherein X is selected from N—$R_b$, O, and a bond.

Another aspect includes a compound of Formula (IV), wherein X is a bond.

One aspect includes a compound of Formula (IV), wherein $R_1$ is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, and wherein each instance of heterocyclyl is optionally substituted where allowed by available valences with one, two, three, or four $R_3$ substituents.

Another aspect includes a compound of Formula (IV), wherein $R_1$ is heterocyclyl selected from pyrrolidinyl, piperidinyl, piperazinyl, 1,2,3,6-tetrahydropyridinyl, octahydroindolizinyl, hexahydropyrrolo[3,4-c]pyrrol-(1H)-yl, 8-azabicyclo[3.2.1]octyl, 8-azabicyclo[3.2.1]oct-2-enyl, 1,6-diazaspiro[3.5]nonyl, 1,7-diazaspiro[3.5]nonyl, 2,7-diazaspiro[3.5]nonyl, and 8'-azaspiro[azetidine-3,3'-bicyclo[3.2.1]octan]-yl, optionally substituted where allowed by available valences with one, two, three, or four $R_3$ substituents.

Another aspect includes a compound of Formula (IV), wherein $R_1$ is piperidinyl, optionally substituted where allowed by available valences with one, two, three, or four $R_3$ substituents.

Another aspect includes a compound of Formula (IV), wherein $R_1$ is heterocyclyl selected from pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,2,3,6-tetrahydropyridin-2-yl, 1,2,3,6-tetrahydropyridin-3-yl, 1,2,3,6-tetrahydropyridin-4-yl, octahydroindolizin-7-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, 8-azabicyclo[3.2.1]oct-3-yl, 8-azabicyclo[3.2.1]oct-2-en-3-yl, 1,6-diazaspiro[3.5]non-1-yl, 1,7-diazaspiro[3.5]non-1-yl, 2,7-diazaspiro[3.5]non-2-yl, and 8'-azaspiro[azetidine-3,3'-bicyclo[3.2.1]octan]-1-yl, optionally substituted where allowed by available valences with one, two, three, or four $R_3$ substituents.

Another aspect includes a compound of Formula (IV), wherein $R_1$ is piperidin-4-yl, optionally substituted where allowed by available valences with one, two, three, or four $R_3$ substituents.

One aspect includes a compound of Formula (IV), wherein $R_3$ is, in each instance, independently selected from cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, amino, $C_{1-6}$alkyl-amino, ($C_{1-6}$alkyl)$_2$-amino, amino-$C_{1-6}$alkyl, hydroxy-$C_{1-6}$alkyl, and $C_{3-10}$cycloalkyl.

One aspect includes a compound of Formula (IV), wherein $R_2$ is selected from phenyl and heteroaryl, wherein heteroaryl is a 3-7 membered monocyclic or 6-10 membered bicyclic ring system having 1, 2, 3, or 4 heteroatom ring members independently selected from N, O, or S, and wherein each instance of phenyl or heteroaryl is optionally substituted where allowed by available valences with one, two, or three $R_4$ substituents and optionally, with one additional $R_5$ substituent or, wherein, alternatively, each instance of phenyl or heteroaryl is optionally substituted where allowed by available valences with one, two, three, or four $R_4$ substituents.

Another aspect includes a compound of Formula (IV), wherein $R_2$ is heteroaryl selected from 1H-pyrazolyl, thiazolyl, isothiazolyl, oxazolyl, 1H-imidazolyl, 1H-1,2,3-triazolyl, 2H-1,2,3-triazolyl, 1H-1,2,4-triazolyl, 2H-tetrazolyl, pyridinyl, pyridin-2(1H)-on-yl, pyrimidinyl, pyrimidin-4 (3H)-on-yl, pyridazinyl, pyrazinyl, 1,2,4-triazinyl, 1H-indolyl, 1H-indazolyl, 2H-indazolyl, 1H-benzimidazolyl, 1H-pyrazolo[3,4-c]pyridinyl, 1H-pyrrolo[2,3-b]pyridinyl, 1H-pyrrolo[2,3-c]pyridinyl, imidazo[1,2-a]pyridinyl, imidazo[1,2-b]pyridazinyl, imidazo[1,2-a]pyrazinyl, imidazo[1,2-c]pyrimidinyl, 1H-imidazo[4,5-c]pyridinyl, 3H-imidazo[4,5-c]pyridinyl, imidazo[2,1-b][1,3]thiazolyl, and [1,2,4]triazolo[4,3-a]pyridinyl, optionally substituted where allowed by available valences with one, two, or three $R_4$ substituents and optionally, with one additional $R_5$ substituent or, alternatively, optionally substituted where allowed by available valences with one, two, three, or four $R_4$ substituents.

Another aspect includes a compound of Formula (IV), wherein $R_2$ is heteroaryl selected from 2H-indazolyl and imidazo[1,2-a]pyridinyl, optionally substituted where allowed by available valences with one, two, or three $R_4$ substituents and optionally, with one additional $R_5$ substituent or, alternatively, optionally substituted where allowed by available valences with one, two, three, or four $R_4$ substituents.

One aspect includes a compound of Formula (IV), wherein $R_4$ is, in each instance, independently selected from cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, $C_{1-6}$alkoxy-carbonyl, amino, $C_{1-6}$alkyl-amino, ($C_{1-6}$alkyl)$_2$-amino, amino-$C_{1-6}$alkyl, and hydroxy-$C_{1-6}$alkyl.

Another aspect includes a compound of Formula (IV), wherein $R_4$ is, in each instance, independently selected from cyano, halogen, and $C_{1-6}$alkyl.

Another aspect includes a compound of Formula (IV), wherein $R_4$ is cyano.

Another aspect includes a compound of Formula (IV), wherein $R_4$ is halogen selected from bromo, chloro, fluoro, and iodo.

Another aspect includes a compound of Formula (IV), wherein $R_4$ is fluoro.

Another aspect includes a compound of Formula (IV), wherein $R_4$ is $C_{1-6}$alkyl selected from methyl, ethyl, propyl, isopropyl, and tert-butyl.

Another aspect includes a compound of Formula (IV), wherein $R_4$ is methyl.

One aspect includes a compound of Formula (IV), wherein $R_5$ is heteroaryl selected from 1H-pyrazolyl, thiazolyl, isothiazolyl, oxazolyl, 1H-imidazolyl, 1H-1,2,3-triazolyl, 2H-1,2,3-triazolyl, 1H-1,2,4-triazolyl, 2H-tetrazolyl, pyridinyl, pyridin-2(1H)-on-yl, pyrimidinyl, pyrimidin-4(3H)-on-yl, pyridazinyl, pyrazinyl, 1,2,4-triazinyl, 1H-indolyl, 1H-indazolyl, 2H-indazolyl, 1H-benzimidazolyl, 1H-pyrazolo[3,4-c]pyridinyl, 1H-pyrrolo[2,3-b]pyridinyl, imidazo[1,2-a]pyridinyl, imidazo[1,2-b]pyridazinyl, imidazo[1,2-a]pyrazinyl, imidazo[1,2-c]pyrimidinyl, 1H-imidazo[4,5-c]pyridinyl, 3H-imidazo[4,5-c]pyridinyl, imidazo[2,1-b][1,3]thiazolyl, and [1,2,4]triazolo[4,3-a]pyridinyl, optionally substituted where allowed by available valences with one, two or three $R_6$ substituents.

One aspect includes a compound of Formula (IV), wherein $R_6$ is, in each instance, independently selected from cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, $C_{1-6}$alkoxy-carbonyl, amino, $C_{1-6}$alkyl-amino, ($C_{1-6}$alkyl)$_2$-amino, amino-$C_{1-6}$alkyl, and hydroxy-$C_{1-6}$alkyl.

An aspect of the compound of Formula (I), Formula (II), Formula (III), or Formula (IV) or a form thereof includes a compound selected from the group consisting of:

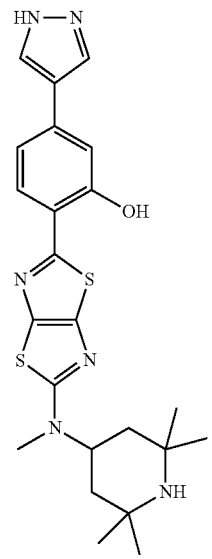

1

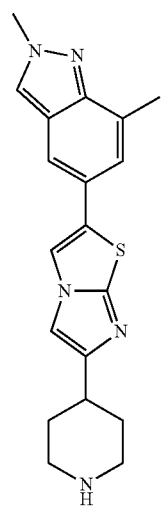

2

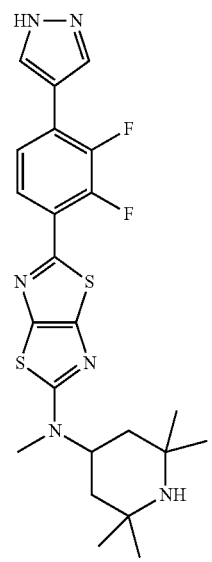

3

4
5
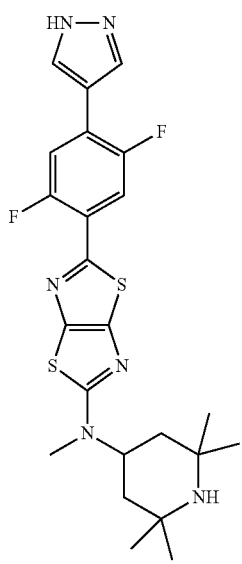
5
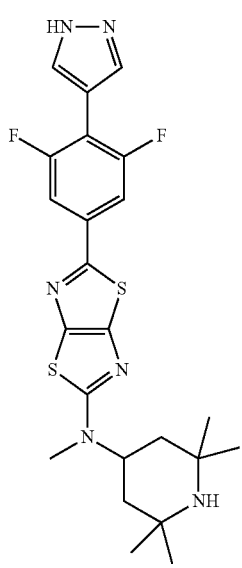
6
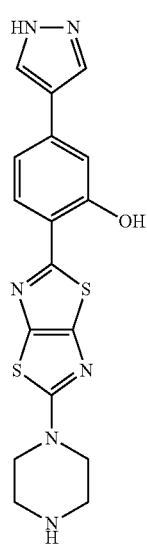
7
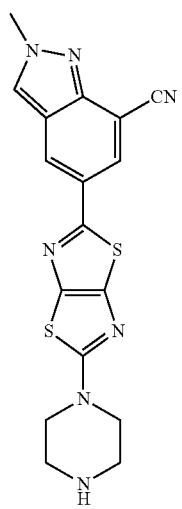
8
9

10
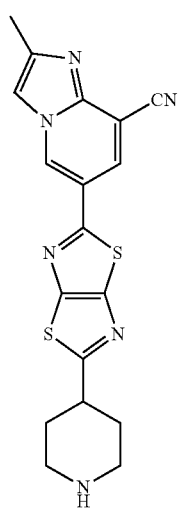
11
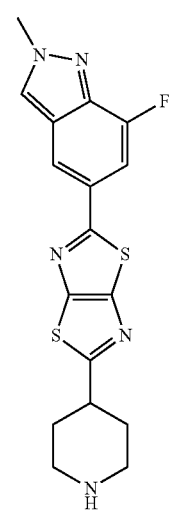
12
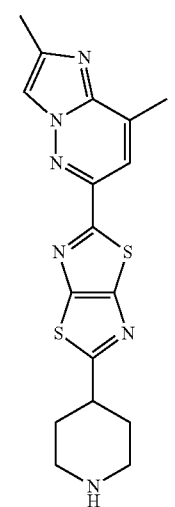
13
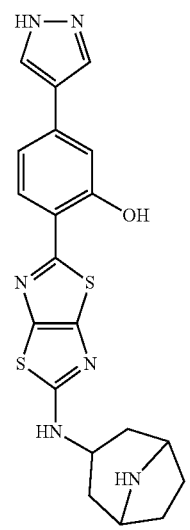
14
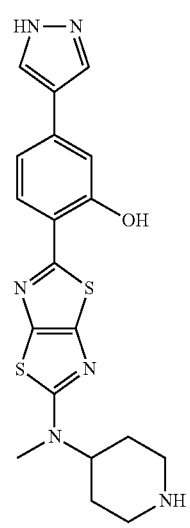
15
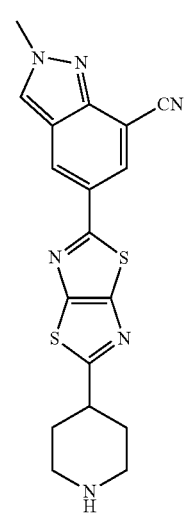

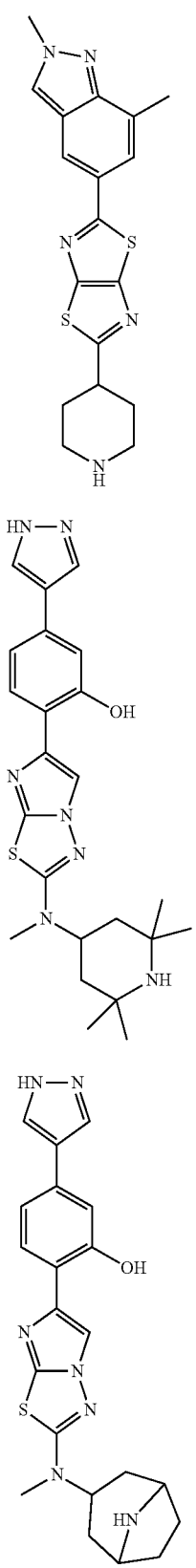
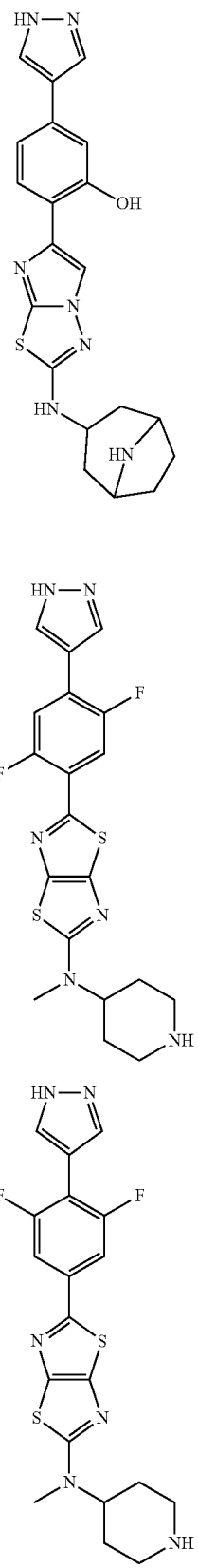

-continued
22
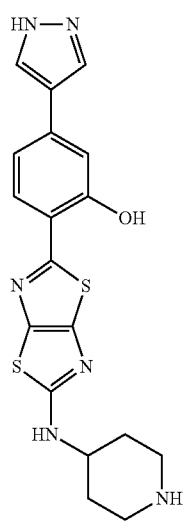
23
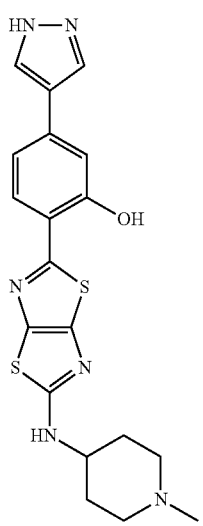
24
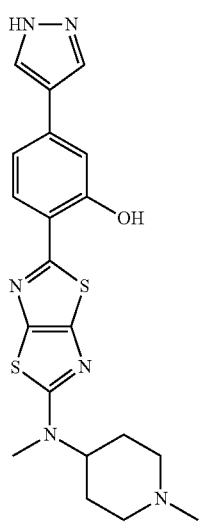
-continued
25
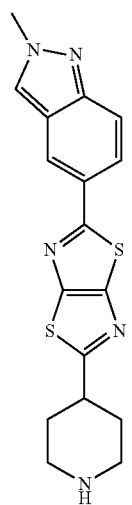
26
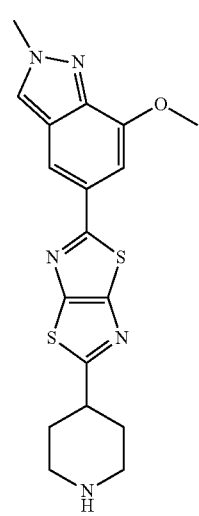
27
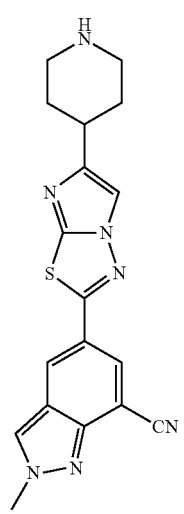

28
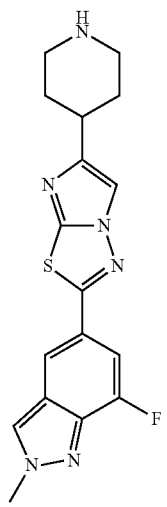
29
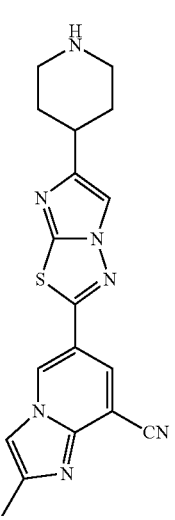
30
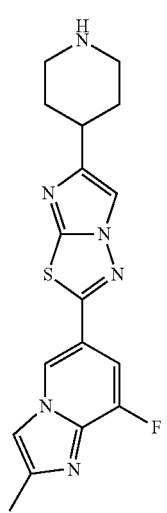
31
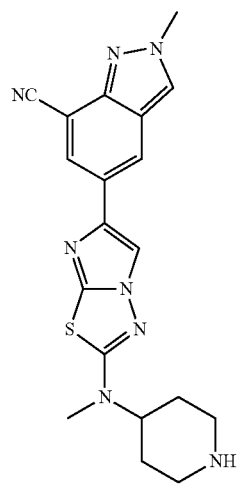
32
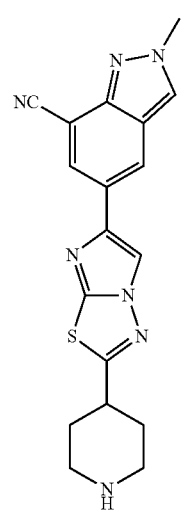
33
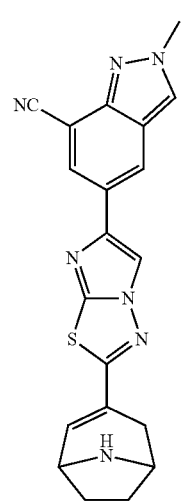

34
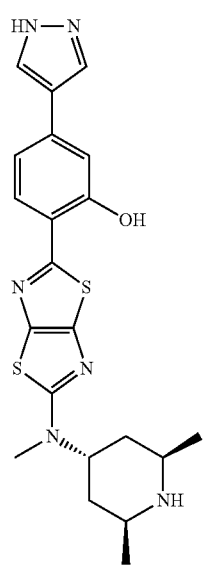
35
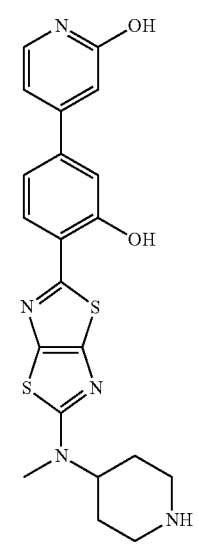
36
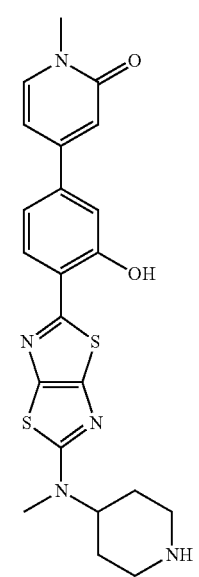
37
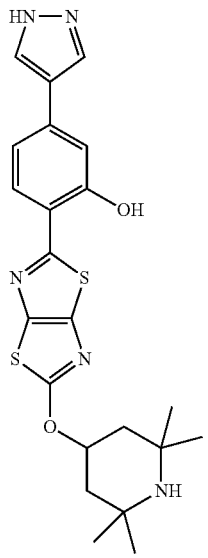
38
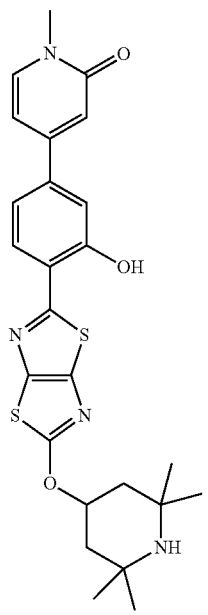

33
-continued
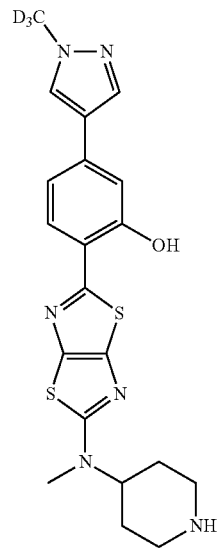
39
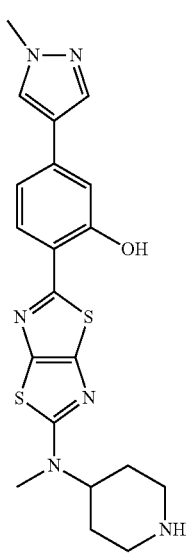
40
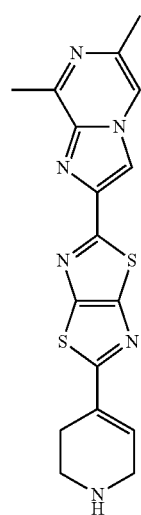
41
34
-continued
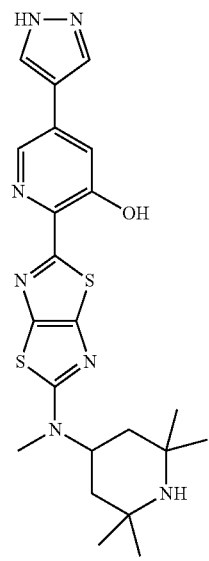
42
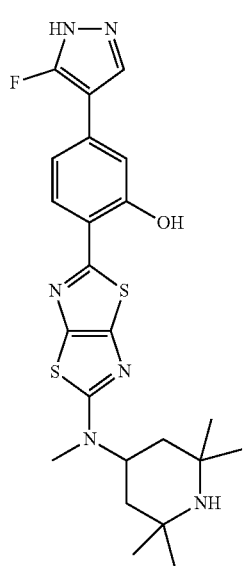
43
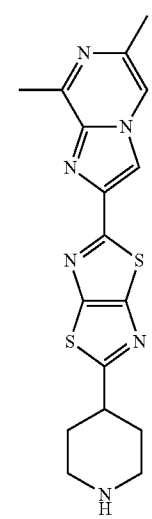
44

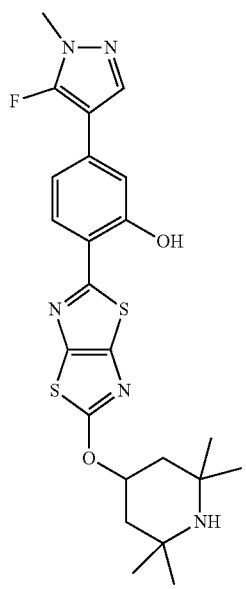
45
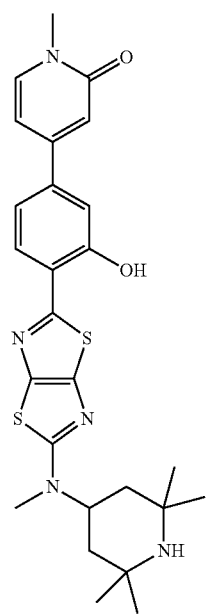
46
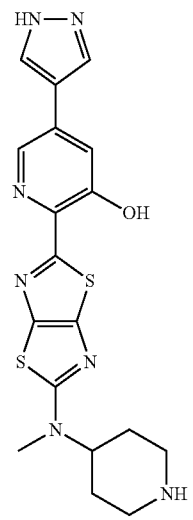
47
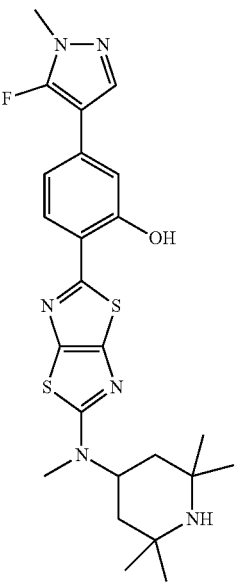
48
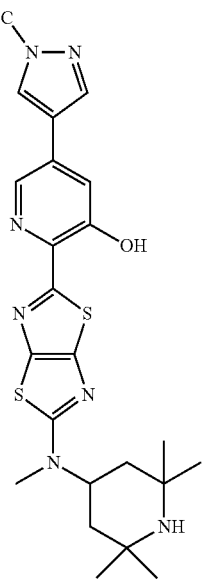
49

37
-continued
38
-continued
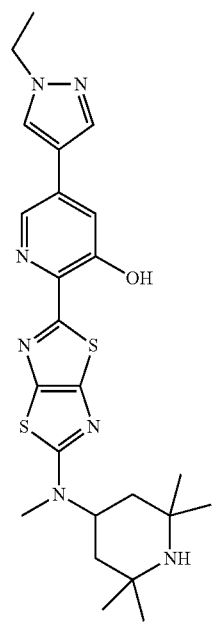
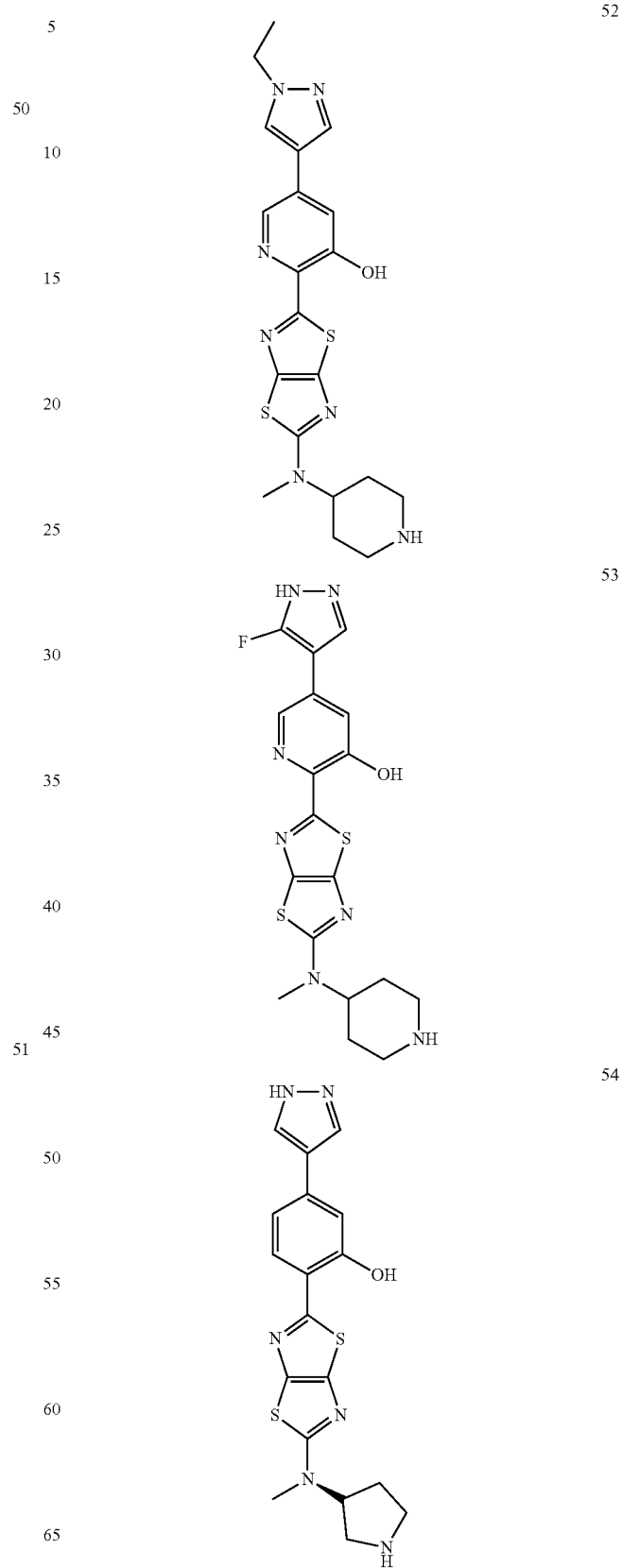

55
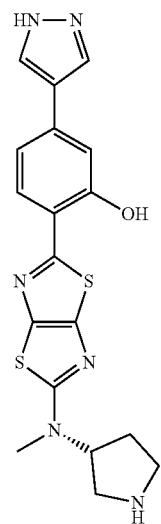
56
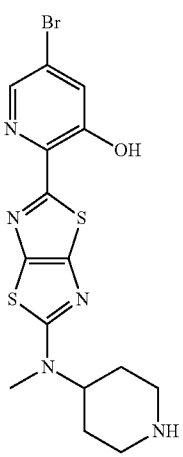
57
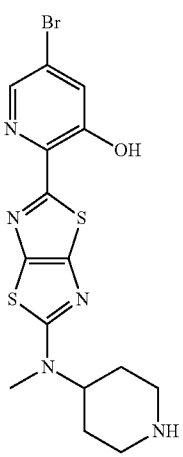
58
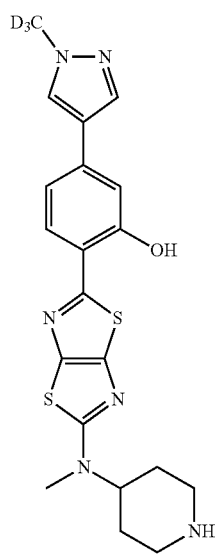
59
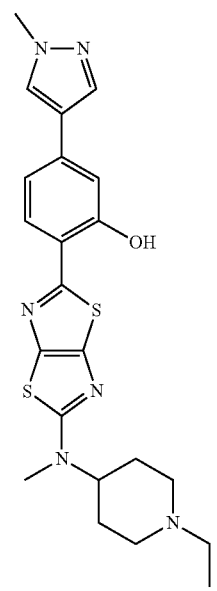
60
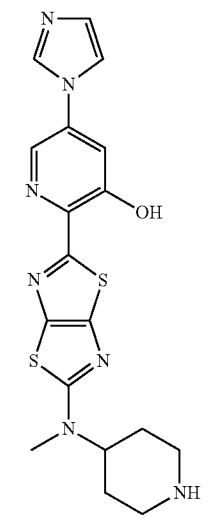

41
-continued
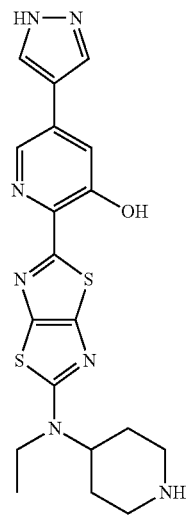
61
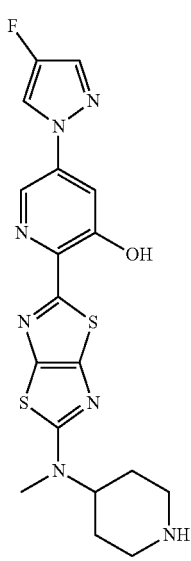
62
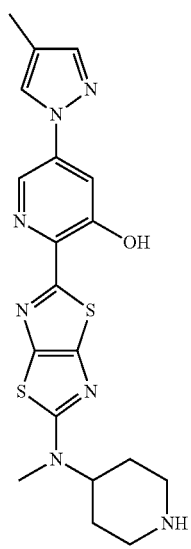
63
42
-continued
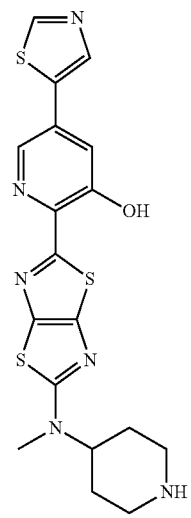
64
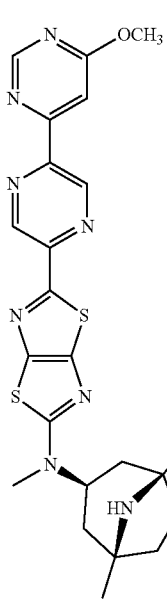
65
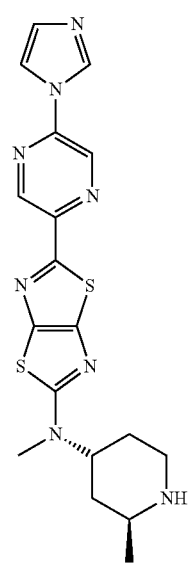
66

67
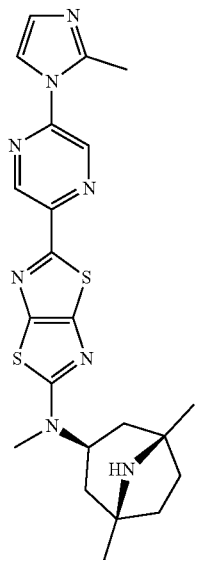
68
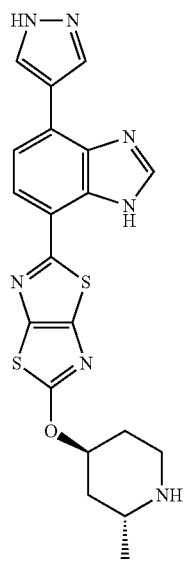
69
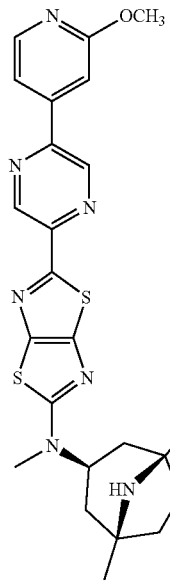
70
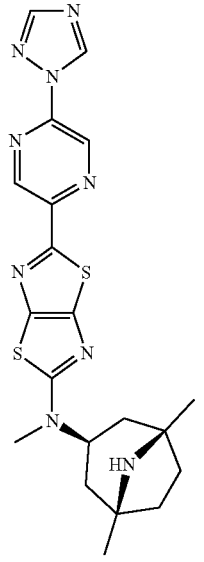

71
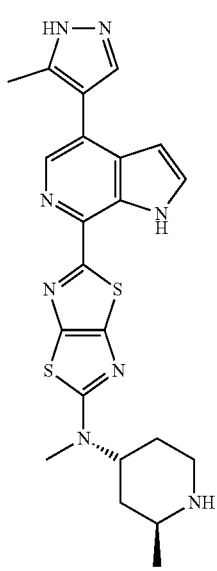
72
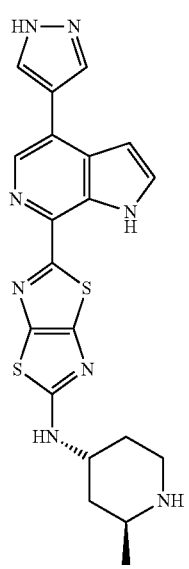
73
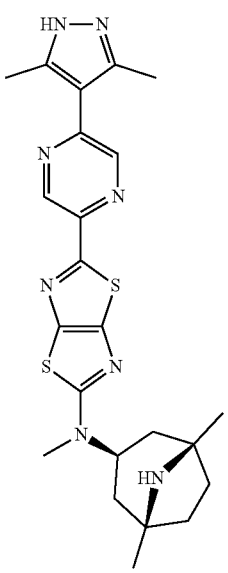
74
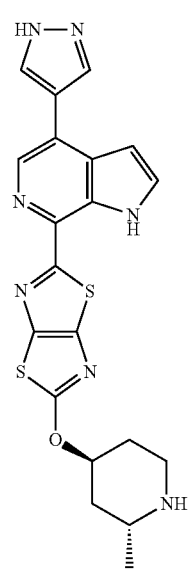
75
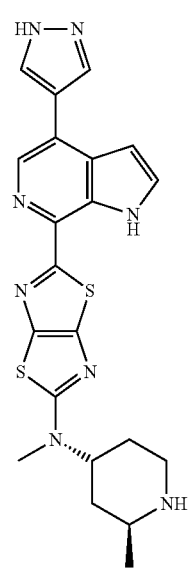
76
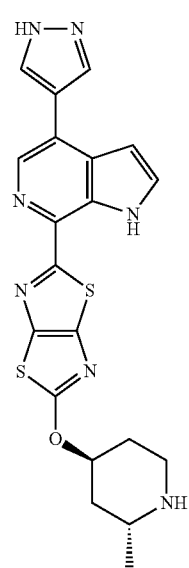

77
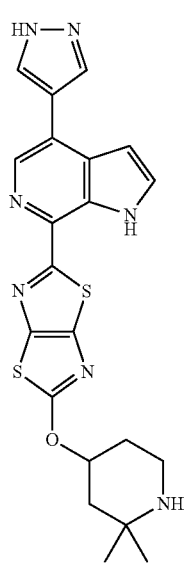
78
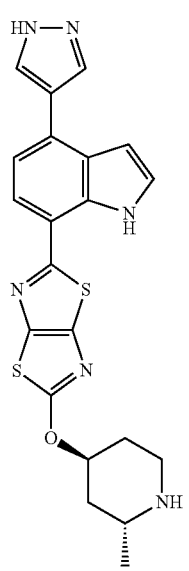
79
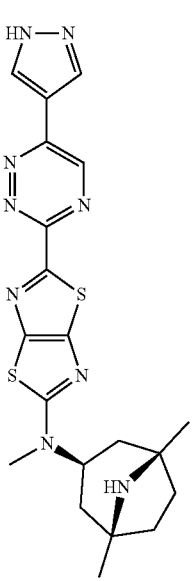
80
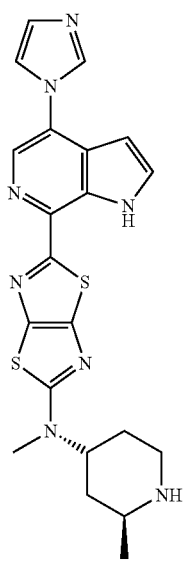
81
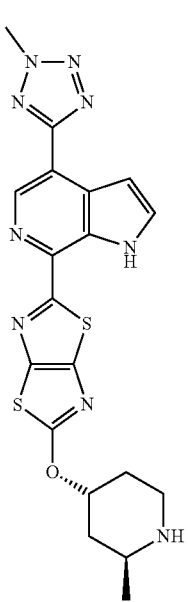

82
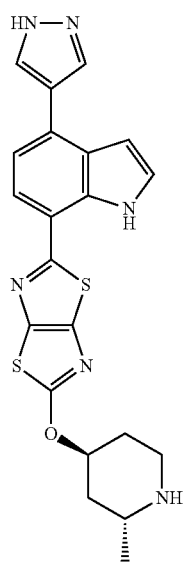
83
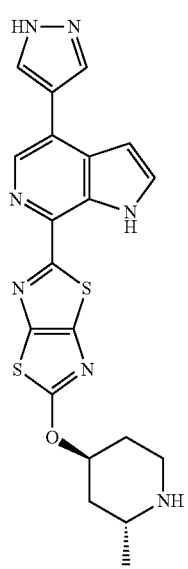
84
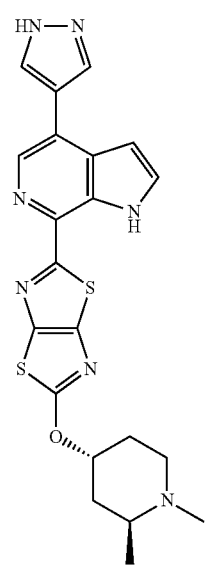
85
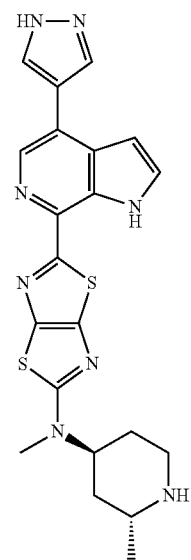
86
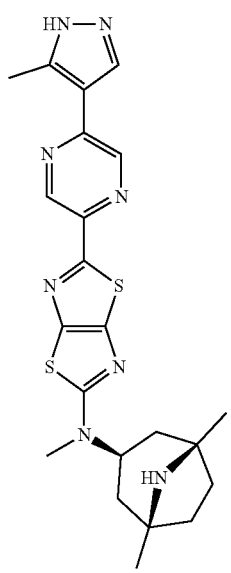
87
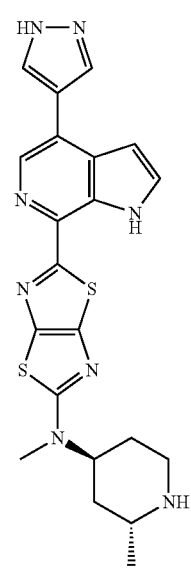

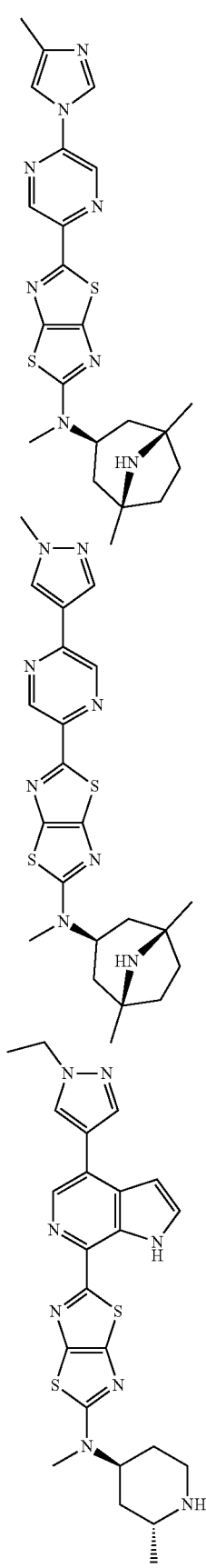
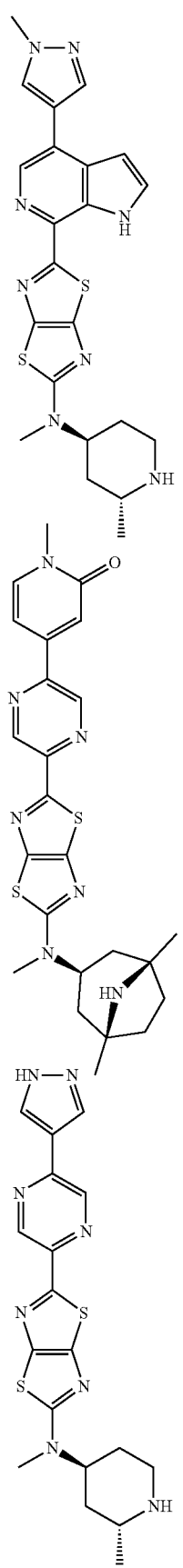

94
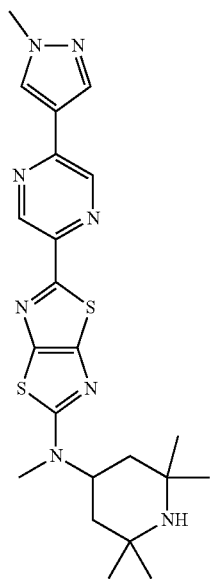
95
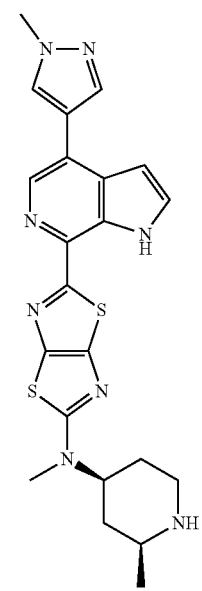
96
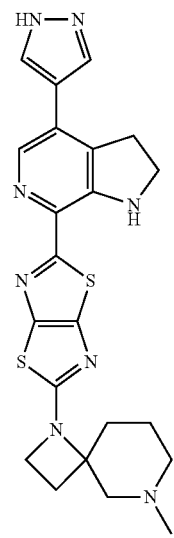
97
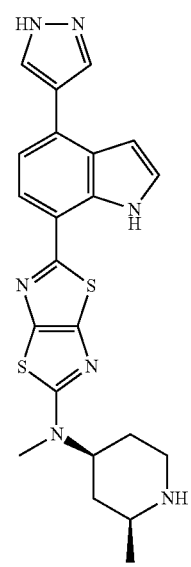
98
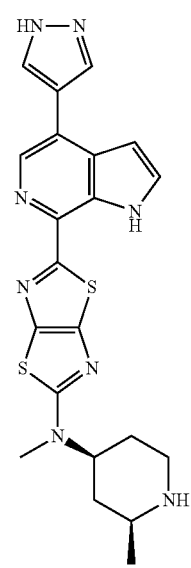

99
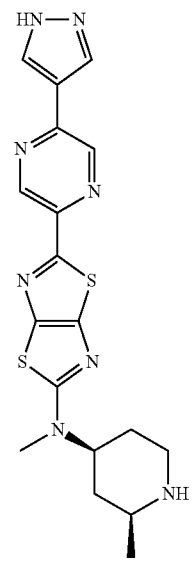
100
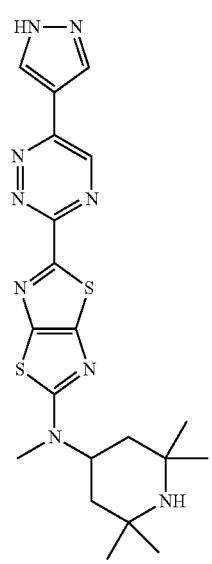
101
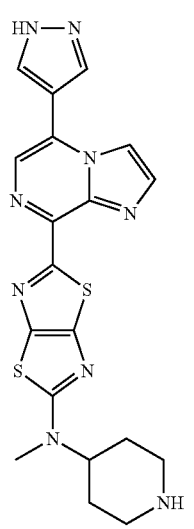
102
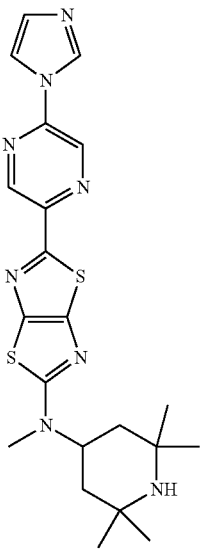
103
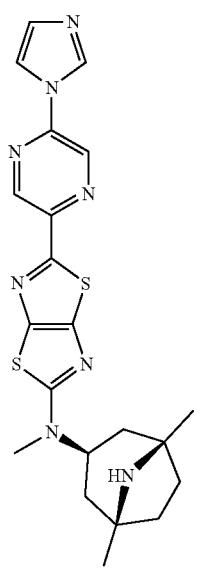
104
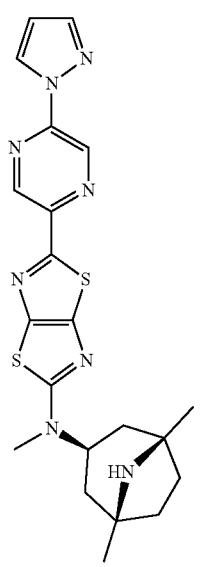

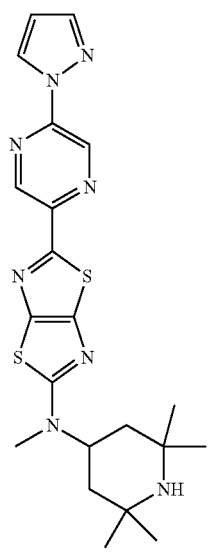
105
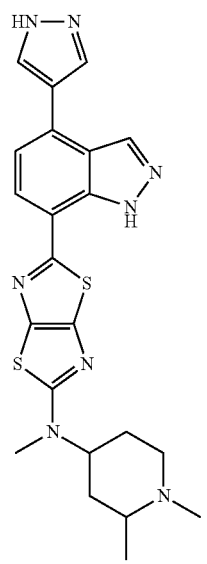
108
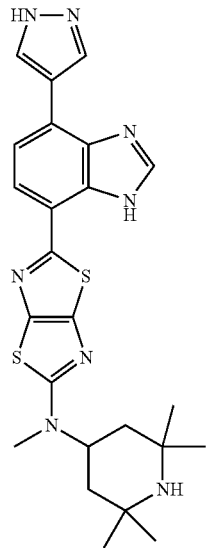
106
109
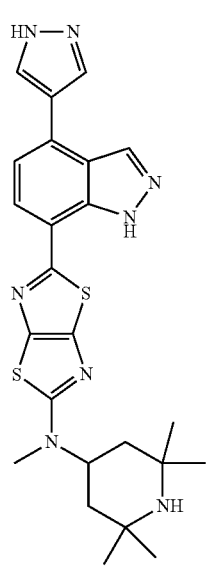
107
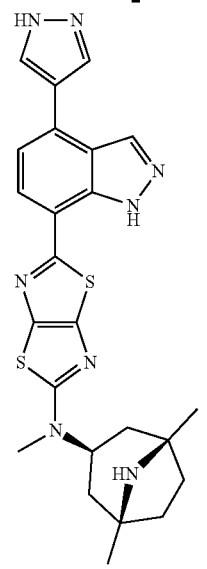
110

| 111 | 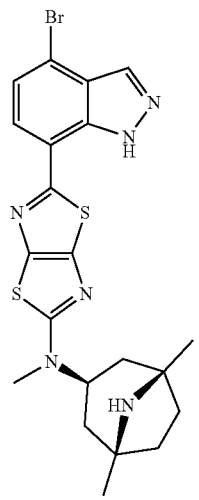 |
| --- | --- |
| 112 | 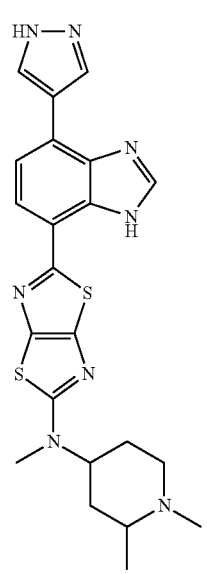 |
| 113 | 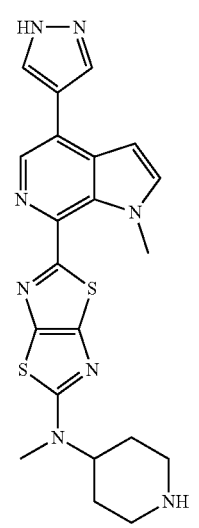 |
| 114 | 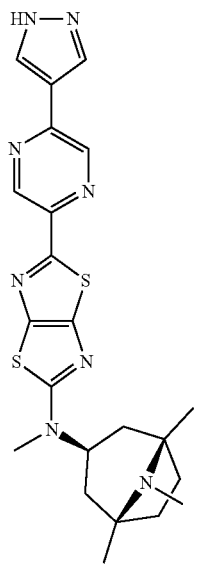 |
| 115 | 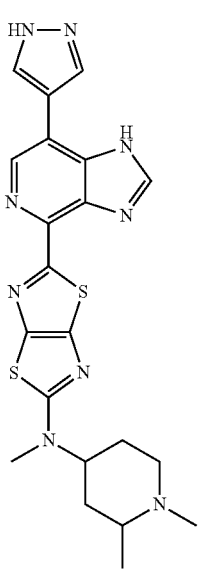 |
| 116 | 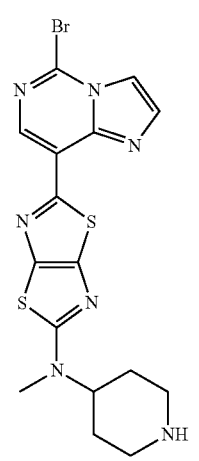 |

61
-continued
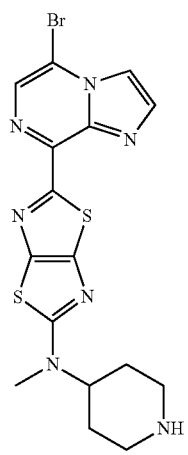
117
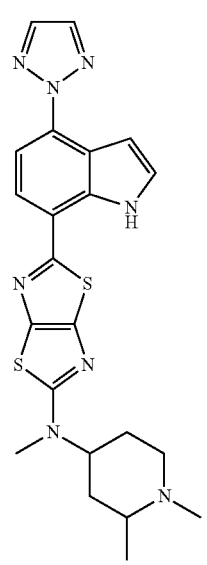
118
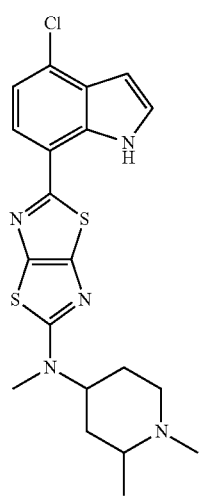
119
62
-continued
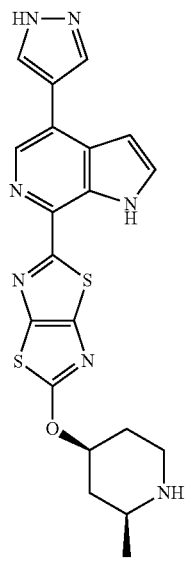
120
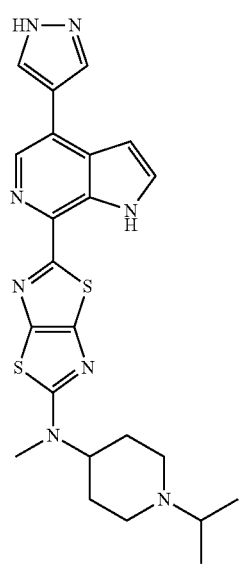
121
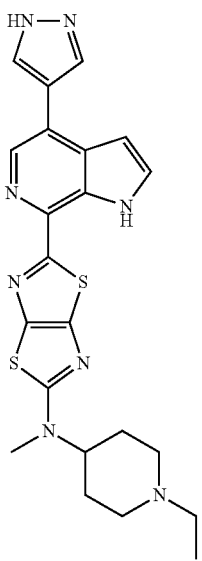
122

123
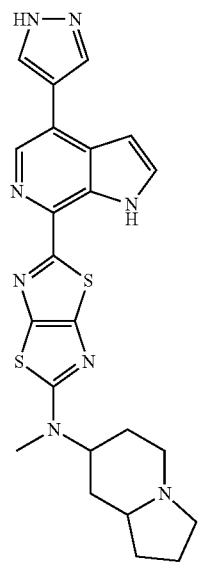
124
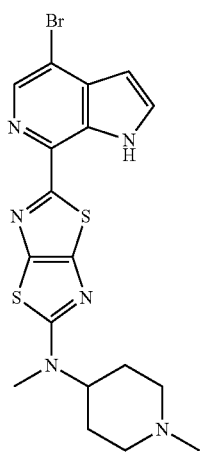
125
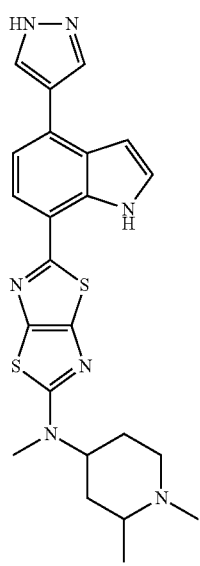
126
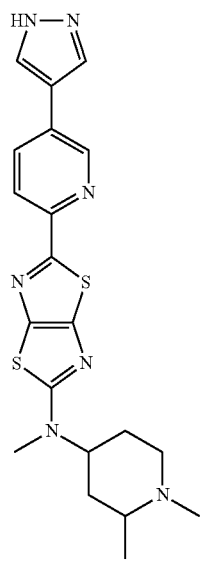
127
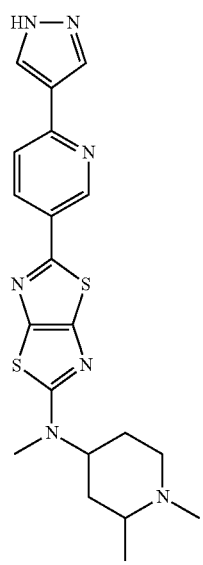
128
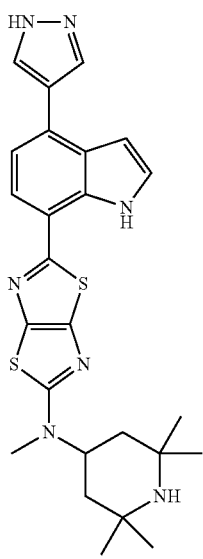

129 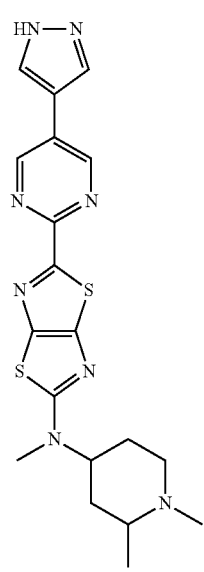
130 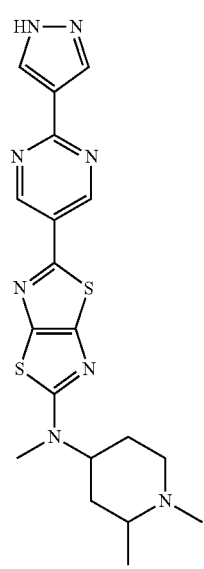
131 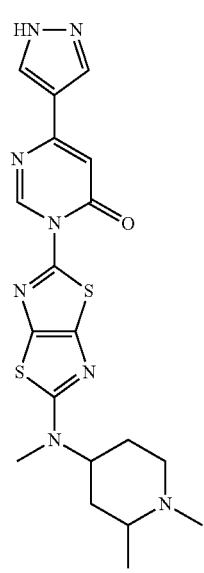
132 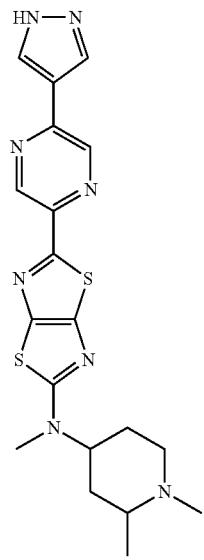
133 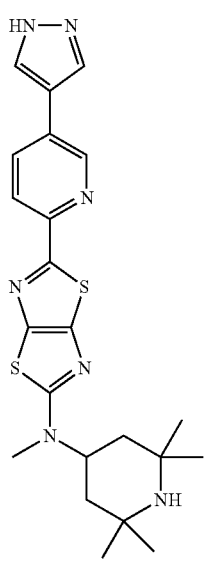
134 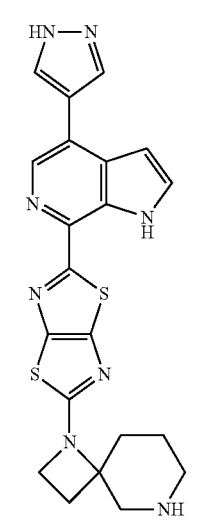

135 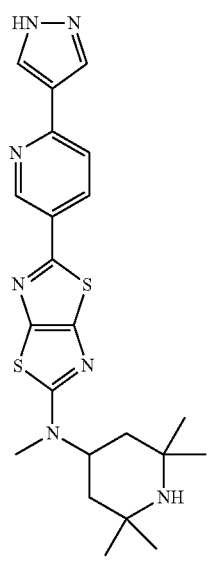
136 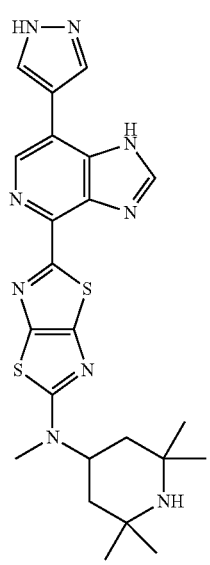
137 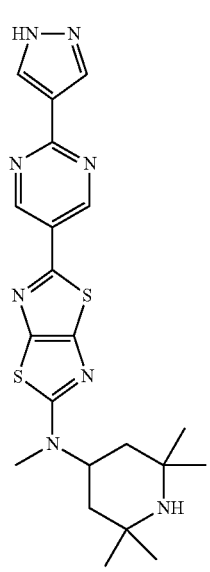
138 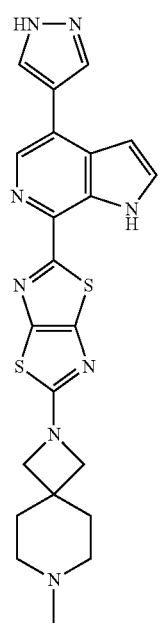
139 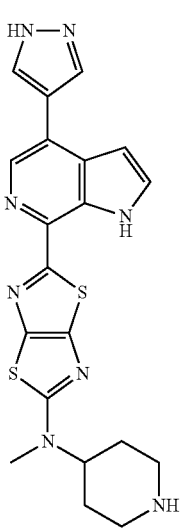
140 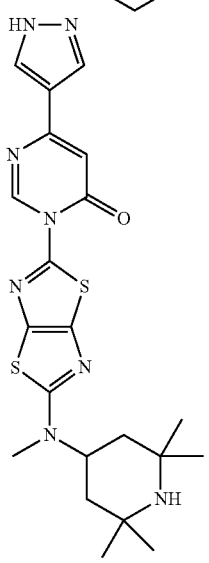

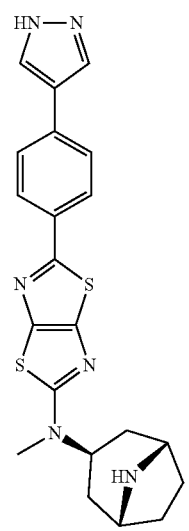
141
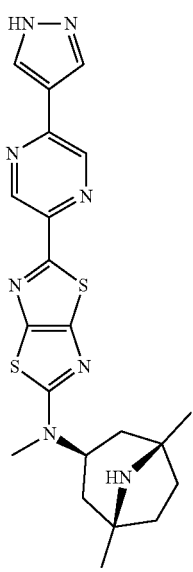
142
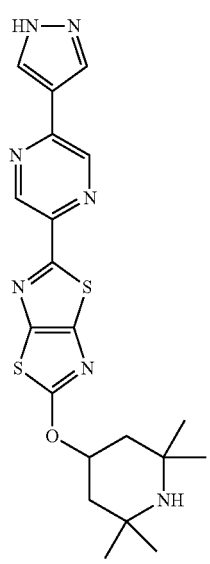
143
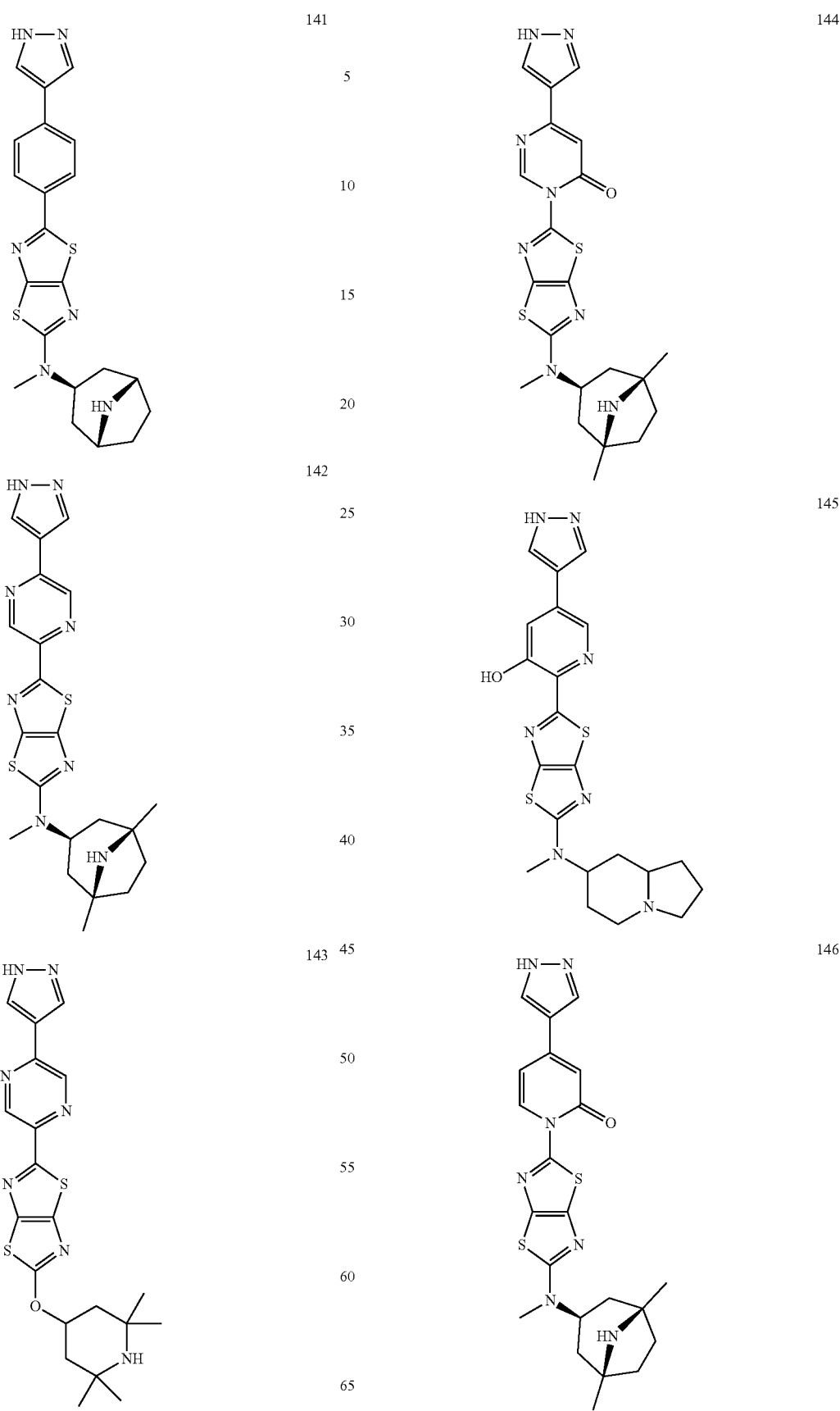

147 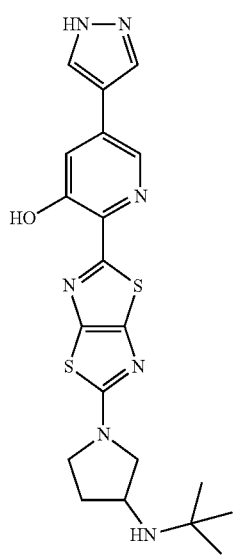
148 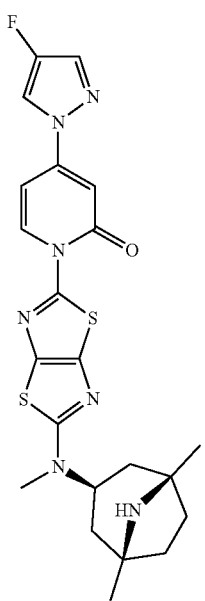
149 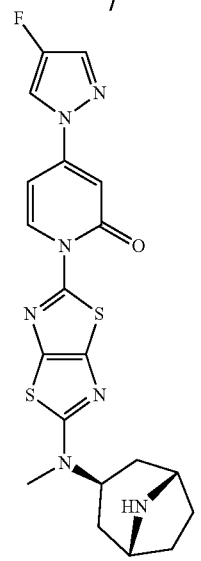
150 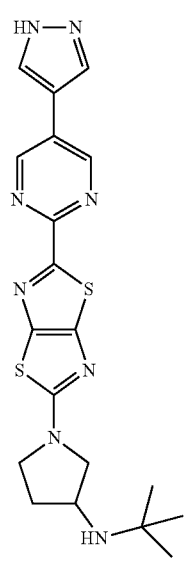
151
152 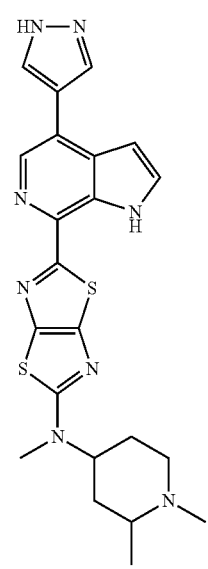

73
-continued
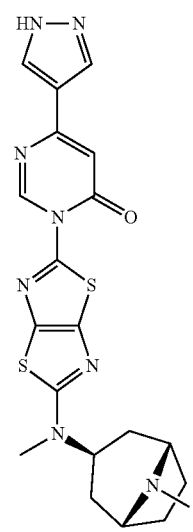
153
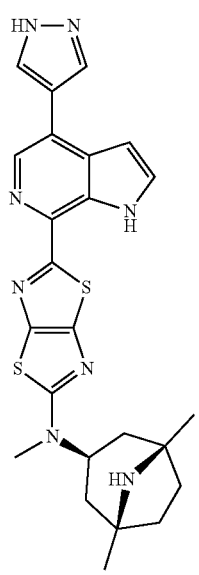
154
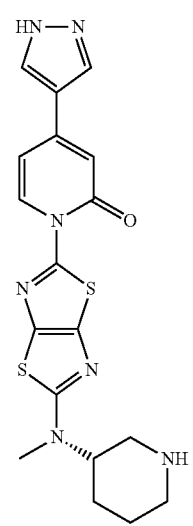
155
74
-continued
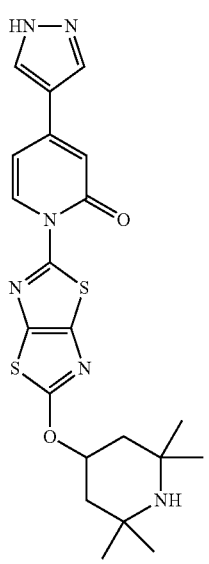
156
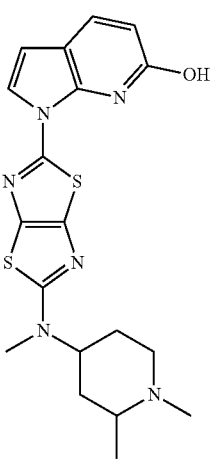
157
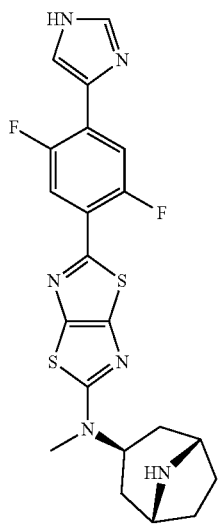
158

159 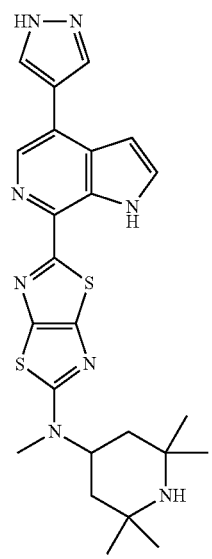
160 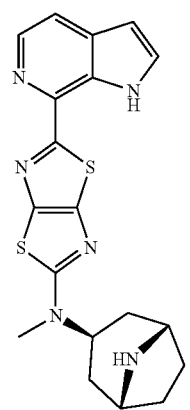
161 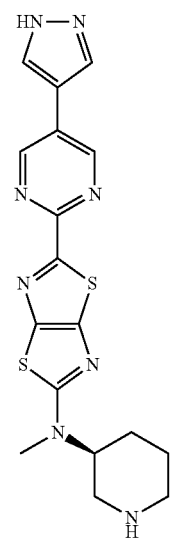
162 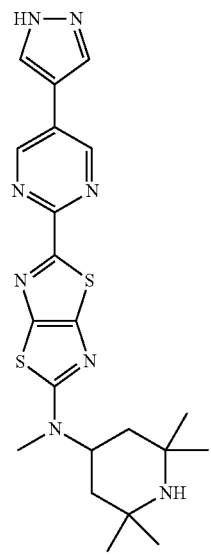
163 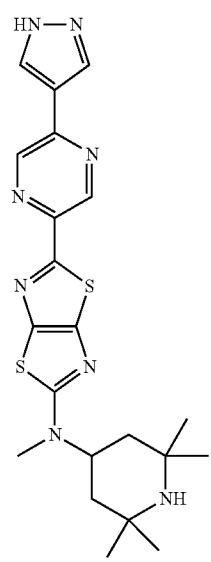
164 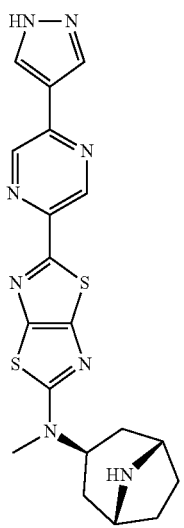

| | |
|---|---|
| 165 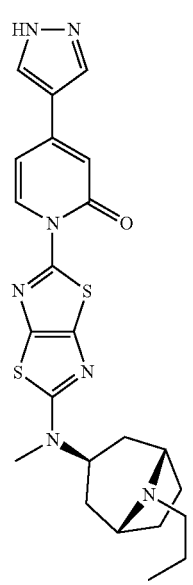 | 168 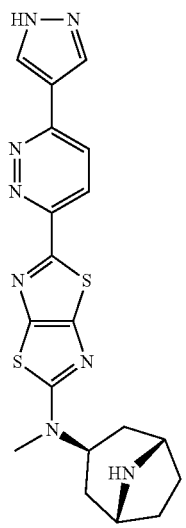 |
| 166 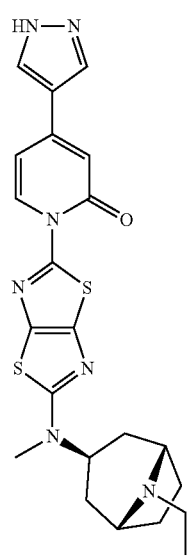 | 169 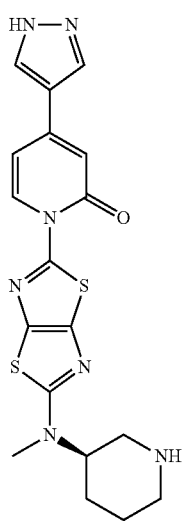 |
| 167 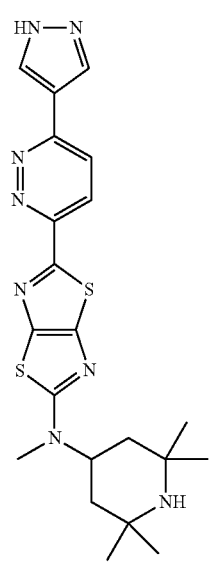 | 170 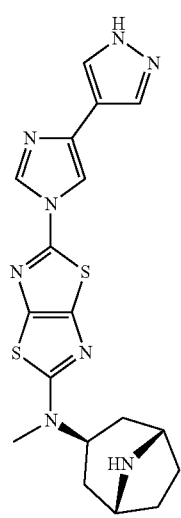 |

79 80
-continued -continued
171
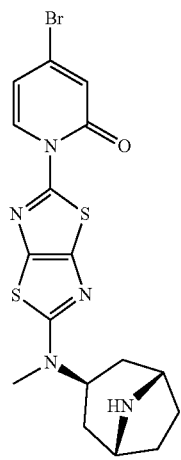
174
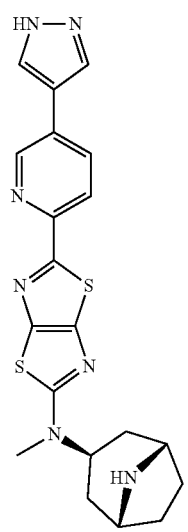
172
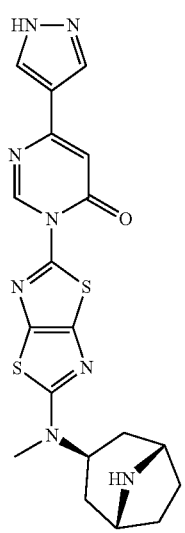
175
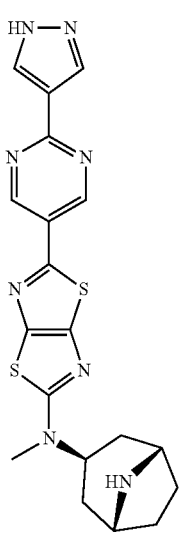
173
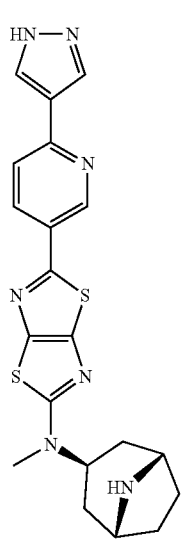
176
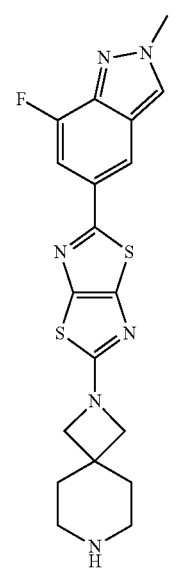

177 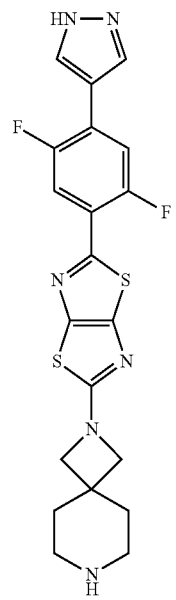
178 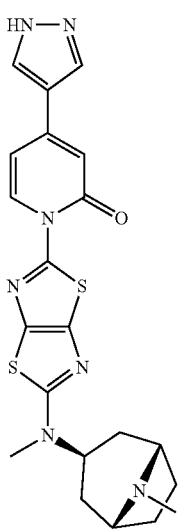
179 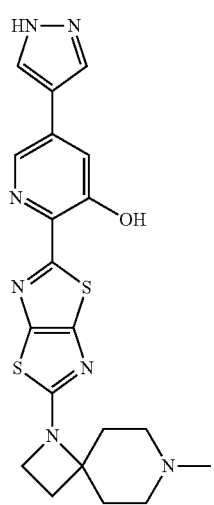
180 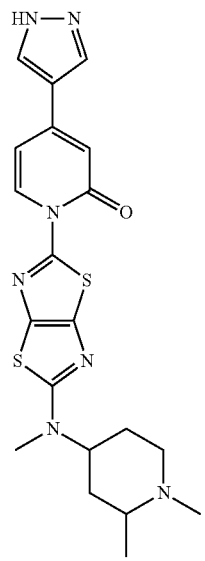
181 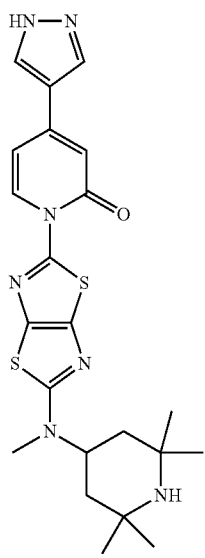
182 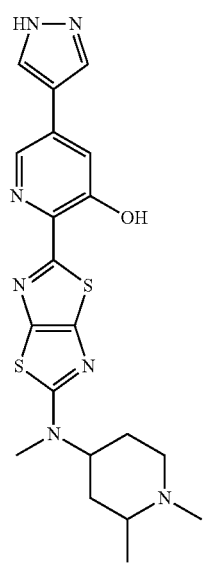

83
-continued
184
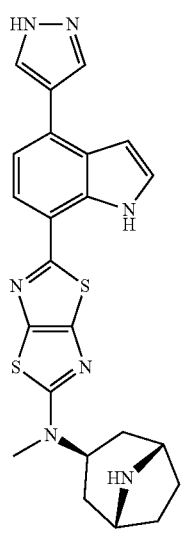
184
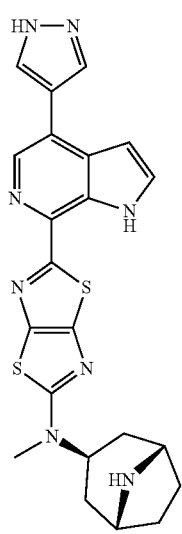
185
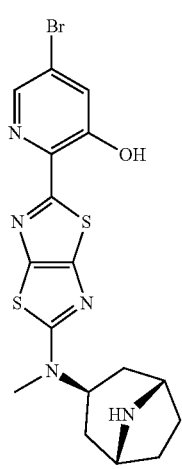
84
-continued
186
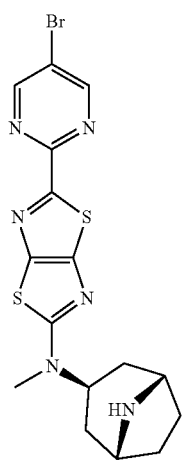
187
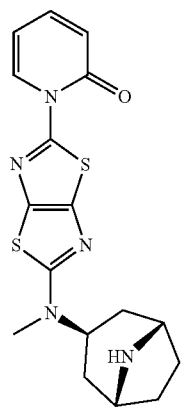
188
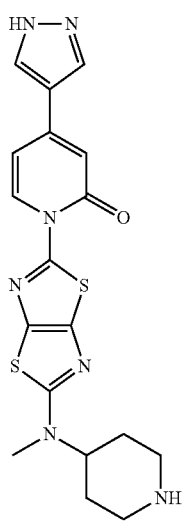

189 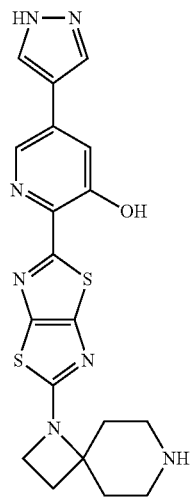
190 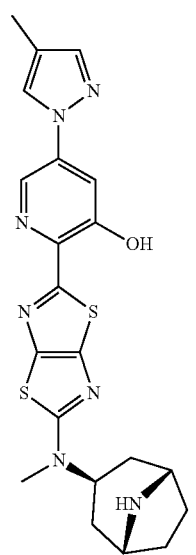
191 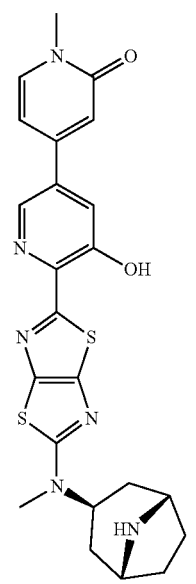
192 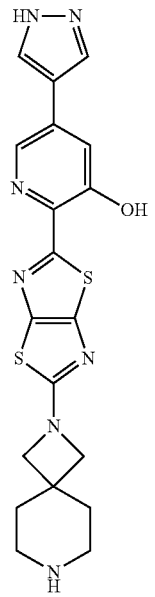
193 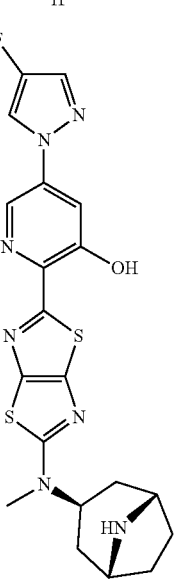
194 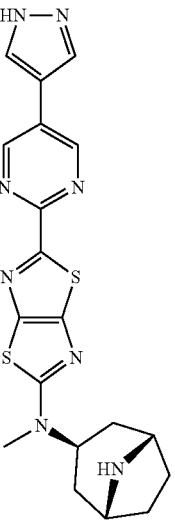

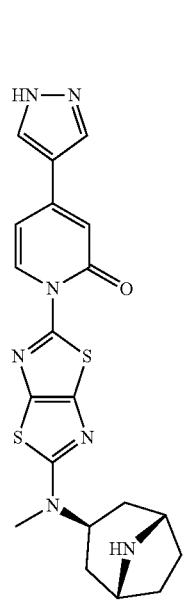
195
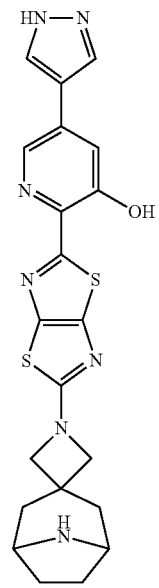
197
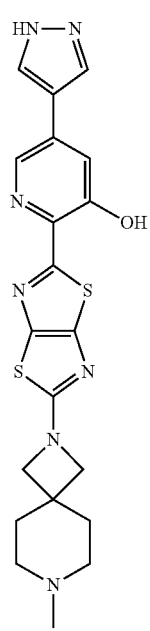
196
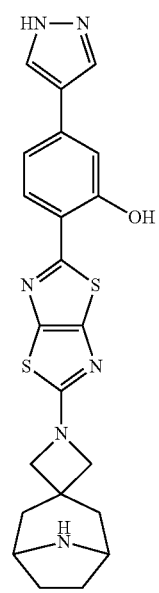
198

199 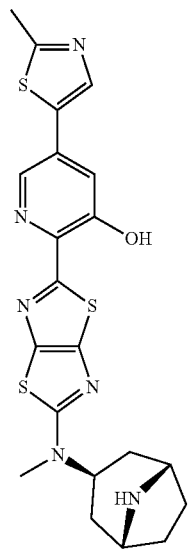
200 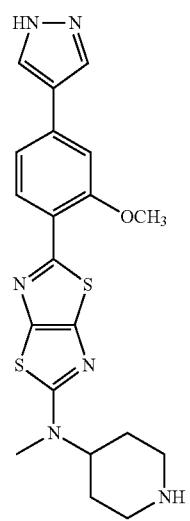
201 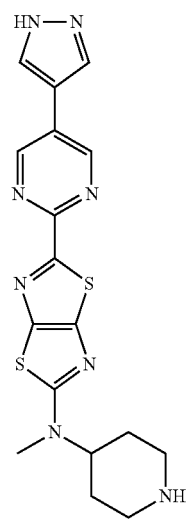
202 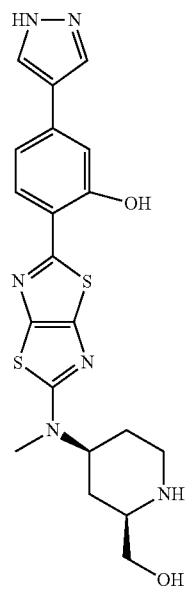
203 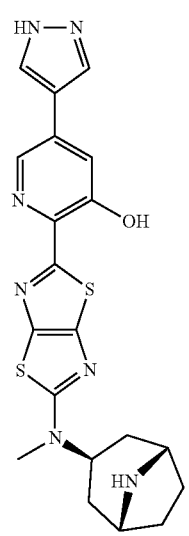
204 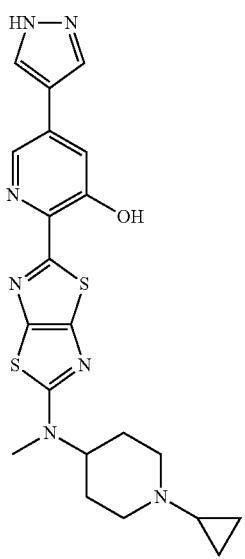

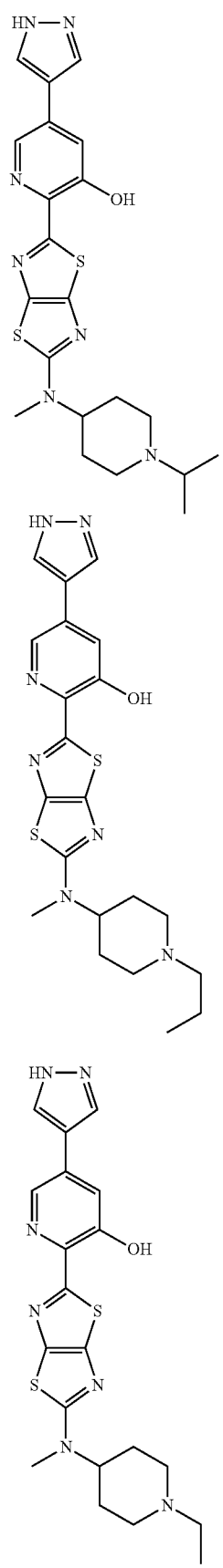
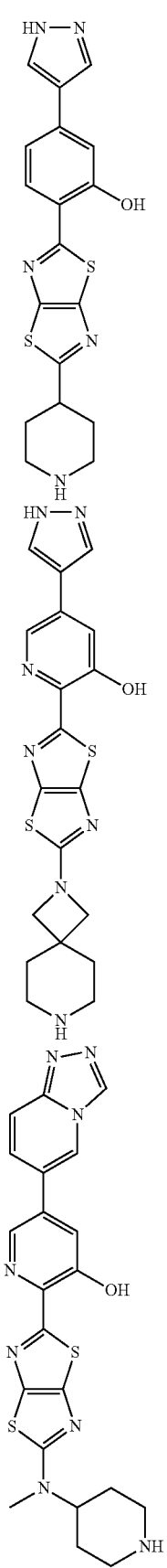

211 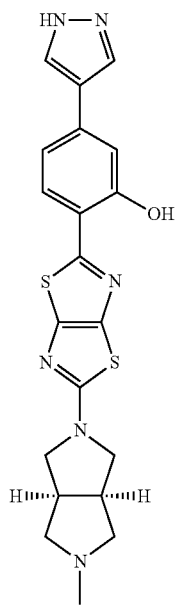
212 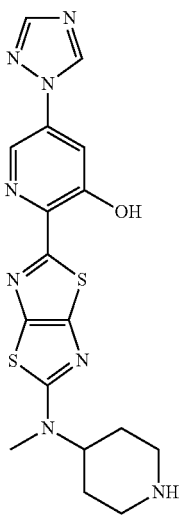
213 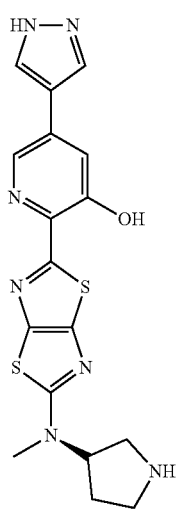
214 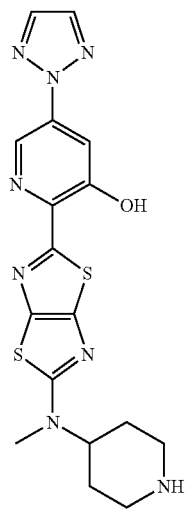
215 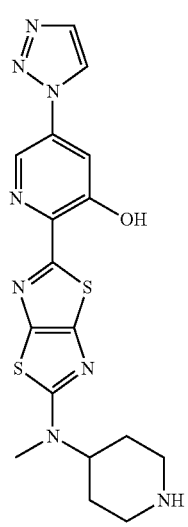
216 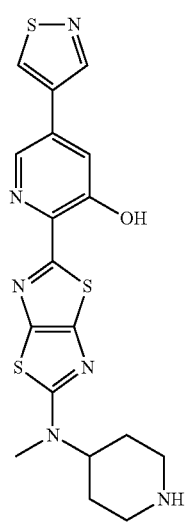

| 217 | 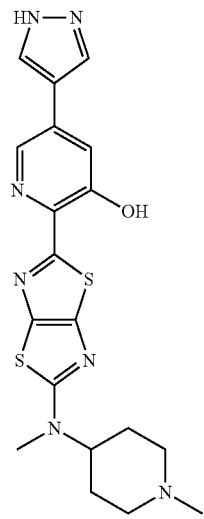 | 220 | 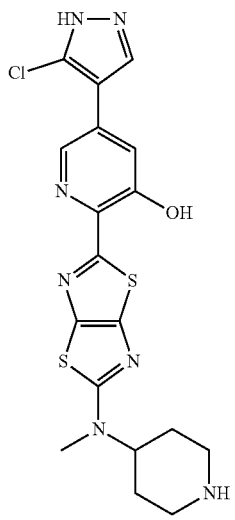 |
| 218 | 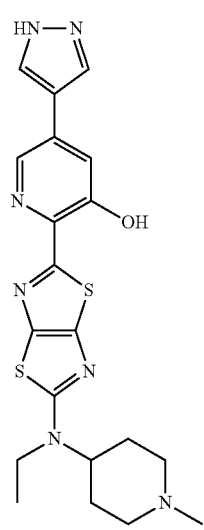 | 221 | 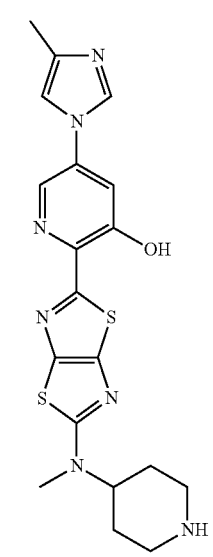 |
| 219 | 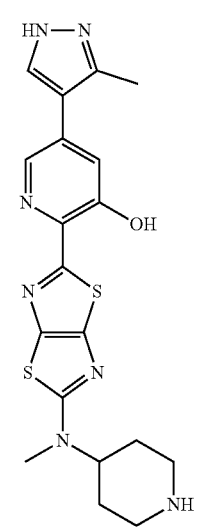 | 222 | 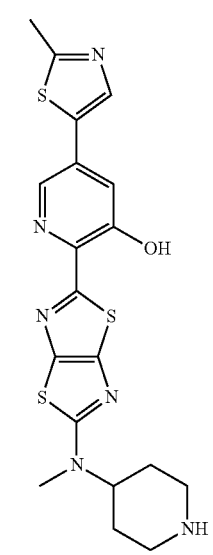 |

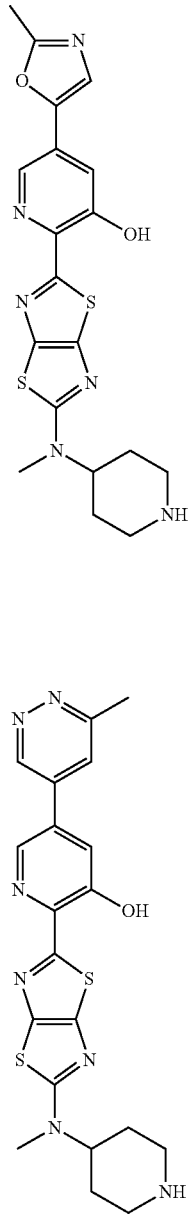

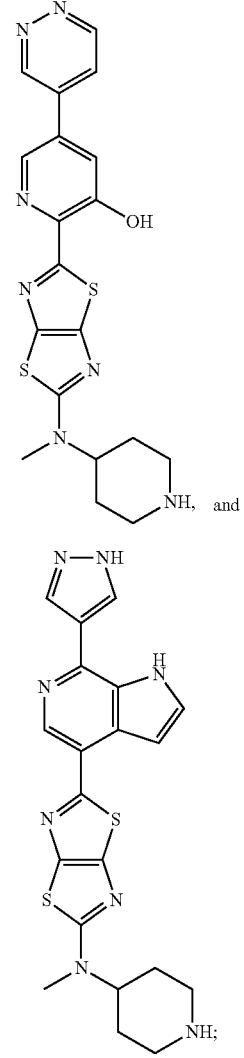

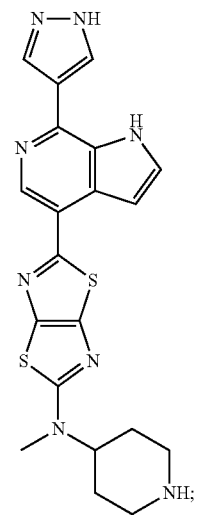

wherein the form of the compound is selected from the group consisting of a salt, prodrug, hydrate, solvate, clathrate, isotopologue, racemate, enantiomer, diastereomer, stereoisomer, polymorph and tautomer form thereof.

An aspect the compound of Formula (I), Formula (II), Formula (III), or Formula (IV) or a form thereof (wherein compound number (#¹) indicates that the salt form was isolated) includes a compound selected from the group consisting of:

| Cpd | Name |
|---|---|
| 1[1] | 2-{5-[methyl(2,2,6,6-tetramethylpiperidin-4-yl)amino][1,3]thiazolo[5,4-d][1,3]thiazol-2-yl}-5-(1H-pyrazol-4-yl)phenol |
| 2[1] | 2,7-dimethyl-5-[6-(piperidin-4-yl)imidazo[2,1-b][1,3]thiazol-2-yl]-2H-indazole |
| 3[1] | 5-[2,3-difluoro-4-(1H-pyrazol-4-yl)phenyl]-N-methyl-N-(2,2,6,6-tetramethylpiperidin-4-yl)[1,3]thiazolo[5,4-d][1,3]thiazol-2-amine |
| 4[1] | 5-[2,5-difluoro-4-(1H-pyrazol-4-yl)phenyl]-N-methyl-N-(2,2,6,6-tetramethylpiperidin-4-yl)[1,3]thiazolo[5,4-d][1,3]thiazol-2-amine |
| 5[1] | 5-[3,5-difluoro-4-(1H-pyrazol-4-yl)phenyl]-N-methyl-N-(2,2,6,6-tetramethylpiperidin-4-yl)[1,3]thiazolo[5,4-d][1,3]thiazol-2-amine |
| 6[1] | 2-[5-(piperazin-1-yl)[1,3]thiazolo[5,4-d][1,3]thiazol-2-yl]-5-(1H-pyrazol-4-yl)phenol |
| 7[1] | 2-methyl-5-[5-(piperazin-1-yl)[1,3]thiazolo[5,4-d][1,3]thiazol-2-yl]-2H-indazole-7-carbonitrile |

-continued

| Cpd | Name |
|---|---|
| 8[1] | 2,8-dimethyl-6-[6-(piperidin-4-yl)imidazo[2,1-b][1,3]thiazol-2-yl]imidazo[1,2-b]pyridazine |
| 9[1] | 2-{5-chloro-2-[methyl(2,2,6,6-tetramethylpiperidin-4-yl)amino]imidazo[2,1-b][1,3,4]thiadiazol-6-yl}-5-(1H-pyrazol-4-yl)phenol |
| 10[1] | 2-methyl-6-[5-(piperidin-4-yl)[1,3]thiazolo[5,4-d][1,3]thiazol-2-yl]imidazo[1,2-a]pyridine-8-carbonitrile |
| 11[1] | 7-fluoro-2-methyl-5-[5-(piperidin-4-yl)[1,3]thiazolo[5,4-d][1,3]thiazol-2-yl]-2H-indazole |
| 12[1] | 2,8-dimethyl-6-[5-(piperidin-4-yl)[1,3]thiazolo[5,4-d][1,3]thiazol-2-yl]imidazo[1,2-b]pyridazine |
| 13[1] | 2-{5-[(3-exo)-8-azabicyclo[3.2.1]oct-3-ylamino][1,3]thiazolo[5,4-d][1,3]thiazol-2-yl}-5-(1H-pyrazol-4-yl)phenol |
| 14[1] | 2-{5-[methyl(piperidin-4-yl)amino][1,3]thiazolo[5,4-d][1,3]thiazol-2-yl}-5-(1H-pyrazol-4-yl)phenol |
| 15[1] | 2-methyl-5-[5-(piperidin-4-yl)[1,3]thiazolo[5,4-d][1,3]thiazol-2-yl]-2H-indazole-7-carbonitrile |
| 16[1] | 2,7-dimethyl-5-[5-(piperidin-4-yl)[1,3]thiazolo[5,4-d][1,3]thiazol-2-yl]-2H-indazole |
| 17[1] | 2-{2-[methyl(2,2,6,6-tetramethylpiperidin-4-yl)amino]imidazo[2,1-b][1,3,4]thiadiazol-6-yl}-5-(1H-pyrazol-4-yl)phenol |
| 18[1] | 2-{2-[(3-exo)-8-azabicyclo[3.2.1]oct-3-yl(methyl)amino]imidazo[2,1-b][1,3,4]thiadiazol-6-yl}-5-(1H-pyrazol-4-yl)phenol |
| 19[1] | 2-(2-{[(3-exo)-8-methyl-8-azabicyclo[3.2.1]oct-3-yl]amino}imidazo[2,1-b][1,3,4]thiadiazol-6-yl)-5-(1H-pyrazol-4-yl)phenol |
| 20[1] | 5-[2,5-difluoro-4-(1H-pyrazol-4-yl)phenyl]-N-methyl-N-(piperidin-4-yl)[1,3]thiazolo[5,4-d][1,3]thiazol-2-amine |
| 21[1] | 5-[3,5-difluoro-4-(1H-pyrazol-4-yl)phenyl]-N-methyl-N-(piperidin-4-yl)[1,3]thiazolo[5,4-d][1,3]thiazol-2-amine |
| 22[1] | 2-[5-(piperidin-4-ylamino)[1,3]thiazolo[5,4-d][1,3]thiazol-2-yl]-5-(1H-pyrazol-4-yl)phenol |
| 23[1] | 2-{5-[(1-methylpiperidin-4-yl)amino][1,3]thiazolo[5,4-d][1,3]thiazol-2-yl}-5-(1H-pyrazol-4-yl)phenol |
| 24[1] | 2-{5-[methyl(1-methylpiperidin-4-yl)amino][1,3]thiazolo[5,4-d][1,3]thiazol-2-yl}-5-(1H-pyrazol-4-yl)phenol |
| 25[1] | 2-methyl-5-[5-(piperidin-4-yl)[1,3]thiazolo[5,4-d][1,3]thiazol-2-yl]-2H-indazole |
| 26[1] | 7-methoxy-2-methyl-5-[5-(piperidin-4-yl)[1,3]thiazolo[5,4-d][1,3]thiazol-2-yl]-2H-indazole |
| 27[1] | 2-methyl-5-[6-(piperidin-4-yl)imidazo[2,1-b][1,3,4]thiadiazol-2-yl]-2H-indazole-7-carbonitrile |
| 28[1] | 7-fluoro-2-methyl-5-[6-(piperidin-4-yl)imidazo[2,1-b][1,3,4]thiadiazol-2-yl]-2H-indazole |
| 29[1] | 2-methyl-6-[6-(piperidin-4-yl)imidazo[2,1-b][1,3,4]thiadiazol-2-yl]imidazo[1,2-a]pyridine-8-carbonitrile |
| 30[1] | 8-fluoro-2-methyl-6-[6-(piperidin-4-yl)imidazo[2,1-b][1,3,4]thiadiazol-2-yl]imidazo[1,2-a]pyridine |
| 31[1] | 2-methyl-5-{2-[methyl(1-methylpiperidin-4-yl)amino]imidazo[2,1-b][1,3,4]thiadiazol-6-yl}-2H-indazole-7-carbonitrile |
| 32[1] | 2-methyl-5-[2-(piperidin-4-yl)imidazo[2,1-b][1,3,4]thiadiazol-6-yl]-2H-indazole-7-carbonitrile |
| 33[1] | 5-[2-(8-azabicyclo[3.2.1]oct-2-en-3-yl)imidazo[2,1-b][1,3,4]thiadiazol-6-yl]-2-methyl-2H-indazole-7-carbonitrile |
| 34[1] | 2-(5-{[(2R,4s,6S)-2,6-dimethylpiperidin-4-yl](methyl)amino}[1,3]thiazolo[5,4-d][1,3]thiazol-2-yl)-5-(1H-pyrazol-4-yl)phenol |
| 35[1] | 4-(3-hydroxy-4-{5-[methyl(piperidin-4-yl)amino][1,3]thiazolo[5,4-d][1,3]thiazol-2-yl}phenyl)pyridin-2-ol |
| 36[1] | 4-(3-hydroxy-4-{5-[methyl(piperidin-4-yl)amino][1,3]thiazolo[5,4-d][1,3]thiazol-2-yl}phenyl)-1-methylpyridin-2(1H)-one |
| 37 | 5-(1H-pyrazol-4-yl)-2-{5-[(2,2,6,6-tetramethylpiperidin-4-yl)oxy][1,3]thiazolo[5,4-d][1,3]thiazol-2-yl}phenol |
| 38[1] | 4-(3-hydroxy-4-{5-[(2,2,6,6-tetramethylpiperidin-4-yl)oxy][1,3]thiazolo[5,4-d][1,3]thiazol-2-yl}phenyl)-1-methylpyridin-2(1H)-one |
| 39[1] | 2-{5-[methyl(piperidin-4-yl)amino][1,3]thiazolo[5,4-d][1,3]thiazol-2-yl}-5-[1-($^2H_3$)methyl-1H-pyrazol-4-yl]phenol |
| 40[1] | 2-{5-[methyl(piperidin-4-yl)amino][1,3]thiazolo[5,4-d][1,3]thiazol-2-yl}-5-(1-methyl-1H-pyrazol-4-yl)phenol |
| 41 | 6,8-dimethyl-2-[5-(1,2,3,6-tetrahydropyridin-4-yl)[1,3]thiazolo[5,4-d][1,3]thiazol-2-yl]imidazo[1,2-a]pyrazine |
| 42[1] | 2-{5-[methyl(2,2,6,6-tetramethylpiperidin-4-yl)amino][1,3]thiazolo[5,4-d][1,3]thiazol-2-yl}-5-(1H-pyrazol-4-yl)pyridin-3-ol |
| 43[1] | 5-(5-fluoro-1H-pyrazol-4-yl)-2-{5-[methyl(2,2,6,6-tetramethylpiperidin-4-yl)amino][1,3]thiazolo[5,4-d][1,3]thiazol-2-yl}phenol |
| 44[1] | 6,8-dimethyl-2-[5-(piperidin-4-yl)[1,3]thiazolo[5,4-d][1,3]thiazol-2-yl]imidazo[1,2-a]pyrazine |
| 45[1] | 5-(5-fluoro-1-methyl-1H-pyrazol-4-yl)-2-{5-[(2,2,6,6-tetramethylpiperidin-4-yl)oxy][1,3]thiazolo[5,4-d][1,3]thiazol-2-yl}phenol |
| 46[1] | 4-(3-hydroxy-4-{5-[methyl(2,2,6,6-tetramethylpiperidin-4-yl)amino][1,3]thiazolo[5,4-d][1,3]thiazol-2-yl}phenyl)-1-methylpyridin-2(1H-one |

| Cpd | Name |
|---|---|
| 47[1] | 2-{5-[methyl(piperidin-4-yl)amino][1,3]thiazolo[5,4-d][1,3]thiazol-2-yl}-5-(1H-pyrazol-4-yl)pyridin-3-ol |
| 48[1] | 5-(5-fluoro-1-methyl-1H-pyrazol-4-yl)-2-{5-[methyl(2,2,6,6-tetramethylpiperidin-4-yl)amino][1,3]thiazolo[5,4-d][1,3]thiazol-2-yl}phenol |
| 49[1] | 5-[1-($^2$H$_3$)methyl-1H-pyrazol-4-yl]-2-{5-[methyl(2,2,6,6-tetramethylpiperidin-4-yl)amino][1,3]thiazolo[5,4-d][1,3]thiazol-2-yl}pyridin-3-ol |
| 50[1] | 5-(1-ethyl-1H-pyrazol-4-yl)-2-{5-[methyl(2,2,6,6-tetramethylpiperidin-4-yl)amino][1,3]thiazolo[5,4-d][1,3]thiazol-2-yl}pyridin-3-ol |
| 51[1] | 2-{5-[methyl(piperidin-4-yl)amino][1,3]thiazolo[5,4-d][1,3]thiazol-2-yl}-5-[1-($^2$H$_3$)methyl-1H-pyrazol-4-yl]pyridin-3-ol |
| 52[1] | 5-(1-ethyl-1H-pyrazol-4-yl)-2-{5-[methyl(piperidin-4-yl)amino][1,3]thiazolo[5,4-d][1,3]thiazol-2-yl}pyridin-3-ol |
| 53[1] | 5-(5-fluoro-1H-pyrazol-4-yl)-2-{5-[methyl(piperidin-4-yl)amino][1,3]thiazolo[5,4-d][1,3]thiazol-2-yl}pyridin-3-ol |
| 54[1] | 2-(5-{methyl[(3S)-pyrrolidin-3-yl]amino}[1,3]thiazolo[5,4-d][1,3]thiazol-2-yl)-5-(1H-pyrazol-4-yl)phenol |
| 55[1] | 2-(5-{methyl[(3R)-pyrrolidin-3-yl]amino}[1,3]thiazolo[5,4-d][1,3]thiazol-2-yl)-5-(1H-pyrazol-4-yl)phenol |
| 56[1] | 2-(5-{methyl[(3R)-pyrrolidin-3-yl]amino}[1,3]thiazolo[5,4-d][1,3]thiazol-2-yl)-5-(1H-pyrazol-4-yl)pyridin-3-ol |
| 57[1] | 5-bromo-2-{5-[methyl(piperidin-4-yl)amino][1,3]thiazolo[5,4-d][1,3]thiazol-2-yl}pyridin-3-ol |
| 58[1] | 2-{5-[methyl(1-methylpiperidin-4-yl)amino][1,3]thiazolo[5,4-d][1,3]thiazol-2-yl}-5-[1-($^2$H$_3$)methyl-1H-pyrazol-4-yl]phenol |
| 59[1] | 2-{5-[(1-ethylpiperidin-4-yl)(methyl)amino][1,3]thiazolo[5,4-d][1,3]thiazol-2-yl}-5-(1-methyl-1H-pyrazol-4-yl)phenol |
| 60[1] | 5-(1H-imidazol-1-yl)-2-{5-[methyl(piperidin-4-yl)amino][1,3]thiazolo[5,4-d][1,3]thiazol-2-yl}pyridin-3-ol |
| 61[1] | 2-{5-[ethyl(piperidin-4-yl)amino][1,3]thiazolo[5,4-d][1,3]thiazol-2-yl}-5-(1H-pyrazol-4-yl)pyridin-3-ol |
| 62[1] | 5-(4-fluoropyrazol-1-yl)-2-[5-[methyl(4-piperidyl)amino]thiazolo[5,4-d]thiazol-2-yl]pyridin-3-ol |
| 63[1] | 5-(4-methylpyrazol-1-yl)-2-[5-[methyl(4-piperidyl)amino]thiazolo[5,4-d]thiazol-2-yl]pyridin-3-ol |
| 64[1] | 5-(thiazol-5-yl)-2-{5-[methyl(piperidin-4-yl)amino][1,3]thiazolo[5,4-d][1,3]thiazol-2-yl}pyridin-3-ol |
| 65 | N-[(1R,3s,5S)-1,5-dimethyl-8-azabicyclo[3.2.1]octan-3-yl]-5-[5-(6-methoxypyrimidin-4-yl)pyrazin-2-yl]-N-methyl[1,3]thiazolo[5,4-d][1,3]thiazol-2-amine |
| 66 | 5-[5-(1H-imidazol-1-yl)pyrazin-2-yl]-N-methyl-N-[(2S,4R)-2-methylpiperidin-4-yl][1,3]thiazolo[5,4-d][1,3]thiazol-2-amine |
| 67 | N-[(1R,3s,5S)-1,5-dimethyl-8-azabicyclo[3.2.1]octan-3-yl]-N-methyl-5-[5-(2-methyl-1H-imidazol-1-yl)pyrazin-2-yl][1,3]thiazolo[5,4-d][1,3]thiazol-2-amine |
| 68 | 7-(5-{[(2R,4S)-2-methylpiperidin-4-yl]oxy}[1,3]thiazolo[5,4-d][1,3]thiazol-2-yl)-4-(1H-pyrazol-4-yl)-1H-benzimidazole |
| 69 | N-[(1R,3s,5S)-1,5-dimethyl-8-azabicyclo[3.2.1]octan-3-yl]-5-[5-(2-methoxypyridin-4-yl)pyrazin-2-yl]-N-methyl[1,3]thiazolo[5,4-d][1,3]thiazol-2-amine |
| 70 | N-[(1R,3s,5S)-1,5-dimethyl-8-azabicyclo[3.2.1]octan-3-yl]-N-methyl-5-[5-(1H-1,2,4-triazol-1-yl)pyrazin-2-yl][1,3]thiazolo[5,4-d][1,3]thiazol-2-amine |
| 71[1] | N-methyl-N-[(2S,4R)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine |
| 72[1] | N-methyl-N-[(2S,4R)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine |
| 73 | N-[(1R,3s,5S)-1,5-dimethyl-8-azabicyclo[3.2.1]octan-3-yl]-5-[5-(3,5-dimethyl-1H-pyrazol-4-yl)pyrazin-2-yl]-N-methyl[1,3]thiazolo[5,4-d][1,3]thiazol-2-amine |
| 74 | 7-(5-{[(2R,4S)-2-methylpiperidin-4-yl]oxy}[1,3]thiazolo[5,4-d][1,3]thiazol-2-yl)-4-(1H-pyrazol-4-yl)-1H-pyrazolo[3,4-c]pyridine |
| 75[1] | N-methyl-N-[(2S,4R)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine |
| 76[1] | 7-(5-{[(2R,4S)-2-methylpiperidin-4-yl]oxy}[1,3]thiazolo[5,4-d][1,3]thiazol-2-yl)-4-(1H-pyrazol-4-yl)-1H-pyrrolo[2,3-c]pyridine |
| 77[1] | 7-{5-[(2,2-dimethylpiperidin-4-yl)oxy][1,3]thiazolo[5,4-d][1,3]thiazol-2-yl}-4-(1H-pyrazol-4-yl)-1H-pyrrolo[2,3-c]pyridine |
| 78[1] | 7-(5-{[(2R,4S)-2-methylpiperidin-4-yl]oxy}[1,3]thiazolo[5,4-d][1,3]thiazol-2-yl)-4-(1H-pyrazol-4-yl)-1H-indazole |
| 79[1] | N-[(1R,3s,5S)-1,5-dimethyl-8-azabicyclo[3.2.1]octan-3-yl]-N-methyl-5-[6-(1H-pyrazol-4-yl)-1,2,4-triazin-3-yl][1,3]thiazolo[5,4-d][1,3]thiazol-2-amine |
| 80[1] | 5-[4-(1H-imidazol-1-yl)-1H-pyrrolo[2,3-c]pyridin-7-yl]-N-methyl-H-[(2S,4R)-2-methylpiperidin-4-yl][1,3]thiazolo[5,4-d][1,3]thiazol-2-amine |
| 81[1] | 7-(5-{[(2S,4R)-2-methylpiperidin-4-yl]oxy}[1,3]thiazolo[5,4-d][1,3]thiazol-2-yl)-4-(2-methyl-2H-tetrazol-5-yl)-1H-pyrrolo[2,3-c]pyridine |
| 82[1] | 7-(5-{[(2R,4S)-2-methylpiperidin-4-yl]oxy}[1,3]thiazolo[5,4-d][1,3]thiazol-2-yl)-4-(1H-pyrazol-4-yl)-1H-indole |
| 83[1] | 4-(5-{[(2R,4S)-2-methylpiperidin-4-yl]oxy}[1,3]thiazolo[5,4-d][1,3]thiazol-2-yl)-7-(1H-pyrazol-4-yl)-3H-imidazo[4,5-c]pyridine |
| 84[1] | 7-(5-{[(2S,4R)-1,2-dimethylpiperidin-4-yl]oxy}[1,3]thiazolo[5,4-d][1,3]thiazol-2-yl)-4-(1H-pyrazol-4-yl)-1H-pyrrolo[2,3-c]pyridine |

| Cpd | Name |
|---|---|
| 85[1] | N-methyl-N-[(2R,4S)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine |
| 86[1] | N-[(1R,3s,5S)-1,5-dimethyl-8-azabicyclo[3.2.1]octan-3-yl]-N-methyl-5-[5-(5-methyl-1H-pyrazol-4-yl)pyrazin-2-yl][1,3]thiazolo[5,4-d][1,3]thiazol-2-amine |
| 87[1] | N-methyl-N-[(2R,4S)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine |
| 88 | N-[(1R,3s,5S)-1,5-dimethyl-8-azabicyclo[3.2.1]octan-3-yl]-N-methyl-5-[5-(4-methyl-1H-imidazol-1-yl)pyrazin-2-yl][1,3]thiazolo[5,4-d][1,3]thiazol-2-amine |
| 89[1] | N-[(1R,3s,5S)-1,5-dimethyl-8-azabicyclo[3.2.1]octan-3-yl]-N-methyl-5-[5-(1-methyl-1H-pyrazol-4-yl)pyrazin-2-yl][1,3]thiazolo[5,4-d][1,3]thiazol-2-amine |
| 90[1] | 5-[4-(1-ethyl-1H-pyrazol-4-yl)-1H-pyrrolo[2,3-c]pyridin-7-yl]-N-methyl-N-[(2R,4S)-2-methylpiperidin-4-yl][1,3]thiazolo[5,4-d][1,3]thiazol-2-amine |
| 91[1] | N-methyl-N-[(2R,4S)-2-methylpiperidin-4-yl]-5-[4-(1-methyl-1H-pyrazol-4-yl)-1H-pyrrolo[2,3-c]pyridin-7-yl][1,3]thiazolo[5,4-d][1,3]thiazol-2-amine |
| 92[1] | 4-[5-(5-{[(1R,3s,5S)-1,5-dimethyl-8-azabicyclo[3.2.1]octan-3-yl](methyl)amino}[1,3]thiazolo[5,4-d][1,3]thiazol-2-yl)pyrazin-2-yl]-1-methylpyridin-2(1H)-one |
| 93[1] | N-methyl-N-[(2R,4S)-2-methylpiperidin-4-yl]-5-[5-(1H-pyrazol-4-yl)pyrazin-2-yl][1,3]thiazolo[5,4-d][1,3]thiazol-2-amine |
| 94[1] | N-methyl-5-[5-(1-methyl-1H-pyrazol-4-yl)pyrazin-2-yl]-N-(2,2,6,6-tetramethylpiperidin-4-yl)[1,3]thiazolo[5,4-d][1,3]thiazol-2-amine |
| 95[1] | N-methyl-N-[(2S,4S)-2-methylpiperidin-4-yl]-5-[4-(1-methyl-1H-pyrazol-4-yl)-1H-pyrrolo[2,3-c]pyridin-7-yl][1,3]thiazolo[5,4-d][1,3]thiazol-2-amine |
| 96[1] | 7-[5-(6-methyl-1,6-diazaspiro[3.5]nonan-1-yl)[1,3]thiazolo[5,4-d][1,3]thiazol-2-yl]-4-(1H-pyrazol-4-yl)-1H-pyrrolo[2,3-c]pyridine |
| 97[1] | N-methyl-N-[(2S,4S)-2-methylpiperidin-4-yl]-5-[4-(1H-pyrazol-4-yl)-1H-indol-7-yl][1,3]thiazolo[5,4-d][1,3]thiazol-2-amine |
| 98[1] | N-methyl-N-[(2S,4S)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine |
| 99[1] | N-methyl-N-[(2S,4S)-2-methylpiperidin-4-yl]-5-[5-(1H-pyrazol-4-yl)pyrazin-2-yl][1,3]thiazolo[5,4-d][1,3]thiazol-2-amine |
| 100 | N-methyl-5-[6-(1H-pyrazol-4-yl)-1,2,4-triazin-3-yl]-N-(2,2,6,6-tetramethylpiperidin-4-yl)[1,3]thiazolo[5,4-d][1,3]thiazol-2-amine |
| 101[1] | N-methyl-N-(piperidin-4-yl)-5-[5-(1H-pyrazol-4-yl)imidazo[1,2-a]pyrazin-8-yl][1,3]thiazolo[5,4-d][1,3]thiazol-2-amine |
| 102[1] | 5-[5-(1H-imidazol-1-yl)pyrazin-2-yl]-N-methyl-N-(2,2,6,6-tetramethylpiperidin-4-yl)[1,3]thiazolo[5,4-d][1,3]thiazol-2-amine |
| 103[1] | N-[(1R,3s,5S)-1,5-dimethyl-8-azabicyclo[3.2.1]octan-3-yl]-5-[5-(1H-imidazol-1-yl)pyrazin-2-yl]-N-methyl[1,3]thiazolo[5,4-d][1,3]thiazol-2-amine |
| 104[1] | N-[(1R,3s,5S)-1,5-dimethyl-8-azabicyclo[3.2.1]octan-3-yl]-N-methyl-5-[5-(1H-pyrazol-1-yl)pyrazin-2-yl][1,3]thiazolo[5,4-d][1,3]thiazol-2-amine |
| 105[1] | N-methyl-5-[5-(1H-pyrazol-1-yl)pyrazin-2-yl]-N-(2,2,6,6-tetramethylpiperidin-4-yl)[1,3]thiazolo[5,4-d][1,3]thiazol-2-amine |
| 106[1] | N-methyl-5-[4-(1H-pyrazol-4-yl)-1H-benzimidazol-7-yl]-N-(2,2,6,6-tetramethylpiperidin-4-yl)[1,3]thiazolo[5,4-d][1,3]thiazol-2-amine |
| 107[1] | N-methyl-5-[4-(1H-pyrazol-4-yl)-1H-indazol-7-yl]-N-(2,2,6,6-tetramethylpiperidin-4-yl)[1,3]thiazolo[5,4-d][1,3]thiazol-2-amine |
| 108[1] | N-(1,2-dimethylpiperidin-4-yl)-N-methyl-5-[4-(1H-pyrazol-4-yl)-1H-indazol-7-yl][1,3]thiazolo[5,4-d][1,3]thiazol-2-amine |
| 109[1] | 7-(5-{[(2S,4R)-2-methylpiperidin-4-yl]oxy}[1,3]thiazolo[5,4-d][1,3]thiazol-2-yl)-4-(1H-pyrazol-4-yl)-1H-pyrrolo[2,3-c]pyridine |
| 110[1] | N-[(1R,3s,5S)-1,5-dimethyl-8-azabicyclo[3.2.1]octan-3-yl]-N-methyl-5-[4-(1H-pyrazol-4-yl)-1H-indazol-7-yl][1,3]thiazolo[5,4-d][1,3]thiazol-2-amine |
| 111[1] | 5-(4-bromo-1H-indazol-7-yl)-N-[(1R,3s,5S)-1,5-dimethyl-8-azabicyclo[3.2.1]octan-3-yl]-N-methyl[1,3]thiazolo[5,4-d][1,3]thiazol-2-amine |
| 112[1] | N-(1,2-dimethylpiperidin-4-yl)-N-methyl-5-[4-(1H-pyrazol-4-yl)-1H-benzimidazol-7-yl][1,3]thiazolo[5,4-d][1,3]thiazol-2-amine |
| 113[1] | N-methyl-5-[1-methyl-4-(1H-pyrazol-4-yl)-1H-pyrrolo[2,3-c]pyridin-7-yl]-N-(piperidin-4-yl)[1,3]thiazolo[5,4-d][1,3]thiazol-2-amine |
| 114[1] | N-methyl-5-[5-(1H-pyrazol-4-yl)pyrazin-2-yl]-N-[(1R,3s,5S)-1,5,8-trimethyl-8-azabicyclo[3.2.1]octan-3-yl][1,3]thiazolo[5,4-d][1,3]thiazol-2-amine |
| 115[1] | N-(1,2-dimethylpiperidin-4-yl)-N-methyl-5-[7-(1H-pyrazol-4-yl)-1H-imidazo[4,5-c]pyridin-4-yl][1,3]thiazolo[5,4-d][1,3]thiazol-2-amine |
| 116[1] | 5-(5-bromoimidazo[1,2-c]pyrimidin-8-yl)-N-methyl-N-(piperidin-4-yl)[1,3]thiazolo[5,4-d][1,3]thiazol-2-amine |
| 117[1] | 5-(5-bromoimidazo[1,2-a]pyrazin-8-yl)-N-methyl-N-(piperidin-4-yl)[1,3]thiazolo[5,4-d][1,3]thiazol-2-amine |
| 118[1] | N-(1,2-dimethylpiperidin-4-yl)-N-methyl-5-[4-(2H-1,2,3-triazol-2-yl)-1H-indol-7-yl][1,3]thiazolo[5,4-d][1,3]thiazol-2-amine |
| 119[1] | 5-(4-chloro-1H-indol-7-yl)-N-(1,2-dimethylpiperidin-4-yl)-N-methyl[1,3]thiazolo[5,4-d][1,3]thiazol-2-amine |
| 120[1] | 7-(5-{[(2S,4S)-2-methylpiperidin-4-yl]oxy}[1,3]thiazolo[5,4-d][1,3]thiazol-2-yl)-4-(1H-pyrazol-4-yl)-1H-pyrrolo[2,3-c]pyridine |
| 121[1] | N-methyl-N-[1-(propan-2-yl)piperidin-4-yl]-5-[4-(1H-pyrazol-4-yl)-1H-pyrrolo[2,3-c]pyridin-7-yl][1,3]thiazolo[5,4-d][1,3]thiazol-2-amine |
| 122[1] | N-(1-ethylpiperidin-4-yl)-N-methyl-5-[4-(1H-pyrazol-4-yl)-1H-pyrrolo[2,3-c]pyridin-7-yl][1,3]thiazolo[5,4-d][1,3]thiazol-2-amine |

| Cpd | Name |
|---|---|
| 123[1] | N-methyl-N-{5-[4-(1H-pyrazol-4-yl)-1H-pyrrolo[2,3-c]pyridin-7-yl][1,3]thiazolo[5,4-d][1,3]thiazol-2-yl}octahydroindolizin-7-amine |
| 124[1] | 5-(4-bromo-1H-pyrrolo[2,3-c]pyridin-7-yl)-N-(1,2-dimethylpiperidin-4-yl)-N-methyl[1,3]thiazolo[5,4-d][1,3]thiazol-2-amine |
| 125[1] | N-(1,2-dimethylpiperidin-4-yl)-N-methyl-5-[4-(1H-pyrazol-4-yl)-1H-indol-7-yl][1,3]thiazolo[5,4-d][1,3]thiazol-2-amine |
| 126[1] | N-(1,2-dimethylpiperidin-4-yl)-N-methyl-5-[5-(1H-pyrazol-4-yl)pyridin-2-yl][1,3]thiazolo[5,4-d][1,3]thiazol-2-amine |
| 127[1] | N-(1,2-dimethylpiperidin-4-yl)-N-methyl-5-[6-(1H-pyrazol-4-yl)pyridin-3-yl][1,3]thiazolo[5,4-d][1,3]thiazol-2-amine |
| 128[1] | N-methyl-5-[4-(1H-pyrazol-4-yl)-1H-indol-7-yl]-N-(2,2,6,6-tetramethylpiperidin-4-yl)[1,3]thiazolo[5,4-d][1,3]thiazol-2-amine |
| 129[1] | N-(1,2-dimethylpiperidin-4-yl)-N-methyl-5-[5-(1H-pyrazol-4-yl)pyrimidin-2-yl][1,3]thiazolo[5,4-d][1,3]thiazol-2-amine |
| 130[1] | N-(1,2-dimethylpiperidin-4-yl)-N-methyl-5-[2-(1H-pyrazol-4-yl)pyrimidin-5-yl][1,3]thiazolo[5,4-d][1,3]thiazol-2-amine |
| 131[1] | 3-{5-[(1,2-dimethylpiperidin-4-yl)(methyl)amino][1,3]thiazolo[5,4-d][1,3]thiazol-2-yl}-6-(1H-pyrazol-4-yl)pyrimidin-4(3H)-one |
| 132[1] | N-(1,2-dimethylpiperidin-4-yl)-N-methyl-5-[5-(1H-pyrazol-4-yl)pyrazin-2-yl][1,3]thiazolo[5,4-d][1,3]thiazol-2-amine |
| 133[1] | N-methyl-5-[5-(1H-pyrazol-4-yl)pyridin-2-yl]-N-(2,2,6,6-tetramethylpiperidin-4-yl)[1,3]thiazolo[5,4-d][1,3]thiazol-2-amine |
| 134[1] | 7-[5-(1,6-diazaspiro[3.5]nonan-1-yl)[1,3]thiazolo[5,4-d][1,3]thiazol-2-yl]-4-(1H-pyrazol-4-yl)-1H-pyrrolo[2,3-c]pyridine |
| 135[1] | N-methyl-5-[6-(1H-pyrazol-4-yl)pyridin-3-yl]-N-(2,2,6,6-tetramethylpiperidin-4-yl)[1,3]thiazolo[5,4-d][1,3]thiazol-2-amine |
| 136[1] | N-methyl-5-[7-(1H-pyrazol-4-yl)-1H-imidazo[4,5-c]pyridin-4-yl]-N-(2,2,6,6-tetramethylpiperidin-4-yl)[1,3]thiazolo[5,4-d][1,3]thiazol-2-amine |
| 137[1] | N-methyl-5-[2-(1H-pyrazol-4-yl)pyrimidin-5-yl]-N-(2,2,6,6-tetramethylpiperidin-4-yl)[1,3]thiazolo[5,4-d][1,3]thiazol-2-amine |
| 138[1] | 7-[5-(7-methyl-2,7-diazaspiro[3.5]nonan-2-yl)[1,3]thiazolo[5,4-d][1,3]thiazol-2-yl]-4-(1H-pyrazol-4-yl)-1H-pyrrolo[2,3-c]pyridine |
| 139[1] | N-methyl-N-(piperidin-4-yl)-5-[4-(1H-pyrazol-4-yl)-1H-pyrrolo[2,3-c]pyridin-7-yl][1,3]thiazolo[5,4-d][1,3]thiazol-2-amine |
| 140[1] | 3-{5-[methyl(2,2,6,6-tetramethylpiperidin-4-yl)amino][1,3]thiazolo[5,4-d][1,3]thiazol-2-yl}-6-(1H-pyrazol-4-yl)pyrimidin-4(3H)-one |
| 141[1] | N-[(1R,3s,5S)-8-azabicyclo[3.2.1]octan-3-yl]-N-methyl-5-[4-(1H-pyrazol-4-yl)phenyl][1,3]thiazolo[5,4-d][1,3]thiazol-2-amine |
| 142[1] | N-[(1R,3s,5S)-1,5-dimethyl-8-azabicyclo[3.2.1]octan-3-yl]-N-methyl-5-[5-(1H-pyrazol-4-yl)pyrazin-2-yl][1,3]thiazolo[5,4-d][1,3]thiazol-2-amine |
| 143[1] | 2-[5-(1H-pyrazol-4-yl)pyrazin-2-yl]-5-[(2,2,6,6-tetramethylpiperidin-4-yl)oxy][1,3]thiazolo[5,4-d][1,3]thiazole |
| 144[1] | 3-(5-{[(1R,3s,5S)-1,5-dimethyl-8-azabicyclo[3.2.1]octan-3-yl](methyl)amino}[1,3]thiazolo[5,4-d][1,3]thiazol-2-yl)-6-(1H-pyrazol-4-yl)pyrimidin-4(3H)-one |
| 145[1] | 2-{5-[methyl(octahydroindolizin-7-yl)amino][1,3]thiazolo[5,4-d][1,3]thiazol-2-yl}-5-(1H-pyrazol-4-yl)pyridin-3-ol |
| 146[1] | 1-(5-{[(1R,3s,5S)-1,5-dimethyl-8-azabicyclo[3.2.1]octan-3-yl](methyl)amino}[1,3]thiazolo[5,4-d][1,3]thiazol-2-yl)-4-(1H-pyrazol-4-yl)pyridin-2(1H)-one |
| 147[1] | 2-{5-[3-(tert-butylamino)pyrrolidin-1-yl][1,3]thiazolo[5,4-d][1,3]thiazol-2-yl}-5-(1H-pyrazol-4-yl)phenol |
| 148[1] | 1-(5-{[(1R,3s,5S)-1,5-dimethyl-8-azabicyclo[3.2.1]octan-3-yl](methyl)amino}[1,3]thiazolo[5,4-d][1,3]thiazol-2-yl)-4-(4-fluoro-1H-pyrazol-1-yl)pyridin-2(1H)-one |
| 149[1] | 1-(5-{[(1R,3s,5S)-8-azabicyclo[3.2.1]octan-3-yl](methyl)amino}[1,3]thiazolo[5,4-d][1,3]thiazol-2-yl)-4-(4-fluoro-1H-pyrazol-1-yl)pyridin-2(1H)-one |
| 150[1] | N-tert-butyl-1-{5-[5-(1H-pyrazol-4-yl)pyrimidin-2-yl][1,3]thiazolo[5,4-d][1,3]thiazol-2-yl}pyrrolidin-3-amine |
| 151[1] | 1-{5-[3-(tert-butylamino)pyrrolidin-1-yl][1,3]thiazolo[5,4-d][1,3]thiazol-2-yl}-4-(1H-pyrazol-4-yl)pyridin-2(1H)-one |
| 152[1] | N-(1,2-dimethylpiperidin-4-yl)-N-methyl-5-[4-(1H-pyrazol-4-yl)-1H-pyrrolo[2,3-c]pyridin-7-yl][1,3]thiazolo[5,4-d][1,3]thiazol-2-amine |
| 153[1] | 3-(5-{methyl[(1R,3s,5S)-8-methyl-8-azabicyclo[3.2.1]octan-3-yl]amino}[1,3]thiazolo[5,4-d][1,3]thiazol-2-yl)-6-(1H-pyrazol-4-yl)pyrimidin-4(3H)-one |
| 154[1] | N-[(1R,3s,5S)-1,5-dimethyl-8-azabicyclo[3.2.1]octan-3-yl]-N-methyl-5-[4-(1H-pyrazol-4-yl)-1H-pyrrolo[2,3-c]pyridin-7-yl][1,3]thiazolo[5,4-d][1,3]thiazol-2-amine |
| 155[1] | 1-(5-{methyl[(3R)-piperidin-3-yl]amino}[1,3]thiazolo[5,4-d][1,3]thiazol-2-yl)-4-(1H-pyrazol-4-yl)pyridin-2(1H)-one |
| 156[1] | 4-(1H-pyrazol-4-yl)-1-{5-[(2,2,6,6-tetramethylpiperidin-4-yl)oxy][1,3]thiazolo[5,4-d][1,3]thiazol-2-yl}pyridin-2(1H)-one |
| 157[1] | 1-{5-[(1,2-dimethylpiperidin-4-yl)(methyl)amino][1,3]thiazolo[5,4-d][1,3]thiazol-2-yl}-1H-pyrrolo[2,3-b]pyridin-6-ol |
| 158[1] | N-[(1R,3s,5S)-8-azabicyclo[3.2.1]octan-3-yl]-5-[2,5-difluoro-4-(1H-pyrazol-4-yl)phenyl]-N-methyl[1,3]thiazolo[5,4-d][1,3]thiazol-2-amine |

-continued

| Cpd | Name |
|---|---|
| 159[1] | N-methyl-5-[4-(1H-pyrazol-4-yl)-1H-pyrrolo[2,3-c]pyridin-7-yl]-N-(2,2,6,6-tetramethylpiperidin-4-yl)[1,3]thiazolo[5,4-d][1,3]thiazol-2-amine |
| 160[1] | N-[(1R,3s,5S)-8-azabicyclo[3.2.1]octan-3-yl]-N-methyl-5-(1H-pyrrolo[2,3-c]pyridin-7-yl)[1,3]thiazolo[5,4-d][1,3]thiazol-2-amine |
| 161[1] | N-methyl-N-[(3S)-piperidin-3-yl]-5-[5-(1H-pyrazol-4-yl)pyrimidin-2-yl][1,3]thiazolo[5,4-d][1,3]thiazol-2-amine |
| 162[1] | N-methyl-5-[5-(1H-pyrazol-4-yl)pyrimidin-2-yl]-N-(2,2,6,6-tetramethylpiperidin-4-yl)[1,3]thiazolo[5,4-d][1,3]thiazol-2-amine |
| 163[1] | N-methyl-5-[5-(1H-pyrazol-4-yl)pyrazin-2-yl]-N-(2,2,6,6-tetramethylpiperidin-4-yl)[1,3]thiazolo[5,4-d][1,3]thiazol-2-amine |
| 164[1] | N-[(1R,3s,5S)-8-azabicyclo[3.2.1]octan-3-yl]-N-methyl-5-[5-(1H-pyrazol-4-yl)pyrazin-2-yl][1,3]thiazolo[5,4-d][1,3]thiazol-2-amine |
| 165 | 1-(5-{methyl[(1R,3s,5S)-8-propyl-8-azabicyclo[3.2.1]octan-3-yl]amino}[1,3]thiazolo[5,4-d][1,3]thiazol-2-yl)-4-(1H-pyrazol-4-yl)pyridin-2(1H)-one |
| 166 | 1-(5-{[(1R,3s,5S)-8-ethyl-8-azabicyclo[3.2.1]octan-3-yl](methyl)amino}[1,3]thiazolo[5,4-d][1,3]thiazol-2-yl)-4-(1H-pyrazol-4-yl)pyridin-2(1H)-one |
| 167[1] | N-methyl-5-[6-(1H-pyrazol-4-yl)pyridazin-3-yl]-N-(2,2,6,6-tetramethylpiperidin-4-yl)[1,3]thiazolo[5,4-d][1,3]thiazol-2-amine |
| 168[1] | N-[(1R,3s,5S)-8-azabicyclo[3.2.1]octan-3-yl]-N-methyl-5-[6-(1H-pyrazol-4-yl)pyridazin-3-yl][1,3]thiazolo[5,4-d][1,3]thiazol-2-amine |
| 169[1] | 1-(5-{methyl[(3S)-piperidin-3-yl]amino}[1,3]thiazolo[5,4-d][1,3]thiazol-2-yl)-4-(1H-pyrazol-4-yl)pyridin-2(1H)-one |
| 170[1] | N-[(1R,3s,5S)-8-azabicyclo[3.2.1]octan-3-yl]-N-methyl-5-[4-(1H-pyrazol-4-yl)-1H-imidazol-1-yl][1,3]thiazolo[5,4-d][1,3]thiazol-2-amine |
| 171[1] | 1-(5-{[(1R,3s,5S)-8-azabicyclo[3.2.1]octan-3-yl](methyl)amino}[1,3]thiazolo[5,4-d][1,3]thiazol-2-yl)-4-bromopyridin-2(1H)-one |
| 172[1] | 3-(5-{[(1R,3s,5S)-8-azabicyclo[3.2.1]octan-3-yl](methyl)amino}[1,3]thiazolo[5,4-d][1,3]thiazol-2-yl)-6-(1H-pyrazol-4-yl)pyrimidin-4(3H)-one |
| 173[1] | N-[(1R,3s,5S)-8-azabicyclo[3.2.1]octan-3-yl]-N-methyl-5-[6-(1H-pyrazol-4-yl)pyridin-3-yl][1,3]thiazolo[5,4-d][1,3]thiazol-2-amine |
| 174[1] | N-[(1R,3s,5S)-8-azabicyclo[3.2.1]octan-3-yl]-N-methyl-5-[5-(1H-pyrazol-4-yl)pyridin-2-yl][1,3]thiazolo[5,4-d][1,3]thiazol-2-amine |
| 175[1] | N-[(1R,3s,5S)-8-azabicyclo[3.2.1]octan-3-yl]-N-methyl-5-[2-(1H-pyrazol-4-yl)pyrimidin-5-yl][1,3]thiazolo[5,4-d][1,3]thiazol-2-amine |
| 176[1] | 5-[5-(2,7-diazaspiro[3.5]nonan-2-yl)[1,3]thiazolo[5,4-d][1,3]thiazol-2-yl]-7-fluoro-2-methyl-2H-indazole |
| 177[1] | 2-{5-[2,5-difluoro-4-(1H-pyrazol-4-yl)phenyl][1,3]thiazolo[5,4-d][1,3]thiazol-2-yl}-2,7-diazaspiro[3.5]nonane |
| 178 | 1-(5-{methyl[(1R,3s,5S)-8-methyl-8-azabicyclo[3.2.1]octan-3-yl]amino}[1,3]thiazolo[5,4-d][1,3]thiazol-2-yl)-4-(1H-pyrazol-4-yl)pyridin-2(1H)-one |
| 179[1] | 2-[5-(7-methyl-1,7-diazaspiro[3.5]nonan-1-yl)[1,3]thiazolo[5,4-d][1,3]thiazol-2-yl]-5-(1H-pyrazol-4-yl)pyridin-3-ol |
| 180 | 1-{5-[(1,2-dimethylpiperidin-4-yl)(methyl)amino][1,3]thiazolo[5,4-d][1,3]thiazol-2-yl}-4-(1H-pyrazol-4-yl)pyridin-2(1H)-one |
| 181 | 1-{5-[methyl(2,2,6,6-tetramethylpiperidin-4-yl)amino][1,3]thiazolo[5,4-d][1,3]thiazol-2-yl}-4-(1H-pyrazol-4-yl)pyridin-2(1H)-one |
| 182[1] | 2-{5-[(1,2-dimethylpiperidin-4-yl)(methyl)amino][1,3]thiazolo[5,4-d][1,3]thiazol-2-yl}-5-(1H-pyrazol-4-yl)pyridin-3-ol |
| 183[1] | N-[(1R,3s,5S)-8-azabicyclo[3.2.1]octan-3-yl]-N-methyl-5-[4-(1H-pyrazol-4-yl)-1H-indol-7-yl][1,3]thiazolo[5,4-d][1,3]thiazol-2-amine |
| 184[1] | N-[(1R,3s,5S)-8-azabicyclo[3.2.1]octan-3-yl]-N-methyl-5-[4-(1H-pyrazol-4-yl)-1H-pyrrolo[2,3-c]pyridin-7-yl][1,3]thiazolo[5,4-d][1,3]thiazol-2-amine |
| 185[1] | 2-(5-{[(1R,3s,5S)-8-azabicyclo[3.2.1]octan-3-yl](methyl)amino}[1,3]thiazolo[5,4-d][1,3]thiazol-2-yl)-5-bromopyridin-3-ol |
| 186[1] | N-[(1R,3s,5S)-8-azabicyclo[3.2.1]octan-3-yl]-5-(5-bromopyrimidin-2-yl)-N-methyl[1,3]thiazolo[5,4-d][1,3]thiazol-2-amine |
| 187[1] | 1-(5-{[(1R,3s,5S)-8-azabicyclo[3.2.1]octan-3-yl](methyl)amino}[1,3]thiazolo[5,4-d][1,3]thiazol-2-yl)pyridin-2(1H)-one |
| 188[1] | 1-{5-[methyl(piperidin-4-yl)amino][1,3]thiazolo[5,4-d][1,3]thiazol-2-yl}-4-(1H-pyrazol-4-yl)pyridin-2(1H)-one |
| 189[1] | 2-[5-(1,7-diazaspiro[3.5]nonan-1-yl)[1,3]thiazolo[5,4-d][1,3]thiazol-2-yl]-5-(1H-pyrazol-4-yl)pyridin-3-ol |
| 190[1] | 2-(5-{[(1R,3s,5S)-8-azabicyclo[3.2.1]octan-3-yl](methyl)amino}[1,3]thiazolo[5,4-d][1,3]thiazol-2-yl)-5-(4-methyl-1H-pyrazol-1-yl)pyridin-3-ol |
| 191[1] | 6-(5-{[(1R,3s,5S)-8-azabicyclo[3.2.1]octan-3-yl](methyl)amino}[1,3]thiazolo[5,4-d][1,3]thiazol-2-yl)-5-hydroxy-1'-methyl[3,4'-bipyridin]-2'(1'H)-one |
| 192[1] | 2-[5-(2,6-diazaspiro[3.5]nonan-2-yl)[1,3]thiazolo[5,4-d][1,3]thiazol-2-yl]-5-(1H-pyrazol-4-yl)pyridin-3-ol |
| 193[1] | 2-(5-{[(1R,3s,5S)-8-azabicyclo[3.2.1]octan-3-yl](methyl)amino}[1,3]thiazolo[5,4-d][1,3]thiazol-2-yl)-5-(4-fluoro-1H-pyrazol-1-yl)pyridin-3-ol |
| 194[1] | N-[(1R,3s,5S)-8-azabicyclo[3.2.1]octan-3-yl]-N-methyl-5-[5-(1H-pyrazol-4-yl)pyrimidin-2-yl][1,3]thiazolo[5,4-d][1,3]thiazol-2-amine |
| 195[1] | 1-(5-{[(1R,3s,5S)-8-azabicyclo[3.2.1]octan-3-yl](methyl)amino}[1,3]thiazolo[5,4-d][1,3]thiazol-2-yl)-4-(1H-pyrazol-4-yl)pyridin-2(1H)-one |

-continued

| Cpd | Name |
|---|---|
| 196[1] | 2-[5-(7-methyl-2,7-diazaspiro[3.5]nonan-2-yl)[1,3]thiazolo[5,4-d][1,3]thiazol-2-yl]-5-(1H-pyrazol-4-yl)pyridin-3-ol |
| 197[1] | 5-(1H-pyrazol-4-yl)-2-[5-(spiro[8-azabicyclo[3.2.1]octane-3,3'-azetidin]-1'-yl)[1,3]thiazolo[5,4-d][1,3]thiazol-2-yl]pyridin-3-ol |
| 198[1] | 5-(1H-pyrazol-4-yl)-2-[5-(spiro[8-azabicyclo[3.2.1]octane-3,3'-azetidin]-1'-yl)[1,3]thiazolo[5,4-d][1,3]thiazol-2-yl]phenol |
| 199[1] | 2-(5-{[(1R,3s,5S)-8-azabicyclo[3.2.1]octan-3-yl](methyl)amino}[1,3]thiazolo[5,4-d][1,3]thiazol-2-yl)-5-(2-methyl-1,3-thiazol-5-yl)pyridin-3-ol |
| 200[1] | 5-[2-methoxy-4-(1H-pyrazol-4-yl)phenyl]-N-methyl-N-(piperidin-4-yl)[1,3]thiazolo[5,4-d][1,3]thiazol-2-amine |
| 201[1] | N-methyl-N-(piperidin-4-yl)-5-[5-(1H-pyrazol-4-yl)pyrimidin-2-yl][1,3]thiazolo[5,4-d][1,3]thiazol-2-amine |
| 202[1] | 2-(5-{[(2R,4S)-2-(hydroxymethyl)piperidin-4-yl](methyl)amino}[1,3]thiazolo[5,4-d][1,3]thiazol-2-yl)-5-(1H-pyrazol-4-yl)phenol |
| 203[1] | 2-(5-{[(1R,3s,5S)-8-azabicyclo[3.2.1]octan-3-yl](methyl)amino}[1,3]thiazolo[5,4-d][1,3]thiazol-2-yl)-5-(1H-pyrazol-4-yl)pyridin-3-ol |
| 204[1] | 2-{5-[(1-cyclopropylpiperidin-4-yl)(methyl)amino][1,3]thiazolo[5,4-d][1,3]thiazol-2-yl}-5-(1H-pyrazol-4-yl)pyridin-3-ol |
| 205[1] | 2-(5-{methyl[1-(propan-2-yl)piperidin-4-yl]amino}[1,3]thiazolo[5,4-d][1,3]thiazol-2-yl)-5-(1H-pyrazol-4-yl)pyridin-3-ol |
| 206[1] | 2-{5-[methyl(1-propylpiperidin-4-yl)amino][1,3]thiazolo[5,4-d][1,3]thiazol-2-yl}-5-(1H-pyrazol-4-yl)pyridin-3-ol |
| 207[1] | 2-{5-[(1-ethylpiperidin-4-yl)(methyl)amino][1,3]thiazolo[5,4-d][1,3]thiazol-2-yl}-5-(1H-pyrazol-4-yl)pyridin-3-ol |
| 208[1] | 2-[5-(piperidin-4-yl)[1,3]thiazolo[5,4-d][1,3]thiazol-2-yl]-5-(1H-pyrazol-4-yl)phenol |
| 209[1] | 2-[5-(2,7-diazaspiro[3.5]nonan-2-yl)[1,3]thiazolo[5,4-d][1,3]thiazol-2-yl]-5-(1H-pyrazol-4-yl)pyridin-3-ol |
| 210[1] | 2-{5-[methyl(piperidin-4-yl)amino][1,3]thiazolo[5,4-d][1,3]thiazol-2-yl}-5-([1,2,4]triazolo[4,3-a]pyridin-6-yl)pyridin-3-ol |
| 211[1] | 2-{5-[(3aR,6aS)-5-methylhexahydropyrrolo[3,4-c]pyrrol-2(1H)-yl][1,3]thiazolo[5,4-d][1,3]thiazol-2-yl}-5-(1H-pyrazol-4-yl)phenol |
| 212[1] | 2-{5-[methyl(piperidin-4-yl)amino][1,3]thiazolo[5,4-d][1,3]thiazol-2-yl}-5-(1H-1,2,4-triazol-1-yl)pyridin-3-ol |
| 213[1] | 2-(5-{methyl[(3S)-pyrrolidin-3-yl]amino}[1,3]thiazolo[5,4-d][1,3]thiazol-2-yl)-5-(1H-pyrazol-4-yl)pyridin-3-ol |
| 214[1] | 2-{5-[methyl(piperidin-4-yl)amino][1,3]thiazolo[5,4-d][1,3]thiazol-2-yl}-5-(2H-1,2,3-triazol-2-yl)pyridin-3-ol |
| 215[1] | 2-{5-[methyl(piperidin-4-yl)amino][1,3]thiazolo[5,4-d][1,3]thiazol-2-yl}-5-(1H-1,2,3-triazol-1-yl)pyridin-3-ol |
| 216[1] | 2-{5-[methyl(piperidin-4-yl)amino][1,3]thiazolo[5,4-d][1,3]thiazol-2-yl}-5-(1,2-thiazol-4-yl)pyridin-3-ol |
| 217[1] | 2-{5-[methyl(1-methylpiperidin-4-yl)amino][1,3]thiazolo[5,4-d][1,3]thiazol-2-yl}-5-(1H-pyrazol-4-yl)pyridin-3-ol |
| 218[1] | 2-{5-[ethyl(1-methylpiperidin-4-yl)amino][1,3]thiazolo[5,4-d][1,3]thiazol-2-yl}-5-(1H-pyrazol-4-yl)pyridin-3-ol |
| 219[1] | 2-{5-[methyl(piperidin-4-yl)amino][1,3]thiazolo[5,4-d][1,3]thiazol-2-yl}-5-(3-methyl-1H-pyrazol-4-yl)pyridin-3-ol |
| 220[1] | 5-(5-chloro-1H-pyrazol-4-yl)-2-{5-[methyl(piperidin-4-yl)amino][1,3]thiazolo[5,4-d][1,3]thiazol-2-yl}pyridin-3-ol |
| 221[1] | 5-(4-methyl-1H-imidazol-1-yl)-2-{5-[methyl(piperidin-4-yl)amino][1,3]thiazolo[5,4-d][1,3]thiazol-2-yl}pyridin-3-ol |
| 222[1] | 2-{5-[methyl(piperidin-4-yl)amino][1,3]thiazolo[5,4-d][1,3]thiazol-2-yl}-5-(2-methyl-1,3-thiazol-5-yl)pyridin-3-ol |
| 223[1] | 5-(2-methyl-1,3-oxazol-5-yl)-2-{5-[methyl(piperidin-4-yl)amino][1,3]thiazolo[5,4-d][1,3]thiazol-2-yl}pyridin-3-ol |
| 224[1] | 2-{5-[methyl(piperidin-4-yl)amino][1,3]thiazolo[5,4-d][1,3]thiazol-2-yl}-5-(6-methylpyridazin-4-yl)pyridin-3-ol |
| 225[1] | 2-{5-[methyl(piperidin-4-yl)amino][1,3]thiazolo[5,4-d][1,3]thiazol-2-yl}-5-(pyridazin-4-yl)pyridin-3-ol, and |
| 226[1] | N-methyl-N-(piperidin-4-yl)-5-[7-(1H-pyrazol-4-yl)-1H-pyrrolo[2,3-c]pyridin-4-yl][1,3]thiazolo[5,4-d][1,3]thiazol-2-amine; | wherein the form of the compound is selected from the group consisting of a salt, hydrate, solvate, racemate, enantiomer, diastereomer, stereoisomer, and tautomer form thereof.

Another aspect of the compound of Formula (I), Formula (II), Formula (III), or Formula (IV) or a form thereof is a compound salt selected from the group consisting of:

| Cpd | Name |
|---|---|
| 1 | 2-{5-[methyl(2,2,6,6-tetramethylpiperidin-4-yl)amino][1,3]thiazolo[5,4-d][1,3]thiazol-2-yl}-5-(1H-pyrazol-4-yl)phenol hydrochloride |
| 2 | 2,7-dimethyl-5-[6-(piperidin-4-yl)imidazo[2,1-b][1,3]thiazol-2-yl]-2H-indazole hydrochloride |

-continued

| Cpd | Name |
|---|---|
| 3 | 5-[2,3-difluoro-4-(1H-pyrazol-4-yl)phenyl]-N-methyl-N-(2,2,6,6-tetramethylpiperidin-4-yl)[1,3]thiazolo[5,4-d][1,3]thiazol-2-amine hydrochloride |
| 4 | 5-[2,5-difluoro-4-(1H-pyrazol-4-yl)phenyl]-N-methyl-N-(2,2,6,6-tetramethylpiperidin-4-yl)[1,3]thiazolo[5,4-d][1,3]thiazol-2-amine hydrochloride |
| 5 | 5-[3,5-difluoro-4-(1H-pyrazol-4-yl)phenyl]-N-methyl-N-(2,2,6,6-tetramethylpiperidin-4-yl)[1,3]thiazolo[5,4-d][1,3]thiazol-2-amine hydrochloride |
| 6 | 2-[5-(piperazin-1-yl)[1,3]thiazolo[5,4-d][1,3]thiazol-2-yl]-5-(1H-pyrazol-4-yl)phenol hydrochloride |
| 7 | 2-methyl-5-[5-(piperazin-1-yl)[1,3]thiazolo[5,4-d][1,3]thiazol-2-yl]-2H-indazole-7-carbonitrile hydrochloride |
| 8 | 2,8-dimethyl-6-[6-(piperidin-4-yl)imidazo[2,1-b][1,3]thiazol-2-yl]imidazo[1,2-b]pyridazine hydrochloride |
| 9 | 2-{5-chloro-2-[methyl(2,2,6,6-tetramethylpiperidin-4-yl)amino]imidazo[2,1-b][1,3,4]thiadiazol-6-yl}-5-(1H-pyrazol-4-yl)phenol hydrochloride |
| 10 | 2-methyl-6-[5-(piperidin-4-yl)[1,3]thiazolo[5,4-d][1,3]thiazol-2-yl]imidazo[1,2-a]pyridine-8-carbonitrile hydrochloride |
| 11 | 7-fluoro-2-methyl-5-[5-(piperidin-4-yl)[1,3]thiazolo[5,4-d][1,3]thiazol-2-yl]-2H-indazole hydrochloride |
| 12 | 2,8-dimethyl-6-[5-(piperidin-4-yl)[1,3]thiazolo[5,4-d][1,3]thiazol-2-yl]imidazo[1,2-b]pyridazine hydrochloride |
| 13 | 2-{5-[(3-exo)-8-azabicyclo[3.2.1]oct-3-ylamino][1,3]thiazolo[5,4-d][1,3]thiazol-2-yl}-5-(1H-pyrazol-4-yl)phenol hydrochloride |
| 14 | 2-{5-[methyl(piperidin-4-yl)amino][1,3]thiazolo[5,4-d][1,3]thiazol-2-yl}-5-(1H-pyrazol-4-yl)phenol hydrochloride |
| 15 | 2-methyl-5-[5-(piperidin-4-yl)[1,3]thiazolo[5,4-d][1,3]thiazol-2-yl]-2H-indazole-7-carbonitrile hydrochloride |
| 16 | 2,7-dimethyl-5-[5-(piperidin-4-yl)[1,3]thiazolo[5,4-d][1,3]thiazol-2-yl]-2H-indazole hydrochloride |
| 17 | 2-{2-[methyl(2,2,6,6-tetramethylpiperidin-4-yl)amino]imidazo[2,1-b][1,3,4]thiadiazol-6-yl}-5-(1H-pyrazol-4-yl)phenol hydrochloride |
| 18 | 2-{2-[(3-exo)-8-azabicyclo[3.2.1]oct-3-yl(methyl)amino]imidazo[2,1-b][1,3,4]thiadiazol-6-yl}-5-(1H-pyrazol-4-yl)phenol hydrochloride |
| 19 | 2-(2-{[(3-exo)-8-methyl-8-azabicyclo[3.2.1]oct-3-yl]amino}imidazo[2,1-b][1,3,4]thiadiazol-6-yl)-5-(1H-pyrazol-4-yl)phenol hydrochloride |
| 20 | 5-[2,5-difluoro-4-(1H-pyrazol-4-yl)phenyl]-N-methyl-N-(piperidin-4-yl)[1,3]thiazolo[5,4-d][1,3]thiazol-2-amine hydrochloride |
| 21 | 5-[3,5-difluoro-4-(1H-pyrazol-4-yl)phenyl]-N-methyl-N-(piperidin-4-yl)[1,3]thiazolo[5,4-d][1,3]thiazol-2-amine hydrochloride |
| 22 | 2-[5-(piperidin-4-ylamino)[1,3]thiazolo[5,4-d][1,3]thiazol-2-yl]-5-(1H-pyrazol-4-yl)phenol hydrochloride |
| 23 | 2-{5-[(1-methylpiperidin-4-yl)amino][1,3]thiazolo[5,4-d][1,3]thiazol-2-yl}-5-(1H-pyrazol-4-yl)phenol hydrochloride |
| 24 | 2-{5-[methyl(1-methylpiperidin-4-yl)amino][1,3]thiazolo[5,4-d][1,3]thiazol-2-yl}-5-(1H-pyrazol-4-yl)phenol hydrochloride |
| 25 | 2-methyl-5-[5-(piperidin-4-yl)[1,3]thiazolo[5,4-d][1,3]thiazol-2-yl]-2H-indazole trifluoroacetate |
| 26 | 7-methoxy-2-methyl-5-[5-(piperidin-4-yl)[1,3]thiazolo[5,4-d][1,3]thiazol-2-yl]-2H-indazole trifluoroacetate |
| 27 | 2-methyl-5-[6-(piperidin-4-yl)imidazo[2,1-b][1,3,4]thiadiazol-2-yl]-2H-indazole-7-carbonitrile trifluoroacetate |
| 28 | 7-fluoro-2-methyl-5-[6-(piperidin-4-yl)imidazo[2,1-b][1,3,4]thiadiazol-2-yl]-2H-indazole trifluoroacetate |
| 29 | 2-methyl-6-[6-(piperidin-4-yl)imidazo[2,1-b][1,3,4]thiadiazol-2-yl]imidazo[1,2-a]pyridine-8-carbonitrile hydrochloride |
| 30 | 8-fluoro-2-methyl-6-[6-(piperidin-4-yl)imidazo[2,1-b][1,3,4]thiadiazol-2-yl]imidazo[1,2-a]pyridine hydrochloride |
| 31 | 2-methyl-5-{2-[methyl(1-methylpiperidin-4-yl)amino]imidazo[2,1-b][1,3,4]thiadiazol-6-yl}-2H-indazole-7-carbonitrile hydrochloride |
| 32 | 2-methyl-5-[2-(piperidin-4-yl)imidazo[2,1-b][1,3,4]thiadiazol-6-yl]-2H-indazole-7-carbonitrile hydrochloride |
| 33 | 5-[2-(8-azabicyclo[3.2.1]oct-2-en-3-yl)imidazo[2,1-b][1,3,4]thiadiazol-6-yl]-2-methyl-2H-indazole-7-carbonitrile hydrochloride |
| 34 | 2-(5-{[(2R,4s,6S)-2,6-dimethylpiperidin-4-yl](methyl)amino}[1,3]thiazolo[5,4-d][1,3]thiazol-2-yl)-5-(1H-pyrazol-4-yl)phenol trifluoroacetate |
| 35 | 4-(3-hydroxy-4-{5-[methyl(piperidin-4-yl)amino][1,3]thiazolo[5,4-d][1,3]thiazol-2-yl}phenyl)pyridin-2-ol hydrochloride |
| 36 | 4-(3-hydroxy-4-{5-[methyl(piperidin-4-yl)amino][1,3]thiazolo[5,4-d][1,3]thiazol-2-yl}phenyl)-1-methylpyridin-2(1H)-one hydrochloride |
| 38 | 4-(3-hydroxy-4-{5-[(2,2,6,6-tetramethylpiperidin-4-yl)oxy][1,3]thiazolo[5,4-d][1,3]thiazol-2-yl}phenyl)-1-methylpyridin-2(1H)-one hydrochloride |
| 39 | 2-{5-[methyl(piperidin-4-yl)amino][1,3]thiazolo[5,4-d][1,3]thiazol-2-yl}-5-[1-($^{2}H_{3}$)methyl-1H-pyrazol-4-yl]phenol hydrochloride |
| 40 | 2-{5-[methyl(piperidin-4-yl)amino][1,3]thiazolo[5,4-d][1,3]thiazol-2-yl}-5-(1-methyl-1H-pyrazol-4-yl)phenol hydrochloride |
| 42 | 2-{5-[methyl(2,2,6,6-tetramethylpiperidin-4-yl)amino][1,3]thiazolo[5,4-d][1,3]thiazol-2-yl}-5-(1H-pyrazol-4-yl)pyridin-3-ol hydrochloride |

-continued

| Cpd | Name |
|---|---|
| 43 | 5-(5-fluoro-1H-pyrazol-4-yl)-2-{5-[methyl(2,2,6,6-tetramethylpiperidin-4-yl)amino][1,3]thiazolo[5,4-d][1,3]thiazol-2-yl}phenol hydrochloride |
| 44 | 6,8-dimethyl-2-[5-(piperidin-4-yl)[1,3]thiazolo[5,4-d][1,3]thiazol-2-yl]imidazo[1,2-a]pyrazine hydrochloride |
| 45 | 5-(5-fluoro-1-methyl-1H-pyrazol-4-yl)-2-{5-[(2,2,6,6-tetramethylpiperidin-4-yl)oxy][1,3]thiazolo[5,4-d][1,3]thiazol-2-yl}phenol trifluoroacetate |
| 46 | 4-(3-hydroxy-4-{5-[methyl(2,2,6,6-tetramethylpiperidin-4-yl)amino][1,3]thiazolo[5,4-d][1,3]thiazol-2-yl}phenyl)-1-methylpyridin-2(1H)-one hydrochloride |
| 47 | 2-{5-[methyl(piperidin-4-yl)amino][1,3]thiazolo[5,4-d][1,3]thiazol-2-yl}-5-(1H-pyrazol-4-yl)pyridin-3-ol hydrochloride |
| 48 | 5-(5-fluoro-1-methyl-1H-pyrazol-4-yl)-2-{5-[methyl(2,2,6,6-tetramethylpiperidin-4-yl)amino][1,3]thiazolo[5,4-d][1,3]thiazol-2-yl}phenol hydrochloride |
| 49 | 5-[1-($^2$H$_3$)methyl-1H-pyrazol-4-yl]-2-{5-[methyl(2,2,6,6-tetramethylpiperidin-4-yl)amino][1,3]thiazolo[5,4-d][1,3]thiazol-2-yl}pyridin-3-ol hydrochloride |
| 50 | 5-(1-ethyl-1H-pyrazol-4-yl)-2-{5-[methyl(2,2,6,6-tetramethylpiperidin-4-yl)amino][1,3]thiazolo[5,4-d][1,3]thiazol-2-yl}pyridin-3-ol hydrochloride |
| 51 | 2-{5-[methyl(piperidin-4-yl)amino][1,3]thiazolo[5,4-d][1,3]thiazol-2-yl}-5-[1-($^2$H$_3$)methyl-1H-pyrazol-4-yl]pyridin-3-ol hydrochloride |
| 52 | 5-(1-ethyl-1H-pyrazol-4-yl)-2-{5-[methyl(piperidin-4-yl)amino][1,3]thiazolo[5,4-d][1,3]thiazol-2-yl}pyridin-3-ol hydrochloride |
| 53 | 5-(5-fluoro-1H-pyrazol-4-yl)-2-{5-[methyl(piperidin-4-yl)amino][1,3]thiazolo[5,4-d][1,3]thiazol-2-yl}pyridin-3-ol trifluoroacetate |
| 54 | 2-(5-{methyl[(3S)-pyrrolidin-3-yl]amino}[1,3]thiazolo[5,4-d][1,3]thiazol-2-yl)-5-(1H-pyrazol-4-yl)phenol hydrochloride |
| 55 | 2-(5-{methyl[(3R)-pyrrolidin-3-yl]amino}[1,3]thiazolo[5,4-d][1,3]thiazol-2-yl)-5-(1H-pyrazol-4-yl)phenol hydrochloride |
| 56 | 2-(5-{methyl[(3R)-pyrrolidin-3-yl]amino}[1,3]thiazolo[5,4-d][1,3]thiazol-2-yl)-5-(1H-pyrazol-4-yl)pyridin-3-ol hydrochloride |
| 57 | 5-bromo-2-{5-[methyl(piperidin-4-yl)amino][1,3]thiazolo[5,4-d][1,3]thiazol-2-yl}pyridin-3-ol hydrochloride |
| 58 | 2-{5-[methyl(1-methylpiperidin-4-yl)amino][1,3]thiazolo[5,4-d][1,3]thiazol-2-yl}-5-[1-($^2$H$_3$)methyl-1H-pyrazol-4-yl]phenol hydrochloride |
| 59 | 2-{5-[(1-ethylpiperidin-4-yl)(methyl)amino][1,3]thiazolo[5,4-d][1,3]thiazol-2-yl}-5-(1-methyl-1H-pyrazol-4-yl)phenol hydrochloride |
| 60 | 5-(1H-imidazol-1-yl)-2-{5-[methyl(piperidin-4-yl)amino][1,3]thiazolo[5,4-d][1,3]thiazol-2-yl}pyridin-3-ol trifluoroacetate |
| 61 | 2-{5-[ethyl(piperidin-4-yl)amino][1,3]thiazolo[5,4-d][1,3]thiazol-2-yl}-5-(1H-pyrazol-4-yl)pyridin-3-ol hydrochloride |
| 62 | 5-(4-fluoropyrazol-1-yl)-2-[5-[methyl(4-piperidyl)amino]thiazolo[5,4-d]thiazol-2-yl]pyridin-3-ol hydrochloride |
| 63 | 5-(4-methylpyrazol-1-yl)-2-[5-[methyl(4-piperidyl)amino]thiazolo[5,4-d]thiazol-2-yl]pyridin-3-ol hydrochloride |
| 64 | 5-(thiazol-5-yl)-2-{5-[methyl(piperidin-4-yl)amino][1,3]thiazolo[5,4-d][1,3]thiazol-2-yl}pyridin-3-ol hydrochloride |
| 71 | N-methyl-N-[(2S,4R)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine hydrochloride |
| 72 | N-methyl-N-[(2S,4R)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine hydrochloride |
| 75 | N-methyl-N-[(2S,4R)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine hydrochloride |
| 76 | 7-(5-{[(2R,4S)-2-methylpiperidin-4-yl]oxy}[1,3]thiazolo[5,4-d][1,3]thiazol-2-yl)-4-(1H-pyrazol-4-yl)-1H-pyrrolo[2,3-c]pyridine hydrochloride |
| 77 | 7-{5-[(2,2-dimethylpiperidin-4-yl)oxy][1,3]thiazolo[5,4-d][1,3]thiazol-2-yl}-4-(1H-pyrazol-4-yl)-1H-pyrrolo[2,3-c]pyridine hydrochloride |
| 78 | 7-(5-{[(2R,4S)-2-methylpiperidin-4-yl]oxy}[1,3]thiazolo[5,4-d][1,3]thiazol-2-yl)-4-(1H-pyrazol-4-yl)-1H-indazole hydrochloride |
| 79 | N-[(1R,3s,5S)-1,5-dimethyl-8-azabicyclo[3.2.1]octan-3-yl]-N-methyl-5-[6-(1H-pyrazol-4-yl)-1,2,4-triazin-3-yl][1,3]thiazolo[5,4-d][1,3]thiazol-2-amine hydrochloride |
| 80 | 5-[4-(1H-imidazol-1-yl)-1H-pyrrolo[2,3-c]pyridin-7-yl]-N-methyl-N-[(2S,4R)-2-methylpiperidin-4-yl][1,3]thiazolo[5,4-d][1,3]thiazol-2-amine hydrochloride |
| 81 | 7-(5-{[(2S,4R)-2-methylpiperidin-4-yl]oxy}[1,3]thiazolo[5,4-d][1,3]thiazol-2-yl)-4-(2-methyl-2H-tetrazol-5-yl)-1H-pyrrolo[2,3-c]pyridine hydrochloride |
| 82 | 7-(5-{[(2R,4S)-2-methylpiperidin-4-yl]oxy}[1,3]thiazolo[5,4-d][1,3]thiazol-2-yl)-4-(1H-pyrazol-4-yl)-1H-indole hydrochloride |
| 83 | 4-(5-{[(2R,4S)-2-methylpiperidin-4-yl]oxy}[1,3]thiazolo[5,4-d][1,3]thiazol-2-yl)-7-(1H-pyrazol-4-yl)-3H-imidazo[4,5-c]pyridine hydrochloride |
| 84 | 7-(5-{[(2S,4R)-1,2-dimethylpiperidin-4-yl]oxy}[1,3]thiazolo[5,4-d][1,3]thiazol-2-yl)-4-(1H-pyrazol-4-yl)-1H-pyrrolo[2,3-c]pyridine formate |
| 85 | N-methyl-N-[(2R,4S)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine hydrochloride |
| 86 | N-[(1R,3s,5S)-1,5-dimethyl-8-azabicyclo[3.2.1]octan-3-yl]-N-methyl-5-[5-(5-methyl-1H-pyrazol-4-yl)pyrazin-2-yl][1,3]thiazolo[5,4-d][1,3]thiazol-2-amine hydrochloride |
| 87 | N-methyl-N-[(2R,4S)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine hydrochloride |

-continued

| Cpd | Name |
|---|---|
| 89 | N-[(1R,3s,5S)-1,5-dimethyl-8-azabicyclo[3.2.1]octan-3-yl]-N-methyl-5-[5-(1-methyl-1H-pyrazol-4-yl)pyrazin-2-yl][1,3]thiazolo[5,4-d][1,3]thiazol-2-amine hydrochloride |
| 90 | 5-[4-(1-ethyl-1H-pyrazol-4-yl)-1H-pyrrolo[2,3-c]pyridin-7-yl]-N-methyl-N-[(2R,4S)-2-methylpiperidin-4-yl][1,3]thiazolo[5,4-d][1,3]thiazol-2-amine hydrochloride |
| 91 | N-methyl-N-[(2R,4S)-2-methylpiperidin-4-yl]-5-[4-(1-methyl-1H-pyrazol-4-yl)-1H-pyrrolo[2,3-c]pyridin-7-yl][1,3]thiazolo[5,4-d][1,3]thiazol-2-amine hydrochloride |
| 92 | 4-[5-(5-{[(1R,3s,5S)-1,5-dimethyl-8-azabicyclo[3.2.1]octan-3-yl](methyl)amino}[1,3]thiazolo[5,4-d][1,3]thiazol-2-yl)pyrazin-2-yl]-1-methylpyridin-2(1H)-one trifluoroacetate |
| 93 | N-methyl-N-[(2R,4S)-2-methylpiperidin-4-yl]-5-[5-(1H-pyrazol-4-yl)pyrazin-2-yl][1,3]thiazolo[5,4-d][1,3]thiazol-2-amine hydrochloride |
| 94 | N-methyl-5-[5-(1-methyl-1H-pyrazol-4-yl)pyrazin-2-yl]-N-(2,2,6,6-tetramethylpiperidin-4-yl)[1,3]thiazolo[5,4-d][1,3]thiazol-2-amine hydrochloride |
| 95 | N-methyl-N-[(2S,4S)-2-methylpiperidin-4-yl]-5-[4-(1-methyl-1H-pyrazol-4-yl)-1H-pyrrolo[2,3-c]pyridin-7-yl][1,3]thiazolo[5,4-d][1,3]thiazol-2-amine hydrochloride |
| 96 | 7-[5-(6-methyl-1,6-diazaspiro[3.5]nonan-1-yl)[1,3]thiazolo[5,4-d][1,3]thiazol-2-yl]-4-(1H-pyrazol-4-yl)-1H-pyrrolo[2,3-c]pyridine formate |
| 97 | N-methyl-N-[(2S,4S)-2-methylpiperidin-4-yl]-5-[4-(1H-pyrazol-4-yl)-1H-indol-7-yl][1,3]thiazolo[5,4-d][1,3]thiazol-2-amine trifluoroacetate |
| 98 | N-methyl-N-[(2S,4S)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine trifluoroacetate |
| 99 | N-methyl-N-[(2S,4S)-2-methylpiperidin-4-yl]-5-[5-(1H-pyrazol-4-yl)pyrazin-2-yl][1,3]thiazolo[5,4-d][1,3]thiazol-2-amine hydrochloride |
| 101 | N-methyl-N-(piperidin-4-yl)-5-[5-(1H-pyrazol-4-yl)imidazo[1,2-a]pyrazin-8-yl][1,3]thiazolo[5,4-d][1,3]thiazol-2-amine hydrochloride |
| 102 | 5-[5-(1H-imidazol-1-yl)pyrazin-2-yl]-N-methyl-N-(2,2,6,6-tetramethylpiperidin-4-yl)[1,3]thiazolo[5,4-d][1,3]thiazol-2-amine hydrochloride |
| 103 | N-[(1R,3s,5S)-1,5-dimethyl-8-azabicyclo[3.2.1]octan-3-yl]-5-[5-(1H-imidazol-1-yl)pyrazin-2-yl]-N-methyl[1,3]thiazolo[5,4-d][1,3]thiazol-2-amine hydrochloride |
| 104 | N-[(1R,3s,5S)-1,5-dimethyl-8-azabicyclo[3.2.1]octan-3-yl]-N-methyl-5-[5-(1H-pyrazol-1-yl)pyrazin-2-yl][1,3]thiazolo[5,4-d][1,3]thiazol-2-amine hydrochloride |
| 105 | N-methyl-5-[5-(1H-pyrazol-1-yl)pyrazin-2-yl]-N-(2,2,6,6-tetramethylpiperidin-4-yl)[1,3]thiazolo[5,4-d][1,3]thiazol-2-amine hydrochloride |
| 106 | N-methyl-5-[4-(1H-pyrazol-4-yl)-1H-benzimidazol-7-yl]-N-(2,2,6,6-tetramethylpiperidin-4-yl)[1,3]thiazolo[5,4-d][1,3]thiazol-2-amine trifluoroacetate |
| 107 | N-methyl-5-[4-(1H-pyrazol-4-yl)-1H-indazol-7-yl]-N-(2,2,6,6-tetramethylpiperidin-4-yl)[1,3]thiazolo[5,4-d][1,3]thiazol-2-amine trifluoroacetate |
| 108 | N-(1,2-dimethylpiperidin-4-yl)-N-methyl-5-[4-(1H-pyrazol-4-yl)-1H-indazol-7-yl][1,3]thiazolo[5,4-d][1,3]thiazol-2-amine hydrochloride |
| 109 | 7-(5-{[(2S,4R)-2-methylpiperidin-4-yl]oxy}[1,3]thiazolo[5,4-d][1,3]thiazol-2-yl)-4-(1H-pyrazol-4-yl)-1H-pyrrolo[2,3-c]pyridine hydrochloride |
| 110 | N-[(1R,3s,5S)-1,5-dimethyl-8-azabicyclo[3.2.1]octan-3-yl]-N-methyl-5-[4-(1H-pyrazol-4-yl)-1H-indazol-7-yl][1,3]thiazolo[5,4-d][1,3]thiazol-2-amine trifluoroacetate |
| 111 | 5-(4-bromo-1H-indazol-7-yl)-N-[(1R,3s,5S)-1,5-dimethyl-8-azabicyclo[3.2.1]octan-3-yl]-N-methyl[1,3]thiazolo[5,4-d][1,3]thiazol-2-amine hydrochloride |
| 112 | N-(1,2-dimethylpiperidin-4-yl)-N-methyl-5-[4-(1H-pyrazol-4-yl)-1H-benzimidazol-7-yl][1,3]thiazolo[5,4-d][1,3]thiazol-2-amine trifluoroacetate |
| 113 | N-methyl-5-[1-methyl-4-(1H-pyrazol-4-yl)-1H-pyrrolo[2,3-c]pyridin-7-yl]-N-(piperidin-4-yl)[1,3]thiazolo[5,4-d][1,3]thiazol-2-amine hydrochloride |
| 114 | N-methyl-5-[5-(1H-pyrazol-4-yl)pyrazin-2-yl]-N-[(1R,3s,5S)-1,5,8-trimethyl-8-azabicyclo[3.2.1]octan-3-yl][1,3]thiazolo[5,4-d][1,3]thiazol-2-amine trifluoroacetate |
| 115 | N-(1,2-dimethylpiperidin-4-yl)-N-methyl-5-[7-(1H-pyrazol-4-yl)-1H-imidazo[4,5-c]pyridin-4-yl][1,3]thiazolo[5,4-d][1,3]thiazol-2-amine trifluoroacetate |
| 116 | 5-(5-bromoimidazo[1,2-c]pyrimidin-8-yl)-N-methyl-N-(piperidin-4-yl)[1,3]thiazolo[5,4-d][1,3]thiazol-2-amine hydrochloride |
| 117 | 5-(5-bromoimidazo[1,2-a]pyrazin-8-yl)-N-methyl-N-(piperidin-4-yl)[1,3]thiazolo[5,4-d][1,3]thiazol-2-amine hydrochloride |
| 118 | N-(1,2-dimethylpiperidin-4-yl)-N-methyl-5-[4-(2H-1,2,3-triazol-2-yl)-1H-indol-7-yl][1,3]thiazolo[5,4-d][1,3]thiazol-2-amine trifluoroacetate |
| 119 | 5-(4-chloro-1H-indol-7-yl)-N-(1,2-dimethylpiperidin-4-yl)-N-methyl[1,3]thiazolo[5,4-d][1,3]thiazol-2-amine trifluoroacetate |
| 120 | 7-(5-{[(2S,4S)-2-methylpiperidin-4-yl]oxy}[1,3]thiazolo[5,4-d][1,3]thiazol-2-yl)-4-(1H-pyrazol-4-yl)-1H-pyrrolo[2,3-c]pyridine formate |
| 121 | N-methyl-N-[1-(propan-2-yl)piperidin-4-yl]-5-[4-(1H-pyrazol-4-yl)-1H-pyrrolo[2,3-c]pyridin-7-yl][1,3]thiazolo[5,4-d][1,3]thiazol-2-amine formate |
| 122 | N-(1-ethylpiperidin-4-yl)-N-methyl-5-[4-(1H-pyrazol-4-yl)-1H-pyrrolo[2,3-c]pyridin-7-yl][1,3]thiazolo[5,4-d][1,3]thiazol-2-amine formate |
| 123 | N-methyl-N-{5-[4-(1H-pyrazol-4-yl)-1H-pyrrolo[2,3-c]pyridin-7-yl][1,3]thiazolo[5,4-d][1,3]thiazol-2-yl}octahydroindolizin-7-amine hydrochloride |
| 124 | 5-(4-bromo-1H-pyrrolo[2,3-c]pyridin-7-yl)-N-(1,2-dimethylpiperidin-4-yl)-N-methyl[1,3]thiazolo[5,4-d][1,3]thiazol-2-amine formate |
| 125 | N-(1,2-dimethylpiperidin-4-yl)-N-methyl-5-[4-(1H-pyrazol-4-yl)-1H-indol-7-yl][1,3]thiazolo[5,4-d][1,3]thiazol-2-amine trifluoroacetate |

-continued

| Cpd | Name |
|---|---|
| 126 | N-(1,2-dimethylpiperidin-4-yl)-N-methyl-5-[5-(1H-pyrazol-4-yl)pyridin-2-yl][1,3]thiazolo[5,4-d][1,3]thiazol-2-amine hydrochloride |
| 127 | N-(1,2-dimethylpiperidin-4-yl)-N-methyl-5-[6-(1H-pyrazol-4-yl)pyridin-3-yl][1,3]thiazolo[5,4-d][1,3]thiazol-2-amine trifluoroacetate |
| 128 | N-methyl-5-[4-(1H-pyrazol-4-yl)-1H-indol-7-yl]-N-(2,2,6,6-tetramethylpiperidin-4-yl)[1,3]thiazolo[5,4-d][1,3]thiazol-2-amine trifluoroacetate |
| 129 | N-(1,2-dimethylpiperidin-4-yl)-N-methyl-5-[5-(1H-pyrazol-4-yl)pyrimidin-2-yl][1,3]thiazolo[5,4-d][1,3]thiazol-2-amine trifluoroacetate |
| 130 | N-(1,2-dimethylpiperidin-4-yl)-N-methyl-5-[2-(1H-pyrazol-4-yl)pyrimidin-5-yl][1,3]thiazolo[5,4-d][1,3]thiazol-2-amine trifluoroacetate |
| 131 | 3-{5-[(1,2-dimethylpiperidin-4-yl)(methyl)amino][1,3]thiazolo[5,4-d][1,3]thiazol-2-yl}-6-(1H-pyrazol-4-yl)pyrimidin-4(3H)-one hydrochloride |
| 13¹ | N-(1,2-dimethylpiperidin-4-yl)-N-methyl-5-[5-(1H-pyrazol-4-yl)pyrazin-2-yl][1,3]thiazolo[5,4-d][1,3]thiazol-2-amine trifluoroacetate |
| 133 | N-methyl-5-[5-(1H-pyrazol-4-yl)pyridin-2-yl]-N-(2,2,6,6-tetramethylpiperidin-4-yl)[1,3]thiazolo[5,4-d][1,3]thiazol-2-amine hydrochloride |
| 134 | 7-[5-(1,6-diazaspiro[3.5]nonan-1-yl)[1,3]thiazolo[5,4-d][1,3]thiazol-2-yl]-4-(1H-pyrazol-4-yl)-1H-pyrrolo[2,3-c]pyridine formate |
| 135 | N-methyl-5-[6-(1H-pyrazol-4-yl)pyridin-3-yl]-N-(2,2,6,6-tetramethylpiperidin-4-yl)[1,3]thiazolo[5,4-d][1,3]thiazol-2-amine hydrochloride |
| 136 | N-methyl-5-[7-(1H-pyrazol-4-yl)-1H-imidazo[4,5-c]pyridin-4-yl]-N-(2,2,6,6-tetramethylpiperidin-4-yl)[1,3]thiazolo[5,4-d][1,3]thiazol-2-amine trifluoroacetate |
| 137 | N-methyl-5-[2-(1H-pyrazol-4-yl)pyrimidin-5-yl]-N-2,2,6,6-tetramethylpiperidin-4-yl)[1,3]thiazolo[5,4-d][1,3]thiazol-2-amine hydrochloride |
| 138 | 7-[5-(7-methyl-2,7-diazaspiro[3.5]nonan-2-yl)[1,3]thiazolo[5,4-d][1,3]thiazol-2-yl]-4-(1H-pyrazol-4-yl)-1H-pyrrolo[2,3-c]pyridine trifluoroacetate |
| 139 | N-methyl-N-(piperidin-4-yl)-5-[4-(1H-pyrazol-4-yl)-1H-pyrrolo[2,3-c]pyridin-7-yl][1,3]thiazolo[5,4-d][1,3]thiazol-2-amine trifluoroacetate |
| 140 | 3-{5-[methyl(2,2,6,6-tetramethylpiperidin-4-yl)amino][1,3]thiazolo[5,4-d][1,3]thiazol-2-yl}-6-(1H-pyrazol-4-yl)pyrimidin-4(3H)-one trifluoroacetate |
| 141 | N-[(1R,3s,5S)-8-azabicyclo[3.2.1]octan-3-yl]-N-methyl-5-[4-(1H-pyrazol-4-yl)phenyl][1,3]thiazolo[5,4-d][1,3]thiazol-2-amine trifluoroacetate |
| 142 | N-[(1R,3s,5S)-1,5-dimethyl-8-azabicyclo[3.2.1]octan-3-yl]-N-methyl-5-[5-(1H-pyrazol-4-yl)pyrazin-2-yl][1,3]thiazolo[5,4-d][1,3]thiazol-2-amine trifluoroacetate |
| 143 | 2-[5-(1H-pyrazol-4-yl)pyrazin-2-yl]-5-[(2,2,6,6-tetramethylpiperidin-4-yl)oxy][1,3]thiazolo[5,4-d][1,3]thiazole trifluoroacetate |
| 144 | 3-(5-{[(1R,3s,5S)-1,5-dimethyl-8-azabicyclo[3.2.1]octan-3-yl](methyl)amino}[1,3]thiazolo[5,4-d][1,3]thiazol-2-yl)-6-(1H-pyrazol-4-yl)pyrimidin-4(3H)-one trifluoroacetate |
| 145 | 2-{5-[methyl(octahydroindolizin-7-yl)amino][1,3]thiazolo[5,4-d][1,3]thiazol-2-yl}-5-(1H-pyrazol-4-yl)pyridin-3-ol trifluoroacetate |
| 146 | 1-(5-{[(1R,3s,5S)-1,5-dimethyl-8-azabicyclo[3.2.1]octan-3-yl](methyl)amino}[1,3]thiazolo[5,4-d][1,3]thiazol-2-yl)-4-(1H-pyrazol-4-yl)pyridin-2(1H)-one hydrochloride |
| 147 | 2-{5-[3-(tert-butylamino)pyrrolidin-1-yl][1,3]thiazolo[5,4-d][1,3]thiazol-2-yl}-5-(1H-pyrazol-4-yl)phenol hydrochloride |
| 148 | 1-(5-{[(1R,3s,5S)-1,5-dimethyl-8-azabicyclo[3.2.1]octan-3-yl](methyl)amino}[1,3]thiazolo[5,4-d][1,3]thiazol-2-yl)-4-(4-fluoro-1H-pyrazol-1-yl)pyridin-2(1H)-one hydrochloride |
| 149 | 1-(5-{[(1R,3s,5S)-8-azabicyclo[3.2.1]octan-3-yl](methyl)amino}[1,3]thiazolo[5,4-d][1,3]thiazol-2-yl)-4-(4-fluoro-1H-pyrazol-1-yl)pyridin-2(1H)-one hydrochloride |
| 150 | N-tert-butyl-1-{5-[5-(1H-pyrazol-4-yl)pyrimidin-2-yl][1,3]thiazolo[5,4-d][1,3]thiazol-2-yl}pyrrolidin-3-amine hydrochloride |
| 151 | 1-{5-[3-(tert-butylamino)pyrrolidin-1-yl][1,3]thiazolo[5,4-d][1,3]thiazol-2-yl}-4-(1H-pyrazol-4-yl)pyridin-2(1H)-one hydrochloride |
| 152 | N-(1,2-dimethylpiperidin-4-yl)-N-methyl-5-[4-(1H-pyrazol-4-yl)-1H-pyrrolo[2,3-c]pyridin-7-yl][1,3]thiazolo[5,4-d][1,3]thiazol-2-amine hydrochloride |
| 153 | 3-(5-{methyl[(1R,3s,5S)-8-methyl-8-azabicyclo[3.2.1]octan-3-yl]amino}[1,3]thiazolo[5,4-d][1,3]thiazol-2-yl)-6-(1H-pyrazol-4-yl)pyrimidin-4(3H)-one hydrochloride |
| 154 | N-[(1R,3s,5S)-1,5-dimethyl-8-azabicyclo[3.2.1]octan-3-yl]-N-methyl-5-[4-(1H-pyrazol-4-yl)-1H-pyrrolo[2,3-c]pyridin-7-yl][1,3]thiazolo[5,4-d][1,3]thiazol-2-amine hydrochloride |
| 155 | 1-(5-{methyl[(3R)-piperidin-3-yl]amino}[1,3]thiazolo[5,4-d][1,3]thiazol-2-yl)-4-(1H-pyrazol-4-yl)pyridin-2(1H)-one hydrochloride |
| 156 | 4-(1H-pyrazol-4-yl)-1-{5-[(2,2,6,6-tetramethylpiperidin-4-yl)oxy][1,3]thiazolo[5,4-d][1,3]thiazol-2-yl}pyridin-2(1H)-one hydrochloride |
| 157 | 1-{5-[(1,2-dimethylpiperidin-4-yl)(methyl)amino][1,3]thiazolo[5,4-d][1,3]thiazol-2-yl}-1H-pyrrolo[2,3-b]pyridin-6-ol hydrochloride |
| 158 | N-[(1R,3s,5S)-8-azabicyclo[3.2.1]octan-3-yl]-5-[2,5-difluoro-4-(1H-pyrazol-4-yl)phenyl]-N-methyl[1,3]thiazolo[5,4-d][1,3]thiazol-2-amine formate |
| 159 | N-methyl-5-[4-(1H-pyrazol-4-yl)-1H-pyrrolo[2,3-c]pyridin-7-yl]-N-(2,2,6,6-tetramethylpiperidin-4-yl)[1,3]thiazolo[5,4-d][1,3]thiazol-2-amine hydrochloride |
| 160 | N-[(1R,3s,5S)-8-azabicyclo[3.2.1]octan-3-yl]-N-methyl-5-(1H-pyrrolo[2,3-c]pyridin-7-yl)[1,3]thiazolo[5,4-d][1,3]thiazol-2-amine hydrochloride |
| 161 | N-methyl-N-[(3S)-piperidin-3-yl]-5-[5-(1H-pyrazol-4-yl)pyrimidin-2-yl][1,3]thiazolo[5,4-d][1,3]thiazol-2-amine hydrochloride |

-continued

| Cpd | Name |
|---|---|
| 162 | N-methyl-5-[5-(1H-pyrazol-4-yl)pyrimidin-2-yl]-N-(2,2,6,6-tetramethylpiperidin-4-yl)[1,3]thiazolo[5,4-d][1,3]thiazol-2-amine hydrochloride |
| 163 | N-methyl-5-[5-(1H-pyrazol-4-yl)pyrazin-2-yl]-N-(2,2,6,6-tetramethylpiperidin-4-yl)[1,3]thiazolo[5,4-d][1,3]thiazol-2-amine hydrochloride |
| 164 | N-[(1R,3s,5S)-8-azabicyclo[3.2.1]octan-3-yl]-N-methyl-5-[5-(1H-pyrazol-4-yl)pyrazin-2-yl][1,3]thiazolo[5,4-d][1,3]thiazol-2-amine hydrochloride |
| 167 | N-methyl-5-[6-(1H-pyrazol-4-yl)pyridazin-3-yl]-N-(2,2,6,6-tetramethylpiperidin-4-yl)[1,3]thiazolo[5,4-d][1,3]thiazol-2-amine hydrochloride |
| 168 | N-[(1R,3s,5S)-8-azabicyclo[3.2.1]octan-3-yl]-N-methyl-5-[6-(1H-pyrazol-4-yl)pyridazin-3-yl][1,3]thiazolo[5,4-d][1,3]thiazol-2-amine hydrochloride |
| 169 | 1-(5-{methyl[(3S)-piperidin-3-yl]amino}[1,3]thiazolo[5,4-d][1,3]thiazol-2-yl)-4-(1H-pyrazol-4-yl)pyridin-2(1H)-one hydrochloride |
| 170 | N-[(1R,3s,5S)-8-azabicyclo[3.2.1]octan-3-yl]-N-methyl-5-[4-(1H-pyrazol-4-yl)-1H-imidazol-1-yl][1,3]thiazolo[5,4-d][1,3]thiazol-2-amine hydrochloride |
| 171 | 1-(5-{[(1R,3s,5S)-8-azabicyclo[3.2.1]octan-3-yl](methyl)amino}[1,3]thiazolo[5,4-d][1,3]thiazol-2-yl)-4-bromopyridin-2(1H)-one hydrochloride |
| 172 | 3-(5-{[(1R,3s,5S)-8-azabicyclo[3.2.1]octan-3-yl](methyl)amino}[1,3]thiazolo[5,4-d][1,3]thiazol-2-yl)-6-(1H-pyrazol-4-yl)pyrimidin-4(3H)-one hydrochloride |
| 173 | N-[(1R,3s,5S)-8-azabicyclo[3.2.1]octan-3-yl]-N-methyl-5-[6-(1H-pyrazol-4-yl)pyridin-3-yl][1,3]thiazolo[5,4-d][1,3]thiazol-2-amine hydrochloride |
| 174 | N-[(1R,3s,5S)-8-azabicyclo[3.2.1]octan-3-yl]-N-methyl-5-[5-(1H-pyrazol-4-yl)pyridin-2-yl][1,3]thiazolo[5,4-d][1,3]thiazol-2-amine hydrochloride |
| 175 | N-[(1R,3s,5S)-8-azabicyclo[3.2.1]octan-3-yl]-N-methyl-5-[2-(1H-pyrazol-4-yl)pyrimidin-5-yl][1,3]thiazolo[5,4-d][1,3]thiazol-2-amine hydrochloride |
| 176 | 5-[5-(2,7-diazaspiro[3.5]nonan-2-yl)[1,3]thiazolo[5,4-d][1,3]thiazol-2-yl]-7-fluoro-2-methyl-2H-indazole hydrochloride |
| 177 | 2-{5-[2,5-difluoro-4-(1H-pyrazol-4-yl)phenyl][1,3]thiazolo[5,4-d][1,3]thiazol-2-yl}-2,7-diazaspiro[3.5]nonane hydrochloride |
| 179 | 2-[5-(7-methyl-1,7-diazaspiro[3.5]nonan-1-yl)[1,3]thiazolo[5,4-d][1,3]thiazol-2-yl]-5-(1H-pyrazol-4-yl)pyridin-3-ol hydrochloride |
| 182 | 2-{5-[(1,2-dimethylpiperidin-4-yl)(methyl)amino][1,3]thiazolo[5,4-d][1,3]thiazol-2-yl}-5-(1H-pyrazol-4-yl)pyridin-3-ol hydrochloride |
| 183 | N-[(1R,3s,5S)-8-azabicyclo[3.2.1]octan-3-yl]-N-methyl-5-[4-(1H-pyrazol-4-yl)-1H-indol-7-yl][1,3]thiazolo[5,4-d][1,3]thiazol-2-amine hydrochloride |
| 184 | N-[(1R,3s,5S)-8-azabicyclo[3.2.1]octan-3-yl]-N-methyl-5-[4-(1H-pyrazol-4-yl)-1H-pyrrolo[2,3-c]pyridin-7-yl][1,3]thiazolo[5,4-d][1,3]thiazol-2-amine hydrochloride |
| 185 | 2-(5-{[(1R,3s,5S)-8-azabicyclo[3.2.1]octan-3-yl](methyl)amino}[1,3]thiazolo[5,4-d][1,3]thiazol-2-yl)-5-bromopyridin-3-ol hydrochloride |
| 186 | N-[(1R,3s,5S)-8-azabicyclo[3.2.1]octan-3-yl]-5-(5-bromopyrimidin-2-yl)-N-methyl[1,3]thiazolo[5,4-d][1,3]thiazol-2-amine hydrochloride |
| 187 | 1-(5-{[(1R,3s,5S)-8-azabicyclo[3.2.1]octan-3-yl](methyl)amino}[1,3]thiazolo[5,4-d][1,3]thiazol-2-yl)pyridin-2(1H)-one hydrochloride |
| 188 | 1-{5-[methyl(piperidin-4-yl)amino][1,3]thiazolo[5,4-d][1,3]thiazol-2-yl}-4-(1H-pyrazol-4-yl)pyridin-2(1H)-one hydrochloride |
| 189 | 2-[5-(1,7-diazaspiro[3.5]nonan-1-yl)[1,3]thiazolo[5,4-d][1,3]thiazol-2-yl]-5-(1H-pyrazol-4-yl)pyridin-3-ol hydrochloride |
| 190 | 2-(5-{[(1R,3s,5S)-8-azabicyclo[3.2.1]octan-3-yl](methyl)amino}[1,3]thiazolo[5,4-d][1,3]thiazol-2-yl)-5-(4-methyl-1H-pyrazol-1-yl)pyridin-3-ol hydrochloride |
| 191 | 6-(5-{[(1R,3s,5S)-8-azabicyclo[3.2.1]octan-3-yl](methyl)amino}[1,3]thiazolo[5,4-d][1,3]thiazol-2-yl)-5-hydroxy-1'-methyl[3,4'-bipyridin]-2'(1'H)-one hydrochloride |
| 192 | 2-[5-(2,6-diazaspiro[3.5]nonan-2-yl)[1,3]thiazolo[5,4-d][1,3]thiazol-2-yl]-5-(1H-pyrazol-4-yl)pyridin-3-ol hydrochloride |
| 193 | 2-(5-{[(1R,3s,5S)-8-azabicyclo[3.2.1]octan-3-yl](methyl)amino}[1,3]thiazolo[5,4-d][1,3]thiazol-2-yl)-5-(4-fluoro-1H-pyrazol-1-yl)pyridin-3-ol hydrochloride |
| 194 | N-[(1R,3s,5S)-8-azabicyclo[3.2.1]octan-3-yl]-N-methyl-5-[5-(1H-pyrazol-4-yl)pyrimidin-2-yl][1,3]thiazolo[5,4-d][1,3]thiazol-2-amine hydrochloride |
| 195 | 1-(5-{[(1R,3s,5S)-8-azabicyclo[3.2.1]octan-3-yl](methyl)amino}[1,3]thiazolo[5,4-d][1,3]thiazol-2-yl)-4-(1H-pyrazol-4-yl)pyridin-2(1H)-one hydrochloride |
| 196 | 2-[5-(7-methyl-2,7-diazaspiro[3.5]nonan-2-yl)[1,3]thiazolo[5,4-d][1,3]thiazol-2-yl]-5-(1H-pyrazol-4-yl)pyridin-3-ol hydrochloride |
| 197 | 5-(1H-pyrazol-4-yl)-2-[5-(spiro[8-azabicyclo[3.2.1]octane-3,3'-azetidin]-1'-yl)[1,3]thiazolo[5,4-d][1,3]thiazol-2-yl]pyridin-3-ol hydrochloride |
| 198 | 5-(1H-pyrazol-4-yl)-2-[5-(spiro[8-azabicyclo[3.2.1]octane-3,3'-azetidin]-1'-yl)[1,3]thiazolo[5,4-d][1,3]thiazol-2-yl]phenol hydrochloride |
| 199 | 2-(5-{[(1R,3s,5S)-8-azabicyclo[3.2.1]octan-3-yl](methyl)amino}[1,3]thiazolo[5,4-d][1,3]thiazol-2-yl)-5-(2-methyl-1,3-thiazol-5-yl)pyridin-3-ol dihydrochloride |
| 200 | 5-[2-methoxy-4-(1H-pyrazol-4-yl)phenyl]-N-methyl-N-(piperidin-4-yl)[1,3]thiazolo[5,4-d][1,3]thiazol-2-amine hydrochloride |
| 201 | N-methyl-N-(piperidin-4-yl)-5-[5-(1H-pyrazol-4-yl)pyrimidin-2-yl][1,3]thiazolo[5,4-d][1,3]thiazol-2-amine hydrochloride |
| 202 | 2-(5-{[(2R,4S)-2-(hydroxymethyl)piperidin-4-yl](methyl)amino}[1,3]thiazolo[5,4-d][1,3]thiazol-2-yl)-5-(1H-pyrazol-4-yl)phenol dihydrochloride |
| 203 | 2-(5-{[(1R,3s,5S)-8-azabicyclo[3.2.1]octan-3-yl](methyl)amino}[1,3]thiazolo[5,4-d][1,3]thiazol-2-yl)-5-(1H-pyrazol-4-yl)pyridin-3-ol dihydrochloride |
| 204 | 2-{5-[(1-cyclopropylpiperidin-4-yl)(methyl)amino][1,3]thiazolo[5,4-d][1,3]thiazol-2-yl}-5-(1H-pyrazol-4-yl)pyridin-3-ol hydrochloride |

-continued

| Cpd | Name |
|---|---|
| 205 | 2-(5-{methyl[1-(propan-2-yl)piperidin-4-yl]amino}[1,3]thiazolo[5,4-d][1,3]thiazol-2-yl)-5-(1H-pyrazol-4-yl)pyridin-3-ol hydrochloride |
| 206 | 2-{5-[methyl(1-propylpiperidin-4-yl)amino][1,3]thiazolo[5,4-d][1,3]thiazol-2-yl}-5-(1H-pyrazol-4-yl)pyridin-3-ol hydrochloride |
| 207 | 2-{5-[(1-ethylpiperidin-4-yl)(methyl)amino][1,3]thiazolo[5,4-d][1,3]thiazol-2-yl}-5-(1H-pyrazol-4-yl)pyridin-3-ol hydrochloride |
| 208 | 2-[5-(piperidin-4-yl)[1,3]thiazolo[5,4-d][1,3]thiazol-2-yl]-5-(1H-pyrazol-4-yl)phenol dihydrochloride |
| 209 | 2-[5-(2,7-diazaspiro[3.5]nonan-2-yl)[1,3]thiazolo[5,4-d][1,3]thiazol-2-yl]-5-(1H-pyrazol-4-yl)pyridin-3-ol hydrochloride |
| 210 | 2-{5-[methyl(piperidin-4-yl)amino][1,3]thiazolo[5,4-d][1,3]thiazol-2-yl}-5-([1,2,4]triazolo[4,3-a]pyridin-6-yl)pyridin-3-ol hydrochloride |
| 211 | 2-{5-[(3aR,6aS)-5-methylhexahydropyrrolo[3,4-c]pyrrol-2(1H)-yl][1,3]thiazolo[5,4-d][1,3]thiazol-2-yl}-5-(1H-pyrazol-4-yl)phenol dihydrochloride |
| 212 | 2-{5-[methyl(piperidin-4-yl)amino][1,3]thiazolo[5,4-d][1,3]thiazol-2-yl}-5-(1H-1,2,4-triazol-1-yl)pyridin-3-ol hydrochloride |
| 213 | 2-(5-{methyl[(3S)-pyrrolidin-3-yl]amino}[1,3]thiazolo[5,4-d][1,3]thiazol-2-yl)-5-(1H-pyrazol-4-yl)pyridin-3-ol hydrochloride |
| 214 | 2-{5-[methyl(piperidin-4-yl)amino][1,3]thiazolo[5,4-d][1,3]thiazol-2-yl}-5-(2H-1,2,3-triazol-2-yl)pyridin-3-ol trifluoroacetate |
| 215 | 2-{5-[methyl(piperidin-4-yl)amino][1,3]thiazolo[5,4-d][1,3]thiazol-2-yl}-5-(1H-1,2,3-triazol-1-yl)pyridin-3-ol trifluoroacetate |
| 216 | 2-{5-[methyl(piperidin-4-yl)amino][1,3]thiazolo[5,4-d][1,3]thiazol-2-yl}-5-(1,2-thiazol-4-yl)pyridin-3-ol hydrochloride |
| 217 | 2-{5-[methyl(1-methylpiperidin-4-yl)amino][1,3]thiazolo[5,4-d][1,3]thiazol-2-yl}-5-(1H-pyrazol-4-yl)pyridin-3-ol hydrochloride |
| 218 | 2-{5-[ethyl(1-methylpiperidin-4-yl)amino][1,3]thiazolo[5,4-d][1,3]thiazol-2-yl}-5-(1H-pyrazol-4-yl)pyridin-3-ol hydrochloride |
| 219 | 2-{5-[methyl(piperidin-4-yl)amino][1,3]thiazolo[5,4-d][1,3]thiazol-2-yl}-5-(3-methyl-1H-pyrazol-4-yl)pyridin-3-ol hydrochloride |
| 220 | 5-(5-chloro-1H-pyrazol-4-yl)-2-{5-[methyl(piperidin-4-yl)amino][1,3]thiazolo[5,4-d][1,3]thiazol-2-yl}pyridin-3-ol hydrochloride |
| 221 | 5-(4-methyl-1H-imidazol-1-yl)-2-{5-[methyl(piperidin-4-yl)amino][1,3]thiazolo[5,4-d][1,3]thiazol-2-yl}pyridin-3-ol hydrochloride |
| 222 | 2-{5-[methyl(piperidin-4-yl)amino][1,3]thiazolo[5,4-d][1,3]thiazol-2-yl}-5-(2-methyl-1,3-thiazol-5-yl)pyridin-3-ol hydrochloride |
| 223 | 5-(2-methyl-1,3-oxazol-5-yl)-2-{5-[methyl(piperidin-4-yl)amino][1,3]thiazolo[5,4-d][1,3]thiazol-2-yl}pyridin-3-ol hydrochloride |
| 224 | 2-{5-[methyl(piperidin-4-yl)amino][1,3]thiazolo[5,4-d][1,3]thiazol-2-yl}-5-(6-methylpyridazin-4-yl)pyridin-3-ol trifluoroacetate |
| 225 | 2-{5-[methyl(piperidin-4-yl)amino][1,3]thiazolo[5,4-d][1,3]thiazol-2-yl}-5-(pyridazin-4-yl)pyridin-3-ol, and trifluoroacetate, and |
| 226 | N-methyl-N-(piperidin-4-yl)-5-[7-(1H-pyrazol-4-yl)-1H-pyrrolo[2,3-c]pyridin-4-yl][1,3]thiazolo[5,4-d][1,3]thiazol-2-amine hydrochloride; | wherein the form of the compound salt is selected from the group consisting of a hydrate, solvate, racemate, enantiomer, diastereomer, stereoisomer, tautomer form thereof.

An aspect of the present description includes a method for preventing, treating or ameliorating D in a subject in need thereof comprising, administering to the subject an effective amount of a compound of Formula (I), Formula (II), Formula (III), or Formula (IV) or a form thereof.

An aspect of the present description includes a method for treating or ameliorating HD in a subject in need thereof comprising, administering to the subject an effective amount of a compound of Formula (I), Formula (II), Formula (III), or Formula (IV) or a form thereof.

Another aspect of the present description includes a method for treating or ameliorating HD in a subject in need thereof comprising, administering to the subject an effective amount of a compound salt of Formula (I), Formula (II), Formula (III), or Formula (IV) or a form thereof.

An aspect of the present description includes a method for use of a compound of Formula (I), Formula (II), Formula (III), or Formula (IV) or a form or composition thereof for treating or ameliorating HD in a subject in need thereof comprising, administering to the subject an effective amount of the compound of Formula (I), Formula (II), Formula (III), or Formula (IV) or a form or composition thereof.

Another aspect of the present description includes a method for use of a compound salt of Formula (I), Formula (II), Formula (III), or Formula (IV) or a form or composition thereof for treating or ameliorating HD in a subject in need thereof comprising, administering to the subject an effective amount of the compound salt of Formula (I), Formula (II), Formula (III), or Formula (IV) or a form thereof.

An aspect of the present description includes a use for a compound of Formula (I), Formula (II), Formula (III), or Formula (IV) or a form thereof for treating or ameliorating HD in a subject in need thereof comprising, administering to the subject an effective amount of the compound of Formula (I), Formula (II), Formula (III), or Formula (IV) or a form thereof.

Another aspect of the present description includes a use for a compound salt of Formula (I), Formula (II), Formula (III), or Formula (IV) or a form thereof for treating or ameliorating HD in a subject in need thereof comprising, administering to the subject an effective amount of the compound salt of Formula (I), Formula (II), Formula (III), or Formula (IV) or a form thereof.

An aspect of the present description includes a use for a compound of Formula (I), Formula (II), Formula (III), or Formula (IV) or a form thereof in the manufacture of a medicament for treating or ameliorating HD in a subject in need thereof comprising, administering to the subject an effective amount of the medicament.

Another aspect of the present description includes a use for a compound salt of Formula (I), Formula (II), Formula (III), or Formula (IV) or a form thereof in the manufacture of a medicament for treating or ameliorating HD in a subject in need thereof comprising, administering to the subject an effective amount of the medicament.

An aspect of the present description includes a use for a compound of Formula (I), Formula (II), Formula (III), or Formula (IV) or a form thereof in a combination product with one or more therapeutic agents for treating or ameliorating HD in a subject in need thereof comprising, administering to the subject an effective amount of the compound of Formula (I), Formula (II), Formula (III), or Formula (IV) or a form thereof in combination with an effective amount of the one or more agents.

Another aspect of the present description includes a use for a compound salt of Formula (I), Formula (II), Formula (III), or Formula (IV) or a form thereof in a combination product with one or more therapeutic agents for treating or ameliorating HD in a subject in need thereof comprising, administering to the subject an effective amount of the compound salt of Formula (I), Formula (II), Formula (III), or Formula (IV) or a form thereof in combination with an effective amount of the one or more agents.

Chemical Definitions

The chemical terms used above and throughout the description herein, unless specifically defined otherwise, shall be understood by one of ordinary skill in the art to have the following indicated meanings.

As used herein, the term "$C_{1-6}$alkyl" generally refers to saturated hydrocarbon radicals having from one to eight carbon atoms in a straight or branched chain configuration, including, but not limited to, methyl, ethyl, n-propyl (also referred to as propyl or propanyl), isopropyl, n-butyl (also referred to as butyl or butanyl), isobutyl, sec-butyl, tert-butyl, n-pentyl (also referred to as pentyl or pentanyl), n-hexyl (also referred to as hexyl or hexanyl), and the like. In certain aspects, $C_{1-6}$alkyl includes, but is not limited to, $C_{1-4}$alkyl and the like. A $C_{1-6}$alkyl radical is optionally substituted with substituent species as described herein where allowed by available valences.

As used herein, the term "$C_{2-8}$alkenyl" generally refers to partially unsaturated hydrocarbon radicals having from two to eight carbon atoms in a straight or branched chain configuration and one or more carbon-carbon double bonds therein, including, but not limited to, ethenyl (also referred to as vinyl), allyl, propenyl and the like. In certain aspects, $C_{2-8}$alkenyl includes, but is not limited to, $C_{2-6}$alkenyl, $C_{2-4}$alkenyl and the like. A $C_{2-8}$alkenyl radical is optionally substituted with substituent species as described herein where allowed by available valences.

As used herein, the term "$C_{2-8}$alkynyl" generally refers to partially unsaturated hydrocarbon radicals having from two to eight carbon atoms in a straight or branched chain configuration and one or more carbon-carbon triple bonds therein, including, but not limited to, ethynyl, propynyl, butynyl and the like. In certain aspects, $C_{2-8}$alkynyl includes, but is not limited to, $C_{2-6}$alkynyl, $C_{2-4}$alkynyl and the like. A $C_{2-8}$alkynyl radical is optionally substituted with substituent species as described herein where allowed by available valences.

As used herein, the term "$C_{1-6}$alkoxy" generally refers to saturated hydrocarbon radicals having from one to eight carbon atoms in a straight or branched chain configuration of the formula: —O—$C_{1-6}$alkyl, including, but not limited to, methoxy, ethoxy, n-propoxy, isopropoxy, n-butoxy, isobutoxy, sec-butoxy, tert-butoxy, n-pentoxy, n-hexoxy and the like. In certain aspects, $C_{1-6}$alkoxy includes, but is not limited to, $C_{1-4}$alkoxy and the like. A $C_{1-6}$alkoxy radical is optionally substituted with substituent species as described herein where allowed by available valences.

As used herein, the term "$C_{3-10}$cycloalkyl" generally refers to a saturated or partially unsaturated monocyclic, bicyclic or polycyclic hydrocarbon radical, including, but not limited to, cyclopropyl, cyclobutyl, cyclopentyl, cyclohexyl, cyclohexenyl, cycloheptyl, cyclooctyl, and the like. In certain aspects, $C_{3-10}$cycloalkyl includes, but is not limited to, $C_{3-8}$cycloalkyl, $C_{5-8}$cycloalkyl, and the like. A $C_{3-10}$cycloalkyl radical is optionally substituted with substituent species as described herein where allowed by available valences.

As used herein, the term "aryl" generally refers to a monocyclic, bicyclic or polycyclic aromatic carbon atom ring structure radical, including, but not limited to, phenyl, naphthyl, anthracenyl, fluorenyl, azulenyl, phenanthrenyl and the like. An aryl radical is optionally substituted with substituent species as described herein where allowed by available valences.

As used herein, the term "heteroaryl" generally refers to a monocyclic, bicyclic or polycyclic aromatic carbon atom ring structure radical in which one or more carbon atom ring members have been replaced, where allowed by structural stability, with one or more heteroatoms, such as an O, S or N atom, including, but not limited to, furanyl, thienyl, pyrrolyl, pyrazolyl, imidazolyl, isoxazolyl, isothiazolyl, oxazolyl, 1,3-thiazolyl, triazolyl, oxadiazolyl, thiadiazolyl, tetrazolyl, pyridinyl, pyrimidinyl, pyrazinyl, pyridazinyl, triazinyl, indolyl, indazolyl, indolizinyl, isoindolyl, benzofuranyl, benzothienyl, benzoimidazolyl, 1,3-benzothiazolyl, 1,3-benzoxazolyl, purinyl, quinolinyl, isoquinolinyl, quinazolinyl, quinoxalinyl, 1,3-diazinyl, 1,2-diazinyl, 1,2-diazolyl, 1,4-diazanaphthalenyl, acridinyl, furo[3,2-b]pyridinyl, furo[3,2-c]pyridinyl, furo[2,3-c]pyridinyl, 6H-thieno[2,3-b]pyrrolyl, thieno[3,2-c]pyridinyl, thieno[2,3-d]pyrimidinyl, 1H-pyrrolo[2,3-b]pyridinyl, 1H-pyrrolo[2,3-c]pyridinyl, 1H-pyrrolo[3,2-b]pyridinyl, pyrrolo[1,2-a]pyrazinyl, pyrrolo[1,2-b]pyridazinyl, pyrazolo[1,5-a]pyridinyl, pyrazolo[1,5-a]pyrazinyl, imidazo[1,2-a]pyridinyl, 3H-imidazo[4,5-b]pyridinyl, imidazo[1,2-a]pyrimidinyl, imidazo[1,2-c]pyrimidinyl, imidazo[1,2-b]pyridazinyl, imidazo[1,2-a]pyrazinyl, imidazo[2,1-b][1,3]thiazolyl, imidazo[2,1-b][1,3,4]thiadiazolyl, [1,2,4]triazolo[1,5-a]pyridinyl, [1,2,4]triazolo[4,3-a]pyridinyl and the like. A heteroaryl radical is optionally substituted on a carbon or nitrogen atom ring member with substituent species as described herein where allowed by available valences.

In certain aspects, the nomenclature for a heteroaryl radical may differ, such as in non-limiting examples where furanyl may also be referred to as furyl, thienyl may also be referred to as thiophenyl, pyridinyl may also be referred to as pyridyl, benzothienyl may also be referred to as benzothiophenyl and 1,3-benzoxazolyl may also be referred to as 1,3-benzooxazolyl.

In certain other aspects, the term for a heteroaryl radical may also include other regioisomers, such as in non-limiting examples where the term pyrrolyl may also include 2H-pyrrolyl, 3H-pyrrolyl and the like, the term pyrazolyl may also include 1H-pyrazolyl and the like, the term imidazolyl may also include 1H-imidazolyl and the like, the term triazolyl may also include 1H-1,2,3-triazolyl and the like, the term oxadiazolyl may also include 1,2,4-oxadiazolyl, 1,3,4-oxadiazolyl and the like, the term tetrazolyl may also include 1H-tetrazolyl, 2H-tetrazolyl and the like, the term indolyl may also include 1H-indolyl and the like, the term indazolyl may also include 1H-indazolyl, 2H-indazolyl and the like, the term benzoimidazolyl may also include 1H-benzoimidazolyl and the term purinyl may also include 9H-purinyl and the like.

As used herein, the term "heterocyclyl" generally refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including, but not limited to, oxiranyl, oxetanyl, azetidinyl, tetrahydrofuranyl, pyrrolinyl, pyrrolidinyl, pyrazolinyl, pyrazolidinyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, pyranyl, dihydro-2H-pyranyl, thiopyranyl, 1,3-dioxanyl, 1,2,5,6-tetrahydropyridinyl, 1,2,3,6-tetrahydropyridinyl, piperidinyl, piperazinyl, morpholinyl, thiomorpholinyl, 1,4-diazepanyl, 1,3-benzodioxolyl, 1,4-benzodioxanyl, 2,3-dihydro-1,4-benzodioxinyl, hexahydropyrrolo[3,4-b]pyrrol-(1H)-yl, (3aS,6aS)-hexahydropyrrolo[3,4-b]pyrrol-(1H)-yl, (3aR,6aR)-hexahydropyrrolo[3,4-b]pyrrol-(1H)-yl, hexahydropyrrolo[3,4-b]pyrrol-(2H)-yl, (3aS,6aS)-hexahydropyrrolo[3,4-b]pyrrol-(2H)-yl, (3aR,6aR)-hexahydropyrrolo[3,4-b]pyrrol-(2H)-yl, hexahydropyrrolo[3,4-c]pyrrol-(1H)-yl, (3aR,6aS)-hexahydropyrrolo[3,4-c]pyrrol-(1H)-yl, (3aR,6aR)-hexahydropyrrolo[3,4-c]pyrrol-(1H)-yl, octahydro-5H-pyrrolo[3,2-c]pyridinyl, octahydro-6H-pyrrolo[3,4-b]pyridinyl, (4aR,7aR)-octahydro-6H-pyrrolo[3,4-b]pyridinyl, (4aS,7aS)-octahydro-6H-pyrrolo[3,4-b]pyridinyl, hexahydropyrrolo[1,2-a]pyrazin-(1H)-yl, (7R,8aS)-hexahydropyrrolo[1,2-a]pyrazin-(1H)-yl, (8aS)-hexahydropyrrolo[1,2-a]pyrazin-(1H)-yl, (8aR)-hexahydropyrrolo[1,2-a]pyrazin-(1H)-yl, (8aS)-octahydropyrrolo[1,2-a]pyrazin-(1H)-yl, (8aR)-octahydropyrrolo[1,2-a]pyrazin-(1H)-yl, hexahydropyrrolo[1,2-a]pyrazin-(2H)-one, octahydro-2H-pyrido[1,2-a]pyrazinyl, 3-azabicyclo[3.1.0]hexyl, (1R,5S)-3-azabicyclo[3.1.0]hexyl, 8-azabicyclo[3.2.1]octyl, (1R,5S)-8-azabicyclo[3.2.1]octyl, 8-azabicyclo[3.2.1]oct-2-enyl, (1R,5S)-8-azabicyclo[3.2.1]oct-2-enyl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]heptyl, 2,5-diazabicyclo[2.2.2]octyl, 3,8-diazabicyclo[3.2.1]octyl, (1R,5S)-3,8-diazabicyclo[3.2.1]octyl, 1,4-diazabicyclo[3.2.2]nonyl, azaspiro[3.3]heptyl, 2,6-diazaspiro[3.3]heptyl, 2,7-diazaspiro[3.5]nonyl, 5,8-diazaspiro[3.5]nonyl, 2,7-diazaspiro[4.4]nonyl, 6,9-diazaspiro[4.5]decyl and the like. A heterocyclyl radical is optionally substituted on a carbon or nitrogen atom ring member with substituent species as described herein where allowed by available valences.

In certain aspects, the nomenclature for a heterocyclyl radical may differ, such as in non-limiting examples where 1,3-benzodioxolyl may also be referred to as benzo[d][1,3]dioxolyl and 2,3-dihydro-1,4-benzodioxinyl may also be referred to as 2,3-dihydrobenzo[b][1,4]dioxinyl.

As used herein, the term "deutero-$C_{1-4}$alkyl," refers to a radical of the formula: —$C_{1-4}$alkyl-deutero, wherein $C_{1-4}$alkyl is partially or completely substituted with one or more deuterium atoms where allowed by available valences.

As used herein, the term "$C_{1-6}$alkoxy-$C_{1-6}$alkyl" refers to a radical of the formula: —$C_{1-6}$alkyl-O—$C_{1-6}$alkyl.

As used herein, the term "$C_{1-6}$alkoxy-carbonyl" refers to a radical of the formula: —C(O)—O—$C_{1-6}$alkyl.

As used herein, the term "$C_{1-6}$alkyl-amino" refers to a radical of the formula: —NH—$C_{1-6}$alkyl.

As used herein, the term "($C_{1-6}$alkyl)$_2$-amino" refers to a radical of the formula: —N($C_{1-6}$alkyl)$_2$.

As used herein, the term "amino-$C_{1-6}$alkyl" refers to a radical of the formula: —$C_{1-6}$alkyl-NH$_2$.

As used herein, the term "halo" or "halogen" generally refers to a halogen atom radical, including fluoro, chloro, bromo and iodo.

As used herein, the term "halo-$C_{1-6}$alkoxy" refers to a radical of the formula: —O—$C_{1-6}$alkyl-halo, wherein $C_{1-6}$alkyl is partially or completely substituted with one or more halogen atoms where allowed by available valences.

As used herein, the term "halo-$C_{1-6}$alkyl" refers to a radical of the formula: —$C_{1-6}$alkyl-halo, wherein $C_{1-6}$alkyl is partially or completely substituted with one or more halogen atoms where allowed by available valences.

As used herein, the term "hydroxy" refers to a radical of the formula: —OH.

As used herein, the term "hydroxy-$C_{1-6}$alkyl" refers to a radical of the formula: —$C_{1-6}$alkyl-OH, wherein $C_{1-6}$alkyl is partially or completely substituted with one or more hydroxy radicals where allowed by available valences.

As used herein, the term "substituent" means positional variables on the atoms of a core molecule that are substituted at a designated atom position, replacing one or more hydrogens on the designated atom, provided that the designated atom's normal valency is not exceeded, and that the substitution results in a stable compound. Combinations of substituents and/or variables are permissible only if such combinations result in stable compounds. A person of ordinary skill in the art should note that any carbon as well as heteroatom with valences that appear to be unsatisfied as described or shown herein is assumed to have a sufficient number of hydrogen atom(s) to satisfy the valences described or shown. In certain instances one or more substituents having a double bond (e.g., "oxo" or "=O") as the point of attachment may be described, shown or listed herein within a substituent group, wherein the structure may only show a single bond as the point of attachment to the core structure of Formula (I), Formula (II), Formula (III), or Formula (IV). A person of ordinary skill in the art would understand that, while only a single bond is shown, a double bond is intended for those substituents.

As used herein, the term "and the like," with reference to the definitions of chemical terms provided herein, means that variations in chemical structures that could be expected by one skilled in the art include, without limitation, isomers (including chain, branching or positional structural isomers), hydration of ring systems (including saturation or partial unsaturation of monocyclic, bicyclic or polycyclic ring structures) and all other variations where allowed by available valences which result in a stable compound.

For the purposes of this description, where one or more substituent variables for a compound of Formula (I), Formula (II), Formula (III), or Formula (IV) or a form thereof encompass functionalities incorporated into a compound of Formula (I), Formula (II), Formula (III), or Formula (IV), each functionality appearing at any location within the disclosed compound may be independently selected, and as appropriate, independently and/or optionally substituted.

As used herein, the terms "independently selected," or "each selected" refer to functional variables in a substituent list that may occur more than once on the structure of Formula (I), Formula (II), Formula (III), or Formula (IV), the pattern of substitution at each occurrence is independent of the pattern at any other occurrence. Further, the use of a generic substituent variable on any formula or structure for a compound described herein is understood to include the replacement of the generic substituent with species substituents that are included within the particular genus, e.g., aryl may be replaced with phenyl or naphthalenyl and the like, and that the resulting compound is to be included within the scope of the compounds described herein.

As used herein, the terms "each instance of" or "in each instance, when present," when used preceding a phrase such as " . . . $C_{3-10}$cycloalkyl, $C_{3-10}$cycloalkyl-$C_{1-4}$alkyl, aryl, aryl-$C_{1-4}$alkyl, heteroaryl, heteroaryl-$C_{1-4}$alkyl, heterocyclyl and heterocyclyl-$C_{1-4}$alkyl," are intended to refer to the $C_{3-10}$cycloalkyl, aryl, heteroaryl and heterocyclyl ring systems when each are present either alone or as a substituent.

As used herein, the term "optionally substituted" means optional substitution with the specified substituent variables, groups, radicals or moieties.

Compound Forms

As used herein, the term "form" means a compound of Formula (I), Formula (II), Formula (III), or Formula (IV) having a form selected from the group consisting of a free acid, free base, prodrug, salt, hydrate, solvate, clathrate, isotopologue, racemate, enantiomer, diastereomer, stereoisomer, polymorph and tautomer form thereof.

In certain aspects described herein, the form of the compound of Formula (I), Formula (II), Formula (III), or Formula (IV) is a free acid, free base or salt thereof.

In certain aspects described herein, the form of the compound of Formula (I), Formula (II), Formula (III), or Formula (IV) is a salt thereof.

In certain aspects described herein, the form of the compound of Formula (I), Formula (II), Formula (III), or Formula (IV) is an isotopologue thereof.

In certain aspects described herein, the form of the compound of Formula (I), Formula (II), Formula (III), or Formula (IV) is a stereoisomer, racemate, enantiomer or diastereomer thereof.

In certain aspects described herein, the form of the compound of Formula (I), Formula (II), Formula (III), or Formula (IV) is a tautomer thereof.

In certain aspects described herein, the form of the compound of Formula (I), Formula (II), Formula (III), or Formula (IV) is a pharmaceutically acceptable form.

In certain aspects described herein, the compound of Formula (I), Formula (II), Formula (III), or Formula (IV) or a form thereof is isolated for use.

As used herein, the term "isolated" means the physical state of a compound of Formula (I), Formula (II), Formula (III), or Formula (IV) or a form thereof after being isolated and/or purified from a synthetic process (e.g., from a reaction mixture) or natural source or combination thereof according to an isolation or purification process or processes described herein or which are well known to the skilled artisan (e.g., chromatography, recrystallization and the like) in sufficient purity to be characterized by standard analytical techniques described herein or well known to the skilled artisan.

As used herein, the term "protected" means that a functional group in a compound of Formula (I), Formula (II), Formula (III), or Formula (IV) or a form thereof is in a form modified to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York. Such functional groups include hydroxy, phenol, amino and carboxylic acid. Suitable protecting groups for hydroxy or phenol include trialkylsilyl or diarylalkylsilyl (e.g., t-butyldimethylsilyl, t-butyldiphenylsilyl or trimethylsilyl), tetrahydropyranyl, benzyl, substituted benzyl, methyl, methoxymethanol, and the like. Suitable protecting groups for amino, amidino and guanidino include t-butoxycarbonyl, benzyloxycarbonyl, and the like. Suitable protecting groups for carboxylic acid include alkyl, aryl or arylalkyl esters. In certain instances, the protecting group may also be a polymer resin, such as a Wang resin or a 2-chlorotrityl-chloride resin. Protecting groups may be added or removed in accordance with standard techniques, which are well-known to those skilled in the art and as described herein. It will also be appreciated by those skilled in the art, although such protected derivatives of compounds described herein may not possess pharmacological activity as such, they may be administered to a subject and thereafter metabolized in the body to form compounds described herein which are pharmacologically active. Such derivatives may therefore be described as "prodrugs". All prodrugs of compounds described herein are included within the scope of the use described herein.

As used herein, the term "prodrug" means a form of an instant compound (e.g., a drug precursor) that is transformed in vivo to yield an active compound of Formula (I), Formula (II), Formula (III), or Formula (IV) or a form thereof. The transformation may occur by various mechanisms (e.g., by metabolic and/or non-metabolic chemical processes), such as, for example, by hydrolysis and/or metabolism in blood, liver and/or other organs and tissues. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

In one example, when a compound of Formula (I), Formula (II), Formula (III), or Formula (IV) or a form thereof contains a carboxylic acid functional group, a prodrug can comprise an ester formed by the replacement of the hydrogen atom of the acid group with a functional group such as alkyl and the like. In another example, when a compound of Formula (I), Formula (II), Formula (III), or Formula (IV) or a form thereof contains a hydroxyl functional group, a prodrug form can be prepared by replacing the hydrogen atom of the hydroxyl with another functional group such as alkyl, alkylcarbonyl or a phosphonate ester and the like. In another example, when a compound of Formula (I), Formula (II), Formula (III), or Formula (IV) or a form thereof contains an amine functional group, a prodrug form can be prepared by replacing one or more amine hydrogen atoms with a functional group such as alkyl or substituted carbonyl. Pharmaceutically acceptable prodrugs of compounds of Formula (I), Formula (II), Formula (III), or Formula (IV) or a form thereof include those compounds substituted with one or more of the following groups: carboxylic acid esters, sulfonate esters, amino acid esters, phosphonate esters and mono-, di- or triphosphate esters or alkyl substituents, where appropriate. As described herein, it is understood by a person of ordinary skill in the art that one or more of such substituents may be used to provide a compound of Formula (I), Formula (II), Formula (III), or Formula (IV) or a form thereof as a prodrug.

One or more compounds described herein may exist in unsolvated as well as solvated forms with pharmaceutically acceptable solvents such as water, ethanol, and the like, and the description herein is intended to embrace both solvated and unsolvated forms.

As used herein, the term "solvate" means a physical association of a compound described herein with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates. Non-limiting examples of suitable solvates include ethanolates, methanolates, and the like.

As used herein, the term "hydrate" means a solvate wherein the solvent molecule is water.

The compounds of Formula (I), Formula (II), Formula (III), or Formula (IV) can form salts, which are intended to be included within the scope of this description. Reference to a compound of Formula (I), Formula (II), Formula (III), or Formula (IV) or a form thereof herein is understood to include reference to salt forms thereof, unless otherwise indicated. The term "salt(s)", as employed herein, denotes acidic salts formed with inorganic and/or organic acids, as well as basic salts formed with inorganic and/or organic bases. In addition, when a compound of Formula (I), Formula (II), Formula (III), or Formula (IV) or a form thereof contains both a basic moiety, such as, without limitation an amine moiety, and an acidic moiety, such as, but not limited to a carboxylic acid, zwitterions ("inner salts") may be formed and are included within the term "salt(s)" as used herein.

The term "pharmaceutically acceptable salt(s)", as used herein, means those salts of compounds described herein that are safe and effective (i.e., non-toxic, physiologically acceptable) for use in mammals and that possess biological activity, although other salts are also useful. Salts of the compounds of the Formula (I), Formula (II), Formula (III), or Formula (IV) may be formed, for example, by reacting a compound of Formula (I), Formula (II), Formula (III), or Formula (IV) or a form thereof with an amount of acid or base, such as an equivalent amount, in a medium such as one in which the salt precipitates or in an aqueous medium followed by lyophilization.

Pharmaceutically acceptable salts include one or more salts of acidic or basic groups present in compounds described herein. Particular aspects of acid addition salts include, and are not limited to, acetate, ascorbate, benzoate, benzenesulfonate, bisulfate, bitartrate, borate, bromide, butyrate, chloride, citrate, camphorate, camphorsulfonate, ethanesulfonate, formate, fumarate, gentisinate, gluconate, glucaronate, glutamate, iodide, isonicotinate, lactate, maleate, methanesulfonate, naphthalenesulfonate, nitrate, oxalate, pamoate, pantothenate, phosphate, propionate, saccharate, salicylate, succinate, sulfate, tartrate, thiocyanate, toluenesulfonate (also known as tosylate), trifluoroacetate salts and the like. Certain particular aspects of acid addition salts include chloride or dichloride.

Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J.* *of Pharmaceutics* (1986) 33, 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Suitable basic salts include, but are not limited to, aluminum, ammonium, calcium, lithium, magnesium, potassium, sodium and zinc salts.

All such acid salts and base salts are intended to be included within the scope of pharmaceutically acceptable salts as described herein. In addition, all such acid and base salts are considered equivalent to the free forms of the corresponding compounds for purposes of this description.

Compounds of Formula (I), Formula (II), Formula (III), or Formula (IV) and forms thereof, may further exist in a tautomeric form. All such tautomeric forms are contemplated and intended to be included within the scope of the compounds of Formula (I), Formula (II), Formula (III), or Formula (IV) or a form thereof as described herein.

The compounds of Formula (I), Formula (II), Formula (III), or Formula (IV) or a form thereof may contain asymmetric or chiral centers, and, therefore, exist in different stereoisomeric forms. The present description is intended to include all stereoisomeric forms of the compounds of Formula (I), Formula (II), Formula (III), or Formula (IV) as well as mixtures thereof, including racemic mixtures.

The compounds described herein may include one or more chiral centers, and as such may exist as racemic mixtures (R/S) or as substantially pure enantiomers and diastereomers. The compounds may also exist as substantially pure (R) or (S) enantiomers (when one chiral center is present). In one particular aspect, the compounds described herein are (S) isomers and may exist as enantiomerically pure compositions substantially comprising only the (S) isomer. In another particular aspect, the compounds described herein are (R) isomers and may exist as enantiomerically pure compositions substantially comprising only the (R) isomer. As one of skill in the art will recognize, when more than one chiral center is present, the compounds described herein may also exist as a (R,R), (R,S), (S,R) or (S,S) isomer, as defined by IUPAC Nomenclature Recommendations.

As used herein, the term "substantially pure" refers to compounds consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

In one aspect of the description, a compound of Formula (I), Formula (II), Formula (III), or Formula (IV) or a form thereof is a substantially pure (S) enantiomer form present in an amount greater than or equal to 90%, in an amount greater than or equal to 92%, in an amount greater than or equal to 95%, in an amount greater than or equal to 98%, in an amount greater than or equal to 99%, or in an amount equal to 100%.

In one aspect of the description, a compound of Formula (I), Formula (II), Formula (III), or Formula (IV) or a form thereof is a substantially pure (R) enantiomer form present in an amount greater than or equal to 90%, in an amount greater than or equal to 92%, in an amount greater than or equal to 95%, in an amount greater than or equal to 98%, in an amount greater than or equal to 99%, or in an amount equal to 100%.

As used herein, a "racemate" is any mixture of isometric forms that are not "enantiomerically pure", including mixtures such as, without limitation, in a ratio of about 50/50, about 60/40, about 70/30, or about 80/20.

In addition, the present description embraces all geometric and positional isomers. For example, if a compound of Formula (I), Formula (II), Formula (III), or Formula (IV) or a form thereof incorporates a double bond or a fused ring, both the cis- and trans-forms, as well as mixtures, are embraced within the scope of the description. Diastereomeric mixtures can be separated into their individual diastereomers on the basis of their physical chemical differences by methods well known to those skilled in the art, such as, for example, by chromatography and/or fractional crystallization. Enantiomers can be separated by use of chiral HPLC column or other chromatographic methods known to those skilled in the art. Enantiomers can also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I), Formula (II), Formula (III), or Formula (IV) may be atropisomers (e.g., substituted biaryls) and are considered as part of this description.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this description, as are positional isomers (such as, for example, 4-pyridyl and 3-pyridyl). Individual stereoisomers of the compounds described herein may, for example, be substantially free of other isomers, or may be present in a racemic mixture, as described supra.

The use of the terms "salt", "solvate", "ester", "prodrug" and the like, is intended to equally apply to the salt, solvate, ester and prodrug of enantiomers, stereoisomers, rotamers, tautomers, positional isomers, racemates or isotopologues of the instant compounds.

The term "isotopologue" refers to isotopically-enriched compounds described herein which are identical to those recited herein, but for the fact that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, $^{35}Cl$ and $^{36}Cl$, respectively, each of which are also within the scope of this description.

Certain isotopically-enriched compounds described herein (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances.

Polymorphic crystalline and amorphous forms of the compounds of Formula (I), Formula (II), Formula (III), or Formula (IV) and of the salts, solvates, hydrates, esters and prodrugs of the compounds of Formula (I), Formula (II), Formula (III), or Formula (IV) are further intended to be included in the present description.

Compound Uses

In accordance with the intended scope of the present description, aspects of the present description include compounds that have been identified and have been demonstrated to be useful in selectively preventing, treating or ameliorating HD and have been provided for use for preventing, treating or ameliorating HD.

An aspect of the present description includes a method for preventing, treating or ameliorating HD in a subject in need thereof comprising, administering to the subject an effective amount of a compound of Formula (I), Formula (II), Formula (III), or Formula (IV) or a form thereof.

An aspect of the present description includes a method for treating or ameliorating HD in a subject in need thereof comprising, administering to the subject an effective amount of a compound of Formula (I), Formula (II), Formula (III), or Formula (IV) or a form thereof.

An aspect of the present description includes a method for preventing HD in a subject in need thereof comprising, administering to the subject an effective amount of a compound of Formula (I), Formula (II), Formula (III), or Formula (IV) or a form thereof.

An aspect of the present description includes a method for treating HD in a subject in need thereof comprising, administering to the subject an effective amount of a compound of Formula (I), Formula (II), Formula (III), or Formula (IV) or a form thereof.

An aspect of the present description includes a method for ameliorating HD in a subject in need thereof comprising, administering to the subject an effective amount of a compound of Formula (I), Formula (II), Formula (III), or Formula (IV), or a form thereof.

Another aspect of the present description includes a method for treating or ameliorating HD in a subject in need thereof comprising, administering to the subject an effective amount of a compound salt of Formula (I), Formula (II), Formula (III), or Formula (IV), or a form thereof.

An aspect of the present description includes a method for use of a compound of Formula (I), Formula (II), Formula (III), or Formula (IV), or a form or composition thereof for treating or ameliorating HD in a subject in need thereof comprising, administering to the subject an effective amount of the compound of Formula (I), Formula (II), Formula (III), or Formula (IV), or a form or composition thereof.

Another aspect of the present description includes a method for use of a compound salt of Formula (I), Formula (II), Formula (III), or Formula (IV), or a form or composition thereof for treating or ameliorating HD in a subject in need thereof comprising, administering to the subject an effective amount of the compound salt of Formula (I), Formula (II), Formula (III), or Formula (IV), or a form thereof.

An aspect of the present description includes a use for a compound of Formula (I), Formula (II), Formula (III), or Formula (IV), or a form thereof for treating or ameliorating HD in a subject in need thereof comprising, administering to the subject an effective amount of the compound of Formula (I), Formula (II), Formula (III), or Formula (IV), or a form thereof.

Another aspect of the present description includes a use for a compound salt of Formula (I), Formula (II), Formula (III), or Formula (IV), or a form thereof for treating or ameliorating HD in a subject in need thereof comprising, administering to the subject an effective amount of the compound salt of Formula (I), Formula (II), Formula (III), or Formula (IV), or a form thereof.

An aspect of the present description includes a use for a compound of Formula (I), Formula (II), Formula (III), or Formula (IV), or a form thereof in the manufacture of a medicament for treating or ameliorating HD in a subject in need thereof comprising, administering to the subject an effective amount of the medicament.

Another aspect of the present description includes a use for a compound salt of Formula (I), Formula (II), Formula (III), or Formula (IV), or a form thereof in the manufacture of a medicament for treating or ameliorating HD in a subject in need thereof comprising, administering to the subject an effective amount of the medicament.

An aspect of the present description includes in vitro or in vivo use of the compound of Formula (I), Formula (II), Formula (III), or Formula (IV), or a form thereof having activity toward HD.

An aspect of the present description includes a use of the compound of Formula (I), Formula (II), Formula (III), or Formula (IV), or a form thereof in a combination therapy to provide additive or synergistic activity, thus enabling the development of a combination product for treating or ameliorating HD.

Another aspect of the present description includes a combination therapy comprising compounds described herein in combination with one or more known drugs or one or more known therapies may be used to treat HD regardless of whether HD is responsive to the known drug.

An aspect of the present description includes a use for a compound of Formula (I), Formula (II), Formula (III), or Formula (IV), or a form thereof in a combination product with one or more therapeutic agents for treating or ameliorating HD in a subject in need thereof comprising, administering to the subject an effective amount of the compound of Formula (I), Formula (II), Formula (III), or Formula (IV), or a form thereof in combination with an effective amount of the one or more agents.

Another aspect of the present description includes a use for a compound salt of Formula (I), Formula (II), Formula (III), or Formula (IV), or a form thereof in a combination product with one or more therapeutic agents for treating or ameliorating HD in a subject in need thereof comprising, administering to the subject an effective amount of the compound salt of Formula (I), Formula (II), Formula (III), or Formula (IV), or a form thereof in combination with an effective amount of the one or more agents.

In an aspect of a use or method provided herein, compounds of Formula (I), Formula (II), Formula (III), or Formula (IV), or a form thereof used in combination with one or more additional agents can be administered to a subject or contacted with a subject or patient cell(s) prior to, concurrently with, or subsequent to administering to the subject or patient or contacting the cell with an additional agent(s). A compound(s) of Formula (I), Formula (II), Formula (III), or Formula (IV), or a form thereof and an additional agent(s) can be administered to a subject or contacted with a cell in single composition or different compositions. In a specific aspect, a compound(s) of Formula (I), Formula (II), Formula (III), or Formula (IV), or a form thereof is used in combination with gene therapy to inhibit HTT expression (using, e.g., viral delivery vectors) or the administration of another small molecule HTT inhibitor. In another specific aspect, a compound(s) of Formula (I), Formula (II), Formula (III), or Formula (IV), or a form thereof are used in combination with cell replacement using differentiated non-mutant HTT stem cells. In another specific aspect, a compound(s) of Formula (I), Formula (II), Formula (III), or Formula (IV), or a form thereof are used in combination with cell replacement using differentiated HTT stem cells.

In one aspect, provided herein is the use of compounds of Formula (I), Formula (II), Formula (III), or Formula (IV), or a form thereof in combination with supportive standard of care therapies, including palliative care.

An aspect of the present description includes a use for a compound of Formula (I), Formula (II), Formula (III), or Formula (IV), or a form thereof in the preparation of a kit for treating or ameliorating HD in a subject in need thereof comprising, the compound of Formula (I), Formula (II), Formula (III), or Formula (IV), or a form thereof and instructions for administering an effective amount of the compound of Formula (I), Formula (II), Formula (III), or Formula (IV), or a form thereof.

An aspect of the present description includes a use for a compound of Formula (I), Formula (II), Formula (III), or Formula (IV), or a form thereof in the preparation of a kit for treating or ameliorating HD in a subject in need thereof comprising, the compound of Formula (I), Formula (II), Formula (III), or Formula (IV), or a form thereof and instructions for administering an effective amount of the compound of Formula (I), Formula (II), Formula (III), or Formula (IV), or a form thereof; and optionally, for administering to the subject an effective amount of the compound of Formula (I), Formula (II), Formula (III), or Formula (IV), or a form thereof in a combination product with an effective amount of one or more therapeutic agents.

An aspect of the present description includes a use for a compound of Formula (I), Formula (II), Formula (III), or Formula (IV), or a form thereof in the preparation of a kit for treating or ameliorating HD in a subject in need thereof comprising, the compound of Formula (I), Formula (II), Formula (III), or Formula (IV), or a form thereof and instructions for administering an effective amount of the compound of Formula (I), Formula (II), Formula (III), or Formula (IV), or a form thereof; and optionally, for administering to the subject an effective amount of the compound of Formula (I), Formula (II), Formula (III), or Formula (IV), or a form thereof in a combination product with an effective amount of the one or more therapeutic agents; and optionally, for administering to the subject an effective amount of the compound of Formula (I), Formula (II), Formula (III), or Formula (IV), or a form thereof in a combination product with an effective amount of the one or more therapeutic agents in a combination therapy with a standard of care supportive therapy, wherein the standard of care supportive therapy is palliative care.

In one respect, for each of such aspects, the subject is treatment naive. In another respect, for each of such aspects, the subject is not treatment naive.

As used herein, the term "preventing" refers to keeping a disease, disorder or condition from occurring in a subject that may be predisposed to the disease, disorder and/or condition but has not yet been diagnosed as having the disease, disorder and/or condition.

As used herein, the term "treating" refers to inhibiting the progression of a disease, disorder or condition in a subject already exhibiting the symptoms of the disease, disorder and/or condition, i.e., arresting the development of a disease, disorder and/or condition that has already affected the subject.

As used herein, the term "ameliorating" refers to relieving the symptoms of a disease, disorder or condition in a subject already exhibiting the symptoms of the disease, disorder and/or condition, i.e., causing regression of the disease, disorder and/or condition that has already affected the subject.

As used herein, the term "subject" refers to an animal or any living organism having sensation and the power of voluntary movement, and which requires oxygen and organic food. Nonlimiting examples include members of the human, primate, equine, porcine, bovine, murine, rattus, canine and feline specie. In certain aspects, the subject is a mammal or a warm-blooded vertebrate animal. In other aspects, the subject is a human. As used herein, the term "patient" may be used interchangeably with "subject" and "human".

As used herein, the terms "effective amount" or "therapeutically effective amount" mean an amount of compound of Formula (I), Formula (II), Formula (III), or Formula (IV), or a form, composition or medicament thereof that achieves a target plasma concentration that is effective in treating or ameliorating HD as described herein and thus producing the desired therapeutic, ameliorative, inhibitory or preventative effect in a subject in need thereof. In one aspect, the effective amount may be the amount required to treat HD in a subject or patient, more specifically, in a human.

In another aspect, the concentration-biological effect relationships observed with regard to a compound of Formula (I), Formula (II), Formula (III), or Formula (IV), or a form thereof indicate a target plasma concentration ranging from approximately 0.001 µg/mL to approximately 50 µg/mL, from approximately 0.01 µg/mL to approximately 20 µg/mL, from approximately 0.05 µg/mL to approximately 10 µg/mL, or from approximately 0.1 µg/mL to approximately 5 µg/mL. To achieve such plasma concentrations, the compounds described herein may be administered at doses that vary, such as, for example, without limitation, from 1.0 ng to 10,000 mg.

In one aspect, the dose administered to achieve an effective target plasma concentration may be administered based upon subject or patient specific factors, wherein the doses administered on a weight basis may be in the range of from about 0.001 mg/kg/day to about 3500 mg/kg/day, or about 0.001 mg/kg/day to about 3000 mg/kg/day, or about 0.001 mg/kg/day to about 2500 mg/kg/day, or about 0.001 mg/kg/day to about 2000 mg/kg/day, or about 0.001 mg/kg/day to about 1500 mg/kg/day, or about 0.001 mg/kg/day to about 1000 mg/kg/day, or about 0.001 mg/kg/day to about 500 mg/kg/day, or about 0.001 mg/kg/day to about 250 mg/kg/day, or about 0.001 mg/kg/day to about 200 mg/kg/day, or about 0.001 mg/kg/day to about 150 mg/kg/day, or about 0.001 mg/kg/day to about 100 mg/kg/day, or about 0.001 mg/kg/day to about 75 mg/kg/day, or about 0.001 mg/kg/day to about 50 mg/kg/day, or about 0.001 mg/kg/day to about 25 mg/kg/day, or about 0.001 mg/kg/day to about 10 mg/kg/day, or about 0.001 mg/kg/day to about 5 mg/kg/day, or about 0.001 mg/kg/day to about 1 mg/kg/day, or about 0.001 mg/kg/day to about 0.5 mg/kg/day, or about 0.001 mg/kg/day to about 0.1 mg/kg/day, or from about 0.01 mg/kg/day to about 3500 mg/kg/day, or about 0.01 mg/kg/day to about 3000 mg/kg/day, or about 0.01 mg/kg/day to about 2500 mg/kg/day, or about 0.01 mg/kg/day to about 2000 mg/kg/day, or about 0.01 mg/kg/day to about 1500 mg/kg/day, or about 0.01 mg/kg/day to about 1000 mg/kg/day, or about 0.01 mg/kg/day to about 500 mg/kg/day, or about 0.01 mg/kg/day to about 250 mg/kg/day, or about 0.01 mg/kg/day to about 200 mg/kg/day, or about 0.01 mg/kg/day to about 150 mg/kg/day, or about 0.01 mg/kg/day to about 100 mg/kg/day, or about 0.01 mg/kg/day to about 75 mg/kg/day, or about 0.01 mg/kg/day to about 50 mg/kg/day, or about 0.01 mg/kg/day to about 25 mg/kg/day, or about 0.01 mg/kg/day to about 10 mg/kg/day, or about 0.01 mg/kg/day to about 5 mg/kg/day, or about 0.01 mg/kg/day to about 1 mg/kg/day, or about 0.01 mg/kg/day to about 0.5 mg/kg/day, or about 0.01 mg/kg/day to about 0.1 mg/kg/day, or from about 0.1 mg/kg/day to about 3500 mg/kg/day, or about 0.1 mg/kg/day to about 3000 mg/kg/day, or about 0.1 mg/kg/day to about 2500 mg/kg/day, or about 0.1 mg/kg/day to about 2000 mg/kg/day, or about 0.1 mg/kg/day to about 1500 mg/kg/day, or about 0.1 mg/kg/day to about 1000 mg/kg/day, or about 0.1 mg/kg/day to about 500 mg/kg/day, or about 0.1 mg/kg/day to about 250 mg/kg/day, or about 0.1 mg/kg/day to about 200 mg/kg/day, or about 0.1 mg/kg/day to about 150 mg/kg/day, or about 0.1 mg/kg/day to about 100 mg/kg/day, or about 0.1 mg/kg/day to about 75 mg/kg/day, or about 0.1 mg/kg/day to about 50 mg/kg/day, or about 0.1 mg/kg/day to about 25 mg/kg/day, or about 0.1 mg/kg/day to about 10 mg/kg/day, or about 0.1 mg/kg/day to about 5 mg/kg/day, or about 0.1 mg/kg/day to about 1 mg/kg/day, or about 0.1 mg/kg/day to about 0.5 mg/kg/day.

Effective amounts for a given subject may be determined by routine experimentation that is within the skill and judgment of a clinician or a practitioner skilled in the art in light of factors related to the subject. Dosage and administration may be adjusted to provide sufficient levels of the active agent(s) or to maintain the desired effect. Factors which may be taken into account include genetic screening, severity of the disease state, status of disease progression, general health of the subject, ethnicity, age, weight, gender, diet, time of day and frequency of administration, drug combination(s), reaction sensitivities, experience with other therapies, and tolerance/response to therapy.

The dose administered to achieve an effective target plasma concentration may be orally administered once (once in approximately a 24 hour period; i.e., "q.d."), twice (once in approximately a 12 hour period; i.e., "b.i.d." or "q.12 h"), thrice (once in approximately an 8 hour period; i.e., "t.i.d." or "q.8 h"), or four times (once in approximately a 6 hour period; i.e., "q.d.s.", "q.i.d." or "q.6 h") daily.

In certain aspects, the dose administered to achieve an effective target plasma concentration may also be administered in a single, divided, or continuous dose for a patient or subject having a weight in a range of between about 40 to about 200 kg (which dose may be adjusted for patients or subjects above or below this range, particularly children under 40 kg). The typical adult subject is expected to have a median weight in a range of about 70 kg. Long-acting pharmaceutical compositions may be administered every 2, 3 or 4 days, once every week, or once every two weeks depending on half-life and clearance rate of the particular formulation.

The compounds and compositions described herein may be administered to the subject via any drug delivery route known in the art. Nonlimiting examples include oral, ocular, rectal, buccal, topical, nasal, sublingual, transdermal, subcutaneous, intramuscular, intravenous (bolus and infusion), intracerebral, and pulmonary routes of administration.

In another aspect, the dose administered may be adjusted based upon a dosage form described herein formulated for delivery at about 0.02, 0.025, 0.03, 0.05, 0.06, 0.075, 0.08, 0.09, 0.10, 0.20, 0.25, 0.30, 0.50, 0.60, 0.75, 0.80, 0.90, 1.0, 1.10, 1.20, 1.25, 1.50, 1.75, 2.0, 3.0, 5.0, 10, 20, 30, 40, 50, 100, 150, 200, 250, 300, 400, 500, 1000, 1500, 2000, 2500, 3000 or 4000 mg/day.

For any compound, the effective amount can be estimated initially either in cell culture assays or in relevant animal models, such as a mouse, guinea pig, chimpanzee, marmoset or tamarin animal model. Relevant animal models may also be used to determine the appropriate concentration range and route of administration. Such information can then be used to determine useful doses and routes for administration in humans. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is therapeutic index, and can be expressed as the ratio, $LD_{50}/ED_{50}$. In certain aspects, the effective amount is such that a large therapeutic index is achieved. In further particular aspects, the dosage is within a range of circulating concentrations that include an $ED_{50}$ with little or no toxicity. The dosage may vary within this range depending upon the dosage form employed, sensitivity of the patient, and the route of administration.

In one aspect, provided herein are methods for modulating the amount of HTT (huntingtin protein), comprising contacting a human cell with a compound of Formula (I), Formula (II), Formula (III), or Formula (IV), or a form thereof. In a specific aspect, provided herein are methods for modulating the amount of HTT, comprising contacting a human cell with a compound of Formula (I), Formula (II), Formula (III), or Formula (IV), or a form thereof that modulates the expression of HTT. The human cell can be contacted with a compound of Formula (I), Formula (II), Formula (III), or Formula (IV), or a form thereof in vitro, or in vivo, e.g., in a non-human animal or in a human. In a specific aspect, the human cell is from or in a human. In another specific aspect, the human cell is from or in a human with HD. In another specific aspect, the human cell is from or in a human with HD, caused by a CAG repeat in the Htt gene, resulting in a loss of HTT expression and/or function. In another aspect, the human cell is from a human with HD. In another aspect, the human cell is in a human with HD. In one aspect, the compound is a form of the compound of Formula (I), Formula (II), Formula (III), or Formula (IV).

In a specific aspect, provided herein is a method for enhancing the inhibition of mutant HTT transcribed from the Htt gene, comprising contacting a human cell with a compound of Formula (I), Formula (II), Formula (III), or Formula (IV), or a form thereof. The human cell can be contacted with a compound of Formula (I) or a form thereof in vitro, or in vivo, e.g., in a non-human animal or in a human. In a specific aspect, the human cell is from or in a human. In another specific aspect, the human cell is from or in a human with HD. In another specific aspect, the human cell is from or in a human with HD, caused by a CAG repeat in the Htt gene, resulting in a loss of wild-type "normal" HTT expression and/or function. In another aspect, the human cell is from a human with HD. In another aspect, the human cell is in a human with HD. In one aspect, the compound is a form of the compound of Formula (I), Formula (II), Formula (III), or Formula (IV).

In another aspect, provided herein is a method for modulating the inhibition of mutant HTT transcribed from the Htt gene, comprising administering to a non-human animal model for HD a compound of Formula (I), Formula (II), Formula (III), or Formula (IV), or a form thereof. In a specific aspect, provided herein is a method for modulating the inhibition of mutant HTT transcribed from the Htt gene, comprising administering to a non-human animal model for HD a compound of Formula (I), Formula (II), Formula (III), or Formula (IV), or a form thereof. In a specific aspect, the compound is a form of the compound of Formula (I), Formula (II), Formula (III), or Formula (IV).

In another aspect, provided herein is a method for decreasing the amount of mutant HTT, comprising contacting a human cell with a compound of Formula (I), Formula (II), Formula (III), or Formula (IV), or a form thereof. In a specific aspect, provided herein is a method for decreasing the amount of mutant HTT, comprising contacting a human cell with a compound of Formula (I), Formula (II), Formula (III), or Formula (IV), that inhibits the transcription of mutant HTT (huntingtin mRNA) from the Htt gene. In another specific aspect, provided herein is a method for decreasing the amount of HTT, comprising contacting a human cell with a compound of Formula (I), Formula (II), Formula (III), or Formula (IV), that inhibits the expression of mutant HTT transcribed from the Htt gene. The human cell can be contacted with a compound of Formula (I), Formula (II), Formula (III), or Formula (IV), or a form thereof in vitro, or in vivo, e.g., in a non-human animal or in a human. In a specific aspect, the human cell is from or in a human. In another specific aspect, the human cell is from or in a human with HD. In another specific aspect, the human cell is from or in a human with HD, caused by a CAG repeat in the Htt gene, resulting in a loss of HTT expression and/or function. In another aspect, the human cell is from a human with HD. In another aspect, the human cell is in a human with HD. In one aspect, the compound is a form of the compound of Formula (I), Formula (II), Formula (III), or Formula (IV).

In certain aspects, treating or ameliorating HD with a compound of Formula (I), Formula (II), Formula (III), or Formula (IV), or a form thereof (alone or in combination with an additional agent) has a therapeutic effect and/or beneficial effect. In a specific aspect, treating HD with a compound of Formula (I), Formula (II), Formula (III), or Formula (IV), or a form thereof (alone or in combination with an additional agent) results in one, two or more of the following effects: (i) reduces or ameliorates the severity of HD; (ii) delays onset of HD; (iii) inhibits the progression of HD; (iv) reduces hospitalization of a subject; (v) reduces hospitalization length for a subject; (vi) increases the survival of a subject; (vii) improves the quality of life for a subject; (viii) reduces the number of symptoms associated with HD; (ix) reduces or ameliorates the severity of a symptom(s) associated with HD; (x) reduces the duration of a symptom associated with HD; (xi) prevents the recurrence of a symptom associated with HD; (xii) inhibits the development or onset of a symptom of HD; and/or (xiii) inhibits of the progression of a symptom associated with HD.

Metabolites

Another aspect included within the scope of the present description are the use of in vivo metabolic products of the compounds described herein. Such products may result, for example, from the oxidation, reduction, hydrolysis, amidation, esterification and the like of the administered compound, primarily due to enzymatic processes. Accordingly, the description includes the use of compounds produced by a process comprising contacting a compound described herein with a mammalian tissue or a mammal for a period of time sufficient to yield a metabolic product thereof.

Such products typically are identified by preparing a radio-labeled isotopologue (e.g., $^{14}C$ or $^{3}H$) of a compound described herein, administering the radio-labeled compound in a detectable dose (e.g., greater than about 0.5 mg/kg) to a mammal such as a rat, mouse, guinea pig, dog, monkey or human, allowing sufficient time for metabolism to occur (typically about 30 seconds to about 30 hours), and identifying the metabolic conversion products from urine, bile, blood or other biological samples. The conversion products are easily isolated since they are "radiolabeled" by virtue of being isotopically-enriched (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds described herein even if they possess no biological activity of their own.

Pharmaceutical Compositions

In accordance with the intended scope of the present description, aspects of the present description include compounds that have been identified and have been demonstrated to be useful in selectively preventing, treating or ameliorating HD and have been provided for use as one or more pharmaceutical compositions for preventing, treating or ameliorating HD.

An aspect of the present description includes a use for a compound of Formula (I), Formula (II), Formula (III), or Formula (IV), or a form thereof in the preparation of a pharmaceutical composition for treating or ameliorating HD in a subject in need thereof comprising, administering to the subject an effective amount of the compound of Formula (I), Formula (II), Formula (III), or Formula (IV), or a form thereof in admixture with one or more pharmaceutically acceptable excipients.

An aspect of the present description includes a use for a pharmaceutical composition of the compound of Formula (I), Formula (II), Formula (III), or Formula (IV), or a form thereof in the preparation of a kit for treating or ameliorating HD in a subject in need thereof comprising, the pharmaceutical composition of the compound of Formula (I), Formula (II), Formula (III), or Formula (IV), or a form thereof and instructions for administering the pharmaceutical composition.

As used herein, the term "composition" means a product comprising the specified ingredients in the specified amounts, as well as any product which results, directly or indirectly, from combination of the specified ingredients in the specified amounts.

The pharmaceutical composition may be formulated to achieve a physiologically compatible pH, ranging from about pH 3 to about pH 11. In certain aspects, the pharmaceutical composition is formulated to achieve a pH of from about pH 3 to about pH 7. In other aspects, the pharmaceutical composition is formulated to achieve a pH of from about pH 5 to about pH 8.

The term "pharmaceutically acceptable excipient" refers to an excipient for administration of a pharmaceutical agent, such as the compounds described herein. The term refers to any pharmaceutical excipient that may be administered without undue toxicity. Pharmaceutically acceptable excipients may be determined in part by the particular composition being administered, as well as by the particular mode of administration and/or dosage form. Nonlimiting examples of pharmaceutically acceptable excipients include carriers, solvents, stabilizers, adjuvants, diluents, etc. Accordingly, there exists a wide variety of suitable formulations of pharmaceutical compositions for the instant compounds described herein (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive antibodies. Other exemplary excipients include antioxidants such as ascorbic acid; chelating agents such as EDTA; carbohydrates such as dextrin, hydroxyalkylcellulose, hydroxyalkylmethylcellulose (e.g., hydroxypropylmethylcellulose, also known as HPMC), stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions described herein may be formulated in any form suitable for the intended use described herein. Suitable formulations for oral administration include solids, liquid solutions, emulsions and suspensions, while suitable inhalable formulations for pulmonary administration include liquids and powders. Alternative formulations include syrups, creams, ointments, tablets, and lyophilized solids which can be reconstituted with a physiologically compatible solvent prior to administration.

When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents, and preserving agents, in order to provide a palatable preparation.

Pharmaceutically acceptable excipients suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid, or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate, or kaolin, or as soft gelatin capsules wherein the active ingredient is mixed with non-aqueous or oil medium, such as glycerin, propylene glycol, polyethylene glycol, peanut oil, liquid paraffin, or olive oil.

In other aspects, pharmaceutical compositions described herein may be formulated as suspensions comprising a compound of Formula (I), Formula (II), Formula (III), or Formula (IV), or a form thereof in admixture with one or more pharmaceutically acceptable excipients suitable for the manufacture of a suspension. In yet other aspects, pharmaceutical compositions described herein may be formulated as dispersible powders and granules suitable for preparation of a suspension by the addition of one or more excipients.

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin, or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions described herein may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions described herein may be in the form of a sterile injectable preparation, such as a sterile injectable aqueous emulsion or oleaginous suspension. Such emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propanediol. The sterile injectable preparation may also be prepared as a lyophilized powder. Among the acceptable vehicles and solvents that may be employed are water, Ringer's solution and isotonic sodium chloride solution. In addition, sterile fixed oils may be employed as a solvent or suspending medium. For this purpose any bland fixed oil may be employed including synthetic mono- or di-glycerides. In addition, fatty acids such as oleic acid may likewise be used in the preparation of injectables.

The compounds described herein may be substantially insoluble in water and sparingly soluble in most pharmaceutically acceptable protic solvents and vegetable oils, but generally soluble in medium-chain fatty acids (e.g., caprylic and capric acids) or triglycerides and in propylene glycol esters of medium-chain fatty acids. Thus, contemplated in the description are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In certain aspects, the compound described herein is formulated for oral administration in a lipid-based composition suitable for low solubility compounds. Lipid-based formulations can generally enhance the oral bioavailability of such compounds. As such, pharmaceutical compositions described herein may comprise a effective amount of a compound of Formula (I), Formula (II), Formula (III), or Formula (IV), or a form thereof, together with at least one pharmaceutically acceptable excipient selected from medium chain fatty acids or propylene glycol esters thereof (e.g., propylene glycol esters of edible fatty acids such as caprylic and capric fatty acids) and pharmaceutically acceptable surfactants, such as polysorbate 20 or 80 (also referred to as Tween® 20 or Tween® 80, respectively) or polyoxyl 40 hydrogenated castor oil.

In other aspects, the bioavailability of low solubility compounds may be enhanced using particle size optimization techniques including the preparation of nanoparticles or nanosuspensions using techniques known to those skilled in the art. The compound forms present in such preparations include amorphous, partially amorphous, partially crystalline or crystalline forms.

In alternative aspects, the pharmaceutical composition may further comprise one or more aqueous solubility enhancer(s), such as a cyclodextrin. Nonlimiting examples of cyclodextrin include hydroxypropyl, hydroxyethyl, glucosyl, maltosyl and maltotriosyl derivatives of α-, β-, and γ-cyclodextrin, and hydroxypropyl-β-cyclodextrin (HPBC). In certain aspects, the pharmaceutical composition further comprises HPBC in a range of from about 0.1% to about 20%, from about 1% to about 15%, or from about 2.5% to about 10%. The amount of solubility enhancer employed may depend on the amount of the compound in the composition.

Preparation of Compounds

General Synthetic Methods

As disclosed herein, general methods for preparing the compounds of Formula (I), Formula (II), Formula (III), or Formula (IV), or a form thereof as described herein are available via standard, well-known synthetic methodology. Many of the starting materials are commercially available or, when not available, can be prepared using the routes described below using techniques known to those skilled in the art. The synthetic schemes provided herein comprise multiple reaction steps, each of which is intended to stand on its own and can be carried out with or without any preceding or succeeding step(s). In other words, each of the individual reaction steps of the synthetic schemes provided herein in isolation is contemplated.

Scheme A:

Compounds of Formula (I), Formula (II), Formula (III), or Formula (IV), wherein $R_1$ is monocyclic, bicyclic, or polycyclic heterocyclyl ring system and $R_2$ is phenyl or monocyclic or bicyclic heteroaryl ring system, may be prepared as described in Scheme A below.

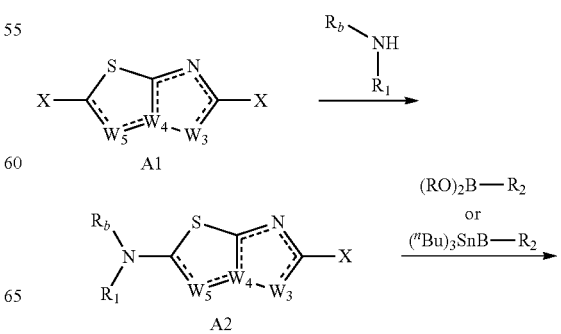

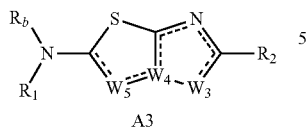

A3

Compound A1 (where X is bromo, chloro and the like, $W_3$ and $W_5$ are independently CH, S or N, and $W_4$ is C or N) is converted to Compound A2 by a nucleophilic substitution with a primary or secondary amine in the presence of a suitable base (such as $Et_3N$ and the like) in a suitable solvent (such as ACN and the like). Alternatively, Compound A1 is converted to Compound A2 via cross coupling with a primary or secondary amine in the presence of a suitable catalyst (such as RuPhos Pd G2 and the like) and base (such as sodium tert-butoxide and the like) in an appropriate solvent such as 1,4-dioxane and the like). Compound A2 is converted to Compound A3 by a Suzuki coupling with an aryl- or heteroaryl-boronic acid (or pinacol boronic ester) in the presence of a catalyst (such as $Pd(dppf)Cl_2$ and the like) and a base (such as aqueous $K_2CO_3$ and the like) in a suitable solvent (such as 1,4-dioxane and the like). Alternatively, Compound A3 can be prepared by a Stille coupling with an aryl- or heteroaryl tributyltin reagent in the presence of a catalyst (such as $Pd(PPh_3)_4$ and the like) in a suitable solvent (such as 1,4-dioxane and the like).

Scheme B:

Compounds of Formula (I), Formula (II), Formula (III), or Formula (IV), wherein $R_1$ is monocyclic, bicyclic, or polycyclic heterocyclyl ring system and $R_2$ is phenyl or monocyclic or bicyclic heteroaryl ring system, may be prepared as described in Scheme B below.

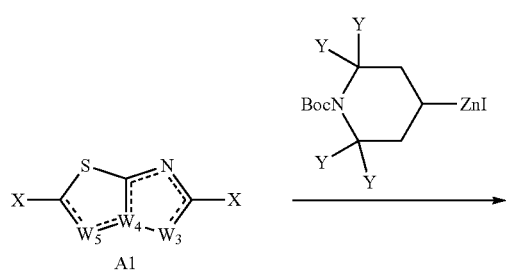

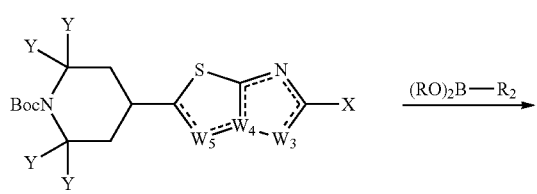

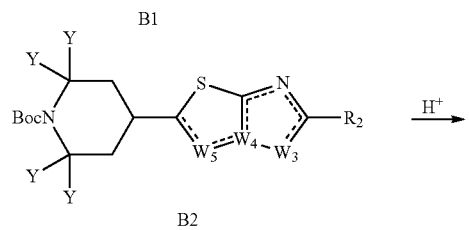

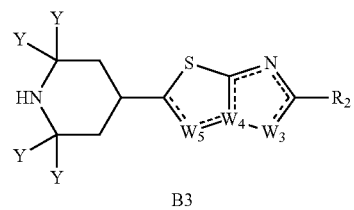

B3

Compound A1 (where X is bromo, chloro and the like, $W_3$ and $W_5$ are independently CH, S or N, and $W_4$ is C or N) is converted to Compound B1 by a Negishi coupling with an optionally substituted N-Boc-piperidinyl zinc iodide in the presence of a catalyst (such as $Pd(dppf)Cl_2$ and the like) in a suitable solvent (such as 1,4-dioxane and the like). Upon treatment with acid (such as TFA or HCl in dioxane and the like), Compound B2 is converted to Compound B3.

Scheme C:

Compounds of Formula (I), Formula (II), Formula (III), or Formula (IV), wherein $R_1$ is monocyclic, bicyclic, or polycyclic heterocyclyl ring system and $R_2$ is phenyl or monocyclic or bicyclic heteroaryl ring system, may be prepared as described in Scheme C below.

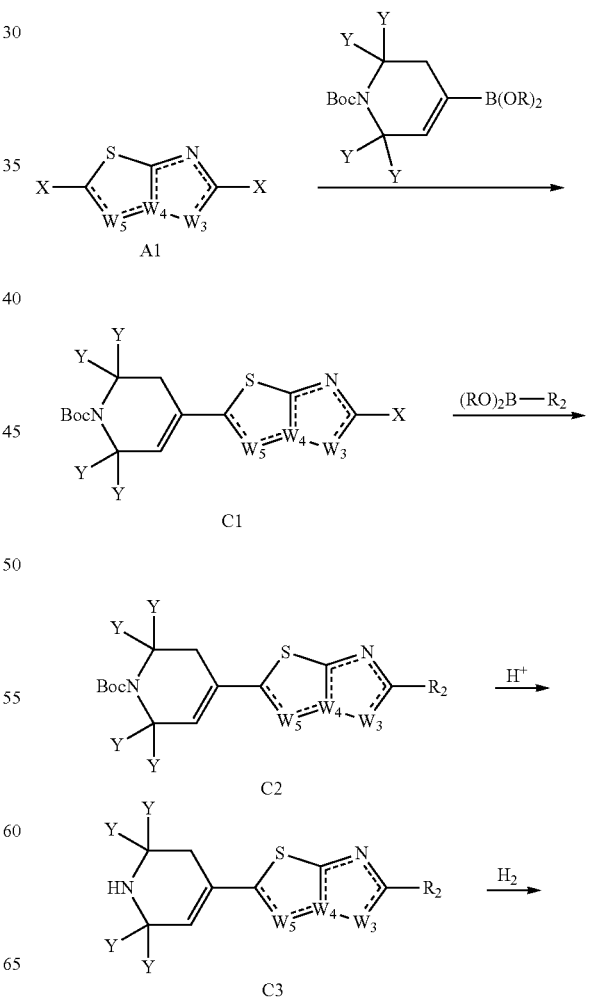

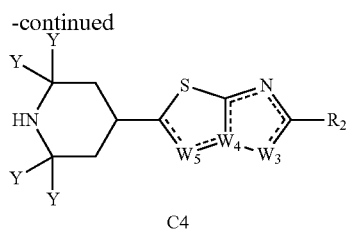

C4

Compound A1 (where X is bromo, chloro and the like, $W_3$ and $W_5$ are independently CH, S or N, and $W_4$ is C or N) is converted to Compound C1 by a Suzuki coupling with an optionally substituted N-Boc-tetrahydropyridinyl pinacol boronic ester in the presence of a catalyst (such as Pd(dppf)$Cl_2$ and the like) and base (such as aqueous $K_2CO_3$ and the like) in a suitable solvent (such as 1,4-dioxane and the like). Compound C1 is converted to Compound C2 by a Suzuki coupling with an aryl- or heteroaryl-boronic acid (or pinacol boronic ester) in the presence of a catalyst (such as Pd(dppf)$Cl_2$ and the like) and base (such as aqueous $K_2CO_3$ and the like) in a suitable solvent (such as 1,4-dioxane and the like). Upon treatment with acid (such as TFA or HCl in dioxane and the like) Compound C2 is converted to Compound C3. Under an atmosphere of $H_2$ in a suitable solvent (such as methanol and the like) and in the presence of catalyst (such as 10% Pd/C and the like) Compound C3 is converted to Compound C4.

Scheme D:

Compounds of Formula (I), Formula (II), Formula (III), or Formula (IV), wherein $R_1$ is monocyclic, bicyclic, or polycyclic heterocyclyl ring system and $R_2$ is phenyl or monocyclic or bicyclic heteroaryl ring system, may be prepared as described in Scheme D below.

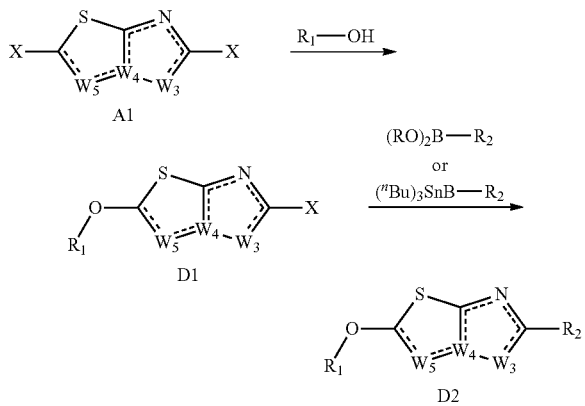

Compound A1 (where X is bromo, chloro and the like, $W_3$ and $W_5$ are independently CH, S or N, and $W_4$ is C or N) is converted to Compound D1 by a nucleophilic substitution with a primary or secondary alcohol in the presence of a suitable base (such as NaH and the like) in a suitable solvent (such as DMF and the like). Compound D1 is converted to Compound D2 by a Suzuki coupling with an aryl- or heteroaryl-boronic acid (or pinacol boronic ester) in the presence of a catalyst (such as Pd(PPh$_3$)$_4$ and the like) and a base (such as aqueous $K_2CO_3$ and the like) in a suitable solvent (such as toluene and the like). Alternatively, Compound D2 can be prepared by a Stille coupling with an aryl- or heteroaryl tributyltin reagent in the presence of a catalyst (such as Pd(PPh$_3$)$_4$ and the like) in a suitable solvent (such as 1,4-dioxane and the like).

Scheme E:

Compounds of Formula (I), Formula (II), Formula (III), or Formula (IV), wherein $R_1$ is monocyclic, bicyclic, or polycyclic heterocyclyl ring system and $R_2$ is phenyl or monocyclic or bicyclic heteroaryl ring system, may be prepared as described in Scheme E below.

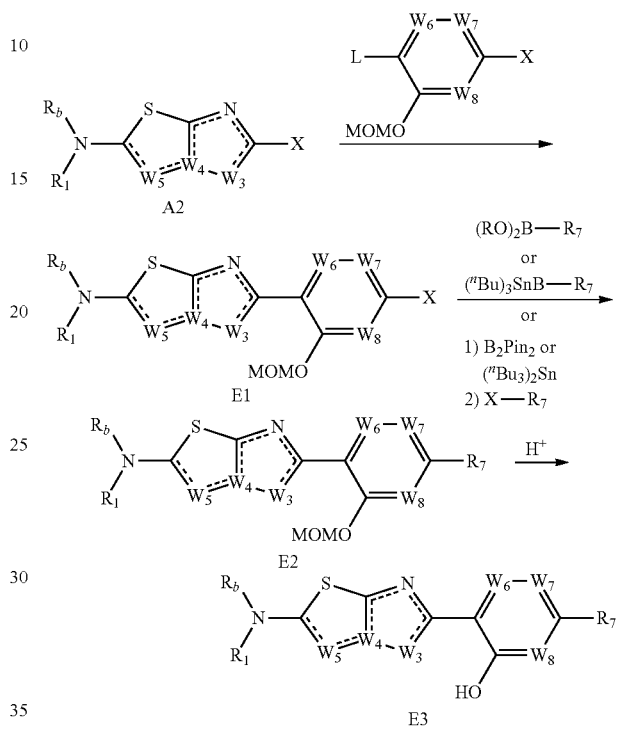

Compound A2 (where X is bromo, chloro and the like, $W_3$ and $W_5$ are independently CH, S or N, and $W_4$ is C or N), prepared according to the chemistry in Scheme A, is converted to Compound E1 by coupling with an aryl halide or heteroaryl halide (where $W_6$, $W_7$ and $W_8$ are independently CH or N) bearing a MOM-protected hydroxyl group and a leaving group L (where L is iodo, bromo, chloro, boronic acid pinacol boronic esters) in the presence of a catalyst (such as Pd(PPh$_3$)$_4$ and the like) and a base (such as aqueous $K_2CO_3$ and the like) in a suitable solvent (such as toluene and the like). Compound E1 is converted to Compound E2 by a Suzuki coupling with an aryl- or heteroaryl-boronic acid (or pinacol boronic ester) in the presence of a catalyst (such as Xphos G4 and the like) and base (such as aqueous $K_2CO_3$ and the like) in a suitable solvent (such as 1,4-dioxane and the like). Upon treatment with acid (such as TFA or HCl in dioxane and the like), Compound E2 is converted to Compound E3. Alternatively, Compound E2 can be prepared by a Stille coupling with an aryl- or heteroaryl tributyltin reagent in the presence of a catalyst (such as Pd(PPh$_3$)$_4$ and the like) in a suitable solvent (such as 1,4-dioxane and the like). E2 can also be prepared from E1 through a in situ generated pinacol boronic ester using a palladium (such as PdCl$_2$(dppf) and the like) catalyzed reaction in a suitable solvent (such as dioxane), followed by a Suzuki coupling with an aryl- or heteroaryl halide in the presence of a catalyst (such as Xphos G 4 and the like) and a base (such as aqueous $K_2CO_3$ and the like) in a suitable solvent (such as 1,4-dioxane and the like); or through a in situ generated tributyltin intermediate using a palladium (such as P(PPh₃)₄ and the like) catalyzed reaction in a suitable solvent (such as dioxane), followed by a Stille coupling with an aryl- or heteroaryl halide in the presence of a catalyst (such as Pd(PPh₃)₄ and the like) in a suitable solvent (such as 1,4-dioxane and the like).

Scheme F:

Compounds of Formula (I), Formula (II), Formula (III), or Formula (IV), wherein $R_1$ is monocyclic, bicyclic, or polycyclic heterocyclyl ring system and $R_2$ is phenyl or monocyclic or bicyclic heteroaryl ring system, may be prepared as described in Scheme F below.

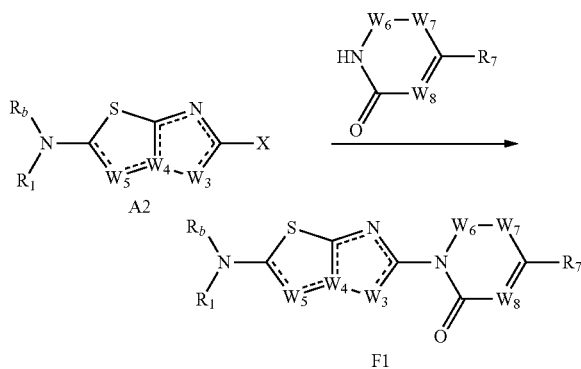

Compound A2 (where X is bromo, chloro and the like, $W_3$ and $W_5$ are independently CH, S or N, and $W_4$ is C or N) is converted to Compound F1 by a Buchwald coupling with an NH containing heteroaryl ($W_6$, $W_7$, and $W_8$ are independently CH or N), in the presence of a Cu(I) catalyst (such as CuI and the like) and a ligand (such as 4,7-dimethoxy-1,10-phenanthroline and the like) in a suitable solvent (such as DMSO and the like).

Scheme G:

Compounds of Formula (I), Formula (II), Formula (III), or Formula (IV), wherein $R_1$ is monocyclic, bicyclic, or polycyclic heterocyclyl ring system and $R_2$ is phenyl or monocyclic or bicyclic heteroaryl ring system, may be prepared as described in Scheme G below.

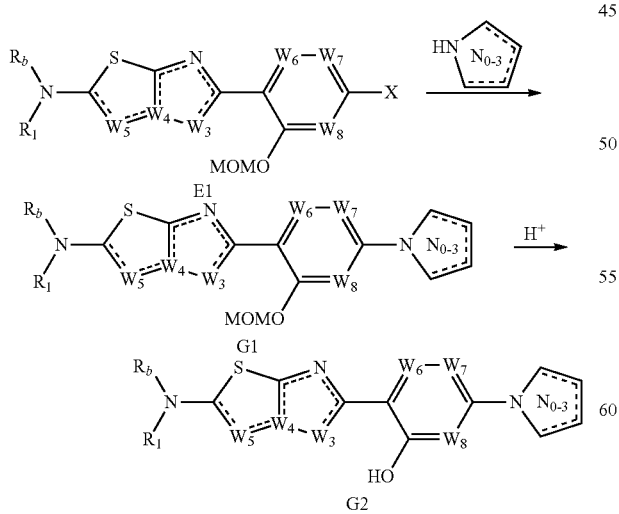

Compound E1 (where X is bromo, chloro and the like, $W_3$ and $W_5$ are independently CH, S or N, $W_4$ is C or N, and $W_6$, $W_7$ and $W_8$ are independently CH or N) is converted to Compound G1 by a Buchwald coupling with an optionally substituted NH-containing 5-membered heteroaryl containing up to 3 additional N atoms, in the presence of a Cu(I) catalyst (such as CuI and the like) and a diamine ligand (such as N,N'-dimethylcyclohexane diamine and the like) in a suitable solvent (such as 1,4-dioxane and the like). Upon treatment with acid (such as TFA or HCl in dioxane and the like), Compound G1 is converted to Compound G2.

Scheme H:

Compounds of Formula (I), Formula (II), Formula (III), or Formula (IV), wherein $R_1$ is monocyclic, bicyclic, or polycyclic heterocyclyl ring system and $R_2$ is phenyl or monocyclic or bicyclic heteroaryl ring system, may be prepared as described in Scheme H below.

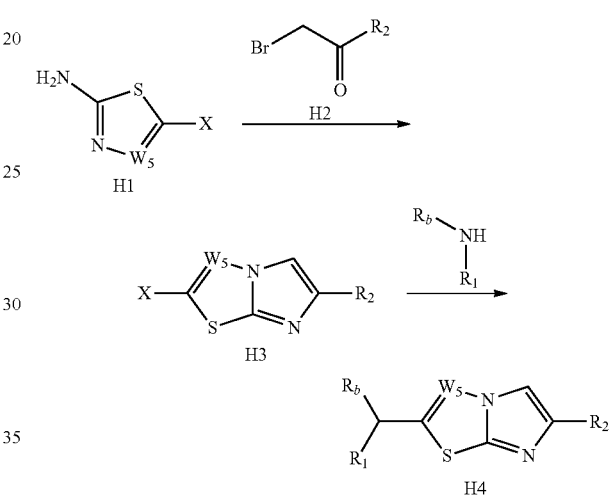

Compound H1 (where X is bromo, chloro and the like and $W_5$ is N) is converted to Compound H3 by a condensation with a bromoketone H2 in a suitable solvent (such as n-butanol and the like). Compound H3 is converted to Compound H4 by a nucleophilic substitution with a primary or secondary amine in the presence of a suitable base (such as Et₃N and the like) in a suitable solvent (such as DMSO and the like).

Scheme I:

Compounds of Formula (I), Formula (II), Formula (III), or Formula (IV), wherein $R_1$ is monocyclic, bicyclic, or polycyclic heterocyclyl ring system and $R_2$ is phenyl or monocyclic or bicyclic heteroaryl ring system, may be prepared as described in Scheme I below.

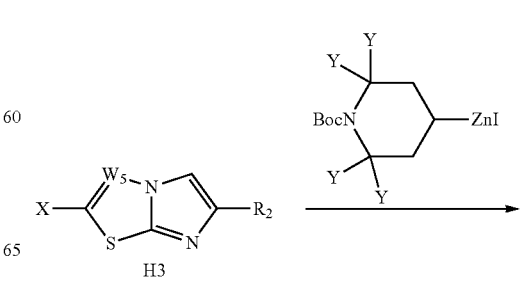

-continued

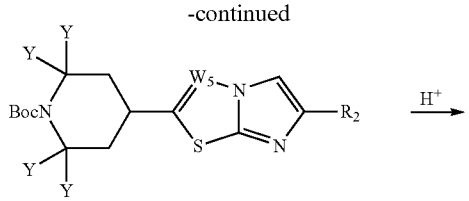

I1

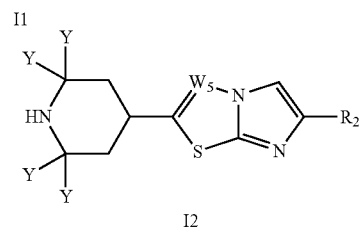

I2

Compound H3 (where X is bromo, chloro and the like and W$_5$ is N) is converted to Compound I1 by a N Negishi coupling with an optionally substituted N-Boc-piperidinyl zinc iodide in the presence of a catalyst (such as Pd(dppf)Cl$_2$ and the like) in a suitable solvent (such as 1,4-dioxane and the like). Upon treatment with acid (such as TFA or HCl in dioxane and the like), Compound I1 is converted to Compound I2.

Scheme J:

Compounds of Formula (I), Formula (II), Formula (III), or Formula (IV), wherein R$_1$ is monocyclic, bicyclic, or polycyclic heterocyclyl ring system and R$_2$ is phenyl or monocyclic or bicyclic heteroaryl ring system, may be prepared as described in Scheme J below.

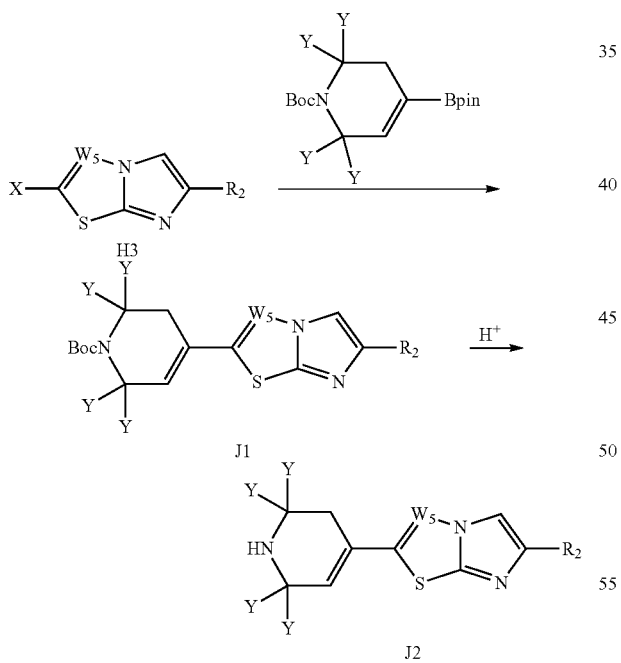

Compound H3 (where X is bromo, chloro and the like and W$_5$ is N) is converted to Compound J1 by a Suzuki coupling with an optionally substituted N-Boc-piperidinyl pinacol boronic ester in the presence of a catalyst (such as Pd(dppf)Cl$_2$ and the like) and base (such as aqueous K$_2$CO$_3$ and the like) in a suitable solvent (such as 1,4-dioxane and the like). Upon treatment with acid (such as TFA or HCl in dioxane and the like), Compound J1 is converted to Compound J2.

Scheme K:

Compounds of Formula (I), Formula (II), Formula (III), or Formula (IV), wherein R$_1$ is monocyclic, bicyclic, or polycyclic heterocyclyl ring system and R$_2$ is phenyl or monocyclic or bicyclic heteroaryl ring system, may be prepared as described in Scheme K below.

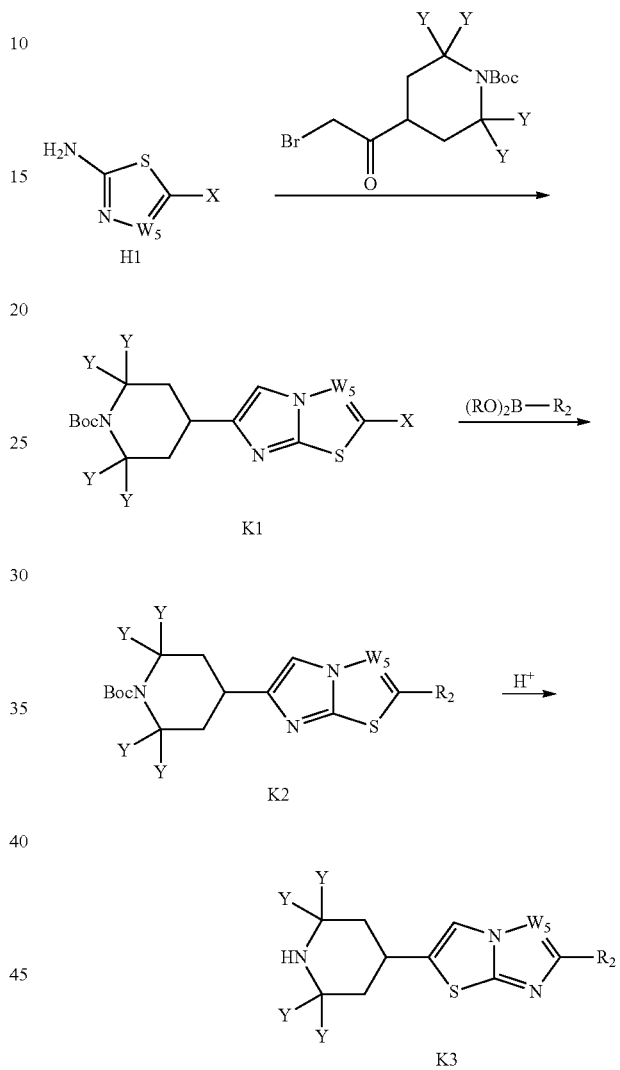

Compound H1 (where X is bromo, chloro and the like and W$_5$ is N) is converted to Compound K1 by a condensation with an optionally substituted N-Boc-tetrahydropyridinyl bromomethylketone in a suitable solvent (such as n-butanol and the like). K1 is converted to K2 by a Suzuki coupling with a boronic acid or pinacol boronic ester in the presence of a catalyst (such as Pd(dppf)Cl$_2$ and the like) and base (such as aqueous K$_2$CO$_3$ and the like) in a suitable solvent (such as 1,4-dioxane and the like). Upon treatment with acid (such as TFA or HCl in dioxane and the like), Compound K2 is converted to Compound K3.

Scheme L:

Compounds of Formula (I), Formula (II), Formula (III), or Formula (IV), wherein R$_1$ is monocyclic, bicyclic, or polycyclic heterocyclyl ring system and R$_2$ is phenyl or monocyclic or bicyclic heteroaryl ring system, may be prepared as described in Scheme L below.

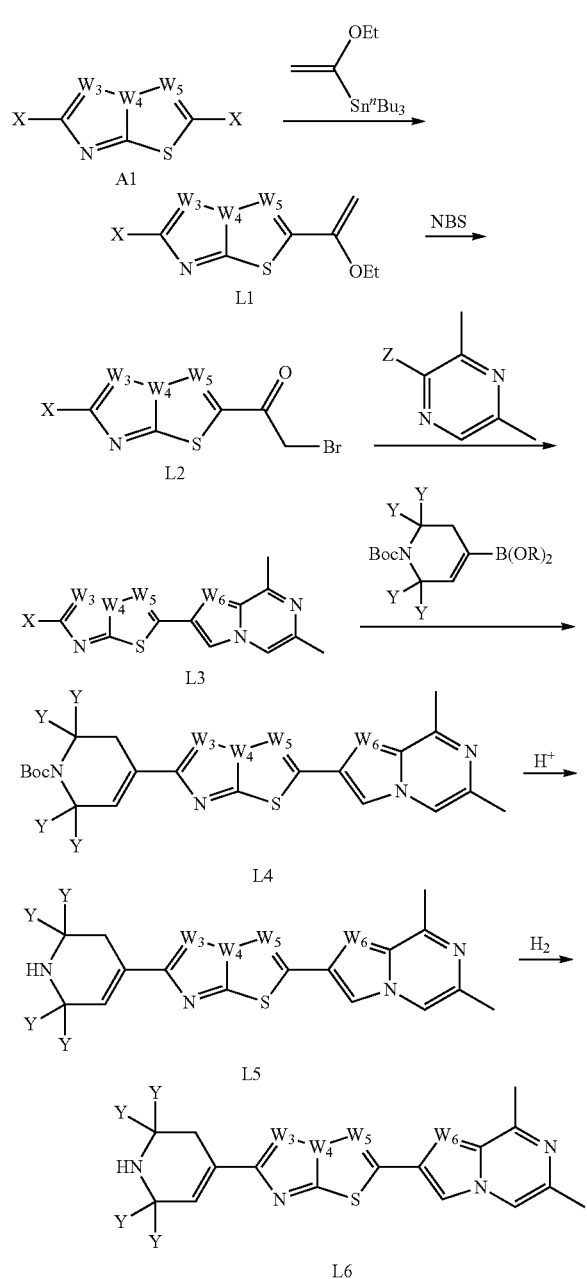

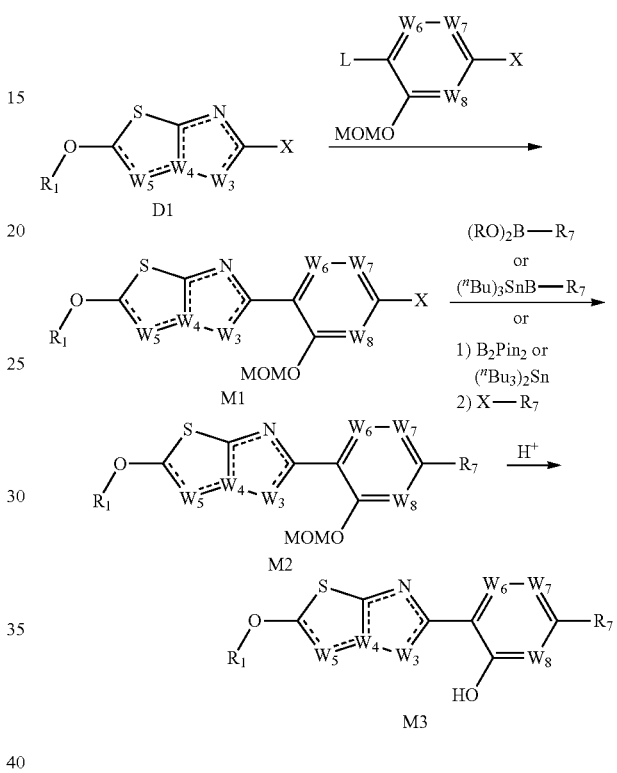

(such as methanol and the like) and in the presence of catalyst (such as 10% Pd/C and the like), Compound L5 is converted to Compound L6.

Scheme M:

Compounds of Formula (I), Formula (II), Formula (III), or Formula (IV), wherein $R_1$ is monocyclic, bicyclic, or polycyclic heterocyclyl ring system and $R_2$ is phenyl or monocyclic or bicyclic heteroaryl ring system, may be prepared as described in Scheme M below.

Compound D1 (where X is bromo, chloro and the like, $W_3$ and $W_5$ are independently CH, S or N, and $W_4$ is C or N), prepared according to the chemistry in Scheme D, is converted to Compound M1 by coupling with an aryl halide or heteroaryl halide (where $W_6$, $W_7$ and $W_8$ are independently CH or N) bearing a MOM-protected hydroxyl group and a leaving group L (where L is iodo, bromo, chloro, boronic acid pinacol boronic esters) in the presence of a catalyst (such as Pd(PPh$_3$)$_4$ and the like) and a base (such as aqueous $K_2CO_3$ and the like) in a suitable solvent (such as toluene and the like). Compound M1 is converted to Compound M2 by a Suzuki coupling with an aryl- or heteroaryl-boronic acid (or pinacol boronic ester) in the presence of a catalyst (such as Xphos G4 and the like) and base (such as aqueous $K_2CO_3$ and the like) in a suitable solvent (such as 1,4-dioxane and the like). Upon treatment with acid (such as TFA or HCl in dioxane and the like), Compound M2 is converted to Compound M3. Alternatively, Compound M2 can be prepared by a Stille coupling with an aryl- or heteroaryl tributyltin reagent in the presence of a catalyst (such as Pd(PPh$_3$)$_4$ and the like) in a suitable solvent (such as 1,4-dioxane and the like). M2 can also be prepared from M1 through a in situ generated pinacol boronic ester using a palladium (such as PdCl$_2$(dppf) and the like) catalyzed reaction in a suitable solvent (such as dioxane), followed by a Suzuki coupling with an aryl- or heteroaryl halide in the presence of a catalyst (such as Xphos G 4 and the like) and Compound A1 (where X is bromo, chloro and the like, $W_3$ and $W_5$ are independently CH, S or N, and $W_4$ is C or N) is converted to Compound L1 by a Stile coupling with a vinylstanane reagent in the presence of a catalyst (such as Pd(PPh$_3$)$_4$ in in a suitable solvent (such as 1,4-dioxane and the like). L1 is then converted to L2 by a brominating agent (such as NBS and the like). Bromoketone L2 is converted to L3 (where $W_6$ is CH or N) by condensation with a pyrazine (where Z is CH$_3$ or NH$_2$) in a suitable solvent (such as n-butanol and the like). L3 is converted to L4 by a Suzuki coupling with an optionally substituted N-Boc-piperidinyl pinacol boronic ester in the presence of a catalyst (such as Pd(dppf)Cl$_2$ and the like) and base (such as aqueous $K_2CO_3$ and the like) in a suitable solvent (such as 1,4-dioxane and the like). Upon treatment with acid (such as TFA or HCl in dioxane and the like) Compound L4 is converted to Compound L5. Under an atmosphere of H$_2$ in a suitable solvent a base (such as aqueous K₂CO₃ and the like) in a suitable solvent (such as 1,4-dioxane and the like); or through a in situ generated tributyltin intermediate using a palladium (such as P(PPh₃)₄ and the like) catalyzed reaction in a suitable solvent (such as dioxane), followed by a Stille coupling with an aryl- or heteroaryl halide in the presence of a catalyst (such as Pd(PPh₃)₄ and the like) in a suitable solvent (such as 1,4-dioxane and the like).

Scheme N:

Compounds of Formula (I), Formula (II), Formula (III), or Formula (IV), wherein $R_1$ is monocyclic, bicyclic, or polycyclic heterocyclyl ring system and $R_2$ is phenyl or monocyclic or bicyclic heteroaryl ring system, may be prepared as described in Scheme N below.

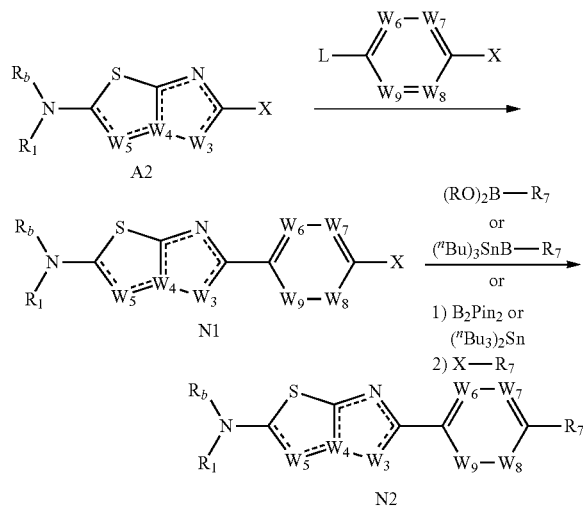

Compound A2 (where X is bromo, chloro and the like, $W_3$ and $W_5$ are independently CH, S or N, and $W_4$ is C or N), prepared according to the chemistry in Scheme A, is converted to Compound N1 by coupling with an aryl halide or heteroaryl halide (where $W_6$, $W_7$, $W_8$ and $W_9$ are independently CH or N) bearing a leaving group L, which is iodo, bromo, chloro or boronic acid (or pinacol boronic esters), or trialkyltin, such as tributyl tin in the presence of a catalyst (such as Pd(PPh₃)₄ and the like) and optionally with a base (such as aqueous K₂CO₃ and the like) in a suitable solvent (such as toluene and the like). Compound N1 is converted to Compound N2 by a Suzuki coupling with an aryl- or heteroaryl-boronic acid (or pinacol boronic ester) in the presence of a catalyst (such as Xphos G 4 and the like) and a base (such as aqueous K₂CO₃ and the like) in a suitable solvent (such as 1,4-dioxane and the like). Compound N2 can also be prepared by a Stille coupling with an aryl- or heteroaryl tributyltin reagent in the presence of a catalyst (such as Pd(PPh₃)₄ and the like) in a suitable solvent (such as 1,4-dioxane and the like). Alternatively, N2 can be prepared from N1 through a in situ generated pinacol boronic ester using a palladium (such as PdCl₂(dppf) and the like) catalyzed reaction in a suitable solvent (such as dioxane), followed by a Suzuki coupling with an aryl- or heteroaryl halide in the presence of a catalyst (such as Xphos G 4 and the like) and a base (such as aqueous K₂CO₃ and the like) in a suitable solvent (such as 1,4-dioxane and the like); or through a in situ generated tributyltin intermediate using a palladium (such as P(PPh₃)₄ and the like) catalyzed reaction in a suitable solvent (such as dioxane), followed by a Stille coupling with an aryl- or heteroaryl halide in the presence of a catalyst (such as Pd(PPh₃)₄ and the like) in a suitable solvent (such as 1,4-dioxane and the like).

Scheme O:

Compounds of Formula (I), Formula (II), Formula (III), or Formula (IV), wherein $R_1$ is monocyclic, bicyclic, or polycyclic heterocyclyl ring system and $R_2$ is phenyl or monocyclic or bicyclic heteroaryl ring system, may be prepared as described in Scheme O below.

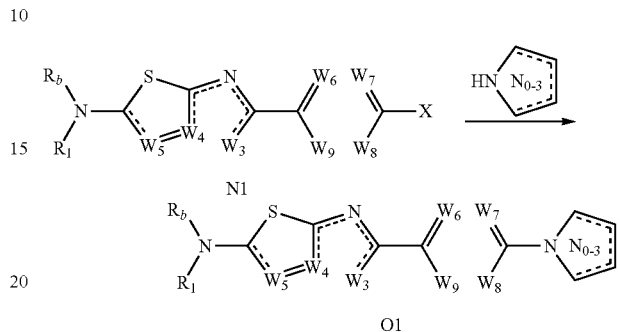

Compound N1 (where X is bromo, chloro and the like, $W_3$ and $W_5$ are independently CH, S or N, $W_4$ is C or N, and $W_6$, $W_7$, $W_8$ and $W_9$ are independently CH or N) is converted to Compound O1 by a Buchwald coupling with an optionally substituted NH-containing 5-membered heteroaryl containing up to 3 additional N atoms, in the presence of a Cu(I) catalyst (such as CuI and the like) and a ligand (such as N,N'-dimethylcyclohexane-1,2-diamine and the like) in a suitable solvent (such as 1,4-dioxane and the like).

Scheme P:

Compounds of Formula (I), Formula (II), Formula (III), or Formula (IV), wherein $R_1$ is monocyclic, bicyclic, or polycyclic heterocyclyl ring system and $R_2$ is phenyl or monocyclic or bicyclic heteroaryl ring system, may be prepared as described in Scheme P below.

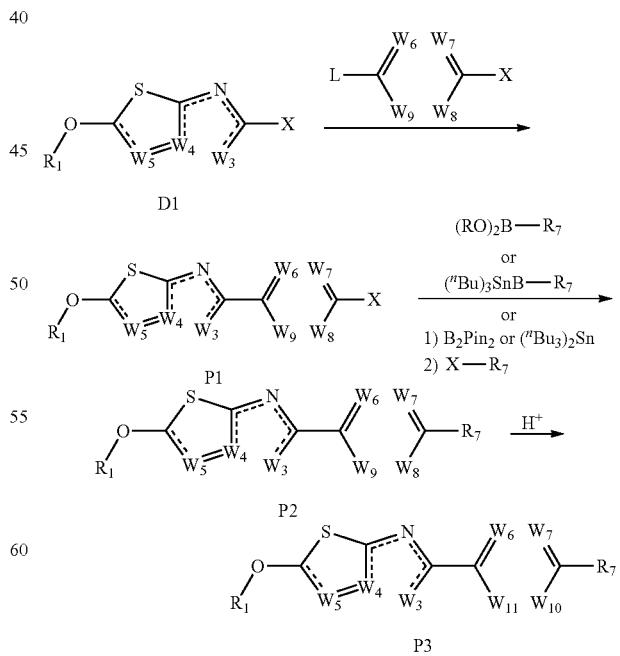

Compound D1 (where X is bromo, chloro and the like, $W_3$ and $W_5$ are independently CH, S or N, and $W_4$ is C or N), prepared according to the chemistry in Scheme D, is converted to Compound P1 by coupling with an aryl halide or heteroaryl halide (where $W_6$, $W_7$, $W_8$ and $W_9$ are independently CH or N) bearing a leaving group L, which is iodo, bromo, chloro or boronic acid (or pinacol boronic esters), or trialkyltin, such as tributyl tin in the presence of a catalyst (such as $Pd(PPh_3)_4$ and the like) and optionally with a base (such as aqueous $K_2CO_3$ and the like) in a suitable solvent (such as toluene and the like). Compound P1 is converted to Compound P2 by a Suzuki coupling with an aryl- or heteroaryl-boronic acid (or pinacol boronic ester) in the presence of a catalyst (such as Xphos G 4 and the like) and a base (such as aqueous $K_2CO_3$ and the like) in a suitable solvent (such as 1,4-dioxane and the like). Compound P2 can also be prepared by a Stille coupling with an aryl- or heteroaryl tributyltin reagent in the presence of a catalyst (such as $Pd(PPh_3)_4$ and the like) in a suitable solvent (such as 1,4-dioxane and the like).

Alternatively, P2 can be prepared from P1 through a in situ generated pinacol boronic ester using a palladium (such as $PdCl_2(dppf)$ and the like) catalyzed reaction in a suitable solvent (such as dioxane), followed by a Suzuki coupling with an aryl- or heteroaryl halide in the presence of a catalyst (such as Xphos G 4 and the like) and a base (such as aqueous $K_2CO_3$ and the like) in a suitable solvent (such as 1,4-dioxane and the like); or through a in situ generated tributyltin intermediate using a palladium (such as $P(PPh_3)_4$ and the like) catalyzed reaction in a suitable solvent (such as dioxane), followed by a Stille coupling with an aryl- or heteroaryl halide in the presence of a catalyst (such as $Pd(PPh_3)_4$ and the like) in a suitable solvent (such as 1,4-dioxane and the like).

Scheme Q:

Compounds of Formula (I), Formula (II), Formula (III), or Formula (IV), wherein $R_1$ is monocyclic, bicyclic, or polycyclic heterocyclyl ring system and $R_2$ is phenyl or monocyclic or bicyclic heteroaryl ring system, may be prepared as described in Scheme Q below.

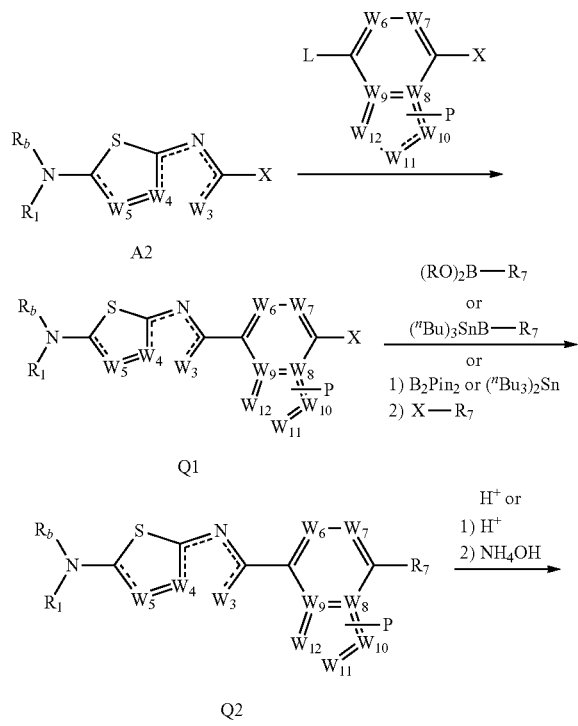

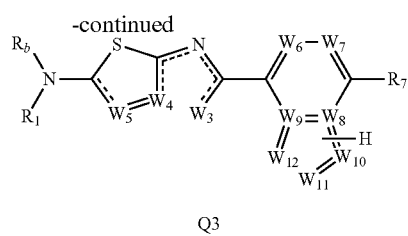

Q3

Compound A2 (where X is bromo, chloro and the like, $W_3$ and $W_5$ are independently CH, S or N, and $W_4$ is C or N), prepared according to the chemistry in Scheme A, is converted to Compound Q1 by coupling with an aryl halide or heteroaryl halide (where $W_6$, $W_7$, $W_8$, $W_9$, $W_{10}$, $W_{11}$ and $W_{12}$ are independently CH or N) bearing a protecting group P (such as Boc, or SEM and the like), a leaving group L, which is iodo, bromo, chloro or boronic acid (or pinacol boronic esters), or trialkyltin, such as tributyl tin in the presence of a catalyst (such as $Pd(PPh_3)_4$ and the like) and optionally with a base (such as aqueous $K_2CO_3$ and the like) in a suitable solvent (such as toluene and the like). Compound Q1 is converted to Compound Q2 by a Suzuki coupling with an aryl- or heteroaryl-boronic acid (or pinacol boronic ester) in the presence of a catalyst (such as Xphos G 4 and the like) and a base (such as aqueous $K_2CO_3$ and the like) in a suitable solvent (such as 1,4-dioxane and the like). Upon treatment with acid (such as TFA or HCl in dioxane and the like; In the case of protecting group P is SEM, $NH_4OH$ treatment can be applied following the acid treatment), Compound Q2 is then converted to Compound Q3 via removal of the protecting group. Compound Q2 can also be prepared by a Stille coupling with an aryl- or heteroaryl tributyltin reagent in the presence of a catalyst (such as $Pd(PPh_3)_4$ and the like) in a suitable solvent (such as 1,4-dioxane and the like). Alternatively, Q2 can be prepared from Q1 through a in situ generated pinacol boronic ester using a palladium (such as $PdCl_2(dppf)$ and the like) catalyzed reaction in a suitable solvent (such as dioxane), followed by a Suzuki coupling with an aryl- or heteroaryl halide in the presence of a catalyst (such as Xphos G 4 and the like) and a base (such as aqueous $K_2CO_3$ and the like) in a suitable solvent (such as 1,4-dioxane and the like); or through a in situ generated tributyltin intermediate using a palladium (such as $P(PPh_3)_4$ and the like) catalyzed reaction in a suitable solvent (such as dioxane), followed by a Stille coupling with an aryl- or heteroaryl halide in the presence of a catalyst (such as $Pd(PPh_3)_4$ and the like) in a suitable solvent (such as 1,4-dioxane and the like).

Scheme R:

Compounds of Formula (I), Formula (II), Formula (III), or Formula (IV), wherein $R_1$ is monocyclic, bicyclic, or polycyclic heterocyclyl ring system and $R_2$ is phenyl or monocyclic or bicyclic heteroaryl ring system, may be prepared as described in Scheme R below.

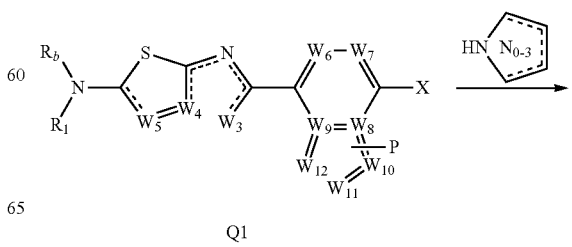

-continued

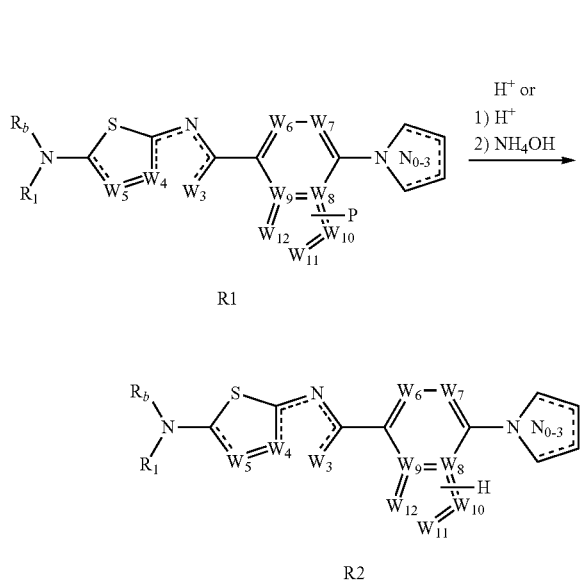

R1

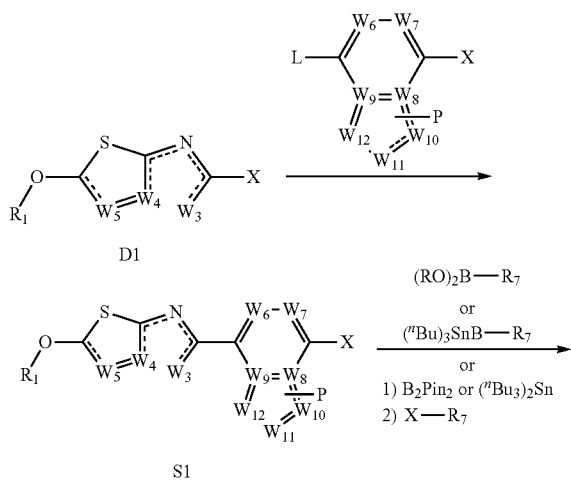

R2

Compound Q1 (where X is bromo, chloro and the like, $W_3$ and $W_5$ are independently CH, S or N, $W_4$ is C or N, and $W_6$, $W_7$, $W_8$, $W_9$, $W_{10}$, $W_{11}$ and $W_{12}$ are independently CH or N), prepared according to the chemistry in Scheme Q, is converted to Compound R1 by a Buchwald coupling with an optionally substituted NH-containing 5-membered heteroaryl containing up to 3 additional N atoms, in the presence of a Cu(I) catalyst (such as CuI and the like) and a ligand (such as N,N'-dimethylcyclohexane-1,2-diamine and the like) in a suitable solvent (such as 1,4-dioxane and the like). Upon treatment with acid (such as TFA or HCl in dioxane and the like; In the case of protecting group P is SEM, $NH_4OH$ treatment can be applied following the acid treatment), Compound R1 is converted to Compound R2.

Scheme S:

Compounds of Formula (I), Formula (II), Formula (III), or Formula (IV), wherein $R_1$ is monocyclic, bicyclic, or polycyclic heterocyclyl ring system and $R_2$ is phenyl or monocyclic or bicyclic heteroaryl ring system, may be prepared as described in Scheme S below.

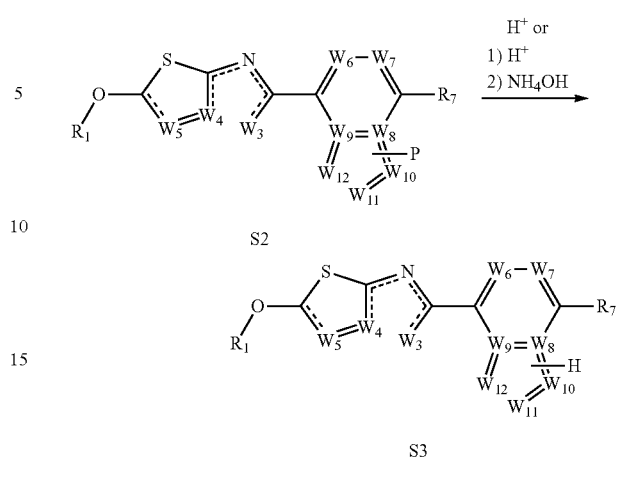

Compound D1 (where X is bromo, chloro and the like, $W_3$ and $W_5$ are independently CH, S or N, and $W_4$ is C or N), prepared according to the chemistry in Scheme D, is converted to Compound S1 by coupling with an aryl halide or heteroaryl halide (where $W_6$, $W_7$, $W_8$, $W_9$, $W_{10}$, $W_{11}$ and $W_{12}$ are independently CH or N) bearing a protecting group P (such as Boc, or SEM and the like), a leaving group L, which is iodo, bromo, chloro or boronic acid (or pinacol boronic esters), or trialkyltin, such as tributyl tin in the presence of a catalyst (such as $Pd(PPh_3)_4$ and the like) and optionally with a base (such as aqueous $K_2CO_3$ and the like) in a suitable solvent (such as toluene and the like). Compound S1 is converted to Compound S2 by a Suzuki coupling with an aryl- or heteroaryl-boronic acid (or pinacol boronic ester) in the presence of a catalyst (such as Xphos G 4 and the like) and a base (such as aqueous $K_2CO_3$ and the like) in a suitable solvent (such as 1,4-dioxane and the like). Upon treatment with acid (such as TFA or HCl in dioxane and the like; In the case of protecting group P is SEM, $NH_4OH$ treatment can be applied following the acid treatment), Compound S2 is converted to Compound S3. Compound S2 can also be prepared by a Stille coupling with an aryl- or heteroaryl tributyltin reagent in the presence of a catalyst (such as $Pd(PPh_3)_4$ and the like) in a suitable solvent (such as 1,4-dioxane and the like). Alternatively, S2 can be prepared from S1 through a in situ generated pinacol boronic ester using a palladium (such as $PdCl_2(dppf)$ and the like) catalyzed reaction in a suitable solvent (such as dioxane), followed by a Suzuki coupling with an aryl- or heteroaryl halide in the presence of a catalyst (such as Xphos G 4 and the like) and a base (such as aqueous $K_2CO_3$ and the like) in a suitable solvent (such as 1,4-dioxane and the like); or through a in situ generated tributyltin intermediate using a palladium (such as $P(PPh_3)_4$ and the like) catalyzed reaction in a suitable solvent (such as dioxane), followed by a Stille coupling with an aryl- or heteroaryl halide in the presence of a catalyst (such as $Pd(PPh_3)_4$ and the like) in a suitable solvent (such as 1,4-dioxane and the like).

Scheme T:

Compounds of Formula (I), Formula (II), Formula (III), or Formula (IV), wherein $R_1$ is monocyclic, bicyclic, or polycyclic heterocyclyl ring system and $R_2$ is phenyl or monocyclic or bicyclic heteroaryl ring system, may be prepared as described in Scheme T below.

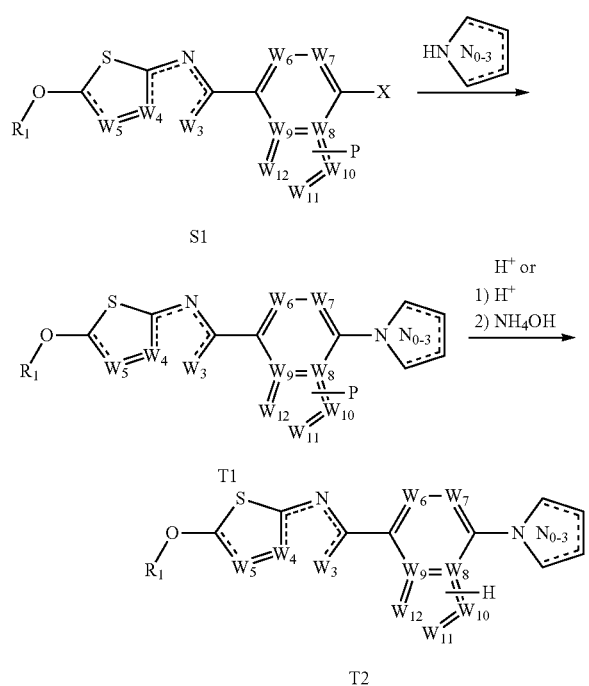

Compound S1 (where X is bromo, chloro and the like, $W_3$ and $W_5$ are independently CH, S or N, $W_4$ is C or N, and $W_6$, $W_7$, $W_8$, $W_9$, $W_{10}$, $W_{11}$ and $W_{12}$ are independently CH or N), prepared according to the chemistry in Scheme S, is converted to Compound T1 by a Buchwald coupling with an optionally substituted NH-containing 5-membered heteroaryl containing up to 3 additional N atoms, in the presence of a Cu(I) catalyst (such as CuI and the like) and a ligand (such as N,N'-dimethylcyclohexane-1,2-diamine and the like) in a suitable solvent (such as 1,4-dioxane and the like). Upon treatment with acid (such as TFA or HCl in dioxane and the like; In the case of protecting group P is SEM, NH$_4$OH treatment can be applied following the acid treatment), Compound T1 is converted to Compound T2.

SPECIFIC SYNTHETIC EXAMPLES

To describe in more detail and assist in understanding, the following non-limiting examples are offered to more fully illustrate the scope of compounds described herein and are not to be construed as specifically limiting the scope thereof.

Such variations of the compounds described herein that may be now known or later developed, which would be within the purview of one skilled in the art to ascertain, are considered to fall within the scope of the compounds as described herein and hereinafter claimed. These examples illustrate the preparation of certain compounds. Those of skill in the art will understand that the techniques described in these examples represent techniques, as described by those of ordinary skill in the art, that function well in synthetic practice, and as such constitute preferred modes for the practice thereof. However, it should be appreciated that those of skill in the art should, in light of the present disclosure, appreciate that many changes can be made in the specific methods that are disclosed and still obtain a like or similar result without departing from the spirit and scope of the present description.

Other than in the following examples of the embodied compounds, unless indicated to the contrary, all numbers expressing quantities of ingredients, reaction conditions, experimental data, and so forth used in the specification and claims are to be understood as being modified by the term "about". Accordingly, all such numbers represent approximations that may vary depending upon the desired properties sought to be obtained by a reaction or as a result of variable experimental conditions. Therefore, within an expected range of experimental reproducibility, the term "about" in the context of the resulting data, refers to a range for data provided that may vary according to a standard deviation from the mean. As well, for experimental results provided, the resulting data may be rounded up or down to present data consistently, without loss of significant figures. At the very least, and not as an attempt to limit the application of the doctrine of equivalents to the scope of the claims, each numerical parameter should be construed in light of the number of significant digits and rounding techniques used by those of skill in the art.

While the numerical ranges and parameters setting forth the broad scope of the present description are approximations, the numerical values set forth in the examples set forth below are reported as precisely as possible. Any numerical value, however, inherently contains certain errors necessarily resulting from the standard deviation found in their respective testing measurements.

COMPOUND EXAMPLES

As used above, and throughout the present description, the following abbreviations, unless otherwise indicated, shall be understood to have the following meanings:

| Abbreviation | Meaning |
| --- | --- |
| Δ | heating (chemistry) or deletion (biology) |
| AcOH or HOAc | acetic acid |
| AC$_2$O | acetic anhydride |
| Ag$_2$SO$_4$ | silver sulfate |
| Ar | argon |
| ACN or CH$_3$CN | acetonitrile |
| atm | atmosphere(s) |
| B$_2$pin$_2$ | bis(pinacolato)diboron |
| BPin | 2 4,4,5,5-tetramethyl-1,3,2-dioxaborolanyl |
| BBr$_3$ | boron tribromide |
| Boc | tert-butoxy-carbonyl |
| Boc$_2$O | di-tert-butyl dicarbonate |
| Br$_2$ | bromine |
| n-BuLi or nBuLi | n-butyl lithium |
| BuOH | n-butanol |
| t-BuOK | potassium t-butoxide |
| Bu$_3$SnCl | tributylchlorostannane or tributyltin chloride |

-continued

| Abbreviation | Meaning |
|---|---|
| ° C. | degrees Centigrade |
| $CCl_4$ | carbon tetrachloride |
| $CDCl_3$ | chloroform-d or deuterochloroform |
| Celite ® or Celite | diatomaceous earth |
| $(COCl)_2$ | oxalyl chloride |
| CPME | cyclopentyl methyl ether |
| $Cs_2CO_3$ | cesium carbonate |
| CuI | copper(I) iodide or cuprous iodide |
| d/h/hr/hrs/min/s | day(d)/hour(h, hr or hrs)/minute(min)/second(s) |
| DABCO | 1,4-diazabicyclo[2.2.2]octane |
| DCE | 1,2-dichloroethane |
| DCM or $CH_2Cl_2$ | dichloromethane |
| DDQ | 2,3-dichloro-5,6-dicyano-p-benzoquinone |
| DMA | dimethylacetamide |
| DME | 1,2-dimethoxyethane |
| DMF | dimethylformamide |
| DMSO | dimethylsulfoxide |
| EtOAc | ethyl acetate |
| EtOH | ethanol |
| $Et_2O$ | diethyl ether |
| eq. | equivalents |
| $H_2$ | hydrogen |
| HCl | hydrochloric acid |
| $H_2SO_4$ | sulfuric acid |
| HCHO | formaldehyde |
| $K_2CO_3$ | potassium carbonate |
| KOAc | potassium acetate |
| KOtBu | potassium t-butoxide |
| KOH | potassium hydroxide |
| LAH | lithium aluminum hydride |
| LC/MS, LCMS or LC-MS | liquid chromatographic mass spectroscopy |
| LDA | lithium diisopropylamine |
| LiHMDS or LHMDS | lithium bis(trimethylsilyl)amide |
| LiOH | lithium hydroxide |
| MeOH | methanol |
| MeI | iodomethane |
| $MeSO_3H$ | methanesulfonic acid |
| Me—THF | 2-methyltetrahydrofuran |
| $Me_2Zn$ or $ZnMe_2$ | dimethylzinc |
| $MgSO_4$ | magnesium sulfate |
| $MnO_2$ | manganese dioxide |
| M | molar |
| MOM-Cl | chloromethyl methyl ether or methoxymethyl chloride |
| MS | mass spectroscopy |
| $NH_4Cl$ | ammonium chloride |
| $NH_4OAc$ | ammonium acetate |
| $NaBH_4$ | sodium borohydride |
| $NaBH(OAc)_3$ | sodium triacetoxyborohydride |
| $Na_2CO_3$ | sodium carbonate |
| NaH | sodium hydride |
| $NaHCO_3$ | sodium bicarbonate |
| $NaHSO_3$ | sodium bisulfite |
| NaHMDS | sodium bis(trimethylsilyl)amide or sodium hexamethyldisilazide |
| NaOAc | sodium acetate |
| NaOH | sodium hydroxide |
| NaOMe | sodium methoxide |
| $NaNO_2$ | sodium nitrite |
| $Na_2SO_4$ | sodium sulfate |
| $N_2$ | nitrogen |
| $NH_4Cl$ | ammonium chloride |
| NBS | 1-bromopyrrolidine-2,5-dione or N-bromosuccinimide |
| NCS | 1-chloropyrrolidine-2,5-dione or N-chlorosuccinimide |
| NIS | 1-iodopyrrolidine-2,5-dione or N-iodosuccinimide |
| NMP | N-methylpyrrolidone |
| NMR | nuclear magnetic resonance |
| $NOBF_4$ | nitrosonium tetrafluoroborate or nitrosyl tetrafluoroborate |
| $Pb(OAc)_4$ | lead(IV) acetate or lead tetraacetate |
| Pd | palladium |
| Pd/C | palladium on carbon |
| $Pd(dba)_2$ | bis(dibenzylideneacetone)palladium |
| $Pd_2(dba)_3$ or $Pd_2dba_3$ | tris(dibenzylideneacetone)dipalladium(0) |
| $PdCl_2(PhCN)_2$ | trans-bis(benzonitrile)dichloropalladium(II) |
| $Pd(dppf)Cl_2$ or | [1,1'- |

| Abbreviation | Meaning |
| --- | --- |
| Pd(dppf)Cl$_2$—CH$_2$Cl$_2$ | bis(diphenylphosphino)ferrocene]dichloropalladium(II), complex with dichloromethane |
| Pd(OAc)$_2$ | palladium(II) acetate |
| Pd(PPh$_3$)$_4$ or Pd(Ph$_3$P)$_4$ | tetrakis(triphenylphosphine)palladium(0) |
| Pd(PPh$_3$)$_2$Cl$_2$, PdCl$_2$(PPh$_3$)$_2$ or PdCl$_2$(Ph$_3$P)$_2$ | bis(triphenylphosphine)palladium(II) dichloride |
| PHBU$_3$BF$_4$ or tBu$_3$PHBF$_4$ | tri-tert-butylphosphonium tetrafluoroborate |
| PhI(OTFA)$_2$ | [bis(trifluoroacetoxy)iodo]benzene |
| PhMe | toluene |
| Ph—N(Tf)$_2$ or PhN(Tf)$_2$ | N-phenyl triflimide, also referred to as N-phenyl-bis(trifluoromethanesulfonimide) |
| POBr$_3$ | phosphoryl bromide or phosphorous(V) oxybromide |
| P$_2$O$_5$ | phosphorous pentoxide or phosphorous(V) oxide |
| POCl$_3$ | phosphoryl chloride or phosphorous(V) oxychloride |
| PPh$_3$ | triphenylphosphine |
| PPA | polyphosphoric acid |
| Psi | pounds per square inch pressure |
| PtO$_2$ | platinum(IV) oxide |
| RT | retention time |
| S$_2$Cl$_2$ | sulfur monochloride |
| SnCl$_2$ | tin(II) chloride or stannous chloride |
| S-Phos, SPhos or Sphos | 2-dicyclohexylphosphino-2',6'-dimethoxybiphenyl |
| S-Phos G$_2$ | chloro(2-dicyclohexylphosphino-2',6'-dimethoxy-1,1'-biphenyl)(2'-amino-1,1'-biphenyl-2-yl) palladium(II) |
| TEA, Et$_3$N or NEt$_3$ | triethylamine |
| TFA | trifluoroacetic acid |
| THF | tetrahydrofuran |
| TIPS | tiisopropylsilane |
| TLC | thin layer chromatography |
| TMEDA | tetramethylethylenediamine |
| TMS | trimethylsilane |
| t-Bu | tert-butyl |

Example 1

Preparation of Compound 1

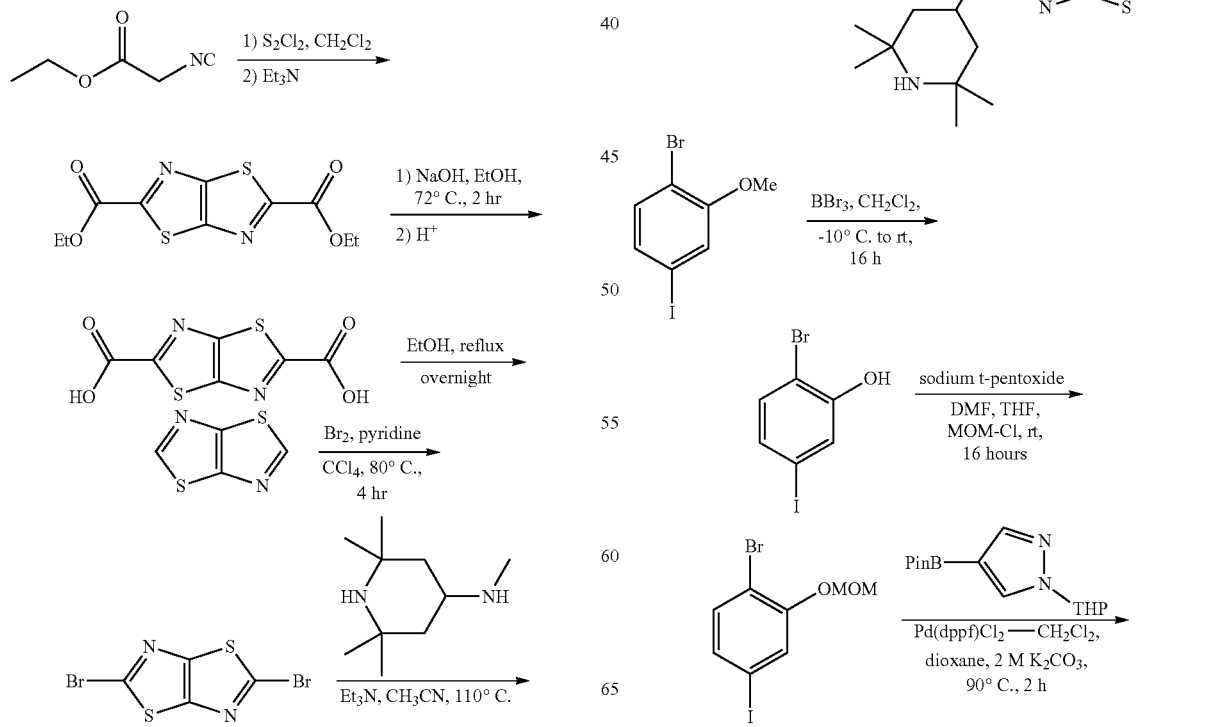

-continued

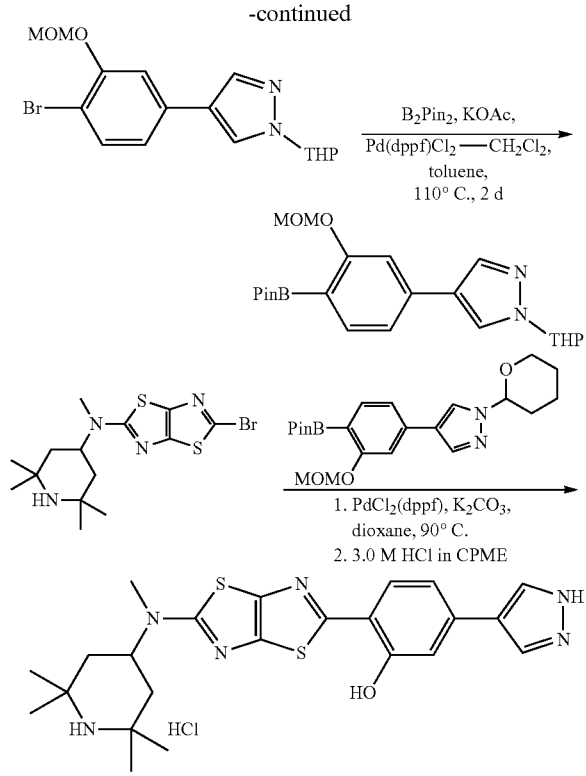

Step 1: To a cooled at −50° C. solution of ethyl isocyanoacetate (100 g, 868.58 mmol) in $CH_2Cl_2$ (1 L) was added sulfur monochloride (34.7 mL, 434 mmol). The mixture was allowed to warm to 10° C. and then re-cooled to −50° C., followed by the addition of triethylamine (121 mL, 866 mmol). The cooling bath was removed after 2 hr (−40° C.), and the mixture was stirred until the temperature reached 10° C. The precipitate was removed by filtration and the solvent was removed under reduced pressure. The residue was treated with EtOH (~10 mL) and the precipitate was collected and washed with additional EtOH and dried under a $N_2$ stream. The filtrate was concentrated, and the residue purified column chromatography (EtOAc in hexanes, 0-30%). Diethyl thiazolo[5,4-d]thiazole-2,5-dicarboxylate was obtained as a white solid (total 16.03 g, 6.4%).

LC-MS 287.2 [M+H]$^+$, RT 1.35 min'; $^1$H NMR (CDCl$_3$) δ: 4.56 (q, J=7.1 Hz, 4H), 1.50 (t, J=7.1 Hz, 6H).

Step 2: The diethyl thiazolo[5,4-d]thiazole-2,5-dicarboxylate (16.03 g, 55.99 mmol) was treated with EtOH (100 mL) and NaOH (24.6 mL, 5 M, 124 mmol) at 76° C. for 2 hr. The reaction was concentrated to dryness and diluted with water, acidified by HCl and the precipitate was collected, washed with water and dried, and then used directly in Step 3, below. LC-MS 231.2 [M+H]$^+$, RT 0.63 min.

Step 3: The material obtained in Step 2 was heated with ethanol (500 mL) at 80° C. for 48 hr. The solvent was concentrated under reduced pressure to provide thiazolo[5,4-d]thiazole which was used directly in step 4, below. LC-MS 143.1 [M+H]$^+$, RT 0.88 min.

Step 4: A mixture of thiazolo[5,4-d]thiazole (56.0 mmol) obtained in Step 3, $CCl_4$ (360 mL), pyridine (9.06 mL, 112 mmol) and bromine (28.8 mL, 560 mmol) was heated at 80° C. for 4 hr. The reaction was cooled, diluted with $CH_2Cl_2$ and treated with saturated aqueous $NaHSO_3$ until the mixture turned light yellow. The organic phase was washed with water and brine, and then dried and chromatographed (silica gel, $CH_2Cl_2$) to furnish 2,5-dibromothiazolo[5,4-d]thiazole (7.5 g, 25 mmol, 45%) as a white solid. LC-MS 298.8, 300.9, 302.8 [M+H]$^+$, RT 1.53 min.

Step 5: A mixture of 2,5-dibromothiazolo[5,4-d]thiazole (370 mg, 1.23 mmol), N,2,2,6,6-pentamethylpiperidin-4-amine (315 mg, 1.85 mmol) and triethylamine (0.34 mL, 2.4 mmol) in $CH_3CN$ (5 mL) was stirred at 110° C. for 12 hr. The reaction was concentrated, diluted with $CH_2Cl_2$ and washed with water, brine and dried. After the removal of the solvent, the residue was chromatographed (1.4 N $NH_3$ in MeOH in $CH_2Cl_2$, 0-20%) to provide 5-bromo-N-methyl-N-(2,2,6,6-tetramethyl-4-piperidyl)thiazolo[5,4-d]thiazol-2-amine (429 mg, 89.3%).

LC-MS 389.1, 391.1 [M+H]$^+$, RT 1.12 min; $^1$H NMR (CDCl$_3$) δ: 4.38 (br t, J=12.1 Hz, 1H), 2.98 (s, 3H), 1.75 (dd, J=12.6, 3.5 Hz, 2H), 1.13-1.51 (m, 14H)

Step 6: 1-Bromo-4-iodo-2-methoxybenzene (50 g, 160 mmol) was suspended in $CH_2Cl_2$ (75 mL) at −10° C. Boron tribromide (250 mL, 250 mmol, 1M in $CH_2Cl_2$,) was cannulated in over 30 min, with the internal temperature remaining below 0° C. throughout the addition. After the addition, the mixture was stirred at 0° C. for 1 hour, and then at room temperature for 16 hours. The mixture was cooled in an ice bath. 10% Aqueous $Na_2CO_3$ (250 mL) was added in portions. The mixture was then partitioned between $H_2O$ and $CH_2Cl_2$. The $CH_2Cl_2$ layer was dried over $MgSO_4$ and then filtered. 2-Bromo-5-iodophenol (46 g, 96%) was obtained from the filtrate as a pinkish-white solid.

$^1$H NMR (acetone-d$_6$) δ: 9.24 (br s, 1H), 7.38 (d, J=2 Hz, 1H), 7.31 (d, J=8.5 Hz, 1H), 7.17 (dd, J=8.5 Hz, 2 Hz, 1H).

Step 7: 2-Bromo-5-iodophenol (54.9 g, 184 mmol), was dissolved in DMF (240 mL) at 0° C. Sodium tert-pentoxide (2.5 M in THF, 90 mL, 230 mmol) was then added dropwise. The reaction was stirred at 0° C. for 15 min after the addition was complete. Chloromethyl methyl ether (18 mL, 225 mmol) was added dropwise over 30 min. The mixture was warmed to ambient temperature and was stirred for 16 hours. The mixture was diluted with $H_2O$ and extracted into EtOAc. The organic layers were washed with $H_2O$ and brine. The organic layer was dried over $MgSO_4$, filtered, and concentrated under vacuum. The crude product was flushed through a silica plug using $CH_2Cl_2$ in hexanes (0-10%) to yield 1-bromo-4-iodo-2-(methoxymethoxy)benzene (61 g, 97%) as a clear liquid.

$^1$H NMR (acetone-d$_6$) δ: 7.56 (d, J=2 Hz, 1H), 7.38 (d, J=8 Hz, 1H), 7.33 (dd, J=8 Hz, 2 Hz, 1H), 5.35 (s, 2H), 3.50 (s, 3H).

Step 8: 1-Bromo-4-iodo-2-(methoxymethoxy)benzene (49 g, 143 mmol), 1-(tetrahydro-2H-pyran-2-yl)-4-(4,4,5,5-tetramethyl-1,3,2-dioxaborolan-2-yl)-1H-pyrazole (48.4 g, 174 mmol), PdCl$_2$(dppf)-dichloromethane adduct (3.1 g, 3.6 mmol), dioxane (500 mL), and aqueous $K_2CO_3$ (350 mL, 350 mmol, 1M) were heated at 90° C. for 2 hours. The reaction mixture was then partitioned between $H_2O$ and EtOAc. The organic layer was dried over $MgSO_4$, filtered, and concentrated under vacuum. Purification by silica gel chromatography (EtOAc in hexane, 20-50%), followed by trituration with hexane, yielded 4-(4-bromo-3-(methoxymethoxy)phenyl)-1-(tetrahydro-2H-pyran-2-yl)-1H-pyrazole (40.4 g, 77%) as an off-white solid.

$^1$H NMR (acetone-d$_6$) δ: 8.22 (s, 1H), 7.88 (s, 1H), 7.55 (d, J=8.5 Hz, 1H), 7.47 (d, J=2 Hz, 1H), 7.23 (dd, J=8.5 Hz, 2 Hz, 1H), 5.44 (dd, J=9.5 Hz, 2.5 Hz, 1H), 5.38 (S, 2H), 4.01 (m, 1H), 3.72 (m, 1H), 3.51 (s, 3H), 2.1-2.23 (m, 1H), 2.0-2.1 (m, 2H), 1.7-1.8 (m, 1H), 1.6-1.7 (m, 2H).

Step 9: Potassium acetate (22 g, 224 mmol) was pumped dry at 180° C. for 2 hours, and then the flask was filled with argon. 4-(4-Bromo-3-(methoxymethoxy)phenyl)-1-(tetrahydro-2H-pyran-2-yl)-1H-pyrazole (20 g, 54.5 mmol), PdCl$_2$(dppf)-dichloromethane adduct (1.22 g, 1.47 mmol), bis(pinacolato)diboron (20.8 g, 81.9 mmol), and dry toluene (200 mL) were added. The mixture was heated at 110° C. for 2 days. The mixture was filtered through Celite®, eluting with ether. The filtrate was concentrated under vacuum, dissolved in ether, and filtered through Celite®. Purification by silica gel chromatography (EtOAc in hexanes, 20-50%) yielded crude product (12 g) that was mostly free of protodeboronated by-product. This was dissolved in ether (100 mL) and washed with aqueous NaHCO$_3$ (2×1.5 L), brine, dried over MgSO$_4$, and then filtered. The filtrate was concentrated to provide pure product (7.05 g, 32%) as a glassy semi-solid.

$^1$H NMR (500 MHz, acetone-d$_6$): δ 8.24 (s, 1H), 7.90 (s, 1H), 7.65 (d, J=8 Hz, 1H), 7.33 (d, J=1.5 Hz, 1H), 7.29 (dd, J=8 Hz, 1.5 Hz, 1H), 5.45 (dd, J=10 Hz, 2.5 Hz, 1H), 5.25 (s, 2H), 4.01 (m, 1H), 3.69-3.74 (m, 1H), 3.52 (s, 3H), 2.15-2.2 (m, 1H), 2.0-2.1 (m, 2H), 1.7-1.8 (m, 1H), 1.6-1.68 (m, 2H), 1.35 (s, 12H).

Step 10: To a mixture of 5-bromo-N-methyl-N-(2,2,6,6-tetramethyl-4-piperidyl)thiazolo[5,4-d]thiazol-2-amine (120 mg, 0.31 mmol), 4-[3-(methoxymethoxy)-4-(4,4,5,5-tetramethyl-1,3,2-dioxaborolan-2-yl)phenyl]-1-tetrahydropyran-2-yl-pyrazole (153 mg, 0.37 mmol), prepared in step 5, above, PdCl$_2$(dppf) (26 mg, 0.03 mmol) in 1,4-dioxane (2.0 mL), under argon was added K$_2$CO$_3$ (0.54 mL, 1.1 mmol, 2.0 M). The mixture was stirred at 90° C. for 24 hr and then cooled and diluted with EtOAc. The precipitate was removed by filtration. The filtrate was concentrated and chromatographed (1.4 N NH$_3$ in MeOH in CH$_2$Cl$_2$, 0-20%) and then further purified by reverse phase preparative HPLC to provide the coupling product. The resultant compound was treated with HCl in CPME (3 mL, 9 mmol, 3 M) at room temperature overnight. The precipitate was collected by filtration and dried to furnish the title compound 2-[5-[methyl-(2,2,6,6-tetramethyl-4-piperidyl)amino]thiazolo[5,4-d]thiazol-2-yl]-5-(1H-pyrazol-4-yl)phenol hydrochloride (51 mg, 87.3%).

LC-MS 469.2 [M+H]$^+$, RT 1.05 min; $^1$H NMR (DMSO-d$_6$) δ: 11.08 (br s, 1H), 9.31 (br d, J=10.7 Hz, 1H), 8.24 (br d, J=11.7 Hz, 1H), 7.97-8.12 (m, 3H), 7.14-7.29 (m, 2H), 4.60 (br t, J=12.5 Hz, 1H), 3.00 (s, 3H), 2.02 (t, J=1.0 Hz, 2H), 1.86 (br dd, J=12.8, 2.7 Hz, 2H), 1.50 (d, J=12.9 Hz, 12H).

Using the procedure described for Example 1, above, additional compounds described herein were prepared by substituting the appropriate starting materials, suitable reagents and reaction conditions, obtaining compounds such as those selected from:

| Cpd | Data |
|---|---|
| 3 | LC-MS 489.2 [M + H]$^+$; $^1$H NMR (DMSO-d$_6$) δ: 9.37 (br d, J = 1.0 Hz, 1H), 8.32 (br d, J = 1.0 Hz, 1H), 8.20 (d, J = 0.9 Hz, 2H), 7.94 (br t, J = 7.1 Hz, 1H), 7.71 (t, J = 7.3 Hz, 1H), 4.65 (br t, J = 12.1 Hz, 2H), 3.03 (s, 3H), 2.07 (br t, J = 12.9 Hz, 2H), 1.86 (br dd, J = 12.8, 2.4 Hz, 2H), 1.51 (d, J = 9.5 Hz, 12H). |
| 4 | LC-MS 489.2 [M + H]$^+$; $^1$H NMR (DMSO-d$_6$) δ: 9.52 (br d, J = 11.0 Hz, 1H), 8.44 (br d, J = 11.0 Hz, 1H), 8.21 (d, J = 1.9 Hz, 2H), 7.94 (dd, J = 11.7, 6.3 Hz, 1H), 7.88 (dd, J = 12.3, 6.3 Hz, 1H), 4.63 (br t, J = 12.1 Hz, 1H), 3.02 (s, 3H), 2.09 (br t, J = 12.8 Hz, 2H), 1.83 (br dd, J = 12.9, 2.2 Hz, 2H), 1.52 (d, J = 2.5 Hz, 12H). |
| 5 | LC-MS 489.2 [M + H]$^+$; $^1$H NMR (DMSO-d$_6$) δ: 9.26 (br s, 1H), 8.31 (s, 2H), 8.20 (br s, 1H), 7.63 (d, J = 10.7 Hz, 2H), 4.64 (br t, J = 12.5 Hz, 1H), 3.04 (s, 3H), 2.04 (t, J = 1.0 Hz, 2H), 1.88 (br dd, J = 13.2, 2.5 Hz, 2H), 1.50 (d, J = 14.2 Hz, 12H). |
| 13 | LC-MS 425.3 [M + H]$^+$; $^1$H NMR (DMSO-d$_6$) δ: 11.05 (br s, 1H), 8.92-9.13 (m, 2H), 8.37 (br d, J = 6.3 Hz, 1H), 8.05 (s, 2H), 7.98 (d, J = 8.8 Hz, 1H), 7.17-7.25 (m, 2H), 4.09-4.21 (m, 1H), 3.98-4.07 (m, 2H), 2.16-2.24 (m, 2H), 1.93-2.06 (m, 4H), 1.74-1.85 (m, 2H). |
| 14 | LC-MS 413.2 [M + H]$^+$; $^1$H NMR (DMSO-d$_6$) δ: 11.04 (br s, 1H), 8.81 (br s, 1H), 8.68 (br s, 1H), 7.98-8.13 (m, 2H), 7.14-7.28 (m, 2H), 4.35-4.49 (m, 1H), 3.33-3.47 (m, 2H), 3.04-3.19 (m, 2H), 2.99 (s, 2H), 1.99-2.18 (m, 2H), 1.81-1.98 (m, 2H). |
| 20 | LC-MS 433.4 [M + H]$^+$; $^1$H NMR (DMSO-d$_6$) δ: 8.84-9.00 (m, 2H), 8.20 (d, J = 1.9 Hz, 2H), 7.93-7.99 (m, 1H), 7.85-7.92 (m, 1H), 4.34-4.52 (m, 1H), 3.29-3.46 (m, 2H), 3.03-3.17 (m, 2H), 2.98-3.03 (m, 3H), 2.06-2.19 (m, 2H), 1.84-1.97 (m, 2H). |
| 21 | LC-MS 433.1 [M + H]$^+$; $^1$H NMR (DMSO-d$_6$) δ: 8.84 (br s, 1H), 8.65 (br s, 1H), 8.09 (s, 1H), 7.67 (d, J = 10.1 Hz, 1H), 4.36-4.51 (m, 1H), 3.32-3.44 (m, 2H), 3.03-3.16 (m, 2H), 2.97-3.03 (m, 3H), 2.01-2.15 (m, 2H), 1.86-1.96 (m, 2H). |
| 22 | LC-MS 399.1 [M + H]$^+$; $^1$H NMR (DMSO-d$_6$) δ: 11.03 (br s, 1H), 8.68-8.90 (m, 2H), 8.44 (br d, J = 6.6 Hz, 1H), 8.05 (s, 2H), 7.99 (d, J = 8.8 Hz, 1H), 7.15-7.26 (m, 2H), 3.97-4.06 (m, 1H), 3.24-3.34 (m, 2H), 2.98-3.11 (m, 2H), 2.11-2.22 (m, 2H), 1.65-1.81 (m, 2H). |
| 23 | LC-MS 413.2 [M + H]$^+$; $^1$H NMR (methanol-d$_4$) δ: 8.21-8.27 (m, 2H), 7.86-7.93 (m, 1H), 7.24-7.29 (m, 2H), 4.00-4.11 (m, 1H), 3.56-3.67 (m, 2H), 3.13-3.26 (m, 2H), 2.86-2.96 (m, 3H), 2.39-2.49 (m, 2H), 1.75-1.92 (m, 2H); NH and OH not observed. |
| 24 | LC-MS 427.4 [M + H]$^+$; $^1$H NMR (methanol-d$_4$) δ: 8.30-8.39 (m, 2H), 7.83-7.90 (m, 1H), 7.26 (s, 2H), 4.45-4.55 (m, 1H), 3.62-3.71 (m, 2H), 3.21-3.30 (m, 2H), 3.07-3.13 (m, 3H), 2.88-2.98 (m, 3H), 2.20-2.35 (m, 2H), 2.08-2.18 (m, 2H); NH and OH not observed. |
| 34 | LC-MS 441.4 [M + H]$^+$; $^1$H NMR (methanol-d) δ: 8.00 (s, 2H), 7.79 (d, J = 8.5 Hz, 1H), 7.12-7.26 (m, 2H), 4.65-4.79 (m, 1H), 3.85-4.03 (m, 1H), 3.60-3.78 (m, 1H), 3.05 (s, 3H), 2.10-2.32 (m, 2H), 1.92-2.02 (m, 1H), 1.78-1.89 (m, 1H), 1.57 (d, J = 1.0 Hz, 3H), 1.39 (d, J = 6.4 Hz, 3H); NH and OH not observed. |

-continued

| Cpd | Data |
|---|---|
| 54 | LC-MS 399.2 [M + H]+; 1H NMR (DMSO-$d_6$) δ: 11.07 (br s, 1H), 9.01-9.30 (m, 2H), 7.98-8.11 (m, 3H), 7.13-7.27 (m, 2H), 4.96-5.06 (m, 1H), 3.40-3.55 (m, 2H), 3.12-3.36 (m, 2H), 3.08 (s, 3H), 2.06-2.34 (m, 2H). |
| 55 | LC-MS 399.2 [M + H]+, RT 1.02 min; 1H NMR (DMSO-$d_6$) δ: 11.07 (br s, 1H), 9.01-9.30 (m, 2H), 7.98-8.11 (m, 3H), 7.13-7.27 (m, 2H), 4.96-5.06 (m, 1H), 3.40-3.55 (m, 2H), 3.12-3.36 (m, 2H), 3.08 (s, 3H), 2.06-2.34 (m, 2H). |
| 141 | LC-MS 423.4 [M + H]+; 1H NMR (DMSO-$d_6$) δ 9.19 (s, 1H), 8.86 (s, 1H), 8.14 (m, 2H), 7.86 (d, J = 8.2 Hz, 2H), 7.73 (d, J = 8.2 Hz, 2H), 4.67-4.55 (m, 1H), 4.15-4.05 (m, 2H), 3.02 (s, 3H), 2.31-2.20 (m, 2H), 2.09-1.95 (m, 4H), 1.91-1.81 (m, 2H). |
| 147 | LC-MS 441.4 [M + H]+; 1H NMR (DMSO-$d_6$) δ 11.08 (s, 1H), 9.29 (s, 2H), 8.07 (s, 2H), 8.04 (d, J = 8.7 Hz, 1H), 7.28-7.16 (m, 2H), 4.22-4.11 (m, 1H), 3.95 (dd, J = 10.8, 7.0 Hz, 1H), 3.76 (dd, J = 10.8, 5.9 Hz, 1H), 3.73-3.66 (m, 1H), 3.54-3.45 (m, 1H), 2.45-2.35 (m, 2H), 1.39 (s, 9H). |
| 158 | LC-MS 459.3 [M + H]+; 1H NMR (methanol-$d_4$) δ 8.52 (s, 1H), 8.14 (s, 2H), 8.01 (dd, J = 11.7, 6.1 Hz, 1H), 7.68 (dd, J = 11.7, 6.2 Hz, 1H), 4.85-4.75 (m, 1H), 4.22-4.16 (m, 2H), 3.08 (s, 3H), 2.27-2.19 (m, 6H), 2.04-2.00 (m, 2H); 2NHs not observed. |
| 198 | LC-MS 451.2 [M + H]+; 1H NMR (methanol-$d_4$) δ 8.53 (s, 2H), 7.94 (d, J = 6.3 Hz, 1H), 7.34-7.25 (m, 2H), 4.38 (s, 2H), 4.17-4.13 (m, 2H), 4.00 (s, 2H), 2.50 (d, J = 15.0 Hz, 2H), 2.25-2.10 (m, 6H); 2NHs and OH not observed. |
| 200 | LC-MS 427.3 [M + H]+; 1H NMR (DMSO-$d_6$) δ: 8.94-9.12 (m, 2H), 8.12-8.31 (m, 3H), 7.33-7.49 (m, 2H), 4.33-4.48 (m, 1H), 4.08 (s, 3H), 3.30-3.44 (m, 2H), 3.03-3.21 (m, 2H), 2.99 (s, 3H), 2.04-2.23 (m, 2H), 1.78-1.98 (m, 2H). |
| 211 | LC-MS 425.2 [M + H]+; 1H NMR (DMSO-$d_6$) δ 8.07 (s, 2H), 8.03 (d, J = 8 Hz, 1H), 7.20-7.24 (m, 2H), 3.80-3.84 (m, 1H), 3.70-3.74 (m, 1H), 3.55-3.65 (m, 4H), 3.37 (m, 1H), 3.28-3.34 (m, 1H), 3.19 (m, 1H), 2.95-3.00 (m, 1H), 2.80-2.87 (m, 3H); NH and OH not observed. |

Example 2

Preparation of Compound 6

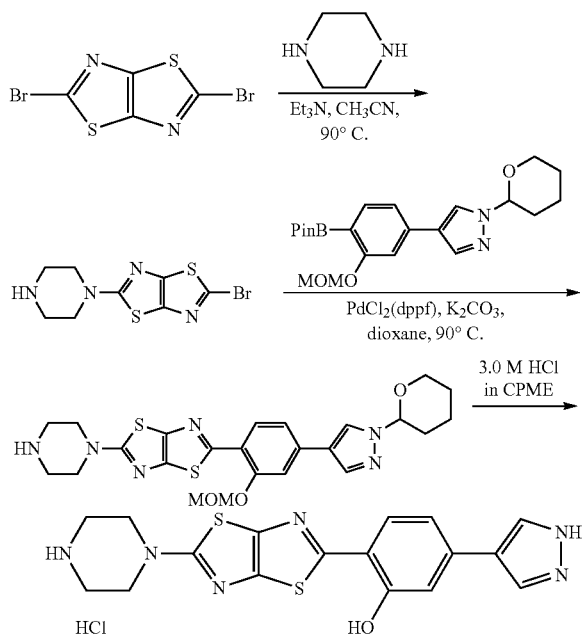

Step 1: A mixture of 2,5-dibromothiazolo[5,4-d]thiazole (299 mg, 1.00 mmol), prepared in Example 1, piperazine (172.3 mg, 2.00 mmol), and $CH_3CN$ (4.0 mL) was stirred at 90° C. for 2 hr. The solvent was evaporated, and the residue was treated with water. The precipitate was collected by filtration, washed with water and dried to provide 5-bromo-2-piperazin-1-yl-thiazolo[5,4-d]thiazole (252 mg, 82.8%). LC-MS 304.9, 306.9 [M+H]+, RT 0.92 min.

Step 2: To a mixture of 5-bromo-2-piperazin-1-yl-thiazolo[5,4-d]thiazole (125 mg, 0.41 mmol), 4-[3-(methoxymethoxy)-4-(4,4,5,5-tetramethyl-1,3,2-dioxaborolan-2-yl)phenyl]-1-tetrahydropyran-2-yl-pyrazole (203 mg, 0.49 mmol), $PdCl_2(dppf)$ (68 mg, 0.082 mmol) in 1,4-dioxane (2.0 mL), under argon was added $K_2CO_3$ (0.51 mL, 1.0 mmol, 2.0 M). The mixture was stirred at 90° C. for 24 hr and evaporated. The residue was treated with $CH_2Cl_2$ and filtered to remove the insoluble material. The filtrate was chromatographed (1.4 N $NH_3$ MeOH in $CH_2Cl_2$ 0-20%) to provide the coupling product, which was further purified by reverse phase preparative LC. The product was converted to the HCl salt by stirring with HCl in CPME (3 mL, 3 mol/L) at room temperature overnight. The precipitate was collected by filtration and dried to provide 2-(5-piperazin-1-ylthiazolo[5,4-d]thiazol-2-yl)-5-(1H-pyrazol-4-yl)phenol hydrochloride (34 mg, 20%).

LC-MS 385.1 [M+H]+, RT 0.91 min; 1H NMR (DMSO-$d_6$) δ: 11.15 (br s, 1H), 9.42-9.45 (m, 2H), 8.06 (t, J=4.3 Hz, 3H), 7.20-7.25 (m, 2H), 3.71-3.85 (m, 4H), 3.20-3.34 (m, 4H).

Using the procedure described for Example 2, above, additional compounds described herein were prepared by substituting the appropriate boronic ester intermediates, suitable reagents and reaction conditions, obtaining compounds such as those selected from:

| Cpd | Data |
|---|---|
| 7 | LC-MS 382.1 [M + H]+; 1H NMR (DMSO-$d_6$) δ: 9.23 (br s, 2H), 8.72 (s, 1H), 8.65 (d, J = 1.6 Hz, 1H), 8.39 (d, J = 1.6 Hz, 1H), 4.28 (s, 3H), 3.75-3.84 (m, 4H), 3.24-3.32 (m, 4H). |

-continued

| Cpd | Data |
|---|---|
| 176 | LC-MS 415.2 [M + H]+; 1H NMR (methanol-d4) δ: 8.33-8.44 (m, 1H), 8.00-8.11 (m, 1H), 7.54-7.69 (m, 1H), 4.25 (s, 2H), 3.96-4.06 (m, 5H), 3.19-3.27 (m, 4H), 2.08-2.20 (m, 4H); NH not observed. |
| 177 | LC-MS 445.2 [M + H]+; 1H NMR (methanol-d4) δ: 8.20 (br s, 2H), 8.01 (dd, J = 11.4, 6.3 Hz, 1H), 7.75 (dd, J = 12.1, 6.3 Hz, 1H), 3.99-4.13 (m, 4H), 3.18-3.27 (m, 4H), 2.09-2.22 (m, 4H); 2NHs not observed. |

Example 3

Preparation of Compound 10

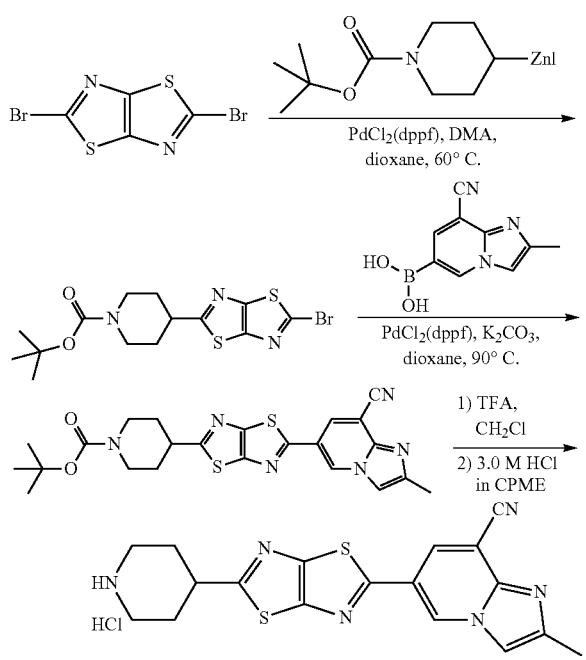

Step 1: A mixture of 2,5-dibromothiazolo[5,4-d]thiazole (1.5 g, 5.0 mmol), (1-tert-butoxycarbonyl-4-piperidyl)-iodo-zinc (6.0 mL, 6.0 mmol, 1.0 mol/L), PdCl2(dppf) (417 mg, 0.50 mmol) in 1,4-dioxane (10 mL) was stirred at 60° C. for 2 days. LC/MS showed approx. 25% conversion. The reaction mixture was evaporated and chromatographed (EtOAc in hexanes 0-50%) to provide tert-butyl 4-(5-bromothiazolo[5,4-d]thiazol-2-yl)piperidine-1-carboxylate (273 mg, 14%) as a yellow powder.

LC-MS 304.0, 305.9 [M+H]+, RT 1.79 min; 1H NMR (CDCl3) δ: 4.15-4.34 (m, 2H), 3.14-3.25 (m, 1H), 2.84-3.00 (m, 2H), 2.08-2.26 (m, 2H), 1.75-1.92 (m, 2H), 1.48 (s, 9H).

Step 2: To a mixture of tert-butyl 4-(5-bromothiazolo[5,4-d]thiazol-2-yl)piperidine-1-carboxylate (102 mg, 0.25 mmol), (8-cyano-2-methyl-imidazo[1,2-a]pyridin-6-yl)boronic acid (60 mg, 0.30 mmol), and PdCl2(dppf) (42 mg, 0.050 mmol) in 1,4-dioxane (1.0 mL), under argon was added K2CO3 (0.31 mL, 0.62 mmol, 2.0 M). The mixture was stirred at 90° C. for 4 hr and cooled. The volatiles were evaporated and the residue was chromatographed (EtOAc in CH2Cl2 0-100%) and further purified by reverse phase preparative LC to provide the coupling product as a light yellow powder.

The above coupling product was treated with 75% TFA in CH2Cl2 at room temperature for 5 min and evaporated. The residue was treated with HCl in ether (3.0 mL, 1.0 M) and stirred at room temperature for 1 hr. The precipitate was collected by filtration, washed with ether and dried to provide the title compound, 2-methyl-6-[5-(4-piperidyl)thiazolo[5,4-d]thiazol-2-yl]imidazo[1,2-a]pyridine-8-carbonitrile hydrochloride (35 mg, 34%)

LC-MS 381.3 [M+H]+, RT 0.92 min; 1H NMR (DMSO-d6) δ: 9.63 (s, 1H), 8.73-9.11 (m, 1H), 8.48 (s, 1H), 8.01 (s, 1H), 3.50-3.60 (m, 1H), 3.34-3.43 (m, 2H), 2.99-3.13 (m, 2H), 2.40-2.45 (m, 3H), 2.23-2.32 (m, 2H), 1.96-2.10 (m, 2H).

Using the procedure described for Example 3, above, additional compounds described herein were prepared by substituting the appropriate boronic ester intermediates, suitable reagents and reaction conditions, obtaining compounds such as those selected from:

| Cpd | Data |
|---|---|
| 11 | LC-MS 374.2 [M + H]+; 1H NMR (DMSO-d6) δ: 8.87-8.99 (m, 1H), 8.68-8.79 (m, 1H), 8.65 (d, J = 1.0 Hz, 1H), 8.29 (d, J = 1.0 Hz, 1H), 7.66 (dd, J = 12.3, 1.3 Hz, 1H), 4.18-4.30 (m, 3H), 3.47-3.57 (m, 1H), 3.29-3.45 (m, 2H, obscured by water signal), 3.00-3.13 (m, 2H), 2.23-2.33 (m, 2H), 1.94-2.08 (m, 2H). |
| 12 | LC-MS 371.2 [M + H]+; 1H NMR (DMSO-d6) δ: 9.02 (br d, J = 1.0 Hz, 2H), 8.33 (s, 1H), 8.04 (s, 1H), 3.50-3.60 (m, 1H, obscured by water signal), 3.34-3.43 (m, 2H), 3.02-3.14 (m, 2H), 2.69 (s, 3H), 2.49 (s, 3H), 2.25-2.34 (m, 2H), 1.99-2.13 (m, 2H). |
| 15 | LC-MS 381.2 [M + H]+; 1H NMR (DMSO-d6) δ: 8.99-9.13 (m, 1H), 8.84-8.97 (m, 1H), 8.75-8.81 (m, 2H), 8.45 (d, J = 1.9 Hz, 1H), 4.23-4.35 (m, 3H), 3.47-3.60 (m, 1H), 3.36-3.43 (m, 2H), 2.97-3.12 (m, 2H), 2.20-2.34 (m, 2H), 1.94-2.10 (m, 2H). |
| 16 | LC-MS 370.2 [M + H]+; 1H NMR (DMSO-d6) δ: 9.05 (br s, 1H), 8.87 (br s, 1H), 8.49 (s, 1H), 8.25 (s, 1H), 7.66 (s, 1H), 4.21 (s, 3H), 3.49-3.56 (m, 1H), 3.29-3.49 (m, 2H), 2.98-3.16 (m, 2H), 2.57 (s, 3H), 2.27 (br d, J = 12.6 Hz, 2H), 1.96-2.18 (m, 2H). |

-continued

| Cpd | Data |
|---|---|
| 25 | LC-MS 356.3 [M + H]+; 1H NMR (DMSO-d6) δ: 6.80 (s, 2H), 6.37-6.43 (m, 1H), 6.11-6.18 (m, 1H), 2.69 (s, 3H), 1.93-2.04 (m, 3H), 1.61-1.71 (m, 2H), 0.81-0.92 (m, 2H), 0.52-0.66 (m, 2H). |
| 26 | LC-MS 386.3 [M + H]+; 1H NMR (methanol-d4) δ: 8.30 (s, 1H), 7.94 (d, J = 1.6 Hz, 1H), 7.34 (d, J = 1.3 Hz, 1H), 4.22 (s, 3H), 4.08 (s, 3H), 3.50-3.60 (m, 3H), 3.18-3.27 (m, 2H), 2.35-2.49 (m, 2H), 2.07-2.23 (m, 2H); NH and OH not observed. |
| 208 | LC-MS 384.2 [M + H]+; 1H NMR (DMSO-d6) δ: 8.17 (d, J = 8 Hz, 1H), 8.09 (br s, 2H), 7.28 (d, J = 8 Hz, 1H), 7.26 (s, 1H), 3.49-3.54 (m, 1H), 3.08 (m, 2H), 2.28 (m, 2H), 2.00 (m, 2H) (2 aliphatic Hs are obscured by the water peak at 3.33 ppm); 2NHs and OH not observed. |

Example 4

Preparation of Compound 17

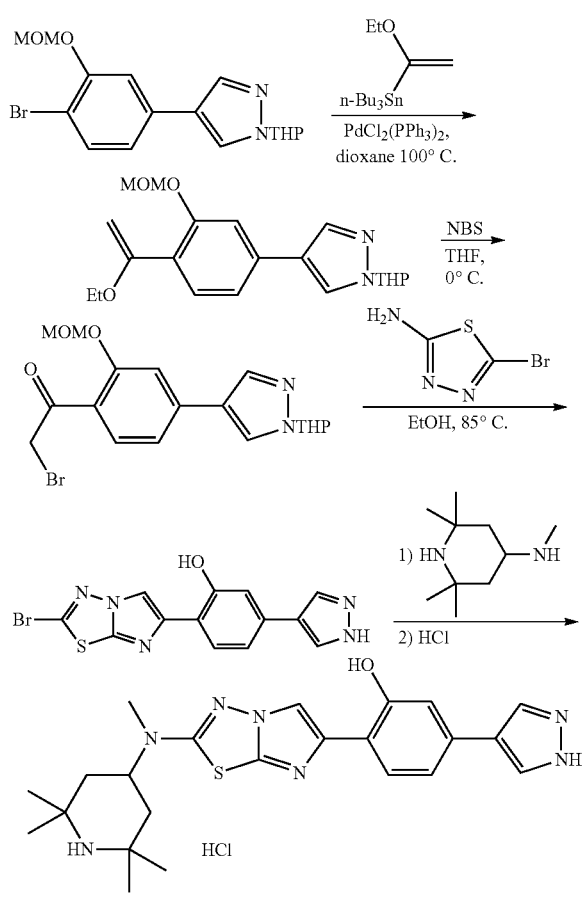

Step 1: A mixture of 4-[4-bromo-3-(methoxymethoxy)phenyl]-1-tetrahydropyran-2-yl-pyrazole, prepared in Example 1, Step 8 (3.36 g, 9.15 mmol), PdCl2(PPh3)2 (642 mg, 0.92 mmol), 1,4-dioxane (20 mL), and tributyl(1-ethoxyvinyl)tin (3.90 mL, 11.0 mmol) was heated at 100° C. overnight. The solvent was removed under reduced pressure and the residue was chromatographed (EtOAc in hexanes 0-100%) to provide 4-[4-(1-ethoxyvinyl)-3-(methoxymethoxy)phenyl]-1-tetrahydropyran-2-yl-pyrazole (1.76 g, 4.91 mmol, 53.7%).

LC-MS 359.3 [M+H]+, RT 1.58 min; 1H NMR (CDCl3) δ: 7.94 (s, 1H), 7.86 (s, 1H), 7.78 (d, J=7.9 Hz, 1H), 7.30 (d, J=1.3 Hz, 1H), 7.19 (dd, J=8.2, 1.6 Hz, 1H), 5.38-5.48 (m, 1H), 5.34 (s, 2H), 4.04-4.20 (m, 1H), 3.73 (q, J=6.9 Hz, 3H), 3.50-3.59 (m, 3H), 2.01-2.20 (m, 4H), 1.58-1.82 (m, 4H), 1.25 (t, J=7.1 Hz, 3H).

Step 2: To a mixture of 4-[4-(1-ethoxyvinyl)-3-(methoxymethoxy)phenyl]-1-tetrahydropyran-2-yl-pyrazole (1.76 g, 4.91 mmol), THF (18 mL) and water (6 mL) was added NBS (874 mg, 4.91 mmol) at 0° C. The reaction was stirred for 0.5 hr. The mixture was diluted with water and then extracted with EtOAc. The organic layer was dried and concentrated to dryness. The residue was chromatographed (EtOAc in hexanes, 0-50%) to provide 2-bromo-1-[2-(methoxymethoxy)-4-(1-tetrahydropyran-2-ylpyrazol-4-yl)phenyl]ethanone (781 mg, 38.9%). LC-MS 409.2, 411.3 [M+H]+, RT 1.48 min.

Step 3: A mixture of 2-bromo-1-[2-(methoxymethoxy)-4-(1-tetrahydropyran-2-ylpyrazol-4-yl)phenyl]ethanone (740 mg, 1.81 mmol) and 5-bromo-1,3,4-thiadiazol-2-amine (326 mg, 1.81 mmol) in EtOH (10 mL) was stirred at 85° C. overnight. The solvent was evaporated, and the residue was treated with water and NaHCO3. The solid was collected, washed with water and CH2Cl2, and then dried under N2 to provide 2-(2-bromoimidazo[2,1-b][1,3,4]thiadiazol-6-yl)-5-(1H-pyrazol-4-yl)phenol (486 mg, 74.2%).

LC-MS 362.2, 364.2 [M+H]+, RT 1.30 min; 1H NMR (DMSO-d6) δ: 11.41-11.54 (m, 1H), 8.61 (s, 1H), 8.04 (s, 1H), 7.84-7.98 (m, 2H), 7.04-7.38 (m, 2H), 5.76-5.98 (m, 1H).

Step 4: A mixture of 2-(2-bromoimidazo[2,1-b][1,3,4]thiadiazol-6-yl)-5-(1H-pyrazol-4-yl)phenol (72.4 mg, 0.20 mmol), N,2,2,6,6-pentamethylpiperidin-4-amine (41 mg, 0.24 mmol), triethylamine (84 μL, 0.60 mmol) and CH3CN (2.0 mL) was stirred at 100° C. for 12 hr. The reaction was concentrated and suspended in water. The precipitate was collected, washed with water and dried, and purified by reverse phase preparative HPLC. The product was converted to the HCl salt using HCl in diethyl ether (2.0 mL, 1.0 M) to provide the title compound, 2-[2-[methyl-(2,2,6,6-tetramethyl-4-piperidyl)amino]imidazo[2,1-b][1,3,4]thiadiazol-6-yl]-5-(1H-pyrazol-4-yl)phenol; hydrochloride (23 mg, 23.6%) as a white solid.

LC-MS 452.5 [M+H]+, RT 0.99 min; 1H NMR (DMSO-d6) δ: 9.41 (br d, J=11.0 Hz, 1H), 8.43 (s, 1H), 8.34 (br d, J=11.3 Hz, 1H), 8.04 (s, 2H), 7.63-7.81 (m, 1H), 7.09-7.25 (m, 2H), 4.23-4.35 (m, 1H), 3.01 (s, 3H), 1.99-2.12 (m, 2H), 1.82-1.95 (m, 2H), 1.50 (d, J=2.8 Hz, 12H).

Using the procedure described for Example 4, above, additional compounds described herein were prepared by substituting the appropriate boronic ester intermediates, suitable reagents and reaction conditions, obtaining compounds such as those selected from:

| Cpd | Data |
|---|---|
| 18 | LC-MS 422.4 [M + H]$^+$; $^1$H NMR (DMSO-d$_6$) δ: 9.06-9.16 (m, 1H), 8.78-8.86 (m, 1H), 8.34 (s, 1H), 8.02 (s, 2H), 7.71 (d, J = 8.5 Hz, 1H), 7.08-7.14 (m, 2H), 4.14-4.30 (m, 1H), 3.95-4.12 (m, 2H), 3.00 (s, 3H), 2.19-2.31 (m, 2H), 1.80-2.13 (m, 6H); NH and OH not observed. |
| 19 | LC-MS 422.4 [M + H]$^+$; $^1$H NMR (DMSO-d$_6$) δ: 10.63 (br s, 1H), 8.68 (br s, 1H), 8.35-8.44 (m, 1H), 8.03 (s, 2H), 7.70 (d, J = 8.5 Hz, 1H), 7.10-7.19 (m, 2H), 4.01-4.12 (m, 1H), 3.93 (br s, 2H), 2.66 (d, J = 5.0 Hz, 3H), 2.19-2.31 (m, 4H), 1.94-2.14 (m, 4H); 1NH not observed. |

Example 5

Preparation of Compound 27

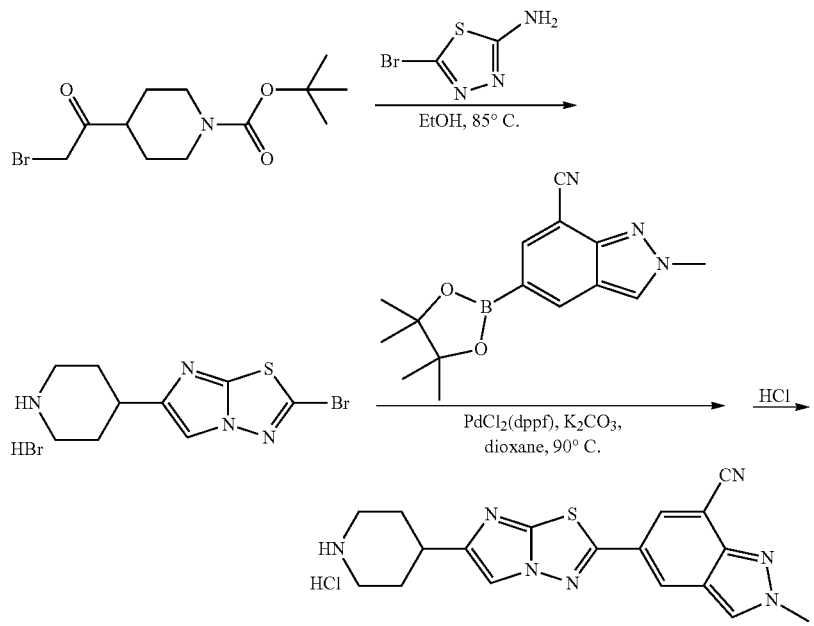

Step 1: A mixture of tert-butyl 4-(2-bromoacetyl)piperidine-1-carboxylate (919 mg, 3.0 mmol) and 5-bromo-1,3,4-thiadiazol-2-amine (540 mg, 3.0 mmol) in ethanol (5.0 mL) was stirred at 85° C. overnight. The mixture was then diluted with EtOAc (10 mL) and stirred for 1 h. The precipitate was collected, washed with EtOAc and dried to provide 2-bromo-6-(4-piperidyl)imidazo[2,1-b][1,3,4]thiadiazole hydrobromide (978 mg, 88.5%).

LC-MS 287.2, 289.2 [M+H]$^+$, RT 0.97 min; $^1$H NMR (DMSO-d$_6$) δ: 8.06 (d, J=0.6 Hz, 1H), 7.82 (br s, 1H), 3.04-3.50 (m, 2H), 2.82-3.01 (m, 3H), 1.97-2.12 (m, 2H), 1.61-1.81 (m, 2H).

Step 2: To a mixture of 2-bromo-6-(4-piperidyl)imidazo[2,1-b][1,3,4]thiadiazole hydrobromide (92 mg, 0.25 mmol), 2-methyl-5-(4,4,5,5-tetramethyl-1,3,2-dioxaborolan-2-yl) indazole-7-carbonitrile (106 mg, 0.38 mmol), and PdCl$_2$(dppf) (21 mg, 0.03 mmol) in 1,4-dioxane (2.0 mL), under argon, was added K$_2$CO$_3$ (0.44 mL, 0.88 mmol, 2.0 M). The mixture was stirred at 90° C. overnight and cooled. The volatiles were evaporated and the residue was purified by reverse phase preparative LC to provide the title compound, 2-methyl-5-[6-(4-piperidyl)imidazo[2,1-b][1,3,4]thiadiazol-2-yl]indazole-7-carbonitrile 2,2,2-trifluoroacetic acid (4.0 mg, 3.4%).

LC-MS 364.3 [M+H]$^+$, RT 0.85 min; $^1$H NMR (methanol-d$_4$) δ: 8.58-8.65 (m, 2H), 8.33-8.41 (m, 1H), 7.91 (s, 1H), 4.32 (s, 3H), 3.47-3.56 (m, 2H), 3.02-3.24 (m, 3H), 2.23-2.35 (m, 2H), 1.89-2.05 (m, 2H); NH and OH not observed.

Using the procedure described for Example 5, above, additional compounds described herein were prepared by substituting the appropriate starting materials, suitable reagents and reaction conditions, obtaining compounds such as those selected from:

| Cpd | Data |
|---|---|
| 28 | LC-MS 357.3 [M + H]$^+$; $^1$H NMR (methanol-d$_4$) δ: 8.45-8.56 (m, 1H), 8.06-8.23 (m, 1H), 7.89 (s, 1H), 7.62 (br d, J = 12.0 Hz, 1H), 4.28 (s, 3H), 3.50 (br d, J = 12.9 Hz, 2H), 3.02-3.24 (m, 3H), 2.22-2.33 (m, 2H), 1.86-2.05 (m, 2H); NH and OH not observed. |
| 29 | LC-MS 364.0 [M + H]$^+$; $^1$H NMR (DMSO-d$_6$) δ: 9.58 (d, J = 1.9 Hz, 1H), 8.78-8.89 (m, 1H), 8.55-8.67 (m, 1H), 8.38 (d, J = 1.9 Hz, 1H), 8.12 (d, J = 0.9 Hz, |

| Cpd | Data |
|---|---|
|  | 1H), 8.01 (d, J = 0.9 Hz, 1H), 3.26-3.37 (m, 2H), 2.92-3.11 (m, 3H), 2.44 (d, J = 0.9 Hz, 3H), 2.10-2.23 (m, 2H), 1.78-1.95 (m, 2H). |
| 30 | LC-MS 357.4 [M + H]$^+$; $^1$H NMR (DMSO-d$_6$) δ: 9.28 (d, J = 1.6 Hz, 1H), 8.97 (br d, J = 9.1 Hz, 1H), 8.76 (br d, J = 8.8 Hz, 1H), 8.12 (d, J = 0.9 Hz, 1H), 8.02 (d, J = 1.9 Hz, 1H), 7.75 (br d, J = 11.0 Hz, 1H), 3.21-3.35 (m, 2H), 2.89-3.09 (m, 3H), 2.43 (d, J = 0.9 Hz, 3H), 2.05-2.21 (m, 2H), 1.75-1.94 (m, 2H). |

Example 6

Preparation of Compound 9

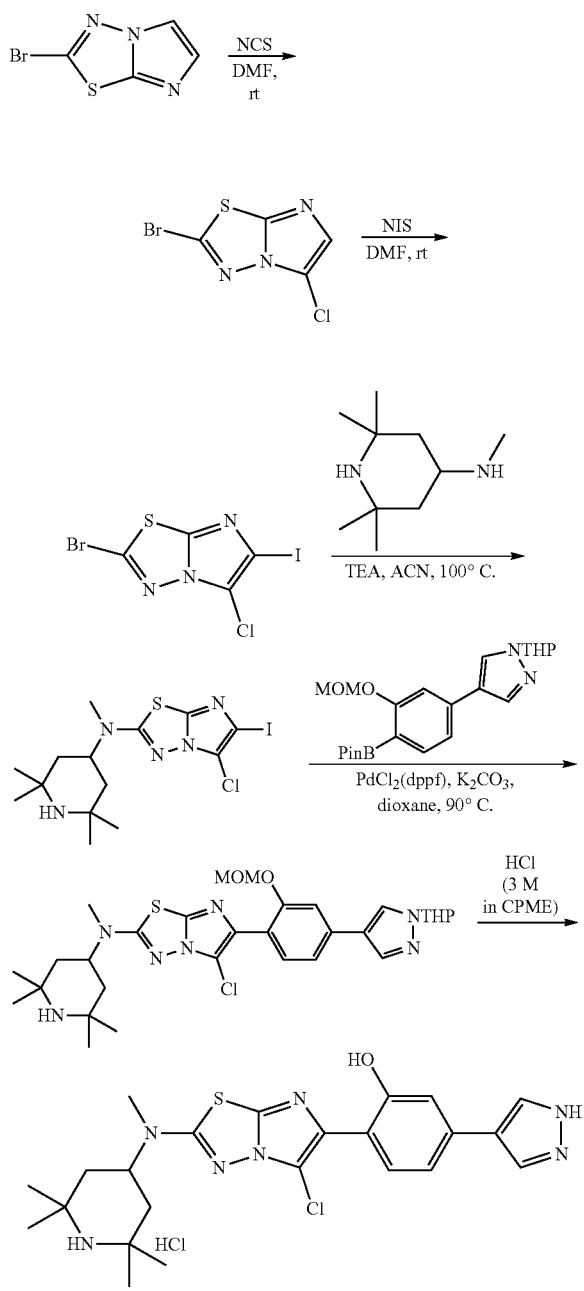

Step 1: A mixture of 2-bromoimidazo[2,1-b][1,3,4]thiadiazole (1.02 g, 5.00 mmol) and 1-chloropyrrolidine-2,5-dione (434 mg, 3.25 mmol) in DMF (10 mL) was stirred at room temperature for 2 h. The mixture was diluted with water and treated with Na$_2$S$_2$O$_3$. The precipitate was collected, washed with water, dried and chromatographed (silica gel, EtOAc in CH$_2$Cl$_2$ 0-30%) to provide 2-bromo-5-chloro-imidazo[2,1-b][1,3,4]thiadiazole (706 mg, 59.2%). LC-MS 239.8 [M+H]$^+$, RT 1.22 min.

Step 2: A mixture of 2-bromo-5-chloro-imidazo[2,1-b][1,3,4]thiadiazole (706 mg, 2.96 mmol), NIS (1.36 g, 5.92 mmol) and DMF (8 mL) was stirred at 60° C. for 2 days. The mixture was diluted with water and treated with Na$_2$S$_2$O$_3$. The precipitate was collected, washed with water, and then dried and chromatographed (silica gel, EtOAc in CH$_2$Cl$_2$ 0-10%) to provide 2-bromo-5-chloro-6-iodo-imidazo[2,1-b][1,3,4]thiadiazole (0.92 g, 85%). LC-MS 365.8 [M+H]$^+$, RT 1.46 min.

Step 3: A mixture of 2-bromo-5-chloro-6-iodo-imidazo[2,1-b][1,3,4]thiadiazole (0.92 g, 2.5 mmol), triethylamine (0.70 mL, 5.0 mmol), CH$_3$CN (10 mL) and N,2,2,6,6-pentamethylpiperidin-4-amine (0.64 g, 3.8 mmol) was stirred at 100° C. for 3 h. After cooling, the solvent was removed. The residue was treated with water, extracted with CH$_2$Cl$_2$ and dried. After the removal of the solvent, the residue was chromatographed (MeOH in CH$_2$Cl$_2$ 0-20%) to provide 5-chloro-6-iodo-N-methyl-N-(2,2,6,6-tetramethyl-4-piperidyl)imidazo[2,1-b][1,3,4]thiadiazol-2-amine (1.05 g, 92%). LC-MS 454.0, 456.0 [M+H]$^+$, RT 1.07 min.

Step 4: To a mixture of 5-chloro-6-iodo-N-methyl-N-(2,2,6,6-tetramethyl-4-piperidyl)imidazo[2,1-b][1,3,4]thiadiazol-2-amine (136 mg, 0.30 mmol), 4-[3-(methoxymethoxy)-4-(4,4,5,5-tetramethyl-1,3,2-dioxaborolan-2-yl)phenyl]-1-tetrahydropyran-2-yl-pyrazole (149 mg, 0.36 mmol), and PdCl$_2$(dppf) (25 mg, 0.03 mmol) in 1,4-dioxane (1.0 mL), under argon, was added K$_2$CO$_3$ (0.38 mL, 0.76 mmol, 2.0 M). The mixture was stirred at 90° C. for 12 h and cooled. The volatiles were evaporated, and the residue was chromatographed (MeOH in CH$_2$Cl$_2$ 0-30%). The product was treated with HCl (3.0 mL, 9.0 mmol, 3 M in CPME) at room temperature overnight, to provide the title compound 2-(5-chloro-2-(methyl(2,2,6,6-tetramethylpiperidin-4-yl)amino)imidazo[2,1-b][1,3,4]thiadiazol-6-yl)-5-(1H-pyrazol-4-yl)phenol hydrochloride (95 mg, 61%).

LC-MS 486.3 [M+H]$^+$, RT 1.06 min; $^1$H NMR (DMSO-d$_6$) δ: 9.44 (br d, J=12.3 Hz, 1H), 8.39 (br d, J=11.7 Hz, 1H), 8.10 (s, 2H), 7.78 (d, J=8.8 Hz, 1H), 7.15-7.20 (m, 2H), 4.18-4.32 (m, 1H), 3.01 (s, 3H), 1.99-2.12 (m, 2H), 1.85-1.94 (m, 2H), 1.42-1.59 (m, 12H).

Example 7

Preparation of Compound 8

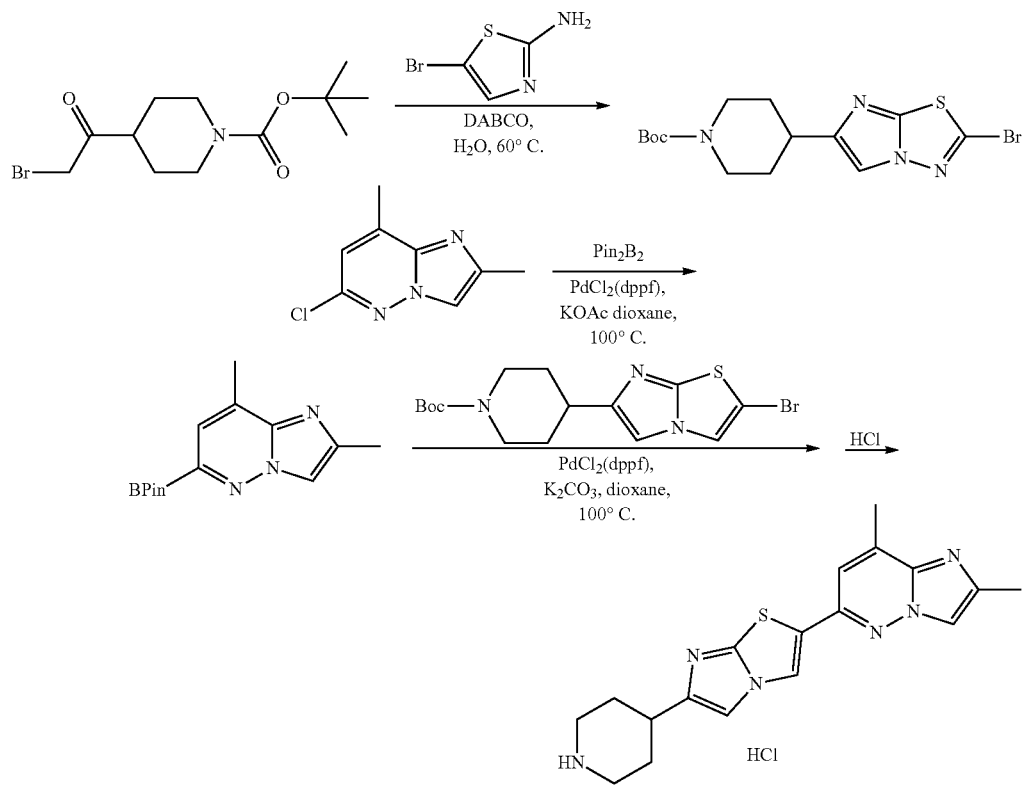

Step 1: A mixture of tert-butyl 4-(2-bromoacetyl)piperidine-1-carboxylate (4.3 g, 14 mmol), 5-bromothiazol-2-amine (3.0 g, 16.8 mmol, 1.2 eq.), and DABCO (0.16 g, 1.4 mmol, 0.1 eq.) in water (20 mL) was stirred at 60° C. for 16 h, then cooled, basified with saturated aqueous NaHCO₃ and extracted with EtOAc. The organic extracts were combined, and dried over Na₂SO₄ and evaporated. The residue was purified by column chromatography to give tert-butyl 4-(2-bromoimidazo[2,1-b]thiazol-6-yl)piperidine-1-carboxylate (2.4 g, 44%).

¹H NMR (DMSO-d₆) δ: 8.18 (s, 1H), 7.50 (s, 1H), 3.97 (d, J=8.8 Hz, 2H), 2.79-2.95 (br. s, 2H), 2.74 (m, 1H), 1.89 (d, J 11.0 Hz, 2H), 1.44 (m, 2H), 1.40 (s, 9H).

Step 2: A mixture of 6-chloro-2,8-dimethyl-imidazo[1,2-b]pyridazine (38 mg, 0.21 mmol), 4,4,4',4',5,5,5',5'-octamethyl-2,2'-bi(1,3,2-dioxaborolane) (80 mg, 0.31 mmol), PdCl₂(dppf) (17 mg, 0.021 mmol) and KOAc (62 mg, 0.63 mmol) in dioxane (2.0 mL) was stirred at 100° C. for 2 h. After cooling, tert-butyl 4-(2-bromoimidazo[2,1-b]thiazol-6-yl)piperidine-1-carboxylate (54 mg, 0.14 mmol), PdCl₂dppf dichloromethane adduct (17 mg, 0.021 mmol) and aqueous K₂CO₃ (0.31 mL, 0.63 mmol, 2.0 M) were added, and the mixture was heated at 100° C. for another 3 h. The mixture was cooled, diluted with EtOAc, washed with water and brine, dried over Na₂SO₄ and concentrated. The residue was purified over silica with MeOH in CH₂Cl₂ (0-10% gradient) to provide tert-butyl 4-[2-(2,8-dimethylimidazo[1,2-b]pyridazin-6-yl)imidazo[2,1-b]thiazol-6-yl] piperidine-1-carboxylate, which was further treated with HCl (4 M in dioxane). After 2 h, the mixture was diluted with ether, filtered and dried to give the title compound, 2-(2,8-dimethylimidazo[1,2-b]pyridazin-6-yl)-6-(4-piperidyl)imidazo[2,1-b]thiazole; hydrochloride (26 mg, 48%).

LC-MS 353.3 [M+H]⁺; ¹H NMR (methanol-d₄) δ: 9.17 (s, 1H), 8.38 (m, 2H), 8.13 (s, 1H), 3.53-3.62 (m, 2H), 3.21-3.29 (m, 3H), 2.84 (s, 3H), 2.68 (s, 3H), 2.34-2.43 (m, 2H), 2.00-2.11 (m, 2H); NH and OH not observed.

Using the procedure described for Example 7, above, additional compounds described herein were prepared by substituting the appropriate starting materials, suitable reagents and reaction conditions, obtaining compounds such as those selected from:

| Cpd | Data |
|-----|------|
| 2 | LC-MS 352.1 [M + H]⁺; ¹H NMR (DMSO-d₆) δ: 8.62 (br s, 1H), 8.37 (m, 3H), 7.72 (s, 1H), 7.63 (s, 1H), 7.36 (s, 1H), 4.19 (s, 3H), 3.35 (d, J = 11.7 Hz, 2H), 2.90-3.11 (m, 3H), 2.55 (s, 3H), 2.12 (d, J = 13.2 Hz, 2H), 1.72-1.86 (m, 2H). |

Example 8

Preparation of Compound 31

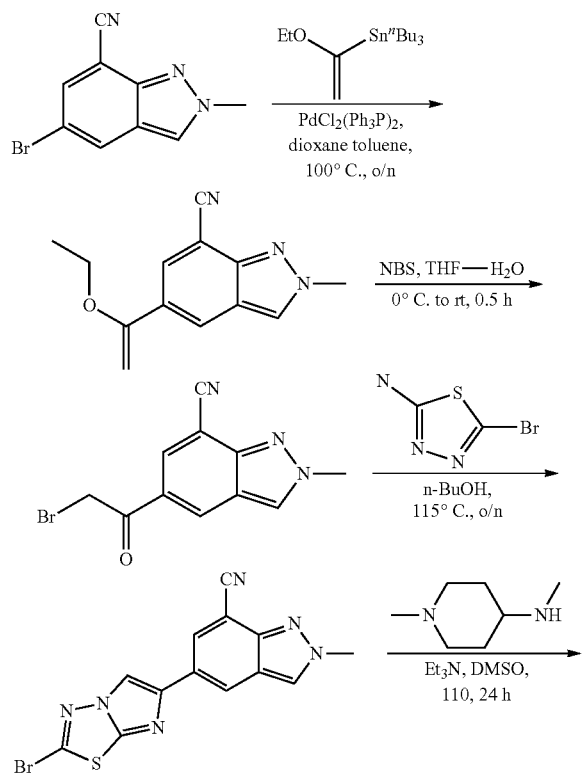

Step 1: A mixture of 5-bromo-2-methyl-indazole-7-carbonitrile (1.65 g, 7.0 mmol), PdCl$_2$(dppf) (491 mg, 0.70 mmol), 1,4-dioxane (25 mL, 292.8 mmol), and tributyl(1-ethoxyvinyl)stannane (2.99 mL, 8.41 mmol) was heated at 100° C. overnight. The solvent was removed under reduced pressure, and the residue was chromatographed (EtOAc in hexanes 0-100%) to provide 5-(1-ethoxyvinyl)-2-methyl-indazole-7-carbonitrile (1.12 g, 70.5%).

LC-MS 228.4 [M+H]$^+$, RT 1.29 min; $^1$H NMR (CDCl$_3$) δ: 8.59 (d, J=1.58 Hz, 1H), 8.34 (d, J=1.58 Hz, 1H), 8.24 (s, 1H), 4.34 (s, 3H), 3.73 (q, J=7.04 Hz, 2H), 2.67 (s, 2H), 1.25 (t, J=6.94 Hz, 3H).

Step 2: To a solution of 5-(1-ethoxyvinyl)-2-methyl-indazole-7-carbonitrile (1.12 g, 4.9 mmol) in THF (18 mL) at 0° C. was added NBS (913 mg, 5.0 mmol). The mixture was stirred for 0.5 h at 0° C. until LC/MS showed a complete disappearance of starting material. The mixture was diluted with water, extracted with EtOAc, dried and then concentrated to dryness. The residue was chromatographed (EtOAc in CH$_2$Cl$_2$, 0-70%) to provide 5-(2-bromoacetyl)-2-methyl-indazole-7-carbonitrile (987 mg, 3.5 mmol, 72.0%).

LC-MS 278.2, 280.2 [M+H]$^+$, RT 1.08 min; $^1$H NMR (CDCl$_3$) δ: 8.66 (d, J=1.58 Hz, 1H), 8.33 (d, J=1.58 Hz, 1H), 8.28 (s, 1H), 4.46 (s, 2H), 4.35 (s, 3H).

Step 3: A mixture of 5-(2-bromoacetyl)-2-methyl-indazole-7-carbonitrile (987 mg, 3.5 mmol) and 5-bromo-1,3,4-thiadiazol-2-amine (639 mg, 3.5 mmol) in 1-butanol (30 mL) was stirred at 115° C. overnight. The mixture was diluted with EtOAc and stirred for 0.5 h. The precipitate was collected by filtration, washed with EtOAc and dried to provide 5-(2-bromoimidazo[2,1-b][1,3,4]thiadiazol-6-yl)-2-methyl-indazole-7-carbonitrile (890 mg, 69.8%) as a white powder.

LC-MS 359.1, 361.1 [M+H]$^+$, RT 1.22 min; $^1$H NMR (DMSO-d$_6$) δ: 8.83 (s, 1H), 8.65 (s, 1H), 8.54 (d, J=1.26 Hz, 1H), 8.38 (d, J=1.58 Hz, 1H), 4.24 (s, 3H).

Step 4: A mixture of 5-(2-bromoimidazo[2,1-b][1,3,4]thiadiazol-6-yl)-2-methyl-indazole-7-carbonitrile (90 mg, 0.25 mmol), N,1-dimethylpiperidin-4-amine (39 mg, 0.30 mmol), triethylamine (87 μL, 0.62 mmol) and DMSO (2.5 mL) was stirred at 110° C. for 24 h. After concentration, the residue was chromatographed (1.4 N NH$_3$ in MeOH in CH$_2$Cl$_2$, 0-25%) to provide the product, which was treated with 2 drops of TFA and dissolved in MeOH/DMSO and purified by prep HPLC. The pure fractions were combined and concentrated to dryness and treated with HCl in diethyl ether (3.0 mL, 1.0 M). The precipitate was collected, washed with diethyl ether and dried to provide 2-methyl-5-[2-[methyl-(1-methyl-4-piperidyl)amino]imidazo[2,1-b][1,3,4]thiadiazol-6-yl]indazole-7-carbonitrile hydrochloride (49 mg, 44.1%).

LC-MS 407.4 [M+H]$^+$, RT 0.80 min; $^1$H NMR (DMSO-d$_6$) δ: 9.14-9.23 (m, 1H), 8.61 (s, 1H), 8.46 (d, J=1.58 Hz, 1H), 8.41 (s, 1H), 8.33 (d, J=1.58 Hz, 1H), 4.23 (s, 3H), 3.86-4.15 (m, 1H), 3.11-3.57 (m, 4H), 2.70-2.79 (m, 3H), 2.53-2.55 (m, 3H), 1.62-2.33 (m, 4H).

Example 9

Preparation of Compound 32

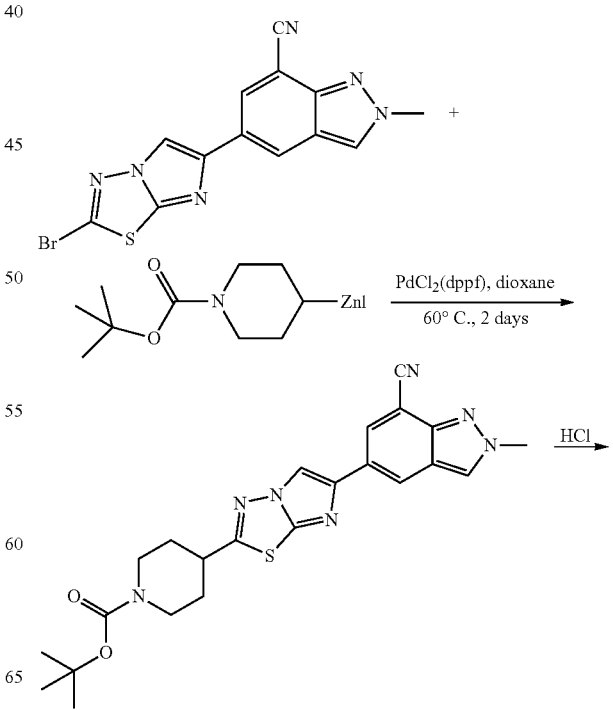

-continued

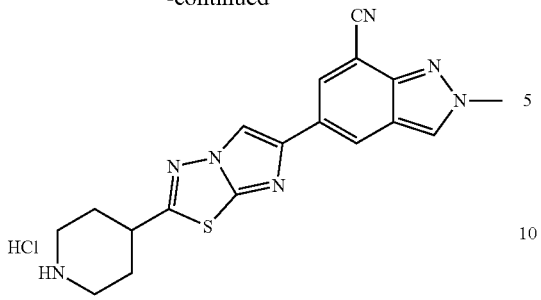

Step 1: A mixture of 5-(2-bromoimidazo[2,1-b][1,3,4]thiadiazol-6-yl)-2-methyl-indazole-7-carbonitrile (36 mg, 0.10 mmol, prepared in Example 8), PdCl$_2$(dppf) dichloromethane complex (8 mg, 0.01 mmol), (1-tert-butoxycarbonyl-4-piperidyl)iodozine (0.12 mL, 0.12 mmol, 1.0 mol/L in DMA) and 1,4-dioxane (0.5 mL) was stirred at 60° C. for 2 days. The solvent was removed under reduced pressure, and the residue was chromatographed (EtOAc in hexanes 0-50%) to provide the coupling product, used directly in Step 2. LC-MS 464.4 [M+H]$^+$, RT 1.37 min.

Step 2: The product from Step 1 was treated with dichloromethane (0.5 mL) and TFA (0.5 mL) at room temperature for 15 min. The mixture was concentrated under reduced pressure, and the residue was purified by HPLC. The desired product fractions were combined and concentrated to dryness. The residue was treated with HCl in diethyl ether (2 mL, 1.0 M) and stirred at room temperature for 4 h. The precipitate was collected by filtration, washed with diethyl ether and dried to provide 2-methyl-5-[2-(4-piperidyl)imidazo[2,1-b][1,3,4]thiadiazol-6-yl]indazole-7-carbonitrile hydrochloride (6.2 mg, 16%) as a white powder.

LC-MS 364.4 [M+H]$^+$, RT 0.78 min; $^1$H NMR (DMSO-d$_6$) δ: 8.78-8.90 (m, 1H), 8.74-8.78 (m, 1H), 8.59-8.69 (m, 2H), 8.55 (d, J=1.58 Hz, 1H), 8.38 (d, J=1.58 Hz, 1H), 4.25 (s, 3H), 3.45-3.56 (m, 1H), 3.33-3.43 (m, 2H), 2.99-3.12 (m, 2H), 2.21-2.32 (m, 2H), 1.90-2.06 (m, 2H).

Example 10

Preparation of Compound 33

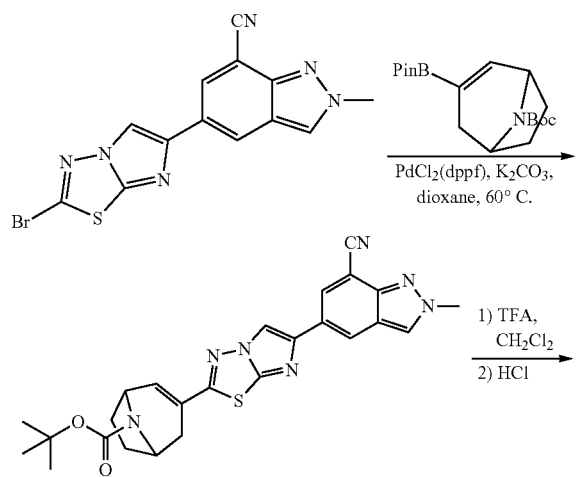

-continued

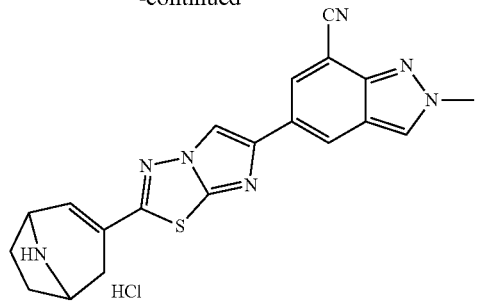

Step 1: To a mixture of 5-(2-bromoimidazo[2,1-b][1,3,4]thiadiazol-6-yl)-2-methyl-indazole-7-carbonitrile (72 mg, 0.20 mmol), prepared in Example 8, tert-butyl 3-(4,4,5,5-tetramethyl-1,3,2-dioxaborolan-2-yl)-8-azabicyclo[3.2.1]oct-3-ene-8-carboxylate (80 mg, 0.24 mmol), and PdCl$_2$(dppf) dichloromethane complex (17 mg, 0.020 mmol) in 1,4-dioxane (1.0 mL), under argon was added K$_2$CO$_3$ (0.25 mL, 0.50 mmol, 2.0 M). The mixture was stirred at 90° C. overnight and cooled. The mixture was concentrated under reduced pressure, and the residue was chromatographed (EtOAc in CH$_2$Cl$_2$ 0-100%) to provide the coupling product, which was used directly in Step 2. LC-MS 488.4 [M+H]$^+$, RT 1.44 min.

Step 2: The product from Step 1, tert-butyl 3-[6-(7-cyano-2-methyl-indazol-5-yl)imidazo[2,1-b][1,3,4]thiadiazol-2-yl]-8-azabicyclo[3.2.1]oct-3-ene-8-carboxylate was treated with CH$_2$Cl$_2$ (0.5 mL) and TFA (0.5 mL) at room temperature for 15 min and evaporated to dryness. The residue was purified by HPLC, and the desired product fractions were combined and concentrated to dryness. The residue was treated with HCl in diethyl ether (2.0 mL, 1.0 M) and stirred at room temperature for 4 h. The precipitate was collected by filtration, washed with ethyl ether and dried to provide 5-[2-(8-azabicyclo[3.2.1]oct-3-en-3-yl)imidazo[2,1-b][1,3,4]thiadiazol-6-yl]-2-methyl-indazole-7-carbonitrile hydrochloride (5.1 mg, 6.0%) as a white powder.

LC-MS 388.4 [M+H]$^+$, RT 0.83 min; $^1$H NMR (DMSO-d$_6$) δ: 9.40 (br d, J=1.0 Hz, 1H), 9.25 (br d, J=9.5 Hz, 1H), 8.80 (s, 1H), 8.66 (s, 1H), 8.56 (d, J=1.6 Hz, 1H), 8.39 (d, J=1.6 Hz, 1H), 6.94 (d, J=5.7 Hz, 1H), 4.42-4.49 (m, 1H), 4.29-4.35 (m, 1H), 4.22-4.27 (m, 3H), 3.14 (br dd, J=17.7, 4.1 Hz, 1H), 2.76 (d, J=1.0 Hz, 1H), 2.07-2.30 (m, 3H), 1.85-1.98 (m, 1H).

Example 11

Preparation of Compound 35

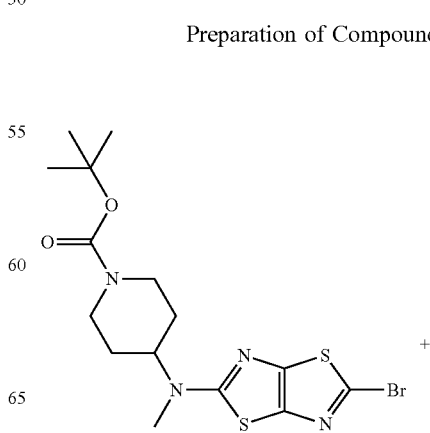

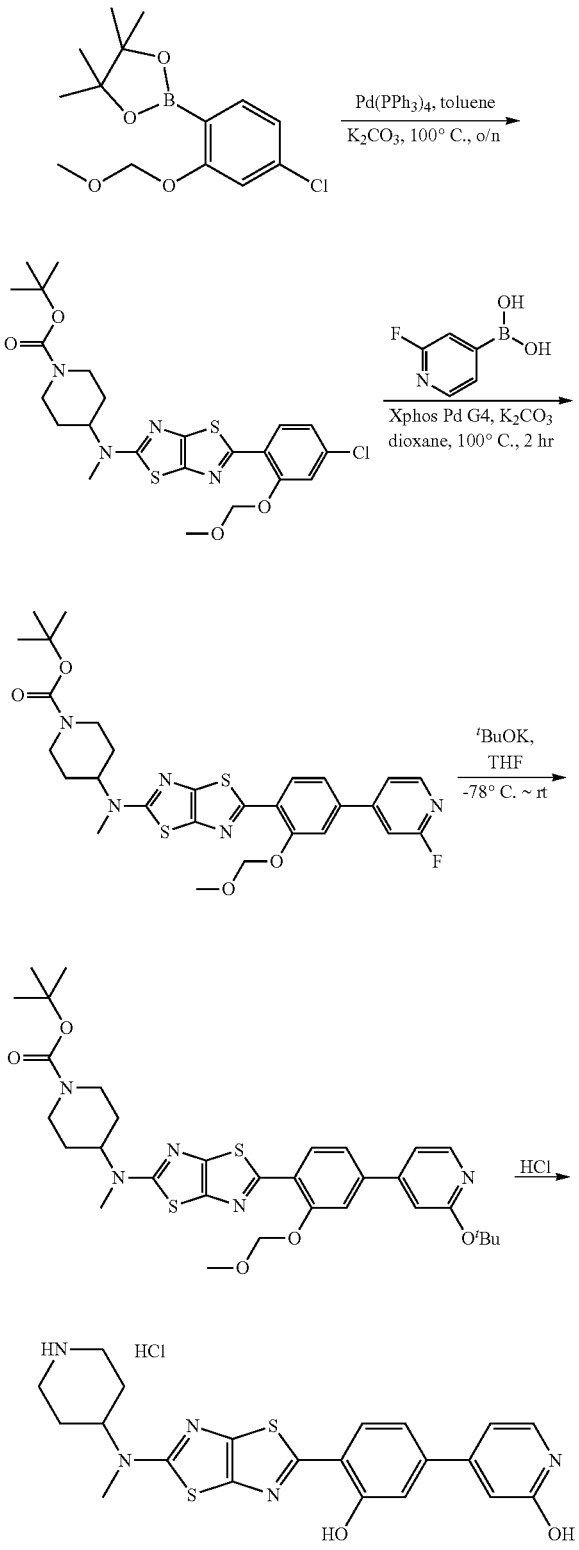

mmol), 2-[4-chloro-2-(methoxymethoxy)phenyl]-4,4,5,5-tetramethyl-1,3,2-dioxaborolane (373 mg, 1.25 mmol), K$_2$CO$_3$ (1.3 mL, 2.6 mmol, 2.0 M) in toluene (5 mL) was stirred at 100° C. overnight. The mixture was chromatographed (EtOAc in CH$_2$Cl$_2$, 0-20%) to provide tert-butyl 4-[[2-[4-chloro-2-(methoxymethoxy)phenyl]thiazolo[5,4-d]thiazol-5-yl]-methyl-amino]piperidine-1-carboxylate (270 mg, 51.5%) as a white powder. LC-MS 525.3, 527.3 [M+H]$^+$, RT 1.91 min.

Step 2: A mixture of tert-butyl 4-[[2-[4-chloro-2-(methoxymethoxy)phenyl]thiazolo[5,4-d]thiazol-5-yl]methyl-amino]piperidine-1-carboxylate (210 mg, 0.40 mmol), (2-fluoro-4-pyridyl)boronic acid (71 mg, 0.50 mmol), Xphos Pd G4 (33 mg, 0.04 mmol) and K$_2$CO$_3$ (0.5 mL, 1 mmol, 2.0 mol/L) in 1,4-dioxane (4.0 mL) was stirred at 100° C. for 2 h. The mixture was diluted with EtOAc, washed with water and brine, dried and concentrated. The residue was chromatographed (EtOAc in CH$_2$Cl$_2$ 0-60%) to provide tert-butyl 4-[[2-[4-(2-fluoro-4-pyridyl)-2-(methoxymethoxy)phenyl]thiazolo[5,4-d]thiazol-5-yl]-methyl-amino]piperidine-1-carboxylate (215 mg, 91.8%) as a yellow solid.

LC-MS 586.5 [M+H]$^+$, RT 1.82 min; $^1$H NMR (CDCl$_3$) δ: 8.47 (d, J=8.24 Hz, 1H), 8.31 (d, J=5.19 Hz, 1H), 7.57 (d, J=1.53 Hz, 1H), 7.44 (dt, J=5.26, 1.64 Hz, 1H), 7.42 (dd, J=8.24, 1.53 Hz, 1H), 5.54 (s, 2H), 7.18 (s, 1H), 4.57-4.75 (m, 1H), 4.23-4.38 (m, 2H), 3.56-3.67 (m, 3H), 3.22 (s, 3H), 2.99-3.15 (m, 2H), 1.90-2.02 (m, 2H), 1.70-1.85 (m, 2H), 1.49 (s, 9H).

Step 3: To a solution of tert-butyl 4-[[2-[4-(2-fluoro-4-pyridyl)-2-(methoxymethoxy)phenyl]thiazolo[5,4-d]thiazol-5-yl]-methyl-amino]piperidine-1-carboxylate (100 mg, 0.17 mmol) in THF (1 mL, 12.3 mmol, 100 mass %) at −78° C. was added KOtBu (0.21 mL, 0.34 mmol, 1.6 M). After stirring for 0.5 h, the mixture was brought to room temperature, stirred for another 0.5 h, quenched with NH$_4$Cl (aq.) and extracted with EtOAc. The organic layer was separated, and the aqueous layer was extracted with EtOAc. The combined organic phases were washed with brine, dried, and concentrated. The residue was chromatographed (EtOAc in CH$_2$Cl$_2$ 0-30%) to provide tert-butyl 4-[[2-[4-(2-tert-butoxy-4-pyridyl)-2-(methoxymethoxy)phenyl]thiazolo[5,4-d]thiazol-5-yl]-methyl-amino]piperidine-1-carboxylate (93.5 mg, 85.6%). LC-MS 640.6 [M+H]$^+$, RT 2.06 min.

Step 4: tert-Butyl 4-[[2-[4-(2-tert-butoxy-4-pyridyl)-2-(methoxymethoxy)phenyl]thiazolo[5,4-d]thiazol-5-yl]-methyl-amino]piperidine-1-carboxylate (23.5 mg, 0.037 mmol) was treated with HCl in CPME (1.5 mL, 3 M) at 50° C. for 4 h, then diluted with diethyl ether. The precipitate was collected, washed with diethyl ether and dried to furnish 4-[3-hydroxy-4-[5-[methyl(4-piperidyl)amino]thiazolo[5,4-d]thiazol-2-yl]phenyl]pyridin-2-ol hydrochloride (18 mg, 103%).

LC-MS 440.4 [M+H]$^+$, RT 0.89 min; $^1$H NMR (DMSO-d$_6$) δ: 11.37 (br s, 1H), 8.64-9.00 (m, 2H), 8.19 (d, J=8.24 Hz, 1H), 7.50 (d, J=7.02 Hz, 1H), 7.31-7.34 (m, 1H), 7.28 (dd, J=8.24, 1.83 Hz, 1H), 6.58 (d, J=1.53 Hz, 1H), 6.51 (dd, J=7.02, 1.83 Hz, 1H), 4.37-4.50 (m, 1H), 3.34-3.46 (m, 1H), 3.03-3.18 (m, 1H), 3.00 (s, 3H), 2.02-2.19 (m, 1H), 1.84-1.97 (m, 1H), 1.38-1.69 (m, 4H).

Step 1: A mixture of tert-butyl 4-[(5-bromothiazolo[5,4-d]thiazol-2-yl)-methyl-amino]piperidine-1-carboxylate (433 mg, 1.00 mmol), prepared based on the chemistry described in Example 1, step 5, Pd(PPh$_3$)$_4$ (116 mg, 0.10

Example 12

Preparation of Compound 36

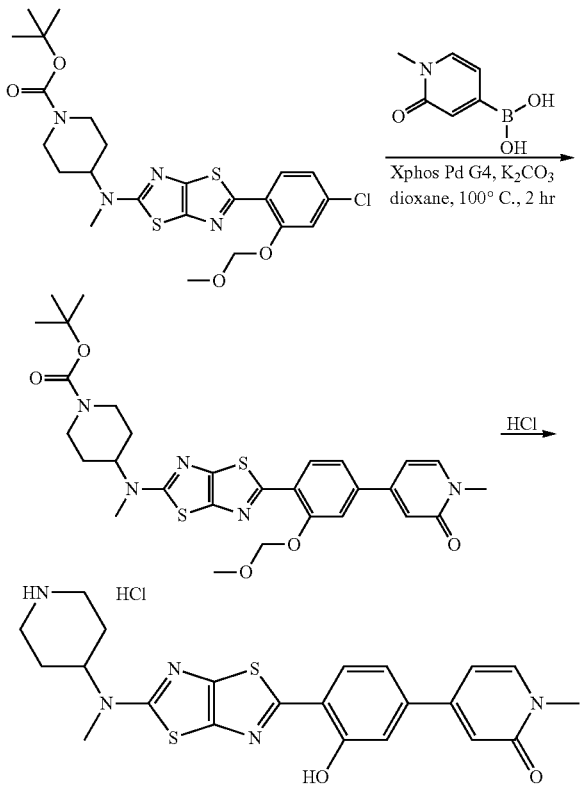

A mixture of tert-butyl 4-[[2-[4-chloro-2-(methoxymethoxy)phenyl]thiazolo[5,4-d]thiazol-5-yl]-methyl-amino]piperidine-1-carboxylate (55 mg, 0.10 mmol), prepared in Example 11, (1-methyl-2-oxo-4-pyridyl)boronic acid (20 mg, 0.13 mmol), Xphos Pd G 4 (9 mg, 0.010 mmol) and $K_2CO_3$ (0.13 mL, 0.26 mmol, 2.0 mol/L) in 1,4-dioxane (1.5 mL) was stirred under argon at 100° C. for 2 h. The mixture was diluted with $CH_2Cl_2$, washed with water and brine, dried and concentrated. The residue was chromatographed (MeOH in $CH_2Cl_2$, 0-20%) to provide tert-butyl 4-[[2-[2-(methoxymethoxy)-4-(1-methyl-2-oxo-4-pyridyl)phenyl]thiazolo[5,4-d]thiazol-5-yl]-methyl-amino]piperidine-1-carboxylate, which was then treated with HCl in diethyl ether (1.5 mL, 2.0 M) at 40° C. for 2 h. The precipitate was collected, washed with diethyl ether and dried to provide 4-[3-hydroxy-4-[5-[methyl(4-piperidyl)amino]thiazolo[5,4-d]thiazol-2-yl]phenyl]-1-methyl-pyridin-2-one hydrochloride (52 mg, 101.4%) as an orange solid.

LC-MS 454.4 [M+H]$^+$, RT 0.95 min; $^1$H NMR (DMSO-$d_6$) δ: 11.38 (br s, 1H), 8.75-9.01 (m, 2H), 8.18 (d, J=1.00 Hz, 1H), 7.79 (d, J=1.00 Hz, 1H), 7.35 (s, 1H), 7.28 (d, J=1.00 Hz, 1H), 6.62 (s, 1H), 6.52 (br d, J=6.41 Hz, 1H), 4.43 (br s, 1H), 3.33-3.53 (m, 2H), 3.03-3.17 (m, 2H), 2.99 (s, 3H), 2.02-2.19 (m, 2H), 1.84-1.96 (m, 2H), 1.59 (s, 3H).

Using the procedure described for Example 12, above, additional compounds described herein were prepared by substituting the appropriate starting materials, suitable reagents and reaction conditions, obtaining compounds such as those selected from:

| Cpd | Data |
|---|---|
| 39 | LC-MS 430.5 [M + H]$^+$; $^1$H NMR (DMSO-$d_6$) δ: 11.07 (br s, 1H), 8.59-9.06 (m, 2H), 8.14 (s, 1H), 7.97-8.08 (m, 1H), 7.83 (s, 1H), 7.08-7.24 (m, 2H), 4.36-4.50 (m, 1H), 3.29-3.47 (m, 2H), 3.04-3.20 (m, 2H), 2.98 (s, 3H), 1.97-2.19 (m, 2H), 1.78-1.96 (m, 2H). |
| 40 | LC-MS 427.4 [M + H]$^+$; $^1$H NMR (DMSO-$d_6$) δ: 11.09 (br s, 1H), 8.76-9.11 (m, 2H), 8.13 (s, 1H), 8.02 (br d, J = 7.93 Hz, 1H), 7.11-7.21 (m, 2H), 7.82 (s, 1H), 4.37-4.48 (m, 1H), 3.87 (s, 3H), 3.31-3.46 (m, 2H), 3.03-3.19 (m, 2H), 2.98 (s, 3H), 2.02-2.22 (m, 2H), 1.81-1.98 (m, 2H). |
| 46 | LC-MS 510.4 [M + H]$^+$; $^1$H NMR (methanol-$d_4$) δ: 8.03 (d, J = 9.16 Hz, 1H), 7.88 (d, J = 7.32 Hz, 1H), 7.29-7.36 (m, 2H), 6.90-7.02 (m, 2H), 4.87-4.93 (m, 1H), 3.71 (s, 3H), 3.09 (s, 3H), 1.92-2.13 (m, 4H), 1.64 (s, 6H), 1.53 (s, 6H); NH and OH not observed. |
| 43 | LC-MS 487.4 [M + H]$^+$; $^1$H NMR (methanol-$d_4$) δ: 7.97 (d, J = 2.1 Hz, 1H), 7.83 (d, J = 8.2 Hz, 1H), 7.20 (d, J = 1.8 Hz, 1H), 7.17 (dd, J = 8.2, 1.5 Hz, 1H), 4.79-4.85 (m, 1H), 3.07 (s, 3H), 1.94-2.11 (m, 4H), 1.63 (s, 6H), 1.53 (s, 6H); NH and OH not observed. |
| 48 | LC-MS 501.4 [M + H]$^+$; $^1$H NMR (methanol-$d_4$) δ: 7.84 (d, J = 7.9 Hz, 1H), 7.79 (d, J = 3.1 Hz, 1H), 7.11-7.18 (m, 2H), 3.80 (s, 3H), 3.00-3.13 (m, 4H), 1.93-2.12 (m, 4H), 1.63 (s, 6H), 1.53 (s, 6H); NH and OH not observed. |

Example 13

Preparation of Compound 38

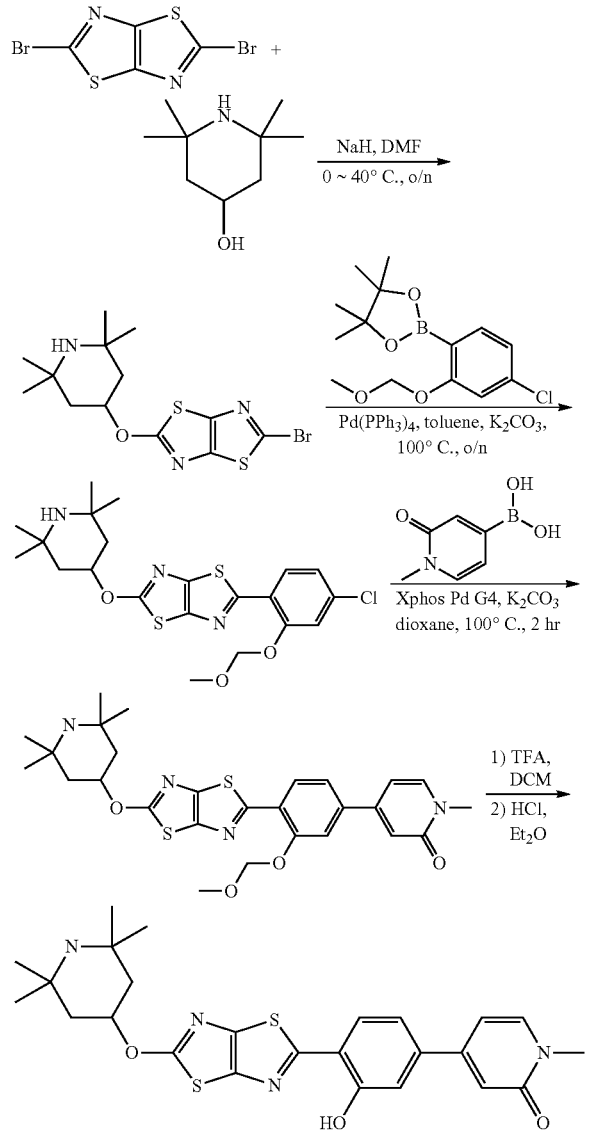

Step 1: To a mixture of 2,2,6,6-tetramethylpiperidin-4-ol (377.4 mg, 2.40 mmol) in DMF (10 mL) in an ice-water bath was added NaH (60 mass % in mineral oil, 112 mg, 2.80 mmol). The reaction was stirred for 5 min, followed by the addition of 2,5-dibromothiazolo[5,4-d]thiazole (600 mg, 2.0 mmol). The mixture was stirred at 40° C. overnight, diluted with water and extracted with EtOAc, and washed with water, brine and dried. After the removal of the solvent, the residue was chromatographed (MeOH in $CH_2Cl_2$, 0-20%) to provide 5-bromo-2-[(2,2,6,6-tetramethyl-4-piperidyl)oxy]thiazolo[5,4-d]thiazole (553 mg, 73.5%). LC-MS 376.3, 378.3 $[M+H]^+$, RT 1.04 min.

Step 2: A mixture of 5-bromo-2-[(2,2,6,6-tetramethyl-4-piperidyl)oxy]thiazolo[5,4-d]thiazole (376 mg, 1.00 mmol), $Pd(PPh_3)_4$ (116 mg, 0.10 mmol), 2-[4-chloro-2-(methoxymethoxy)phenyl]-4,4,5,5-tetramethyl-1,3,2-dioxaborolane (373 mg, 1.25 mmol) and $K_2CO_3$ (1.3 mL, 2.6 mmol, 2.0 M) in toluene (10 mL) was stirred at 100° C. for 6 h. The mixture was diluted with EtOAc and washed with water and brine, and then dried and concentrated. The residue was chromatographed (EtOAc in $CH_2Cl_2$ 0-30%) to provide 2-[4-chloro-2-(methoxymethoxy)phenyl]-5-[(2,2,6,6-tetramethyl-4-piperidyl)oxy]thiazolo[5,4-d]thiazole (420 mg, 80.83%) as a brown solid. LC-MS 468.4, 470.4 $[M+H]^+$, RT 1.36 min.

Step 3: A mixture of 2-[4-chloro-2-(methoxymethoxy)phenyl]-5-[(2,2,6,6-tetramethyl-4-piperidyl)oxy]thiazolo[5,4-d]thiazole (70 mg, 0.15 mmol), Xphos G 4 (13 mg, 0.015 mmol), (1-methyl-2-oxo-4-pyridyl)boronic acid (29 mg, 0.19 mmol) and $K_2CO_3$ (0.19 mL, 0.38 mmol, 2.0 M) in 1,4-dioxane (1.5 mL) was stirred under argon at 100° C. overnight. After the reaction mixture was concentrated, the residue was chromatographed (MeOH in $CH_2Cl_2$ 0-30%) to provide 4-[3-(methoxymethoxy)-4-[5-[(2,2,6,6-tetramethyl-4-piperidyl)oxy]thiazolo[5,4-d]thiazol-2-yl]phenyl]-1-methyl-pyridin-2-one, which was treated with TFA (1 mL) at 40° C. for 2 hr. The TFA was evaporated to dryness, and the residue was treated with HCl in diethyl ether (2 mL, 2.0 M). The precipitate was collected, washed with diethyl ether and dried to provide 4-[3-hydroxy-4-[5-[(2,2,6,6-tetramethyl-4-piperidyl)oxy]thiazolo[5,4-d]thiazol-2-yl]phenyl]-1-methyl-pyridin-2-one hydrochloride (32 mg, 40.0%).

LC-MS 497.4 $[M+H]^+$, RT 1.04 min; $^1H$ NMR (DMSO-$d_6$) δ: 11.58 (s, 1H), 9.16 (br d, J=11.90 Hz, 1H), 8.40 (br d, J=11.60 Hz, 1H), 8.25 (d, J=8.24 Hz, 1H), 7.80 (d, J=7.02 Hz, 1H), 7.26-7.38 (m, 2H), 6.62 (d, J=1.53 Hz, 1H), 6.52 (dd, J=1.00 Hz, 1H), 5.54-5.62 (m, 1H), 3.41-3.56 (m, 3H), 2.28-2.44 (m, 3H), 1.76-1.93 (m, 2H), 1.50 (d, J=4.27 Hz, 12H).

Using the procedure described for Example 13, above, additional compounds described herein were prepared by substituting the appropriate starting materials, suitable reagents and reaction conditions, obtaining compounds such as those selected from:

| Cpd | Data |
|---|---|
| 37 | LC-MS 456.4 $[M + H]^+$; $^1H$ NMR (DMSO-$d_6$) δ: 12.81-13.28 (m, 1H), 7.66-8.44 (m, 4H), 7.10-7.29 (m, 3H), 5.39-5.53 (m, 1H), 2.03-2.23 (m, 2H), 1.29-1.47 (m, 2H), 1.22 (s, 6H), 1.13 (s, 6H). |
| 45 | LC-MS 488.4 $[M + H]^+$; $^1H$ NMR (methanol-$d_4$) δ: 7.99 (d, J = 8.8 Hz, 1H), 7.80 (d, J = 1.0 Hz, 1H), 7.14-7.22 (m, 2H), 5.62-5.74 (m, 1H), 3.80 (s, 3H), 2.52 (dd, J = 13.9, 4.1 Hz, 2H), 1.83-1.92 (m, 2H), 1.58-1.65 (m, 6H), 1.55 (s, 6H); NH and OH not observed. |

Example 14

Preparation of Compound 41

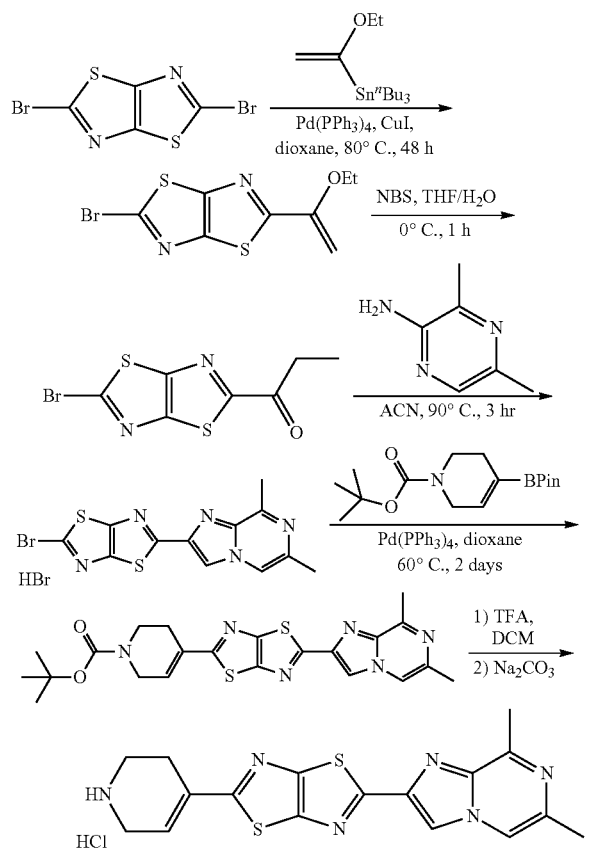

Step 1: A mixture of 2,5-dibromothiazolo[5,4-d]thiazole (600 mg, 2.0 mmol), tributyl(1-ethoxyvinyl)tin (0.85 mL, 2.4 mmol), Pd(PPh₃)₄ (231 mg, 0.20 mmol), copper(I) iodide (7.6 mg, 0.040 mmol) in 1,4-dioxane (6 mL) was stirred under argon at 80° C. for 48 h. The mixture was cooled and evaporated to dryness. The residue was chromatographed (EtOAc in CH₂Cl₂ 0-5%) to give 5-bromo-2-(1-ethoxyvinyl)thiazolo[5,4-d]thiazole (309 mg, 33.4%). LC-MS 291.1, 293.1 [M+H]⁺, RT 1.75 min.

Step 2: The product from Step 1 was dissolved in THF (3.0 mL, 37 mmol), cooled in an ice-water bath and treated with NBS (134 mg, 0.74 mmol). The mixture was stirred for 1 h and diluted with EtOAc, washed with water and brine, dried and then concentrated to dryness. The residue was chromatographed (silica gel, EtOAc in CH₂Cl₂, 0-5%) to give 2-bromo-1-(5-bromothiazolo[5,4-d]thiazol-2-yl)ethanone (135 mg, 59.1%). LC-MS 343.4, 345.4, 347.4 [M+H]⁺, RT 1.58 min.

Step 3: A mixture of 2-bromo-1-(5-bromothiazolo[5,4-d]thiazol-2-yl)ethanone (121 mg, 0.35 mmol), 3,5-dimethylpyrazin-2-amine (44 mg, 0.36 mmol) and acetonitrile (2.0 mL) was stirred at 90° C. for 3 h and diluted with EtOAc. The precipitate was collected and washed with EtOAc and dried to provide 5-bromo-2-(6,8-dimethylimidazo[1,2-a]pyrazin-2-yl)thiazolo[5,4-d]thiazole hydrobromide (140 mg, 88.5%). LC-MS 366.2, 368.2 [M+H]⁺, RT 1.49 min.

Step 4: A mixture of 5-bromo-2-(6,8-dimethylimidazo[1,2-a]pyrazin-2-yl)thiazolo[5,4-d]thiazole hydrobromide (170 mg, 0.38 mmol), tert-butyl 4-(4,4,5,5-tetramethyl-1,3,2-dioxaborolan-2-yl)-3,6-dihydro-2H-pyridine-1-carboxylate (147 mg, 0.48 mmol), Pd(PPh₃)₄ (44 mg, 0.038 mmol), and K₂CO₃ (0.67 mL, 1.30 mmol, 2.0 M) in 1,4-dioxane (4.0 mL) was stirred at 100° C. for 2 h. The reaction mixture was diluted with EtOAc and washed with water and brine, and then dried and concentrated. The residue was chromatographed (EtOAc in CH₂Cl₂ 0-60%) to provide tert-butyl 4-[2-(6,8-dimethylimidazo[1,2-a]pyrazin-2-yl)thiazolo[5,4-d]thiazol-5-yl]-3,6-dihydro-2H-pyridine-1-carboxylate as a yellow solid which was used directly in Step 5. LC-MS 469.4 [M+H]⁺, RT 1.69 min.

Step 5: tert-Butyl 4-[2-(6,8-dimethylimidazo[1,2-a]pyrazin-2-yl)thiazolo[5,4-d]thiazol-5-yl]-3,6-dihydro-2H-pyridine-1-carboxylate, obtained in Step 4, was treated with CH₂Cl₂ (2 mL) and TFA (2.0 mL) at room temperature for 1 h, and then neutralized with Na₂CO₃. The organic solvent was evaporated and the precipitate was collected by filtration and washed with water, diethyl ether and dried to provide 2-(6,8-dimethylimidazo[1,2-a]pyrazin-2-yl)-5-(1,2,3,6-tetrahydropyridin-4-yl)thiazolo[5,4-d]thiazole (63 mg, 45%).

LC-MS 369.4 [M+H]⁺, RT 0.89 min; ¹H NMR (DMSO-d₆) δ: 8.58 (s, 1H), 8.29 (s, 1H), 6.80 (br s, 1H), 3.44 (br d, J=2.7 Hz, 2H), 3.28-3.38 (m, 2H), 2.92 (t, J=5.5 Hz, 2H), 2.74 (s, 3H), 2.39 (s, 3H).

Example 15

Preparation of Compound 44

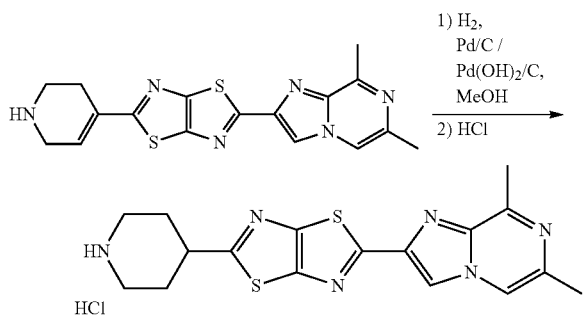

2-(6,8-Dimethylimidazo[1,2-a]pyrazin-2-yl)-5-(1,2,3,6-tetrahydropyridin-4-yl)thiazolo[5,4-d]thiazole (42 mg, 0.11 mmol,) was hydrogenated in the presence of Pd/C (20 mg, 10 wt. %) and Pd(OH)₂/C (20 mg, 20 wt. %) in methanol (10 mL) using a balloon at room temperature overnight. The mixture was filtered and then washed with MeOH. The filtrate was concentrated and treated with HCl (2 mL, 1.0 M in diethyl ether) at room temperature for 4 h. The precipitate was collected and washed with diethyl ether, and dried to provide 2-(6,8-dimethylimidazo[1,2-a]pyrazin-2-yl)-5-(4-piperidyl)thiazolo[5,4-d]thiazole hydrochloride (35 mg, 75.5%).

LC-MS 371.3 [M+H]⁺, RT 0.87 min; ¹H NMR (methanol-d₄) δ: 8.87 (s, 1H), 8.65 (s, 1H), 3.51-3.64 (m, 2H), 3.15-3.28 (m, 3H), 3.10 (s, 3H), 2.62 (s, 3H), 2.37-2.53 (m, 2H), 2.10-2.27 (m, 2H); NH and OH not observed.

Example 16

Preparation of Compound 42

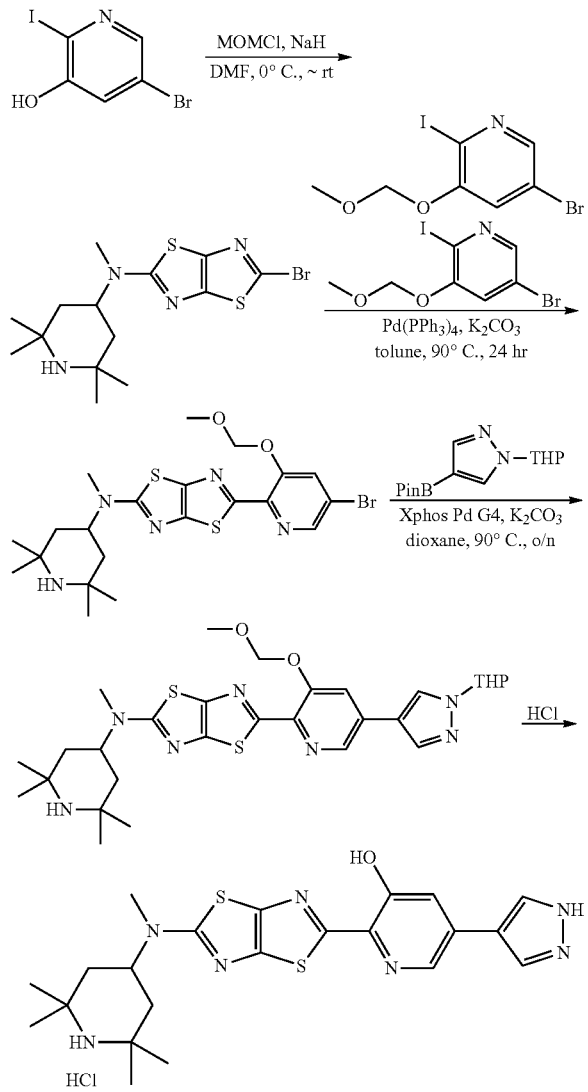

Step 1: A mixture of 5-bromo-2-iodo-pyridin-3-ol (7.57 g, 25.2 mmol) in DMF (50 mL) was treated with NaH (1.51 g, 37.8 mmol, 60 mass %) at 0° C. for 0.5 h, followed by the addition of chloro(methoxy)methane (2.30 mL, 30.3 mmol). The mixture was stirred at room temperature for 4 h and quenched with ice, water, and extracted with EtOAc, washed with water and brine, dried over $Na_2SO_4$ and evaporated. The residue was chromatographed (EtOAc in hexanes, 0-20%) to provide 5-bromo-2-iodo-3-(methoxymethoxy)pyridine (7.90 g, 91.0%).

LC-MS 344.0, 346.0 [M+H]$^+$, RT 1.45 min. $^1$H NMR (CDCl$_3$) δ: 8.15 (d, J=1.8 Hz, 1H), 7.44 (d, J=1.8 Hz, 1H), 5.27 (s, 2H), 3.53 (s, 3H).

Step 2: A mixture of 5-bromo-N-methyl-N-(2,2,6,6-tetramethylpiperidin-4-yl)thiazolo[5,4-d]thiazol-2-amine (prepared in Example 1, step 5, 1.17 g, 3.00 mmol), 5-bromo-2-iodo-3-(methoxymethoxy)pyridine (1.14 g, 3.30 mmol), Pd(PPh$_3$)$_4$ (1.04 g, 0.90 mmol), and K$_2$CO$_3$ (3.8 mL, 7.5 mmol, 2.0 M) in toluene (15 mL) was stirred at 90° C. for 24 h. The reaction was evaporated to dryness and chromatographed (1.4 N NH$_3$ in MeOH in CH$_2$Cl$_2$, 0-20%) to provide 5-(5-bromo-3-(methoxymethoxy)pyridin-2-yl)-N-methyl-N-(2,2,6,6-tetramethylpiperidin-4-yl)thiazolo[5,4-d]thiazol-2-amine (669 mg, 42.3%) as a brown solid. LC-MS 526.3, 528.3 [M+H]$^+$, RT 1.45 min.

Step 3: A mixture of 2-[5-bromo-3-(methoxymethoxy)-2-pyridyl]-N-methyl-N-(2,2,6,6-tetramethyl-4-piperidyl)thiazolo[5,4-d]thiazol-5-amine (29 mg, 0.06 mmol), 1-tetrahydropyran-2-yl-4-(4,4,5,5-tetramethyl-1,3,2-dioxaborolan-2-yl)pyrazole (18 mg, 0.07 mmol), Xphos Pd G4 (5 mg, 0.006 mmol), and K$_2$CO$_3$ (0.07 mL, 0.1 mmol, 2.0 M) in 1,4-dioxane (0.5 mL) was stirred at 100° C. for 24 h and concentrated. This was chromatographed (silica gel, 1.4 N NH$_3$ in MeOH in CH$_2$Cl$_2$, 0-30%) to provide 2-[3-(methoxymethoxy)-5-(1-tetrahydropyran-2-ylpyrazol-4-yl)-2-pyridyl]-N-methyl-N-(2,2,6,6-tetramethyl-4-piperidyl)thiazolo[5,4-d]thiazol-5-amine, which was treated with HCl in diethyl ether (1 mL, 2.0 mmol, 2.0 M) at 40° C. for 4 hr. The precipitate was collected and washed with diethyl ether and dried to provide 2-[5-[methyl-(2,2,6,6-tetramethyl-4-piperidyl)amino]thiazolo[5,4-d]thiazol-2-yl]-5-(1H-pyrazol-4-yl)pyridin-3-ol hydrochloride (12 mg, 43%).

LC-MS 470.5 [M+H]$^+$, RT 1.05 min; $^1$H NMR (DMSO-d$_6$) δ: 10.87 (br s, 1H), 9.11 (br d, J=11.9 Hz, 1H), 8.49 (d, J=1.5 Hz, 1H), 8.21-8.31 (m, 2H), 8.08 (br d, J=13.4 Hz, 1H), 7.71 (d, J=1.8 Hz, 1H), 4.57-4.73 (m, 1H), 3.03 (s, 3H), 1.96-2.10 (m, 2H), 1.83-1.95 (m, 2H), 1.51 (s, 6H), 1.46 (s, 6H).

Using the procedure described for Example 16, above, additional compounds described herein were prepared by substituting the appropriate starting materials, suitable reagents and reaction conditions, obtaining compounds such as those selected from:

| Cpd | Data |
| --- | --- |
| 47 | LC-MS 414.4 [M + H]$^+$; $^1$H NMR (methanol-d$_4$) δ: 8.52 (d, J = 1.5 Hz, 1H), 8.31 (s, 2H), 8.09 (d, J = 1.5 Hz, 1H), 4.54-4.67 (m, 1H), 3.54-3.62 (m, 2H), 3.18-3.28 (m, 2H), 3.12-3.17 (m, 3H), 2.08-2.28 (m, 4H); NH and OH not observed. |
| 49 | LC-MS 487.5 [M + H]$^+$; $^1$H NMR (methanol-d$_4$) δ: 8.42 (br s, 1H), 8.23 (br s, 1H), 8.00 (br s, 1H), 7.86 (br s, 1H), 4.91-5.03 (m, 1H), 3.13 (s, 5H), 1.95-2.16 (m, 4H), 1.64 (s, 6H), 1.54 (s, 6H); NH and OH not observed. |
| 50 | LC-MS 498.4 [M + H]$^+$; $^1$H NMR (methanol-d$_4$) δ: 8.43 (s, 1H), 8.28 (s, 1H), 8.01 (s, 1H), 7.84 (s, 1H), 4.90-5.03 (m, 1H), 4.27 (q, J = 7.3 Hz, 2H), 3.13 (s, 3H), 1.97-2.15 (m, 4H), 1.64 (s, 6H), 1.44-1.61 (m, 9H); NH and OH not observed. |
| 51 | LC-MS 431.4 [M + H]$^+$; $^1$H NMR (DMSO-d$_6$) δ: 11.00 (br s, 1H), 8.74-8.99 (m, 2H), 8.43 (d, J = 1.8 Hz, 1H), 8.35 (s, 1H), 8.05 (s, 1H), 7.69 (d, J = 1.2 Hz, 1H), 4.37-4.57 (m, 1H), 3.33-3.44 (m, 2H), 3.04-3.18 (m, 2H), 3.01 (s, 3H), 2.03-2.21 (m, 2H), 1.84-1.98 (m, 2H). |

| Cpd | Data |
|---|---|
| 52 | LC-MS 442.4 [M + H]⁺; ¹H NMR (DMSO-d₆) δ: 10.78-11.30 (m, 1H), 8.78-9.00 (m, 2H), 8.44 (d, J = 1.5 Hz, 1H), 8.41 (s, 1H), 8.06 (s, 1H), 7.70 (s, 1H), 4.39-4.57 (m, 1H), 4.18 (q, J = 7.3 Hz, 2H), 3.32-3.43 (m, 2H), 3.04-3.19 (m, 2H), 3.01 (s, 3H), 2.04-2.20 (m, 2H), 1.85-1.98 (m, 2H), 1.42 (t, J = 7.2 Hz, 3H). |
| 53 | LC-MS 432.2 [M + H]⁺; ¹H NMR (DMSO-d₆) δ: 12.85 (br s, 1H), 10.88 (s, 1H), 8.67 (br s, 1H), 8.18-8.49 (m, 3H), 7.60 (d, J = 1.5 Hz, 1H), 4.39-4.55 (m, 1H), 3.36-3.46 (m, 2H), 3.05-3.19 (m, 2H), 3.01 (s, 3H), 1.87-2.11 (m, 4H). |
| 56 | LC-MS 400.2 [M + H]⁺; ¹H NMR (DMSO-d₆) δ: 11.15 (br s, 1H), 9.30-9.61 (m, 2H), 8.50 (d, J = 1.8 Hz, 1H), 8.28 (s, 2H), 7.78 (s, 1H), 4.95-5.11 (m, 1H), 3.15-3.55 (m, 4H), 3.11 (s, 3H), 2.07-2.34 (m, 2H). |
| 61 | LC-MS 428.5 [M + H]⁺; ¹H NMR (DMSO-d₆) δ: 11.04 (br s, 1H), 8.92 (br s, 2H), 8.49 (d, J = 1.8 Hz, 1H), 8.27 (s, 2H), 7.76 (s, 1H), 4.26-4.40 (m, 1H), 3.44-3.53 (m, 2H), 3.32-3.43 (m, 2H), 3.00-3.18 (m, 2H), 2.10-2.28 (m, 2H), 1.91-2.05 (m, 2H), 1.26 (t, J = 7.2 Hz, 3H). |
| 145 | LC-MS 454.3 [M + H]⁺; ¹H NMR (methanol-d₄) 8.33-8.47 (m, 1H), 8.11 (s, 2H), 7.52-7.63 (m, 1H), 4.53-4.66 (m, 1H), 3.56-3.88 (m, 2H), 3.33-3.44 (m, 1H), 3.03-3.27 (m, 5H), 1.90-2.51 (m, 7H), 1.72-1.88 (m, 1H); NH and OH not observed. |
| 179 | LC-MS 440.2 [M + H]⁺; ¹H NMR (methanol-d₄) δ 8.48 (s, 1H), 8.23 (s, 2H), 7.92 (s, 1H), 4.14 (t, J = 7.4 Hz, 2H), 3.66-3.58 (m, 2H), 3.35 (s, 3H), 3.23-3.13 (m, 2H), 2.98-2.87 (m, 2H), 2.56 (t, J = 7.4 Hz, 2H), 2.32-2.25 (m, 2H); NH and OH not observed. |
| 182 | LC-MS 442.2 [M + H]⁺; ¹H NMR (methanol-d₄) δ: 8.46-8.56 (m, 1H), 8.23-8.34 (m, 2H), 8.02-8.11 (m, 1H), 4.60-4.74 (m, 1H), 3.63-3.75 (m, 1H), 3.37-3.52 (m, 1H), 3.09-3.19 (m, 3H), 2.84-3.01 (m, 4H), 2.07-2.40 (m, 4H), 1.49 (br d, J = 6.1 Hz, 3H); NH and OH not observed. |
| 189 | LC-MS 426.2 [M + H]⁺; ¹H NMR (DMSO-d₆) δ: 10.70-10.87 (m, 1H), 8.60-8.85 (m, 1H), 8.44-8.52 (m, 1H), 8.19-8.33 (m, 1H), 7.67-7.76 (m, 1H), 3.93-4.09 (m, 2H), 2.87-3.01 (m, 2H), 2.55-2.68 (m, 2H), 2.31-2.44 (m, 4H), 2.01-2.16 (m, 2H); NH and OH not observed. |
| 191 | LC-MS 481.3 [M + H]⁺; ¹H NMR (methanol-d₄) δ 8.55 (s, 1H), 8.07 (s, 1H), 7.91 (d, J = 7.1 Hz, 1H), 6.97 (s, 1H), 6.86 (d, J = 7.1 Hz, 1H), 5.01-4.90 (m, 1H), 4.27-4.20 (m, 2H), 3.68 (s, 3H), 3.16 (s, 3H), 2.36 (t, J = 12.8 Hz, 2H), 2.30-2.19 (m, 4H), 2.10-2.03 (m, 2H); NH and OH not observed. |
| 192 | LC-MS 426.4 [M + H]⁺; ¹H NMR (methanol-d₄) δ 8.52 (s, 1H), 8.29 (s, 2H), 8.07 (s, 1H), 4.17 (d, J = 8.7 Hz, 2H), 4.06 (d, J = 8.7 Hz, 2H), 3.54-3.49 (m, 2H), 3.19 (t, J = 5.6 Hz, 2H), 2.09 (t, J = 5.9 Hz, 2H), 1.96-1.88 (m, 2H); 2NHs and OH not observed. |
| 196 | LC-MS 440.2 [M + H]⁺; ¹H NMR (DMSO-d₆) δ: 11.01 (br s, 1H), 10.38 (br s, 1H), 8.49 (s, 1H), 8.27 (s, 2H), 7.74 (s, 1H), 3.97-4.03 (m, 2H), 3.90-3.96 (m, 2H), 3.29-3.42 (m, 2H), 2.88-3.05 (m, 2H), 2.60-2.78 (m, 3H), 2.11-2.28 (m, 2H), 1.93-2.09 (m, 2H). |
| 197 | LC-MS 452.2 [M + H]⁺; ¹H NMR (methanol-d₄) δ 8.53 (d, J = 1.8 Hz, 1H), 8.30 (s, 2H), 8.09 (d, J = 1.8 Hz, 1H), 4.45 (s, 2H), 4.17-4.13 (m, 2H), 4.06 (s, 2H), 2.51 (d, J = 14.9 Hz, 2H), 2.24-2.14 (m, 6H); 2NHs and OH not observed. |
| 203 | LC-MS 440.4 [M + H]⁺; ¹H NMR (methanol-d₄) δ 8.52 (s, 1H), 8.28 (s, 2H), 8.07 (s, 1H), 5.02-4.90 (m, 1H), 4.27-4.20 (m, 2H), 3.14 (s, 3H), 2.36-2.19 (m, 6H), 2.11-2.02 (m, 2H); 2NHs and OH not observed. |
| 204 | LC-MS 454.1 [M + H]⁺; ¹H NMR (DMSO-d₆) δ: 11.00 (br s, 1H), 10.55-10.72 (m, 1H), 8.49 (d, J = 1.5 Hz, 1H), 8.27 (s, 2H), 7.75 (br s, 1H), 4.49-4.58 (m, 1H), 3.53-3.61 (m, 2H), 3.30-3.43 (m, 2H), 2.99 (s, 3H), 2.69-2.78 (m, 1H), 2.26-2.39 (m, 2H), 1.90-2.02 (m, 2H), 1.11-1.18 (m, 2H), 0.76-0.87 (m, 2H). |
| 205 | LC-MS 456.1 [M + H]⁺; ¹H NMR (DMSO-d₆) δ: 10.69 (br s, 1H), 8.49 (d, J = 1.8 Hz, 1H), 8.28 (s, 2H), 7.81 (s, 1H), 4.51-4.60 (m, 1H), 3.36-3.56 (m, 3H), 3.12-3.27 (m, 2H), 3.03 (s, 3H), 2.40-2.49 (m, 2H), 1.90-2.00 (m, 2H), 1.29 (d, J = 6.7 Hz, 6H); NH or OH not observed. |
| 206 | LC-MS 456.2 [M + H]⁺; ¹H NMR (DMSO-d₆) δ: 10.69 (br s, 2H), 8.48 (d, J = 1.5 Hz, 1H), 8.27 (s, 2H), 7.77 (s, 1H), 4.46-4.56 (m, 1H), 3.49-3.60 (m, 2H), 3.07-3.20 (m, 2H), 2.91-3.05 (m, 5H), 2.30-2.44 (m, 2H), 1.89-2.01 (m, 2H), 1.68-1.81 (m, 2H), 0.92 (t, J = 7.3 Hz, 3H). |
| 207 | LC-MS 442.2 [M + H]⁺; ¹H NMR (DMSO-d₆) δ: 10.93 (br s, 1H), 10.37 (br s, 1H), 8.48 (d, J = 1.5 Hz, 1H), 8.27 (s, 2H), 7.73 (s, 1H), 4.44-4.54 (m, 1H), 3.48-3.61 (m, 2H), 3.05-3.20 (m, 4H), 2.96-3.05 (m, 3H), 2.21-2.35 (m, 2H), 1.90-2.04 (m, 2H), 1.27 (t, J = 7.3 Hz, 3H. |
| 209 | LC-MS 426.2 [M + H]⁺; ¹H NMR (DMSO-d₆) δ: 11.05 (s, 1H), 8.79 (br s, 2H), 8.50 (d, J = 1.8 Hz, 1H), 8.27 (s, 2H), 7.75 (s, 1H), 3.97 (s, 4H), 3.07 (br s, 4H), 1.92-2.13 (m, 4H). |
| 210 | LC-MS 465.2 [M + H]⁺; ¹H NMR (DMSO-d₆) δ: 11.11 (br s, 1H), 9.47 (s, 1H), 9.26 (s, 1H), 8.97 (br s, 2H), 8.57 (s, 1H), 7.98-8.18 (m, 2H), 7.90 (s, 1H), 4.40-4.56 (m, 1H), 3.30-3.46 (m, 2H), 3.05-3.20 (m, 2H), 3.02 (s, 3H), 2.04-2.25 (m, 2H), 1.87-1.98 (m, 2H). |

| Cpd | Data |
|---|---|
| 213 | LC-MS 400.4 [M + H]$^+$; $^1$H NMR (methanol-$d_4$) δ: 8.47 (s, 1H), 8.21 (s, 2H), 7.89 (s, 1H), 3.69-3.82 (m, 2H), 3.54-3.63 (m, 1H), 3.40-3.35 (m, 2H, obscured by methanol peak), 3.26-3.37 (m, 1H), 3.16-3.28 (m, 2H), 2.33-2.62 (m, 2H); NH and OH not observed. |
| 216 | LC-MS 431.1 [M + H]$^+$; $^1$H NMR (DMSO-$d_6$) δ: 10.96 (br s, 1H), 9.61 (s, 1H), 9.20 (s, 1H), 8.71-8.94 (m, 2H), 8.65 (d, J = 1.8 Hz, 1H), 7.95 (d, J = 1.5 Hz, 1H), 4.43-4.54 (m, 1H), 3.34-3.44 (m, 2H), 3.05-3.18 (m, 2H), 3.02 (s, 3H), 2.03-2.19 (m, 2H), 1.86-1.99 (m, 2H). |
| 219 | LC-MS 428.2 [M + H]$^+$; $^1$H NMR (DMSO-$d_6$) δ: 11.47 (br s, 1H), 9.04 (br s, 2H), 8.25-8.42 (m, 1H), 8.08 (s, 1H), 7.73 (br s, 1H), 4.48 (br t, J = 11.9 Hz, 1H), 3.28-3.45 (m, 2H), 3.04-3.18 (m, 2H), 3.02 (s, 3H), 2.45 (s, 3H), 2.02-2.22 (m, 2H), 1.85-1.96 (m, 2H). |
| 220 | LC-MS 448.4, 450.4 [M + H]$^+$; $^1$H NMR (DMSO-$d_6$) δ13.39-13.61 (m, 1H), 10.77-11.06 (m, 1H), 8.51-8.95 (m, 2H), 8.40-8.51 (m, 2H), 7.71 (s, 1H), 4.43-4.54 (m, 1H), 3.34-3.44 (m, 2H), 3.04-3.17 (m, 2H), 3.01 (s, 3H), 2.00-2.14 (m, 2H), 1.87-1.99 (m, 2H). |
| 224 | LC-MS 440.4 [M + H]$^+$; $^1$H NMR (DMSO-$d_6$) δ: 9.60 (br s, 1H), 8.67 (br s, 1H), 8.34 (br s, 1H), 7.96 (br s, 1H), 4.46-4.61 (m, 1H), 3.53-3.62 (m, 2H), 3.15-3.27 (m, 2H), 3.13 (s, 3H), 2.85 (s, 3H), 2.05-2.30 (m, 4H); NH and OH not observed |
| 225 | LC-MS 426.4 [M + H]$^+$; $^1$H NMR (methanol-$d_4$) δ 9.62 (br s, 1H), 9.27 (br d, J = 4.6 Hz, 1H), 8.58 (br s, 1H), 8.10 (br s, 1H), 7.86 (br d, J = 1.8 Hz, 1H), 4.45-4.60 (m, 1H), 3.50-3.64 (m, 2H), 3.16-3.26 (m, 2H), 3.09 (br s, 3H), 2.04-2.26 (m, 4H); NH and OH not observed. |

Example 17

Preparation of Compound 57

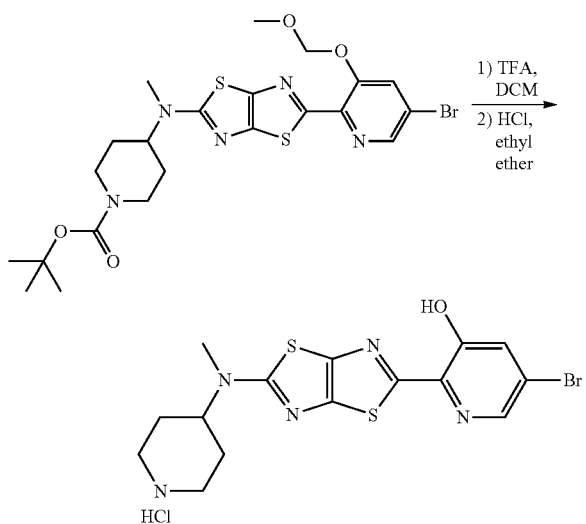

To a solution of tert-butyl 4-[[2-[5-bromo-3-(methoxymethoxy)-2-pyridyl]thiazolo[5,4-d]thiazol-5-yl]-methyl-amino]piperidine-1-carboxylate (340 mg, 0.60 mmol), obtained using the chemistry described in Example 16, Step 2, in $CH_2Cl_2$ (10 mL) was added TFA (1 mL). The mixture was stirred at room temperature for 15 min and neutralized with $NaHCO_3$, washed with brine and chromatographed on a C-18 column, eluting with 0.1% TFA in $H_2O$/0.1% TFA in $CH_3CN$, to provide 5-bromo-2-[5-[methyl(4-piperidyl)amino]thiazolo[5,4-d]thiazol-2-yl]pyridin-3-ol 2,2,2-trifluoroacetic acid, which was treated with HCl in diethyl ether (2.0 mL, 1.0 M) at room temperature for 4 h. The precipitate was collected, washed with diethyl ether and dried to provide 5-bromo-2-[5-[methyl(4-piperidyl)amino]thiazolo[5,4-d]thiazol-2-yl]pyridin-3-ol hydrochloride (49 mg, 18%).

LC-MS 426.1, 428.1 [M+H]$^+$, RT 1.38 min; $^1$H NMR (DMSO-$d_6$) δ: 11.17 (br s, 1H), 8.77-9.11 (m, 2H), 8.26 (d, J=1.8 Hz, 1H), 7.79 (d, J=1.8 Hz, 1H), 4.38-4.57 (m, 1H), 3.31-3.47 (m, 2H), 3.04-3.15 (m, 2H), 3.01 (s, 3H), 2.04-2.20 (m, 2H), 1.82-1.97 (m, 2H).

Using the procedure described for Example 17, above, additional compounds described herein were prepared by substituting the appropriate starting materials, suitable reagents and reaction conditions, obtaining compounds such as those selected from:

| Cpd | Data |
|---|---|
| 185 | LC-MS 452.1, 454.1 [M + H]$^+$; $^1$H NMR (methanol-$d_4$) δ 8.23 (s, 1H), 7.69 (s, 1H), 4.95-4.86 (m, 1H), 4.25-4.19 (m, 2H), 3.10 (s, 3H), 2.32 (t, J = 13.3 Hz, 2H), 2.27-2.19 (m, 4H), 2.08-2.00 (m, 2H); NH and OH not observed. |

Example 18

Preparation of Compound 58

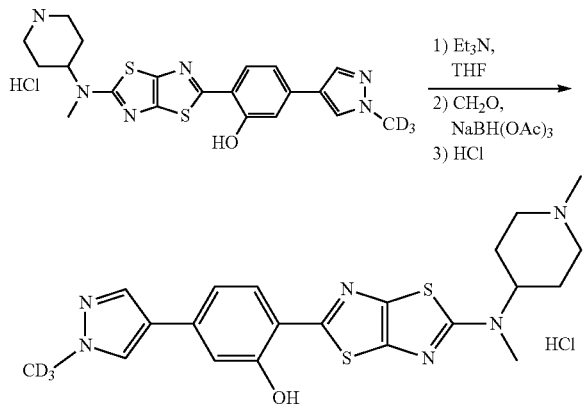

To a mixture of 2-[5-[methyl(4-piperidyl)amino]thiazolo[5,4-d]thiazol-2-yl]-5-[1-(trideuteriomethyl)pyrazol-4-yl]phenol hydrochloride (30 mg, 0.064 mmol), obtained using the chemistry described in Example 12, in THF (1 mL) was added triethylamine (31 μL, 0.22 mmol). The mixture was stirred for 0.5 h, followed by the addition of aqueous formaldehyde (48 μL, 0.64 mmol, 13.31 M) and sodium triacetoxyborohydride (34 mg, 0.16 mmol), and the mixture was stirred overnight. The solvent was evaporated and the residue was suspended in MeOH and filtered, and then purified by preparative LC. The fractions containing the product were combined, concentrated, and treated with 2 M HCl in diethyl ether. The precipitate was collected by filtration, washed with diethyl ether and dried to provide 2-[5-[methyl-(1-methyl-4-piperidyl)amino]thiazolo[5,4-d]thiazol-2-yl]-5-[1-(trideuteriomethyl)pyrazol-4-yl]phenol hydrochloride (17.5 mg, 57%).

LC-MS 444.2 [M+H]+, RT 1.21 min; $^1$H NMR (DMSO-$d_6$) δ: 11.11 (br s, 1H), 10.73 (br s, 1H), 8.14 (d, J=0.6 Hz, 1H), 8.03 (d, J=7.9 Hz, 1H), 7.83 (d, J=0.6 Hz, 1H), 7.08-7.24 (m, 2H), 4.36-4.49 (m, 1H), 3.43-3.56 (m, 2H), 3.12-3.25 (m, 2H), 2.98 (s, 3H), 2.74 (d, J=1.0 Hz, 3H), 2.17-2.34 (m, 2H), 1.88-2.00 (m, 2H).

Using the procedure described for Example 18, above, additional compounds described herein were prepared by substituting the appropriate starting materials, suitable reagents and reaction conditions, obtaining compounds such as those selected from:

| Cpd | Data |
|---|---|
| 59 | LC-MS 455.2 [M + H]+; $^1$H NMR (DMSO-$d_6$) δ: 11.10 (br s, 1H), 10.59 (br s, 1H), 8.14 (s, 1H), 8.03 (d, J = 7.9 Hz, 1H), 7.80-7.88 (m, 1H), 7.10-7.23 (m, 2H), 4.36-4.54 (m, 1H), 3.87 (s, 3H), 3.46-3.62 (m, 2H), 3.02-3.25 (m, 4H), 2.99 (s, 3H), 2.24-2.37 (m, 2H), 1.88-2.01 (m, 2H), 1.27 (t, J = 7.3 Hz, 3H). |
| 84 | LC-MS 452.6 [M + H]+; $^1$H NMR (methanol-$d_4$) δ: 8.28-8.43 (m, 3H), 8.10 (br s, 1H), 7.21 (br s, 1H), 5.41-5.57 (m, 1H), 3.68-3.77 (m, 1H), 3.39-3.55 (m, 2H), 2.96 (s, 3H), 2.62-2.77 (m, 2H), 1.88-2.21 (m, 2H), 1.51 (br d, J = 5.8 Hz, 3H); 2NHs not observed. |
| 96 | LC-MS 463.6 [M + H]+; $^1$H NMR (methanol-$d_4$) δ: 8.19-8.52 (m, 4H), 7.73 (br s, 1H), 6.97 (br s, 1H), 3.97-4.25 (m, 2H), 3.38-3.80 (m, 2H), 3.00-3.19 (m, 1H), 2.27-2.86 (m, 7H), 1.53-2.19 (m, 3H); NH not observed. |
| 114 | LC-MS 467.3 [M + H]+; $^1$H NMR (methanol-$d_4$) δ 9.19 (s, 1H), 8.89 (s, 1H), 8.33 (s, 2H), 4.60-4.50 (m, 1H), 3.19 (s, 3H), 2.97 (s, 3H), 2.53 (t, J = 13.4 Hz, 2H), 2.42-2.34 (m, 2H), 2.06-1.96 (m, 2H), 1.88 (dd, J = 14.8, 6.1 Hz, 2H), 1.51 (s, 6H); NH not observed. |
| 153 | LC-MS 455.3 [M + H]+; $^1$H NMR (DMSO-$d_6$) δ 10.86 (s, 1H), 9.34 (s, 1H), 8.33 (s, 2H), 7.00 (s, 1H), 4.70-4.60 (m, 1H), 4.02-3.95 (m, 2H), 3.05 (s, 3H), 2.69 (s, 3H), 2.50-2.40 (m, 2H), 2.33-2.25 (m, 2H), 2.07-1.98 (m, 2H), 1.95-1.86 (m, 2H). |
| 165 | LC-MS 482.2 [M + H]+; $^1$H NMR (DMSO-$d_6$) δ 13.36 (br s, 1H), 10.85 (br s, 1H), 8.68 (d, J = 7.5 Hz, 1H), 8.55 (s, 1H), 8.19 (s, 1H), 7.05-6.94 (m, 2H), 4.75-4.60 (m, 1H), 4.15-4.05 (m, 2H), 3.08 (s, 3H), 2.95-2.84 (m, 2H), 2.65-2.55 (m, 2H), 2.32-2.28 (m, 2H), 2.10-1.95 (m, 2H), 1.92-1.85 (m, 2H), 1.85-1.72 (m, 2H), 0.93 (t, J = 7.3 Hz, 3H). |
| 166 | LC-MS 468.2 [M + H]+; $^1$H NMR (DMSO-$d_6$) δ 13.34 (s, 1H), 10.25 (br s, 1H), 8.68 (d, J = 7.4 Hz, 1H), 8.36 (m, 2H), 7.00 (m, 2H), 4.75-4.60 (m, 1H), 4.15-4.05 (m, 2H), 3.02 (s, 3H), 2.25-1.55 (m, 10H), 1.15 (t, J = 7.3 Hz, 3H). |
| 178 | LC-MS 454.2 [M + H]+; $^1$H NMR (DMSO-$d_6$) δ 13.35 (s, 1H), 10.79 (s, 1H), 8.68 (d, J = 7.5 Hz, 1H), 8.55 (s, 1H), 8.19 (s, 1H), 7.03-6.95 (m, 2H), 4.71-4.59 (m, 1H), 4.15-3.90 (m, 2H), 3.04 (s, 3H), 2.69 (s, 3H), 2.48-2.40 (m, 2H), 2.34-2.24 (m, 2H), 2.10-1.98 (m, 2H), 1.97-1.85 (m, 2H). |
| 217 | LC-MS 428.5 [M + H]+; $^1$H NMR (DMSO-$d_6$) δ: 11.02 (br s, 1H), 10.66 (br s, 1H), 8.49 (d, J = 1.5 Hz, 2H), 8.27 (s, 1H), 7.75 (s, 1H), 4.41-4.53 (m, 1H), 3.45-3.55 (m, 2H), 3.13-3.25 (m, 2H), 3.00 (s, 3H), 2.74 (d, J = 4.6 Hz, 3H), 2.18-2.31 (m, 2H), 1.89-2.03 (m, 2H). |
| 218 | LC-MS 442.4 [M + H]+; $^1$H NMR (DMSO-$d_6$) δ: 11.19 (br s, 1H), 8.50 (s, 1H), 8.30 (s, 2H), 7.92 (br s, 1H), 4.35 (br t, J = 11.6 Hz, 1H), 3.42-3.54 (m, 4H), 3.13-3.27 (m, 2H), 2.72 (d, J = 4.6 Hz, 3H), 2.28-2.43 (m, 2H), 1.95-2.09 (m, 2H), 1.26 (t, J = 7.0 Hz, 3H); NH and OH not observed. |

Example 19

Preparation of Compound 62

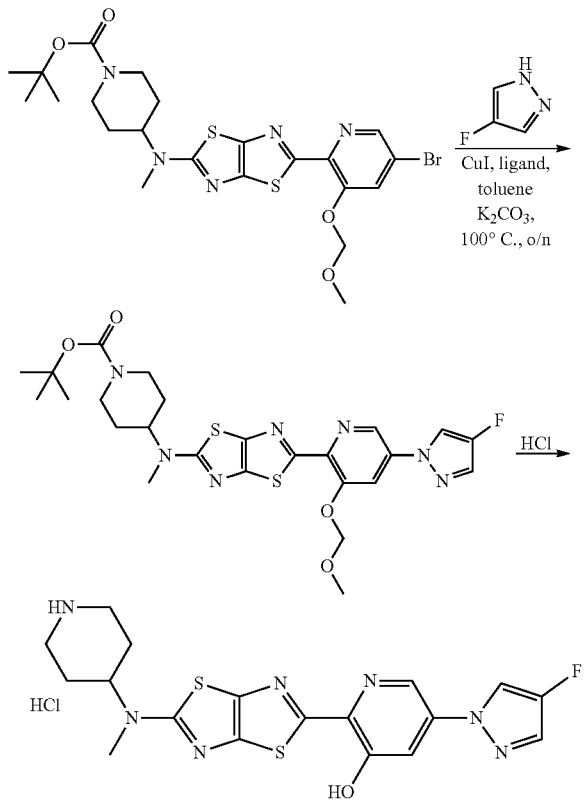

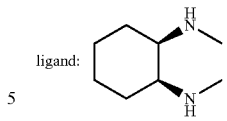
ligand:

A mixture of tert-butyl 4-[[2-[5-bromo-3-(methoxymethoxy)-2-pyridyl]thiazolo[5,4-d]thiazol-5-yl]-methyl-amino]piperidine-1-carboxylate (86 mg, 0.15 mmol), obtained using the chemistry described in Example 16, Step 2, 4-fluoro-1H-pyrazole (19 mg, 0.22 mmol), cuprous iodide (3 mg, 0.016 mmol), trans-N,N'-dimethyl-cyclohexane-1,2-diamine (5 mg, 0.034 mmol) and $K_2CO_3$ (52 mg, 0.38 mmol) in toluene (0.3 mL) was stirred at 100° C. for 12 h. The reaction was concentrated, diluted with $CH_2Cl_2$ and washed with aqueous $NH_4Cl$, brine and dried. After the removal of the solvent, the residue was chromatographed (EtOAc in $CH_2Cl_2$, 0-100%) to provide tert-butyl 4-[[2-[5-(4-fluoropyrazol-1-yl)-3-(methoxymethoxy)-2-pyridyl]thiazolo[5,4-d]thiazol-5-yl]-methyl-amino]piperidine-1-carboxylate. The product was treated with HCl in dioxane (3.0 mL, 4.0 M) at room temperature for 4 h and the precipitate was collected, washed with diethyl ether and dried to provide 5-(4-fluoropyrazol-1-yl)-2-[5-[methyl(4-piperidyl)amino]thiazolo[5,4-d]thiazol-2-yl]pyridin-3-ol hydrochloride (46 mg, 65.2%).

LC-MS 432.4 [M+H]$^+$, RT 1.21 min, $^1$H NMR (DMSO-d$_6$) δ: 11.15 (br s, 1H), 8.69-8.94 (m, 3H), 8.65 (d, J=2.1 Hz, 1H), 7.97 (d, J=4.0 Hz, 1H), 7.86 (d, J=2.1 Hz, 1H), 4.37-4.62 (m, 1H), 3.33-3.42 (m, 2H), 3.04-3.19 (m, 2H), 3.01 (s, 3H), 2.03-2.18 (m, 2H), 1.84-1.97 (m, 2H).

Using the procedure described for Example 19, above, additional compounds described herein were prepared by substituting the appropriate starting materials, suitable reagents and reaction conditions, obtaining compounds such as those selected from:

| Cpd | Data |
|---|---|
| 60 | LC-MS 414.2 [M + H]$^+$; $^1$H NMR (methanol-d$_4$) δ: 9.54 (br s, 1H), 8.51 (d, J = 2.14 Hz, 1H), 8.17 (br s, 1H), 7.76-7.91 (m, 2H), 4.50-4.61 (m, 1H), 3.52-3.63 (m, 2H), 3.16-3.27 (m, 2H), 3.12 (s, 3H), 2.08-2.30 (m, 4H); NH and OH not observed. |
| 63 | LC-MS 428.5 [M + H]$^+$; $^1$H NMR (DMSO-d$_6$) δ: 11.09 (br s, 1H), 8.70-8.99 (m, 2H), 8.66 (d, J = 1.83 Hz, 1H), 8.43 (s, 1H), 7.84 (d, J = 1.83 Hz, 1H), 7.67 (s, 1H), 4.41-4.57 (m, 1H), 3.32-3.47 (m, 2H), 3.04-3.19 (m, 2H), 3.01 (s, 3H), 2.04-2.16 (m, 5H), 1.87-1.96 (m, 2H). |
| 190 | LC-MS 454.4 [M + H]$^+$; $^1$H NMR (methanol-d$_4$) δ 9.48 (s, 1H), 8.51 (s, 1H), 7.91 (s, 1H), 7.82 (s, 1H), 4.96-4.86 (m, 1H), 4.26-4.17 (m, 2H), 3.12 (s, 3H), 2.49 (s, 3H), 2.35-2.20 (m, 6H), 2.10-2.02 (m, 2H); NH and OH not observed. |
| 193 | LC-MS 458.4 [M + H]$^+$; $^1$H NMR (methanol-d$_4$) δ 8.60 (s, 1H), 8.45 (d, J = 4.3 Hz, 1H), 7.78 (s, 1H), 7.76 (d, J = 4.3 Hz, 1H), 4.85-4.70 (m, 1H), 4.23-4.15 (m, 2H), 3.09 (s, 3H), 2.30-2.19 (m, 6H), 2.10-2.00 (m, 2H); NH and OH not observed. |
| 212 | LC-MS 415.4 [M + H]$^+$; $^1$H NMR (DMSO-d$_6$) δ: 11.24 (br s, 1H), 9.44 (s, 1H), 8.75-8.98 (m, 2H), 8.70 (d, J = 1.8 Hz, 1H), 8.33 (s, 1H), 7.98 (d, J = 2.1 Hz, 1H), 4.39-4.59 (m, 1H), 3.32-3.46 (m, 2H), 3.05-3.20 (m, 2H), 3.02 (s, 3H), 2.04-2.21 (m, 2H), 1.83-1.99 (m, 2H). |
| 214 | LC-MS 415.5 [M + H]$^+$; $^1$H NMR (methanol-d$_4$) δ: 8.83 (br s, 1H), 8.03 (s, 2H), 7.98 (s, 1H), 4.46-4.55 (m, 1H), 3.53-3.62 (m, 2H), 3.15-3.27 (m, 2H), 3.09 (s, 3H), 2.08-2.23 (m, 4H); NH and OH not observed. |
| 215 | LC-MS 415.4 [M + H]$^+$; $^1$H NMR (methanol-d$_4$) δ: 8.66 (br s, 2H), 7.98 (s, 1H), 7.90 (s, 1H), 4.44-4.57 (m, 1H), 3.51-3.62 (m, 2H), 3.15-3.26 (m, 2H), 3.10 (s, 3H), 2.07-2.28 (m, 4H); NH and OH not observed. |
| 221 | LC-MS 428.5 [M + H]$^+$; $^1$H NMR (DMSO-d$_6$) δ: 11.31 (br s, 1H), 9.52 (br s, 1H), 8.81-9.01 (m, 2H), 8.59 (d, J = 2.1 Hz, 1H), 8.03 (s, 1H), 7.96 (d, J = 1.8 Hz, 1H), 4.42-4.55 (m, 1H), 3.64-3.75 (m, 1H), 3.49-3.55 (m, 1H), 3.05-3.18 (m, 2H), 3.03 (s, 3H), 2.34 (s, 3H), 2.07-2.19 (m, 2H), 1.85-1.97 (m, 2H). |

Example 20

Preparation of Compound 64

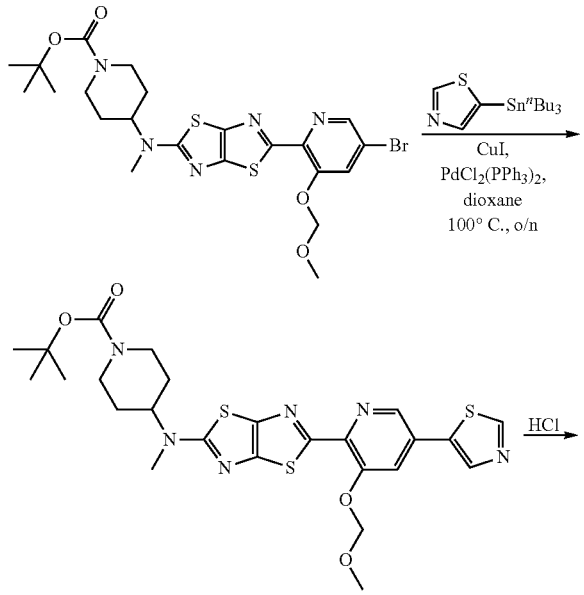

A mixture of tert-butyl 4-[[2-[5-bromo-3-(methoxymethoxy)-2-pyridyl]thiazolo[5,4-d]thiazol-5-yl]-methyl-amino]piperidine-1-carboxylate (86 mg, 0.15 mmol), obtained using the chemistry described in Example 16, Step 2, tributylthiazol-5-yl-stannane (87 mg, 0.22 mmol), cuprous iodide (0.7 mg, 0.004 mmol), and PdCl$_2$(PPh$_3$)$_2$ (11 mg, 0.016 mmol) in 1,4-dioxane (0.5 mL) was stirred at 100° C. for 12 h. The reaction mixture was concentrated, diluted with CH$_2$Cl$_2$ and washed with aqueous NH$_4$Cl, brine and then dried. After removal of the solvent, the residue was chromatographed (EtOAc in CH$_2$Cl$_2$, 0-100%) to provide tert-butyl 4-[[2-[3-(methoxymethoxy)-5-thiazol-5-yl-2-pyridyl]thiazolo[5,4-d]thiazol-5-yl]-methyl-amino]piperidine-1-carboxylate. This was treated with HCl in dioxane (3.0 mL, 4.0 M) at room temperature for 4 h and then concentrated to dryness. The residue was purified by preparative LC using 0.2% TFA in CH$_3$CN and 0.2% TFA in water. The fractions containing the desired product were combined and concentrated to dryness. The residue was stirred with 2 N HCl in diethyl ether (2 mL) at room temperature for 4 h. The precipitate was collected, washed with diethyl ether and dried to provide 2-[5-[methyl(4-piperidyl)amino]thiazolo[5,4-d]thiazol-2-yl]-5-thiazol-5-yl-pyridin-3-ol; hydrochloride (34 mg, 49%).

LC-MS 431.4 [M+H]$^+$, RT 1.11 min; $^1$H NMR (DMSO-d$_6$) δ: 10.99 (br s, 1H), 9.21 (s, 1H), 8.63-8.98 (m, 2H), 8.53 (s, 1H), 8.51 (d, J=1.8 Hz, 1H), 7.80 (d, J=1.8 Hz, 1H), 4.42-4.57 (m, 1H), 3.32-3.46 (m, 2H), 3.05-3.19 (m, 2H), 2.96-3.05 (m, 3H), 2.02-2.18 (m, 2H), 1.85-1.98 (m, 2H).

Using the procedure described for Example 20, above, additional compounds described herein were prepared by substituting the appropriate starting materials, suitable reagents and reaction conditions, obtaining compounds such as those selected from:

| Cpd | Data |
|---|---|
| 199 | LC-MS 471.2 [M + H]$^+$; $^1$H NMR (methanol-d$_4$) δ 8.42 (s, 1H), 8.15 (s, 1H), 7.68 (s, 1H), 4.86-4.75 (m, 1H), 4.26-4.19 (m, 2H), 3.10 (s, 3H), 2.81 (s, 3H), 2.32-2.20 (m, 6H), 2.10-2.03 (m, 2H); NH and OH not observed. |
| 222 | LC-MS 445.4 [M + H]$^+$; $^1$H NMR (DMSO-d$_6$) δ: 11.01 (br s, 1H), 8.79-9.00 (m, 2H), 8.43 (d, J = 1.8 Hz, 1H), 8.26 (s, 1H), 7.72 (d, J = 1.8 Hz, 1H), 4.48 (br s, 1H), 3.38 (br d, J = 12.2 Hz, 2H), 3.09 (q, J = 11.8 Hz, 2H), 3.01 (s, 3H), 2.71 (s, 3H), 2.04-2.18 (m, 2H), 1.91 (br d, J = 11.9 Hz, 2H). |
| 223 | LC-MS 429.4 [M + H]$^+$; $^1$H NMR (DMSO-d$_6$) δ: 11.05 (br s, 1H), 8.72-8.94 (m, 2H), 8.47 (d, J = 1.8 Hz, 1H), 7.77 (s, 1H), 7.70 (d, J = 1.5 Hz, 1H), 4.42-4.56 (m, 1H), 3.34-3.44 (m, 2H), 3.04-3.19 (m, 2H), 3.01 (s, 3H), 2.52 (s, 3H), 2.04-2.20 (m, 2H), 1.85-1.98 (m, 2H). |

Example 21

Preparation of Compound 201

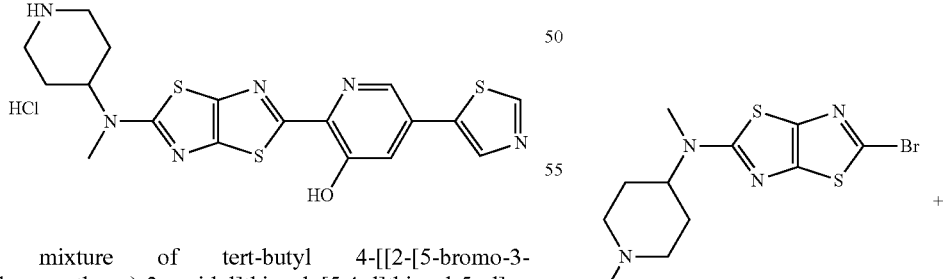

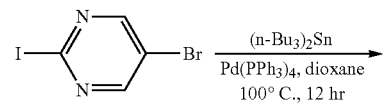

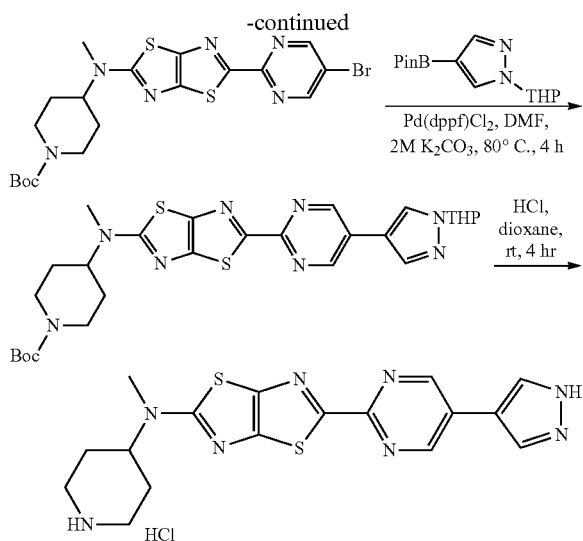

Step 1: A mixture of tert-butyl 4-[(5-bromothiazolo[5,4-d]thiazol-2-yl)-methyl-amino]piperidine-1-carboxylate (65 mg, 0.15 mmol), prepared in Example 11, Pd(PPh₃)₄ (17 mg, 0.015 mmol), 5-bromo-2-iodo-pyrimidine (64 mg, 0.22 mmol), and hexabutylditin (0.23 mL, 0.44 mmol) in 1,4-dioxane (2.0 mL) was stirred at 100° C. under an argon atmosphere for 12 h. The reaction was then cooled and concentrated. The residue was chromatographed on a silica gel column (ethyl acetate in dichloromethane, 0-100%) to provide tert-butyl 4-[[2-(5-bromopyrimidin-2-yl)thiazolo[5,4-d]thiazol-5-yl]-methyl-amino]piperidine-1-carboxylate (59 mg, 76%).

LC-MS 511.0, 513.0 [M+H]⁺, RT 1.67 min.

Step 2: A mixture of tert-butyl 4-[[2-(5-bromopyrimidin-2-yl)thiazolo[5,4-d]thiazol-5-yl]-methyl-amino]piperidine-1-carboxylate (59 mg, 0.12 mmol), 1-tetrahydropyran-2-yl-4-(4,4,5,5-tetramethyl-1,3,2-dioxaborolan-2-yl)pyrazole (50 mg, 0.18 mmol), DMF (1.0 mL), PdCl₂(dppf) (13 mg, 0.016 mmol) and K₂CO₃ (0.19 mL, 0.38 mmol) was stirred at 80° C. overnight under an argon atmosphere. The reaction was then diluted with dichloromethane, washed with water and brine, dried, and then evaporated to dryness. The residue was chromatographed on a silica column (ethyl acetate in dichloromethane 0-100%) to provide tert-butyl 4-[methyl-[2-[5-(1-tetrahydropyran-2-ylpyrazol-4-yl)pyrimidin-2-yl]thiazolo[5,4-d]thiazol-5-yl]amino]piperidine-1-carboxylate, which was then treated with HCl in dioxane (3.0 mL, 4.0 M) at room temperature for 4 h. The mixture was diluted with diethyl ether and the precipitate was collected, washed with diethyl ether and dried to provide N-methyl-N-(4-piperidyl)-2-[5-(1H-pyrazol-4-yl)pyrimidin-2-yl]thiazolo[5,4-d]thiazol-5-amine; hydrochloride (23 mg, 46%).

LC-MS 399.2 [M+H]⁺, RT 0.82 min; ¹H NMR (DMSO-d₆) δ: 9.14 (s, 2H), 8.65-8.97 (m, 2H), 8.34 (s, 2H), 4.36-4.60 (m, 1H), 3.32-3.45 (m, 2H), 3.05-3.17 (m, 2H), 3.03 (s, 3H), 2.02-2.22 (m, 2H), 1.81-2.00 (m, 2H).

Using the procedure described for Example 21, above, additional compounds described herein were prepared by substituting the appropriate starting materials, suitable reagents and reaction conditions, obtaining compounds such as those selected from:

| Cpd | Data |
|---|---|
| 101 | LC-MS 438.3 [M + H]⁺; ¹H NMR (methanol-d₄) δ: 8.64 (d, J = 2.1 Hz, 1H), 8.59 (br s, 1H), 8.43 (br s, 2H), 8.33 (d, J = 2.1 Hz, 1H), 4.60-4.71 (m, 1H), 3.54-3.63 (m, 2H), 3.15-3.29 (m, 5H), 2.07-2.33 (m, 4H); NH not observed. |
| 126 | LC-MS 426.4 [M + H]⁺; ¹H NMR (DMSO-d₆) δ 10.76 (br s, 1H), 8.88 (s, 1H), 8.26 (s, 2H), 8.14 (d, J = 8.3 Hz, 1H), 8.02 (d, J = 8.3 Hz, 1H), 4.60-4.45 (m, 1H), 3.55-3.45 (m, 1H), 3.42-3.30 (m, 1H), 3.27-3.18 (m, 1H), 3.01 (s, 3H), 2.75 (s, 3H), 2.39-2.23 (m, 1H), 2.18-2.07 (m, 1H), 2.05-1.91 (m, 2H), 1.35 (d, J = 6.3 Hz, 3H). |
| 129 | LC-MS 427.3 [M + H]⁺; ¹H NMR (methanol-d₄) δ 8.98 (s, 2H), 8.11 (s, 2H), 4.50-4.40 (m, 1H), 3.60-3.50 (m, 1H), 3.32-3.25 (m, 1H), 3.19-3.13 (m, 1H), 3.00 (s, 3H), 2.84 (s, 3H), 2.17-2.00 (m, 3H), 1.97-1.87 (m, 1H), 1.35 (d, J = 6.4 Hz, 3H); NH not observed. |
| 133 | LC-MS 454.3 [M + H]⁺; ¹H NMR (DMSO-d₆) δ 9.11 (br s, 1H), 8.89 (s, 1H), 8.25 (s, 2H), 8.14 (d, J = 8.2 Hz, 1H), 8.09 (br s, 1H), 8.03 (d, J = 8.2 Hz, 1H), 4.70-4.60 (m, 1H), 3.03 (s, 3H), 2.01 (t, J = 13.1 Hz, 2H), 1.89 (dd, J = 13.1, 3.7 Hz, 2H), 1.51 (s, 6H), 1.47 (s, 6H). |
| 150 | LC-MS 427.4 [M + H]⁺; ¹H NMR (DMSO-d₆) δ 9.26-9.05 (m, 4H), 8.34 (s, 2H), 4.25-4.15 (m, 1H), 3.99 (dd, J = 10.9, 7.0 Hz, 1H), 3.81-3.75 (m, 1H), 3.61-3.50 (m, 1H), 3.43-3.35 (m, 1H), 2.43-2.35 (m, 2H), 1.38 (s, 9H). |
| 161 | LC-MS 399.3 [M + H]⁺; ¹H NMR (DMSO-d₆) δ 9.33 (br s, 1H), 9.16 (s, 2H), 8.95 (br s, 1H), 8.35 (s, 2H), 4.65-4.50 (m, 1H), 3.37-3.29 (m, 1H), 3.29-3.23 (m, 1H), 3.23-3.13 (m, 1H), 3.08 (s, 3H), 2.89-2.76 (m, 1H), 2.02-1.88 (m, 3H), 1.87-1.74 (m, 1H). |
| 162 | LC-MS 455.4 [M + H]⁺; ¹H NMR (DMSO-d₆) δ 9.25-9.10 (m, 2H), 8.34 (s, 2H), 8.15 (br s, 1H), 4.74-4.62 (m, 1H), 3.05 (s, 3H), 2.10-1.97 (m, 2H), 1.90 (dd, J = 13.0, 3.5 Hz, 2H), 1.52 (s, 6H), 1.48 (s, 6H); NH not observed. |
| 167 | LC-MS 455.4 [M + H]⁺; ¹H NMR (DMSO-d₆) δ 9.20 (br s, 1H), 8.41 (s, 2H), 8.23 (d, J = 8.9 Hz, 1H), 8.17 (br s, 1H), 8.11 (d, J = 8.9 Hz, 1H), 4.75-4.64 (m, 1H), 3.05 (s, 3H), 2.10-2.00 (m, 2H), 1.93-1.85 (m, 2H), 1.52 (s, 6H), 1.48 (s, 6H). |
| 168 | LC-MS 425.4 [M + H]⁺; ¹H NMR (DMSO-d₆) δ 9.52 (br s, 1H), 9.02 (brs, 1H), 8.42 (s, 2H), 8.23 (d, J = 8.9 Hz, 1H), 8.12 (d, J = 8.9 Hz, 1H), 4.72-4.62 (m, 1H), 4.14-4.05 (m, 2H), 3.06 (s, 3H), 2.39-2.30 (m, 2H), 2.11-1.95 (m, 4H), 1.89-1.82 (m, 2H). |
| 174 | LC-MS 424.4 [M + H]⁺; ¹H NMR (DMSO-d₆) δ 9.48 (br s, 1H), 9.01 (br s, 1H), 8.88 (s, 1H), 8.26 (s, 2H), 8.14 (d, J = 8.2 Hz, 1H), 8.02 (d, J = 8.2 Hz, 1H), 4.70-4.60 (m, 1H), 4.15-4.05 (m, 2H), 3.04 (s, 3H), 2.38-2.24 (m, 2H), 2.09-1.95 (m, 4H), 1.89-1.78 (m, 2H). |

| Cpd | Data |
|---|---|
| 194 | LC-MS 425.4 [M + H]+; 1H NMR (methanol-d4) δ 9.10 (s, 2H), 8.26 (s, 2H), 4.85-4.70 (m, 1H), 4.26-4.15 (m, 2H), 3.10 (s, 3H), 2.32-2.20 (m, 6H), 2.11-2.02 (m, 2H); 2NHs not observed. |

Example 22

Preparation of Compound 188

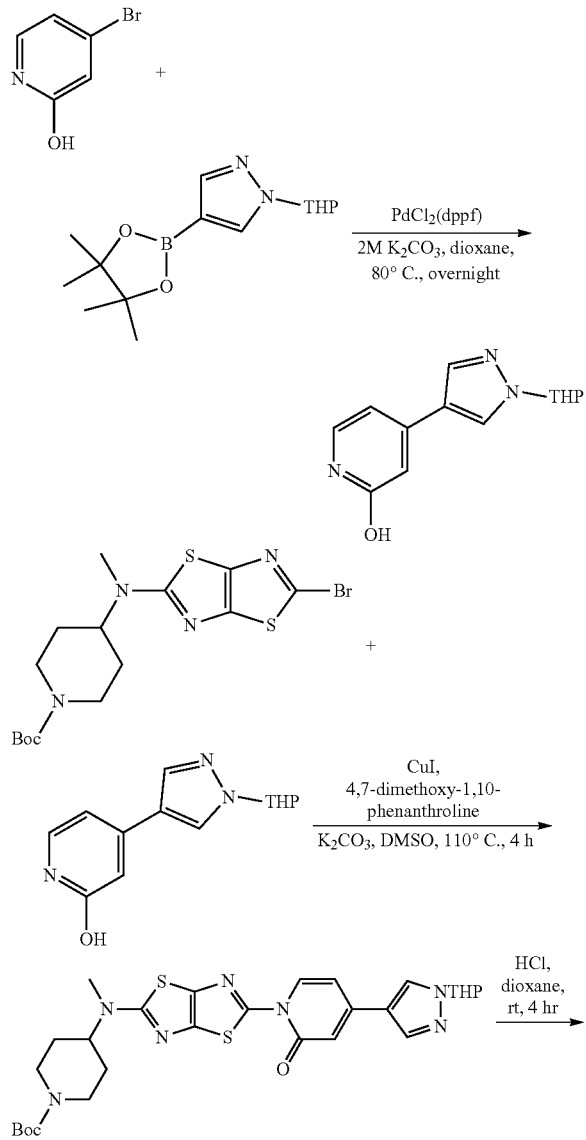

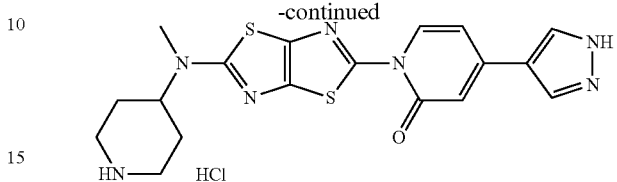

Step 1: A mixture of 4-bromopyridin-2-ol (0.49 g, 2.82 mmol), 1-tetrahydropyran-2-yl-4-(4,4,5,5-tetramethyl-1,3,2-dioxaborolan-2-yl)pyrazole (0.86 g, 3.10 mmol), granular $K_2CO_3$ (1.17 g, 8.47 mmol), $PdCl_2$(dppf) (0.10 g, 0.14 mmol), 1,4-dioxane (12 mL), and $H_2O$ (5 mL) was stirred at 80° C. under an argon atmosphere overnight. The reaction mixture was diluted with brine (40 mL), and extracted with dichloromethane (2×60 mL). The extracts were combined, dried over anhydrous $MgSO_4$, filtered, and the filtrate was concentrated to dryness on a rotovap. The crude material was purified on a silica gel column (methanol in dichloromethane, 0-50%) to afford the desired 4-(1-tetrahydropyran-2-ylpyrazol-4-yl)pyridin-2-ol (0.56 g, 81%) as a white, fluffy powder. LC-MS 246.3 [M+H]+, RT 1.05 min.

Step 2: A mixture of tert-butyl 4-[(5-bromothiazolo[5,4-d]thiazol-2-yl)-methyl-amino]piperidine-1-carboxylate (65 mg, 0.15 mmol), prepared in Example 11, 4-(1-tetrahydropyran-2-ylpyrazol-4-yl)-1H-pyridin-2-one (48 mg, 0.20 mmol), 4,7-dimethoxy-1,10-phenanthroline (26 mg, 0.11 mmol), CuI (14 mg, 0.074 mmol), and $K_2CO_3$ (46 mg, 0.33 mmol) in DMSO (1.0 mL) was stirred at 110° C. under an argon atmosphere for 4 h and was then evaporated to dryness. The residue was suspended in dichloromethane and filtered. The filtrate was loaded on a silica gel column and chromatographed (methanol in dichloromethane 0-20%) to provide tert-butyl 4-[methyl-[2-[2-oxo-4-(1-tetrahydropyran-2-ylpyrazol-4-yl)-1-pyridyl]thiazolo[5,4-d]thiazol-5-yl]amino]piperidine-1-carboxylate, which was treated with HCl in dioxane (3.0 mL, 12 mmol, 4.0 M) at room temperature for 4 h. The resulting mixture was diluted with ethyl ether. The precipitate was collected and triturated with MeOH, and dried to furnish 1-[5-[methyl(4-piperidyl)amino]thiazolo[5,4-d]thiazol-2-yl]-4-(1H-pyrazol-4-yl)pyridin-2-one hydrochloride (56 mg, 83%). LC-MS 414.2 [M+H]+, RT 0.87 min; 1H NMR (DMSO-d6) δ: 8.99 (br s, 2H), 8.67 (d, J=7.3 Hz, 1H), 8.36 (br s, 2H), 6.88-7.08 (m, 2H), 4.34-4.51 (m, 1H), 3.33-3.47 (m, 2H), 3.01-3.16 (m, 2H), 2.97 (s, 3H), 2.03-2.22 (m, 2H), 1.80-1.98 (m, 2H).

Using the procedure described for Example 22, above, additional compounds described herein were prepared by substituting the appropriate starting materials, suitable reagents and reaction conditions, obtaining compounds such as those selected from:

| Cpd | Data |
|---|---|
| 131 | LC-MS 443.3 [M + H]+; 1H NMR (DMSO-d6) δ 10.74 (br s, 1H), 9.34 (s, 1H), 8.34 (s, 2H), 7.01 (s, 1H), 4.56-4.52 (m, 1H), 3.60-3.50 (m, 1H), 3.32-3.25 (m, 1H), 3.19-3.13 (m, 1H), 2.99 (s, 3H), 2.74 (s, 3H), 2.35-2.25 (m, 1H), 2.16-2.05 (m, 1H), 2.04-1.90 (m, 2H), 1.35 (d, J = 6.4 Hz, 3H). |

| Cpd | Data |
|---|---|
| 140 | LC-MS 471.4 [M + H]$^+$; $^1$H NMR (DMSO-d$_6$) δ 13.37 (s, 1H), 9.34 (s, 1H), 8.71 (br s, 1H), 8.48 (s, 1H), 8.19 (s, 1H), 7.73 (br s, 1H), 7.01 (s, 1H), 4.66-4.50 (m, 1H), 3.03 (s, 3H), 1.98-1.85 (m, 4H), 1.50 (s, 6H), 1.42 (s, 6H). |
| 144 | LC-MS 469.4 [M + H]$^+$; $^1$H NMR (DMSO-d$_6$) δ 13.36 (s, 1H), 9.34 (s, 1H), 8.68 (s, 2H), 8.48 (br s, 1H), 8.19 (br s, 1H), 7.01 (s, 1H), 4.70-4.60 (m, 1H), 3.00 (s, 3H), 2.14 (d, J = 9.0 Hz, 2H), 2.02-1.85 (m, 6H), 1.44 (s, 6H). |
| 146 | LC-MS 468.4 [M + H]$^+$; $^1$H NMR (DMSO-d$_6$) δ 9.68 (br s, 1H), 9.02 (br s, 1H), 8.68 (d, J = 7.4 Hz, 1H), 8.37 (s, 2H), 7.00 (m, 2H), 4.70-4.60 (m, 1H), 3.03 (s, 3H), 2.19 (t, J = 12.7 Hz, 2H), 2.10 (d, J = 8.6 Hz, 2H), 1.94-1.84 (m, 4H), 1.47 (s, 6H). |
| 148 | LC-MS 486.3 [M + H]$^+$; $^1$H NMR (DMSO-d$_6$) δ 9.24 (br s, 1H), 8.98 (d, J = 4.1 Hz, 1H), 8.86 (m, 2H), 8.10 (d, J = 4.1 Hz, 1H), 7.30 (d, J = 8.2 Hz, 1H), 7.09 (s, 1H), 4.70-4.60 (m, 1H), 3.02 (s, 3H), 2.16-2.07 (m, 4H), 1.95-1.85 (m, 4H), 1.46 (s, 6H). |
| 149 | LC-MS 458.3 [M + H]$^+$; $^1$H NMR (DMSO-d$_6$) δ 9.48 (br s, 1H), 8.99 (br s, 1H), 8.97 (d, J = 4.2 Hz, 1H), 8.84 (d, J = 7.9 Hz, 1H), 8.09 (d, J = 4.2 Hz, 1H), 7.28 (d, J = 7.9 Hz, 1H), 7.08 (s, 1H), 4.65-4.55 (m, 1H), 4.13-4.06 (m, 2H), 3.02 (s, 3H), 2.32 (t, J = 12.7 Hz, 2H), 2.12-2.02 (m, 2H), 2.02-1.92 (m, 2H), 1.89-1.80 (m, 2H). |
| 151 | LC-MS 442.3 [M + H]$^+$; $^1$H NMR (DMSO-d$_6$) δ 9.30-9.10 (m, 2H), 8.68 (d, J = 7.9 Hz, 1H), 8.37 (s, 2H), 7.00 (m, 2H), 4.25-4.15 (m, 1H), 3.94 (dd, J = 10.8, 6.9 Hz, 1H), 3.76-3.65 (m, 1H), 3.54-3.40 (m, 1H), 3.42-3.35 (m, 1H), 2.43-2.35 (m, 2H), 1.38 (s, 9H). |
| 155 | LC-MS 414.4 [M + H]$^+$; $^1$H NMR (DMSO-d$_6$) δ 9.36 (br s, 1H), 8.99 (br s, 1H), 8.69 (d, J = 7.4 Hz, 1H), 8.38 (s, 2H), 7.03-6.98 (m, 2H), 4.58-4.49 (m, 1H), 3.34-3.27 (m, 1H), 3.27-3.21 (m, 1H), 3.21-3.10 (m, 1H), 3.03 (s, 3H), 2.89-2.76 (m, 1H), 2.00-1.86 (m, 3H), 1.86-1.75 (m, 1H) |
| 156 | LC-MS 457.3 [M + H]$^+$; $^1$H NMR (DMSO-d$_6$) δ 9.21 (br s, 1H), 8.71 (d, J = 7.6 Hz, 1H), 8.48 (br s, 1H), 8.39 (s, 2H), 7.07-6.99 (m, 2H), 5.63-5.54 (m, 1H), 2.37 (dd, J = 13.3,4.2 Hz, 2H), 1.87 (dd,J = 13.3, 10.5 Hz, 2H), 1.51 (s, 12H). |
| 157 | LC-MS 415.4 [M + H]$^+$; $^1$H NMR (DMSO-d$_6$) δ: 12.37 (br s, 1H), 10.81 (br s, 1H), 7.92 (br d, J = 9.2 Hz, 1H), 7.02 (br s, 1H), 6.46 (br s, 1H), 6.33 (d, J = 9.2 Hz, 1H), 4.51-4.66 (m, 1H), 3.46-3.57 (m, 1H), 3.17-3.43 (m, 2H), 2.96-3.11 (m, 3H), 2.69-2.81 (m, 3H), 2.23-2.39 (m, 1H), 1.89-2.21 (m, 3H), 1.21-1.45 (m, 3H). |
| 169 | LC-MS 414.4 [M + H]$^+$; $^1$H NMR (DMSO-d$_6$) δ 9.32 (br s, 1H), 9.04-8.90 (m, 1H), 8.69 (d, J = 7.4 Hz, 1H), 8.38 (s, 2H), 7.05-6.95 (m, 2H), 4.58-4.51 (m, 1H), 3.35-3.28 (m, 1H), 3.28-3.21 (m, 1H), 3.21-3.11 (m, 1H), 3.03 (s, 3H), 2.88-2.77 (m, 1H), 1.98-1.86 (m, 3H), 1.85-1.75 (m, 1H). |
| 171 | LC-MS 450.2, 452.2 [M + H]$^+$; $^1$H NMR (DMSO-d$_6$) δ 9.48-9.32 (br s, 1H), 8.97 (br s, 1H), 8.65 (d, J = 7.8 Hz, 1H), 7.13 (s, 1H), 6.85 (d, J = 7.8 Hz, 1H), 4.66-4.54 (m, 1H), 4.14-4.05 (m, 2H), 3.57 (s, 3H), 2.30 (t, J = 12.0 Hz, 2H), 2.09-2.02 (m, 2H), 2.02-1.95 (m, 2H), 1.90-1.79 (m, 2H). |
| 172 | LC-MS 441.2 [M + H]$^+$; $^1$H NMR (DMSO-d$_6$) δ 9.38 (br s, 1H), 9.33 (s, 1H), 8.97 (br s, 1H), 8.34 (s, 2H), 7.00 (s, 1H), 4.66-4.56 (m, 1H), 4.14-4.05 (m, 2H), 3.03 (s, 3H), 2.34-2.23 (m, 2H), 2.10-1.95 (m, 4H), 1.90-1.83 (m, 2H). |
| 180 | LC-MS 442.2 [M + H]$^+$; $^1$H NMR (DMSO-d$_6$) δ: 13.18-13.40 (m, 1H), 8.63-8.75 (m, 1H), 8.45-8.62 (m, 1H), 8.10-8.31 (m, 1H), 6.92-7.05 (m, 2H), 3.91-4.18 (m, 1H), 2.84-3.11 (m, 4H), 1.42-2.36 (m, 9H), 0.98-1.25 (m, 3H). |
| 181 | LC-MS 470.2 [M + H]$^+$; $^1$H NMR (DMSO-d$_6$) δ: 13.25-13.47 (m, 1H), 9.11-9.42 (m, 1H), 7.96-8.83 (m, 4H), 6.90-7.09 (m, 2H), 4.38-4.70 (m, 1H), 2.99 (s, 3H), 0.93-2.14 (m, 16H). |
| 187 | LC-MS 374.3 [M + H]$^+$; $^1$H NMR (methanol-d$_4$) δ 8.84 (d, J = 7.2 Hz, 1H), 7.69-7.61 (m, 1H), 6.78 (d, J = 9.3 Hz, 1H), 6.66 (t, J = 7.2 Hz, 1H), 4.88-4.78 (m, 1H), 4.24-4.17 (m, 2H), 3.07 (s, 3H), 2.32-2.20 (m, 6H), 2.08-2.02 (m, 2H); NH not observed. |
| 195 | LC-MS 440.3 [M + H]$^+$; $^1$H NMR (methanol-d$_4$) δ 8.82 (d, J = 6.9 Hz, 1H), 8.34 (s, 2H), 7.00 (m, 2H), 4.86-4.79 (m, 1H), 4.25-4.17 (m, 2H), 3.07 (s, 3H), 2.33-2.19 (m, 6H), 2.08-2.00 (m, 2H); 2NHs not observed. |

Example 23

Preparation of Compound 152

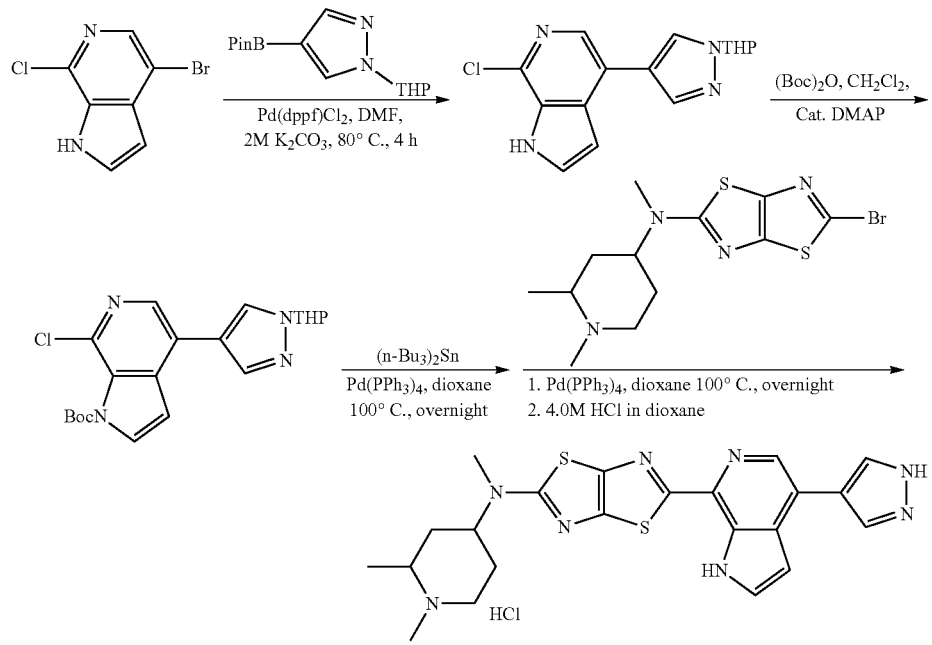

Step 1: A mixture of 4-bromo-7-chloro-3a,7a-dihydro-1H-pyrrolo[2,3-c]pyridine (5.00 g, 21.4 mmol), 1-tetrahydropyran-2-yl-4-(4,4,5,5-tetramethyl-1,3,2-dioxaborolan-2-yl)pyrazole (7.15 g, 25.7 mmol), PdCl$_2$(dppf) (1.78 g, 2.14 mmol), and K$_2$CO$_3$ (21 mL, 42 mmol, 2.0 M) in DMF (100 mL) was stirred at 80° C. under an argon atmosphere for 4 h. The solvent was removed under vacuum on a rotovap and the residue was suspended in dichloromethane and filtered. The filtrate was washed with water and brine, dried and concentrated to dryness and used directly in Step 2, below. LC-MS 303.3, 305.3 [M+H]$^+$, RT 1.15 min.

Step 2: The material obtained above was dissolved in dichloromethane (50 mL) and treated with tert-butoxycarbonyl tert-butyl carbonate (6.1 mL, 27 mmol) and a few crystals of 4-dimethylaminopyridine. This was stirred for 60 min at room temperature, and then concentrated and chromatographed on a silica gel column (ethyl acetate in hexanes, 0-100%) to provide tert-butyl 7-chloro-4-(1-tetrahydropyran-2-ylpyrazol-4-yl)-3a,7a-dihydropyrrolo[2,3-c]pyridine-1-carboxylate (6.4 g, 74%) as an oil.

LC-MS 403.5, 405.5 [M+H]$^+$, RT 1.54 min; $^1$H NMR (CDCl$_3$) δ: 8.27 (s, 1H), 7.93-7.98 (m, 1H), 7.90 (s, 1H), 7.77-7.84 (m, 1H), 6.82 (d, J=3.7 Hz, 1H), 5.42-5.51 (m, 1H), 4.09-4.19 (m, 1H), 3.71-3.80 (m, 1H), 2.02-2.25 (m, 3H), 1.63-1.80 (m, 12H).

Step 3: A mixture of tert-butyl 7-chloro-4-(1-tetrahydropyran-2-ylpyrazol-4-yl)pyrrolo[2,3-c]pyridine-1-carboxylate (73 mg, 0.18 mmol), obtained in Step 2 above, hexabutylditin (0.19 mL, 0.36 mmol), and Pd(Ph$_3$)$_4$ (35 mg, 0.030 mmol) in 1,4-dioxane (1.0 mL) was stirred at 100° C. under argon overnight, followed by the addition of 5-bromo-N-(1,2-dimethyl-4-piperidyl)-N-methyl-thiazolo[5,4-d]thiazol-2-amine (54 mg, 0.15 mmol, prepared based on the chemistry described in Example 1, step 5), and another batch of Pd(Ph$_3$)$_4$ (35 mg, 0.030 mmol). This was then stirred at 100° C. under argon for 24 h. After cooling, the solvent was removed and the residue was treated with HCl in dioxane (2.0 mL, 4.0 M) at room temperature for 4 h. The volatiles were evaporated and the residue was chromatographed on a C18 column, eluting with 0.1 TFA modified acetonitrile in H$_2$O (0-100%). The fractions containing the desired product were combined and concentrated to dryness, and treated with HCl in diethyl ether (2.0 mL, 2.0 M). The precipitate was collected, washed with diethyl ether and dried to provide N-(1,2-dimethyl-4-piperidyl)-N-methyl-2-[4-(1H-pyrazol-4-yl)-1H-pyrrolo[2,3-c]pyridin-7-yl]thiazolo[5,4-d]thiazol-5-amine; hydrochloride (9.4 mg, 13%).

LC-MS 465.3 [M+H]$^+$, RT 0.93 min; $^1$H NMR (methanol-d$_4$) δ: 8.65 (s, 1H), 8.36-8.50 (m, 2H), 8.32 (s, 1H), 8.19 (br s, 1H), 7.28 (br s, 1H), 4.64-4.74 (m, 1H), 3.62-3.74 (m, 1H), 3.38-3.53 (m, 2H), 3.00-3.24 (m, 3H), 2.90-2.99 (m, 3H), 1.98-2.43 (m, 4H), 1.43-1.53 (m, 3H).

Using the procedure described for Example 23, above, additional compounds described herein were prepared by substituting the appropriate starting materials, suitable reagents and reaction conditions, obtaining compounds such as those selected from:

| Cpd | Data |
|---|---|
| 72 | LC-MS 437.6 [M + H]$^+$; $^1$H NMR (methanol-d$_4$) δ: 8.23-8.42 (m, 3H), 8.09 (br s, 1H), 7.20 (br s, 1H), 4.35-4.48 (m, 1H), 3.34-3.64 (m, 3H), 2.22-2.39 (m, 2H), 1.86-2.18 (m, 2H), 1.40 (br d, J = 6.4 Hz, 3H); 4NHs not observed. |

| Cpd | Data |
|---|---|
| 75 | LC-MS 451.6 [M + H]⁺; ¹H NMR (methanol-d₄) δ: 8.25-8.41 (m, 3H), 8.08-8.19 (m, 1H), 7.19-7.29 (m, 1H), 3.95-4.06 (m, 1H), 3.60-3.71 (m, 1H), 3.36-3.55 (m, 2H), 3.17 (s, 3H), 2.30-2.45 (m, 1H), 2.10-2.27 (m, 2H), 1.95-2.06 (m, 1H), 1.57 (br d, J = 6.7 Hz, 3H); 3NHs not observed. |
| 76 | LC-MS 438.5 [M + H]⁺; ¹H NMR (methanol-d₄) δ: 8.28-8.49 (m, 3H), 8.08-8.18 (m, 1H), 7.19-7.30 (m, 1H), 5.64-5.75 (m, 1H), 3.58-3.73 (m, 1H), 3.36-3.50 (m, 2H), 2.44-2.61 (m, 2H), 2.08-2.24 (m, 1H), 1.89-2.05 (m, 1H), 1.39 (br d, J = 6.4 Hz, 3H); 3NHs not observed. |
| 77 | LC-MS 452.6 [M + H]⁺; ¹H NMR (methanol-d₄) δ: 8.34-8.55 (m, 3H), 8.18-8.27 (m, 1H), 7.27-7.38 (m, 1H), 5.60-5.72 (m, 1H), 3.37-3.59 (m, 2H), 2.37-2.61 (m, 2H), 2.02-2.22 (m, 2H), 1.53 (br d, J = 9.2 Hz, 6H); 3NHs not observed. |
| 83 | LC-MS 439.5 [M + H]⁺; ¹H NMR (methanol-d₄) δ 9.07 (s, 1H), 8.75 (s, 1H), 8.44 (s, 2H), 5.75-5.68 (m, 1H), 3.70-3.60 (m, 1H), 3.48-3.38 (m, 2H), 2.60-2.45 (m, 2H), 2.25-2.12 (m, 1H), 2.03-1.94 (m, 1H), 1.41 (d, J = 6.4 Hz, 3H); 3NHs not observed. |
| 85 | LC-MS 451.6 [M + H]⁺; ¹H NMR (DMSO-d₆) δ: 11.69-11.96 (m, 1H), 9.06-9.31 (m, 1H), 8.69-8.92 (m, 1H), 8.43 (s, 1H), 8.31 (s, 2H), 7.73 (br s, 1H), 6.98 (br s, 1H), 4.55-4.74 (m, 1H), 3.76-3.94 (m, 1H), 3.16-3.44 (m, 2H), 3.03 (s, 3H), 2.05-2.35 (m, 2H), 1.72-2.00 (m, 2H), 1.43 (br d, J = 6.7 Hz, 3H). |
| 87 | LC-MS 451.6 [M + H]⁺; ¹H NMR (methanol-d₄) δ 8.35 (s, 1H), 8.21 (s, 2H), 7.70 (s, 1H), 6.91 (s, 1H), 4.81-4.73 (m, 1H), 4.02-3.92 (m, 1H), 3.50-3.38 (m, 2H), 3.11 (s, 3H), 2.33 (td, J = 13.1, 4.9 Hz, 1H), 2.20-2.10 (m, 2H), 2.04-1.98 (m, 1H), 1.57 (d, J = 6.8 Hz, 3H); 2NHs not observed. |
| 90 | LC-MS 479.6 [M + H]⁺; ¹H NMR (DMSO-d₆) δ: 11.78 (br s, 1H), 9.11-9.30 (m, 1H), 8.69-8.87 (m, 1H), 8.44-8.55 (m, 1H), 8.40 (s, 1H), 8.11 (s, 1H), 7.73 (br s, 1H), 6.98 (br s, 1H), 4.55-4.72 (m, 1H), 4.11-4.37 (m, 2H), 3.77-3.94 (m, 1H), 3.16-3.47 (m, 2H), 3.03 (s, 3H), 2.02-2.34 (m, 2H), 1.71-1.98 (m, 2H), 1.28-1.61 (m, 6H). |
| 91 | LC-MS 465.6 [M + H]⁺; ¹H NMR (methanol-d₄) δ: 8.45 (s, 1H), 8.29 (s, 1H), 8.12-8.20 (m, 2H), 7.25 (br s, 1H), 4.28-4.43 (m, 1H), 3.95-4.12 (m, 1H), 3.68 (s, 3H), 3.39-3.55 (m, 2H), 3.19 (s, 3H), 1.95-2.46 (m, 4H), 1.52-1.67 (m, 3H); 3 NHs not observed. |
| 95 | LC-MS 465.6 [M + H]⁺; ¹H NMR (methanol-d₄) δ: 8.18 (s, 1H), 8.11 (s, 1H), 7.94 (s, 1H), 7.85 (s, 1H), 6.96 (s, 1H), 4.55-4.40 (m, 1H), 3.91 (s, 3H), 3.50-3.42 (m, 1H), 3.40-3.30 (m, 1H), 3.16-3.04 (m, 1H), 3.02 (s, 3H), 2.10-1.96 (m, 3H), 1.90-1.80 (m, 1H), 1.31 (d, J = 6.5, 3H); 2NHs not observed. |
| 98 | LC-MS 451.6 [M + H]⁺; ¹H NMR (methanol-d₄) δ: 8.36-8.30 (m, 3H), 8.05 (d, J = 3.0 Hz, 1H), 7.18 (d, J = 3.0 Hz, 1H), 4.70-4.61 (m, 1H), 3.66-3.55 (m, 1H), 3.52-3.43 (m, 1H), 3.31-3.22 (m, 1H), 3.18 (s, 3H), 2.23-2.09 (m, 3H), 2.04-1.94 (m, 1H), 1.44 (d, J = 6.5 Hz, 3H); 3NHs not observed. |
| 109 | LC-MS 438.5 [M + H]⁺; ¹H NMR (methanol-d₄) δ: 8.29-8.51 (m, 3H), 8.12 (br d, J = 2.7 Hz, 1H), 7.23 (d, J = 2.7 Hz, 1H), 5.40-5.55 (m, 1H), 3.41-3.65 (m, 2H), 3.17-3.29 (m, 1H), 2.57-2.75 (m, 2H), 1.73-2.08 (m, 2H), 1.44 (d, J = 6.4 Hz, 3H); 3 NHs not observed. |
| 115 | LC-MS 466.3 [M + H]⁺; ¹H NMR (methanol-d₄) δ: 8.52 (s, 1H), 8.48 (s, 1H), 8.31 (s, 2H), 4.56-4.46 (m, 1H), 3.62-3.54 (m, 1H), 3.35-3.25 (m, 1H), 3.10-3.04 (m, 1H), 3.01 (s, 3H), 2.84 (s, 3H), 2.20-2.02 (m, 3H), 2.00-1.86 (m, 1H), 1.36 (d, J = 6.4 Hz, 3H); 2NHs not observed. |
| 120 | LC-MS 438.3 [M + H]⁺; ¹H NMR (methanol-d₄) δ: 8.57 (br s, 1H), 8.34 (s, 1H), 8.19 (br s, 2H), 7.66 (br s, 1H), 6.88 (br s, 1H), 5.54 (br s, 1H), 3.40-3.59 (m, 1H), 3.14-3.30 (m, 2H), 2.27-2.51 (m, 2H), 1.93-2.13 (m, 1H), 1.76-1.91 (m, 1H), 1.32 (br d, J = 6.4 Hz, 3H); 2NHs not observed. |
| 121 | LC-MS 479.3 [M + H]⁺; ¹H NMR (methanol-d₄) δ: 8.54 (br s, 1H), 8.31 (s, 1H), 8.18 (br s, 2H), 7.66 (br s, 1H), 6.87 (br s, 1H), 4.31-4.49 (m, 1H), 3.38-3.58 (m, 3H), 2.97-3.15 (m, 5H), 2.00-2.34 (m, 4H), 1.33 (br d, J = 6.4 Hz, 6H); NH not observed. |
| 122 | LC-MS 465.3 [M + H]⁺; ¹H NMR (methanol-d₄) δ: 8.53 (br s, 1H), 8.31 (s, 1H), 8.18 (br s, 1H), 7.66 (br s, 1H), 6.87 (br s, 1H), 4.30-4.45 (m, 1H), 3.42-3.63 (m, 2H), 3.02-3.17 (m, 3H), 2.90-3.02 (m, 2H), 2.73-2.90 (m, 2H), 1.96-2.24 (m, 4H), 1.23-1.40 (m, 3H); 2NHs not observed. |
| 123 | LC-MS 477.3 [M + H]⁺; ¹H NMR (methanol-d₄) δ: 8.35 (br s, 2H), 8.29 (br s, 1H), 8.16 (br s, 1H), 7.23 (br s, 1H), 4.63-4.76 (m, 1H), 3.37-3.91 (m, 5H), 3.01-3.26 (m, 5H), 2.11-2.60 (m, 6H); 2NHs not observed. |
| 134 | LC-MS 449.3 [M + H]⁺; ¹H NMR (methanol-d₄) δ: 8.50 (br s, 1H), 8.32 (s, 1H), 8.19 (s, 2H), 7.67 (d, J = 3.1 Hz, 1H), 6.89 (d, J = 3.1 Hz, 1H), 4.08-4.20 (m, 1H), 3.91-4.03 (m, 1H), 3.79-3.91 (m, 1H), 3.36-3.47 (m, 2H), 3.09-3.22 (m, 1H), 2.48-2.67 (m, 2H), 2.30-2.44 (m, 1H), 2.13-2.27 (m, 1H), 1.96-2.10 (m, 1H), 1.81-1.96 (m, 1H); 2NHs not observed. |
| 136 | LC-MS 494.3 [M + H]⁺; ¹H NMR (DMSO-d₆) δ 13.07 (s, 1H), 8.77 (s, 1H), 8.73 (s, 1H), 8.57 (s, 1H), 8.52 (s, 1H), 7.83 (br s, 1H), 4.76-4.64 (m, 1H), 3.06 (s, 3H), 2.05-1.90 (m, 4H), 1.52 (s, 6H), 1.43 (s, 6H). |
| 138 | LC-MS 463.4 [M + H]⁺; ¹H NMR (methanol-d₄) δ: 8.23 (s, 2H), 8.19 (s, 1H), 7.89 (d, J = 2.7 Hz, 1H), 7.02 (d, J = 3.1 Hz, 1H), 4.02 (s, 2H), 3.93 (s, 2H), 3.48-3.58 (m, 2H), 3.01-3.16 (m, 2H), 2.90 (s, 3H), 2.23-2.37 (m, 2H), 1.98-2.17 (m, 2H); 2NHs not observed. |

-continued

| Cpd | Data |
|---|---|
| 139 | LC-MS 437.4 [M + H]$^+$; $^1$H NMR (methanol-$d_4$) δ: 8.21-8.35 (m, 3H), 7.94 (d, J = 3.1 Hz, 1H), 7.09 (d, J = 3.1 Hz, 1H), 4.53-4.64 (m, 1H), 3.55-3.65 (m, 2H), 3.18-3.28 (m, 2H), 3.14 (s, 3H), 2.05-2.26 (m, 4H); 2NHs not observed. |
| 154 | LC-MS 491.3 [M + H]$^+$; $^1$H NMR (DMSO-$d_6$) δ 11.76 (s, 1H), 9.78 (br s, 1H), 9.04 (br s, 1H), 8.44 (s, 1H), 8.31 (s, 2H), 7.73 (s, 1H), 6.98 (s, 1H), 4.82-4.72 (m, 1H), 3.08 (s, 3H), 2.28-2.20 (m, 2H), 2.15-2.08 (m, 2H), 1.95-1.85 (m, 4H), 1.48 (s, 6H). |
| 159 | LC-MS 493.4 [M + H]$^+$; $^1$H NMR (DMSO-$d_6$) δ 11.74 (s, 1H), 9.24 (br s, 1H), 8.44 (s, 1H), 8.31 (s, 2H), 8.23 (br s, 1H), 7.71 (s, 1H), 6.97 (s, 1H), 4.75-4.65 (m, 1H), 3.06 (s, 3H), 2.10-2.02 (m, 2H), 1.94-1.85 (m, 2H), 1.53 (s, 6H), 1.50 (s, 6H). |
| 160 | LC-MS 397.3 [M + H]$^+$; $^1$H NMR (DMSO-$d_6$) δ 11.71 (s, 1H), 9.37 (br s, 1H), 8.95 (br s, 1H), 8.14 (d, J = 5.2 Hz, 1H), 7.73-7.62 (m, 2H), 6.66 (s, 1H), 4.78-4.68 (m, 1H), 4.15-4.08 (m, 2H), 3.07 (s, 3H), 2.32 (t, J = 12.8 Hz, 2H), 2.09-1.97 (m, 4H), 1.91-1.84 (m, 2H). |
| 184 | LC-MS 463.2 [M + H]$^+$; $^1$H NMR (methanol-$d_4$) δ 8.45 (s, 2H), 8.35 (s, 1H), 8.22 (d, J = 3.0 Hz, 1H), 7.32-7.28 (m, 1H), 5.05-4.95 (m, 1H), 4.30-4.24 (m, 2H), 3.19 (s, 3H), 2.36 (t, J = 13.0 Hz, 2H), 2.31-2.21 (m, 4H), 2.13-2.05 (m, 2H); 3NHs not observed. |

Example 24

Preparation of Compounds 117 and 116

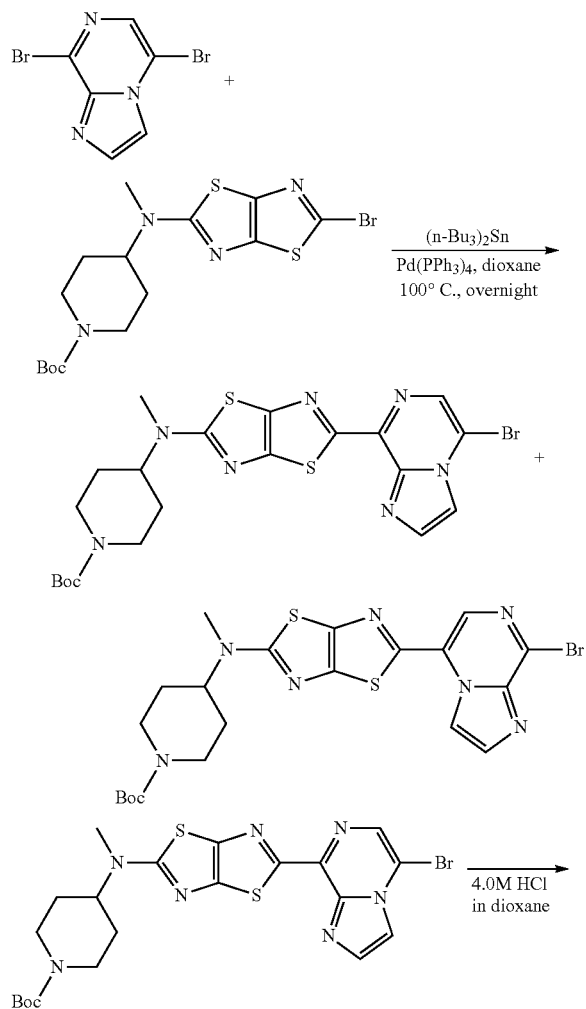

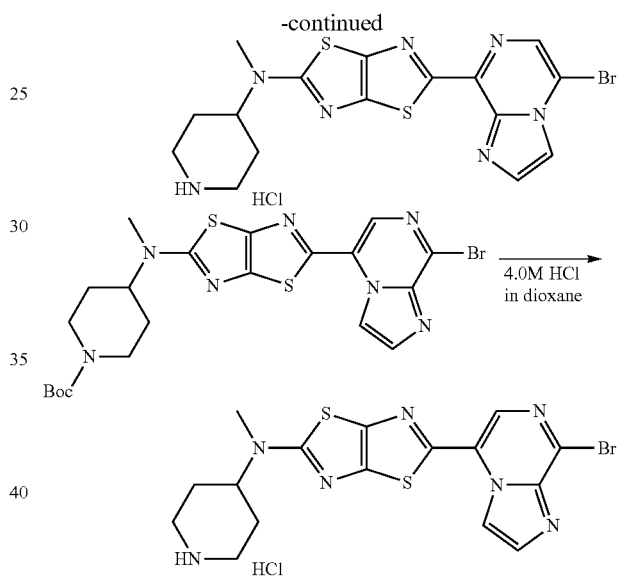

Step 1: A mixture of 5,8-dibromoimidazo[1,2-a]pyrazine (276 mg, 1.00 mmol), tert-butyl 4-[(5-bromothiazolo[5,4-d]thiazol-2-yl)-methyl-amino]piperidine-1-carboxylate (108 mg, 0.25 mmol), prepared in Example 11, Pd(PPh$_3$)$_4$ (35 mg, 0.030 mmol), and hexabutylditin (0.38 mL, 0.73 mmol) in 1,4-dioxane (2.0 mL) was stirred at 100° C. under argon overnight. After cooling, the solvent was removed and the residue was chromatographed on a silica gel column (ethyl acetate in dichloromethane, 0-100%) to provide a mixture of desired product which was further purified on a C-18 column (acetonitrile in water, 0-100%) to provide two isomers of coupling product, tert-butyl 4-[[2-(5-bromoimidazo[1,2-a]pyrazin-8-yl)thiazolo[5,4-d]thiazol-5-yl]-methyl-amino]piperidine-1-carboxylate (10 mg, 7.4%). LC-MS 550.1, 552.1 [M+H]$^+$, RT 1.61 min., and tert-butyl 4-[[2-(8-bromoimidazo[1,2-a]pyrazin-5-yl)thiazolo[5,4-d]thiazol-5-yl]-methyl-amino]piperidine-1-carboxylate (2.8 mg, 2.0%). LC-MS 550.1, 552.1 [M+H]$^+$, RT 1.68 min.

Step 2: tert-Butyl 4-[[2-(5-bromoimidazo[1,2-a]pyrazin-8-yl)thiazolo[5,4-d]thiazol-5-yl]-methyl-amino]piperidine-1-carboxylate (10 mg, 0.018 mmol) was treated with HCl in dioxane (1.0 mL, 4.0 M) at room temperature for 4 h. This was diluted with ether and the precipitates were collected, washed with ether and dried to provide 2-(5-bromoimidazo[1,2-a]pyrazin-8-yl)-N-methyl-N-(4-piperidyl)thiazolo[5,4-d]thiazol-5-amine hydrochloride (9.4 mg 102%).

LC-MS 450.2, 452.2 [M+H]+, RT 0.93 min; $^1$H NMR (methanol-$d_4$) δ: 8.54-8.72 (m, 2H), 8.33-8.46 (m, 1H), 4.58-4.70 (m, 1H), 3.52-3.82 (m, 4H), 3.12-3.28 (m, 5H), 2.06-2.32 (m, 2H); NH not observed.

Similarly, treatment of tert-butyl 4-[[2-(8-bromoimidazo[1,2-a]pyrazin-5-yl)thiazolo[5,4-d]thiazol-5-yl]-methylamino]piperidine-1-carboxylate (2.8 mg, 0.0051 mmol) with HCl in dioxane (1.0 mL, 4.0 M) furnished 2-(8-bromoimidazo[1,2-a]pyrazin-5-yl)-N-methyl-N-(4-piperidyl)thiazolo[5,4-d]thiazol-5-amine; hydrochloride (1.9 mg, 76% Yield).

LC-MS 450.2, 452.2 [M+H]+, RT 0.93 min; $^1$H NMR (methanol-$d_4$) δ: 9.52 (d, J=1.5 Hz, 1H), 8.53 (s, 1H), 8.18 (d, J=1.2 Hz, 1H), 4.51-4.68 (m, 1H), 3.53-3.85 (m, 4H), 3.05-3.27 (m, 5H), 2.08-2.29 (m, 2H); NH not observed.

Using the procedure described for Example 24, above, additional compounds described herein were prepared by substituting the appropriate starting materials, suitable reagents and reaction conditions, obtaining compounds such as those selected from:

| Cpd | Data |
|---|---|
| 124 | LC-MS 477.3, 479.3 [M + H]+; $^1$H NMR (methanol-$d_4$) δ: 8.50 (br s, 1H), 8.18 (s, 1H), 7.61-7.73 (m, 1H), 6.57-6.67 (m, 1H), 4.33-4.46 (m, 1H), 3.33-3.41 (m, 1H), 3.08 (s, 3H), 2.73-2.90 (m, 2H), 2.62 (br s, 3H), 1.74-2.22 (m, 4H), 1.32 (br d, J = 6.1 Hz, 3H); NH not observed. |
| 186 | LC-MS 437.2, 439.2 [M + H]+; $^1$H NMR (methanol-$d_4$) δ 8.95 (s, 2H), 4.95-4.88 (m, 1H), 4.26-4.17 (m, 2H), 3.11 (s, 3H), 2.33-2.18 (m, 6H), 2.11-2.01 (m, 2H); NH not observed. |

Example 25

Preparation of Compound 113

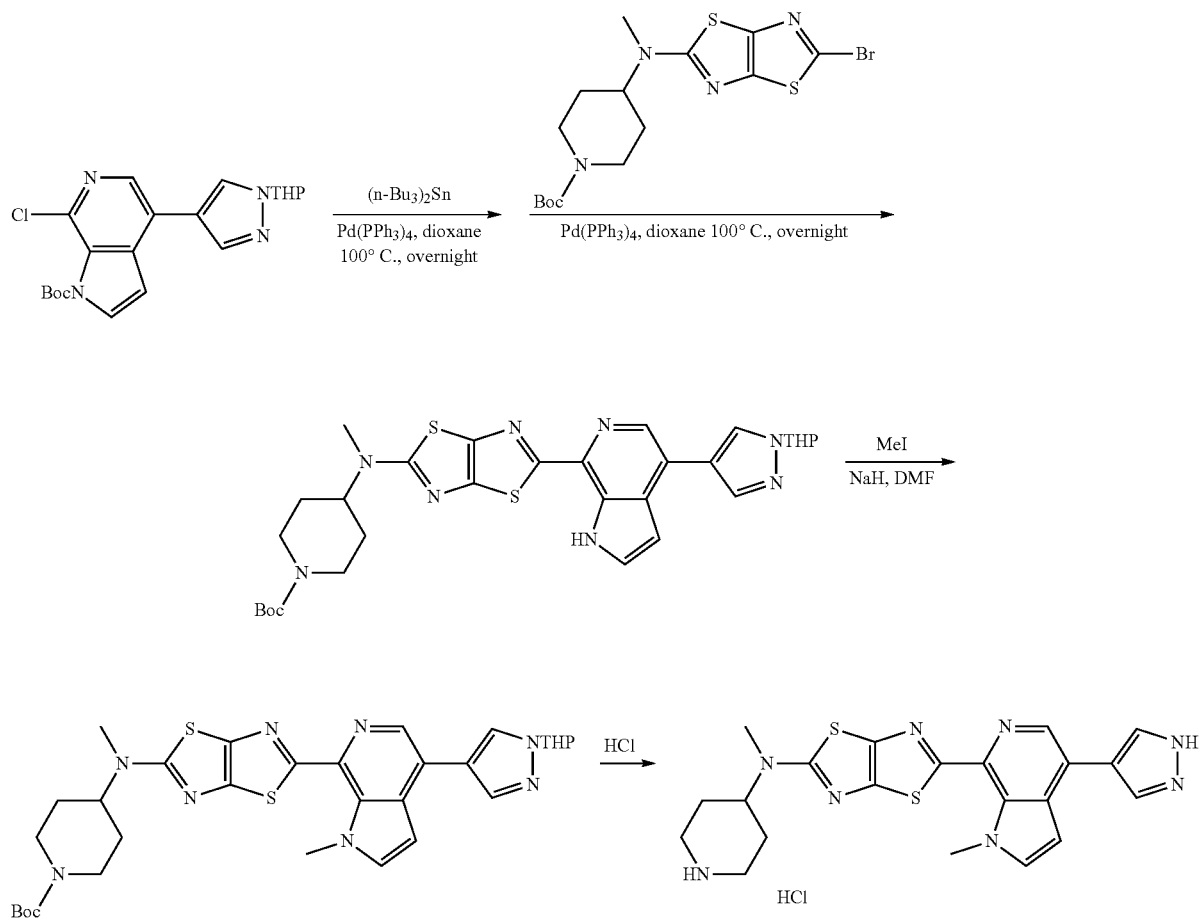

Step 1: A mixture of tert-butyl 7-chloro-4-(1-tetrahydropyran-2-ylpyrazol-4-yl)pyrrolo[2,3-c]pyridine-1-carboxylate (218 mg, 0.54 mmol), prepared in Example 23, hexabutylditin (0.56 mL, 1.1 mmol), and Pd(PPh$_3$)$_4$ (52 mg, 0.045 mmol) in 1,4-dioxane (2.0 mL) was stirred at 100° C. under argon overnight, followed by the addition of tert-butyl 4-[(5-bromothiazolo[5,4-d]thiazol-2-yl)-methyl-amino]piperidine-1-carboxylate (195 mg, 0.45 mmol), prepared in Example 11, and another batch of Pd(PPh$_3$)$_4$ (52 mg, 0.045 mmol). The resulting mixture was stirred at 100° C. under argon for 24 hr. After cooling, the solvent was removed and the residue was suspended in dichloromethane and filtered. The filtrate was concentrated and the residue was chromatographed first on a silica gel column (ethyl acetate in dichloromethane, 0-70%) and then a C-18 column (acetonitrile in water, 0-100%) to obtain tert-butyl 4-[methyl-[2-[4-(1-tetrahydropyran-2-ylpyrazol-4-yl)-1H-pyrrolo[2,3-c]pyridin-7-yl]thiazolo[5,4-d]thiazol-5-yl]amino]piperidine-1-carboxylate (16 mg, 5.8%). LC-MS 621.4 [M+H]$^+$, RT 1.69 min.

Step 2: tert-Butyl 4-[methyl-[2-[4-(1-tetrahydropyran-2-ylpyrazol-4-yl)-1H-pyrrolo[2,3-c]pyridin-7-yl]thiazolo[5,4-d]thiazol-5-yl]amino]piperidine-1-carboxylate (16 mg, 0.026 mmol), obtained in Step 1 above, was treated with NaH (4.0 mg, 0.10 mmol, 60 mass % in mineral oil) in DMF (0.2 mL) followed by the addition of iodomethane (4.0 μL, 0.064 mmol) and stirred at 30° C. overnight. This was treated with water and the precipitate was collected, washed with water and hexanes, and then dried and chromatographed on a C18 column, eluting with 0.1% TFA modified acetonitrile in water (0-100%). The fractions containing the desired product were combined and concentrated to dryness and treated with HCl in dioxane (2.0 mL, 4.0 M) at room temperature for 4 h. The precipitate was collected, washed with diethyl ether and dried to provide N-methyl-2-[1-methyl-4-(1H-pyrazol-4-yl)pyrrolo[2,3-c]pyridin-7-yl]-N-(4-piperidyl)thiazolo[5,4-d]thiazol-5-amine; hydrochloride (13 mg, 102%).

LC-MS 451.4 [M+H]$^+$, RT 0.84 min; $^1$H NMR (DMSO-d$_6$) δ: 8.78-9.04 (m, 2H), 8.48 (s, 1H), 8.34 (s, 2H), 7.88 (br s, 1H), 7.07 (br s, 1H), 4.41-4.54 (m, 1H), 4.05 (s, 3H), 3.34-3.47 (m, 2H), 3.06-3.18 (m, 2H), 3.03 (s, 3H), 2.05-2.24 (m, 2H), 1.83-2.01 (m, 2H).

Example 26

Preparation of Compound 226

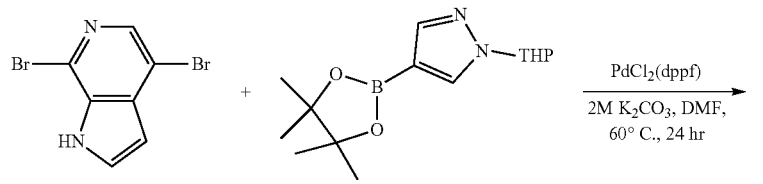

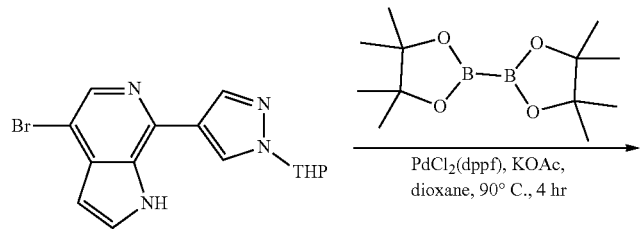

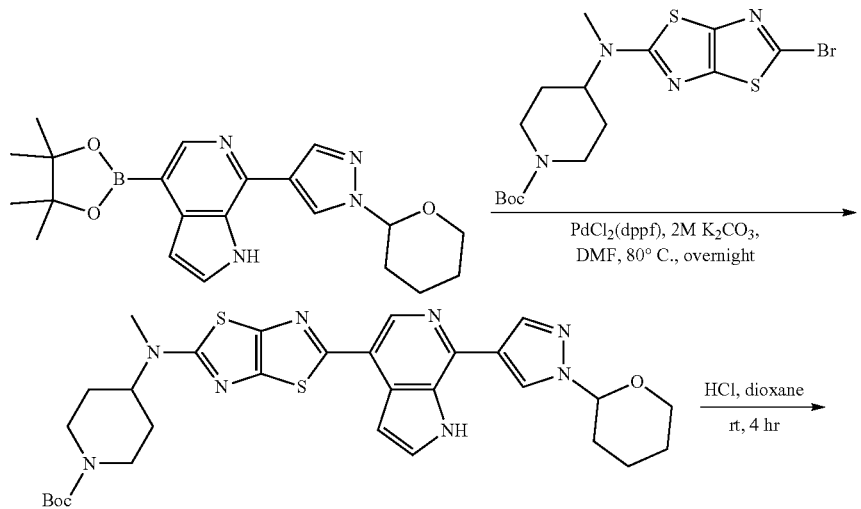

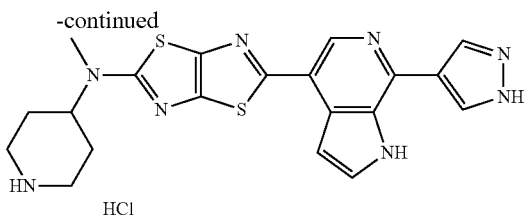

Step 1: A mixture of 4,7-dibromo-1H-pyrrolo[2,3-c]pyridine (207 mg, 0.75 mmol), 1-tetrahydropyran-2-yl-4-(4,4,5,5-tetramethyl-1,3,2-dioxaborolan-2-yl)pyrazole (250 mg, 0.90 mmol), (63 mg, 0.076 mmol), and $K_2CO_3$ (0.94 mL, 1.9 mmol, 2.0 M) in DMF (4.0 mL) was stirred at 60° C. for 24 h under argon. After cooling, the solvent was evaporated and the residue was chromatographed on a silica gel column (ethyl acetate in dichloromethane 0-100%) to provide 4-bromo-7-(1-tetrahydropyran-2-ylpyrazol-4-yl)-1H-pyrrolo[2,3-c]pyridine (229 mg, 88%). LC-MS 347.1, 349.1 [M+H]$^+$, RT 0.98 min.

Step 2: 4-Bromo-7-(1-tetrahydropyran-2-ylpyrazol-4-yl)-1H-pyrrolo[2,3-c]pyridine (87 mg, 0.25 mmol), obtained in Step 1, 4,4,5,5-tetramethyl-2-(4,4,5,5-tetramethyl-1,3,2-dioxaborolan-2-yl)-1,3,2-dioxaborolane (76 mg, 0.30 mmol), potassium acetate (49 mg, 0.50 mmol), and $PdCl_2$(dppf) (21 mg, 0.025 mmol) in 1,4-dioxane (1.0 mL) were placed in a sealed tube and stirred at 90° C. for 4 h under an argon atmosphere. After cooling to room temperature, a mixture of tert-butyl 4-[(5-bromothiazolo[5,4-d]thiazol-2-yl)-methyl-amino]piperidine-1-carboxylate (87 mg, 0.20 mmol), prepared in Example 11, $PdCl_2$(dppf) (17 mg, 0.020 mmol), $K_2CO_3$ (0.25 mL, 0.50 mmol, 2.0 mol/L) and DMF (2.0 mL) was added and the resulting mixture was stirred at 80° C. under argon overnight. The solvent was evaporated and the residue was chromatographed, first on a silica gel column (ethyl acetate in dichloromethane, 0-100%), then on a C18 column (acetonitrile in water, 0-100%) to provide tert-butyl 4-[methyl-[2-[7-(1-tetrahydropyran-2-ylpyrazol-4-yl)-1H-pyrrolo[2,3-c]pyridin-4-yl]thiazolo[5,4-d]thiazol-5-yl]amino]piperidine-1-carboxylate (13.0 mg, 10%). LC-MS 621.8 [M+H]$^+$, RT 1.35 min.

Step 3: tert-Butyl 4-[methyl-[2-[7-(1-tetrahydropyran-2-ylpyrazol-4-yl)-1H-pyrrolo[2,3-c]pyridin-4-yl]thiazolo[5,4-d]thiazol-5-yl]amino]piperidine-1-carboxylate (13 mg, 0.021 mmol), obtained in Step 2, was treated with HCl in dioxane (1.0 mL, 4.0M) at room temperature for 6 h. The precipitate formed was collected and washed with diethyl ether and dried to provide the title compound, N-methyl-N-(4-piperidyl)-2-[7-(1H-pyrazol-4-yl)-1H-pyrrolo[2,3-c]pyridin-4-yl]thiazolo[5,4-d]thiazol-5-amine; hydrochloride (8 mg, 81%).

LC-MS 437.5 [M+H]$^+$, RT 0.73 min; $^1$H NMR (methanol-$d_4$) δ: 8.65 (s, 1H), 8.56 (s, 2H), 8.28 (d, J=2.7 Hz, 1H), 7.67 (d, J=2.7 Hz, 1H), 4.50-4.66 (m, 1H), 3.52-3.62 (m, 2H), 3.19-3.27 (m, 2H), 3.15 (s, 3H), 2.04-2.33 (m, 4H); 3NHs not observed.

Example 27

Preparation of Compound 81

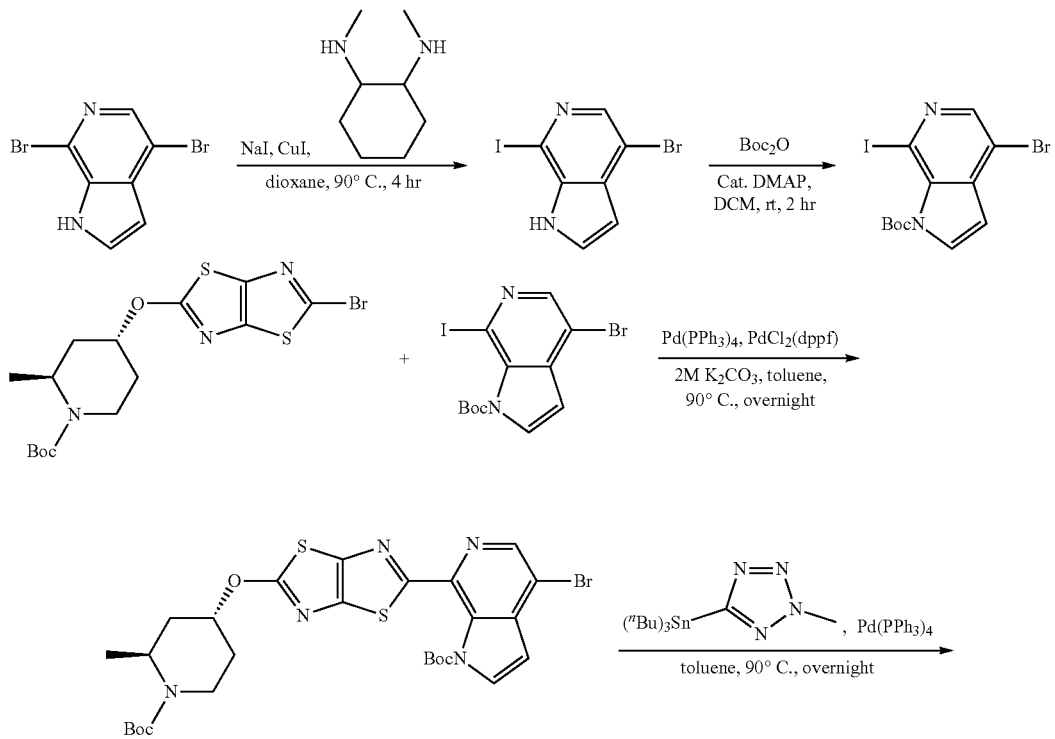

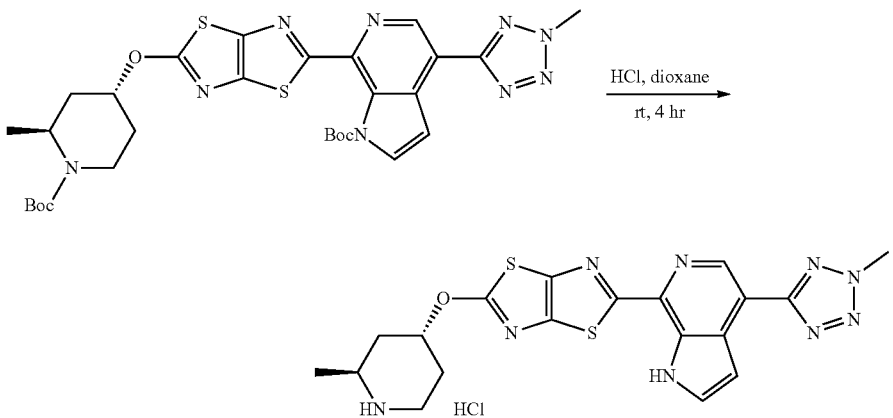

Step 1: A mixture of 4,7-dibromo-1H-pyrrolo[2,3-c]pyridine (946 mg, 3.43 mmol), NaI (2.08 g, 13.7 mmol), CuI (33 mg, 0.17 mmol), and trans-N,N'-dimethylcyclohexane-1,2-diamine (51 mg, 0.35 mmol) in 1,4-dioxane (10 mL) was stirred at 90° C. under argon for 4 h. LC/MS showed complete conversion was achieved (LC-MS 323.0, 325.0 [M+H]$^+$, RT 1.30 min). The solvent was removed and the residue was suspended in ethyl acetate and filtered. The filtrate was washed with NH$_4$Cl (aq.), water and brine, dried over anhydrous Na$_2$SO$_4$ and concentrated. The material obtained was dissolved in dichloromethane (20 mL) and treated with di-tert-butyl dicarbonate (1.20 mL, 5.1 mmol) and a few crystals of 4-dimethylaminopyridine. After stirring at room temperature for 2 h, the mixture was concentrated and chromatographed on a silica gel column (ethyl acetate in hexanes, 0-50%) to provide tert-butyl 4-bromo-7-iodo-pyrrolo[2,3-c]pyridine-1-carboxylate (1.41 g, 97%) as a pink oil. LC-MS 423.3, 425.3 [M+H]$^+$, RT 1.69 min.

Step 2: A mixture of tert-butyl (2R*,4S*)-4-(5-bromothiazolo[5,4-d]thiazol-2-yl)oxy-2-methyl-piperidine-1-carboxylate (869 mg, 2.00 mmol), prepared based on the chemistry described in Example 13, tert-butyl 4-bromo-7-iodo-pyrrolo[2,3-c]pyridine-1-carboxylate (1.27 g, 3.00 mmol), Pd(PPh$_3$)$_4$ (694 mg, 0.60 mmol), PdCl$_2$(dppf)(167 mg, 0.20 mmol), and K$_2$CO$_3$ (2.00 mL, 4.0 mmol, 2.0M) in toluene (10.0 mL) was stirred under an argon atmosphere overnight. After cooling, the mixture was partitioned with ethyl acetate and water. The organic layer was separated and washed with water and brine, and then dried over anhydrous Na$_2$SO$_4$. The solvent was removed and the crude material was chromatographed first on a silica gel column (ethyl acetate in hexanes, 0-50%) then on a C18 column (acetonitrile in water, 0-100%) to provide tert-butyl 4-bromo-7-[5-[[(2R*,4S*)-1-tert-butoxycarbonyl-2-methyl-4-piperidyl]oxy]thiazolo[5,4-d]thiazol-2-yl]pyrrolo[2,3-c]pyridine-1-carboxylate (350 mg, 27%). LC-MS 650.8, 652.3 [M+H]$^+$, RT 2.04 min;

Step 3: A mixture of tert-butyl 4-bromo-7-[5-[[(2R*,4S*)-1-tert-butoxycarbonyl-2-methyl-4-piperidyl]oxy]thiazolo[5,4-d]thiazol-2-yl]pyrrolo[2,3-c]pyridine-1-carboxylate (82 mg, 0.13 mmol), Pd(PPh$_3$)$_4$ (15 mg, 0.013 mmol), and tributyl-(2-methyltetrazol-5-yl)stannane (56 mg, 0.15 mmol) in toluene (2.0 mL) was stirred at 90° C. under argon overnight and then cooled. The solvent was removed in vacuo and the residue was chromatographed on a silica gel column (ethyl acetate in hexanes, 0-60%) to provide tert-butyl 7-[5-[[(2R*,4S*)-1-tert-butoxycarbonyl-2-methyl-4-piperidyl]oxy]thiazolo[5,4-d]thiazol-2-yl]-4-(2-methyltetrazol-5-yl)pyrrolo[2,3-c]pyridine-1-carboxylate, which was treated with HCl in dioxane (2.0 mL, 4.0 M) at room temperature for 3 h. This was diluted with diethyl ether and the precipitate was collected, washed with ether and dried to furnish 5-[[(2R*,4S*)-2-methyl-4-piperidyl]oxy]-2-[4-(2-methyltetrazol-5-yl)-1H-pyrrolo[2,3-c]pyridin-7-yl]thiazolo[5,4-d]thiazole; hydrochloride (10 mg, 16%)

LC-MS 454.6 [M+H]$^+$, RT 1.07 min; $^1$H NMR (methanol-d$_4$) δ: 8.91 (s, 1H), 7.97 (br s, 1H), 7.46 (br s, 1H), 5.67 (br s, 1H), 4.53 (s, 3H), 3.60-3.70 (m, 1H), 3.37-3.50 (m, 2H), 2.45-2.63 (m, 2H), 2.09-2.27 (m, 1H), 1.89-2.05 (m, 1H), 1.40 (br d, J=6.1 Hz, 3H); 2NHs not observed.

Example 28

Preparation of Compound 71

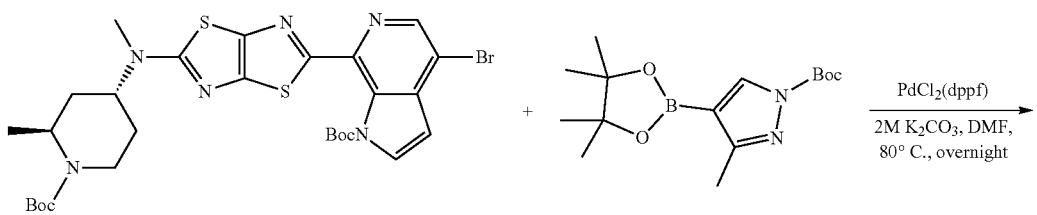

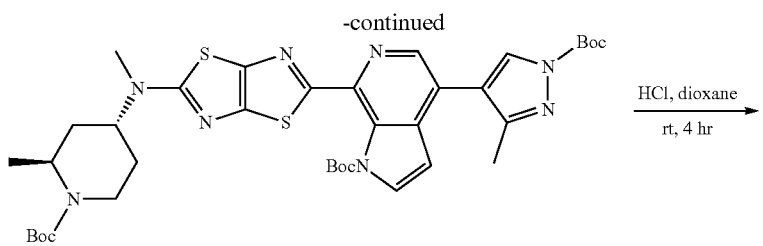

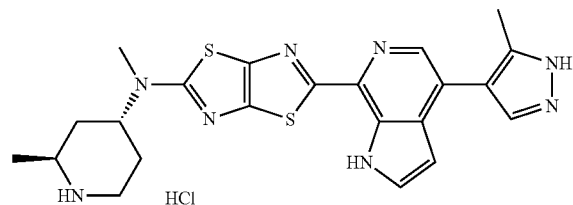

A mixture of tert-butyl 4-bromo-7-[5-[[(2R*,4S*)-1-tert-butoxycarbonyl-2-methyl-4-piperidyl]-methyl-amino]thiazolo[5,4-d]thiazol-2-yl]pyrrolo[2,3-c]pyridine-1-carboxylate (100 mg, 0.15 mmol), prepared based on the chemistry described in Example 27, tert-butyl 3-methyl-4-(4,4,5,5-tetramethyl-1,3,2-dioxaborolan-2-yl)pyrazole-1-carboxylate (56 mg, 0.18 mmol), PdCl$_2$(dppf) (12.5 mg, 0.015 mmol), and K$_2$CO$_3$ (0.15 mL, 0.30 mmol, 2.0 M) in DMF (1.0 mL) was stirred at 80° C. under argon overnight and then cooled and concentrated. The residue was chromatographed (ethyl acetate in dichloromethane, 0-100%) to provide tert-butyl 7-[5-[[(2R*,4S*)-1-tert-butoxycarbonyl-2-methyl-4-piperidyl]-methyl-amino]thiazolo[5,4-d]thiazol-2-yl]-4-(1-tert-butoxycarbonyl-3-methyl-pyrazol-4-yl)pyrrolo[2,3-c]pyridine-1-carboxylate, which was treated with HCl in dioxane (3.0 mL, 4.0 M)) at room temperature for 4 h and diluted with diethyl ether. The precipitate was collected by filtration and washed with diethyl ether then dried under a N$_2$ stream to provide N-methyl-N-[(2R*,4S*)-2-methyl-4-piperidyl]-2-[4-(3-methyl-1H-pyrazol-4-yl)-1H-pyrrolo[2,3-c]pyridin-7-yl]thiazolo[5,4-d]thiazol-5-amine; hydrochloride (13 mg, 17%).

LC-MS 465.6 [M+H]$^+$, RT 0.91 min. $^1$H NMR (methanol-d$_4$) δ: 7.99-8.19 (m, 3H), 6.93-7.01 (m, 1H), 3.92-4.07 (m, 1H), 3.37-3.58 (m, 3H), 3.18 (s, 3H), 2.47 (s, 3H), 2.11-2.40 (m, 3H), 1.94-2.08 (m, 1H), 1.57 (br d, J=6.7 Hz, 3H); 3NHs not observed.

Example 29

Preparation of Compound 183

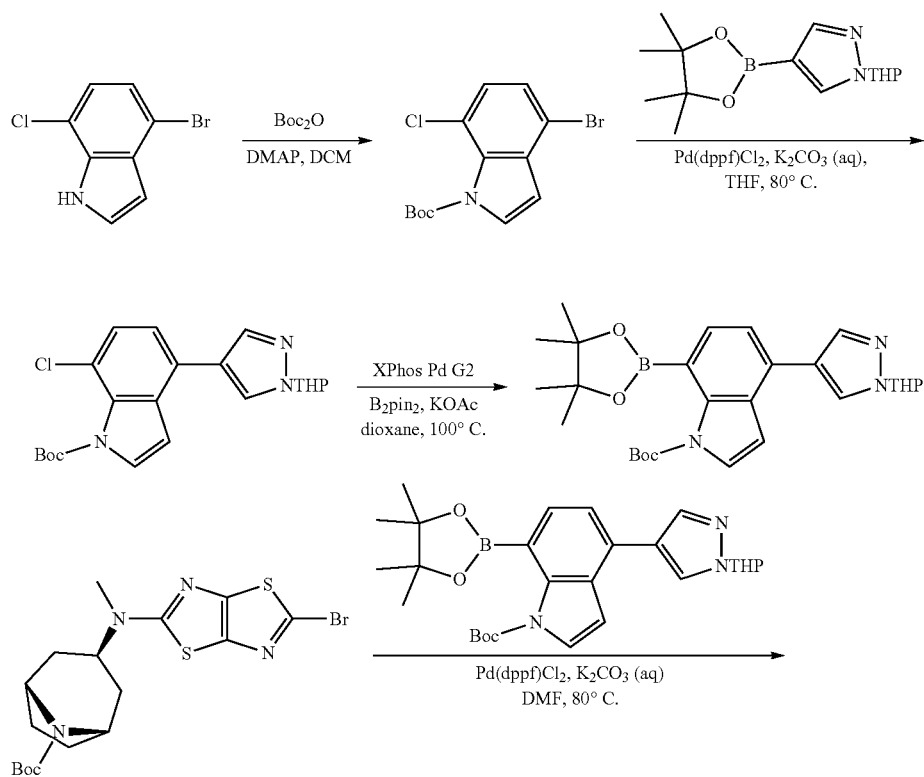

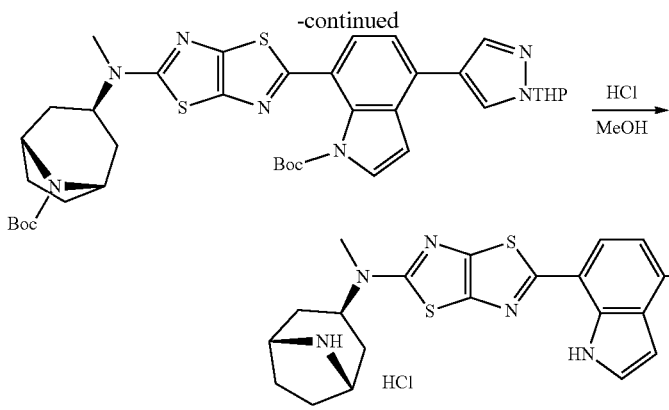

Step 1: 4-Bromo-7-chloro-1H-indole (230.5 mg, 1 mmol), Boc$_2$O (327.4 mg, 1.5 mmol), and DMAP (12.2 mg, 0.1 mmol) were dissolved in dichloromethane (10 mL) and the reaction mixture was allowed to stir for 2 h at room temperature. The solvent was removed and the residue was purified by silica gel chromatography (ethyl acetate in hexanes, 0-50%), to yield tert-butyl 4-bromo-7-chloro-1H-indole-1-carboxylate (314.1 mg, 95%) as an off-white solid.

Step 2: tert-Butyl 4-bromo-7-chloro-1H-indole-1-carboxylate (330.6 mg, 1 mmol), 1-(tetrahydro-2H-pyran-2-yl)-4-(4,4,5,5-tetramethyl-1,3,2-dioxaborolan-2-yl)-1H-pyrazole (417.2 mg, 1.5 mmol), PdCl$_2$(dppf)-dichloromethane adduct (81.7 mg, 0.1 mmol), dioxane (10 mL), and aqueous K$_2$CO$_3$ (1.5 mL, 3 mmol, 2M) were heated at 80° C. for 2 h. The reaction mixture was then partitioned between H$_2$O and ethyl acetate. The organic layer was dried over MgSO$_4$, filtered, and concentrated under vacuum. Purification by silica gel chromatography (ethyl acetate in hexanes, 0-100%), yielded tert-butyl 7-chloro-4-(1-(tetrahydro-2H-pyran-2-yl)-1H-pyrazol-4-yl)-1H-indole-1-carboxylate (309.5 mg, 77%) as an off-white solid. LC-MS 402.3 [M+H]+, RT 1.68 min.

Step 3: Potassium acetate (294.4 mg, 3 mmol) was pumped dry at 180° C. for 2 h, and then the flask was filled with argon. tert-Butyl 7-chloro-4-(1-(tetrahydro-2H-pyran-2-yl)-1H-pyrazol-4-yl)-1H-indole-1-carboxylate (401.9 mg, 1 mmol), XPhos Pd G2 (78.7 mg, 0.1 mmol), bis(pinacolato)diboron (330.1 mg, 1.3 mmol), and dry dioxane (5 mL) were added to the reaction. The mixture was heated at 100° C. for 16 h. The resultant crude mixture of tert-butyl 4-(1-(tetrahydro-2H-pyran-2-yl)-1H-pyrazol-4-yl)-7-(4,4,5,5-tetramethyl-1,3,2-dioxaborolan-2-yl)-1H-indole-1-carboxylate was used in the next step without purification.

Step 4: To the crude mixture of tert-butyl 4-(1-(tetrahydro-2H-pyran-2-yl)-1H-pyrazol-4-yl)-7-(4,4,5,5-tetramethyl-1,3,2-dioxaborolan-2-yl)-1H-indole-1-carboxylate from the last step was added tert-butyl (1r,3s,5s)-3-((5-bromothiazolo[5,4-d]thiazol-2-yl)(methyl)amino)-8-azabicyclo[3.2.1]octane-8-carboxylate (307.8 mg, 0.67 mmol), prepared based on the chemistry described in Example 1, step 5, PdCl$_2$(dppf) (57.2 mg, 0.07 mmol), K$_2$CO$_3$ (1.0 mL, 2 mmol, 2.0 M) and DMF (5 mL). The mixture was sparged by argon for 5 min and stirred at 80° C. for 24 h and then cooled and diluted with ethyl acetate. The precipitate was removed by filtration. The filtrate was concentrated and chromatographed (1 M NH$_3$ in MeOH in CH$_2$Cl$_2$, 0-20%) and then further purified by reverse phase preparative HPLC to provide the coupling product. The resultant compound was treated with HCl in MeOH (3 mL, 3 mmol, 1 M) at room temperature overnight. The precipitate was collected by filtration and dried to furnish the title compound 5-(4-(1H-pyrazol-4-yl)-1H-indol-7-yl)-N-((1r,3 s,5 s)-8-azabicyclo[3.2.1]octan-3-yl)-N-methylthiazolo[5,4-d]thiazol-2-amine (184.6 mg, 40%).

LC-MS 462.4 [M+H]+; $^1$H NMR (methanol-d$_4$) δ 8.20 (s, 2H), 7.61 (d, J=7.9 Hz, 1H), 7.49 (d, J=3.1 Hz, 1H), 7.33 (d, J=7.9 Hz, 1H), 6.84 (d, J=3.1 Hz, 1H), 4.95-4.88 (m, 1H), 4.26-4.17 (m, 2H), 3.08 (s, 3H), 2.33-2.18 (m, 6H), 2.12-2.00 (m, 2H); 3NHs not observed.

Using the procedure described for Example 29, above, additional compounds described herein were prepared by substituting the appropriate starting materials, suitable reagents and reaction conditions, obtaining compounds such as those selected from:

| Cpd | Data |
|---|---|
| 68 | LC-MS 438.5 [M + H]+; $^1$H NMR (methanol-d$_4$) δ 9.57 (s, 1H), 8.28 (s, 2H), 8.12 (d, J = 7.8 Hz, 1H), 7.85 (d, J = 7.8 Hz, 1H), 5.69-5.63 (m, 1H), 3.70-3.60 (m, 1H), 3.47-3.39 (m, 2H), 3.40-3.34 (m, 1H), 2.60-2.46 (m, 1H), 2.21-2.12 (m, 1H), 2.02-1.93 (m, 1H), 1.41 (d, J = 6.7 Hz, 3H); 3NHs not observed. |
| 82 | LC-MS 437.6 [M + H]+; $^1$H NMR (methanol-d$_4$) 11.16 (br s, 1H), 8.15 (s, 2H), 7.66 (d, J = 7.7 Hz, 1H), 7.50 (s, 1H), 7.34 (d, J = 7.7 Hz, 1H), 6.86 (s, 1H), 5.61-5.55 (m, 1H), 3.73-3.57 (m, 1H), 3.43-3.36 (m, 2H), 2.55-2.40 (m, 2H), 2.22-2.08 (m, 1H), 1.95 (dd, J = 15.2, 12.5 Hz, 1H), 1.40 (d, J = 6.5 Hz, 3H); 2NHs not observed. |
| 97 | LC-MS 450.6 [M + H]+; $^1$H NMR (methanol-d$_4$) δ 11.13 (s, 1H), 8.13 (s, 2H), 7.61 (d, J = 7.7 Hz, 1H), 7.49 (d, J = 3.0 Hz, 1H), 7.33 (d, J = 7.7 Hz, 1H), 6.85 (d, J = 3.0 Hz, 1H), 4.60-4.50 (m, 1H), 3.61-3.55 (m, 1H), 3.51-3.40 (m, 1H), 3.27-3.17 (m, 1H), 3.11 (s, 3H), 2.21-2.05 (m, 3H), 1.98-1.85 (m, 1H), 1.42 (d, J = 6.5 Hz, 3H); 2NHs not observed. |

-continued

| Cpd | Data |
|---|---|
| 106 | LC-MS 493.4 [M + H]+; 1H NMR (methanol-d4) δ 9.30 (s, 1H), 8.27 (s, 2H), 7.98 (d, J = 8.0 Hz, 1H), 7.77 (d, J = 8.0 Hz, 1H), 5.05-4.95 (m, 1H), 3.13 (s, 3H), 2.13-2.00 (m, 4H), 1.66 (s, 6H), 1.55 (s, 6H); 3NHs not observed. |
| 112 | LC-MS 465.3 [M + H]+; 1H NMR (methanol-d4) δ 9.07 (s, 1H), 8.15 (s, 2H), 7.82 (d, J = 8.0 Hz, 1H), 7.63 (d, J = 8.0 Hz, 1H), 4.55-4.45 (m, 1H), 3.64-3.50 (m, 1H), 3.62-3.50 (m, 1H), 3.07-3.03 (m, 1H), 3.00 (s, 3H), 2.84 (s, 3H), 2.19-2.01 (m, 3H), 2.02-1.86 (m, 1H), 1.36 (d, J = 6.4 Hz, 3H); 2NHs not observed. |
| 119 | LC-MS 432.3, 434.3 [M + H]+; 1H NMR (methanol-d4) δ 7.52 (d, J = 8.1 Hz, 1H), 7.47 (s, 1H), 7.13 (d, J = 8.1 Hz, 1H), 6.64 (s, 1H), 4.63-4.48 (m, 1H), 3.74-3.65 (m, 1H), 3.44-3.34 (m, 1H), 3.33-3.25 (m, 1H), 3.09 (s, 3H), 2.96 (s, 3H), 2.30-2.12 (m, 3H), 2.12-1.95 (m, 1H), 1.48 (d, J = 6.4 Hz, 3H); 2NHs not observed. |
| 125 | LC-MS 464.3 [M + H]+; 1H NMR (methanol-d4) δ 8.22 (s, 2H), 7.60 (d, J = 7.8 Hz, 1H), 7.49 (s, 1H), 7.32 (d, J = 7.8 Hz, 1H), 6.84 (s, 1H), 4.60-4.45 (m, 1H), 3.70-3.60 (m, 1H), 3.44-3.34 (m, 1H), 3.33-3.25 (m, 1H), 3.07 (s, 3H), 2.95 (s, 3H), 2.27-2.10 (m, 3H), 2.09-1.94 (m, 1H), 1.46 (d, J = 6.4 Hz, 3H); 2NHs not observed. |
| 127 | LC-MS 426.4 [M + H]+; 1H NMR (DMSO-d6) δ 9.25 (br s, 1H), 9.02 (s, 1H), 8.28 (s, 2H), 8.19 (d, J = 8.4 Hz, 1H), 7.81 (d, J = 8.4 Hz, 1H), 4.55-4.42 (m, 1H), 3.63-3.55 (m, 1H), 3.45-3.32 (m, 1H), 3.31-3.20 (m, 1H), 3.00 (s, 3H), 2.82 (s, 3H), 2.13-1.99 (m, 3H), 1.96-1.84 (m, 1H), 1.32 (d, J = 6.3 Hz, 3H). |
| 128 | LC-MS 492.3 [M + H]+; 1H NMR (methanol-d4) δ 8.15 (s, 2H), 7.62 (d, J = 7.8 Hz, 1H), 7.49 (d, J = 3.3 Hz, 1H), 7.33 (d, J = 7.8 Hz, 1H), 6.85 (d, J = 3.3 Hz, 1H), 4.96-4.86 (m, 1H), 3.10 (s, 3H), 2.09 (dd, J = 13.4, 3.7 Hz, 2H), 1.99 (t, J = 13.4 Hz, 2H), 1.66 (s, 6H), 1.54 (s, 6H); 3NHs not observed. |
| 132 | LC-MS 427.4 [M + H]+; 1H NMR (DMSO-d6) δ 9.28 (br s, 1H), 9.16 (s, 1H), 8.98 (s, 1H), 8.37 (s, 2H), 4.60-4.45 (m, 1H), 3.63-3.53 (m, 1H), 3.35-3.20 (m, 2H), 3.02 (s, 3H), 2.82 (s, 3H), 2.12-1.98 (m, 3H), 1.95-1.80 (m, 1H), 1.32 (d, J = 6.3 Hz, 3H). |
| 135 | LC-MS 454.3 [M + H]+; 1H NMR (DMSO-d6) δ 9.43 (br s, 1H), 9.01 (s, 1H), 8.41 (s, 2H), 8.34 (d, J = 8.6 Hz, 1H), 7.95 (d, J = 8.6 Hz, 1H), 4.70-4.60 (m, 1H), 3.03 (s, 3H), 2.08 (t, J = 13.1 Hz, 2H), 1.85 (dd, J = 13.1, 3.5 Hz, 2H), 1.52 (s, 6H), 1.50 (s, 6H). |
| 173 | LC-MS 424.2 [M + H]+; 1H NMR (DMSO-d6) δ 9.54 (br s, 1H), 9.04 (br s, 1H), 9.00 (s, 1H), 8.43 (s, 2H), 8.37 (d, J = 8.6 Hz, 1H), 7.97 (d, J = 8.6 Hz, 1H), 4.69-4.58 (m, 1H), 4.15-4.05 (m, 2H), 3.05 (s, 3H), 2.40-2.28 (m, 2H), 2.11-2.03 (m, 2H), 2.02-1.95 (m, 2H), 1.89-1.80 (m, 2H). |

Example 30

Preparation of Compound 164

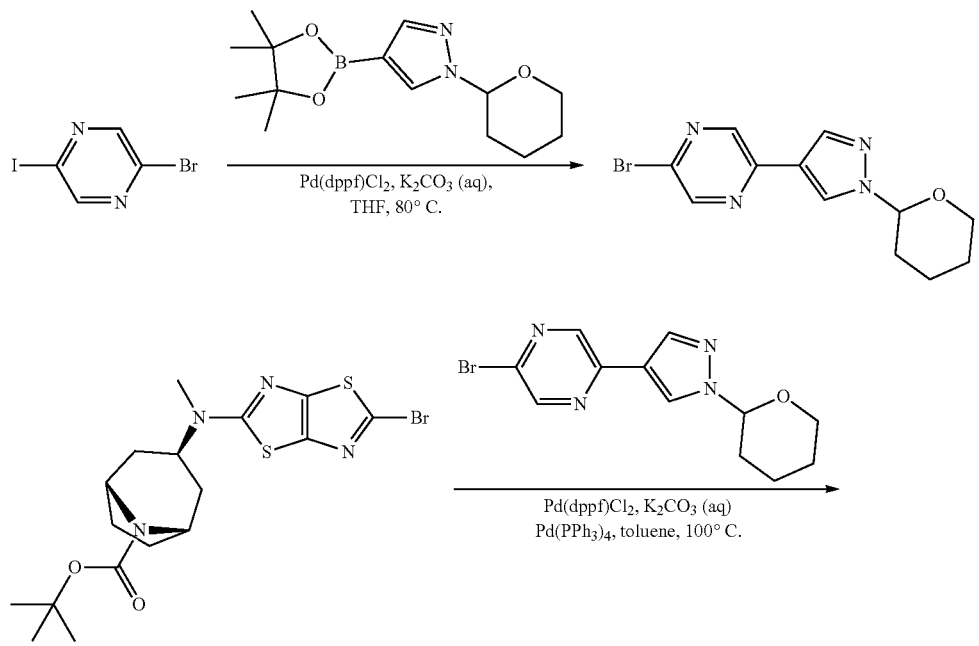

-continued

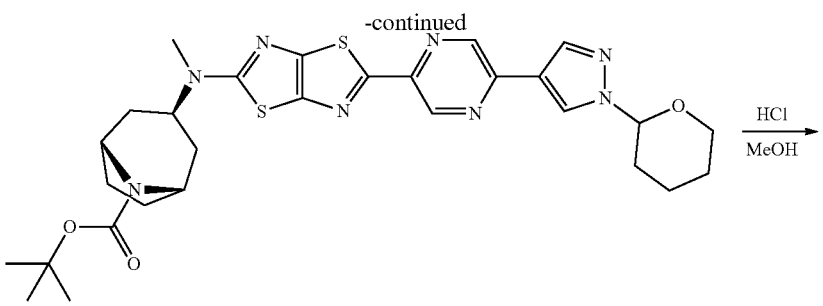

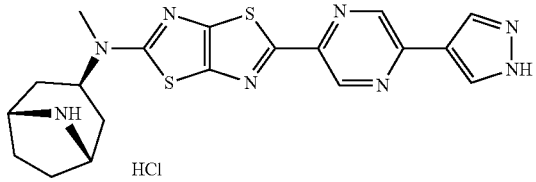

Step 1: 2-Bromo-5-iodopyrazine (284.9 mg, 1 mmol), 1-(tetrahydro-2H-pyran-2-yl)-4-(4,4,5,5-tetramethyl-1,3,2-dioxaborolan-2-yl)-1H-pyrazole (306.0 mg, 1.1 mmol), PdCl$_2$(dppf)-dichloromethane adduct (81.7 mg, 0.1 mmol), dioxane (10 mL), and aqueous K$_2$CO$_3$ (1.5 mL, 3 mmol, 2 M) were heated at 80° C. for 2 h. The reaction mixture was then partitioned between H$_2$O and ethyl acetate. The organic layer was dried over MgSO$_4$, filtered, and concentrated under vacuum. Purification by silica gel chromatography (ethyl acetate in hexanes, 0-100%), yielded 2-bromo-5-(1-(tetrahydro-2H-pyran-2-yl)-1H-pyrazol-4-yl)pyrazine (216.4 mg, 70%) as an off-white solid. LC-MS 225.1, 227.1 [M−THP+H]$^+$, RT 1.32 min.

Step 2: tert-Butyl (1r,3s,5s)-3-((5-bromothiazolo[5,4-d]thiazol-2-yl)(methyl)amino)-8-azabicyclo[3.2.1]octane-8-carboxylate (137.8 mg, 0.3 mmol), prepared based on the chemistry described in Example 1, step 5, 2-bromo-5-(1-(tetrahydro-2H-pyran-2-yl)-1H-pyrazol-4-yl)pyrazine (139.1 mg, 0.45 mmol), Pd(PPh$_3$)$_4$ (104.0 mg, 0.09 mmol), PdCl$_2$(dppf) (24.5 mg, 0.03 mmol), K$_2$CO$_3$ (0.38 mL, 0.75 mmol, 2.0 M) were mixed in toluene (3 mL) and the mixture was sparged by argon for 5 min. The reaction mixture was allowed to stir at 100° C. for 16 h and then cooled and diluted with dichloromethane. Purification by silica gel chromatography (ethyl acetate in hexanes, 0-100% then 1 M NH$_3$ in MeOH in CH$_2$Cl$_2$, 0-20%), yielded tert-butyl (1r,3s,5s)-3-(methyl(5-(5-(1-(tetrahydro-2H-pyran-2-yl)-1H-pyrazol-4-yl)pyrazin-2-yl)thiazolo[5,4-d]thiazol-2-yl)amino)-8-azabicyclo[3.2.1]octane-8-carboxylate as an oil. The resultant compound was then treated with HCl in MeOH (3 mL, 3 mmol, 1 M) at room temperature overnight. The precipitate was collected by filtration and dried to furnish the title compound 5-(4-(1H-pyrazol-4-yl)-1H-indol-7-yl)-N-((1r,3s,5s)-8-azabicyclo[3.2.1]octan-3-yl)-N-methylthiazolo[5,4-d]thiazol-2-amine (44.6 mg, 35%).

LC-MS 425.2 [M+H]$^+$; $^1$H NMR (DMSO-d$_6$) δ 9.45-9.35 (br s, 1H), 9.15 (d, J=1.6 Hz, 1H), 8.99 (d, J=1.6 Hz, 1H), 8.99-8.90 (br s, 1H), 8.37 (s, 2H), 4.74-4.60 (m, 1H), 4.15-4.05 (m, 2H), 3.05 (s, 3H), 2.36-2.27 (m, 2H), 2.10-1.95 (m, 4H), 1.90-1.82 (m, 2H).

Using the procedure described for Example 30, above, additional compounds described herein were prepared by substituting the appropriate starting materials, suitable reagents and reaction conditions, obtaining compounds such as those selected from:

| Cpd | Data |
|---|---|
| 69 | LC-MS 494.6 [M + H]$^+$; $^1$H NMR (DMSO-d$_6$) δ 9.35 (s, 1H), 9.08 (br s, 1H), 8.81 (br s, 1H), 8.36 (d, J = 5.4 Hz, 1H), 7.75 (d, J = 5.4 Hz, 1H), 7.58 (s, 1H), 4.80-4.70 (m, 1H), 3.94 (s, 3H), 3.06 (s, 3H), 2.20-2.02 (m, 4H), 1.98-1.86 (m, 4H), 1.45 (s, 6H). |
| 73 | LC-MS 481.6 [M + H]$^+$; $^1$H NMR (methanol-d$_4$) δ 9.29 (s, 1H), 8.68 (s, 1H), 5.00-4.90 (m, 1H) 3.10 (s, 3H), 2.53 (s, 6H), 2.32 (d, J = 8.8 Hz, 2H), 2.19-2.00 (m, 6H), 1.57 (s, 6H); 2NHs not observed. |
| 86 | LC-MS 467.6 [M + H]$^+$; $^1$H NMR (methanol-d$_4$) δ 9.16 (s, 1H), 8.90 (s, 1H), 8.24 (s, 1H), 4.63-4.53 (m, 1H), 3.01 (s, 3H), 2.57 (s, 3H), 1.95 (d, J = 8.5 Hz, 2H), 1.86 (t, J = 12.4 Hz, 2H), 1.82-1.68 (m, 4H), 1.33 (s, 6H); 2NHs not observed. |
| 89 | LC-MS 467.6 [M + H]$^+$; $^1$H NMR (methanol-d$_4$) δ 9.16 (s, 1H), 8.83 (s, 1H), 8.32 (s, 1H), 8.14 (s, 1H), 4.95-4.90 (m, 1H), 4.00 (s, 3H), 3.09 (s, 3H), 2.31 (t, J = 7.5 Hz, 2H), 2.15-1.93 (m, 6H), 1.57 (s, 6H); 2NHs not observed. |
| 92 | LC-MS 494.6 [M + H]$^+$; $^1$H NMR (methanol-d$_4$) δ 9.35 (s, 1H), 9.11 (s, 1H), 7.82 (d, J = 6.9 Hz, 1H), 7.32 (s, 1H), 7.16 (d, J = 6.9 Hz, 1H), 4.95-4.90 (m, 1H), 3.65 (s, 3H), 3.11 (s, 3H), 2.33 (d, J = 8.6 Hz, 2H), 2.17-2.04 (m, 6H), 1.57 (s, 6H); NH not observed. |
| 93 | LC-MS 413.5 [M + H]$^+$; $^1$H NMR (methanol-d$_4$) δ 8.97 (s, 1H), 8.69 (s, 1H), 8.17 (s, 2H), 4.62-4.52 (m, 1H), 3.90-3.79 (m, 1H), 3.38-3.23 (m, 2H), 2.93 (s, 3H), 2.22-2.09 (m, 1H), 2.05-1.93 (m, 2H), 1.83 (d, J = 13.9 Hz, 1H), 1.43 (d, J = 7.2, 3H); 2NHs not observed. |

| Cpd | Data |
|---|---|
| 94 | LC-MS 469.3 [M + H]$^+$; $^1$H NMR (DMSO-d$_6$) δ 9.13 (s, 1H), 8.92 (s, 1H), 8.45 (s, 1H), 8.18 (s, 1H), 8.13 (s, 1H), 4.60-4.45 (m, 1H), 3.91 (s, 3H), 3.01 (s, 3H), 1.80-1.66 (m, 4H), 1.35 (s, 6H), 1.25 (s, 6H). |
| 99 | LC-MS 413.3 [M + H]$^+$; $^1$H NMR (DMSO-d$_6$) δ 9.22 (m, 2H), 9.14 (s, 1H), 8.98 (s, 1H), 8.38 (s, 2H), 4.56-4.45 (m, 1H), 3.43-3.30 (m, 2H), 3.14-3.03 (m, 1H), 3.01 (s, 3H), 2.22-2.10 (m, 1H), 2.03-1.84 (m, 3H), 1.31 (d, J = 6.4 Hz, 3H). |
| 142 | LC-MS 453.3 [M + H]$^+$; $^1$H NMR (DMSO-d$_6$) δ 13.34 (s, 1H), 9.16 (s, 1H), 8.99 (s, 1H), 8.74 (s, 2H), 8.53 (brs, 1H), 8.22 (brs, 1H), 4.76-4.65 (m, 1H), 3.02 (s, 3H), 2.14 (d, J = 9.0 Hz, 2H), 2.06-1.79 (m, 6H), 1.44 (s, 6H). |
| 143 | LC-MS 442.4 [M + H]$^+$; $^1$H NMR (methanol-d$_4$) δ 9.25 (s, 1H), 8.94 (s, 1H), 8.35 (s, 2H), 5.78-5.64 (m, 1H), 2.55 (dd, J = 13.9, 4.1 Hz, 2H), 1.91 (dd, J = 13.9, 10.6 Hz, 2H), 1.63 (s, 6H), 1.57 (s, 6H); 2NHs not observed. |
| 163 | LC-MS 455.3 [M + H]$^+$; $^1$H NMR (DMSO-d$_6$) δ 9.49-9.31 (m, 1H), 9.15 (d, J = 1.5 Hz, 1H), 8.99 (d, J = 1.5 Hz, 1H), 8.40-8.30 (m, 3H), 4.72-4.64 (m, 1H), 3.03 (s, 3H), 2.08 (t, J = 13.1 Hz, 2H), 1.86 (dd, J = 13.1, 3.6 Hz, 2H), 1.52 (s, 6H), 1.50 (s, 6H). |

Example 31

Preparation of Compound 175

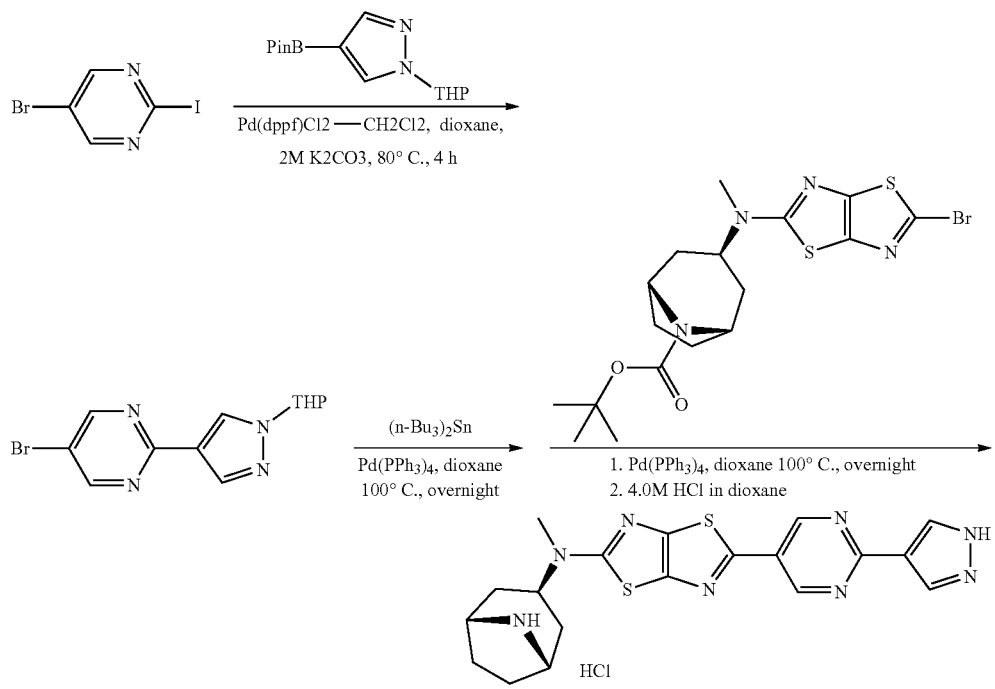

Step 1: A mixture of 5-bromo-2-iodopyrimidine (284.9 mg, 1 mmol), 1-tetrahydropyran-2-yl-4-(4,4,5,5-tetramethyl-1,3,2-dioxaborolan-2-yl)pyrazole (306.0 mg, 1.1 mmol), PdCl$_2$(dppf)-dichloromethane adduct (81.7 mg, 0.1 mmol), dioxane (10 mL), and aqueous K$_2$CO$_3$ (1.5 mL, 3 mmol, 2M) were heated at 80° C. for 4 h. The reaction mixture was then partitioned between H$_2$O and ethyl acetate. The organic layer was dried over MgSO$_4$, filtered, and concentrated under vacuum. Purification by silica gel chromatography (ethyl acetate in hexanes, 0-100%), yielded 5-bromo-2-(1-(tetrahydro-2H-pyran-2-yl)-1H-pyrazol-4-yl)pyrimidine (247.3 mg, 80%) as an off-white solid. LC-MS 225.1, 227.1 [M–THP+H]$^+$, RT 1.32 min.

Step 2: A mixture of 2-bromo-5-(1-(tetrahydro-2H-pyran-2-yl)-1H-pyrazol-4-yl)pyrimidine (55.7 mg, 0.18 mmol), hexabutylditin (0.19 mL, 0.36 mmol), Pd(PPh$_3$)$_4$ (35 mg, 0.030 mmol) in 1,4-dioxane (1.0 mL) was stirred at 100° C. under argon overnight, followed by the addition of tert-butyl (1r,3s,5s)-3-((5-bromothiazolo[5,4-d]thiazol-2-yl)(methyl)amino)-8-azabicyclo[3.2.1]octane-8-carboxylate (68.9 mg, 0.15 mmol), prepared based on the chemistry described in Example 1, step 5, and another batch of Pd(PPh$_3$)$_4$ (35 mg, 0.030 mmol), This was then stirred at 100° C. under argon for 24 h. After cooling, the solvent was removed and the residue was treated with HCl in dioxane (2.0 mL, 4.0 M) at room temperature for 4 h. The volatiles were evaporated and the residue was chromatographed on a C18 column, eluted with ACN in H$_2$O (0-100%). The fractions containing the desire product were combined and concentrated to dryness to provide 5-(2-(1H-pyrazol-4-yl)pyrimidin-5-yl)-N-((1R, 3s,5S)-8-azabicyclo[3.2.1]octan-3-yl)-N-methylthiazolo[5,4-d]thiazol-2-amine (7.6 mg, 10%).

LC-MS 425.4 [M+H]$^+$; $^1$H NMR (methanol-d$_4$) δ 9.17 (s, 2H), 8.36 (s, 2H), 4.86-4.80 (m, 1H), 4.28-4.18 (s, 2H), 3.07 (s, 3H), 2.30-2.19 (m, 6H), 2.09-2.01 (m, 2H); 2NHs not observed.

Using the procedure described for Example 31, above, additional compounds described herein were prepared by substituting the appropriate starting materials, suitable reagents and reaction conditions, obtaining compounds such as those selected from:

| Cpd | Data |
|---|---|
| 130 | LC-MS 427.4 [M + H]$^+$; $^1$H NMR (methanol-d$_4$) δ 9.15 (s, 2H), 8.31 (s, 2H), 4.60-4.50 (m, 1H), 3.75-3.60 (m, 1H), 3.42-3.33 (m, 1H), 3.29-3.25 (m, 1H), 3.08 (s, 3H), 2.93 (s, 3H), 2.24-2.09 (m, 3H), 2.06-1.97 (m, 1H), 1.45 (d, J = 6.5 Hz, 3H); NH not observed. |
| 137 | LC-MS 455.3 [M + H]$^+$; $^1$H NMR (DMSO-d$_6$) δ 9.20 (s, 2H), 9.11 (br s, 1H), 8.44 (s, 2H), 8.08 (br s, 1H), 4.71-4.57 (m, 1H), 3.04 (s, 3H), 2.05-1.95 (m, 2H), 1.95-1.85 (m, 2H), 1.51 (s, 6H), 1.47 (s, 6H). |

Example 32

Preparation of Compound 170

Step 1: A mixture of 4-bromopyridin-2-ol (150.0 mg, 1 mmol), 1-tetrahydropyran-2-yl-4-(4,4,5,5-tetramethyl-1,3,2-dioxaborolan-2-yl)pyrazole (417.2 mg, 1.5 mmol), PdCl$_2$(dppf)-dichloromethane adduct (81.7 mg, 0.1 mmol), dioxane (10 mL), and aqueous K$_2$CO$_3$ (1.5 mL, 3 mmol, 2M) were heated at 80° C. overnight. The reaction mixture was then partitioned between H$_2$O and ethyl acetate. The organic layer was dried over MgSO$_4$, filtered, and concentrated under vacuum. Purification by silica gel chromatography (ethyl acetate in hexanes, 0-100%), yielded 4-(1H-imidazol-4-yl)-1-(tetrahydro-2H-pyran-2-yl)-1H-pyrazole (141.9 mg, 65%) as an off-white solid. LC-MS 219.3 [M+H]$^+$, RT 0.86 min.

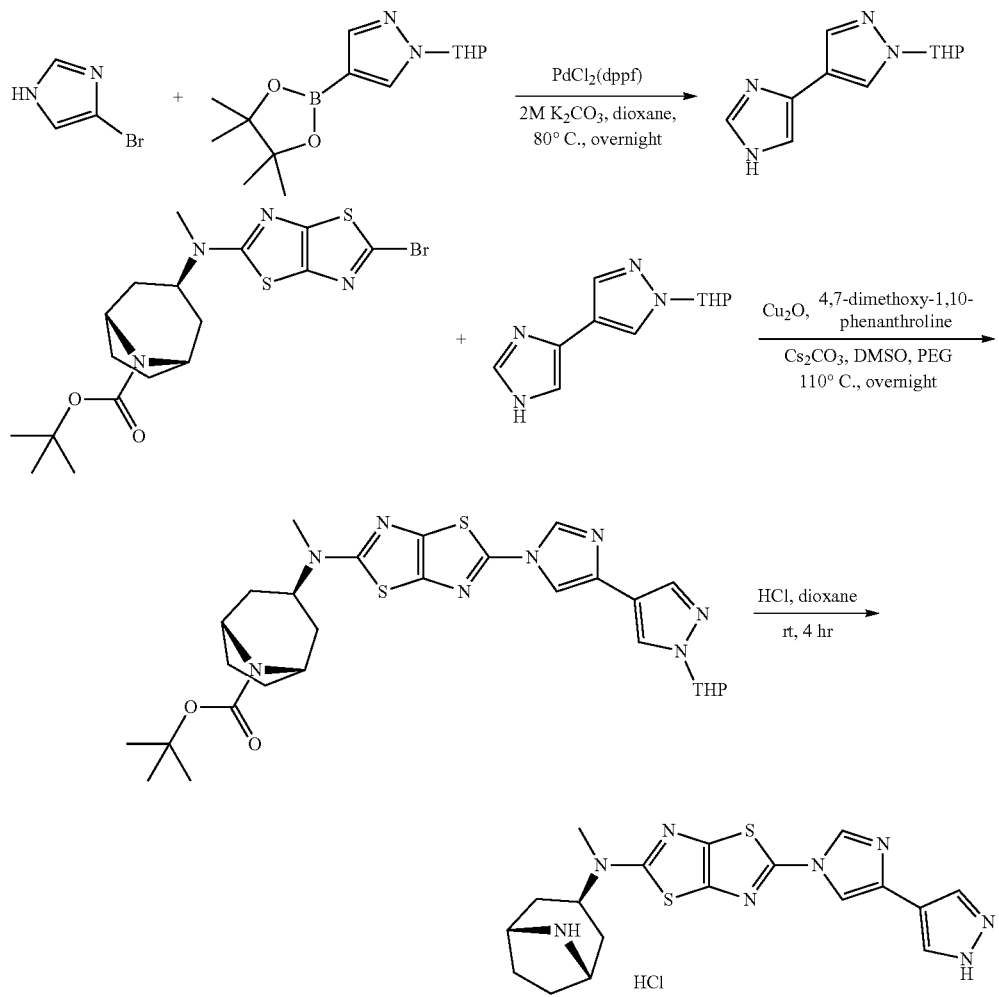

Step 2: A mixture of tert-butyl (1r,3s,5s)-3-((5-bromothiazolo[5,4-d]thiazol-2-yl)(methyl)amino)-8-azabicyclo[3.2.1]octane-8-carboxylate (68.9 mg, 0.15 mmol), prepared based on the chemistry described in Example 1, step 5, 4-(1H-imidazol-4-yl)-1-(tetrahydro-2H-pyran-2-yl)-1H-pyrazole (43.7 mg, 0.20 mmol), 4,7-dimethoxy-1,10-phenanthroline (26.4 mg, 0.11 mmol), $Cu_2O$ (10.6 mg, 0.074 mmol), $Cs_2CO_3$ (107.5 mg, 0.33 mmol) and PEG-1500 (100.0 mg) in DMSO (1.0 mL) was stirred at 110° C. under argon overnight and then evaporated to dryness. The residue was suspended in dichloromethane and filtered, and the filtrate was loaded on a silica gel column and chromatographed (methanol in dichloromethane 0-20%) to provide tert-butyl (1r,3s,5s)-3-(methyl(5-(4-(1-(tetrahydro-2H-pyran-2-yl)-1H-pyrazol-4-yl)-1H-imidazol-1-yl)thiazolo[5,4-d]thiazol-2-yl)amino)-8-azabicyclo[3.2.1]octane-8-carboxylate (49.2 mg, 55%).

Step 3: tert-Butyl (1r,3s,5s)-3-(methyl(5-(4-(1-(tetrahydro-2H-pyran-2-yl)-1H-pyrazol-4-yl)-1H-imidazol-1-yl)thiazolo[5,4-d]thiazol-2-yl)amino)-8-azabicyclo[3.2.1]octane-8-carboxylate (49.2 mg, 0.083 mmol) was treated with HCl in MeOH (2.0 mL, 4 mmol, 2.0 M) at room temperature for 4 h. The resulting mixture was purified by reverse phase chromatography ($CH_3CN$ in water, 0-100%) and the desired fractions were collected and dried to furnish 5-(4-(1H-pyrazol-4-yl)-1H-imidazol-1-yl)-N-((1r,3 s,5 s)-8-azabicyclo[3.2.1]octan-3-yl)-N-methylthiazolo[5,4-d]thiazol-2-amine (29.1 mg, 85%).

LC-MS 413.4 $[M+H]^+$; $^1$H NMR (DMSO-$d_6$) δ 9.61 (brs, 1H), 9.25 (s, 1H), 9.07 (s, 1H), 8.32 (s, 1H), 8.16 (s, 2H), 4.66-4.55 (m, 1H), 4.15-4.05 (m, 2H), 3.05 (s, 3H), 2.40-2.29 (m, 2H), 2.12-1.92 (m, 4H), 1.91-1.78 (m, 2H).

Example 33

Preparation of Compound 118

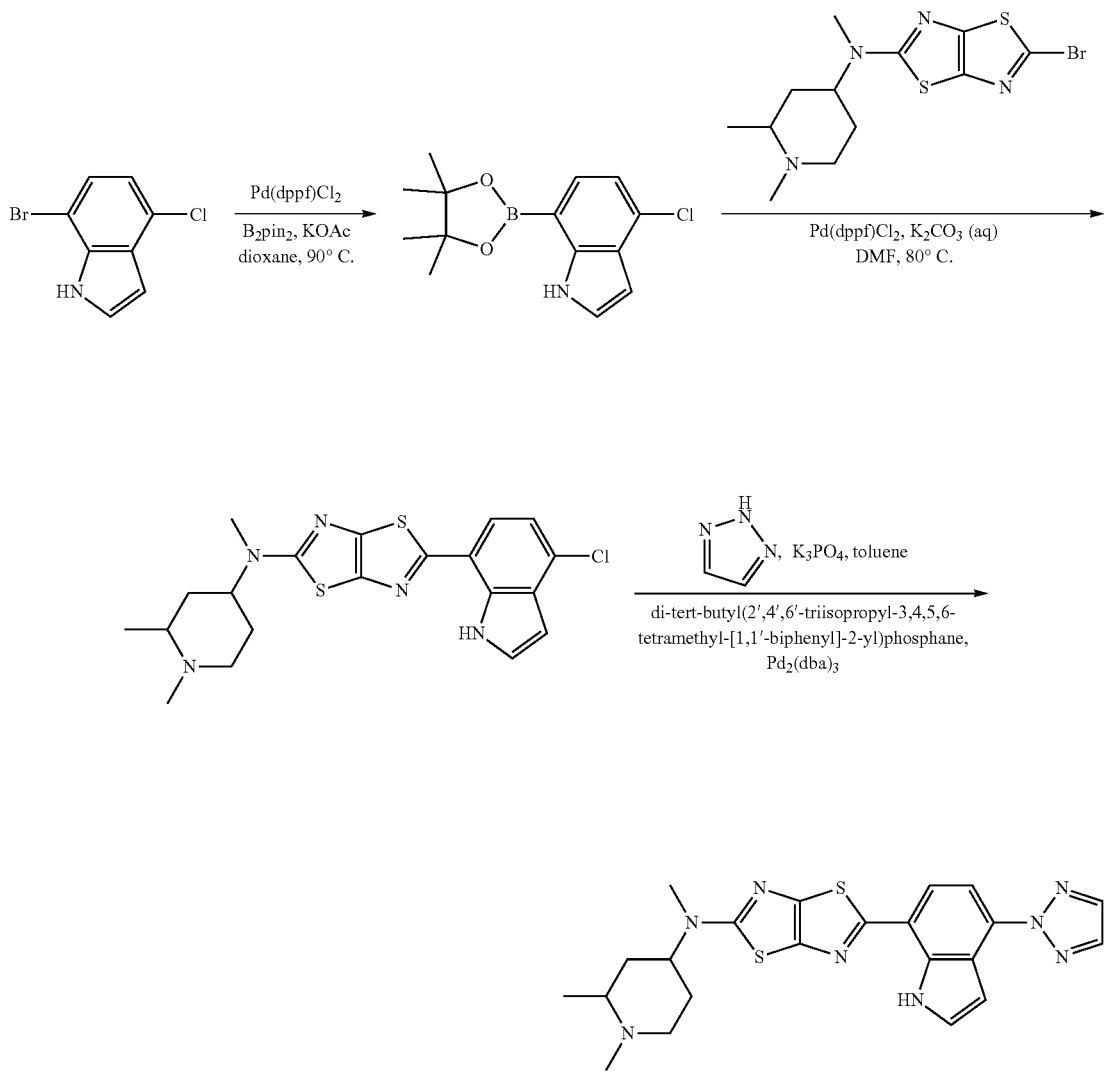

Step 1: Potassium acetate (294.4 mg, 3 mmol) was pumped dry at 180° C. for 2 h, and then the flask was filled with argon. 7-Bromo-4-chloro-1H-indole (230.5 mg, 1 mmol), PdCl$_2$(dppf) (81.7 mg, 0.1 mmol), bis(pinacolato) diboron (330.1 mg, 1.3 mmol), and dry dioxane (5 mL) were added. The mixture was heated at 90° C. for 16 h. The crude mixture of 4-chloro-7-(4,4,5,5-tetramethyl-1,3,2-dioxaborolan-2-yl)-1H-indole was used in the next step without purification.

Step 2: To the crude mixture of 4-chloro-7-(4,4,5,5-tetramethyl-1,3,2-dioxaborolan-2-yl)-1H-indole from the last step was added 5-bromo-N-(1,2-dimethylpiperidin-4-yl)-N-methylthiazolo[5,4-d]thiazol-2-amine (242.1 mg, 0.67 mmol), prepared based on the chemistry described in Example 1, step 5, PdCl$_2$(dppf) (57.2 mg, 0.07 mmol), K$_2$CO$_3$ (1 mL, 2 mmol, 2.0 M) and DMF (5 mL). The mixture was sparged by argon for 5 min and stirred at 80° C. for 24 h and then cooled and diluted with ethyl acetate. The mixture was chromatographed (1 M NH$_3$ in MeOH in CH$_2$Cl$_2$, 0-20%) and then further purified by reverse phase preparative HPLC (CH$_3$CN in water 0-100%) to provide the coupling product 5-(4-chloro-1H-indol-7-yl)-N-(1,2-dimethylpiperidin-4-yl)-N-methylthiazolo[5,4-d]thiazol-2-amine (101.3 mg, 35%). LC-MS 432.3, 434.3 [M+H]$^+$, RT 1.46 min.

Step 3: A mixture of Pd$_2$(dba)$_3$ (18.3 mg, 0.02 mmol) and di-tert-butyl(2',4',6'-triisopropyl-3,4,5,6-tetramethyl-[1,1'-biphenyl]-2-yl)phosphane (19.2 mg, 0.04 mmol) was heated in toluene (2.0 ml) at 120° C. for 5 min under argon. To the resultant mixture was added 5-(4-chloro-1H-indol-7-yl)-N-(1,2-dimethylpiperidin-4-yl)-N-methylthiazolo[5,4-d]thiazol-2-amine (86.4 mg, 0.20 mmol), 2H-1,2,3-triazole (20.7 mg, 0.30 mmol), and K$_3$PO$_4$ (84.9 mg, 0.40 mmol). The mixture was stirred at 120° C. for 2 h and then evaporated to dryness. The residue was suspended in dichloromethane and filtered. The filtrate was loaded on a silica gel column and chromatographed (methanol in dichloromethane 0-20%) to provide 5-(4-(2H-1,2,3-triazol-2-yl)-1H-indol-7-yl)-N-(1,2-dimethylpiperidin-4-yl)-N-methylthiazolo[5,4-d]thiazol-2-amine (23.2 mg, 25%).

LC-MS 465.3 [M+H]$^+$; $^1$H NMR (methanol-d$_4$) δ 8.03 (d, J=2.0 Hz, 2H), 7.86 (d, J=8.3 Hz, 1H), 7.70 (d, J=8.3 Hz, 1H), 7.53 (s, 1H), 7.35 (s, 1H), 4.65-4.50 (m, 1H), 3.75-3.65 (m, 1H), 3.49-3.35 (m, 1H), 3.33-3.25 (m, 1H), 3.11 (s, 3H), 2.97 (s, 3H), 2.28-2.15 (m, 3H), 2.10-2.00 (m, 1H), 1.48 (d, J=6.4, 3H); NH not observed.

Example 34

Preparation of Compound 105

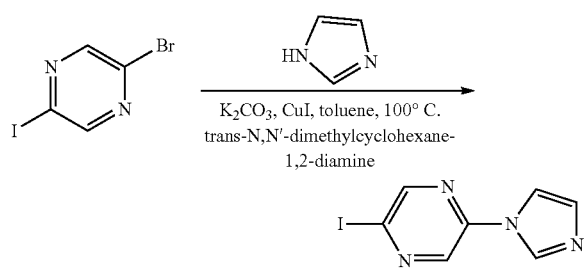

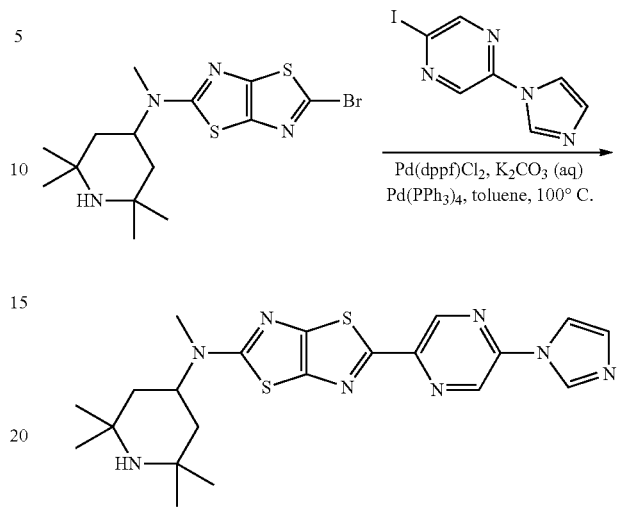

Step 1: 2-Bromo-5-iodopyrazine (284.9 mg, 1 mmol), 1H-imidazole (64.7 mg, 0.95 mmol), toluene (10 mL), and K$_2$CO$_3$ (345.5 mg, 2.5 mmol), CuI (19.0 mg, 0.1 mmol), trans-N,N'-dimethylcyclohexane-1,2-diamine (0.032 mL, 0.2 mmol) were heated at 100° C. overnight. The reaction mixture was then partitioned between H$_2$O and ethyl acetate. The organic layer was dried over MgSO$_4$, filtered, and concentrated under vacuum. Purification by silica gel chromatography (ethyl acetate in hexane, 0-100%), yielded 2-(1H-imidazol-1-yl)-5-iodopyrazine (219.7 mg, 85%) as an off-white solid which contains a small amount of inseparable byproduct 2-(1H-imidazol-1-yl)-5-bromopyrazine. LC-MS 273.1 [M+H]$^+$, RT 0.74 min.

Step 2: 5-Bromo-N-methyl-N-(2,2,6,6-tetramethylpiperidin-4-yl)thiazolo[5,4-d]thiazol-2-amine (116.8 mg, 0.3 mmol), prepared in Example 1, 2-(1H-imidazol-1-yl)-5-iodopyrazine (122.4 mg, 0.45 mmol), Pd(PPh$_3$)$_4$ (104.0 mg, 0.09 mmol), PdCl$_2$(dppf) (24.5 mg, 0.03 mmol), and K$_2$CO$_3$ (0.38 mL, 0.75 mmol, 2.0 M) were mixed in toluene (3 mL) and the mixture was sparged by argon for 5 min. The reaction mixture was allowed to stir at 100° C. for 16 h and then cooled and diluted with dichloromethane. Purification by silica gel chromatography (ethyl acetate in hexanes, 0-100%), followed by reverse phase chromatography (CH$_3$CN in water, 0-100%) and salt formation with HCl in diethyl ether (2.0 M) yielded 5-(5-(1H-imidazol-1-yl) pyrazin-2-yl)-N-methyl-N-(2,2,6,6-tetramethylpiperidin-4-yl)thiazolo[5,4-d]thiazol-2-amine hydrochloride (47.7 mg, 35%).

LC-MS 455.4 [M+H]$^+$; $^1$H NMR (DMSO-d$_6$) δ 9.20 (s, 1H), 9.13 (s, 1H), 9.04 (br s, 1H), 8.68-8.65 (m, 1H), 8.03 (br s, 1H), 7.99-7.96 (m, 1H), 6.73-6.67 (m, 1H), 4.75-4.60 (m, 1H), 3.05 (s, 3H), 2.05-1.97 (m, 2H), 1.96-1.88 (m, 2H), 1.51 (s, 6H), 1.46 (s, 6H). HCl salt.

Using the procedure described for Example 34, above, additional compounds described herein were prepared by substituting the appropriate starting materials, suitable reagents and reaction conditions, obtaining compounds such as those selected from:

| Cpd | Data |
|---|---|
| 66 | LC-MS 413.5 [M + H]+; $^1$H NMR (methanol-$d_4$) δ 9.82 (s, 1H), 9.29 (s, 1H), 9.17 (s, 1H), 8.46 (s, 1H), 7.83 (s, 1H), 4.83-4.70 (m, 1H), 4.05-3.95 (m, 1H), 3.51-3.36 (m, 2H), 3.13 (s, 3H), 2.38-2.28 (m, 1H), 2.23-2.09 (m, 2H), 2.03-1.95 (m, 1H), 1.57 (d, J = 7.0 Hz, 3H); NH not observed. |
| 67 | LC-MS 467.6 [M + H]+; $^1$H NMR (methanol-$d_4$) δ 9.35 (s, 1H), 8.99 (s, 1H), 8.10 (s, 1H), 7.72 (s, 1H), 5.00-4.90 (m, 1H), 3.12 (s, 3H), 2.91 (s, 3H), 2.32 (d, J = 8.7 Hz, 2H), 2.15-2.05 (m, 6H), 1.57 (s, 6H); NH not observed. |
| 70 | LC-MS 454.6 [M + H]+; $^1$H NMR (DMSO-$d_6$) δ 9.48 (s, 1H), 9.17 (s, 1H), 9.14 (s, 1H), 8.44 (s, 1H), 4.60-4.40 (m, 1H), 3.01 (s, 3H), 1.85-1.75 (m, 2H), 1.75-1.50 (m, 6H), 1.23 (s, 6H); NH not observed. |
| 88 | LC-MS 467.6 [M + H]+; $^1$H NMR (DMSO-$d_6$) δ 9.09 (s, 2H), 8.53 (s, 1H), 7.75 (s, 1H), 4.74-4.60 (m, 1H), 3.03 (s, 3H), 2.21 (s, 3H), 2.15-1.95 (m, 2H), 1.95-1.80 (m, 6H), 1.42 (s, 6H); NH not observed. |
| 102 | LC-MS 455.4 [M + H]+; $^1$H NMR (DMSO-$d_6$) δ 10.10 (s, 1H), 9.64 (br s, 1H), 9.38 (d, J = 1.4 Hz, 1H), 9.24 (d, J = 1.4 Hz, 1H), 8.60-8.49 (m, 2H), 7.97 (s, 1H), 4.77-4.65 (m, 1H), 3.06 (s, 3H), 2.23-2.13 (m, 2H), 1.87-1.77 (m, 2H), 1.54 (s, 12H). |
| 103 | LC-MS 453.4 [M + H]+; $^1$H NMR (DMSO-$d_6$) δ 9.98 (br s, 1H), 9.69 (s, 1H), 9.29 (s, 1H), 9.21 (s, 1H), 9.12 (br s, 1H), 8.40 (s, 1H), 7.78 (s, 1H), 4.80-4.65 (m, 1H), 3.10 (s, 3H), 2.28 (t, J = 12.7 Hz, 2H), 2.14-2.06 (m, 2H), 1.95-1.83 (m, 4H), 1.48 (s, 6H). |
| 104 | LC-MS 453.4 [M + H]+; $^1$H NMR (DMSO-$d_6$) δ 9.56 (br s, 1H), 9.19 (s, 1H), 9.12 (s, 1H), 8.95 (br s, 1H), 8.70-8.65 (m, 1H), 8.00-7.96 (m, 1H), 6.73-6.68 (m, 1H), 4.80-4.65 (m, 1H), 3.07 (s, 3H), 2.23-2.07 (m, 4H), 1.95-1.85 (m, 4H), 1.46 (s, 6H). |

Example 35

Preparation of Compound 100

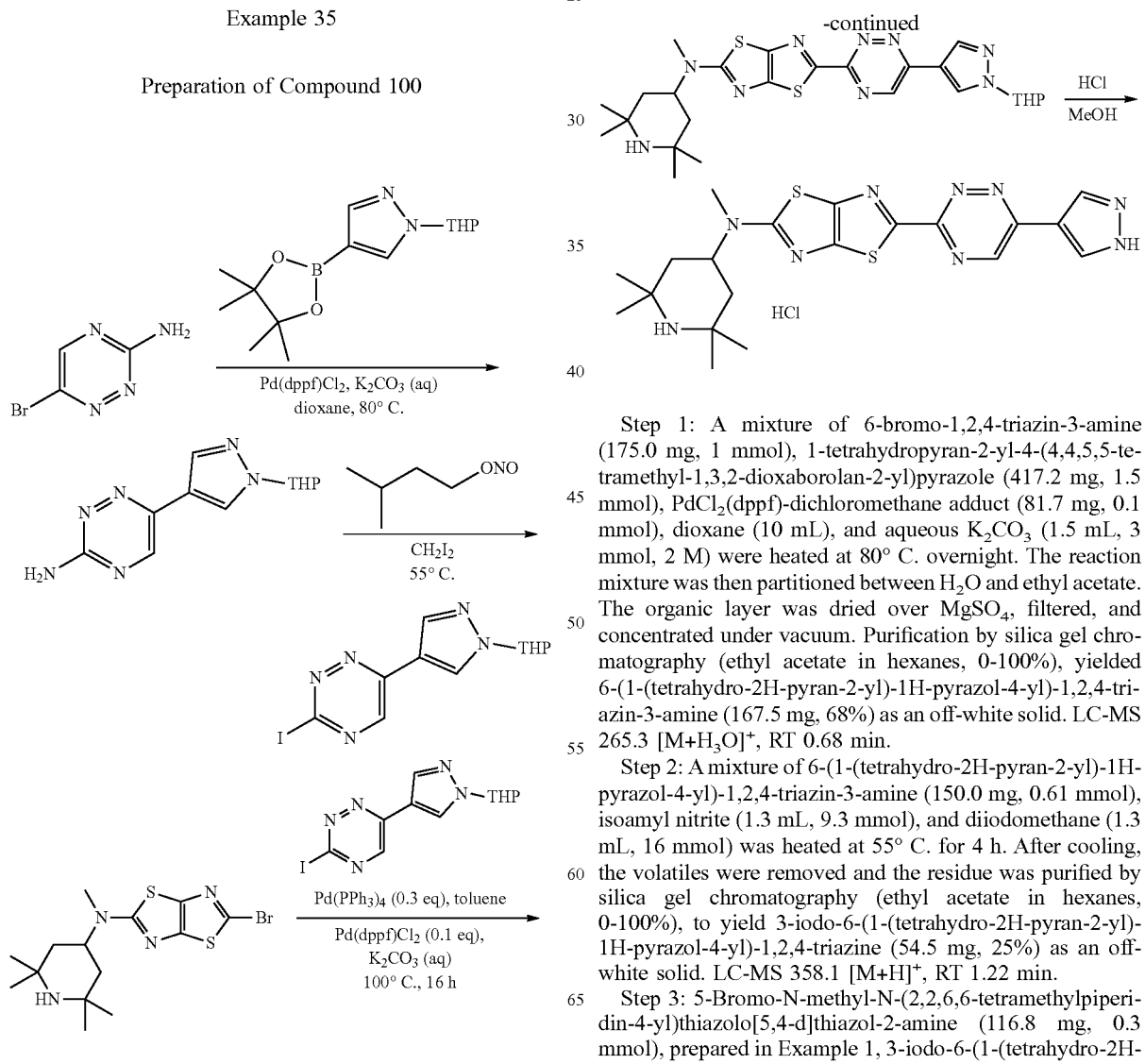

Step 1: A mixture of 6-bromo-1,2,4-triazin-3-amine (175.0 mg, 1 mmol), 1-tetrahydropyran-2-yl-4-(4,4,5,5-tetramethyl-1,3,2-dioxaborolan-2-yl)pyrazole (417.2 mg, 1.5 mmol), PdCl$_2$(dppf)-dichloromethane adduct (81.7 mg, 0.1 mmol), dioxane (10 mL), and aqueous K$_2$CO$_3$ (1.5 mL, 3 mmol, 2 M) were heated at 80° C. overnight. The reaction mixture was then partitioned between H$_2$O and ethyl acetate. The organic layer was dried over MgSO$_4$, filtered, and concentrated under vacuum. Purification by silica gel chromatography (ethyl acetate in hexanes, 0-100%), yielded 6-(1-(tetrahydro-2H-pyran-2-yl)-1H-pyrazol-4-yl)-1,2,4-triazin-3-amine (167.5 mg, 68%) as an off-white solid. LC-MS 265.3 [M+H$_3$O]+, RT 0.68 min.

Step 2: A mixture of 6-(1-(tetrahydro-2H-pyran-2-yl)-1H-pyrazol-4-yl)-1,2,4-triazin-3-amine (150.0 mg, 0.61 mmol), isoamyl nitrite (1.3 mL, 9.3 mmol), and diiodomethane (1.3 mL, 16 mmol) was heated at 55° C. for 4 h. After cooling, the volatiles were removed and the residue was purified by silica gel chromatography (ethyl acetate in hexanes, 0-100%), to yield 3-iodo-6-(1-(tetrahydro-2H-pyran-2-yl)-1H-pyrazol-4-yl)-1,2,4-triazine (54.5 mg, 25%) as an off-white solid. LC-MS 358.1 [M+H]+, RT 1.22 min.

Step 3: 5-Bromo-N-methyl-N-(2,2,6,6-tetramethylpiperidin-4-yl)thiazolo[5,4-d]thiazol-2-amine (116.8 mg, 0.3 mmol), prepared in Example 1, 3-iodo-6-(1-(tetrahydro-2H- pyran-2-yl)-1H-pyrazol-4-yl)-1,2,4-triazine (160.7 mg, 0.45 mmol), Pd(PPh₃)₄ (104.0 mg, 0.09 mmol), PdCl₂(dppf) (24.5 mg, 0.03 mmol), and K₂CO₃ (0.38 mL, 0.75 mmol, 2.0 M) were mixed in toluene (3 mL) and the mixture was sparged by argon for 5 min. The reaction mixture was stirred at 100° C. for 16 h and then cooled and diluted with dichloromethane. Purification by silica gel chromatography (ethyl acetate in hexanes, 0-100%), followed by reverse phase chromatography ($CH_3CN$ in water, 0-100%) yielded N-methyl-5-(6-(1-(tetrahydro-2H-pyran-2-yl)-1H-pyrazol-4-yl)-1,2,4-triazin-3-yl)-N-(2,2,6,6-tetramethylpiperidin-4-yl)thiazolo[5,4-d]thiazol-2-amine (48.6 mg, 30%). LC-MS 540.3 $[M+H]^+$, RT 1.04 min.

Step 4: N-methyl-5-(6-(1-(tetrahydro-2H-pyran-2-yl)-1H-pyrazol-4-yl)-1,2,4-triazin-3-yl)-N-(2,2,6,6-tetramethylpiperidin-4-yl)thiazolo[5,4-d]thiazol-2-amine (48.6 mg, 0.09 mmol) was treated with HCl in MeOH (2.0 mL, 4 mmol, 2.0 M) at room temperature for 4 h. The resulting mixture was purified by reverse phase chromatography ($CH_3CN$ in water, 0-100%) and the desired fractions were collected and dried to furnish the title compound 5-(6-(1H-pyrazol-4-yl)-1,2,4-triazin-3-yl)-N-methyl-N-(2,2,6,6-tetramethylpiperidin-4-yl)thiazolo[5,4-d]thiazol-2-amine (39.0 mg, 95%).

LC-MS 456.4 $[M+H]^+$; $^1$H NMR (methanol-$d_4$) δ 9.12 (s, 1H), 8.46 (s, 2H), 4.97-4.88 (m, 1H), 3.14 (s, 3H), 2.14-1.93 (m, 4H), 1.63 (s, 6H), 1.52 (s, 6H); 2NHs not observed.

Using the procedure described for Example 35, above, additional compounds described herein were prepared by substituting the appropriate starting materials, suitable reagents and reaction conditions, obtaining compounds such as those selected from:

| Cpd | Data |
|---|---|
| 65 | LC-MS 495.6 $[M + H]^+$; $^1$H NMR (DMSO-$d_6$) δ 9.48 (s, 1H), 9.37 (s, 1H), 8.98 (s, 1H), 7.69 (s, 1H), 4.79-4.69 (m, 1H), 4.02 (s, 3H), 3.04 (s, 3H), 2.14 (d, J = 9.1 Hz, 2H), 2.09-2.00 (m, 2H), 1.98-1.86 (m, 4H), 1.45 (s, 6H); NH not observed. |
| 79 | LC-MS 454.6 $[M + H]^+$; $^1$H NMR (methanol-$d_4$) δ 9.14 (s, 1H), 8.47 (s, 2H), 5.02-4.90 (m, 1H), 3.13 (s, 3H), 2.33 (d, J = 8.9 Hz, 2H), 2.19-2.01 (m, 6H), 1.57 (s, 6H); 2NHs not observed. |

Example 36

Preparation of Compounds 110 and 111

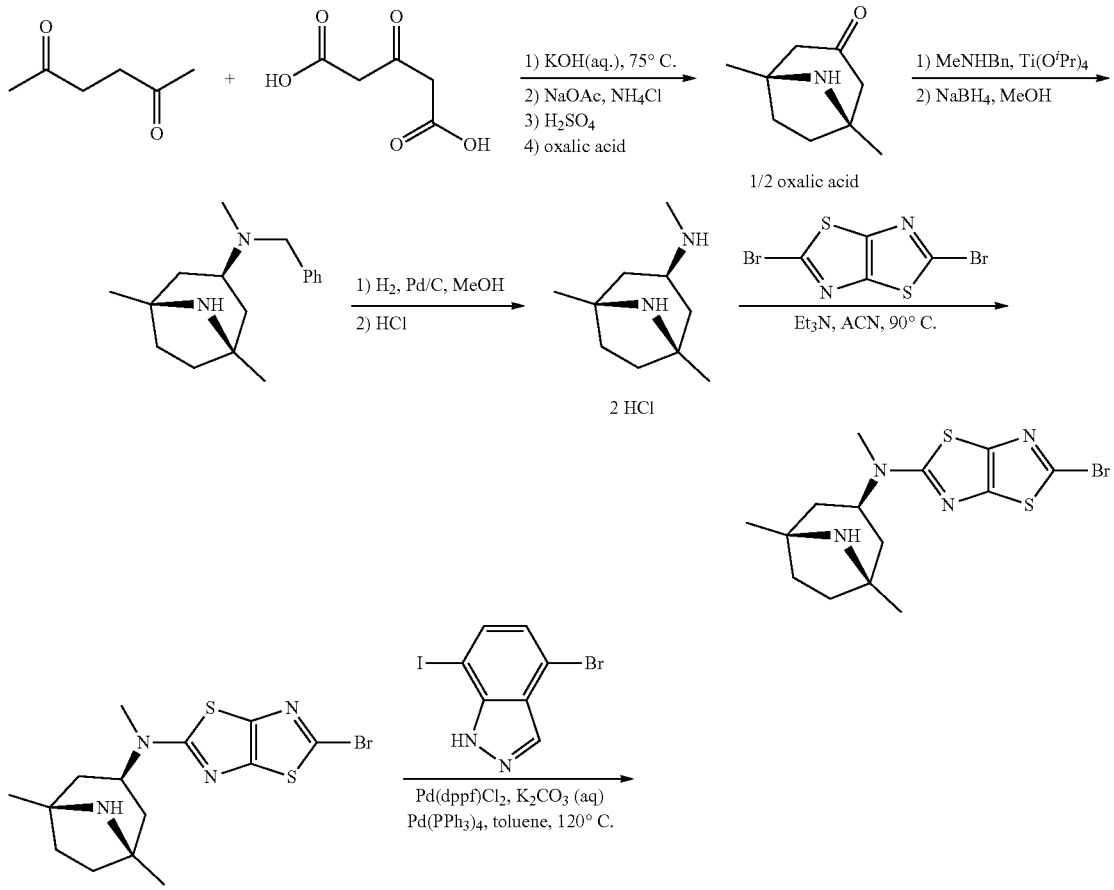

-continued

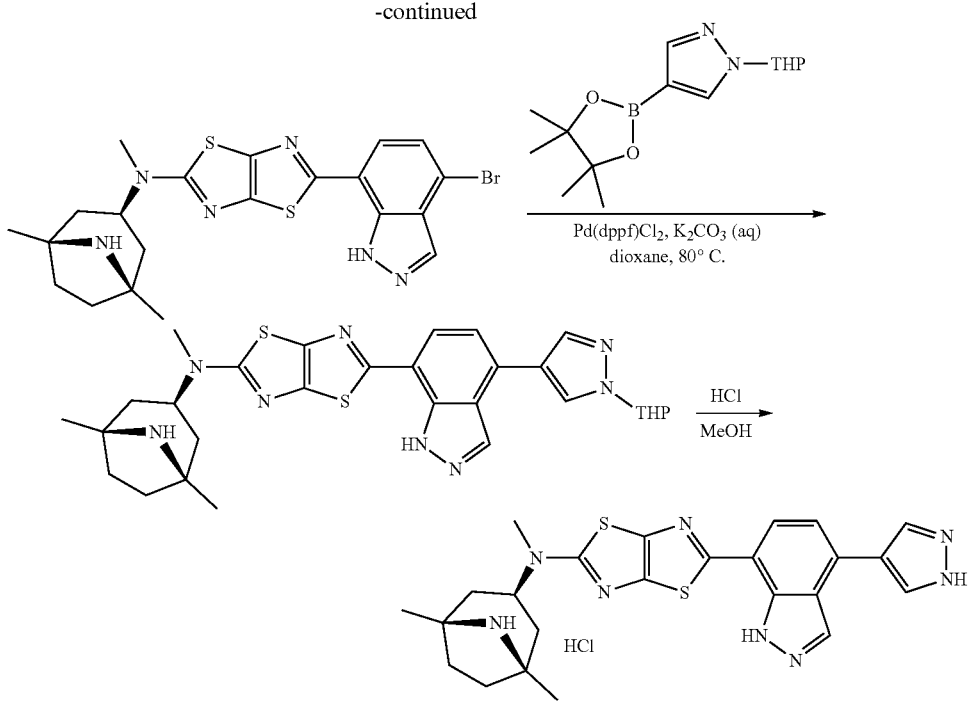

Step 1: Hexane-2,5-dione (10.8 mL, 92.1 mmol) and 3-oxopentanedioic acid (26 g, 177.96 mmol) were dissolved in $H_2O$ (75 mL) at 0° C. A solution of KOH (23.2 g, 414 mmol) in $H_2O$ (15 mL) was added dropwise, followed by a solution of NaOAc (9 g, 109.711 mmol) and $NH_4Cl$ (15 g, 280.418 mmol) in $H_2O$ (135 mL). Aqueous 50% w/w KOH (ca. 8 mL) was added to adjust the pH to 9. More $H_2O$ (60 mL) was added. This was stirred at room temperature over 5 days. The reaction mixture was then re-cooled to 0° C. 50% w/w $H_2SO_4$ (120 mL) was added slowly, resulting in $CO_2$ evolution, until the pH=2. This mixture was then washed with dichloromethane (2×300 mL). The aqueous layer was made basic with solid KOH. This was extracted into EtOAc (2×450 mL). The EtOAc layer was back-washed with brine, dried over $MgSO_4$, filtered, and evaporated to dryness, yielding crude amine. This was treated with a solution of oxalic acid dihydrate (5.4 g) in ether (600 mL). The solid was filtered off, washed with ether, then EtOH, then ether again to yield 1,5-dimethyl-8-azabicyclo[3.2.1]octan-3-one oxalic acid salt (7.00 g, 31%) as a white solid.

$^1$H NMR ($D_2O$) δ: 2.84-2.88 (m, 1H), 2.81-2.84 (m, 1H), 2.65-2.68 (m, 1H), 2.61-2.64 (m, 1H), 2.05-2.09 (m, 4H), 1.54 (s, 6H).

Step 2: A mixture of 1,5-dimethyl-8-azabicyclo[3.2.1]octan-3-one (9.19 g, 60.0 mmol), titanium isopropoxide (30 mL), and N-methyl-1-phenyl-methanamine (9.3 mL, 72 mmol) was stirred under argon at room temperature overnight. This was diluted with MeOH (250 mL) and treated with $NaBH_4$ (3.71 g, 96.1 mmol) portionwise. After the addition, the mixture was stirred for 0.5 h, and then quenched with NaOH (0.1 N, 60 mL). The precipitate was removed by filtration and washed with ether, dichloromethane and then the combined filtrates were dried over $Na_2SO_4$ and filtered. After the removal of the volatiles, the residue was chromatographed (1.4 N ammonia in MeOH in dichloromethane, 0-15%) to provide N,1,5-trimethyl-8-azabicyclo[3.2.1]octan-3-amine.

$^1$H NMR (methanol-$d_4$) δ: 7.21-7.38 (m, 5H), 3.59 (s, 2H), 2.83-2.95 (m, 1H), 2.20 (s, 3H), 1.50-1.73 (m, 6H), 1.38-1.48 (m, 2H), 1.25 (s, 6H).

N,1,5-trimethyl-8-azabicyclo[3.2.1]octan-3-amine was then dissolved in MeOH (250 mL) and hydrogenated with $H_2$ using a balloon at room temperature overnight, catalyzed by Pd/C (3.3 g, 10 mass %). The reaction mixture was diluted with MeOH and filtered over Celite, concentrated to dryness and then treated with HCl in diethyl ether (70 mL, 2.0 M). The precipitate was collected by filtration, washed with ether and dried to provide N,1,5-trimethyl-8-azabicyclo[3.2.1]octan-3-amine dihydrochloride (13.27 g, 92%).

$^1$H NMR (methanol-$d_4$) δ: 3.27 (s, 2H), 2.76-2.88 (m, 1H), 2.36 (s, 3H), 1.72-1.91 (m, 4H), 1.52-1.65 (m, 2H), 1.23 (s, 6H).

Step 3: A mixture of 2,5-dibromothiazolo[5,4-d]thiazole (1.00 g, 3.33 mmol), N,1,5-trimethyl-8-azabicyclo[3.2.1]octan-3-amine dihydrochloride (1.05 g, 4.35 mmol), triethylamine (3 mL, 21.5 mmol) and acetonitrile (10 mL) was stirred at 90° C. overnight. This was concentrated and treated with water and extracted with dichloromethane. The organic phase was washed with brine, dried, and concentrated. The residue was chromatographed (EtOAc in hexanes 0-100%) to provide 5-bromo-N-[1,5-dimethyl-8-azabicyclo[3.2.1]octan-3-yl]-N-methyl-thiazolo[5,4-d]thiazol-2-amine (1.2 g, 93% Yield) as white solid. LC-MS 387.1, 389.1 $[M+H]^+$, RT 1.14 min.

Step 4: 5-Bromo-N-((1r,3s,5s)-1,5-dimethyl-8-azabicyclo[3.2.1]octan-3-yl)-N-methylthiazolo[5,4-d]thiazol-2-amine (116.2 mg, 0.3 mmol), prepared based on the chemistry described in Example 1, step 5, 4-bromo-7-iodo-1H-indazole (145.3 mg, 0.45 mmol), Pd(PPh$_3$)$_4$ (104.0 mg, 0.09 mmol), PdCl$_2$(dppf) (24.5 mg, 0.03 mmol), and $K_2CO_3$ (0.38 mL, 0.75 mmol, 2.0 M) were mixed in toluene (3 mL) and the mixture was sparged by argon for 5 min. The reaction mixture was allowed to stir at 120° C. for 16 h and then cooled and diluted with dichloromethane. Purification by silica gel chromatography (ethyl acetate in hexanes, 0-100%), followed by reverse phase chromatography ($CH_3CN$ in water, 0-100%) yielded 5-(4-bromo-1H-indazol-7-yl)-N-((1r,3s,5s)-1,5-dimethyl-8-azabicyclo[3.2.1]octan-3-yl)-N-methylthiazolo[5,4-d]thiazol-2-amine (45.3 mg, 30%).

LC-MS 503.4, 505.4 [M+H]$^+$, RT 1.27 min; $^1$H NMR (methanol-$d_4$) δ 8.14 (s, 1H), 7.72 (d, J=7.8 Hz, 1H), 7.43 (d, J=7.8 Hz, 1H), 4.95-4.87 (m, 1H), 3.10 (s, 3H), 2.36-2.30 (m, 2H), 2.13-2.02 (m, 6H), 1.57 (s, 6H); 2NHs not observed.

Step 5: A mixture of 5-(4-bromo-1H-indazol-7-yl)-N-((1r,3s,5s)-1,5-dimethyl-8-azabicyclo[3.2.1]octan-3-yl)-N-methylthiazolo[5,4-d]thiazol-2-amine (50.3 mg, 0.1 mmol), 1-tetrahydropyran-2-yl-4-(4,4,5,5-tetramethyl-1,3,2-dioxaborolan-2-yl)pyrazole (41.7 mg, 0.15 mmol), $PdCl_2$(dppf)-dichloromethane adduct (8.2 mg, 0.01 mmol), dioxane (1 mL), and aqueous $K_2CO_3$ (0.15 mL, 0.3 mmol, 2 M) were heated at 80° C. overnight. The reaction mixture was then partitioned between $H_2O$ and ethyl acetate. The organic layer was dried over $MgSO_4$, filtered, and concentrated under vacuum. Purification by silica gel chromatography (ethyl acetate in hexanes, 0-100%), yielded N-((1r,3s,5s)-1,5-dimethyl-8-azabicyclo[3.2.1]octan-3-yl)-N-methyl-5-(4-(1-(tetrahydro-2H-pyran-2-yl)-1H-pyrazol-4-yl)-1H-indazol-7-yl)thiazolo[5,4-d]thiazol-2-amine. This was then treated with HCl in MeOH (2.0 mL, 4 mmol, 2.0 M) at room temperature for 4 h. The resulting mixture was purified by reverse phase chromatography and the desired fractions were collected and dried to furnish 5-(4-(1H-pyrazol-4-yl)-1H-indazol-7-yl)-N-((1r,3s,5s)-1,5-dimethyl-8-azabicyclo[3.2.1]octan-3-yl)-N-methylthiazolo[5,4-d]thiazol-2-amine (27 mg, 55%).

LC-MS 491.6 [M+H]$^+$; $^1$H NMR (methanol-$d_4$) δ 8.45 (s, 1H), 8.25 (s, 2H), 7.80 (d, J=7.6 Hz, 1H), 7.44 (d, J=7.6 Hz, 1H), 4.87-4.82 (m, 1H), 3.07 (s, 3H), 2.35-2.28 (m, 2H), 2.13-1.98 (m, 6H), 1.56 (s, 6H); 3NHs not observed.

Using the procedure described for Example 36, above, additional compounds described herein were prepared by substituting the appropriate starting materials, suitable reagents and reaction conditions, obtaining compounds such as those selected from:

| Cpd | Data |
|---|---|
| 78 | LC-MS 438.5 [M + H]$^+$; $^1$H NMR (methanol-$d_4$) δ 8.48 (s, 1H), 8.27 (s, 2H), 7.92 (d, J = 7.4 Hz, 1H), 7.49 (d, J = 7.4 Hz, 1H), 5.68-5.65 (m, 1H), 3.70-3.60 (m, 1H), 3.50-3.40 (m, 2H), 2.59-2.46 (m, 2H), 2.15-2.05 (m, 1H), 1.97-1.89 (m, 1H), 1.39 (d, J = 6.2 Hz, 3H); 3NHs not observed. |
| 107 | LC-MS 493.6 [M + H]$^+$; $^1$H NMR (methanol-$d_4$) δ 8.44 (s, 1H), 8.25 (s, 2H), 7.77 (d, J = 7.5 Hz, 1H), 7.42 (d, J = 7.5 Hz, 1H), 4.90-4.82 (m, 1H), 3.06 (s, 3H), 2.07-1.92 (m, 4H), 1.64 (s, 6H), 1.52 (s, 6H); 3NHs not observed. |
| 108 | LC-MS 465.3 [M + H]$^+$; $^1$H NMR (methanol-$d_4$) δ 8.31 (s, 1H), 8.12 (s, 2H), 7.66 (d, J = 7.6 Hz, 1H), 7.31 (d, J = 7.6 Hz, 1H), 4.47-4.37 (m, 1H), 3.61-3.52 (m, 1H), 3.33-3.22 (m, 1H), 3.17-3.11 (m, 1H), 2.97 (s, 3H), 2.84 (s, 3H), 2.15-2.00 (m, 3H), 1.96-1.85 (m, 1H), 1.35 (d, J = 6.4 Hz, 3H); 2NHs not observed. |

Example 37

Preparation of Compound 74

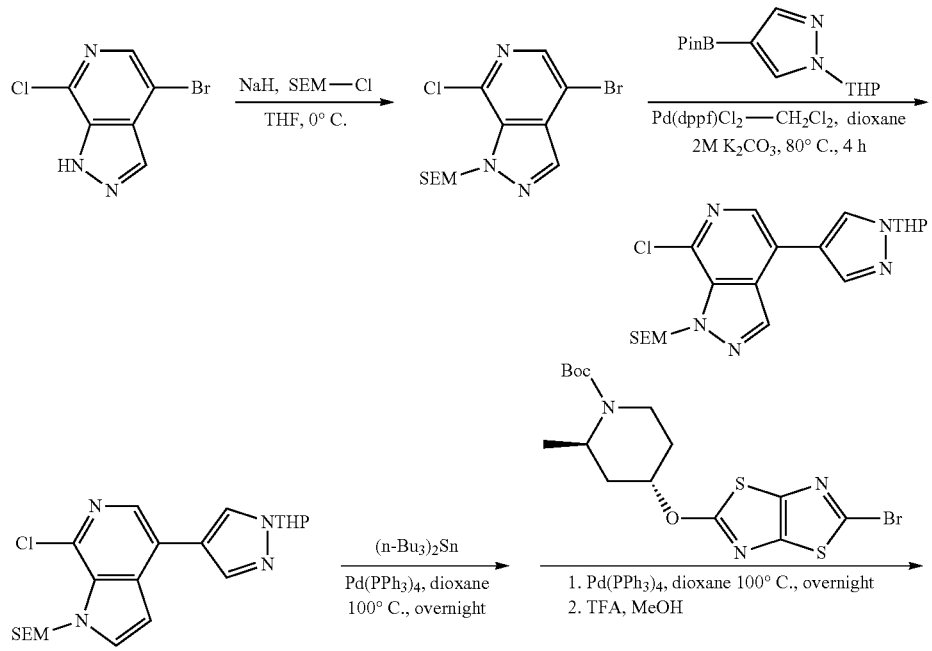

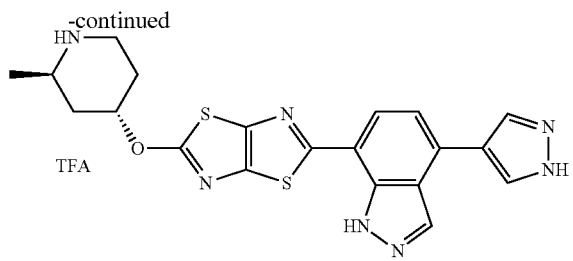

TFA

Step 1: 4-Bromo-7-chloro-1H-pyrazolo[3,4-c]pyridine (232.5 mg, 1 mmol) was dissolved in THF (5 mL) and the mixture was cooled to 0° C. To the cooled mixture was added sodium hydride (60 mg, 1.5 mmol, 60% dispersion in mineral oil) slowly. After 10 min, 2-(trimethylsilyl)ethoxymethyl chloride (0.23 L, 1.3 mmol) was added to the reaction mixture and the reaction was allowed to stir for 1 h. Purification by silica gel chromatography (ethyl acetate in hexane, 0-100%), yielded a combined mixture of 4-bromo-7-chloro-1-((2-(trimethylsilyl)ethoxy)methyl)-1H-pyrazolo[3,4-c]pyridine and 4-bromo-7-chloro-2-((2-(trimethylsilyl)ethoxy)methyl)-2H-pyrazolo[3,4-c]pyridine (308.3 mg, 85%). LC-MS 362.3, 364.3 [M+H]$^+$, RT 1.76 min.

Step 2: A mixture of 4-bromo-7-chloro-1-((2-(trimethylsilyl)ethoxy)methyl)-1H-pyrazolo[3,4-c]pyridine (362.7 mg, 1 mmol), 1-tetrahydropyran-2-yl-4-(4,4,5,5-tetramethyl-1,3,2-dioxaborolan-2-yl)pyrazole (417.2 mg, 1.5 mmol), PdCl$_2$(dppf)-dichloromethane adduct (81.7 mg, 0.1 mmol), dioxane (10 mL), and aqueous K$_2$CO$_3$ (1.5 mL, 3 mmol, 2M) were heated at 80° C. for 4 h. The reaction mixture was then partitioned between H$_2$O and ethyl acetate. The organic layer was dried over MgSO$_4$, filtered, and concentrated under vacuum. Purification by silica gel chromatography (ethyl acetate in hexanes, 0-100%), yielded 7-chloro-4-(1-(tetrahydro-2H-pyran-2-yl)-1H-pyrazol-4-yl)-1-((2-(trimethylsilyl)ethoxy)methyl)-1H-pyrazolo[3,4-c]pyridine (325.5 mg, 75%) as an off-white solid. LC-MS 434.6, 436.6 [M+H]$^+$, RT 1.68 min.

Step 3: A mixture of 7-chloro-4-(1-(tetrahydro-2H-pyran-2-yl)-1H-pyrazol-4-yl)-1-((2-(trimethylsilyl)ethoxy)methyl)-1H-pyrazolo[3,4-c]pyridine (78.1 mg, 0.18 mmol), hexabutylditin (0.19 mL, 0.36 mmol), Pd(PPh$_3$)$_4$ (35 mg, 0.030 mmol) in 1,4-dioxane (1.0 mL) was stirred at 100° C. under argon overnight, followed by the addition of tert-butyl trans-4-((5-bromothiazolo[5,4-d]thiazol-2-yl)oxy)-2-methylpiperidine-1-carboxylate (65.2 mg, 0.15 mmol) and another batch of Pd(PPh$_3$)$_4$ (35 mg, 0.030 mmol), This was then stirred at 100° C. under argon for 24 h. After cooling, the solvent was removed and the residue was purified by silica gel chromatography (ethyl acetate in hexanes, 0-100%). The desired fractions were combined and concentrated, and treated with TFA (2.0 mL) at room temperature overnight. The volatiles were evaporated and the residue was chromatographed on a C18 column, eluting with CH$_3$CN in H$_2$O (0-100%). The fractions containing the desired product were combined and concentrated to dryness to provide 2-(4-(1H-pyrazol-4-yl)-1H-pyrazolo[3,4-c]pyridin-7-yl)-5-(((2R,4S)-2-methylpiperidin-4-yl)oxy)thiazolo[5,4-d]thiazole (9.9 mg, 15%).

LC-MS 439.5 [M+H]$^+$; $^1$H NMR (methanol-d$_4$) δ 8.59 (s, 1H), 8.55 (s, 1H), 8.37 (s, 2H), 5.68-5.65 (m, 1H), 3.70-3.60 (m, 1H), 3.50-3.40 (m, 2H), 2.62-2.44 (m, 2H), 2.18-2.08 (m, 1H), 2.00-1.84 (m, 1H), 1.40 (d, J=6.6 Hz, 3H); 3NHs not observed.

Example 38

Preparation of Compound 202

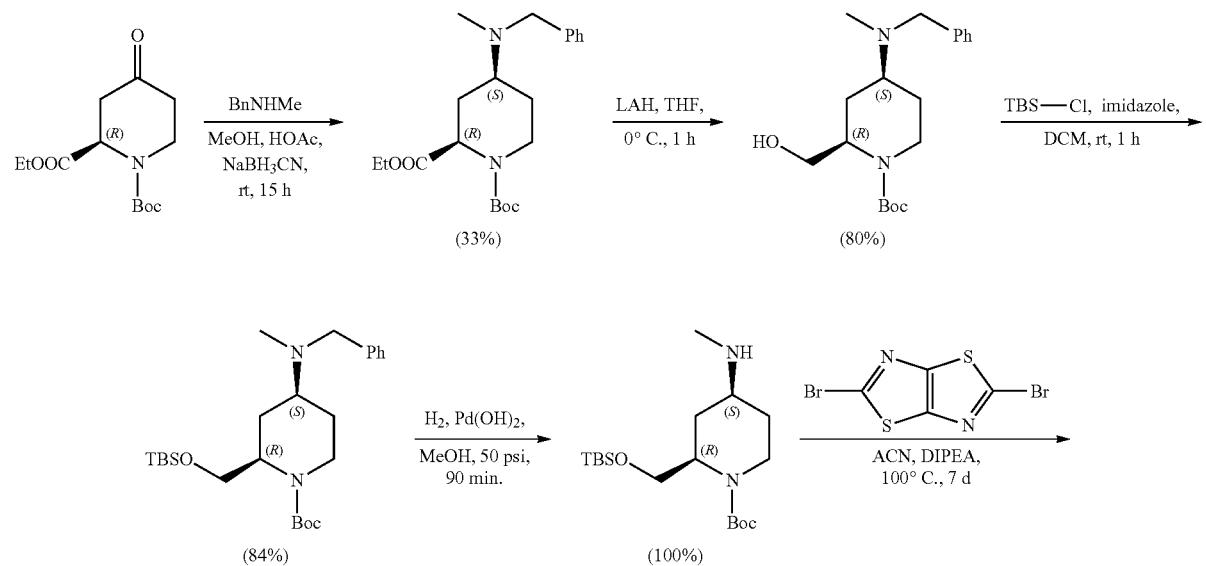

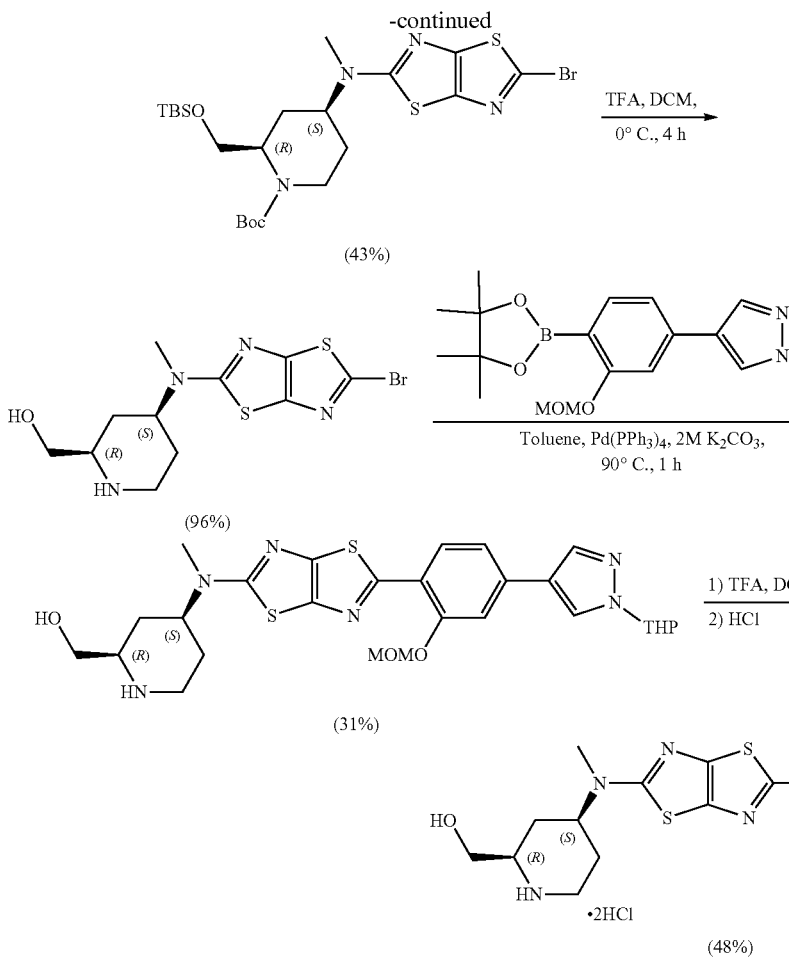

Step 1: 1-(tert-Butyl) 2-ethyl (R)-4-oxopiperidine-1,2-dicarboxylate (2.71 g, 10.1 mmol) was dissolved in MeOH (14 mL). N-methylbenzylamine (2.2 mL, 17 mmol) was added, followed by acetic acid (0.25 mL). This was stirred at room temperature for 1 h. The mixture was cooled to 0° C. and NaBH$_3$CN (1 g, 15.9 mmol) was added in one portion. This was warmed to room temperature over 15 h. The mixture was partitioned between H$_2$O and ethyl acetate. The organic layer was dried over MgSO$_4$, filtered, and concentrated under vacuum. Purification by silica chromatography (10% ethyl acetate in hexanes) yielded 1-(tert-butyl) 2-ethyl (2R,4S)-4-(benzyl(methyl)amino)piperidine-1,2-dicarboxylate (1.256 g, 33%) as the lowest major mobile TLC spot (iodine visualization) as an oil.

$^1$H NMR (methanol-d$_4$) δ 7.28-7.33 (m, 4H), 7.20-7.25 (m, 1H), 4.47 (m, 1H), 4.10-4.23 (m, 1H), 4.00-4.09 (m, 1H), 3.68-3.80 (m, 2H), 3.42 (m, 1H), 2.50-2.59 (m, 2H), 2.03-2.12 (m, 4H), 1.95-2.00 (m, 1H), 1.71-1.78 (m, 1H), 1.47 (m, 10H), 1.21 (t, J=7 Hz, 3H).

Step 2: 1-(tert-Butyl) 2-ethyl (2R,4S)-4-(benzyl(methyl)amino)piperidine-1,2-dicarboxylate (1.25 g, 3.32 mmol) was dissolved in THF (5 mL) at 0° C. LiAlH$_4$ (1M in THF, 2.5 mL, 2.5 mmol) was added dropwise. This was stirred at 0° C. for 1 h. Ethyl acetate (1 mL) was then added dropwise, followed by 1.5 mL of 10% aqueous NaOH. More ethyl acetate was added, and this was filtered. The filtrate was concentrated under vacuum. Purification by silica chromatography (20-40% acetone in dichloromethane) yielded tert-butyl (2R,4S)-4-(benzyl(methyl)amino)-2-(hydroxymethyl)piperidine-1-carboxylate (887 mg, 80%) as a clear oil.

$^1$H NMR (methanol-d$_4$) δ 7.33 (m, 4H), 7.27-7.30 (m, 1H), 3.92-3.95 (m, 1H), 3.75-3.83 (m, 2H), 3.66-3.70 (m, 2H), 3.62 (d, J=13 Hz, 1H), 3.34 (m, 1H, partially obscured by residual solvent peak), 2.65 (pentet, J=6 Hz, 1H), 2.20 (s, 3H), 2.01 (t, J=6 Hz, 2H), 1.90-1.95 (m, 1H), 1.80-1.88 (m, 1H), 1.48 (s, 9H).

Step 3: tert-Butyl (2R,4S)-4-(benzyl(methyl)amino)-2-(hydroxymethyl)piperidine-1-carboxylate (840 mg, 2.51 mmol) was dissolved in dichloromethane (10 mL). TBDMS-Cl (630 mg, 4.05 mmol) was added, followed by imidazole (270 mg, 4 mmol). This was stirred at room temperature for 1 h. The reaction mixture was loaded onto a silica column and was eluted with 9:1:0.1 dichloromethane/MeOH/NH$_4$OH to yield tert-butyl (2R,4S)-4-(benzyl(methyl)amino)-2-(((tert-butyldimethylsilyl)oxy)methyl)piperidine-1-carboxylate (950 mg, 84%) as a clear oil.

$^1$H NMR (methanol-d$_4$) δ 7.30-7.35 (m, 4H), 7.25-7.29 (m, 1H), 3.80-3.95 (m, 3H), 3.75 (m, 1H), 3.62 (d, J=13 Hz, 1H), 3.56 (d, J=13 Hz, 1H), 3.23 (m, 1H), 2.68 (m, 1H), 2.20 (s, 3H), 1.83-2.00 (m, 3H), 1.77 (m, 1H), 1.49 (s, 9H), 0.92 (s, 9H), 0.08 (d, J=11.5 Hz, 6H).

Step 4: tert-Butyl (2R,4S)-4-(benzyl(methyl)amino)-2-(((tert-butyldimethylsilyl)oxy)methyl)piperidine-1-carboxylate (872 mg, 1.94 mmol) was dissolved in MeOH (10 mL). Pd(OH)$_2$ (20% on charcoal, 100 mg) was added. This was hydrogenated at 50 psi for 90 min. The reaction mixture was filtered through Celite. The filtrate was concentrated, redissolved in ether, and was filtered again through Celite to remove particulate impurities. The filtrate was concentrated to provide tert-butyl (2R,4S)-2-(((tert-butyldimethylsilyl)oxy)methyl)-4-(methylamino)piperidine-1-carboxylate (697 mg, 100%).

$^1$H NMR (methanol-d$_4$) δ 3.83-3.95 (m, 2H), 3.72-3.82 (m, 2H), 3.22-3.28 (m, 1H), 2.68-2.72 (m, 1H), 2.38 (s, 3H), 1.89-2.00 (m, 2H), 1.70-1.80 (m, 1H), 1.47 (m, 10H), 0.93 (s, 9H), 0.095 (d, J=2.5 Hz, 6H).

Step 5: tert-Butyl (2R,4S)-2-(((tert-butyldimethylsilyl)oxy)methyl)-4-(methylamino)piperidine-1-carboxylate (690 mg, 1.92 mmol), 2,5-dibromothiazolo[5,4-d]thiazole (600 mg, 2.0 mmol), acetonitrile (5 mL), and DIPEA (0.7 mL, 4 mmol) were heated at 100° C. for 7 days. This was cooled to room temperature and was concentrated under vacuum. Purification by silica chromatography (0-5% ethyl acetate in dichloromethane) yielded tert-butyl (2R,4S)-4-((5-bromothiazolo[5,4-d]thiazol-2-yl)(methyl)amino)-2-(((tert-butyldimethylsilyl)oxy)methyl)piperidine-1-carboxylate (532 mg, 43%) as a yellow oil.

$^1$H NMR (methanol-d$_4$) δ 4.29-4.38 (m, 1H), 3.83-3.99 (m, 3H), 3.72 (dd, J=10 Hz, 3 Hz, 1H), 3.37-3.42 (m, 1H), 3.05 (s, 3H), 2.10-2.28 (m, 2H), 1.90 (m, 1H), 1.79 (m, 1H), 1.51 (s, 9H), 0.94 (s, 9H), 0.10 (d, J=5 Hz, 6H).

Step 6: tert-Butyl (2R,4S)-4-((5-bromothiazolo[5,4-d]thiazol-2-yl)(methyl)amino)-2-(((tert-butyldimethylsilyl)oxy)methyl)piperidine-1-carboxylate (520 mg, 0.81 mmol), dichloromethane (3 mL), and TFA (1 mL) were stirred at 0° C. for 4 h. This was added to aqueous NaHCO$_3$, and the mixture was extracted into dichloromethane. Purification by silica (10-20% MeOH in dichloromethane, then 9:1:0.1 dichloromethane/MeOH/NH$_4$OH) yielded ((2R,4S)-4-((5-bromothiazolo[5,4-d]thiazol-2-yl)(methyl)amino)piperidin-2-yl)methanol (282 mg, 96%) as an off-white solid.

$^1$H NMR (methanol-d$_4$) δ 4.38-4.45 (m, 1H), 3.74 (dd, J=11.5 Hz, 5 Hz, 1H), 3.58 (dd, J=11.5 Hz, 6.5 Hz, 1H), 3.41-3.48 (m, 1H), 3.17-3.26 (m, 1H), 3.10-3.20 (m, 1H), 3.05 (s, 3H), 1.95-2.04 (m, 3H), 1.85 (q, J=12.5 Hz, 1H); NH and OH not observed.

Step 7: ((2R,4S)-4-((5-Bromothiazolo[5,4-d]thiazol-2-yl)(methyl)amino)piperidin-2-yl)methanol (40 mg, 0.11 mmol), 4-(3-(methoxymethoxy)-4-(4,4,5,5-tetramethyl-1,3,2-dioxaborolan-2-yl)phenyl)-1-(tetrahydro-2H-pyran-2-yl)-1H-pyrazole (58 mg, 0.13 mmol), Pd(PPh$_3$)$_4$ (15 mg, 0.013 mmol), toluene (0.9 mL), and aqueous 2M K$_2$CO$_3$ (0.15 mL) were heated at 90° C. for 1 h. The mixture was partitioned between dichloromethane and H$_2$O. The organic layer was dried over MgSO$_4$, filtered, and concentrated under vacuum. Purification by silica chromatography (95:5 dichloromethane/MeOH, then 9:1:0.1 dichloromethane/MeOH/NH$_4$OH), followed by ether trituration, yielded ((2R,4S)-4-((5-(2-(methoxymethoxy)-4-(1-(tetrahydro-2H-pyran-2-yl)-1H-pyrazol-4-yl)phenyl)thiazolo[5,4-d]thiazol-2-yl)(methyl)amino)piperidin-2-yl)methanol (24 mg, 31%) as a yellow solid which was used directly into the next step.

Step 8: Crude ((2R,4S)-4-((5-(2-(methoxymethoxy)-4-(1-(tetrahydro-2H-pyran-2-yl)-1H-pyrazol-4-yl)phenyl)thiazolo[5,4-d]thiazol-2-yl)(methyl)amino)piperidin-2-yl)methanol (22 mg, 0.031 mmol), dichloromethane (0.3 mL), and TFA (0.1 mL) were stirred at 0° C. to room temperature over 15 h. The mixture was pipetted into aqueous NaHCO$_3$. The solids were filtered. The solids were purified by reverse-phase chromatography (CH$_3$CN/H$_2$O/TFA modifier) to yield 10 mg of the trifluoroacetate salt. This was dissolved in MeOH and 1M HCl in ether was added to this mixture. The volatiles were removed by a nitrogen stream. The product was triturated with ether to yield the title product (8 mg, 48%) as a yellow solid.

MS m/z 443.2 [M+H]$^+$; $^1$H NMR (methanol-d$_4$) δ: 8.47 (br s, 2H), 7.89 (d, J=8 Hz, 1H), 7.26-7.30 (m, 2H), 4.54-4.62 (m, 1H), 3.84 (dd, J=12 Hz, 3.5 Hz, 1H), 3.65 (dd, J=12 Hz, 6.5 Hz, 1H), 3.55-3.59 (m, 1H), 3.41-3.50 (m, 1H), 3.20-3.30 (m, 1H), 3.11 (s, 3H), 2.00-2.20 (m, 4H); 2NHs and 2OHs not observed.

Example 39

Preparation of Compound 80

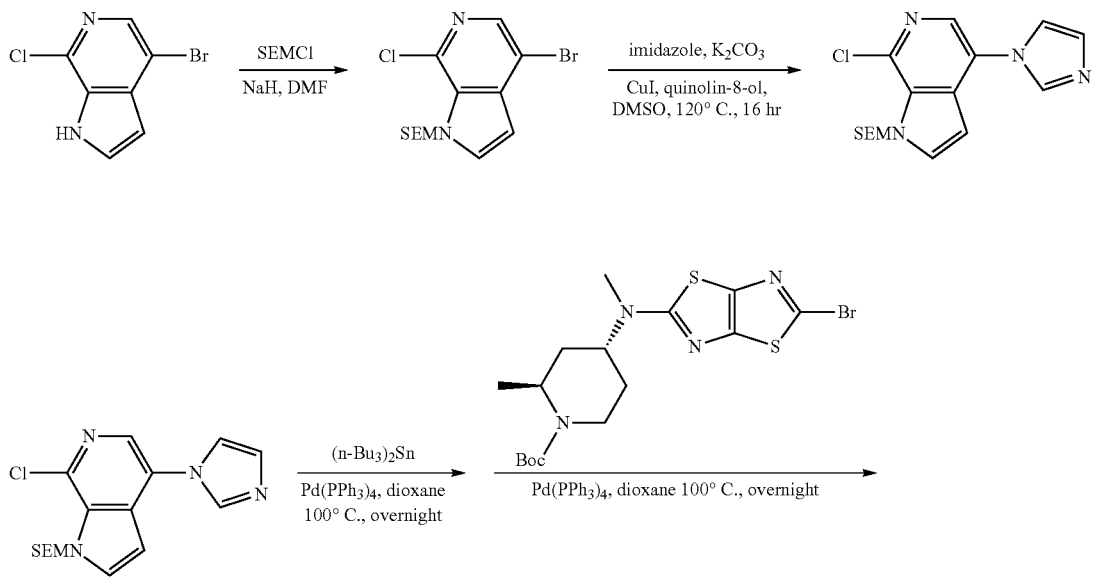

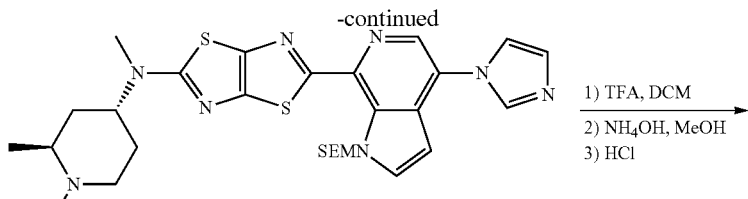

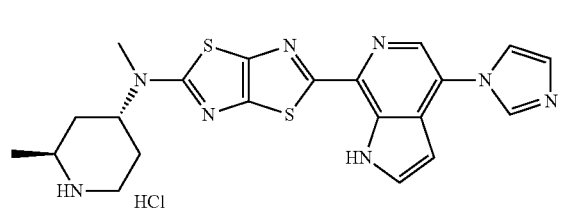

Step 1: At room temperature, 4-bromo-7-chloro-1H-pyrrolo[2,3-c]pyridine (3.00 g, 13.0 mmol) was treated with NaH (778 mg, 19.5 mmol, 60% in mineral oil) in DMF (30 mL) and stirred for 10 min., followed by the addition of 2-(chloromethoxy)ethyl-trimethyl-silane (2.98 mL, 16.8 mmol). The mixture was stirred at room temperature overnight and diluted with water, extracted with EtOAc, washed with water and brine, dried, and then concentrated. The residue was chromatographed (EtOAc in hexanes, 0-20%) to provide 2-[(4-bromo-7-chloro-pyrrolo[2,3-c]pyridin-1-yl)methoxy]ethyl-trimethyl-silane (4.02 g, 86%) as a colorless oil, which solidified on standing as white solid. LC-MS 361.3, 363.3, 365.3 [M+H]$^+$, RT 1.76 min.

Step 2: A mixture of 2-[(4-bromo-7-chloro-pyrrolo[2,3-c]pyridin-1-yl)methoxy]ethyl-trimethyl-silane (330 mg, 0.91 mmol), imidazole (60 mg, 0.88 mmol), quinolin-8-ol (13 mg, 0.090 mmol), CuI (17 mg, 0.090 mmol), and $K_2CO_3$ (400 mg, 2.89 mmol) in DMSO (20 mL) was stirred under argon at 120° C. for 16 h. After cooling to room temperature, the reaction mixture was diluted with EtOAc (50 mL), filtered through Celite and concentrated. The organic layer was washed with water and brine, dried over anhydrous $MgSO_4$, filtered, concentrated, and then purified by silica gel column chromatography (45% EtOAC in petroleum ether) to furnish 2-[(7-chloro-4-imidazol-1-yl-pyrrolo[2,3-c]pyridin-1-yl)methoxy]ethyl-trimethyl-silane (100 mg, 31%). LC-MS 348.9, 350.9 [M+H]$^+$, RT 1.65 min.

Step 3: A mixture of 2-[(7-chloro-4-imidazol-1-yl-pyrrolo[2,3-c]pyridin-1-yl)methoxy]ethyl-trimethyl-silane (84 mg, 0.24 mmol), hexabutylditin (0.25 mL, 0.48 mmol), Pd(PPh$_3$)$_4$ (23 mg, 0.020 mmol), and 1,4-dioxane (1.5 mL) was stirred at 100° C. overnight, followed by the addition of tert-butyl (2R*,4S*)-4-[(5-bromothiazolo[5,4-d]thiazol-2-yl)-methyl-amino]-2-methyl-piperidine-1-carboxylate (90 mg, 0.20 mmol), prepared based on the chemistry described in Example 1, step 5, and Pd(PPh$_3$)$_4$ (23 mg, 0.020 mmol). This was then stirred at 90° C. overnight. After the removal of the solvent, the residue was chromatographed first on a silica gel column (ethyl acetate in hexanes, 0-60%), then on a C-18 column (acetonitrile in water, 0-100%) to provide tert-butyl (2R*,4S*)-4-[[2-[4-imidazol-1-yl-1-(2-trimethylsilylethoxymethyl)pyrrolo[2,3-c]pyridin-7-yl]thiazolo[5,4-d]thiazol-5-yl]-methyl-amino]-2-methyl-piperidine-1-carboxylate which was treated with trifluoroacetic acid (0.75 mL) in dichloromethane (0.25 mL) at room temperature for 1 h and evaporated to dryness, followed by treatment with methanol (0.5 mL) and ammonium hydroxide (1.0 mL, 23%) at room temperature for 1 h. After removal of the volatiles, the residue was chromatographed on a C-18 column (acetonitrile in water, 0-100%). The fractions containing the desired product were combined and concentrated to dryness and stirred with HCl in diethyl ether (2.0 mL, 2 M)) at room temperature for 2 h. The precipitate was collected, washed with diethyl ether and dried to furnish 2-(4-imidazol-1-yl-1H-pyrrolo[2,3-c]pyridin-7-yl)-N-methyl-N-[(2R*,4S*)-2-methyl-4-piperidyl]thiazolo[5,4-d]thiazol-5-amine hydrochloride (14 mg, 14%).

LC-MS 451.6 [M+H]$^+$, RT 0.77 min; $^1$H NMR (DMSO-d$_6$) δ: 12.14-12.40 (m, 1H), 9.75 (br s, 1H), 9.40-9.62 (m, 1H), 8.99 (br d, J=12.5 Hz, 1H), 8.49 (s, 1H), 8.33 (br s, 1H), 8.05 (br s, 1H), 7.88 (br d, J=1.8 Hz, 1H), 6.79 (br s, 1H), 4.58-4.75 (m, 1H), 3.75-3.91 (m, 1H), 3.15-3.47 (m, 2H), 3.05 (s, 3H), 2.08-2.42 (m, 2H), 1.65-1.97 (m, 2H), 1.43 (br d, J=6.4 Hz, 3H).

Endogenous Huntingtin Protein Assay

Meso Scale Discovery (MSD) 96-well or 384-well plates were coated overnight at 4° C. with MW1 (expanded polyglutamine) or MAB2166 monoclonal antibody (for capture) at a concentration of 1 μg/mL in PBS (30 μL per well). Plates were then washed three times with 300 μL wash buffer (0.05% Tween-20 in PBS) and blocked (100 μL blocking buffer; 5% BSA in PBS) for 4-5 hours at room temperature with rotational shaking and then washed three times with wash buffer.

Samples (25 μL) were transferred to the antibody-coated MSD plate and incubated overnight at 4° C. After removal of the lysates, the plate was washed three times with wash buffer, and 25 μL of #5656S (Cell signaling; rabbit monoclonal) secondary antibody (diluted to 0.25 μg/mL in 0.05% Tween-20 in blocking buffer) was added to each well and incubated with shaking for 1 Hour at room temperature. Following incubation with the secondary antibody, the wells were rinsed with wash buffer after which 25 μL of goat anti-rabbit SULFO TAG secondary detection antibody (required aspect of the MSD system) (diluted to 0.25 μg/mL in 0.05% Tween-20 in blocking buffer) was added to each well and incubated with shaking for 1 hour at room temperature. After rinsing three times with wash buffer, 150 μL of read buffer T with surfactant (MSD) were added to each empty well, and the plate was imaged on a SI 6000 imager (MSD) according to manufacturers' instructions provided for 96- or 384-well plates. The resulting IC$_{50}$ values (μM) for compounds tested are shown in Table 1.

As shown in Table 1, test compounds described herein had the following IC$_{50}$ values, an IC$_{50}$ value between >3 μM and ≤9 μM is indicated by a single star (*), an IC$_{50}$ value between >1 μM and ≤3 μM is indicated by two stars (), an IC$_{50}$ value between >0.5 μM and ≤1 μM is indicated by three stars (*), an $IC_{50}$ value between >0.1 µM and ≤0.5 µM is indicated by four stars (**) and an $IC_{50}$ value of ≤0.1 µM is indicated by five stars (***).

TABLE 1

| Cpd | $IC_{50}$ |
|---|---|
| 1 | ***** |
| 2 | ***** |
| 3 | **** |
| 4 | ***** |
| 5 | ***** |
| 6 | ** |
| 7 | *** |
| 8 | ***** |
| 9 | **** |
| 10 | **** |
| 11 | ***** |
| 12 | **** |
| 13 | ***** |
| 14 | ***** |
| 15 | ***** |
| 16 | ***** |
| 17 | *** |
| 18 | **** |
| 19 | **** |
| 20 | **** |
| 21 | ** |
| 22 | ***** |
| 23 | ***** |
| 24 | ***** |
| 25 | **** |
| 26 | ***** |
| 27 | ***** |
| 28 | ***** |
| 29 | **** |
| 30 | **** |
| 31 | * |
| 32 | **** |
| 33 | ** |
| 34 | ***** |
| 35 | * |
| 36 | **** |
| 37 | ***** |
| 38 | **** |
| 39 | ***** |
| 40 | ***** |
| 41 | **** |
| 42 | ***** |
| 43 | ***** |
| 44 | ** |
| 45 | ***** |
| 46 | ***** |
| 47 | ***** |
| 48 | **** |
| 49 | ***** |
| 50 | **** |
| 51 | ***** |
| 52 | ** |
| 53 | ***** |
| 54 | ***** |
| 55 | ***** |
| 56 | ***** |
| 57 | ** |
| 58 | ***** |
| 59 | ***** |
| 60 | ** |
| 61 | ***** |
| 62 | ** |
| 63 | * |
| 64 | **** |
| 65 | **** |
| 66 | ***** |
| 67 | ***** |
| 68 | ***** |
| 69 | **** |
| 70 | ***** |
| 71 | **** |
| 72 | ***** |
| 73 | ** |
| 74 | ***** |
| 75 | ***** |
| 76 | ***** |
| 77 | ***** |
| 78 | ***** |
| 79 | ***** |
| 80 | ***** |
| 81 | ***** |
| 82 | ***** |
| 83 | ***** |
| 84 | ***** |
| 85 | ***** |
| 86 | ***** |
| 87 | ***** |
| 88 | ***** |
| 89 | ***** |
| 90 | ***** |
| 91 | ***** |
| 92 | ***** |
| 93 | ***** |
| 94 | ***** |
| 95 | ***** |
| 96 | ***** |
| 97 | ***** |
| 98 | ***** |
| 99 | *** |
| 100 | ***** |
| 101 | ** |
| 102 | ***** |
| 103 | ***** |
| 104 | *** |
| 105 | *** |
| 107 | ***** |
| 108 | ***** |
| 109 | ***** |
| 110 | ***** |
| 111 | ***** |
| 112 | ***** |
| 113 | **** |
| 114 | ***** |
| 115 | ***** |
| 116 | *** |
| 117 | ** |
| 118 | *** |
| 119 | ** |
| 120 | ***** |
| 121 | ***** |
| 122 | ***** |
| 123 | ***** |
| 124 | **** |
| 125 | ***** |
| 126 | **** |
| 127 | ** |
| 128 | ***** |
| 129 | **** |
| 130 | ** |
| 131 | **** |
| 132 | **** |
| 133 | ***** |
| 134 | ***** |
| 135 | **** |
| 136 | ***** |
| 137 | ***** |
| 138 | ***** |
| 139 | ***** |
| 140 | ***** |
| 141 | ***** |
| 142 | ***** |
| 143 | ***** |
| 144 | ***** |
| 145 | ***** |
| 146 | ***** |
| 147 | ** |
| 148 | ***** |
| 149 | ***** |
| 150 | ** |
| 151 | **** |
| 152 | ***** |

TABLE 1-continued

| Cpd | IC$_{50}$ |
|---|---|
| 153 | ***** |
| 154 | ***** |
| 155 | **** |
| 156 | ***** |
| 157 | **** |
| 158 | ***** |
| 159 | ***** |
| 160 | **** |
| 161 | **** |
| 162 | ***** |
| 163 | ***** |
| 164 | ***** |
| 165 | ***** |
| 166 | ***** |
| 167 | **** |
| 168 | ***** |
| 169 | ***** |
| 170 | **** |
| 171 | ***** |
| 172 | ***** |
| 173 | ***** |
| 174 | ***** |
| 175 | ***** |
| 176 | **** |
| 177 | ** |
| 178 | ***** |
| 179 | ***** |
| 180 | ***** |
| 181 | ***** |
| 182 | ***** |
| 183 | ***** |
| 184 | ***** |
| 185 | ***** |
| 186 | ***** |
| 187 | **** |
| 188 | ***** |
| 189 | **** |
| 190 | ***** |
| 191 | ***** |
| 192 | ***** |
| 193 | ***** |
| 194 | ***** |
| 195 | ***** |
| 196 | ***** |
| 197 | ** |
| 198 | *** |
| 199 | ***** |
| 200 | ** |
| 201 | *** |
| 202 | ***** |
| 203 | ***** |
| 204 | **** |
| 205 | ***** |
| 206 | ***** |
| 207 | ***** |
| 208 | ** |
| 209 | ***** |
| 210 | * |
| 211 | ** |
| 212 | **** |
| 213 | ***** |
| 214 | *** |
| 215 | **** |
| 216 | ***** |
| 217 | ***** |
| 218 | ***** |
| 219 | ***** |
| 220 | ***** |
| 221 | ***** |
| 222 | ***** |
| 223 | ***** |
| 224 | ***** |
| 225 | ***** |
| 226 | ***** |

Without regard to whether a document cited herein was specifically and individually indicated as being incorporated by reference, all documents referred to herein are incorporated by reference into the present application for any and all purposes to the same extent as if each individual reference was fully set forth herein.

Having now fully described the subject matter of the claims, it will be understood by those having ordinary skill in the art that the same can be performed within a wide range of equivalents without affecting the scope of the subject matter or particular aspects described herein. It is intended that the appended claims be interpreted to include all such equivalents.

What is claimed is:

1. A compound of Formula (I):

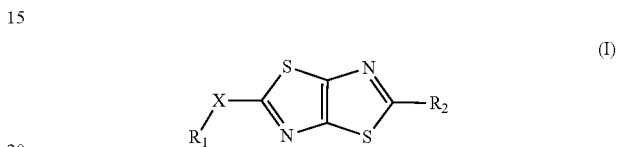

or a form thereof, wherein:
X is selected from the group consisting of N—R$_b$, O, and a bond;
R$_b$ is selected from the group consisting of hydrogen and C$_{1-6}$ alkyl;
R$_1$ is heterocyclyl,
wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, and
wherein heterocyclyl is optionally substituted where allowed by available valences with one, two, three, or four R$_3$ substituents;
R$_3$ is, in each instance, independently selected from the group consisting of cyano, halogen, hydroxy, C$_{1-6}$ alkyl, deutero-C$_{1-4}$alkyl, halo-C$_{1-6}$alkyl, C$_{1-6}$ alkoxy, halo-C$_{1-6}$ alkoxy, C$_{1-6}$alkoxy-C$_{1-6}$ alkyl, amino, C$_{1-6}$ alkyl-amino, (C$_{1-6}$ alkyl)$_2$-amino, amino-C$_{1-6}$alkyl, hydroxy-C$_{1-6}$ alkyl, and C$_{3-10}$ cycloalkyl;
R$_2$ is selected from the group consisting of phenyl and heteroaryl,
wherein heteroaryl is a 3-7 membered monocyclic or 6-10 membered bicyclic ring system having 1, 2, 3, or 4 heteroatom ring members independently selected from N, O, or S, and
wherein phenyl or heteroaryl is optionally substituted where allowed by available valences with one, two, or three R$_4$ substituents and optionally, with one additional R$_5$ substituent, or
wherein, alternatively, phenyl or heteroaryl is optionally substituted where allowed by available valences with one, two, three, or four R$_4$ substituents;
R$_4$ is, in each instance, independently selected from the group consisting of cyano, halogen, hydroxy, C$_{1-6}$ alkyl, deutero-C$_{1-4}$alkyl, halo-C$_{1-6}$alkyl, C$_{1-6}$ alkoxy, halo-C$_{1-6}$ alkoxy, C$_{1-6}$alkoxy-C$_{1-6}$ alkyl, C$_{1-6}$ alkoxy-carbonyl, amino, C$_{1-6}$alkyl-amino, (C$_{1-6}$ alkyl)$_2$-amino, amino-C$_{1-6}$alkyl, and hydroxy-C$_{1-6}$ alkyl;
R$_5$ is heteroaryl;
wherein heteroaryl is a 3-7 membered monocyclic or 6-10 membered bicyclic ring system having 1, 2, 3, or 4 heteroatom ring members independently selected from N, O, or S, and wherein, each instance of heteroaryl is optionally substituted where allowed by available valences with one, two or three $R_6$ substituents; and $R_6$ is, in each instance, independently selected from the group consisting of cyano, halogen, hydroxy, $C_{1-6}$ alkyl, deutero-$C_{1-4}$alkyl, halo-$C_{1-6}$alkyl, $C_{1-6}$ alkoxy, halo-$C_{1-6}$ alkoxy, $C_{1-6}$alkoxy-$C_{1-6}$ alkyl, $C_{1-6}$ alkoxy-carbonyl, amino, $C_{1-6}$alkyl-amino, $(C_{1-6}$ alkyl$)_2$-amino, amino-$C_{1-8}$alkyl, and hydroxy-$C_{1-6}$ alkyl;

wherein a form of the compound is selected from the group consisting of a salt, hydrate, solvate, racemate, enantiomer, diastereomer, stereoisomer, and tautomer form thereof.

2. The compound of claim 1, wherein $R_1$ is heterocyclyl selected from the group consisting of pyrrolidinyl, piperidinyl, piperazinyl, 1,2,3,6-tetrahydropyridinyl, octahydroindolizinyl, hexahydropyrrolo[3,4-c]pyrrol-(1H)-yl, 8-azabicyclo[3.2.1]octyl, 8-azabicyclo[3.2.1]oct-2-enyl, 1,6-diazaspiro[3.5]nonyl, 1,7-diazaspiro[3.5]nonyl, 2,7-diazaspiro[3.5]nonyl, and 8'-azaspiro[azetidine-3,3'-bicyclo[3.2.1]octan]-yl, wherein heterocyclyl is optionally substituted where allowed by available valences with one, two, three, or four $R_3$ substituents.

3. The compound of claim 1, wherein the form of the compound is a compound salt selected from the group consisting of hydrochloride, hydrobromide, trifluoroacetate, formate, dihydrochloride, and dihydrobromide salts.

4. A compound selected from the group consisting of:
2-{5-[methyl(2,2,6,6-tetramethylpiperidin-4-yl)amino][1,3]thiazolo[5,4-d][1,3]thiazol-2-yl}-5-(1H-pyrazol-4-yl)phenol;
5-[2,3-difluoro-4-(1H-pyrazol-4-yl)phenyl]-N-methyl-N-(2,2,6,6-tetramethylpiperidin-4-yl)[1,3]thiazolo[5,4-d][1,3]thiazol-2-amine;
5-[2,5-difluoro-4-(1H-pyrazol-4-yl)phenyl]-N-methyl-N-(2,2,6,6-tetramethylpiperidin-4-yl)[1,3]thiazolo[5,4-d][1,3]thiazol-2-amine;
5-[3,5-difluoro-4-(1H-pyrazol-4-yl)phenyl]-N-methyl-N-(2,2,6,6-tetramethylpiperidin-4-yl)[1,3]thiazolo[5,4-d][1,3]thiazol-2-amine;
2-[5-(piperazin-1-yl)[1,3]thiazolo[5,4-d][1,3]thiazol-2-yl]-5-(1H-pyrazol-4-yl)phenol;
2-methyl-5-[5-(piperazin-1-yl)[1,3]thiazolo[5,4-d][1,3]thiazol-2-yl]-2H-indazole-7-carbonitrile;
2-methyl-6-[5-(piperidin-4-yl)[1,3]thiazolo[5,4-d][1,3]thiazol-2-yl]imidazo[1,2-a]pyridine-8-carbonitrile;
7-fluoro-2-methyl-5-[5-(piperidin-4-yl)[1,3]thiazolo[5,4-d][1,3]thiazol-2-yl]-2H-indazole;
2,8-dimethyl-6-[5-(piperidin-4-yl)[1,3]thiazolo[5,4-d][1,3]thiazol-2-yl]imidazo[1,2-b]pyridazine;
2-{5-[(3-exo)-8-azabicyclo[3.2.1]oct-3-ylamino][1,3]thiazolo[5,4-d][1,3]thiazol-2-yl}-5-(1H-pyrazol-4-yl)phenol;
2-{5-[methyl(piperidin-4-yl)amino][1,3]thiazolo[5,4-d][1,3]thiazol-2-yl}-5-(1H-pyrazol-4-yl)phenol;
2-methyl-5-[5-(piperidin-4-yl)[1,3]thiazolo[5,4-d][1,3]thiazol-2-yl]-2H-indazole-7-carbonitrile;
2,7-dimethyl-5-[5-(piperidin-4-yl)[1,3]thiazolo[5,4-d][1,3]thiazol-2-yl]-2H-indazole;
5-[2,5-difluoro-4-(1H-pyrazol-4-yl)phenyl]-N-methyl-N-(piperidin-4-yl)[1,3]thiazolo[5,4-d][1,3]thiazol-2-amine;
5-[3,5-difluoro-4-(1H-pyrazol-4-yl)phenyl]-N-methyl-N-(piperidin-4-yl)[1,3]thiazolo[5,4-d][1,3]thiazol-2-amine;
2-[5-(piperidin-4-ylamino)[1,3]thiazolo[5,4-d][1,3]thiazol-2-yl]-5-(1H-pyrazol-4-yl)phenol;
2-{5-[(1-methylpiperidin-4-yl)amino][1,3]thiazolo[5,4-d][1,3]thiazol-2-yl}-5-(1H-pyrazol-4-yl)phenol;
2-{5-[methyl(1-methylpiperidin-4-yl)amino][1,3]thiazolo[5,4-d][1,3]thiazol-2-yl}-5-(1H-pyrazol-4-yl)phenol;
2-methyl-5-[5-(piperidin-4-yl)[1,3]thiazolo[5,4-d][1,3]thiazol-2-yl]-2H-indazole;
7-methoxy-2-methyl-5-[5-(piperidin-4-yl)[1,3]thiazolo[5,4-d][1,3]thiazol-2-yl]-2H-indazole;
2-(5-{[(2R,6S)-2,6-dimethylpiperidin-4-yl](methyl)amino}[1,3]thiazolo[5,4-d][1,3]thiazol-2-yl)-5-(1H-pyrazol-4-yl)phenol;
4-(3-hydroxy-4-{5-[methyl(piperidin-4-yl)amino][1,3]thiazolo[5,4-d][1,3]thiazol-2-yl}phenyl)pyridin-2-ol;
4-(3-hydroxy 4-{5-[methyl(piperidin-4-yl)amino][1,3]thiazolo[5,4-d][1,3]thiazol-2-yl}phenyl)-1-methylpyridin-2(1H)-one;
5-(1H-pyrazol-4-yl)-2-{5-[(2,2,6,6-tetramethylpiperidin-4-yl)oxy][1,3]thiazolo[5,4-d][1,3]thiazol-2-yl}phenol;
4-(3-hydroxy-4-{5-[(2,2,6,6-tetramethylpiperidin-4-yl)oxy][1,3]thiazolo[5,4-d][1,3]thiazol-2-yl}phenyl)-1-methylpyridin-2(1H)-one;
2-{5-[methyl(piperidin-4-yl)amino][1,3]thiazolo[5,4-d][1,3]thiazol-2-yl}-5-(1-($^2$H$_3$)methyl-1H-pyrazol-4-yl)phenol;
2-{5-[methyl(piperidin-4-yl)amino][1,3]thiazolo[5,4-d][1,3]thiazol-2-yl}-5-(1-methyl-1H-pyrazol-4-yl)phenol;
6,8-dimethyl-2-[5-(1,2,3,6-tetrahydropyridin-4-yl))[1,3]thiazolo[5,4-d][1,3]thiazol-2-yl]imidazo[1,2-a]pyrazine;
2-{5-[methyl(2,2,6,6-tetrahydropyridin-4-yl)amino][1,3]thiazolo[5,4-d][1,3]thiazol-2-yl}-5-(1H-pyrazol-4-yl)pyridin-3-ol;
5-(5-fluoro-1H-pyrazol-4-yl)-2-{5-[methyl(2,2,6,6-tetramethylpiperidin-4-yl)amino][1,3]thiazolo[5,4-d][1,3]thiazol-2-yl}phenol;
6,8-dimethyl-2-[5-(piperidin-4-yl)[1,3]thiazolo[5,4-d][1,3]thiazol-2-yl]imidazo[1,2-a]pyrazine;
5-(5-fluoro-1-methyl-1H-pyrazol-4-yl)-2-{5-[(2,2,6,6-tetramethylpiperidin-4-yl)oxy][1,3]thiazolo[5,4-d][1,3]thiazol-2-yl}phenol;
4-(3-hydroxy-4-{5-[methyl(2,2,6,6-tetramethylpiperidin-4-yl)amino][1,3]thiazolo[5,4-d][1,3]thiazol-2-yl}phenyl)-1-methylpyridin-2(1H)-one;
2-{5-[methyl(piperidin-4-yl)amino][1,3]thiazolo[5,4-d][1,3]thiazol-2-yl}-5-(1H-pyrazol-4-yl)pyridin-3-ol;
5-(5-fluoro-1-methyl-1H-pyrazol-4-yl)-2-{5-[methyl(2,2,6,6-tetramethylpiperidin-4-yl)amino][1,3]thiazolo[5,4-d][1,3]thiazol-2-yl}phenol;
5-[1-($^2$H$_3$)methyl-1H-pyrazol-4-yl]-2-{5-[methyl(2,2,6,6-tetramethylpiperidin-4-yl)amino][1,3]thiazolo[5,4-d][1,3]thiazol-2-yl}pyridin-3-ol;
5-(1-ethyl-1H-pyrazol-4-yl)-2-{5-[methyl(2,2,6,6-tetramethylpiperidin-4-yl)amino][1,3]thiazolo[5,4-d][1,3]thiazol-2-yl}pyridin-3-ol;
2-{5-[methyl(piperidin-4-yl)amino][1,3]thiazolo[5,4-d][1,3]thiazol-2-yl}-5-[1-($^2$H$_3$)methyl-1H-pyrazol-4-yl]pyridin-3-ol;
5-(1-ethyl-1H-pyrazol-4-yl)-2-{5-[methyl(piperidin-4-yl)amino][1,3]thiazolo[5,4-d][1,3]thiazol-2-yl}pyridin-3-ol;
5-(5-fluoro-1H-pyrazol-4-yl)-2-{5-[methyl(piperidin-4-yl)amino][1,3]thiazolo[5,4-d][1,3]thiazol-2-yl}pyridin-3-ol;
2-(5-{methyl[(3S)-pyrrolidin-3-yl]amino}[1,3]thiazolo[5,4-d][1,3]thiazol-2-yl)-5-(1H-pyrazol-4-yl)phenol;

2-(5-{methyl[(3R)-pyrrolidin-3-yl]amino}[1,3]thiazolo [5,4-d][1,3]thiazol-2-yl)-5-(1H-pyrazol-4-yl)phenol;
2-(5-{methyl[(3R)-pyrrolidin-3-yl]amino}[1,3]thiazolo [5,4-d][1,3]thiazol-2-yl)-5-(1H-pyrazol-4-yl)pyridin-3-ol;
5-bromo-2-{5-[methyl(piperidin-4-yl)amino][1,3]thiazolo[5,4-d][1,3]thiazol-2-yl}pyridin-3-ol;
2-{5-[methyl(1-methylpiperidin-4-yl)amino][1,3]thiazolo[5,4-d][1,3]thiazol-2-yl}-5-[1-($^{2}H_3$)methyl-1H-pyrazol-4-yl]phenol;
2-{5-[(1-ethylpiperidin-4-yl)(methyl)amino][1,3]thiazolo[5,4-d][1,3]thiazol-2-yl}-5-(1-methyl-1H-pyrazol-4-yl)phenol;
5-(1H-imidazol-1-yl)-2-{5-[methyl(piperidin-4-yl) amino][1,3]thiazolo[5,4-d][1,3]thiazol-2-yl}pyridin-3-ol;
2-{5-[ethyl(piperidin-4-yl)amino][1,3]thiazolo[5,4-d][1, 3]thiazol-2-yl}-5-(1H-pyrazol-4-yl)pyridin-3-ol;
5-(4-fluoropyrazol-1-yl)-2-[5-[methyl(4-piperidyl) amino]thiazolo[5,4-d]thiazol-2-yl]pyridin-3-ol;
5-(4-methylpyrazol-1-yl)-2-[5-[methyl(4-piperidyl) amino]thiazolo[5,4-d]thiazol-2-yl]pyridin-3-ol;
5-(thiazol-5-yl)-2-{5-[methyl(piperidin-4-yl)amino][1,3] thiazolo[5,4-d][1,3]thiazol-2-yl}pyridin-3-ol;
N-[(1R,3s,5S)-1,5-dimethyl-8-azabicyclo[3.2.1]octan-3-yl]-5-[5-(6-methoxypyrimidin-4-yl)pyrazin-2-yl]-N-methyl[1,3]thiazolo[5,4-d][1,3]thiazol-2-amine;
5-[5-(1H-imidazol-1-yl)pyrazin-2-yl]-N-methyl-N-[(2S,4R)-2-methylpiperidin-4-yl][1,3]thiazolo[5,4-d][1,3]thiazol-2-amine;
N-[(1R,3s,5S)-1,5-dimethyl-8-azabicyclo[3.2.1]octan-3-yl]-N-methyl-5-[5-(2-methyl-1H-imidazol-1-yl)pyrazin-2-yl][1,3]thiazolo[5,4-d][1,3]thiazol-2-amine;
7-(5-{1[(2R,4S)-2-methylpiperidin-4-yl]oxy}[1,3]thiazolo[5,4-d][1,3]thiazol-2-yl)-4-(1H-pyrazol-4-yl)-1H-benzimidazole;
N-[(1R,3s,5S)-1,5-dimethyl-8-azabicyclo[3.2.1]octan-3-yl]-5-[5-(2-methoxypyridin-4-yl)pyrazin-2-yl]-N-methyl[1,3]thiazolo[5,4-d][1,3]thiazol-2-amine;
N-[(1R,3s,5S)-1,5-dimethyl-8-azabicyclo[3.2.1]octan-3-yl]-N-methyl-5-[5-(1H-1,2,4-triazol-1-yl)pyrazin-2-yl][1,3]thiazolo[5,4-d][1,3]thiazol-2-amine;
N-methyl-N-[(2S,4R)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine;
N-methyl-N-[(2S,4R)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine;
N-[(1R,3s,5S)-1,5-dimethyl-8-azabicyclo[3.2.1]octan-3-yl]-5-[5-(3,5-dimethyl-1H-pyrazol-4-yl)pyrazin-2-yl]-N-methyl[1,3]thiazolo[5,4-d][1,3]thiazol-2-amine;
7-(5-{1[(2R,4S)-2-methylpiperidin-4-yl]oxy}[1,3]thiazolo[5,4-d][1,3]thiazol-2-yl)-4-(1H-pyrazol-4-yl)-1H-pyrazolo[3,4-c]pyridine;
N-methyl-N-[(2S,4R)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine;
7-(5-{1[(2R,4S)-2-methylpiperidin-4-yl]oxy}[1,3]thiazolo[5,4-d][1,3]thiazol-2-yl)-4-(1H-pyrazol-4-yl)-1H-pyrrolo[2,3-c]pyridine;
7-{5-[(2,2-dimethylpiperidin-4-yl)oxy][1,3]thiazolo[5,4-d][1,3]thiazol-2-yl}-4-(1H-pyrazol-4-yl)-1H-pyrrolo[2,3-c]pyridine;
7-(5-{[(2R,4S)-2-methylpiperidin-4-yl]oxy}[1,3]thiazolo[5,4-d][1,3]thiazol-2-yl)-4-(1H-pyrazol-4-yl)-1H-indazole;
N-[(1R,3s,5S)-1,5-dimethyl-8-azabicyclo[3.2.1]octan-3-yl]-N-methyl-5-[6-(1H-pyrazol-4-yl)-1,2,4-triazin-3-yl][1,3]thiazolo[5,4-d][1,3]thiazol-2-amine;
5-[4-(1H-imidazol-1-yl)-1H-pyrrolo[2,3-c]pyridin-7-yl]-N-methyl-N-[(2S,4R)-2-methylpiperidin-4-yl][1,3]thiazolo[5,4-d][1,3]thiazol-2-amine;
7-(5-{[(2S,4R)-2-methylpiperidin-4-yl]oxy}[1,3]thiazolo[5,4-d][1,3]thiazol-2-yl)-4-(2-methyl-2H-tetrazol-5-yl)-1H-pyrrolo[2,3-c]pyridine;
7-(5-{[(2R,4S)-2-methylpiperidin-4-yl]oxy}[1,3]thiazolo[5,4-d][1,3]thiazol-2-yl)-4-(1H-pyrazol-4-yl)-1H-indole;
4-(5-{[(2S,4S)-2-methylpiperidin-4-yl]oxy}[1,3]thiazolo[5,4-d][1,3]thiazol-2-yl)-7-(1H-pyrazol-4-yl)-3H-imidazo[4,5-c]pyridine;
7-(5-{[(2S,4R)-1,2-dimethylpiperidin-4-yl]oxy}[1,3]thiazolo[5,4-d][1,3]thiazol-2-yl)-4-(1H-pyrazol-4-yl)-1H-pyrrolo[2,3-c]pyridine;
N-methyl-N-[(2R,4S)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine;
N-[(1R,3s,5S)-1,5-dimethyl-8-azabicyclo[3.2.1]octan-3-yl]-N-methyl-5-[5-(5-methyl-1H-pyrazol-4-yl)pyrazin-2-yl][1,3]thiazolo[5,4-d][1,3]thiazol-2-amine;
N-methyl-N-[(2R,4S)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine;
N-[(1R,3s,5S)-1,5-dimethyl-8-azabicyclo[3.2.1]octan-3-yl]-N-methyl-5-[5-(4-methyl-1H-imidazol-1-yl)pyrazin-2-yl][1,3]thiazolo[5,4-d][1,3]thiazol-2-amine;
N-[(1R,3s,5S)-1,5-dimethyl-8-azabicyclo[3.2.1]octan-3-yl]-N-methyl-5-[5-(1-methyl-1H-pyrazol-4-yl)pyrazin-2-yl][1,3]thiazolo[5,4-d][1,3]thiazol-2-amine;
5-[4-(1-ethyl-1H-pyrazol-4-yl)-1H-pyrrolo[2,3-c]pyridin-7-yl]-N-methyl-N-[(2R,4S)-2-methylpiperidin-4-yl][1,3]thiazolo[5,4-d][1,3]thiazol-2-amine;
N-methyl-N-[(2R,4S)-2-methylpiperidin-4-yl]-5-[4-(1-methyl-1H-pyrazol-4-yl)-1H-pyrrolo[2,3-c]pyridin-7-yl][1,3]thiazolo[5,4-d][1,3]thiazol-2-amine;
4-[5-(5-{[(1R,3s,5S)-1,5-dimethyl-8-azabicyclo[3.2.1]octan-3-yl](methyl)amino}[1,3]thiazolo[5,4-d][1,3]thiazol-2-yl)pyrazin-2-yl]-1-methylpyridin-2(1H)-one;
N-methyl-N-[(2R,4S)-2-methylpiperidin-4-yl]-5-[5-(1H-pyrazol-4-yl)pyrazin-2-yl][1,3]thiazolo[5,4-d][1,3]thiazol-2-amine;
N-methyl-5-[5-(1-methyl-1H-pyrazol-4-yl)pyrazin-2-yl]-N-(2,2,6,6-tetramethylpiperidin-4-yl)[1,3]thiazolo[5,4-d][1,3]thiazol-2-amine;
N-methyl-N-[(2S,4S)-2-methylpiperidin-4-yl]-5-[4-(1-methyl-1H-pyrazol-4-yl)-1H-pyrrolo[2,3-c]pyridin-7-yl][1,3]thiazolo[5,4-d][1,3]thiazol-2-amine;
7-[5-(6-methyl-1,6-diazaspiro[3.5]nonan-1-yl)[1,3]thiazolo[5,4-d][1,3]thiazol-2-yl]-4-(1H-pyrazol-4-yl)-1H-pyrrolo[2,3-c]pyridine;
N-methyl-N-[(2S,4S)-2-methylpiperidin-4-yl]-5-[4-(1H-pyrazol-4-yl)-1H-indol-7-yl][1,3]thiazolo[5,4-d][1,3]thiazol-2-amine;
N-methyl-N-[(2S,4S)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine;
N-methyl-N-[(2S,4S)-2-methylpiperidin-4-yl]-5-[5-(1H-pyrazol-4-yl)pyrazin-2-yl][1,3]thiazolo[5,4-d][1,3]thiazol-2-amine;
N-methyl-5-[6-(1H-pyrazol-4-yl)-1,2,4-triazin-3-yl]-N-(2,2,6,6-tetramethylpiperidin-4-yl)[1,3]thiazolo[5,4-d][1,3]thiazol-2-amine;

N-methyl-N-(piperidin-4-yl)-5-[5-(1H-pyrazol-4-yl)imidazo[1,2-a]pyrazin-8-yl][1,3]thiazolo[5,4-d][1,3]thiazol-2-amine;

5-[5-(1H-imidazol-1-yl)pyrazin-2-yl]-N-methyl-N-(2,2,6,6-tetramethylpiperidin-4-yl)[1,3]thiazolo[5,4-d][1,3]thiazol-2-amine;

N-[(1R,3s,5S)-1,5-dimethyl-8-azabicyclo[3.2.1]octan-3-yl]-5-[5-(1H-imidazol-1-yl)pyrazin-2-yl]-N-methyl[1,3]thiazolo[5,4-d][1,3]thiazol-2-amine;

N-[(1R,3s,5S)-1,5-dimethyl-8-azabicyclo[3.2.1]octan-3-yl]-N-methyl-5-[5-(1H-pyrazol-1-yl)pyrazin-2-yl][1,3]thiazolo[5,4-d][1,3]thiazol-2-amine;

N-methyl-5-[5-(1H-pyrazol-1-yl)pyrazin-2-yl]-N-(2,2,6,6-tetramethylpiperidin-4-yl)[1,3]thiazolo[5,4-d][1,3]thiazol-2-amine;

N-methyl-5-[4-(1H-pyrazol-4-yl)-1H-benzimidazol-7-yl]-N-(2,2,6,6-tetramethylpiperidin-4-yl)[1,3]thiazolo[5,4-d][1,3]thiazol-2-amine;

N-methyl-5-[4-(1H-pyrazol-4-yl)-1H-indazol-7-yl]-N-(2,2,6,6-tetramethylpiperidin-4-yl)[1,3]thiazolo[5,4-d][1,3]thiazol-2-amine;

N-(1,2-dimethylpiperidin-4-yl)-N-methyl-5-[4-(1H-pyrazol-4-yl)-1H-indazol-7-yl][1,3]thiazolo[5,4-d][1,3]thiazol-2-amine;

7-(5-{[(2S,4R)-2-methylpiperidin-4-yl]oxy}[1,3]thiazolo[5,4-d][1,3]thiazol-2-yl)-4-(1H-pyrazol-4-yl)-1H-pyrrolo[2,3-c]pyridine;

N-[(1R,3s,5S)-1,5-dimethyl-8-azabicyclo[3.2.1]octan-3-yl]-N-methyl-5-[4-(1H-pyrazol-4-yl)-1H-indazol-7-yl][1,3]thiazolo[5,4-d][1,3]thiazol-2-amine;

5-(4-bromo-1H-indazol-7-yl)-N-[(1R,3s,5S)-1,5-dimethyl-8-azabicyclo[3.2.1]octan-3-yl]-N-methyl[1,3]thiazolo[5,4-d][1,3]thiazol-2-amine;

N-(1,2-dimethylpiperidin-4-yl)-N-methyl-5-[4-(1H-pyrazol-4-yl)-1H-benzimidazol-7-yl][1,3]thiazolo[5,4-d][1,3]thiazol-2-amine;

N-methyl-5-[1-methyl-4-(1H-pyrazol-4-yl)-1H-pyrrolo[2,3-c]pyridin-7-yl]-N-(piperidin-4-yl)[1,3]thiazolo[5,4-d][1,3]thiazol-2-amine;

N-methyl-5-[5-(1H-pyrazol-4-yl)pyrazin-2-yl]-N-[(1R,3s,5S)-1,5,8-trimethyl-8-azabicyclo[3.2.1]octan-3-yl][1,3]thiazolo[5,4-d][1,3]thiazol-2-amine;

N-(1,2-dimethylpiperidin-4-yl)-N-methyl-5-[7-(1H-pyrazol-4-yl)-1H-imidazo[4,5-c]pyridin-4-yl][1,3]thiazolo[5,4-d][1,3]thiazol-2-amine;

5-(5-bromoimidazo[1,2-c]pyrimidin-8-yl)-N-methyl-N-(piperidin-4-yl)[1,3]thiazolo[5,4-d][1,3]thiazol-2-amine 5-(5-bromoimidazo[1,2-a]pyrazin-8-yl)-N-methyl-N-(piperidin-4-yl)[1,3]thiazolo[5,4-d][1,3]thiazol-2-amine;

N-(1,2-dimethylpiperidin-4-yl)-N-methyl-5-[4-(2H-1,2,3-triazol-2-yl)-1H-indol-7-yl][1,3]thiazolo[5,4-d][1,3]thiazol-2-amine;

5-(4-chloro-1H-indol-7-yl)-N-(1,2-dimethylpiperidin-4-yl)-N-methyl[1,3]thiazolo[5,4-d][1,3]thiazol-2-amine;

7-(5-{[(2S,4S)-2-methylpiperidin-4-yl]oxy}[1,3]thiazolo[5,4-d][1,3]thiazol-2-yl)-4-(1H-pyrazol-4-yl)-1H-pyrrolo[2,3-c]pyridine;

N-methyl-N-[1-(propan-2-yl)piperidin-4-yl]-5-[4-(1H-pyrazol-4-yl)-1H-pyrrolo[2,3-c]pyridin-7-yl][1,3]thiazolo[5,4-d][1,3]thiazol-2-amine;

N-(1-ethylpiperidin-4-yl)-N-methyl-5-[4-(1H-pyrazol-4-yl)-1H-pyrrolo[2,3-c]pyridin-7-yl][1,3]thiazolo[5,4-d][1,3]thiazol-2-amine;

N-methyl-N-{5-[4-(1H-pyrazol-4-yl)-1H-pyrrolo[2,3-c]pyridin-7-yl][1,3]thiazolo[5,4-d][1,3]thiazol-2-yl}octahydroindolizin-7-amine;

5-(4-bromo-1H-pyrrolo[2,3-c]pyridin-7-yl)-N-(1,2-dimethylpiperidin-4-yl)-N-methyl[1,3]thiazolo[5,4-d][1,3]thiazol-2-amine;

N-(1,2-dimethylpiperidin-4-yl)-N-methyl-5-[4-(1H-pyrazol-4-yl)-1H-indol-7-yl][1,3]thiazolo[5,4-d][1,3]thiazol-2-amine;

N-(1,2-dimethylpiperidin-4-yl)-N-methyl-5-[5-(1H-pyrazol-4-yl)pyridin-2-yl][1,3]thiazolo[5,4-d][1,3]thiazol-2-amine;

N-(1,2-dimethylpiperidin-4-yl)-N-methyl-5-[6-(1H-pyrazol-4-yl)pyridin-3-yl][1,3]thiazolo[5,4-d][1,3]thiazol-2-amine;

N-methyl-5-[4-(1H-pyrazol-4-yl)-1H-indol-7-yl]-N-(2,2,6,6-tetramethylpiperidin-4-yl)[1,3]thiazolo[5,4-d][1,3]thiazol-2-amine;

N-(1,2-dimethylpiperidin-4-yl)-N-methyl-5-[5-(1H-pyrazol-4-yl)pyrimidin-2-yl][1,3]thiazolo[5,4-d][1,3]thiazol-2-amine;

N-(1,2-dimethylpiperidin-4-yl)-N-methyl-5-[2-(1H-pyrazol-4-yl)pyrimidin-5-yl][1,3]thiazolo[5,4-d][1,3]thiazol-2-amine;

3-{5-[(1,2-dimethylpiperidin-4-yl)(methyl)amino][1,3]thiazolo[5,4-d][1,3]thiazol-2-yl}-6-(1H-pyrazol-4-yl)pyrimidin-4(3H)-one;

N-(1,2-dimethylpiperidin-4-yl)-N-methyl-5-[5-(1H-pyrazol-4-yl)pyrazin-2-yl][1,3]thiazolo[5,4-d][1,3]thiazol-2-amine;

N-methyl-5-[5-(1H-pyrazol-4-yl)pyridin-2-yl]-N-(2,2,6,6-tetramethylpiperidin-4-yl)[1,3]thiazolo[5,4-d][1,3]thiazol-2-amine;

7-[5-(1,6-diazaspiro[3.5]nonan-1-yl) [1,3]thiazolo[5,4-d][1,3]thiazol-2-yl]-4-(1H-pyrazol-4-yl)-1H-pyrrolo[2,3-c]pyridine;

N-methyl-5-[6-(1H-pyrazol-4-yl)pyridin-3-yl]-N-(2,2,6,6-tetramethylpiperidin-4-yl)[1,3]thiazolo[5,4-d][1,3]thiazol-2-amine;

N-methyl-5-[7-(1H-pyrazol-4-yl)-1H-imidazo[4,5-c]pyridin-4-yl]-N-(2,2,6,6-tetramethylpiperidin-4-yl)[1,3]thiazolo[5,4-d][1,3]thiazol-2-amine;

N-methyl-5-[2-(1H-pyrazol-4-yl)pyrimidin-5-yl]-N-(2,2,6,6-tetramethylpiperidin-4-yl)[1,3]thiazolo[5,4-d][1,3]thiazol-2-amine;

7-[5-(7-methyl-2,7-diazaspiro[3.5]nonan-2-yl) [1,3]thiazolo[5,4-d][1,3]thiazol-2-yl]-4-(1H-pyrazol-4-yl)-1H-pyrrolo[2,3-c]pyridine;

N-methyl-N-(piperidin-4-yl)-5-[4-(1H-pyrazol-4-yl)-1H-pyrrolo[2,3-c]pyridin-7-yl][1,3]thiazolo[5,4-d][1,3]thiazol-2-amine;

3-{5-[methyl(2,2,6,6-tetramethylpiperidin-4-yl)amino][1,3]thiazolo[5,4-d][1,3]thiazol-2-yl}-6-(1H-pyrazol-4-yl)pyrimidin-4(3H)-one;

N-[(1R,3s,5S)-8-azabicyclo[3.2.1]octan-3-yl]-N-methyl-5-[4-(1H-pyrazol-4-yl)phenyl][1,3]thiazolo[5,4-d][1,3]thiazol-2-amine;

N-[(1R,3s,5S)-1,5-dimethyl-8-azabicyclo[3.2.1]octan-3-yl]-N-methyl-5-[5-(1H-pyrazol-4-yl)pyrazin-2-yl][1,3]thiazolo[5,4-d][1,3]thiazol-2-amine;

2-[5-(1H-pyrazol-4-yl)pyrazin-2-yl]-5-[(2,2,6,6-tetramethylpiperidin-4-yl)oxy][1,3]thiazolo[5,4-d][1,3]thiazole;

3-(5-{[(1R,3s,5S)-1,5-dimethyl-8-azabicyclo[3.2.1]octan-3-yl](methyl)amino}[1,3]thiazolo[5,4-d][1,3]thiazol-2-yl)-6-(1H-pyrazol-4-yl)pyrimidin-4(3H)-one;

2-{5-[methyl(octahydroindolizin-7-yl)amino][1,3]thiazolo[5,4-d][1,3]thiazol-2-yl}-5-(1H-pyrazol-4-yl)pyridin-3-ol;

1-(5-{1[(1R,3s,5S)-1,5-dimethyl-8-azabicyclo[3.2.1]octan-3-yl](methyl)amino}[1,3]thiazolo[5,4-d][1,3]thiazol-2-yl)-4-(1H-pyrazol-4-yl)pyridin-2(1H)-one;

2-{5-[3-(tert-butylamino)pyrrolidin-1-yl][1,3]thiazolo[5,4-d][1,3]thiazol-2-yl}-5-(1H-pyrazol-4-yl)phenol;

1-(5-{1[(1R,3s,5S)-1,5-dimethyl-8-azabicyclo[3.2.1]octan-3-yl](methyl)amino}[1,3]thiazolo[5,4-d][1,3]thiazol-2-yl)-4-(4-fluoro-1H-pyrazol-1-yl)pyridin-2(1H)-one;

1-(5-{1[(1R,3s,5S)-8-azabicyclo[3.2.1]octan-3-yl](methyl)amino}[1,3]thiazolo[5,4-d][1,3]thiazol-2-yl)-4-(4-fluoro-1H-pyrazol-1-yl)pyridin-2(1H)-one;

N-tert-butyl-1-{5-[5-(1H-pyrazol-4-yl)pyrimidin-2-yl][1,3]thiazolo[5,4-d][1,3]thiazol-2-yl}pyrrolidin-3-amine;

1-{5-[3-(tert-butylamino)pyrrolidin-1-yl][1,3]thiazolo[5,4-d][1,3]thiazol-2-yl}-4-(1H-pyrazol-4-yl)pyridin-2(1H)-one;

N-(1,2-dimethylpiperidin-4-yl)-N-methyl-5-[4-(1H-pyrazol-4-yl)-1H-pyrrolo[2,3-c]pyridin-7-yl][1,3]thiazolo[5,4-d][1,3]thiazol-2-amine;

3-(5-{methyl[(1R,3s,5S)-8-methyl-8-azabicyclo[3.2.1]octan-3-yl]amino}[1,3]thiazolo[5,4-d][1,3]thiazol-2-yl)-6-(1H-pyrazol-4-yl)pyrimidin-4(3H)-one;

N-[(1R,3s,5S)-1,5-dimethyl-8-azabicyclo[3.2.1]octan-3-yl]-N-methyl-5-[4-(1H-pyrazol-4-yl)-1H-pyrrolo[2,3-c]pyridin-7-yl][1,3]thiazolo[5,4-d][1,3]thiazol-2-amine;

1-(5-{methyl[(3R)-piperidin-3-yl]amino}[1,3]thiazolo[5,4-d][1,3]thiazol-2-yl)-4-(1H-pyrazol-4-yl)pyridin-2(1H)-one;

4-(1H-pyrazol-4-yl)-1-{5-[(2,2,6,6-tetramethylpiperidin-4-yl)oxy][1,3]thiazolo[5,4-d][1,3]thiazol-2-yl}pyridin-2(1H)-one;

1-{5-[(1,2-dimethylpiperidin-4-yl)(methyl)amino][1,3]thiazolo[5,4-d][1,3]thiazol-2-yl}-1H-pyrrolo[2,3-b]pyridin-6-ol;

N-[(1R,3s,5S)-8-azabicyclo[3.2.1]octan-3-yl]-5-[2,5-difluoro-4-(1H-pyrazol-4-yl)phenyl]-N-methyl[1,3]thiazolo[5,4-d][1,3]thiazol-2-amine;

N-methyl-5-[4-(1H-pyrazol-4-yl)-1H-pyrrolo[2,3-c]pyridin-7-yl]-N-(2,2,6,6-tetramethylpiperidin-4-yl)[1,3]thiazolo[5,4-d][1,3]thiazol-2-amine;

N-[(1R,3s,5S)-8-azabicyclo[3.2.1]octan-3-yl]-N-methyl-5-(1H-pyrrolo[2,3-c]pyridin-7-yl)[1,3]thiazolo[5,4-d][1,3]thiazol-2-amine N-methyl-N-[(3S)-piperidin-3-yl]-5-[5-(1H-pyrazol-4-yl)pyrimidin-2-yl][1,3]thiazolo[5,4-d][1,3]thiazol-2-amine;

N-methyl-5-[5-(1H-pyrazol-4-yl)pyrimidin-2-yl]-N-(2,2,6,6-tetramethylpiperidin-4-yl)[1,3]thiazolo[5,4-d][1,3]thiazol-2-amine;

N-methyl-5-[5-(1H-pyrazol-4-yl)pyrazin-2-yl]-N-(2,2,6,6-tetramethylpiperidin-4-yl)[1,3]thiazolo[5,4-d][1,3]thiazol-2-amine;

N-[(1R,3s,5S)-8-azabicyclo[3.2.1]octan-3-yl]-N-methyl-5-[5-(1H-pyrazol-4-yl)pyrazin-2-yl][1,3]thiazolo[5,4-d][1,3]thiazol-2-amine;

1-(5-{methyl[(1R,3s,5S)-8-propyl-8-azabicyclo[3.2.1]octan-3-yl]amino}[1,3]thiazolo[5,4-d][1,3]thiazol-2-yl)-4-(1H-pyrazol-4-yl)pyridin-2(1H)-one;

1-(5-{[(1R,3s,5S)-8-ethyl-8-azabicyclo[3.2.1]octan-3-yl](methyl)amino}[1,3]thiazolo[5,4-d][1,3]thiazol-2-yl)-4-(1H-pyrazol-4-yl)pyridin-2(1H)-one;

N-methyl-5-[6-(1H-pyrazol-4-yl)pyridazin-3-yl]-N-(2,2,6,6-tetramethylpiperidin-4-yl)[1,3]thiazolo[5,4-d][1,3]thiazol-2-amine;

N-[(1R,3s,5S)-8-azabicyclo[3.2.1]octan-3-yl]-N-methyl-5-[6-(1H-pyrazol-4-yl)pyridazin-3-yl][1,3]thiazolo[5,4-d][1,3]thiazol-2-amine;

1-(5-{methyl[(3S)-piperidin-3-yl]amino}[1,3]thiazolo[5,4-d][1,3]thiazol-2-yl)-4-(1H-pyrazol-4-yl)pyridin-2(11H)-one;

N-[(1R,3s,5S)-8-azabicyclo[3.2.1]octan-3-yl]-N-methyl-5-[4-(1H-pyrazol-4-yl)-1H-imidazol-1-yl][1,3]thiazolo[5,4-d][1,3]thiazol-2-amine;

1-(5-{1[(1R,3s,5S)-8-azabicyclo[3.2.1]octan-3-yl](methyl)amino}[1,3]thiazolo[5,4-d][1,3]thiazol-2-yl)-4-bromopyridin-2(1H)-one;

3-(5-{1[(1R,3s,5S)-8-azabicyclo[3.2.1]octan-3-yl](methyl)amino}[1,3]thiazolo[5,4-d][1,3]thiazol-2-yl)-6-(1H-pyrazol-4-yl)pyrimidin-4(3H)-one;

N-[(1R,3s,5S)-8-azabicyclo[3.2.1]octan-3-yl]-N-methyl-5-[6-(1H-pyrazol-4-yl)pyridazin-3-yl][1,3]thiazolo[5,4-d][1,3]thiazol-2-amine;

N-[(1R,3s,5S)-8-azabicyclo[3.2.1]octan-3-yl]-N-methyl-5-[5-(1H-pyrazol-4-yl)pyridin-2-yl][1,3]thiazolo[5,4-d][1,3]thiazol-2-amine;

N-[(1R,3s,5S)-8-azabicyclo[3.2.1]octan-3-yl]-N-methyl-5-[2-(1H-pyrazol-4-yl)pyrimidin-5-yl][1,3]thiazolo[5,4-d][1,3]thiazol-2-amine;

5-[5-(2,7-diazaspiro[3.5]nonan-2-yl)[1,3]thiazolo[5,4-d][1,3]thiazol-2-yl]-7-fluoro-2-methyl-2H-indazole;

2-{5-[2,5-difluoro-4-(1H-pyrazol-4-yl)phenyl][1,3]thiazolo[5,4-d][1,3]thiazol-2-yl}-2,7-diazaspiro[3.5]nonane;

1-(5-{methyl[(1R,3s,5S)-8-methyl-8-azabicyclo[3.2.1]octan-3-yl]amino}[1,3]thiazolo[5,4-d][1,3]thiazol-2-yl)-4-(1H-pyrazol-4-yl)pyridin-2(1H)-one;

2-[5-(7-methyl-1,7-diazaspiro[3.5]nonan-1-yl)[1,3]thiazolo[5,4-d][1,3]thiazol-2-yl]-5-(1H-pyrazol-4-yl)pyridin-3-ol;

1-{5-[(1,2-dimethylpiperidin-4-yl)(methyl)amino][1,3]thiazolo[5,4-d][1,3]thiazol-2-yl}-4-(1H-pyrazol-4-yl)pyridin-2(11H)-one;

1-{5-[methyl(2,2,6,6-tetramethylpiperidin-4-yl)amino][1,3]thiazolo[5,4-d][1,3]thiazol-2-yl}-4-(1H-pyrazol-4-yl)pyridin-2(1H)-one;

2-{5-[(1,2-dimethylpiperidin-4-yl)(methyl)amino][1,3]thiazolo[5,4-d][1,3]thiazol-2-yl}-5-(1H-pyrazol-4-yl)pyridin-3-ol;

N-[(1R,3s,5S)-8-azabicyclo[3.2.1]octan-3-yl]-N-methyl-5-[4-(1H-pyrazol-4-yl)-1H-indol-7-yl][1,3]thiazolo[5,4-d][1,3]thiazol-2-amine;

N-[(1R,3s,5S)-8-azabicyclo[3.2.1]octan-3-yl]-N-methyl-5-[4-(1H-pyrazol-4-yl)-1H-pyrrolo[2,3-c]pyridin-7-yl][1,3]thiazolo[5,4-d][1,3]thiazol-2-amine;

2-(5-{1[(1R,3s,5S)-8-azabicyclo[3.2.1]octan-3-yl](methyl)amino}[1,3]thiazolo[5,4-d][1,3]thiazol-2-yl)-5-bromopyridin-3-ol;

N-[(1R,3s,5S)-8-azabicyclo[3.2.1]octan-3-yl]-5-(5-bromopyrimidin-2-yl)-N-methyl[1,3]thiazolo[5,4-d][1,3]thiazol-2-amine;

1-(5-{1[(1R,3s,5S)-8-azabicyclo[3.2.1]octan-3-yl](methyl)amino}[1,3]thiazolo[5,4-d][1,3]thiazol-2-yl)pyridin-2(1H)-one;

1-{5-[methyl(piperidin-4-yl)amino][1,3]thiazolo[5,4-d][1,3]thiazol-2-yl}-4-(1H-pyrazol-4-yl)pyridin-2(1H)-one;

2-[5-(1,7-diazaspiro[3.5]nonan-1-yl)[1,3]thiazolo[5,4-d][1,3]thiazol-2-yl]-5-(1H-pyrazol-4-yl)pyridin-3-ol;

2-(5-{1[(1R,3s,5S)-8-azabicyclo[3.2.1]octan-3-yl](methyl)amino}[1,3]thiazolo[5,4-d][1,3]thiazol-2-yl)-5-(4-methyl-1H-pyrazol-1-yl)pyridin-3-ol;

6-(5-{1[(1R,3s,5S)-8-azabicyclo[3.2.1]octan-3-yl](methyl)amino}[1,3]thiazolo[5,4-d][1,3]thiazol-2-yl)-5-hydroxy-1'-methyl[3,4'-bipyridin]-2'(1'H)-one;

2-[5-(2,6-diazaspiro[3.5]nonan-2-yl)[1,3]thiazolo[5,4-d][1,3]thiazol-2-yl]-5-(1H-pyrazol-4-yl)pyridin-3-ol;

2-(5-{[(1R,3s,5S)-8-azabicyclo[3.2.1]octan-3-yl](methyl)amino}[1,3]thiazolo[5,4-d][1,3]thiazol-2-yl)-5-(4-fluoro-1H-pyrazol-1-yl)pyridin-3-ol;

N-[(1R,3s,5S)-8-azabicyclo[3.2.1]octan-3-yl]-N-methyl-5-[5-(1H-pyrazol-4-yl)pyrimidin-2-yl][1,3]thiazolo[5,4-d][1,3]thiazol-2-amine;

1-(5-{1[(1R,3s,5S)-8-azabicyclo[3.2.1]octan-3-yl](methyl)amino}[1,3]thiazolo[5,4-d][1,3]thiazol-2-yl)-4-(1H-pyrazol-4-yl)pyridin-2(1H)-one;

2-[5-(7-methyl-2,7-diazaspiro[3.5]nonan-2-yl)[1,3]thiazolo[5,4-d][1,3]thiazol-2-yl]-5-(1H-pyrazol-4-yl)pyridin-3-ol;

5-(1H-pyrazol-4-yl)-2-[5-(spiro[8-azabicyclo[3.2.1]octane-3,3'-azetidin]-1'-yl)[1,3]thiazolo[5,4-d][1,3]thiazol-2-yl]pyridin-3-ol;

5-(1H-pyrazol-4-yl)-2-[5-(spiro[8-azabicyclo[3.2.1]octane-3,3'-azetidin]-1'-yl)[1,3]thiazolo[5,4-d][1,3]thiazol-2-yl]phenol;

2-(5-{1[(1R,3s,5S)-8-azabicyclo[3.2.1]octan-3-yl](methyl)amino}[1,3]thiazolo[5,4-d][1,3]thiazol-2-yl)-5-(2-methyl-1,3-thiazol-5-yl)pyridin-3-ol;

5-[2-methoxy-4-(1H-pyrazol-4-yl)phenyl]-N-methyl-N-(piperidin-4-yl)[1,3]thiazolo[5,4-d][1,3]thiazol-2-amine;

N-methyl-N-(piperidin-4-yl)-5-[5-(1H-pyrazol-4-yl)pyrimidin-2-yl][1,3]thiazolo[5,4-d][1,3]thiazol-2-amine;

2-(5-1{[(2R,4S)-2-(hydroxymethyl)piperidin-4-yl](methyl)amino}[1,3]thiazolo[5,4-d][1,3]thiazol-2-yl)-5-(1H-pyrazol-4-yl)phenol;

2-(5-{1[(1R,3s,5S)-8-azabicyclo[3.2.1]octan-3-yl](methyl)amino}[1,3]thiazolo[5,4-d][1,3]thiazol-2-yl)-5-(1H-pyrazol-4-yl)pyridin-3-ol;

2-{5-[(1-cyclopropylpiperidin-4-yl)(methyl)amino][1,3]thiazolo[5,4-d][1,3]thiazol-2-yl}-5-(1H-pyrazol-4-yl)pyridin-3-ol;

2-(5-{methyl[1-(propan-2-yl)piperidin-4-yl]amino}[1,3]thiazolo[5,4-d][1,3]thiazol-2-yl)-5-(1H-pyrazol-4-yl)pyridin-3-ol;

2-{5-[methyl(1-propylpiperidin-4-yl)amino][1,3]thiazolo[5,4-d][1,3]thiazol-2-yl}-5-(1H-pyrazol-4-yl)pyridin-3-ol;

2-{5-[(1-ethylpiperidin-4-yl)(methyl)amino][1,3]thiazolo[5,4-d][1,3]thiazol-2-yl}-5-(1H-pyrazol-4-yl)pyridin-3-ol;

2-[5-(piperidin-4-yl)[1,3]thiazolo[5,4-d][1,3]thiazol-2-yl]-5-(1H-pyrazol-4-yl)phenol;

2-[5-(2,7-diazaspiro[3.5]nonan-2-yl)[1,3]thiazolo[5,4-d][1,3]thiazol-2-yl]-5-(1H-pyrazol-4-yl)pyridin-3-ol;

2-{5-[methyl(piperidin-4-yl)amino][1,3]thiazolo[5,4-d][1,3]thiazol-2-yl}-5-([1,2,4]triazolo[4,3-a]pyridin-6-yl)pyridin-3-ol;

2-{5-[(3aR,6aS)-5-methylhexahydropyrrolo[3,4-c]pyrrol-2(1H)-yl][1,3]thiazolo[5,4-d][1,3]thiazol-2-yl}-5-(1H-pyrazol-4-yl)phenol;

2-{5-[methyl(piperidin-4-yl)amino][1,3]thiazolo[5,4-d][1,3]thiazol-2-yl}-5-(1H-1,2,4-triazol-1-yl)pyridin-3-ol;

2-(5-{methyl[(3S)-pyrrolidin-3-yl]amino}[1,3]thiazolo[5,4-d][1,3]thiazol-2-yl)-5-(1H-pyrazol-4-yl)pyridin-3-ol;

2-{5-[methyl(piperidin-4-yl)amino][1,3]thiazolo[5,4-d][1,3]thiazol-2-yl}-5-(2H-1,2,3-triazol-2-yl)pyridin-3-ol;

2-{5-[methyl(piperidin-4-yl)amino][1,3]thiazolo[5,4-d][1,3]thiazol-2-yl}-5-(1H-1,2,3-triazol-1-yl)pyridin-3-ol;

2-{5-[methyl(piperidin-4-yl)amino][1,3]thiazolo[5,4-d][1,3]thiazol-2-yl}-5-(1,2-thiazol-4-yl)pyridin-3-ol;

2-{5-[methyl(1-methylpiperidin-4-yl)amino][1,3]thiazolo[5,4-d][1,3]thiazol-2-yl}-5-(1H-pyrazol-4-yl)pyridin-3-ol;

2-{5-[ethyl(1-methylpiperidin-4-yl)amino][1,3]thiazolo[5,4-d][1,3]thiazol-2-yl}-5-(1H-pyrazol-4-yl)pyridin-3-ol;

2-{5-[methyl(piperidin-4-yl)amino][1,3]thiazolo[5,4-d][1,3]thiazol-2-yl}-5-(3-methyl-1H-pyrazol-4-yl)pyridin-3-ol;

5-(5-chloro-1H-pyrazol-4-yl)-2-{5-[methyl(piperidin-4-yl)amino][1,3]thiazolo[5,4-d][1,3]thiazol-2-yl}pyridin-3-ol;

5-(4-methyl-1H-imidazol-1-yl)-2-{5-[methyl(piperidin-4-yl)amino][1,3]thiazolo[5,4-d][1,3]thiazol-2-yl}pyridin-3-ol;

2-{5-[methyl(piperidin-4-yl)amino][1,3]thiazolo[5,4-d][1,3]thiazol-2-yl}-5-(2-methyl-1,3-thiazol-5-yl)pyridin-3-ol;

5-(2-methyl-1,3-oxazol-5-yl)-2-{5-[methyl(piperidin-4-yl)amino][1,3]thiazolo[5,4-d][1,3]thiazol-2-yl}pyridin-3-ol;

2-{5-[methyl(piperidin-4-yl)amino][1,3]thiazolo[5,4-d][1,3]thiazol-2-yl}-5-(6-methylpyridazin-4-yl)pyridin-3-ol;

2-{5-[methyl(piperidin-4-yl)amino][1,3]thiazolo[5,4-d][1,3]thiazol-2-yl}-5-(pyridazin-4-yl)pyridin-3-ol; and N-methyl-N-(piperidin-4-yl)-5-[7-(1H-pyrazol-4-yl)-1H-pyrrolo[2,3-c]pyridin-4-yl][1,3]thiazolo[5,4-d][1,3]thiazol-2-amine;

wherein a form of the compound is selected from the group consisting of salt, hydrate, solvate, racemate, enantiomer, diastereomer, stereoisomer, and tautomer form thereof.

5. The compound of claim 3, wherein the form of the compound is a compound salt or a form thereof selected from the group consisting of:

2-{5-[methyl(2,2,6,6-tetramethylpiperidin-4-yl)amino][1,3]thiazolo[5,4-d][1,3]thiazol-2-yl}-5-(1H-pyrazol-4-yl)phenol hydrochloride;

5-[2,3-difluoro-4-(1H-pyrazol-4-yl)phenyl]-N-methyl-N-(2,2,6,6-tetramethylpiperidin-4-yl)[1,3]thiazolo[5,4-d][1,3]thiazol-2-amine hydrochloride;

5-[2,5-difluoro-4-(1H-pyrazol-4-yl)phenyl]-N-methyl-N-(2,2,6,6-tetramethylpiperidin-4-yl)[1,3]thiazolo[5,4-d][1,3]thiazol-2-amine hydrochloride;

5-[3,5-difluoro-4-(1H-pyrazol-4-yl)phenyl]-N-methyl-N-(2,2,6,6-tetramethylpiperidin-4-yl)[1,3]thiazolo[5,4-d][1,3]thiazol-2-amine hydrochloride;

2-[5-(piperazin-1-yl)[1,3]thiazolo[5,4-d][1,3]thiazol-2-yl]-5-(1H-pyrazol-4-yl)phenol hydrochloride;

2-methyl-5-[5-(piperazin-1-yl)[1,3]thiazolo[5,4-d][1,3]thiazol-2-yl]-2H-indazole-7-carbonitrile hydrochloride;

2-methyl-6-[5-(piperidin-4-yl)[1,3]thiazolo[5,4-d][1,3]thiazol-2-yl]imidazo[1,2-a]pyridine-8-carbonitrile hydrochloride;

7-fluoro-2-methyl-5-[5-(piperidin-4-yl)[1,3]thiazolo[5,4-d][1,3]thiazol-2-yl]-2H-indazole hydrochloride;

2,8-dimethyl-6-[5-(piperidin-4-yl)[1,3]thiazolo[5,4-d][1,3]thiazol-2-yl]imidazo[1,2-b]pyridazine hydrochloride;

2-{5-[(3-exo)-8-azabicyclo[3.2.1]oct-3-ylamino][1,3]thiazolo[5,4-d][1,3]thiazol-2-yl}-5-(1H-pyrazol-4-yl)phenol hydrochloride;

2-{5-[methyl(piperidin-4-yl)amino][1,3]thiazolo[5,4-d][1,3]thiazol-2-yl}-5-(1H-pyrazol-4-yl)phenol hydrochloride;

2-methyl-5-[5-(piperidin-4-yl)[1,3]thiazolo[5,4-d][1,3]thiazol-2-yl]-2H-indazole-7-carbonitrile hydrochloride;

2,7-dimethyl-5-[5-(piperidin-4-yl)[1,3]thiazolo[5,4-d][1,3]thiazol-2-yl]-2H-indazole hydrochloride;

5-[2,5-difluoro-4-(1H-pyrazol-4-yl)phenyl]-N-methyl-N-(piperidin-4-yl)[1,3]thiazolo[5,4-d][1,3]thiazol-2-amine hydrochloride;

5-[3,5-difluoro-4-(1H-pyrazol-4-yl)phenyl]-N-methyl-N-(piperidin-4-yl)[1,3]thiazolo[5,4-d][1,3]thiazol-2-amine hydrochloride;

2-[5-(piperidin-4-ylamino)[1,3]thiazolo[5,4-d][1,3]thiazol-2-yl]-5-(1H-pyrazol-4-yl)phenol hydrochloride;

2-{5-[(1-methylpiperidin-4-yl)amino][1,3]thiazolo[5,4-d][1,3]thiazol-2-yl}-5-(1H-pyrazol-4-yl)phenol hydrochloride;

2-{5-[methyl(1-methylpiperidin-4-yl)amino][1,3]thiazolo[5,4-d][1,3]thiazol-2-yl}-5-(1H-pyrazol-4-yl)phenol hydrochloride;

2-methyl-5-[5-(piperidin-4-yl)[1,3]thiazolo[5,4-d][1,3]thiazol-2-yl]-2H-indazole trifluoroacetate;

7-methoxy-2-methyl-5-[5-(piperidin-4-yl)[1,3]thiazolo[5,4-d][1,3]thiazol-2-yl]-2H-indazole trifluoroacetate;

2-(5-{[(2R,4s,6S)-2,6-dimethylpiperidin-4-yl](methyl)amino}[1,3]thiazolo[5,4-d][1,3]thiazol-2-yl)-5-(1H-pyrazol-4-yl)phenol trifluoroacetate;

4-(3-hydroxy-4-{5-[methyl(piperidin-4-yl)amino][1,3]thiazolo[5,4-d][1,3]thiazol-2-yl}phenyl)pyridin-2-ol hydrochloride;

4-(3-hydroxy-4-{5-[methyl(piperidin-4-yl)amino][1,3]thiazolo[5,4-d][1,3]thiazol-2-yl}phenyl)-1-methylpyridin-2(1H)-one hydrochloride;

4-(3-hydroxy-4-{5-[(2,2,6,6-tetramethylpiperidin-4-yl)oxy][1,3]thiazolo[5,4-d][1,3]thiazol-2-yl}phenyl)-1-methylpyridin-2(1H)-one hydrochloride;

2-{5-[methyl(piperidin-4-yl)amino][1,3]thiazolo[5,4-d][1,3]thiazol-2-yl}-5-[1-($^2$H$_3$)methyl-1H-pyrazol-4-yl]phenol hydrochloride;

2-{5-[methyl(piperidin-4-yl)amino][1,3]thiazolo[5,4-d][1,3]thiazol-2-yl}-5-(1-methyl-1H-pyrazol-4-yl)phenol hydrochloride;

2-{5-[methyl(2,2,6,6-tetramethylpiperidin-4-yl)amino][1,3]thiazolo[5,4-d][1,3]thiazol-2-yl}-5-(1H-pyrazol-4-yl)pyridin-3-ol hydrochloride;

5-(5-fluoro-H-pyrazol-4-yl)-2-{5-[methyl(2,2,6,6-tetramethylpiperidin-4-yl)amino][1,3]thiazolo[5,4-d][1,3]thiazol-2-yl}phenol hydrochloride;

6,8-dimethyl-2-[5-(piperidin-4-yl)[1,3]thiazolo[5,4-d][1,3]thiazol-2-yl]imidazo[1,2-a]pyrazine hydrochloride;

5-(5-fluoro-1l-methyl-1H-pyrazol-4-yl)-2-{5-[(2,2,6,6-tetramethylpiperidin-4-yl)oxy][1,3]thiazolo[5,4-d][1,3]thiazol-2-yl}phenol trifluoroacetate;

4-(3-hydroxy-4-{5-[methyl(2,2,6,6-tetramethylpiperidin-4-yl)amino][1,3]thiazolo[5,4-d][1,3]thiazol-2-yl}phenyl)-1-methylpyridin-2(1H)-one hydrochloride;

2-{5-[methyl(piperidin-4-yl)amino][1,3]thiazolo[5,4-d][1,3]thiazol-2-yl}-5-(1H-pyrazol-4-yl)pyridin-3-ol hydrochloride;

5-(5-fluoro-1-methyl-1H-pyrazol-4-yl)-2-{5-[methyl(2,2,6,6-tetramethylpiperidin-4-yl)amino][1,3]thiazolo[5,4-d][1,3]thiazol-2-yl}phenol hydrochloride;

5-[1-($^2$H$_3$)methyl-1H-pyrazol-4-yl]-2-{5-[methyl(2,2,6,6-tetramethylpiperidin-4-yl)amino][1,3]thiazolo[5,4-d][1,3]thiazol-2-yl}pyridin-3-ol hydrochloride;

5-(1-ethyl-1H-pyrazol-4-yl)-2-{5-[methyl(2,2,6,6-tetramethylpiperidin-4-yl)amino][1,3]thiazolo[5,4-d][1,3]thiazol-2-yl}pyridin-3-ol hydrochloride;

2-{5-[methyl(piperidin-4-yl)amino][1,3]thiazolo[5,4-d][1,3]thiazol-2-yl}-5-[1-($^2$H$_3$)methyl-1H-pyrazol-4-yl]pyridin-3-ol hydrochloride;

5-(1-ethyl-1H-pyrazol-4-yl)-2-{5-[methyl(piperidin-4-yl)amino][1,3]thiazolo[5,4-d][1,3]thiazol-2-yl}pyridin-3-ol hydrochloride;

5-(5-fluoro-1H-pyrazol-4-yl)-2-{5-[methyl(piperidin-4-yl)amino][1,3]thiazolo[5,4-d][1,3]thiazol-2-yl}pyridin-3-ol trifluoroacetate;

2-(5-{methyl[(3S)-pyrrolidin-3-yl]amino}[1,3]thiazolo[5,4-d][1,3]thiazol-2-yl)-5-(1H-pyrazol-4-yl)phenol hydrochloride;

2-(5-{methyl[(3R)-pyrrolidin-3-yl]amino}[1,3]thiazolo[5,4-d][1,3]thiazol-2-yl)-5-(1H-pyrazol-4-yl)phenol hydrochloride;

2-(5-{methyl[(3R)-pyrrolidin-3-yl]amino}[1,3]thiazolo[5,4-d][1,3]thiazol-2-yl)-5-(1H-pyrazol-4-yl)pyridin-3-ol hydrochloride;

5-bromo-2-{5-[methyl(piperidin-4-yl)amino][1,3]thiazolo[5,4-d][1,3]thiazol-2-yl}pyridin-3-ol hydrochloride;

2-{5-[methyl(1-methylpiperidin-4-yl)amino][1,3]thiazolo[5,4-d][1,3]thiazol-2-yl}-5-[1-($^2$H$_3$)methyl-1H-pyrazol-4-yl]phenol hydrochloride;

2-{5-[(1-ethylpiperidin-4-yl)(methyl)amino][1,3]thiazolo[5,4-d][1,3]thiazol-2-yl}-5-(1-methyl-1H-pyrazol-4-yl)phenol hydrochloride;

5-(1H-imidazol-1-yl)-2-{5-[methyl(piperidin-4-yl)amino][1,3]thiazolo[5,4-d][1,3]thiazol-2-yl}pyridin-3-ol trifluoroacetate;

2-{5-[ethyl(piperidin-4-yl)amino][1,3]thiazolo[5,4-d][1,3]thiazol-2-yl}-5-(1H-pyrazol-4-yl)pyridin-3-ol hydrochloride;

5-(4-fluoropyrazol-1-yl)-2-[5-[methyl(4-piperidyl)amino]thiazolo[5,4-d]thiazol-2-yl]pyridin-3-ol hydrochloride;

5-(4-methylpyrazol-1-yl)-2-[5-[methyl(4-piperidyl)amino]thiazolo[5,4-d]thiazol-2-yl]pyridin-3-ol hydrochloride;

5-(thiazol-5-yl)-2-{5-[methyl(piperidin-4-yl)amino][1,3]thiazolo[5,4-d][1,3]thiazol-2-yl}pyridin-3-ol hydrochloride;

N-methyl-N-[(2S,4R)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine hydrochloride;

N-methyl-N-[(2S,4R)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine hydrochloride;

N-methyl-N-[(2S,4R)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine hydrochloride;

7-(5-{[(2R,4S)-2-methylpiperidin-4-yl]oxy}[1,3]thiazolo[5,4-d][1,3]thiazol-2-yl)-4-(1H-pyrazol-4-yl)-1H-pyrrolo[2,3-c]pyridine hydrochloride;

7-{5-[(2,2-dimethylpiperidin-4-yl)oxy][1,3]thiazolo[5,4-d][1,3]thiazol-2-yl}-4-(1H-pyrazol-4-yl)-1H-pyrrolo[2,3-c]pyridine hydrochloride;

7-(5-{[(2R,4S)-2-methylpiperidin-4-yl]oxy}[1,3]thiazolo[5,4-d][1,3]thiazol-2-yl)-4-(1H-pyrazol-4-yl)-1H-indazole hydrochloride;

N-[(1R,3s,5S)-1,5-dimethyl-8-azabicyclo[3.2.1]octan-3-yl]-N-methyl-5-[6-(1H-pyrazol-4-yl)-1,2,4-triazin-3-yl][1,3]thiazolo[5,4-d][1,3]thiazol-2-amine hydrochloride;

5-[4-(1H-imidazol-1-yl)-1H-pyrrolo[2,3-c]pyridin-7-yl]-N-methyl-N-[(2S,4R)-2-methylpiperidin-4-yl][1,3]thiazolo[5,4-d][1,3]thiazol-2-amine hydrochloride;

7-(5-{[(2S,4R)-2-methylpiperidin-4-yl]oxy}[1,3]thiazolo[5,4-d][1,3]thiazol-2-yl)-4-(2-methyl-2H-tetrazol-5-yl)-1H-pyrrolo[2,3-c]pyridine hydrochloride;

7-(5-{[(2R,4S)-2-methylpiperidin-4-yl]oxy}[1,3]thiazolo[5,4-d][1,3]thiazol-2-yl)-4-(1H-pyrazol-4-yl)-1H-indole hydrochloride;

4-(5-{[(2R,4S)-2-methylpiperidin-4-yl]oxy}[1,3]thiazolo[5,4-d][1,3]thiazol-2-yl)-7-(1H-pyrazol-4-yl)-3H-imidazo[4,5-c]pyridine hydrochloride;

7-(5-{[(2S,4R)-1,2-dimethylpiperidin-4-yl]oxy}[1,3]thiazolo[5,4-d][1,3]thiazol-2-yl)-4-(1H-pyrazol-4-yl)-1H-pyrrolo[2,3-c]pyridine formate;

N-methyl-N-[(2R,4S)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine hydrochloride;

N-[(1R,3s,5S)-1,5-dimethyl-8-azabicyclo[3.2.1]octan-3-yl]-N-methyl-5-[5-(5-methyl-1H-pyrazol-4-yl)pyrazin-2-yl][1,3]thiazolo[5,4-d][1,3]thiazol-2-amine hydrochloride;

N-methyl-N-[(2R,4S)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine hydrochloride;

N-[(1R,3s,5S)-1,5-dimethyl-8-azabicyclo[3.2.1]octan-3-yl]-N-methyl-5-[5-(1-methyl-1H-pyrazol-4-yl)pyrazin-2-yl][1,3]thiazolo[5,4-d][1,3]thiazol-2-amine hydrochloride;

5-[4-(1-ethyl-1H-pyrazol-4-yl)-1H-pyrrolo[2,3-c]pyridin-7-yl]-N-methyl-N-[(2R,4S)-2-methylpiperidin-4-yl][1,3]thiazolo[5,4-d][1,3]thiazol-2-amine hydrochloride;

N-methyl-N-[(2R,4S)-2-methylpiperidin-4-yl]-5-[4-(1-methyl-1H-pyrazol-4-yl)-1H-pyrrolo[2,3-c]pyridin-7-yl][1,3]thiazolo[5,4-d][1,3]thiazol-2-amine hydrochloride;

4-[5-(5-{[(1R,3s,5S)-1,5-dimethyl-8-azabicyclo[3.2.1]octan-3-yl](methyl)amino}[1,3]thiazolo[5,4-d][1,3]thiazol-2-yl)pyrazin-2-yl]-1-methylpyridin-2(1H)-one trifluoroacetate;

N-methyl-N-[(2R,4S)-2-methylpiperidin-4-yl]-5-[5-(1H-pyrazol-4-yl)pyrazin-2-yl][1,3]thiazolo[5,4-d][1,3]thiazol-2-amine hydrochloride;

N-methyl-5-[5-(1-methyl-1H-pyrazol-4-yl)pyrazin-2-yl]-N-(2,2,6,6-tetramethylpiperidin-4-yl)[1,3]thiazolo[5,4-d][1,3]thiazol-2-amine hydrochloride;

N-methyl-N-[(2S,4S)-2-methylpiperidin-4-yl]-5-[4-(1-methyl-1H-pyrazol-4-yl)-1H-pyrrolo[2,3-c]pyridin-7-yl][1,3]thiazolo[5,4-d][1,3]thiazol-2-amine hydrochloride;

7-[5-(6-methyl-1,6-diazaspiro[3.5]nonan-1-yl) [1,3]thiazolo[5,4-d][1,3]thiazol-2-yl]-4-(1H-pyrazol-4-yl)-1H-pyrrolo[2,3-c]pyridine formate;

N-methyl-N-[(2S,4S)-2-methylpiperidin-4-yl]-5-[4-(1H-pyrazol-4-yl)-1H-indol-7-yl][1,3]thiazolo[5,4-d][1,3]thiazol-2-amine trifluoroacetate;

N-methyl-N-[(2S,4S)-2-methylpiperidin-4-yl]-5-[4-(1H-pyrazol-4-yl)-1H-pyrrolo[2,3-c]pyridin-7-yl][1,3]thiazolo[5,4-d][1,3]thiazol-2-amine trifluoroacetate;

N-methyl-N-[(2S,4S)-2-methylpiperidin-4-yl]-5-[5-(1H-pyrazol-4-yl)pyrazin-2-yl][1,3]thiazolo[5,4-d][1,3]thiazol-2-amine hydrochloride;

N-methyl-N-(piperidin-4-yl)-5-[5-(1H-pyrazol-4-yl)imidazo[1,2-a]pyrazin-8-yl][1,3]thiazolo[5,4-d][1,3]thiazol-2-amine hydrochloride;

5-[5-(1H-imidazol-1-yl)pyrazin-2-yl]-N-methyl-N-(2,2,6,6-tetramethylpiperidin-4-yl)[1,3]thiazolo[5,4-d][1,3]thiazol-2-amine hydrochloride;

N-[(1R,3s,5S)-1,5-dimethyl-8-azabicyclo[3.2.1]octan-3-yl]-5-[5-(1H-imidazol-1-yl)pyrazin-2-yl]-N-methyl[1,3]thiazolo[5,4-d][1,3]thiazol-2-amine hydrochloride;

N-[(1R,3s,5S)-1,5-dimethyl-8-azabicyclo[3.2.1]octan-3-yl]-N-methyl-5-[5-(1H-pyrazol-1-yl)pyrazin-2-yl][1,3]thiazolo[5,4-d][1,3]thiazol-2-amine hydrochloride;

N-methyl-5-[5-(1H-pyrazol-1-yl)pyrazin-2-yl]-N-(2,2,6,6-tetramethylpiperidin-4-yl)[1,3]thiazolo[5,4-d][1,3]thiazol-2-amine hydrochloride;

N-methyl-5-[4-(1H-pyrazol-4-yl)-1H-benzimidazol-7-yl]-N-(2,2,6,6-tetramethylpiperidin-4-yl)[1,3]thiazolo[5,4-d][1,3]thiazol-2-amine trifluoroacetate;

N-methyl-5-[4-(1H-pyrazol-4-yl)-1H-indazol-7-yl]-N-(2,2,6,6-tetramethylpiperidin-4-yl)[1,3]thiazolo[5,4-d][1,3]thiazol-2-amine trifluoroacetate;

N-(1,2-dimethylpiperidin-4-yl)-N-methyl-5-[4-(1H-pyrazol-4-yl)-1H-indazol-7-yl][1,3]thiazolo[5,4-d][1,3]thiazol-2-amine hydrochloride;

7-(5-{[(2S,4R)-2-methylpiperidin-4-yl]oxy}[1,3]thiazolo[5,4-d][1,3]thiazol-2-yl)-4-(1H-pyrazol-4-yl)-1H-pyrrolo[2,3-c]pyridine hydrochloride;

N-[(1R,3s,5S)-1,5-dimethyl-8-azabicyclo[3.2.1]octan-3-yl]-N-methyl-5-[4-(1H-pyrazol-4-yl)-1H-indazol-7-yl][1,3]thiazolo[5,4-d][1,3]thiazol-2-amine trifluoroacetate;

5-(4-bromo-1H-indazol-7-yl)-N-[(1R,3s,5S)-1,5-dimethyl-8-azabicyclo[3.2.1]octan-3-yl]-N-methyl[1,3]thiazolo[5,4-d][1,3]thiazol-2-amine hydrochloride;

N-(1,2-dimethylpiperidin-4-yl)-N-methyl-5-[4-(1H-pyrazol-4-yl)-1H-benzimidazol-7-yl][1,3]thiazolo[5,4-d][1,3]thiazol-2-amine trifluoroacetate;

N-methyl-5-[1-methyl-4-(1H-pyrazol-4-yl)-1H-pyrrolo[2,3-c]pyridin-7-yl]-N-(piperidin-4-yl)[1,3]thiazolo[5,4-d][1,3]thiazol-2-amine hydrochloride;

N-methyl-5-[5-(1H-pyrazol-4-yl)pyrazin-2-yl]-N-[(1R,3s,5S)-1,5,8-trimethyl-8-azabicyclo[3.2.1]octan-3-yl][1,3]thiazolo[5,4-d][1,3]thiazol-2-amine trifluoroacetate;

N-(1,2-dimethylpiperidin-4-yl)-N-methyl-5-[7-(1H-pyrazol-4-yl)-1H-imidazo[4,5-c]pyridin-4-yl][1,3]thiazolo[5,4-d][1,3]thiazol-2-amine trifluoroacetate;

5-(5-bromoimidazo[1,2-c]pyrimidin-8-yl)-N-methyl-N-(piperidin-4-yl)[1,3]thiazolo[5,4-d][1,3]thiazol-2-amine hydrochloride;

5-(5-bromoimidazo[1,2-a]pyrazin-8-yl)-N-methyl-N-(piperidin-4-yl)[1,3]thiazolo[5,4-d][1,3]thiazol-2-amine hydrochloride;

N-(1,2-dimethylpiperidin-4-yl)-N-methyl-5-[4-(2H-1,2,3-triazol-2-yl)-1H-indol-7-yl][1,3]thiazolo[5,4-d][1,3]thiazol-2-amine trifluoroacetate;

5-(4-chloro-1H-indol-7-yl)-N-(1,2-dimethylpiperidin-4-yl)-N-methyl[1,3]thiazolo[5,4-d][1,3]thiazol-2-amine trifluoroacetate;

7-(5-{1[(2S,4S)-2-methylpiperidin-4-yl]oxy}[1,3]thiazolo[5,4-d][1,3]thiazol-2-yl)-4-(1H-pyrazol-4-yl)-1H-pyrrolo[2,3-c]pyridine formate;

N-methyl-N-[1-(propan-2-yl)piperidin-4-yl]-5-[4-(1H-pyrazol-4-yl)-1H-pyrrolo[2,3-c]pyridin-7-yl][1,3]thiazolo[5,4-d][1,3]thiazol-2-amine formate;

N-(1-ethylpiperidin-4-yl)-N-methyl-5-[4-(1H-pyrazol-4-yl)-1H-pyrrolo[2,3-c]pyridin-7-yl][1,3]thiazolo[5,4-d][1,3]thiazol-2-amine formate;

N-methyl-N-{5-[4-(1H-pyrazol-4-yl)-1H-pyrrolo[2,3-c]pyridin-7-yl][1,3]thiazolo[5,4-d][1,3]thiazol-2-yl}octahydroindolizin-7-amine hydrochloride;

5-(4-bromo-1H-pyrrolo[2,3-c]pyridin-7-yl)-N-(1,2-dimethylpiperidin-4-yl)-N-methyl[1,3]thiazolo[5,4-d][1,3]thiazol-2-amine formate;

N-(1,2-dimethylpiperidin-4-yl)-N-methyl-5-[4-(1H-pyrazol-4-yl)-1H-indol-7-yl][1,3]thiazolo[5,4-d][1,3]thiazol-2-amine trifluoroacetate;

N-(1,2-dimethylpiperidin-4-yl)-N-methyl-5-[5-(1H-pyrazol-4-yl)pyridin-2-yl][1,3]thiazolo[5,4-d][1,3]thiazol-2-amine hydrochloride;

N-(1,2-dimethylpiperidin-4-yl)-N-methyl-5-[6-(1H-pyrazol-4-yl)pyridin-3-yl][1,3]thiazolo[5,4-d][1,3]thiazol-2-amine trifluoroacetate;

N-methyl-5-[4-(1H-pyrazol-4-yl)-1H-indol-7-yl]-N-(2,2,6,6-tetramethylpiperidin-4-yl)[1,3]thiazolo[5,4-d][1,3]thiazol-2-amine trifluoroacetate;

N-(1,2-dimethylpiperidin-4-yl)-N-methyl-5-[5-(1H-pyrazol-4-yl)pyrimidin-2-yl][1,3]thiazolo[5,4-d][1,3]thiazol-2-amine trifluoroacetate;

N-(1,2-dimethylpiperidin-4-yl)-N-methyl-5-[2-(1H-pyrazol-4-yl)pyrimidin-5-yl][1,3]thiazolo[5,4-d][1,3]thiazol-2-amine trifluoroacetate;

3-{5-[(1,2-dimethylpiperidin-4-yl)(methyl)amino][1,3]thiazolo[5,4-d][1,3]thiazol-2-yl}-6-(1H-pyrazol-4-yl)pyrimidin-4(3H)-one hydrochloride;

N-(1,2-dimethylpiperidin-4-yl)-N-methyl-5-[5-(1H-pyrazol-4-yl)pyrazin-2-yl][1,3]thiazolo[5,4-d][1,3]thiazol-2-amine trifluoroacetate;

N-methyl-5-[5-(1H-pyrazol-4-yl)pyridin-2-yl]-N-(2,2,6,6-tetramethylpiperidin-4-yl)[1,3]thiazolo[5,4-d][1,3]thiazol-2-amine hydrochloride;

7-[5-(1,6-diazaspiro[3.5]nonan-1-yl)[1,3]thiazolo[5,4-d][1,3]thiazol-2-yl]-4-(1H-pyrazol-4-yl)-1H-pyrrolo[2,3-c]pyridine formate;

N-methyl-5-[6-(1H-pyrazol-4-yl)pyridin-3-yl]-N-(2,2,6,6-tetramethylpiperidin-4-yl)[1,3]thiazolo[5,4-d][1,3]thiazol-2-amine hydrochloride;

N-methyl-5-[7-(1H-pyrazol-4-yl)-1H-imidazo[4,5-c]pyridin-4-yl]-N-(2,2,6,6-tetramethylpiperidin-4-yl)[1,3]thiazolo[5,4-d][1,3]thiazol-2-amine trifluoroacetate;

N-methyl-5-[2-(1H-pyrazol-4-yl)pyrimidin-5-yl]-N-(2,2,6,6-tetramethylpiperidin-4-yl)[1,3]thiazolo[5,4-d][1,3]thiazol-2-amine hydrochloride;

7-[5-(7-methyl-2,7-diazaspiro[3.5]nonan-2-yl)[1,3]thiazolo[5,4-d][1,3]thiazol-2-yl]-4-(1H-pyrazol-4-yl)-1H-pyrrolo[2,3-c]pyridine trifluoroacetate;

N-methyl-N-(piperidin-4-yl)-5-[4-(1H-pyrazol-4-yl)-1H-pyrrolo[2,3-c]pyridin-7-yl][1,3]thiazolo[5,4-d][1,3]thiazol-2-amine trifluoroacetate;

3-{5-[methyl(2,2,6,6-tetramethylpiperidin-4-yl)amino][1,3]thiazolo[5,4-d][1,3]thiazol-2-yl}-6-(1H-pyrazol-4-yl)pyrimidin-4(3H)-one trifluoroacetate;

N-[(1R,3s,5S)-8-azabicyclo[3.2.1]octan-3-yl]-N-methyl-5-[4-(1H-pyrazol-4-yl)phenyl][1,3]thiazolo[5,4-d][1,3]thiazol-2-amine trifluoroacetate;

N-[(1R,3s,5S)-1,5-dimethyl-8-azabicyclo[3.2.1]octan-3-yl]-N-methyl-5-[5-(1H-pyrazol-4-yl)pyrazin-2-yl][1,3]thiazolo[5,4-d][1,3]thiazol-2-amine trifluoroacetate;

2-[5-(1H-pyrazol-4-yl)pyrazin-2-yl]-5-[(2,2,6,6-tetramethylpiperidin-4-yl)oxy][1,3]thiazolo[5,4-d][1,3]thiazole trifluoroacetate;

3-(5-{[(1R,3s,5S)-1,5-dimethyl-8-azabicyclo[3.2.1]octan-3-yl](methyl)amino}[1,3]thiazolo[5,4-d][1,3]thiazol-2-yl)-6-(1H-pyrazol-4-yl)pyrimidin-4(3H)-one trifluoroacetate;

2-{5-[methyl(octahydroindolizin-7-yl)amino][1,3]thiazolo[5,4-d][1,3]thiazol-2-yl}-5-(1H-pyrazol-4-yl)pyridin-3-ol trifluoroacetate;

1-(5-{[(1R,3s,5S)-1,5-dimethyl-8-azabicyclo[3.2.1]octan-3-yl](methyl)amino}[1,3]thiazolo[5,4-d][1,3]thiazol-2-yl)-4-(1H-pyrazol-4-yl)pyridin-2(1H)-one hydrochloride;

2-{5-[3-(tert-butylamino)pyrrolidin-1-yl][1,3]thiazolo[5,4-d][1,3]thiazol-2-yl}-5-(1H-pyrazol-4-yl)phenol hydrochloride;

1-(5-{[(1R,3s,5S)-1,5-dimethyl-8-azabicyclo[3.2.1]octan-3-yl](methyl)amino}[1,3]thiazolo[5,4-d][1,3]thiazol-2-yl)-4-(4-fluoro-1H-pyrazol-1-yl)pyridin-2(1H)-one hydrochloride;

1-(5-{[(1R,3s,5S)-8-azabicyclo[3.2.1]octan-3-yl](methyl)amino}[1,3]thiazolo[5,4-d][1,3]thiazol-2-yl)-4-(4-fluoro-1H-pyrazol-1-yl)pyridin-2(1H)-one hydrochloride;

N-tert-butyl-1-{5-[5-(1H-pyrazol-4-yl)pyrimidin-2-yl][1,3]thiazolo[5,4-d][1,3]thiazol-2-yl}pyrrolidin-3-amine hydrochloride;

1-{5-[3-(tert-butylamino)pyrrolidin-1-yl][1,3]thiazolo[5,4-d][1,3]thiazol-2-yl}-4-(1H-pyrazol-4-yl)pyridin-2(1H)-one hydrochloride;

N-(1,2-dimethylpiperidin-4-yl)-N-methyl-5-[4-(1H-pyrazol-4-yl)-1H-pyrrolo[2,3-c]pyridin-7-yl][1,3]thiazolo[5,4-d][1,3]thiazol-2-amine hydrochloride;

3-(5-{methyl[(1R,3s,5S)-8-methyl-8-azabicyclo[3.2.1]octan-3-yl]amino}[1,3]thiazolo[5,4-d][1,3]thiazol-2-yl)-6-(1H-pyrazol-4-yl)pyrimidin-4(3H)-one hydrochloride;

N-[(1R,3s,5S)-1,5-dimethyl-8-azabicyclo[3.2.1]octan-3-yl]-N-methyl-5-[4-(1H-pyrazol-4-yl)-1H-pyrrolo[2,3-c]pyridin-7-yl][1,3]thiazolo[5,4-d][1,3]thiazol-2-amine hydrochloride;

1-(5-{methyl[(3R)-piperidin-3-yl]amino}[1,3]thiazolo[5,4-d][1,3]thiazol-2-yl)-4-(1H-pyrazol-4-yl)pyridin-2(1H)-one hydrochloride;

4-(1H-pyrazol-4-yl)-1-{5-[(2,2,6,6-tetramethylpiperidin-4-yl)oxy][1,3]thiazolo[5,4-d][1,3]thiazol-2-yl}pyridin-2(1H)-one hydrochloride;

1-{5-[(1,2-dimethylpiperidin-4-yl)(methyl)amino][1,3]thiazolo[5,4-d][1,3]thiazol-2-yl}-1H-pyrrolo[2,3-b]pyridin-6-ol hydrochloride;

N-[(1R,3s,5S)-8-azabicyclo[3.2.1]octan-3-yl]-5-[2,5-difluoro-4-(1H-pyrazol-4-yl)phenyl]-N-methyl[1,3]thiazolo[5,4-d][1,3]thiazol-2-amine formate;

N-methyl-5-[4-(1H-pyrazol-4-yl)-1H-pyrrolo[2,3-c]pyridin-7-yl]-N-(2,2,6,6-tetramethylpiperidin-4-yl)[1,3]thiazolo[5,4-d][1,3]thiazol-2-amine hydrochloride;

N-[(1R,3s,5S)-8-azabicyclo[3.2.1]octan-3-yl]-N-methyl-5-(1H-pyrrolo[2,3-c]pyridin-7-yl)[1,3]thiazolo[5,4-d][1,3]thiazol-2-amine hydrochloride;

N-methyl-N-[(3S)-piperidin-3-yl]-5-[5-(1H-pyrazol-4-yl)pyrimidin-2-yl][1,3]thiazolo[5,4-d][1,3]thiazol-2-amine hydrochloride;

N-methyl-5-[5-(1H-pyrazol-4-yl)pyrimidin-2-yl]-N-(2,2,6,6-tetramethylpiperidin-4-yl)[1,3]thiazolo[5,4-d][1,3]thiazol-2-amine hydrochloride;

N-methyl-5-[5-(1H-pyrazol-4-yl)pyrazin-2-yl]-N-(2,2,6,6-tetramethylpiperidin-4-yl)[1,3]thiazolo[5,4-d][1,3]thiazol-2-amine hydrochloride;

N-[(1R,3s,5S)-8-azabicyclo[3.2.1]octan-3-yl]-N-methyl-5-[5-(1H-pyrazol-4-yl)pyrazin-2-yl][1,3]thiazolo[5,4-d][1,3]thiazol-2-amine hydrochloride;

N-methyl-5-[6-(1H-pyrazol-4-yl)pyridazin-3-yl]-N-(2,2,6,6-tetramethylpiperidin-4-yl)[1,3]thiazolo[5,4-d][1,3]thiazol-2-amine hydrochloride;

N-[(1R,3s,5S)-8-azabicyclo[3.2.1]octan-3-yl]-N-methyl-5-[6-(1H-pyrazol-4-yl)pyridazin-3-yl][1,3]thiazolo[5,4-d][1,3]thiazol-2-amine hydrochloride;

1-(5-{methyl[(3S)-piperidin-3-yl]amino}[1,3]thiazolo[5,4-d][1,3]thiazol-2-yl)-4-(1H-pyrazol-4-yl)pyridin-2(1H)-one hydrochloride;

N-[(1R,3s,5S)-8-azabicyclo[3.2.1]octan-3-yl]-N-methyl-5-[4-(1H-pyrazol-4-yl)-1H-imidazol-1-yl][1,3]thiazolo[5,4-d][1,3]thiazol-2-amine hydrochloride;

1-(5-{[(1R,3s,5S)-8-azabicyclo[3.2.1]octan-3-yl](methyl)amino}[1,3]thiazolo[5,4-d][1,3]thiazol-2-yl)-4-bromopyridin-2(1H)-one hydrochloride;

3-(5-{1[(1R,3s,5S)-8-azabicyclo[3.2.1]octan-3-yl](methyl)amino}[1,3]thiazolo[5,4-d][1,3]thiazol-2-yl)-6-(1H-pyrazol-4-yl)pyrimidin-4(3H)-one hydrochloride;

N-[(1R,3s,5S)-8-azabicyclo[3.2.1]octan-3-yl]-N-methyl-5-[6-(1H-pyrazol-4-yl)pyridin-3-yl][1,3]thiazolo[5,4-d][1,3]thiazol-2-amine hydrochloride;

N-[(1R,3s,5S)-8-azabicyclo[3.2.1]octan-3-yl]-N-methyl-5-[5-(1H-pyrazol-4-yl)pyridin-2-yl][1,3]thiazolo[5,4-d][1,3]thiazol-2-amine hydrochloride;

N-[(1R,3s,5S)-8-azabicyclo[3.2.1]octan-3-yl]-N-methyl-5-[2-(1H-pyrazol-4-yl)pyrimidin-5-yl][1,3]thiazolo[5,4-d][1,3]thiazol-2-amine hydrochloride;

5-[5-(2,7-diazaspiro[3.5]nonan-2-yl)[1,3]thiazolo[5,4-d][1,3]thiazol-2-yl]-7-fluoro-2-methyl-2H-indazole hydrochloride;

2-{5-[2,5-difluoro-4-(1H-pyrazol-4-yl)phenyl][1,3]thiazolo[5,4-d][1,3]thiazol-2-yl}-2,7-diazaspiro[3.5]nonane hydrochloride;

2-[5-(7-methyl-1,7-diazaspiro[3.5]nonan-1-yl)[1,3]thiazolo[5,4-d][1,3]thiazol-2-yl]-5-(1H-pyrazol-4-yl)pyridin-3-ol hydrochloride;

2-{5-[(1,2-dimethylpiperidin-4-yl)(methyl)amino][1,3]thiazolo[5,4-d][1,3]thiazol-2-yl}-5-(1H-pyrazol-4-yl)pyridin-3-ol hydrochloride;

N-[(1R,3s,5S)-8-azabicyclo[3.2.1]octan-3-yl]-N-methyl-5-[4-(1H-pyrazol-4-yl)-1H-indol-7-yl][1,3]thiazolo[5,4-d][1,3]thiazol-2-amine hydrochloride N-[(1R,3s,5S)-8-azabicyclo[3.2.1]octan-3-yl]-N-methyl-5-[4-(1H-pyrazol-4-yl)-1H-pyrrolo[2,3-c]pyridin-7-yl][1,3]thiazolo[5,4-d][1,3]thiazol-2-amine hydrochloride;

2-(5-{1[(1R,3s,5S)-8-azabicyclo[3.2.1]octan-3-yl](methyl)amino}[1,3]thiazolo[5,4-d][1,3]thiazol-2-yl)-5-bromopyridin-3-ol hydrochloride;

N-[(1R,3s,5S)-8-azabicyclo[3.2.1]octan-3-yl]-5-(5-bromopyrimidin-2-yl)-N-methyl[1,3]thiazolo[5,4-d][1,3]thiazol-2-amine hydrochloride;

1-(5-{1[(1R,3s,5S)-8-azabicyclo[3.2.1]octan-3-yl](methyl)amino}[1,3]thiazolo[5,4-d][1,3]thiazol-2-yl)pyridin-2(1H)-one hydrochloride;

1-{5-[methyl(piperidin-4-yl)amino][1,3]thiazolo[5,4-d][1,3]thiazol-2-yl}-4-(1H-pyrazol-4-yl)pyridin-2(1H1)-one hydrochloride;

2-[5-(1,7-diazaspiro[3.5]nonan-1-yl) [1,3]thiazolo[5,4-d][1,3]thiazol-2-yl]-5-(1H-pyrazol-4-yl)pyridin-3-ol hydrochloride;

2-(5-{[(1R,3s,5S)-8-azabicyclo[3.2.1]octan-3-yl](methyl)amino}[1,3]thiazolo[5,4-d][1,3]thiazol-2-yl)-5-(4-methyl-1H-pyrazol-1-yl)pyridin-3-ol hydrochloride;

6-(5-{1[(1R,3s,5S)-8-azabicyclo[3.2.1]octan-3-yl](methyl)amino}[1,3]thiazolo[5,4-d][1,3]thiazol-2-yl)-5-hydroxy-1'-methyl[3,4'-bipyridin]-2'(1'H)-one hydrochloride;

2-[5-(2,6-diazaspiro[3.5]nonan-2-yl)[1,3]thiazolo[5,4-d][1,3]thiazol-2-yl]-5-(1H-pyrazol-4-yl)pyridin-3-ol hydrochloride;

2-(5-{1[(1R,3s,5S)-8-azabicyclo[3.2.1]octan-3-yl](methyl)amino}[1,3]thiazolo[5,4-d][1,3]thiazol-2-yl)-5-(4-fluoro-1H-pyrazol-1-yl)pyridin-3-ol hydrochloride;

N-[(1R,3s,5S)-8-azabicyclo[3.2.1]octan-3-yl]-N-methyl-5-[5-(1H-pyrazol-4-yl)pyrimidin-2-yl][1,3]thiazolo[5,4-d][1,3]thiazol-2-amine hydrochloride;

1-(5-{1[(1R,3s,5S)-8-azabicyclo[3.2.1]octan-3-yl](methyl)amino}[1,3]thiazolo[5,4-d][1,3]thiazol-2-yl)-4-(1H-pyrazol-4-yl)pyridin-2(1H)-one hydrochloride;

2-[5-(7-methyl-2,7-diazaspiro[3.5]nonan-2-yl)[1,3]thiazolo[5,4-d][1,3]thiazol-2-yl]-5-(1H-pyrazol-4-yl)pyridin-3-ol hydrochloride;

5-(1H-pyrazol-4-yl)-2-[5-(spiro[8-azabicyclo[3.2.1]octane-3,3'-azetidin]-1'-yl)[1,3]thiazolo[5,4-d][1,3]thiazol-2-yl]pyridin-3-ol hydrochloride;

5-(1H-pyrazol-4-yl)-2-[5-(spiro[8-azabicyclo[3.2.1]octane-3,3'-azetidin]-1'-yl)[1,3]thiazolo[5,4-d][1,3]thiazol-2-yl]phenol hydrochloride;

2-(5-{1[(1R,3s,5S)-8-azabicyclo[3.2.1]octan-3-yl](methyl)amino}[1,3]thiazolo[5,4-d][1,3]thiazol-2-yl)-5-(2-methyl-1,3-thiazol-5-yl)pyridin-3-ol dihydrochloride;

5-[2-methoxy-4-(1H-pyrazol-4-yl)phenyl]-N-methyl-N-(piperidin-4-yl)[1,3]thiazolo[5,4-d][1,3]thiazol-2-amine hydrochloride;

N-methyl-N-(piperidin-4-yl)-5-[5-(1H-pyrazol-4-yl)pyrimidin-2-yl][1,3]thiazolo[5,4-d][1,3]thiazol-2-amine hydrochloride;

2-(5-{1[(2R,4S)-2-(hydroxymethyl)piperidin-4-yl](methyl)amino}[1,3]thiazolo[5,4-d][1,3]thiazol-2-yl)-5-(1H-pyrazol-4-yl)phenol dihydrochloride;

2-(5-{1[(1R,3s,5S)-8-azabicyclo[3.2.1]octan-3-yl](methyl)amino}[1,3]thiazolo[5,4-d][1,3]thiazol-2-yl)-5-(1H-pyrazol-4-yl)pyridin-3-ol dihydrochloride;

2-{5-[(1-cyclopropylpiperidin-4-yl)(methyl)amino][1,3]thiazolo[5,4-d][1,3]thiazol-2-yl}-5-(1H-pyrazol-4-yl)pyridin-3-ol hydrochloride;

2-(5-{methyl[1-(propan-2-yl)piperidin-4-yl]amino}[1,3]thiazolo[5,4-d][1,3]thiazol-2-yl)-5-(1H-pyrazol-4-yl)pyridin-3-ol hydrochloride;

2-{5-[methyl(1-propylpiperidin-4-yl)amino][1,3]thiazolo[5,4-d][1,3]thiazol-2-yl}-5-(1H-pyrazol-4-yl)pyridin-3-ol hydrochloride;

2-{5-[(1-ethylpiperidin-4-yl)(methyl)amino][1,3]thiazolo[5,4-d][1,3]thiazol-2-yl}-5-(1H-pyrazol-4-yl)pyridin-3-ol hydrochloride;

2-[5-(piperidin-4-yl) [1,3]thiazolo[5,4-d][1,3]thiazol-2-yl]-5-(1H-pyrazol-4-yl)phenol dihydrochloride;

2-[5-(2,7-diazaspiro[3.5]nonan-2-yl) [1,3]thiazolo[5,4-d][1,3]thiazol-2-yl]-5-(1H-pyrazol-4-yl)pyridin-3-ol hydrochloride;

2-{5-[methyl(piperidin-4-yl)amino][1,3]thiazolo[5,4-d][1,3]thiazol-2-yl}-5-([1,2,4]triazolo[4,3-a]pyridin-6-yl)pyridin-3-ol hydrochloride;

2-{5-[(3aR,6aS)-5-methylhexahydropyrrolo[3,4-c]pyrrol-2(1H)-yl][1,3]thiazolo[5,4-d][1,3]thiazol-2-yl}-5-(1H-pyrazol-4-yl)phenol dihydrochloride;

2-{5-[methyl(piperidin-4-yl)amino][1,3]thiazolo[5,4-d][1,3]thiazol-2-yl}-5-(1H-1,2,4-triazol-1-yl)pyridin-3-ol hydrochloride;

2-(5-{methyl[(3S)-pyrrolidin-3-yl]amino}[1,3]thiazolo[5,4-d][1,3]thiazol-2-yl)-5-(1H-pyrazol-4-yl)pyridin-3-ol hydrochloride;

2-{5-[methyl(piperidin-4-yl)amino][1,3]thiazolo[5,4-d][1,3]thiazol-2-yl}-5-(2H-1,2,3-triazol-2-yl)pyridin-3-ol trifluoroacetate;

2-{5-[methyl(piperidin-4-yl)amino][1,3]thiazolo[5,4-d][1,3]thiazol-2-yl}-5-(1H-1,2,3-triazol-1-yl)pyridin-3-ol trifluoroacetate;

2-{5-[methyl(piperidin-4-yl)amino][1,3]thiazolo[5,4-d][1,3]thiazol-2-yl}-5-(1,2-thiazol-4-yl)pyridin-3-ol hydrochloride;

2-{5-[methyl(1-methylpiperidin-4-yl)amino][1,3]thiazolo[5,4-d][1,3]thiazol-2-yl}-5-(1H-pyrazol-4-yl)pyridin-3-ol hydrochloride;

2-{5-[ethyl(1-methylpiperidin-4-yl)amino][1,3]thiazolo[5,4-d][1,3]thiazol-2-yl}-5-(1H-pyrazol-4-yl)pyridin-3-ol hydrochloride;

2-{5-[methyl(piperidin-4-yl)amino][1,3]thiazolo[5,4-d][1,3]thiazol-2-yl}-5-(3-methyl-1H-pyrazol-4-yl)pyridin-3-ol hydrochloride;

5-(5-chloro-1H-pyrazol-4-yl)-2-{5-[methyl(piperidin-4-yl)amino][1,3]thiazolo[5,4-d][1,3]thiazol-2-yl}pyridin-3-ol hydrochloride;

5-(4-methyl-1H-imidazol-1-yl)-2-{5-[methyl(piperidin-4-yl)amino][1,3]thiazolo[5,4-d][1,3]thiazol-2-yl}pyridin-3-ol hydrochloride;

2-{5-[methyl(piperidin-4-yl)amino][1,3]thiazolo[5,4-d][1,3]thiazol-2-yl}-5-(2-methyl-1,3-thiazol-5-yl)pyridin-3-ol hydrochloride;

5-(2-methyl-1,3-oxazol-5-yl)-2-{5-[methyl(piperidin-4-yl)amino][1,3]thiazolo[5,4-d][1,3]thiazol-2-yl}pyridin-3-ol hydrochloride;

2-{5-[methyl(piperidin-4-yl)amino][1,3]thiazolo[5,4-d][1,3]thiazol-2-yl}-5-(6-methylpyridazin-4-yl)pyridin-3-ol trifluoroacetate;

2-{5-[methyl(piperidin-4-yl)amino][1,3]thiazolo[5,4-d][1,3]thiazol-2-yl}-5-(pyridazin-4-yl)pyridin-3-ol, and trifluoroacetate; and N-methyl-N-(piperidin-4-yl)-5-[7-(1H-pyrazol-4-yl)-1H-pyrrolo[2,3-c]pyridin-4-yl][1,3]thiazolo[5,4-d][1,3]thiazol-2-amine; hydrochloride;

wherein a form of the compound salt is selected from the group consisting of a hydrate, solvate, racemate, enantiomer, diastereomer, stereoisomer, and tautomer form thereof.

6. A method for treating or ameliorating HD in a subject in need thereof comprising administering to the subject an effective amount of the compound of claim 1.

7. The method of claim 6, wherein the effective amount of the compound is in a range of from about 0.001 mg/kg/day to about 500 mg/kg/day.

8. A pharmaceutical composition comprising the compound of claim 1 and at least one pharmaceutically acceptable excipient.

9. A pharmaceutical composition comprising the compound of claim 4 and at least one pharmaceutically acceptable excipient.

* * * * *